US010336826B2

(12) United States Patent
Karpusas et al.

(10) Patent No.: US 10,336,826 B2
(45) Date of Patent: *Jul. 2, 2019

(54) ANTIBODIES TO VLA-1

(71) Applicant: BIOGEN MA INC., Cambridge, MA (US)

(72) Inventors: Michael Karpusas, Upper Darby, PA (US); Paul D. Lyne, Arlington, MA (US); Ellen A. Garber Stark, Cambridge, MA (US); Jose William Saldanha, Enfield (GB)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/470,442

(22) Filed: Mar. 27, 2017

(65) Prior Publication Data

US 2017/0335000 A1 Nov. 23, 2017

Related U.S. Application Data

(60) Continuation of application No. 14/597,262, filed on Jan. 15, 2015, now Pat. No. 9,644,030, which is a division of application No. 13/297,124, filed on Nov. 15, 2011, now abandoned, which is a continuation of application No. 13/017,919, filed on Jan. 31, 2011, now Pat. No. 8,084,028, which is a continuation of application No. 12/727,965, filed on Mar. 19, 2010, now Pat. No. 7,910,099, which is a division of application No. 12/015,213, filed on Jan. 16, 2008, now Pat. No. 7,723,073, which is a division of application No. 10/474,832, filed as application No. PCT/US02/11521 on Apr. 12, 2002, now Pat. No. 7,358,054.

(60) Provisional application No. 60/303,689, filed on Jul. 6, 2001, provisional application No. 60/283,794, filed on Apr. 13, 2001.

(51) Int. Cl.

| | |
|---|---|
| ***A61K 39/395*** | (2006.01) |
| ***C07K 16/28*** | (2006.01) |
| *A61K 39/00* | (2006.01) |

(52) U.S. Cl.

CPC .... *C07K 16/2842* (2013.01); *A61K 2039/505* (2013.01); *C07K 2299/00* (2013.01); *C07K 2317/24* (2013.01); *C07K 2317/34* (2013.01); *C07K 2317/51* (2013.01); *C07K 2317/515* (2013.01); *C07K 2317/56* (2013.01); *C07K 2317/565* (2013.01); *Y02A 90/26* (2018.01)

(58) Field of Classification Search

None

See application file for complete search history.

(56) References Cited

PUBLICATIONS

Conrad et al. α1β1 integrin is crucial for accumulation of epidermal T cells and the development of psoriasis. Nat Med. Jul. 2007;13(7):836-42. (Year: 2007).*

* cited by examiner

*Primary Examiner* — Maher M Haddad

(74) *Attorney, Agent, or Firm* — McCarter & English, LLP; Jonathan M. Sparks; Marcie B. Clarke

(57) ABSTRACT

Antibodies that specifically bind to VLA-1 integrin and methods of using these antibodies to treat immunological disorders in a subject. Also included are crystal structures of complexes formed by VLA-1 antibodies and their ligands, and VLA-1 antagonists and agonists identified by using the structure coordinates of these structures.

15 Claims, 133 Drawing Sheets

Specification includes a Sequence Listing.

| | | | | | | | | | | | | | | | | | | | | |
|---|---|---|---|---|---|---|---|---|---|---|---|---|---|---|---|---|---|---|---|---|
| 1 | V | S | P | T | F | Q | V | V | N | S | F | A | P | V | Q | E | C | S | T | Q |
| | | | | | | | | | | | I | | | | | | | | | |
| 21 | L | D | I | V | I | V | L | D | G | S | N | S | I | Y | P | W | E | S | V | I |
| | | | | | | | | | | | | | | | | | D | | | T |
| 41 | A | F | L | N | D | L | L | K | R | M | D | I | G | P | K | Q | T | Q | V | G |
| 61 | I | V | Q | Y | G | E | N | V | T | H | E | F | N | L | N | K | Y | S | S | T |
| 81 | E | E | V | L | V | A | A | K | K | I | G | R | Q | G | G | L | Q | T | M | T |
| | | | | | | | | | | | V | Q | R | G | G | R | | | | |
| 101 | A | L | G | I | D | T | A | R | K | E | A | F | T | E | A | R | G | A | R | R |
| | | | | T | | | | | | | | | | | | | | | | |
| 121 | G | V | K | K | V | M | V | I | V | T | D | G | E | S | H | D | N | Y | R | L |
| | | | | | | | | | | | | | | | | | | H | | |
| 141 | K | Q | V | I | Q | D | C | E | D | E | N | I | Q | R | F | S | I | A | I | L |
| | | K | | | | | | | | | | | | | | | | | | |
| 161 | G | H | Y | N | R | G | N | L | S | T | E | K | F | V | E | E | I | K | S | I |
| | | S | | | | | | | | | | | | | | | | | | |
| 181 | A | S | E | P | T | E | K | H | F | F | N | V | S | D | E | L | A | L | V | T |
| 201 | I | V | K | A | L | G | E | R | I | F | A | L | E | A | | | | | | |
| | | | | T | | | | | | | | | | | | | | | | |

| | | | | | | | | | | | | | | | | | | | | |
|---|---|---|---|---|---|---|---|---|---|---|---|---|---|---|---|---|---|---|---|---|
| 1 | V | S | P | T | F | Q | V | V | N | S | I | A | P | V | Q | E | C | S | T | Q |
| 21 | L | D | I | V | I | V | L | D | G | S | N | S | I | Y | P | W | D | S | V | T |
| 41 | A | F | L | N | D | L | L | K | R | M | D | I | G | P | K | Q | T | Q | V | G |
| 61 | I | V | Q | Y | G | E | N | V | T | H | E | F | N | L | N | K | Y | S | S | T |
| 81 | E | E | V | L | V | A | A | K | K | I | V | Q | R | G | G | R | Q | T | M | T |
| 101 | A | L | G | T | D | T | A | R | K | E | A | F | T | E | A | R | G | A | R | R |
| 121 | G | V | K | K | V | M | V | I | V | T | D | G | E | S | H | D | N | H | R | L |
| 141 | K | K | V | I | Q | D | C | E | D | E | N | I | Q | R | F | S | I | A | I | L |
| 161 | G | S | Y | N | R | G | N | L | S | T | E | K | F | V | E | E | I | K | S | I |
| 181 | A | S | E | P | T | E | K | H | R | F | N | V | S | D | E | L | A | L | V | T |
| 201 | I | V | K | T | L | G | E | R | I | F | A | L | E | A | | | | | | |

| ATOM | 1 | CB | THR | 145 | 131.250 | 52.244 | -9.297 | 1.00 | 82.68 | A | C |
|---|---|---|---|---|---|---|---|---|---|---|---|
| ATOM | 2 | OG1 | THR | 145 | 131.373 | 51.127 | -10.191 | 1.00 | 82.68 | A | O |
| ATOM | 3 | CG2 | THR | 145 | 132.601 | 52.936 | -9.145 | 1.00 | 82.68 | A | C |
| ATOM | 4 | C | THR | 145 | 129.280 | 51.301 | -8.080 | 1.00 | 146.54 | A | C |
| ATOM | 5 | O | THR | 145 | 128.489 | 51.352 | -7.134 | 1.00 | 146.94 | A | O |
| ATOM | 6 | N | THR | 145 | 131.576 | 50.663 | -7.360 | 1.00 | 144.92 | A | N |
| ATOM | 7 | CA | THR | 145 | 130.726 | 51.757 | -7.915 | 1.00 | 144.52 | A | C |
| ATOM | 8 | N | GLN | 146 | 128.941 | 50.856 | -9.288 | 1.00 | 36.14 | A | N |
| ATOM | 9 | CA | GLN | 146 | 127.592 | 50.397 | -9.569 | 1.00 | 34.29 | A | C |
| ATOM | 10 | CB | GLN | 146 | 127.046 | 51.086 | -10.823 | 1.00 | 99.89 | A | C |
| ATOM | 11 | CG | GLN | 146 | 127.887 | 50.902 | -12.065 | 1.00 | 99.89 | A | C |
| ATOM | 12 | CD | GLN | 146 | 127.274 | 51.575 | -13.279 | 1.00 | 99.89 | A | C |
| ATOM | 13 | OE1 | GLN | 146 | 127.787 | 51.454 | -14.392 | 1.00 | 99.89 | A | O |
| ATOM | 14 | NE2 | GLN | 146 | 126.170 | 52.290 | -13.070 | 1.00 | 99.89 | A | N |
| ATOM | 15 | C | GLN | 146 | 127.535 | 48.883 | -9.721 | 1.00 | 34.71 | A | C |
| ATOM | 16 | O | GLN | 146 | 128.084 | 48.314 | -10.667 | 1.00 | 36.57 | A | O |
| ATOM | 17 | N | LEU | 147 | 126.876 | 48.240 | -8.762 | 1.00 | 33.54 | A | N |
| ATOM | 18 | CA | LEU | 147 | 126.718 | 46.794 | -8.767 | 1.00 | 32.67 | A | C |
| ATOM | 19 | CB | LEU | 147 | 127.491 | 46.143 | -7.609 | 1.00 | 35.25 | A | C |
| ATOM | 20 | CG | LEU | 147 | 128.963 | 46.398 | -7.301 | 1.00 | 35.44 | A | C |
| ATOM | 21 | CD1 | LEU | 147 | 129.205 | 47.877 | -7.087 | 1.00 | 30.65 | A | C |
| ATOM | 22 | CD2 | LEU | 147 | 129.325 | 45.637 | -6.037 | 1.00 | 35.29 | A | C |
| ATOM | 23 | C | LEU | 147 | 125.247 | 46.451 | -8.575 | 1.00 | 31.65 | A | C |
| ATOM | 24 | O | LEU | 147 | 124.506 | 47.194 | -7.939 | 1.00 | 32.95 | A | O |
| ATOM | 25 | N | ASP | 148 | 124.832 | 45.325 | -9.142 | 1.00 | 25.19 | A | N |
| ATOM | 26 | CA | ASP | 148 | 123.477 | 44.817 | -8.976 | 1.00 | 22.65 | A | C |
| ATOM | 27 | CB | ASP | 148 | 122.907 | 44.329 | -10.302 | 1.00 | 27.55 | A | C |
| ATOM | 28 | CG | ASP | 148 | 122.330 | 45.446 | -11.125 | 1.00 | 27.17 | A | C |
| ATOM | 29 | OD1 | ASP | 148 | 121.787 | 45.158 | -12.208 | 1.00 | 26.28 | A | O |
| ATOM | 30 | OD2 | ASP | 148 | 122.413 | 46.612 | -10.686 | 1.00 | 25.35 | A | O |
| ATOM | 31 | C | ASP | 148 | 123.664 | 43.638 | -8.025 | 1.00 | 19.03 | A | C |
| ATOM | 32 | O | ASP | 148 | 124.119 | 42.567 | -8.422 | 1.00 | 18.33 | A | O |
| ATOM | 33 | N | ILE | 149 | 123.341 | 43.848 | -6.760 | 1.00 | 16.75 | A | N |
| ATOM | 34 | CA | ILE | 149 | 123.502 | 42.809 | -5.761 | 1.00 | 15.69 | A | C |
| ATOM | 35 | CB | ILE | 149 | 124.041 | 43.391 | -4.442 | 1.00 | 18.53 | A | C |
| ATOM | 36 | CG2 | ILE | 149 | 124.401 | 42.269 | -3.485 | 1.00 | 13.54 | A | C |
| ATOM | 37 | CG1 | ILE | 149 | 125.271 | 44.251 | -4.718 | 1.00 | 14.25 | A | C |
| ATOM | 38 | CD1 | ILE | 149 | 125.819 | 44.932 | -3.497 | 1.00 | 17.00 | A | C |
| ATOM | 39 | C | ILE | 149 | 122.185 | 42.129 | -5.456 | 1.00 | 17.34 | A | C |
| ATOM | 40 | O | ILE | 149 | 121.191 | 42.794 | -5.181 | 1.00 | 17.74 | A | O |
| ATOM | 41 | N | VAL | 150 | 122.175 | 40.805 | -5.526 | 1.00 | 11.00 | A | N |
| ATOM | 42 | CA | VAL | 150 | 120.987 | 40.036 | -5.193 | 1.00 | 12.56 | A | C |
| ATOM | 43 | CB | VAL | 150 | 120.571 | 39.089 | -6.336 | 1.00 | 16.85 | A | C |
| ATOM | 44 | CG1 | VAL | 150 | 119.409 | 38.210 | -5.885 | 1.00 | 19.04 | A | C |
| ATOM | 45 | CG2 | VAL | 150 | 120.164 | 39.894 | -7.555 | 1.00 | 18.66 | A | C |
| ATOM | 46 | C | VAL | 150 | 121.367 | 39.212 | -3.970 | 1.00 | 10.12 | A | C |
| ATOM | 47 | O | VAL | 150 | 122.387 | 38.526 | -3.973 | 1.00 | 8.27 | A | O |
| ATOM | 48 | N | ILE | 151 | 120.573 | 39.303 | -2.912 | 1.00 | 20.50 | A | N |
| ATOM | 49 | CA | ILE | 151 | 120.856 | 38.537 | -1.699 | 1.00 | 19.30 | A | C |
| ATOM | 50 | CB | ILE | 151 | 120.653 | 39.392 | -0.439 | 1.00 | 14.22 | A | C |
| ATOM | 51 | CG2 | ILE | 151 | 121.039 | 38.601 | 0.785 | 1.00 | 10.58 | A | C |
| ATOM | 52 | CG1 | ILE | 151 | 121.515 | 40.659 | -0.532 | 1.00 | 12.64 | A | C |
| ATOM | 53 | CD1 | ILE | 151 | 121.283 | 41.660 | 0.593 | 1.00 | 14.62 | A | C |
| ATOM | 54 | C | ILE | 151 | 119.931 | 37.329 | -1.646 | 1.00 | 17.42 | A | C |
| ATOM | 55 | O | ILE | 151 | 118.715 | 37.459 | -1.777 | 1.00 | 17.66 | A | O |
| ATOM | 56 | N | VAL | 152 | 120.511 | 36.150 | -1.470 | 1.00 | 17.56 | A | N |
| ATOM | 57 | CA | VAL | 152 | 119.741 | 34.915 | -1.428 | 1.00 | 18.41 | A | C |
| ATOM | 58 | CB | VAL | 152 | 120.395 | 33.849 | -2.309 | 1.00 | 11.45 | A | C |
| ATOM | 59 | CG1 | VAL | 152 | 119.470 | 32.664 | -2.460 | 1.00 | 10.58 | A | C |
| ATOM | 60 | CG2 | VAL | 152 | 120.758 | 34.458 | -3.667 | 1.00 | 7.89 | A | C |
| ATOM | 61 | C | VAL | 152 | 119.675 | 34.404 | -0.003 | 1.00 | 16.31 | A | C |
| ATOM | 62 | O | VAL | 152 | 120.602 | 33.755 | 0.469 | 1.00 | 9.91 | A | O |
| ATOM | 63 | N | LEU | 153 | 118.568 | 34.692 | 0.672 | 1.00 | 19.79 | A | N |
| ATOM | 64 | CA | LEU | 153 | 118.367 | 34.297 | 2.061 | 1.00 | 19.90 | A | C |
| ATOM | 65 | CB | LEU | 153 | 117.530 | 35.361 | 2.766 | 1.00 | 21.44 | A | C |
| ATOM | 66 | CG | LEU | 153 | 118.250 | 36.403 | 3.623 | 1.00 | 23.22 | A | C |
| ATOM | 67 | CD1 | LEU | 153 | 119.699 | 36.561 | 3.185 | 1.00 | 23.73 | A | C |
| ATOM | 68 | CD2 | LEU | 153 | 117.494 | 37.721 | 3.530 | 1.00 | 25.76 | A | C |
| ATOM | 69 | C | LEU | 153 | 117.732 | 32.929 | 2.300 | 1.00 | 20.96 | A | C |
| ATOM | 70 | O | LEU | 153 | 116.724 | 32.574 | 1.690 | 1.00 | 19.96 | A | O |
| ATOM | 71 | N | ASP | 154 | 118.336 | 32.165 | 3.200 | 1.00 | 19.89 | A | N |
| ATOM | 72 | CA | ASP | 154 | 117.820 | 30.854 | 3.554 | 1.00 | 19.37 | A | C |
| ATOM | 73 | CB | ASP | 154 | 118.952 | 29.983 | 4.129 | 1.00 | 22.72 | A | C |

Fig. 19: A-2

| | | | | | | | | | | | |
|---|---|---|---|---|---|---|---|---|---|---|---|
| ATOM | 74 | CG | ASP | 154 | 118.486 | 28.601 | 4.546 | 1.00 | 21.92 | A | C |
| ATOM | 75 | OD1 | ASP | 154 | 117.266 | 28.363 | 4.537 | 1.00 | 25.43 | A | O |
| ATOM | 76 | OD2 | ASP | 154 | 119.340 | 27.754 | 4.893 | 1.00 | 18.24 | A | O |
| ATOM | 77 | C | ASP | 154 | 116.770 | 31.153 | 4.623 | 1.00 | 22.71 | A | C |
| ATOM | 78 | O | ASP | 154 | 117.062 | 31.802 | 5.630 | 1.00 | 19.03 | A | O |
| ATOM | 79 | N | GLY | 155 | 115.540 | 30.718 | 4.393 | 1.00 | 3.06 | A | N |
| ATOM | 80 | CA | GLY | 155 | 114.491 | 30.948 | 5.370 | 1.00 | 5.13 | A | C |
| ATOM | 81 | C | GLY | 155 | 113.840 | 29.638 | 5.788 | 1.00 | 6.39 | A | C |
| ATOM | 82 | O | GLY | 155 | 112.751 | 29.633 | 6.368 | 1.00 | 8.88 | A | O |
| ATOM | 83 | N | SER | 156 | 114.512 | 28.521 | 5.494 | 1.00 | 19.70 | A | N |
| ATOM | 84 | CA | SER | 156 | 114.011 | 27.191 | 5.832 | 1.00 | 24.28 | A | C |
| ATOM | 85 | CB | SER | 156 | 114.994 | 26.111 | 5.353 | 1.00 | 33.45 | A | C |
| ATOM | 86 | OG | SER | 156 | 116.261 | 26.252 | 5.967 | 1.00 | 36.37 | A | O |
| ATOM | 87 | C | SER | 156 | 113.773 | 27.054 | 7.330 | 1.00 | 21.27 | A | C |
| ATOM | 88 | O | SER | 156 | 114.270 | 27.843 | 8.128 | 1.00 | 24.45 | A | O |
| ATOM | 89 | N | ASN | 157 | 113.008 | 26.037 | 7.700 | 1.00 | 21.98 | A | N |
| ATOM | 90 | CA | ASN | 157 | 112.686 | 25.802 | 9.091 | 1.00 | 19.06 | A | C |
| ATOM | 91 | CB | ASN | 157 | 112.027 | 24.435 | 9.247 | 1.00 | 21.82 | A | C |
| ATOM | 92 | CG | ASN | 157 | 110.586 | 24.434 | 8.785 | 1.00 | 23.31 | A | C |
| ATOM | 93 | OD1 | ASN | 157 | 109.944 | 23.385 | 8.706 | 1.00 | 20.38 | A | O |
| ATOM | 94 | ND2 | ASN | 157 | 110.066 | 25.612 | 8.479 | 1.00 | 20.59 | A | N |
| ATOM | 95 | C | ASN | 157 | 113.859 | 25.913 | 10.048 | 1.00 | 17.03 | A | C |
| ATOM | 96 | O | ASN | 157 | 113.720 | 26.498 | 11.132 | 1.00 | 15.01 | A | O |
| ATOM | 97 | N | SER | 158 | 115.006 | 25.367 | 9.653 | 1.00 | 15.99 | A | N |
| ATOM | 98 | CA | SER | 158 | 116.179 | 25.378 | 10.510 | 1.00 | 14.20 | A | C |
| ATOM | 99 | CB | SER | 158 | 117.327 | 24.603 | 9.864 | 1.00 | 26.18 | A | C |
| ATOM | 100 | OG | SER | 158 | 117.597 | 25.067 | 8.562 | 1.00 | 28.89 | A | O |
| ATOM | 101 | C | SER | 158 | 116.656 | 26.753 | 10.941 | 1.00 | 14.97 | A | C |
| ATOM | 102 | O | SER | 158 | 117.053 | 26.930 | 12.097 | 1.00 | 12.14 | A | O |
| ATOM | 103 | N | ILE | 159 | 116.623 | 27.730 | 10.039 | 1.00 | 8.33 | A | N |
| ATOM | 104 | CA | ILE | 159 | 117.050 | 29.083 | 10.379 | 1.00 | 12.93 | A | C |
| ATOM | 105 | CB | ILE | 159 | 116.801 | 30.035 | 9.193 | 1.00 | 9.66 | A | C |
| ATOM | 106 | CG2 | ILE | 159 | 117.138 | 31.479 | 9.592 | 1.00 | 9.57 | A | C |
| ATOM | 107 | CG1 | ILE | 159 | 117.650 | 29.609 | 8.000 | 1.00 | 14.44 | A | C |
| ATOM | 108 | CD1 | ILE | 159 | 119.134 | 29.804 | 8.204 | 1.00 | 19.60 | A | C |
| ATOM | 109 | C | ILE | 159 | 116.292 | 29.604 | 11.616 | 1.00 | 17.24 | A | C |
| ATOM | 110 | O | ILE | 159 | 115.059 | 29.575 | 11.659 | 1.00 | 16.65 | A | O |
| ATOM | 111 | N | TYR | 160 | 117.032 | 30.084 | 12.611 | 1.00 | 29.54 | A | N |
| ATOM | 112 | CA | TYR | 160 | 116.438 | 30.600 | 13.849 | 1.00 | 31.67 | A | C |
| ATOM | 113 | CB | TYR | 160 | 115.775 | 29.455 | 14.639 | 1.00 | 16.89 | A | C |
| ATOM | 114 | CG | TYR | 160 | 115.094 | 29.869 | 15.941 | 1.00 | 13.65 | A | C |
| ATOM | 115 | CD1 | TYR | 160 | 113.717 | 30.089 | 15.993 | 1.00 | 16.07 | A | C |
| ATOM | 116 | CE1 | TYR | 160 | 113.088 | 30.466 | 17.186 | 1.00 | 13.67 | A | C |
| ATOM | 117 | CD2 | TYR | 160 | 115.828 | 30.038 | 17.116 | 1.00 | 11.30 | A | C |
| ATOM | 118 | CE2 | TYR | 160 | 115.211 | 30.416 | 18.304 | 1.00 | 15.01 | A | C |
| ATOM | 119 | CZ | TYR | 160 | 113.841 | 30.627 | 18.338 | 1.00 | 14.36 | A | C |
| ATOM | 120 | OH | TYR | 160 | 113.227 | 30.987 | 19.522 | 1.00 | 19.36 | A | O |
| ATOM | 121 | C | TYR | 160 | 117.498 | 31.264 | 14.734 | 1.00 | 33.39 | A | C |
| ATOM | 122 | O | TYR | 160 | 118.567 | 30.703 | 14.970 | 1.00 | 39.31 | A | O |
| ATOM | 123 | N | PRO | 161 | 117.206 | 32.467 | 15.248 | 1.00 | 31.87 | A | N |
| ATOM | 124 | CD | PRO | 161 | 117.988 | 33.002 | 16.380 | 1.00 | 14.17 | A | C |
| ATOM | 125 | CA | PRO | 161 | 115.969 | 33.234 | 15.055 | 1.00 | 30.15 | A | C |
| ATOM | 126 | CB | PRO | 161 | 115.831 | 33.976 | 16.379 | 1.00 | 18.55 | A | C |
| ATOM | 127 | CG | PRO | 161 | 117.278 | 34.291 | 16.703 | 1.00 | 21.71 | A | C |
| ATOM | 128 | C | PRO | 161 | 116.038 | 34.183 | 13.852 | 1.00 | 28.81 | A | C |
| ATOM | 129 | O | PRO | 161 | 117.074 | 34.792 | 13.580 | 1.00 | 28.13 | A | O |
| ATOM | 130 | N | TRP | 162 | 114.919 | 34.320 | 13.149 | 1.00 | 29.23 | A | N |
| ATOM | 131 | CA | TRP | 162 | 114.839 | 35.170 | 11.967 | 1.00 | 30.30 | A | C |
| ATOM | 132 | CB | TRP | 162 | 113.388 | 35.250 | 11.493 | 1.00 | 29.17 | A | C |
| ATOM | 133 | CG | TRP | 162 | 113.214 | 35.826 | 10.120 | 1.00 | 29.69 | A | C |
| ATOM | 134 | CD2 | TRP | 162 | 113.838 | 35.375 | 8.912 | 1.00 | 24.53 | A | C |
| ATOM | 135 | CE2 | TRP | 162 | 113.338 | 36.175 | 7.859 | 1.00 | 28.08 | A | C |
| ATOM | 136 | CE3 | TRP | 162 | 114.768 | 34.373 | 8.615 | 1.00 | 23.94 | A | C |
| ATOM | 137 | CD1 | TRP | 162 | 112.387 | 36.854 | 9.758 | 1.00 | 28.88 | A | C |
| ATOM | 138 | NE1 | TRP | 162 | 112.455 | 37.071 | 8.403 | 1.00 | 30.75 | A | N |
| ATOM | 139 | CZ2 | TRP | 162 | 113.741 | 36.000 | 6.532 | 1.00 | 26.62 | A | C |
| ATOM | 140 | CZ3 | TRP | 162 | 115.167 | 34.202 | 7.288 | 1.00 | 22.27 | A | C |
| ATOM | 141 | CH2 | TRP | 162 | 114.652 | 35.012 | 6.268 | 1.00 | 27.18 | A | C |
| ATOM | 142 | C | TRP | 162 | 115.381 | 36.579 | 12.210 | 1.00 | 32.08 | A | C |
| ATOM | 143 | O | TRP | 162 | 116.074 | 37.133 | 11.352 | 1.00 | 31.23 | A | O |
| ATOM | 144 | N | GLU | 163 | 115.077 | 37.147 | 13.381 | 1.00 | 25.22 | A | N |
| ATOM | 145 | CA | GLU | 163 | 115.510 | 38.504 | 13.734 | 1.00 | 27.00 | A | C |
| ATOM | 146 | CB | GLU | 163 | 115.108 | 38.857 | 15.172 | 1.00 | 105.95 | A | C |

Fig. 19: A-3

| | | | | | | | | | | | |
|---|---|---|---|---|---|---|---|---|---|---|---|
| ATOM | 147 | CG | GLU | 163 | 115.906 | 38.145 | 16.248 | 1.00 | 112.26 | A | C |
| ATOM | 148 | CD | GLU | 163 | 115.816 | 38.833 | 17.603 | 1.00 | 114.40 | A | C |
| ATOM | 149 | OE1 | GLU | 163 | 116.310 | 39.975 | 17.732 | 1.00 | 116.11 | A | O |
| ATOM | 150 | OE2 | GLU | 163 | 115.253 | 38.232 | 18.541 | 1.00 | 113.36 | A | O |
| ATOM | 151 | C | GLU | 163 | 117.008 | 38.723 | 13.557 | 1.00 | 26.66 | A | C |
| ATOM | 152 | O | GLU | 163 | 117.448 | 39.799 | 13.136 | 1.00 | 22.83 | A | O |
| ATOM | 153 | N | SER | 164 | 117.800 | 37.709 | 13.865 | 1.00 | 20.71 | A | N |
| ATOM | 154 | CA | SER | 164 | 119.241 | 37.850 | 13.715 | 1.00 | 17.90 | A | C |
| ATOM | 155 | CB | SER | 164 | 119.955 | 36.647 | 14.335 | 1.00 | 27.61 | A | C |
| ATOM | 156 | OG | SER | 164 | 119.716 | 36.582 | 15.731 | 1.00 | 33.50 | A | O |
| ATOM | 157 | C | SER | 164 | 119.601 | 37.988 | 12.235 | 1.00 | 18.66 | A | C |
| ATOM | 158 | O | SER | 164 | 120.436 | 38.813 | 11.863 | 1.00 | 21.86 | A | O |
| ATOM | 159 | N | VAL | 165 | 118.956 | 37.179 | 11.398 | 1.00 | 9.03 | A | N |
| ATOM | 160 | CA | VAL | 165 | 119.189 | 37.213 | 9.961 | 1.00 | 8.42 | A | C |
| ATOM | 161 | CB | VAL | 165 | 118.303 | 36.166 | 9.226 | 1.00 | 21.53 | A | C |
| ATOM | 162 | CG1 | VAL | 165 | 118.296 | 36.430 | 7.721 | 1.00 | 22.92 | A | C |
| ATOM | 163 | CG2 | VAL | 165 | 118.826 | 34.760 | 9.505 | 1.00 | 24.53 | A | C |
| ATOM | 164 | C | VAL | 165 | 118.873 | 38.595 | 9.411 | 1.00 | 9.58 | A | C |
| ATOM | 165 | O | VAL | 165 | 119.610 | 39.131 | 8.574 | 1.00 | 11.40 | A | O |
| ATOM | 166 | N | ILE | 166 | 117.772 | 39.169 | 9.887 | 1.00 | 17.73 | A | N |
| ATOM | 167 | CA | ILE | 166 | 117.351 | 40.482 | 9.427 | 1.00 | 17.05 | A | C |
| ATOM | 168 | CB | ILE | 166 | 115.903 | 40.763 | 9.840 | 1.00 | 21.02 | A | C |
| ATOM | 169 | CG2 | ILE | 166 | 115.489 | 42.162 | 9.413 | 1.00 | 20.23 | A | C |
| ATOM | 170 | CG1 | ILE | 166 | 114.997 | 39.737 | 9.164 | 1.00 | 20.88 | A | C |
| ATOM | 171 | CD1 | ILE | 166 | 113.538 | 39.919 | 9.499 | 1.00 | 17.28 | A | C |
| ATOM | 172 | C | ILE | 166 | 118.281 | 41.564 | 9.929 | 1.00 | 16.50 | A | C |
| ATOM | 173 | O | ILE | 166 | 118.560 | 42.520 | 9.206 | 1.00 | 18.25 | A | O |
| ATOM | 174 | N | ALA | 167 | 118.774 | 41.413 | 11.157 | 1.00 | 25.46 | A | N |
| ATOM | 175 | CA | ALA | 167 | 119.711 | 42.391 | 11.710 | 1.00 | 26.06 | A | C |
| ATOM | 176 | CB | ALA | 167 | 120.095 | 42.021 | 13.100 | 1.00 | 7.73 | A | C |
| ATOM | 177 | C | ALA | 167 | 120.941 | 42.371 | 10.823 | 1.00 | 27.27 | A | C |
| ATOM | 178 | O | ALA | 167 | 121.546 | 43.414 | 10.544 | 1.00 | 23.87 | A | O |
| ATOM | 179 | N | PHE | 168 | 121.303 | 41.167 | 10.383 | 1.00 | 18.13 | A | N |
| ATOM | 180 | CA | PHE | 168 | 122.442 | 40.989 | 9.498 | 1.00 | 16.65 | A | C |
| ATOM | 181 | CB | PHE | 168 | 122.626 | 39.513 | 9.158 | 1.00 | 32.51 | A | C |
| ATOM | 182 | CG | PHE | 168 | 123.514 | 39.273 | 7.970 | 1.00 | 31.01 | A | C |
| ATOM | 183 | CD1 | PHE | 168 | 122.968 | 39.066 | 6.701 | 1.00 | 32.61 | A | C |
| ATOM | 184 | CD2 | PHE | 168 | 124.894 | 39.290 | 8.106 | 1.00 | 29.32 | A | C |
| ATOM | 185 | CE1 | PHE | 168 | 123.792 | 38.882 | 5.585 | 1.00 | 31.09 | A | C |
| ATOM | 186 | CE2 | PHE | 168 | 125.724 | 39.109 | 7.000 | 1.00 | 31.14 | A | C |
| ATOM | 187 | CZ | PHE | 168 | 125.173 | 38.906 | 5.738 | 1.00 | 33.63 | A | C |
| ATOM | 188 | C | PHE | 168 | 122.222 | 41.796 | 8.227 | 1.00 | 17.51 | A | C |
| ATOM | 189 | O | PHE | 168 | 123.139 | 42.475 | 7.750 | 1.00 | 13.95 | A | O |
| ATOM | 190 | N | LEU | 169 | 121.007 | 41.719 | 7.680 | 1.00 | 16.88 | A | N |
| ATOM | 191 | CA | LEU | 169 | 120.677 | 42.467 | 6.471 | 1.00 | 19.47 | A | C |
| ATOM | 192 | CB | LEU | 169 | 119.262 | 42.140 | 6.000 | 1.00 | 14.12 | A | C |
| ATOM | 193 | CG | LEU | 169 | 119.041 | 40.860 | 5.213 | 1.00 | 13.28 | A | C |
| ATOM | 194 | CD1 | LEU | 169 | 117.662 | 40.952 | 4.603 | 1.00 | 9.74 | A | C |
| ATOM | 195 | CD2 | LEU | 169 | 120.100 | 40.694 | 4.127 | 1.00 | 10.14 | A | C |
| ATOM | 196 | C | LEU | 169 | 120.777 | 43.966 | 6.731 | 1.00 | 21.77 | A | C |
| ATOM | 197 | O | LEU | 169 | 121.409 | 44.694 | 5.968 | 1.00 | 23.20 | A | O |
| ATOM | 198 | N | ASN | 170 | 120.150 | 44.419 | 7.815 | 1.00 | 20.45 | A | N |
| ATOM | 199 | CA | ASN | 170 | 120.159 | 45.832 | 8.175 | 1.00 | 17.58 | A | C |
| ATOM | 200 | CB | ASN | 170 | 119.534 | 46.018 | 9.562 | 1.00 | 31.53 | A | C |
| ATOM | 201 | CG | ASN | 170 | 119.017 | 47.426 | 9.791 | 1.00 | 34.95 | A | C |
| ATOM | 202 | OD1 | ASN | 170 | 119.740 | 48.282 | 10.284 | 1.00 | 30.48 | A | O |
| ATOM | 203 | ND2 | ASN | 170 | 117.762 | 47.671 | 9.421 | 1.00 | 32.86 | A | N |
| ATOM | 204 | C | ASN | 170 | 121.587 | 46.341 | 8.151 | 1.00 | 17.59 | A | C |
| ATOM | 205 | O | ASN | 170 | 121.941 | 47.174 | 7.321 | 1.00 | 17.80 | A | O |
| ATOM | 206 | N | ASP | 171 | 122.412 | 45.812 | 9.040 | 1.00 | 11.82 | A | N |
| ATOM | 207 | CA | ASP | 171 | 123.816 | 46.218 | 9.120 | 1.00 | 13.94 | A | C |
| ATOM | 208 | CB | ASP | 171 | 124.588 | 45.282 | 10.048 | 1.00 | 56.27 | A | C |
| ATOM | 209 | CG | ASP | 171 | 124.405 | 45.627 | 11.508 | 1.00 | 63.92 | A | C |
| ATOM | 210 | OD1 | ASP | 171 | 123.248 | 45.689 | 11.971 | 1.00 | 66.14 | A | O |
| ATOM | 211 | OD2 | ASP | 171 | 125.427 | 45.834 | 12.196 | 1.00 | 65.78 | A | O |
| ATOM | 212 | C | ASP | 171 | 124.509 | 46.244 | 7.760 | 1.00 | 15.43 | A | C |
| ATOM | 213 | O | ASP | 171 | 125.223 | 47.194 | 7.435 | 1.00 | 14.15 | A | O |
| ATOM | 214 | N | LEU | 172 | 124.289 | 45.200 | 6.966 | 1.00 | 15.45 | A | N |
| ATOM | 215 | CA | LEU | 172 | 124.910 | 45.099 | 5.650 | 1.00 | 16.13 | A | C |
| ATOM | 216 | CB | LEU | 172 | 124.633 | 43.717 | 5.047 | 1.00 | 10.67 | A | C |
| ATOM | 217 | CG | LEU | 172 | 125.667 | 43.058 | 4.123 | 1.00 | 10.16 | A | C |
| ATOM | 218 | CD1 | LEU | 172 | 124.905 | 42.379 | 2.979 | 1.00 | 7.76 | A | C |
| ATOM | 219 | CD2 | LEU | 172 | 126.672 | 44.070 | 3.594 | 1.00 | 8.33 | A | C |

Fig. 19: A-4

| | | | | | | | | | | | |
|---|---|---|---|---|---|---|---|---|---|---|---|
| ATOM | 220 | C | LEU | 172 | 124.401 | 46.178 | 4.699 | 1.00 | 16.47 | A | C |
| ATOM | 221 | O | LEU | 172 | 125.182 | 46.951 | 4.156 | 1.00 | 16.46 | A | O |
| ATOM | 222 | N | LEU | 173 | 123.088 | 46.226 | 4.509 | 1.00 | 30.03 | A | N |
| ATOM | 223 | CA | LEU | 173 | 122.475 | 47.193 | 3.609 | 1.00 | 32.78 | A | C |
| ATOM | 224 | CB | LEU | 173 | 120.967 | 46.932 | 3.474 | 1.00 | 23.11 | A | C |
| ATOM | 225 | CG | LEU | 173 | 120.357 | 45.803 | 2.627 | 1.00 | 24.46 | A | C |
| ATOM | 226 | CD1 | LEU | 173 | 121.069 | 45.702 | 1.292 | 1.00 | 27.98 | A | C |
| ATOM | 227 | CD2 | LEU | 173 | 120.456 | 44.501 | 3.353 | 1.00 | 25.01 | A | C |
| ATOM | 228 | C | LEU | 173 | 122.675 | 48.663 | 3.984 | 1.00 | 34.21 | A | C |
| ATOM | 229 | O | LEU | 173 | 122.937 | 49.495 | 3.105 | 1.00 | 30.93 | A | O |
| ATOM | 230 | N | LYS | 174 | 122.558 | 48.989 | 5.271 | 1.00 | 33.34 | A | N |
| ATOM | 231 | CA | LYS | 174 | 122.684 | 50.379 | 5.693 | 1.00 | 33.56 | A | C |
| ATOM | 232 | CB | LYS | 174 | 122.428 | 50.508 | 7.193 | 1.00 | 32.34 | A | C |
| ATOM | 233 | CG | LYS | 174 | 123.590 | 50.195 | 8.102 | 1.00 | 32.67 | A | C |
| ATOM | 234 | CD | LYS | 174 | 123.170 | 50.471 | 9.551 | 1.00 | 31.92 | A | C |
| ATOM | 235 | CE | LYS | 174 | 124.365 | 50.601 | 10.504 | 1.00 | 27.17 | A | C |
| ATOM | 236 | NZ | LYS | 174 | 125.178 | 49.351 | 10.664 | 1.00 | 23.64 | A | N |
| ATOM | 237 | C | LYS | 174 | 124.004 | 51.046 | 5.317 | 1.00 | 31.92 | A | C |
| ATOM | 238 | O | LYS | 174 | 124.060 | 52.256 | 5.142 | 1.00 | 32.79 | A | O |
| ATOM | 239 | N | ARG | 175 | 125.059 | 50.255 | 5.176 | 1.00 | 34.34 | A | N |
| ATOM | 240 | CA | ARG | 175 | 126.385 | 50.759 | 4.797 | 1.00 | 36.57 | A | C |
| ATOM | 241 | CB | ARG | 175 | 127.468 | 49.712 | 5.125 | 1.00 | 50.56 | A | C |
| ATOM | 242 | CG | ARG | 175 | 127.708 | 49.400 | 6.606 | 1.00 | 57.49 | A | C |
| ATOM | 243 | CD | ARG | 175 | 128.550 | 48.120 | 6.760 | 1.00 | 61.77 | A | C |
| ATOM | 244 | NE | ARG | 175 | 129.398 | 48.107 | 7.957 | 1.00 | 66.67 | A | N |
| ATOM | 245 | CZ | ARG | 175 | 128.954 | 48.049 | 9.211 | 1.00 | 70.25 | A | C |
| ATOM | 246 | NH1 | ARG | 175 | 127.653 | 47.997 | 9.461 | 1.00 | 70.45 | A | N |
| ATOM | 247 | NH2 | ARG | 175 | 129.819 | 48.039 | 10.219 | 1.00 | 71.15 | A | N |
| ATOM | 248 | C | ARG | 175 | 126.461 | 51.051 | 3.288 | 1.00 | 34.10 | A | C |
| ATOM | 249 | O | ARG | 175 | 127.487 | 51.522 | 2.796 | 1.00 | 33.94 | A | O |
| ATOM | 250 | N | MET | 176 | 125.384 | 50.766 | 2.557 | 1.00 | 18.81 | A | N |
| ATOM | 251 | CA | MET | 176 | 125.371 | 50.959 | 1.104 | 1.00 | 15.29 | A | C |
| ATOM | 252 | CB | MET | 176 | 124.758 | 49.728 | 0.431 | 1.00 | 45.67 | A | C |
| ATOM | 253 | CG | MET | 176 | 125.646 | 48.505 | 0.474 | 1.00 | 42.57 | A | C |
| ATOM | 254 | SD | MET | 176 | 124.887 | 47.063 | -0.292 | 1.00 | 46.71 | A | S |
| ATOM | 255 | CE | MET | 176 | 124.633 | 46.046 | 1.139 | 1.00 | 40.22 | A | C |
| ATOM | 256 | C | MET | 176 | 124.679 | 52.199 | 0.546 | 1.00 | 18.80 | A | C |
| ATOM | 257 | O | MET | 176 | 123.797 | 52.768 | 1.176 | 1.00 | 18.87 | A | O |
| ATOM | 258 | N | ASP | 177 | 125.098 | 52.605 | -0.652 | 1.00 | 31.75 | A | N |
| ATOM | 259 | CA | ASP | 177 | 124.504 | 53.744 | -1.344 | 1.00 | 34.24 | A | C |
| ATOM | 260 | CB | ASP | 177 | 125.584 | 54.671 | -1.903 | 1.00 | 129.70 | A | C |
| ATOM | 261 | CG | ASP | 177 | 126.196 | 55.556 | -0.838 | 1.00 | 132.65 | A | C |
| ATOM | 262 | OD1 | ASP | 177 | 127.004 | 56.437 | -1.194 | 1.00 | 132.32 | A | O |
| ATOM | 263 | OD2 | ASP | 177 | 125.869 | 55.372 | 0.354 | 1.00 | 134.30 | A | O |
| ATOM | 264 | C | ASP | 177 | 123.638 | 53.207 | -2.480 | 1.00 | 34.16 | A | C |
| ATOM | 265 | O | ASP | 177 | 124.085 | 53.107 | -3.617 | 1.00 | 33.88 | A | O |
| ATOM | 266 | N | ILE | 178 | 122.402 | 52.848 | -2.153 | 1.00 | 22.62 | A | N |
| ATOM | 267 | CA | ILE | 178 | 121.464 | 52.307 | -3.122 | 1.00 | 22.76 | A | C |
| ATOM | 268 | CB | ILE | 178 | 120.326 | 51.524 | -2.407 | 1.00 | 26.30 | A | C |
| ATOM | 269 | CG2 | ILE | 178 | 119.208 | 51.207 | -3.390 | 1.00 | 24.58 | A | C |
| ATOM | 270 | CG1 | ILE | 178 | 120.866 | 50.222 | -1.803 | 1.00 | 27.36 | A | C |
| ATOM | 271 | CD1 | ILE | 178 | 121.188 | 50.292 | -0.325 | 1.00 | 29.20 | A | C |
| ATOM | 272 | C | ILE | 178 | 120.848 | 53.398 | -4.009 | 1.00 | 21.90 | A | C |
| ATOM | 273 | O | ILE | 178 | 120.532 | 54.501 | -3.539 | 1.00 | 23.89 | A | O |
| ATOM | 274 | N | GLY | 179 | 120.669 | 53.077 | -5.292 | 1.00 | 18.17 | A | N |
| ATOM | 275 | CA | GLY | 179 | 120.091 | 54.029 | -6.226 | 1.00 | 17.89 | A | C |
| ATOM | 276 | C | GLY | 179 | 120.123 | 53.536 | -7.658 | 1.00 | 18.65 | A | C |
| ATOM | 277 | O | GLY | 179 | 121.019 | 52.786 | -8.023 | 1.00 | 16.80 | A | O |
| ATOM | 278 | N | PRO | 180 | 119.150 | 53.937 | -8.498 | 1.00 | 18.34 | A | N |
| ATOM | 279 | CD | PRO | 180 | 117.980 | 54.770 | -8.159 | 1.00 | 16.60 | A | C |
| ATOM | 280 | CA | PRO | 180 | 119.094 | 53.512 | -9.901 | 1.00 | 19.40 | A | C |
| ATOM | 281 | CB | PRO | 180 | 118.044 | 54.442 | -10.498 | 1.00 | 15.44 | A | C |
| ATOM | 282 | CG | PRO | 180 | 117.074 | 54.573 | -9.365 | 1.00 | 17.83 | A | C |
| ATOM | 283 | C | PRO | 180 | 120.432 | 53.622 | -10.597 | 1.00 | 21.18 | A | C |
| ATOM | 284 | O | PRO | 180 | 120.706 | 52.877 | -11.529 | 1.00 | 21.82 | A | O |
| ATOM | 285 | N | LYS | 181 | 121.262 | 54.553 | -10.139 | 1.00 | 25.85 | A | N |
| ATOM | 286 | CA | LYS | 181 | 122.581 | 54.751 | -10.732 | 1.00 | 26.27 | A | C |
| ATOM | 287 | CB | LYS | 181 | 122.737 | 56.187 | -11.253 | 1.00 | 26.21 | A | C |
| ATOM | 288 | CG | LYS | 181 | 121.801 | 56.557 | -12.403 | 1.00 | 26.81 | A | C |
| ATOM | 289 | CD | LYS | 181 | 122.014 | 55.683 | -13.627 | 1.00 | 25.67 | A | C |
| ATOM | 290 | CE | LYS | 181 | 121.014 | 56.031 | -14.719 | 1.00 | 28.19 | A | C |
| ATOM | 291 | NZ | LYS | 181 | 121.097 | 55.146 | -15.923 | 1.00 | 27.76 | A | N |
| ATOM | 292 | C | LYS | 181 | 123.684 | 54.451 | -9.729 | 1.00 | 25.62 | A | C |

Fig. 19: A-5

| | | | | | | | | | | | |
|---|---|---|---|---|---|---|---|---|---|---|---|
| ATOM | 293 | O | LYS | 181 | 124.854 | 54.742 | -9.975 | 1.00 | 23.94 | A | O |
| ATOM | 294 | N | GLN | 182 | 123.300 | 53.870 | -8.599 | 1.00 | 34.95 | A | N |
| ATOM | 295 | CA | GLN | 182 | 124.246 | 53.513 | -7.548 | 1.00 | 33.61 | A | C |
| ATOM | 296 | CB | GLN | 182 | 123.797 | 54.096 | -6.207 | 1.00 | 89.66 | A | C |
| ATOM | 297 | CG | GLN | 182 | 123.331 | 55.528 | -6.251 | 1.00 | 90.94 | A | C |
| ATOM | 298 | CD | GLN | 182 | 124.443 | 56.478 | -6.597 | 1.00 | 92.56 | A | C |
| ATOM | 299 | OE1 | GLN | 182 | 125.007 | 56.418 | -7.686 | 1.00 | 93.40 | A | O |
| ATOM | 300 | NE2 | GLN | 182 | 124.772 | 57.364 | -5.667 | 1.00 | 93.92 | A | N |
| ATOM | 301 | C | GLN | 182 | 124.258 | 51.991 | -7.439 | 1.00 | 32.52 | A | C |
| ATOM | 302 | O | GLN | 182 | 124.398 | 51.278 | -8.429 | 1.00 | 36.85 | A | O |
| ATOM | 303 | N | THR | 183 | 124.096 | 51.507 | -6.216 | 1.00 | 26.87 | A | N |
| ATOM | 304 | CA | THR | 183 | 124.052 | 50.083 | -5.953 | 1.00 | 23.79 | A | C |
| ATOM | 305 | CB | THR | 183 | 124.642 | 49.767 | -4.584 | 1.00 | 30.55 | A | C |
| ATOM | 306 | OG1 | THR | 183 | 125.983 | 50.262 | -4.526 | 1.00 | 27.00 | A | O |
| ATOM | 307 | CG2 | THR | 183 | 124.629 | 48.274 | -4.331 | 1.00 | 28.23 | A | C |
| ATOM | 308 | C | THR | 183 | 122.590 | 49.687 | -5.944 | 1.00 | 23.45 | A | C |
| ATOM | 309 | O | THR | 183 | 121.752 | 50.380 | -5.368 | 1.00 | 21.98 | A | O |
| ATOM | 310 | N | GLN | 184 | 122.269 | 48.592 | -6.608 | 1.00 | 25.73 | A | N |
| ATOM | 311 | CA | GLN | 184 | 120.897 | 48.127 | -6.612 | 1.00 | 21.38 | A | C |
| ATOM | 312 | CB | GLN | 184 | 120.399 | 47.898 | -8.042 | 1.00 | 35.06 | A | C |
| ATOM | 313 | CG | GLN | 184 | 120.016 | 49.181 | -8.770 | 1.00 | 34.81 | A | C |
| ATOM | 314 | CD | GLN | 184 | 118.982 | 48.942 | -9.856 | 1.00 | 34.28 | A | C |
| ATOM | 315 | OE1 | GLN | 184 | 119.215 | 48.164 | -10.781 | 1.00 | 29.98 | A | O |
| ATOM | 316 | NE2 | GLN | 184 | 117.834 | 49.604 | -9.748 | 1.00 | 32.58 | A | N |
| ATOM | 317 | C | GLN | 184 | 120.862 | 46.839 | -5.800 | 1.00 | 21.76 | A | C |
| ATOM | 318 | O | GLN | 184 | 121.832 | 46.087 | -5.780 | 1.00 | 19.15 | A | O |
| ATOM | 319 | N | VAL | 185 | 119.753 | 46.599 | -5.112 | 1.00 | 33.23 | A | N |
| ATOM | 320 | CA | VAL | 185 | 119.634 | 45.408 | -4.298 | 1.00 | 31.60 | A | C |
| ATOM | 321 | CB | VAL | 185 | 119.868 | 45.742 | -2.810 | 1.00 | 20.42 | A | C |
| ATOM | 322 | CG1 | VAL | 185 | 119.572 | 44.535 | -1.938 | 1.00 | 20.41 | A | C |
| ATOM | 323 | CG2 | VAL | 185 | 121.294 | 46.148 | -2.614 | 1.00 | 6.28 | A | C |
| ATOM | 324 | C | VAL | 185 | 118.297 | 44.701 | -4.445 | 1.00 | 32.19 | A | C |
| ATOM | 325 | O | VAL | 185 | 117.237 | 45.322 | -4.469 | 1.00 | 29.34 | A | O |
| ATOM | 326 | N | GLY | 186 | 118.369 | 43.382 | -4.554 | 1.00 | 17.76 | A | N |
| ATOM | 327 | CA | GLY | 186 | 117.177 | 42.573 | -4.672 | 1.00 | 19.39 | A | C |
| ATOM | 328 | C | GLY | 186 | 117.355 | 41.424 | -3.711 | 1.00 | 17.37 | A | C |
| ATOM | 329 | O | GLY | 186 | 118.470 | 40.929 | -3.543 | 1.00 | 22.73 | A | O |
| ATOM | 330 | N | ILE | 187 | 116.278 | 40.995 | -3.073 | 1.00 | 15.41 | A | N |
| ATOM | 331 | CA | ILE | 187 | 116.395 | 39.906 | -2.133 | 1.00 | 14.00 | A | C |
| ATOM | 332 | CB | ILE | 187 | 116.117 | 40.403 | -0.675 | 1.00 | 10.12 | A | C |
| ATOM | 333 | CG2 | ILE | 187 | 116.053 | 39.225 | 0.299 | 1.00 | 7.45 | A | C |
| ATOM | 334 | CG1 | ILE | 187 | 117.232 | 41.364 | -0.253 | 1.00 | 10.64 | A | C |
| ATOM | 335 | CD1 | ILE | 187 | 117.156 | 41.817 | 1.176 | 1.00 | 11.69 | A | C |
| ATOM | 336 | C | ILE | 187 | 115.496 | 38.731 | -2.485 | 1.00 | 13.29 | A | C |
| ATOM | 337 | O | ILE | 187 | 114.301 | 38.896 | -2.768 | 1.00 | 12.19 | A | O |
| ATOM | 338 | N | VAL | 188 | 116.097 | 37.546 | -2.473 | 1.00 | 16.67 | A | N |
| ATOM | 339 | CA | VAL | 188 | 115.403 | 36.303 | -2.769 | 1.00 | 16.34 | A | C |
| ATOM | 340 | CB | VAL | 188 | 116.082 | 35.567 | -3.951 | 1.00 | 11.96 | A | C |
| ATOM | 341 | CG1 | VAL | 188 | 115.642 | 34.122 | -3.993 | 1.00 | 7.23 | A | C |
| ATOM | 342 | CG2 | VAL | 188 | 115.742 | 36.251 | -5.248 | 1.00 | 12.38 | A | C |
| ATOM | 343 | C | VAL | 188 | 115.464 | 35.404 | -1.536 | 1.00 | 14.88 | A | C |
| ATOM | 344 | O | VAL | 188 | 116.509 | 35.286 | -0.895 | 1.00 | 14.29 | A | O |
| ATOM | 345 | N | GLN | 189 | 114.348 | 34.774 | -1.194 | 1.00 | 30.23 | A | N |
| ATOM | 346 | CA | GLN | 189 | 114.335 | 33.873 | -0.049 | 1.00 | 29.91 | A | C |
| ATOM | 347 | CB | GLN | 189 | 113.374 | 34.363 | 1.039 | 1.00 | 26.02 | A | C |
| ATOM | 348 | CG | GLN | 189 | 113.277 | 33.399 | 2.210 | 1.00 | 23.53 | A | C |
| ATOM | 349 | CD | GLN | 189 | 112.257 | 33.807 | 3.267 | 1.00 | 24.24 | A | C |
| ATOM | 350 | OE1 | GLN | 189 | 111.891 | 32.998 | 4.125 | 1.00 | 25.46 | A | O |
| ATOM | 351 | NE2 | GLN | 189 | 111.800 | 35.058 | 3.219 | 1.00 | 25.28 | A | N |
| ATOM | 352 | C | GLN | 189 | 113.911 | 32.490 | -0.520 | 1.00 | 26.90 | A | C |
| ATOM | 353 | O | GLN | 189 | 113.056 | 32.366 | -1.401 | 1.00 | 25.26 | A | O |
| ATOM | 354 | N | TYR | 190 | 114.516 | 31.455 | 0.063 | 1.00 | 12.87 | A | N |
| ATOM | 355 | CA | TYR | 190 | 114.196 | 30.084 | -0.310 | 1.00 | 16.39 | A | C |
| ATOM | 356 | CB | TYR | 190 | 115.267 | 29.539 | -1.257 | 1.00 | 17.86 | A | C |
| ATOM | 357 | CG | TYR | 190 | 116.599 | 29.241 | -0.590 | 1.00 | 13.63 | A | C |
| ATOM | 358 | CD1 | TYR | 190 | 116.887 | 27.963 | -0.092 | 1.00 | 13.63 | A | C |
| ATOM | 359 | CE1 | TYR | 190 | 118.104 | 27.687 | 0.517 | 1.00 | 13.63 | A | C |
| ATOM | 360 | CD2 | TYR | 190 | 117.569 | 30.233 | -0.453 | 1.00 | 13.63 | A | C |
| ATOM | 361 | CE2 | TYR | 190 | 118.787 | 29.968 | 0.159 | 1.00 | 13.63 | A | C |
| ATOM | 362 | CZ | TYR | 190 | 119.053 | 28.698 | 0.640 | 1.00 | 13.63 | A | C |
| ATOM | 363 | OH | TYR | 190 | 120.278 | 28.442 | 1.228 | 1.00 | 13.63 | A | O |
| ATOM | 364 | C | TYR | 190 | 114.035 | 29.135 | 0.878 | 1.00 | 18.24 | A | C |
| ATOM | 365 | O | TYR | 190 | 114.456 | 29.424 | 2.003 | 1.00 | 18.32 | A | O |

Fig. 19: A-6

| | | | | | | | | | | | |
|---|---|---|---|---|---|---|---|---|---|---|---|
| ATOM | 366 | N | GLY | 191 | 113.417 | 27.994 | 0.588 | 1.00 | 15.40 | A | N |
| ATOM | 367 | CA | GLY | 191 | 113.171 | 26.954 | 1.572 | 1.00 | 13.15 | A | C |
| ATOM | 368 | C | GLY | 191 | 112.683 | 25.776 | 0.764 | 1.00 | 14.59 | A | C |
| ATOM | 369 | O | GLY | 191 | 113.482 | 25.084 | 0.139 | 1.00 | 17.97 | A | O |
| ATOM | 370 | N | GLU | 192 | 111.371 | 25.552 | 0.769 | 1.00 | 27.03 | A | N |
| ATOM | 371 | CA | GLU | 192 | 110.764 | 24.475 | -0.020 | 1.00 | 29.04 | A | C |
| ATOM | 372 | CB | GLU | 192 | 109.400 | 24.089 | 0.537 | 1.00 | 28.96 | A | C |
| ATOM | 373 | CG | GLU | 192 | 109.412 | 23.507 | 1.929 | 1.00 | 29.34 | A | C |
| ATOM | 374 | CD | GLU | 192 | 108.020 | 23.089 | 2.390 | 1.00 | 29.53 | A | C |
| ATOM | 375 | OE1 | GLU | 192 | 107.890 | 22.532 | 3.505 | 1.00 | 32.42 | A | O |
| ATOM | 376 | OE2 | GLU | 192 | 107.051 | 23.322 | 1.633 | 1.00 | 27.40 | A | O |
| ATOM | 377 | C | GLU | 192 | 110.562 | 25.062 | -1.410 | 1.00 | 28.85 | A | C |
| ATOM | 378 | O | GLU | 192 | 110.692 | 24.380 | -2.422 | 1.00 | 30.22 | A | O |
| ATOM | 379 | N | ASN | 193 | 110.236 | 26.350 | -1.433 | 1.00 | 34.68 | A | N |
| ATOM | 380 | CA | ASN | 193 | 110.019 | 27.088 | -2.668 | 1.00 | 35.89 | A | C |
| ATOM | 381 | CB | ASN | 193 | 108.566 | 27.527 | -2.769 | 1.00 | 60.91 | A | C |
| ATOM | 382 | CG | ASN | 193 | 107.606 | 26.388 | -2.564 | 1.00 | 64.08 | A | C |
| ATOM | 383 | OD1 | ASN | 193 | 107.545 | 25.804 | -1.488 | 1.00 | 68.19 | A | O |
| ATOM | 384 | ND2 | ASN | 193 | 106.849 | 26.058 | -3.601 | 1.00 | 66.19 | A | N |
| ATOM | 385 | C | ASN | 193 | 110.910 | 28.315 | -2.640 | 1.00 | 34.07 | A | C |
| ATOM | 386 | O | ASN | 193 | 111.759 | 28.459 | -1.760 | 1.00 | 35.07 | A | O |
| ATOM | 387 | N | VAL | 194 | 110.712 | 29.206 | -3.598 | 1.00 | 31.94 | A | N |
| ATOM | 388 | CA | VAL | 194 | 111.511 | 30.423 | -3.660 | 1.00 | 34.28 | A | C |
| ATOM | 389 | CB | VAL | 194 | 112.524 | 30.365 | -4.803 | 1.00 | 32.89 | A | C |
| ATOM | 390 | CG1 | VAL | 194 | 113.514 | 31.495 | -4.671 | 1.00 | 33.92 | A | C |
| ATOM | 391 | CG2 | VAL | 194 | 113.227 | 29.036 | -4.799 | 1.00 | 30.16 | A | C |
| ATOM | 392 | C | VAL | 194 | 110.601 | 31.608 | -3.914 | 1.00 | 32.05 | A | C |
| ATOM | 393 | O | VAL | 194 | 109.651 | 31.507 | -4.688 | 1.00 | 30.17 | A | O |
| ATOM | 394 | N | THR | 195 | 110.877 | 32.730 | -3.261 | 1.00 | 26.46 | A | N |
| ATOM | 395 | CA | THR | 195 | 110.058 | 33.915 | -3.474 | 1.00 | 27.64 | A | C |
| ATOM | 396 | CB | THR | 195 | 109.050 | 34.135 | -2.307 | 1.00 | 36.45 | A | C |
| ATOM | 397 | OG1 | THR | 195 | 109.728 | 34.654 | -1.163 | 1.00 | 40.46 | A | O |
| ATOM | 398 | CG2 | THR | 195 | 108.396 | 32.820 | -1.918 | 1.00 | 38.08 | A | C |
| ATOM | 399 | C | THR | 195 | 110.927 | 35.161 | -3.656 | 1.00 | 28.48 | A | C |
| ATOM | 400 | O | THR | 195 | 111.977 | 35.309 | -3.032 | 1.00 | 31.07 | A | O |
| ATOM | 401 | N | HIS | 196 | 110.492 | 36.040 | -4.545 | 1.00 | 36.83 | A | N |
| ATOM | 402 | CA | HIS | 196 | 111.196 | 37.281 | -4.819 | 1.00 | 36.93 | A | C |
| ATOM | 403 | CB | HIS | 196 | 110.843 | 37.772 | -6.225 | 1.00 | 33.18 | A | C |
| ATOM | 404 | CG | HIS | 196 | 111.434 | 36.951 | -7.326 | 1.00 | 29.68 | A | C |
| ATOM | 405 | CD2 | HIS | 196 | 110.933 | 35.910 | -8.032 | 1.00 | 30.31 | A | C |
| ATOM | 406 | ND1 | HIS | 196 | 112.707 | 37.169 | -7.813 | 1.00 | 28.33 | A | N |
| ATOM | 407 | CE1 | HIS | 196 | 112.965 | 36.296 | -8.772 | 1.00 | 25.05 | A | C |
| ATOM | 408 | NE2 | HIS | 196 | 111.905 | 35.521 | -8.924 | 1.00 | 23.26 | A | N |
| ATOM | 409 | C | HIS | 196 | 110.730 | 38.315 | -3.802 | 1.00 | 36.79 | A | C |
| ATOM | 410 | O | HIS | 196 | 109.687 | 38.933 | -3.997 | 1.00 | 35.45 | A | O |
| ATOM | 411 | N | GLU | 197 | 111.480 | 38.508 | -2.721 | 1.00 | 21.51 | A | N |
| ATOM | 412 | CA | GLU | 197 | 111.069 | 39.488 | -1.732 | 1.00 | 18.84 | A | C |
| ATOM | 413 | CB | GLU | 197 | 112.091 | 39.588 | -0.604 | 1.00 | 43.52 | A | C |
| ATOM | 414 | CG | GLU | 197 | 112.094 | 38.384 | 0.339 | 1.00 | 43.86 | A | C |
| ATOM | 415 | CD | GLU | 197 | 110.717 | 38.043 | 0.882 | 1.00 | 42.93 | A | C |
| ATOM | 416 | OE1 | GLU | 197 | 109.909 | 38.967 | 1.100 | 1.00 | 41.51 | A | O |
| ATOM | 417 | OE2 | GLU | 197 | 110.444 | 36.847 | 1.111 | 1.00 | 44.59 | A | O |
| ATOM | 418 | C | GLU | 197 | 110.882 | 40.832 | -2.442 | 1.00 | 16.31 | A | C |
| ATOM | 419 | O | GLU | 197 | 109.802 | 41.419 | -2.403 | 1.00 | 21.51 | A | O |
| ATOM | 420 | N | PHE | 198 | 111.921 | 41.325 | -3.098 | 1.00 | 11.53 | A | N |
| ATOM | 421 | CA | PHE | 198 | 111.786 | 42.562 | -3.845 | 1.00 | 13.33 | A | C |
| ATOM | 422 | CB | PHE | 198 | 111.803 | 43.785 | -2.901 | 1.00 | 15.90 | A | C |
| ATOM | 423 | CG | PHE | 198 | 113.092 | 44.003 | -2.153 | 1.00 | 14.15 | A | C |
| ATOM | 424 | CD1 | PHE | 198 | 114.262 | 44.390 | -2.823 | 1.00 | 20.29 | A | C |
| ATOM | 425 | CD2 | PHE | 198 | 113.115 | 43.912 | -0.756 | 1.00 | 10.34 | A | C |
| ATOM | 426 | CE1 | PHE | 198 | 115.427 | 44.685 | -2.113 | 1.00 | 16.32 | A | C |
| ATOM | 427 | CE2 | PHE | 198 | 114.274 | 44.208 | -0.039 | 1.00 | 14.80 | A | C |
| ATOM | 428 | CZ | PHE | 198 | 115.431 | 44.594 | -0.719 | 1.00 | 18.60 | A | C |
| ATOM | 429 | C | PHE | 198 | 112.829 | 42.652 | -4.956 | 1.00 | 16.01 | A | C |
| ATOM | 430 | O | PHE | 198 | 113.974 | 42.239 | -4.771 | 1.00 | 17.30 | A | O |
| ATOM | 431 | N | ASN | 199 | 112.418 | 43.152 | -6.123 | 1.00 | 19.42 | A | N |
| ATOM | 432 | CA | ASN | 199 | 113.321 | 43.265 | -7.276 | 1.00 | 19.71 | A | C |
| ATOM | 433 | CB | ASN | 199 | 112.540 | 43.562 | -8.548 | 1.00 | 30.06 | A | C |
| ATOM | 434 | CG | ASN | 199 | 111.465 | 42.548 | -8.824 | 1.00 | 31.32 | A | C |
| ATOM | 435 | OD1 | ASN | 199 | 111.726 | 41.350 | -8.934 | 1.00 | 32.85 | A | O |
| ATOM | 436 | ND2 | ASN | 199 | 110.236 | 43.029 | -8.948 | 1.00 | 30.20 | A | N |
| ATOM | 437 | C | ASN | 199 | 114.458 | 44.288 | -7.173 | 1.00 | 22.17 | A | C |
| ATOM | 438 | O | ASN | 199 | 114.430 | 45.215 | -6.351 | 1.00 | 19.98 | A | O |

Fig. 19: A-7

| | | | | | | | | | | | |
|---|---|---|---|---|---|---|---|---|---|---|---|
| ATOM | 439 | N | LEU | 200 | 115.445 | 44.107 | -8.044 | 1.00 | 18.99 | A | N |
| ATOM | 440 | CA | LEU | 200 | 116.619 | 44.958 | -8.078 | 1.00 | 20.95 | A | C |
| ATOM | 441 | CB | LEU | 200 | 117.556 | 44.524 | -9.212 | 1.00 | 24.87 | A | C |
| ATOM | 442 | CG | LEU | 200 | 118.631 | 43.490 | -8.869 | 1.00 | 22.72 | A | C |
| ATOM | 443 | CD1 | LEU | 200 | 119.348 | 43.048 | -10.130 | 1.00 | 27.84 | A | C |
| ATOM | 444 | CD2 | LEU | 200 | 119.617 | 44.089 | -7.869 | 1.00 | 23.89 | A | C |
| ATOM | 445 | C | LEU | 200 | 116.282 | 46.415 | -8.246 | 1.00 | 21.35 | A | C |
| ATOM | 446 | O | LEU | 200 | 116.960 | 47.274 | -7.688 | 1.00 | 22.37 | A | O |
| ATOM | 447 | N | ASN | 201 | 115.231 | 46.691 | -9.011 | 1.00 | 18.94 | A | N |
| ATOM | 448 | CA | ASN | 201 | 114.816 | 48.061 | -9.284 | 1.00 | 20.79 | A | C |
| ATOM | 449 | CB | ASN | 201 | 114.546 | 48.208 | -10.773 | 1.00 | 21.69 | A | C |
| ATOM | 450 | CG | ASN | 201 | 113.401 | 47.336 | -11.236 | 1.00 | 23.97 | A | C |
| ATOM | 451 | OD1 | ASN | 201 | 113.119 | 47.246 | -12.424 | 1.00 | 24.11 | A | O |
| ATOM | 452 | ND2 | ASN | 201 | 112.727 | 46.684 | -10.292 | 1.00 | 21.81 | A | N |
| ATOM | 453 | C | ASN | 201 | 113.572 | 48.510 | -8.509 | 1.00 | 20.84 | A | C |
| ATOM | 454 | O | ASN | 201 | 112.969 | 49.522 | -8.851 | 1.00 | 16.74 | A | O |
| ATOM | 455 | N | LYS | 202 | 113.182 | 47.770 | -7.477 | 1.00 | 23.30 | A | N |
| ATOM | 456 | CA | LYS | 202 | 111.998 | 48.137 | -6.710 | 1.00 | 23.42 | A | C |
| ATOM | 457 | CB | LYS | 202 | 111.621 | 47.022 | -5.741 | 1.00 | 34.18 | A | C |
| ATOM | 458 | CG | LYS | 202 | 110.337 | 47.265 | -4.944 | 1.00 | 35.72 | A | C |
| ATOM | 459 | CD | LYS | 202 | 109.099 | 47.092 | -5.803 | 1.00 | 37.63 | A | C |
| ATOM | 460 | CE | LYS | 202 | 109.162 | 45.813 | -6.678 | 1.00 | 43.38 | A | C |
| ATOM | 461 | NZ | LYS | 202 | 109.316 | 44.491 | -5.962 | 1.00 | 42.40 | A | N |
| ATOM | 462 | C | LYS | 202 | 112.188 | 49.428 | -5.930 | 1.00 | 22.29 | A | C |
| ATOM | 463 | O | LYS | 202 | 111.338 | 50.313 | -5.984 | 1.00 | 19.57 | A | O |
| ATOM | 464 | N | TYR | 203 | 113.292 | 49.538 | -5.203 | 1.00 | 24.72 | A | N |
| ATOM | 465 | CA | TYR | 203 | 113.538 | 50.731 | -4.407 | 1.00 | 24.40 | A | C |
| ATOM | 466 | CB | TYR | 203 | 113.769 | 50.348 | -2.942 | 1.00 | 32.57 | A | C |
| ATOM | 467 | CG | TYR | 203 | 112.679 | 49.461 | -2.396 | 1.00 | 31.24 | A | C |
| ATOM | 468 | CD1 | TYR | 203 | 112.869 | 48.086 | -2.282 | 1.00 | 31.85 | A | C |
| ATOM | 469 | CE1 | TYR | 203 | 111.842 | 47.251 | -1.844 | 1.00 | 28.32 | A | C |
| ATOM | 470 | CD2 | TYR | 203 | 111.427 | 49.986 | -2.050 | 1.00 | 34.13 | A | C |
| ATOM | 471 | CE2 | TYR | 203 | 110.393 | 49.161 | -1.611 | 1.00 | 36.88 | A | C |
| ATOM | 472 | CZ | TYR | 203 | 110.607 | 47.794 | -1.512 | 1.00 | 36.50 | A | C |
| ATOM | 473 | OH | TYR | 203 | 109.590 | 46.962 | -1.095 | 1.00 | 41.50 | A | O |
| ATOM | 474 | C | TYR | 203 | 114.713 | 51.541 | -4.938 | 1.00 | 25.04 | A | C |
| ATOM | 475 | O | TYR | 203 | 115.755 | 50.986 | -5.280 | 1.00 | 23.21 | A | O |
| ATOM | 476 | N | SER | 204 | 114.536 | 52.861 | -4.998 | 1.00 | 28.94 | A | N |
| ATOM | 477 | CA | SER | 204 | 115.557 | 53.764 | -5.513 | 1.00 | 30.79 | A | C |
| ATOM | 478 | CB | SER | 204 | 114.892 | 54.863 | -6.338 | 1.00 | 29.83 | A | C |
| ATOM | 479 | OG | SER | 204 | 113.945 | 55.577 | -5.558 | 1.00 | 31.66 | A | O |
| ATOM | 480 | C | SER | 204 | 116.372 | 54.402 | -4.412 | 1.00 | 33.37 | A | C |
| ATOM | 481 | O | SER | 204 | 117.247 | 55.214 | -4.680 | 1.00 | 33.88 | A | O |
| ATOM | 482 | N | SER | 205 | 116.089 | 54.027 | -3.173 | 1.00 | 27.33 | A | N |
| ATOM | 483 | CA | SER | 205 | 116.787 | 54.615 | -2.048 | 1.00 | 26.99 | A | C |
| ATOM | 484 | CB | SER | 205 | 115.874 | 55.628 | -1.378 | 1.00 | 50.70 | A | C |
| ATOM | 485 | OG | SER | 205 | 116.409 | 56.032 | -0.137 | 1.00 | 56.19 | A | O |
| ATOM | 486 | C | SER | 205 | 117.251 | 53.608 | -1.016 | 1.00 | 25.12 | A | C |
| ATOM | 487 | O | SER | 205 | 116.650 | 52.551 | -0.857 | 1.00 | 21.38 | A | O |
| ATOM | 488 | N | THR | 206 | 118.318 | 53.949 | -0.301 | 1.00 | 23.44 | A | N |
| ATOM | 489 | CA | THR | 206 | 118.854 | 53.075 | 0.735 | 1.00 | 24.79 | A | C |
| ATOM | 490 | CB | THR | 206 | 120.176 | 53.614 | 1.286 | 1.00 | 12.85 | A | C |
| ATOM | 491 | OG1 | THR | 206 | 121.137 | 53.683 | 0.227 | 1.00 | 11.66 | A | O |
| ATOM | 492 | CG2 | THR | 206 | 120.696 | 52.712 | 2.392 | 1.00 | 11.22 | A | C |
| ATOM | 493 | C | THR | 206 | 117.889 | 52.879 | 1.900 | 1.00 | 25.38 | A | C |
| ATOM | 494 | O | THR | 206 | 117.798 | 51.785 | 2.447 | 1.00 | 28.17 | A | O |
| ATOM | 495 | N | GLU | 207 | 117.173 | 53.926 | 2.299 | 1.00 | 23.18 | A | N |
| ATOM | 496 | CA | GLU | 207 | 116.238 | 53.746 | 3.394 | 1.00 | 22.34 | A | C |
| ATOM | 497 | CB | GLU | 207 | 115.800 | 55.083 | 3.986 | 1.00 | 114.79 | A | C |
| ATOM | 498 | CG | GLU | 207 | 115.317 | 56.095 | 2.992 | 1.00 | 115.51 | A | C |
| ATOM | 499 | CD | GLU | 207 | 114.757 | 57.325 | 3.675 | 1.00 | 116.92 | A | C |
| ATOM | 500 | OE1 | GLU | 207 | 115.428 | 57.857 | 4.587 | 1.00 | 116.15 | A | O |
| ATOM | 501 | OE2 | GLU | 207 | 113.648 | 57.761 | 3.302 | 1.00 | 115.82 | A | O |
| ATOM | 502 | C | GLU | 207 | 115.038 | 52.937 | 2.908 | 1.00 | 22.84 | A | C |
| ATOM | 503 | O | GLU | 207 | 114.515 | 52.094 | 3.640 | 1.00 | 22.79 | A | O |
| ATOM | 504 | N | GLU | 208 | 114.614 | 53.163 | 1.668 | 1.00 | 31.71 | A | N |
| ATOM | 505 | CA | GLU | 208 | 113.485 | 52.412 | 1.126 | 1.00 | 33.44 | A | C |
| ATOM | 506 | CB | GLU | 208 | 113.168 | 52.841 | -0.308 | 1.00 | 38.62 | A | C |
| ATOM | 507 | CG | GLU | 208 | 112.661 | 54.265 | -0.441 | 1.00 | 36.09 | A | C |
| ATOM | 508 | CD | GLU | 208 | 112.288 | 54.633 | -1.875 | 1.00 | 35.61 | A | C |
| ATOM | 509 | OE1 | GLU | 208 | 111.943 | 55.811 | -2.111 | 1.00 | 41.38 | A | O |
| ATOM | 510 | OE2 | GLU | 208 | 112.338 | 53.757 | -2.767 | 1.00 | 34.33 | A | O |
| ATOM | 511 | C | GLU | 208 | 113.808 | 50.920 | 1.148 | 1.00 | 34.14 | A | C |

Fig. 19: A-8

| | | | | | | | | | | |
|---|---|---|---|---|---|---|---|---|---|---|
| ATOM | 512 | O | GLU | 208 | 112.942 | 50.093 | 1.426 | 1.00 | 35.14 | A | O |
| ATOM | 513 | N | VAL | 209 | 115.057 | 50.575 | 0.855 | 1.00 | 17.60 | A | N |
| ATOM | 514 | CA | VAL | 209 | 115.472 | 49.180 | 0.853 | 1.00 | 16.52 | A | C |
| ATOM | 515 | CB | VAL | 209 | 116.790 | 48.982 | 0.077 | 1.00 | 10.63 | A | C |
| ATOM | 516 | CG1 | VAL | 209 | 117.501 | 47.719 | 0.538 | 1.00 | 10.96 | A | C |
| ATOM | 517 | CG2 | VAL | 209 | 116.491 | 48.889 | -1.398 | 1.00 | 11.65 | A | C |
| ATOM | 518 | C | VAL | 209 | 115.656 | 48.691 | 2.276 | 1.00 | 14.54 | A | C |
| ATOM | 519 | O | VAL | 209 | 115.278 | 47.558 | 2.596 | 1.00 | 13.50 | A | O |
| ATOM | 520 | N | LEU | 210 | 116.230 | 49.548 | 3.123 | 1.00 | 19.45 | A | N |
| ATOM | 521 | CA | LEU | 210 | 116.459 | 49.205 | 4.521 | 1.00 | 19.78 | A | C |
| ATOM | 522 | CB | LEU | 210 | 117.148 | 50.354 | 5.242 | 1.00 | 21.61 | A | C |
| ATOM | 523 | CG | LEU | 210 | 118.589 | 50.100 | 5.683 | 1.00 | 21.85 | A | C |
| ATOM | 524 | CD1 | LEU | 210 | 119.093 | 51.347 | 6.358 | 1.00 | 18.40 | A | C |
| ATOM | 525 | CD2 | LEU | 210 | 118.687 | 48.916 | 6.632 | 1.00 | 15.30 | A | C |
| ATOM | 526 | C | LEU | 210 | 115.148 | 48.894 | 5.223 | 1.00 | 18.04 | A | C |
| ATOM | 527 | O | LEU | 210 | 115.078 | 48.022 | 6.093 | 1.00 | 18.81 | A | O |
| ATOM | 528 | N | VAL | 211 | 114.107 | 49.618 | 4.839 | 1.00 | 25.49 | A | N |
| ATOM | 529 | CA | VAL | 211 | 112.798 | 49.443 | 5.432 | 1.00 | 25.25 | A | C |
| ATOM | 530 | CB | VAL | 211 | 111.916 | 50.685 | 5.175 | 1.00 | 19.83 | A | C |
| ATOM | 531 | CG1 | VAL | 211 | 110.457 | 50.391 | 5.537 | 1.00 | 22.01 | A | C |
| ATOM | 532 | CG2 | VAL | 211 | 112.446 | 51.859 | 5.989 | 1.00 | 20.44 | A | C |
| ATOM | 533 | C | VAL | 211 | 112.107 | 48.214 | 4.871 | 1.00 | 24.50 | A | C |
| ATOM | 534 | O | VAL | 211 | 111.437 | 47.483 | 5.593 | 1.00 | 25.18 | A | O |
| ATOM | 535 | N | ALA | 212 | 112.262 | 47.986 | 3.577 | 1.00 | 29.23 | A | N |
| ATOM | 536 | CA | ALA | 212 | 111.624 | 46.839 | 2.964 | 1.00 | 28.21 | A | C |
| ATOM | 537 | CB | ALA | 212 | 111.725 | 46.935 | 1.439 | 1.00 | 1.87 | A | C |
| ATOM | 538 | C | ALA | 212 | 112.275 | 45.559 | 3.465 | 1.00 | 26.02 | A | C |
| ATOM | 539 | O | ALA | 212 | 111.603 | 44.543 | 3.657 | 1.00 | 25.96 | A | O |
| ATOM | 540 | N | ALA | 213 | 113.587 | 45.618 | 3.680 | 1.00 | 33.07 | A | N |
| ATOM | 541 | CA | ALA | 213 | 114.339 | 44.464 | 4.147 | 1.00 | 34.24 | A | C |
| ATOM | 542 | CB | ALA | 213 | 115.803 | 44.787 | 4.176 | 1.00 | 20.72 | A | C |
| ATOM | 543 | C | ALA | 213 | 113.875 | 44.011 | 5.522 | 1.00 | 33.04 | A | C |
| ATOM | 544 | O | ALA | 213 | 113.659 | 42.824 | 5.746 | 1.00 | 30.67 | A | O |
| ATOM | 545 | N | ASN | 214 | 113.723 | 44.952 | 6.446 | 1.00 | 10.19 | A | N |
| ATOM | 546 | CA | ASN | 214 | 113.268 | 44.608 | 7.788 | 1.00 | 14.06 | A | C |
| ATOM | 547 | CB | ASN | 214 | 113.357 | 45.817 | 8.713 | 1.00 | 18.34 | A | C |
| ATOM | 548 | CG | ASN | 214 | 114.763 | 46.094 | 9.158 | 1.00 | 20.07 | A | C |
| ATOM | 549 | OD1 | ASN | 214 | 115.597 | 46.563 | 8.377 | 1.00 | 22.00 | A | O |
| ATOM | 550 | ND2 | ASN | 214 | 115.045 | 45.794 | 10.425 | 1.00 | 20.49 | A | N |
| ATOM | 551 | C | ASN | 214 | 111.847 | 44.081 | 7.828 | 1.00 | 16.45 | A | C |
| ATOM | 552 | O | ASN | 214 | 111.448 | 43.500 | 8.825 | 1.00 | 17.17 | A | O |
| ATOM | 553 | N | LYS | 215 | 111.080 | 44.289 | 6.764 | 1.00 | 16.88 | A | N |
| ATOM | 554 | CA | LYS | 215 | 109.705 | 43.817 | 6.744 | 1.00 | 17.32 | A | C |
| ATOM | 555 | CB | LYS | 215 | 108.804 | 44.772 | 5.926 | 1.00 | 20.45 | A | C |
| ATOM | 556 | CG | LYS | 215 | 108.670 | 46.176 | 6.531 | 1.00 | 28.03 | A | C |
| ATOM | 557 | CD | LYS | 215 | 107.387 | 46.902 | 6.115 | 1.00 | 31.57 | A | C |
| ATOM | 558 | CE | LYS | 215 | 107.304 | 47.155 | 4.607 | 1.00 | 35.03 | A | C |
| ATOM | 559 | NZ | LYS | 215 | 106.135 | 48.007 | 4.237 | 1.00 | 36.02 | A | N |
| ATOM | 560 | C | LYS | 215 | 109.617 | 42.399 | 6.193 | 1.00 | 15.45 | A | C |
| ATOM | 561 | O | LYS | 215 | 108.529 | 41.825 | 6.124 | 1.00 | 16.67 | A | O |
| ATOM | 562 | N | ILE | 216 | 110.757 | 41.824 | 5.812 | 1.00 | 28.84 | A | N |
| ATOM | 563 | CA | ILE | 216 | 110.754 | 40.475 | 5.262 | 1.00 | 25.66 | A | C |
| ATOM | 564 | CB | ILE | 216 | 112.088 | 40.123 | 4.594 | 1.00 | 13.08 | A | C |
| ATOM | 565 | CG2 | ILE | 216 | 112.088 | 38.681 | 4.163 | 1.00 | 9.86 | A | C |
| ATOM | 566 | CG1 | ILE | 216 | 112.298 | 41.002 | 3.362 | 1.00 | 9.76 | A | C |
| ATOM | 567 | CD1 | ILE | 216 | 113.597 | 40.713 | 2.626 | 1.00 | 6.72 | A | C |
| ATOM | 568 | C | ILE | 216 | 110.459 | 39.445 | 6.333 | 1.00 | 24.10 | A | C |
| ATOM | 569 | O | ILE | 216 | 111.076 | 39.441 | 7.404 | 1.00 | 24.80 | A | O |
| ATOM | 570 | N | VAL | 217 | 109.503 | 38.574 | 6.017 | 1.00 | 14.68 | A | N |
| ATOM | 571 | CA | VAL | 217 | 109.065 | 37.511 | 6.904 | 1.00 | 16.45 | A | C |
| ATOM | 572 | CB | VAL | 217 | 107.535 | 37.425 | 6.901 | 1.00 | 9.81 | A | C |
| ATOM | 573 | CG1 | VAL | 217 | 107.065 | 36.144 | 7.569 | 1.00 | 9.81 | A | C |
| ATOM | 574 | CG2 | VAL | 217 | 106.967 | 38.647 | 7.626 | 1.00 | 9.81 | A | C |
| ATOM | 575 | C | VAL | 217 | 109.641 | 36.173 | 6.483 | 1.00 | 17.61 | A | C |
| ATOM | 576 | O | VAL | 217 | 109.794 | 35.895 | 5.298 | 1.00 | 17.07 | A | O |
| ATOM | 577 | N | GLN | 218 | 109.959 | 35.348 | 7.474 | 1.00 | 15.74 | A | N |
| ATOM | 578 | CA | GLN | 218 | 110.512 | 34.024 | 7.234 | 1.00 | 16.40 | A | C |
| ATOM | 579 | CB | GLN | 218 | 111.064 | 33.446 | 8.531 | 1.00 | 14.26 | A | C |
| ATOM | 580 | CG | GLN | 218 | 111.752 | 32.109 | 8.372 | 1.00 | 14.26 | A | C |
| ATOM | 581 | CD | GLN | 218 | 112.331 | 31.589 | 9.675 | 1.00 | 14.26 | A | C |
| ATOM | 582 | OE1 | GLN | 218 | 113.166 | 30.685 | 9.668 | 1.00 | 14.26 | A | O |
| ATOM | 583 | NE2 | GLN | 218 | 111.887 | 32.156 | 10.802 | 1.00 | 14.26 | A | N |
| ATOM | 584 | C | GLN | 218 | 109.392 | 33.151 | 6.719 | 1.00 | 15.85 | A | C |

Fig. 19: A-9

| | | | | | | | | | | | |
|---|---|---|---|---|---|---|---|---|---|---|---|
| ATOM | 585 | O | GLN | 218 | 108.335 | 33.103 | 7.328 | 1.00 | 19.60 | A | O |
| ATOM | 586 | N | ARG | 219 | 109.622 | 32.464 | 5.604 | 1.00 | 16.04 | A | N |
| ATOM | 587 | CA | ARG | 219 | 108.599 | 31.602 | 5.005 | 1.00 | 15.69 | A | C |
| ATOM | 588 | CB | ARG | 219 | 108.595 | 31.786 | 3.489 | 1.00 | 43.49 | A | C |
| ATOM | 589 | CG | ARG | 219 | 109.053 | 33.163 | 3.054 | 1.00 | 43.49 | A | C |
| ATOM | 590 | CD | ARG | 219 | 108.719 | 33.421 | 1.606 | 1.00 | 43.49 | A | C |
| ATOM | 591 | NE | ARG | 219 | 107.365 | 33.952 | 1.454 | 1.00 | 43.49 | A | N |
| ATOM | 592 | CZ | ARG | 219 | 107.042 | 35.232 | 1.606 | 1.00 | 43.49 | A | C |
| ATOM | 593 | NH1 | ARG | 219 | 107.978 | 36.122 | 1.915 | 1.00 | 43.49 | A | N |
| ATOM | 594 | NH2 | ARG | 219 | 105.786 | 35.621 | 1.443 | 1.00 | 43.49 | A | N |
| ATOM | 595 | C | ARG | 219 | 108.814 | 30.127 | 5.350 | 1.00 | 16.90 | A | C |
| ATOM | 596 | O | ARG | 219 | 108.073 | 29.253 | 4.886 | 1.00 | 16.91 | A | O |
| ATOM | 597 | N | GLY | 220 | 109.838 | 29.867 | 6.160 | 1.00 | 9.58 | A | N |
| ATOM | 598 | CA | GLY | 220 | 110.148 | 28.513 | 6.567 | 1.00 | 9.19 | A | C |
| ATOM | 599 | C | GLY | 220 | 110.442 | 27.562 | 5.422 | 1.00 | 8.86 | A | C |
| ATOM | 600 | O | GLY | 220 | 110.682 | 27.993 | 4.288 | 1.00 | 7.20 | A | O |
| ATOM | 601 | N | GLY | 221 | 110.435 | 26.266 | 5.730 | 1.00 | 16.50 | A | N |
| ATOM | 602 | CA | GLY | 221 | 110.682 | 25.265 | 4.718 | 1.00 | 15.07 | A | C |
| ATOM | 603 | C | GLY | 221 | 111.117 | 23.954 | 5.314 | 1.00 | 15.49 | A | C |
| ATOM | 604 | O | GLY | 221 | 112.038 | 23.928 | 6.124 | 1.00 | 12.29 | A | O |
| ATOM | 605 | N | ARG | 222 | 110.459 | 22.865 | 4.927 | 1.00 | 35.34 | A | N |
| ATOM | 606 | CA | ARG | 222 | 110.815 | 21.543 | 5.433 | 1.00 | 36.05 | A | C |
| ATOM | 607 | CB | ARG | 222 | 109.652 | 20.567 | 5.235 | 1.00 | 22.30 | A | C |
| ATOM | 608 | CG | ARG | 222 | 108.505 | 20.791 | 6.201 | 1.00 | 22.30 | A | C |
| ATOM | 609 | CD | ARG | 222 | 107.252 | 20.047 | 5.779 | 1.00 | 22.30 | A | C |
| ATOM | 610 | NE | ARG | 222 | 106.621 | 20.647 | 4.614 | 1.00 | 22.30 | A | N |
| ATOM | 611 | CZ | ARG | 222 | 105.459 | 20.247 | 4.103 | 1.00 | 22.30 | A | C |
| ATOM | 612 | NH1 | ARG | 222 | 104.795 | 19.241 | 4.654 | 1.00 | 22.30 | A | N |
| ATOM | 613 | NH2 | ARG | 222 | 104.951 | 20.857 | 3.042 | 1.00 | 22.30 | A | N |
| ATOM | 614 | C | ARG | 222 | 112.062 | 21.036 | 4.723 | 1.00 | 36.10 | A | C |
| ATOM | 615 | O | ARG | 222 | 112.626 | 20.017 | 5.107 | 1.00 | 36.87 | A | O |
| ATOM | 616 | N | GLN | 223 | 112.473 | 21.750 | 3.678 | 1.00 | 27.48 | A | N |
| ATOM | 617 | CA | GLN | 223 | 113.672 | 21.428 | 2.912 | 1.00 | 25.77 | A | C |
| ATOM | 618 | CB | GLN | 223 | 113.328 | 20.858 | 1.535 | 1.00 | 13.17 | A | C |
| ATOM | 619 | CG | GLN | 223 | 112.830 | 19.417 | 1.508 | 1.00 | 14.61 | A | C |
| ATOM | 620 | CD | GLN | 223 | 111.346 | 19.312 | 1.790 | 1.00 | 15.02 | A | C |
| ATOM | 621 | OE1 | GLN | 223 | 110.533 | 20.016 | 1.190 | 1.00 | 15.42 | A | O |
| ATOM | 622 | NE2 | GLN | 223 | 110.981 | 18.417 | 2.698 | 1.00 | 15.46 | A | N |
| ATOM | 623 | C | GLN | 223 | 114.498 | 22.706 | 2.724 | 1.00 | 26.51 | A | C |
| ATOM | 624 | O | GLN | 223 | 114.057 | 23.799 | 3.069 | 1.00 | 25.99 | A | O |
| ATOM | 625 | N | THR | 224 | 115.696 | 22.567 | 2.172 | 1.00 | 24.40 | A | N |
| ATOM | 626 | CA | THR | 224 | 116.581 | 23.704 | 1.948 | 1.00 | 22.28 | A | C |
| ATOM | 627 | CB | THR | 224 | 117.795 | 23.633 | 2.897 | 1.00 | 14.98 | A | C |
| ATOM | 628 | OG1 | THR | 224 | 117.328 | 23.565 | 4.246 | 1.00 | 14.97 | A | O |
| ATOM | 629 | CG2 | THR | 224 | 118.683 | 24.849 | 2.747 | 1.00 | 11.28 | A | C |
| ATOM | 630 | C | THR | 224 | 117.061 | 23.662 | 0.500 | 1.00 | 19.29 | A | C |
| ATOM | 631 | O | THR | 224 | 118.122 | 23.129 | 0.202 | 1.00 | 15.78 | A | O |
| ATOM | 632 | N | MET | 225 | 116.272 | 24.234 | -0.395 | 1.00 | 14.15 | A | N |
| ATOM | 633 | CA | MET | 225 | 116.607 | 24.236 | -1.810 | 1.00 | 15.04 | A | C |
| ATOM | 634 | CB | MET | 225 | 115.346 | 24.481 | -2.636 | 1.00 | 22.98 | A | C |
| ATOM | 635 | CG | MET | 225 | 114.183 | 23.602 | -2.267 | 1.00 | 20.41 | A | C |
| ATOM | 636 | SD | MET | 225 | 114.421 | 21.883 | -2.704 | 1.00 | 28.15 | A | S |
| ATOM | 637 | CE | MET | 225 | 112.675 | 21.302 | -2.554 | 1.00 | 24.73 | A | C |
| ATOM | 638 | C | MET | 225 | 117.653 | 25.275 | -2.204 | 1.00 | 16.07 | A | C |
| ATOM | 639 | O | MET | 225 | 117.426 | 26.054 | -3.136 | 1.00 | 17.53 | A | O |
| ATOM | 640 | N | THR | 226 | 118.791 | 25.297 | -1.513 | 1.00 | 16.19 | A | N |
| ATOM | 641 | CA | THR | 226 | 119.841 | 26.259 | -1.840 | 1.00 | 15.66 | A | C |
| ATOM | 642 | CB | THR | 226 | 121.155 | 25.905 | -1.129 | 1.00 | 25.30 | A | C |
| ATOM | 643 | OG1 | THR | 226 | 120.925 | 25.825 | 0.284 | 1.00 | 27.32 | A | O |
| ATOM | 644 | CG2 | THR | 226 | 122.216 | 26.959 | -1.414 | 1.00 | 23.02 | A | C |
| ATOM | 645 | C | THR | 226 | 120.100 | 26.337 | -3.356 | 1.00 | 14.26 | A | C |
| ATOM | 646 | O | THR | 226 | 120.229 | 27.418 | -3.917 | 1.00 | 8.95 | A | O |
| ATOM | 647 | N | ALA | 227 | 120.158 | 25.190 | -4.019 | 1.00 | 9.41 | A | N |
| ATOM | 648 | CA | ALA | 227 | 120.408 | 25.162 | -5.448 | 1.00 | 8.35 | A | C |
| ATOM | 649 | CB | ALA | 227 | 120.422 | 23.738 | -5.939 | 1.00 | 23.80 | A | C |
| ATOM | 650 | C | ALA | 227 | 119.342 | 25.951 | -6.188 | 1.00 | 9.01 | A | C |
| ATOM | 651 | O | ALA | 227 | 119.644 | 26.759 | -7.067 | 1.00 | 9.81 | A | O |
| ATOM | 652 | N | LEU | 228 | 118.085 | 25.711 | -5.842 | 1.00 | 28.18 | A | N |
| ATOM | 653 | CA | LEU | 228 | 116.985 | 26.410 | -6.489 | 1.00 | 26.62 | A | C |
| ATOM | 654 | CB | LEU | 228 | 115.649 | 25.860 | -5.988 | 1.00 | 14.81 | A | C |
| ATOM | 655 | CG | LEU | 228 | 114.372 | 26.485 | -6.557 | 1.00 | 22.70 | A | C |
| ATOM | 656 | CD1 | LEU | 228 | 114.356 | 26.363 | -8.080 | 1.00 | 20.29 | A | C |
| ATOM | 657 | CD2 | LEU | 228 | 113.163 | 25.801 | -5.947 | 1.00 | 19.75 | A | C |

Fig. 19: A-10

| | | | | | | | | | | | |
|---|---|---|---|---|---|---|---|---|---|---|---|
| ATOM | 658 | C | LEU | 228 | 117.067 | 27.909 | -6.221 | 1.00 | 25.80 | A | C |
| ATOM | 659 | O | LEU | 228 | 116.885 | 28.719 | -7.129 | 1.00 | 28.78 | A | O |
| ATOM | 660 | N | GLY | 229 | 117.341 | 28.274 | -4.971 | 1.00 | 23.50 | A | N |
| ATOM | 661 | CA | GLY | 229 | 117.449 | 29.679 | -4.624 | 1.00 | 25.86 | A | C |
| ATOM | 662 | C | GLY | 229 | 118.464 | 30.407 | -5.495 | 1.00 | 28.42 | A | C |
| ATOM | 663 | O | GLY | 229 | 118.149 | 31.428 | -6.108 | 1.00 | 29.01 | A | O |
| ATOM | 664 | N | ILE | 230 | 119.682 | 29.876 | -5.562 | 1.00 | 20.49 | A | N |
| ATOM | 665 | CA | ILE | 230 | 120.736 | 30.498 | -6.354 | 1.00 | 21.82 | A | C |
| ATOM | 666 | CB | ILE | 230 | 122.096 | 29.779 | -6.195 | 1.00 | 2.66 | A | C |
| ATOM | 667 | CG2 | ILE | 230 | 123.168 | 30.546 | -6.953 | 1.00 | 2.66 | A | C |
| ATOM | 668 | CG1 | ILE | 230 | 122.486 | 29.692 | -4.720 | 1.00 | 2.66 | A | C |
| ATOM | 669 | CD1 | ILE | 230 | 123.773 | 28.920 | -4.474 | 1.00 | 2.66 | A | C |
| ATOM | 670 | C | ILE | 230 | 120.386 | 30.508 | -7.830 | 1.00 | 22.08 | A | C |
| ATOM | 671 | O | ILE | 230 | 120.614 | 31.498 | -8.511 | 1.00 | 20.01 | A | O |
| ATOM | 672 | N | ASP | 231 | 119.841 | 29.409 | -8.333 | 1.00 | 32.19 | A | N |
| ATOM | 673 | CA | ASP | 231 | 119.473 | 29.352 | -9.743 | 1.00 | 30.59 | A | C |
| ATOM | 674 | CB | ASP | 231 | 118.959 | 27.958 | -10.103 | 1.00 | 35.41 | A | C |
| ATOM | 675 | CG | ASP | 231 | 118.860 | 27.739 | -11.604 | 1.00 | 42.41 | A | C |
| ATOM | 676 | OD1 | ASP | 231 | 119.910 | 27.778 | -12.281 | 1.00 | 41.17 | A | O |
| ATOM | 677 | OD2 | ASP | 231 | 117.735 | 27.525 | -12.103 | 1.00 | 45.95 | A | O |
| ATOM | 678 | C | ASP | 231 | 118.392 | 30.395 | -10.048 | 1.00 | 31.57 | A | C |
| ATOM | 679 | O | ASP | 231 | 118.429 | 31.048 | -11.090 | 1.00 | 28.79 | A | O |
| ATOM | 680 | N | THR | 232 | 117.443 | 30.554 | -9.126 | 1.00 | 18.29 | A | N |
| ATOM | 681 | CA | THR | 232 | 116.347 | 31.510 | -9.296 | 1.00 | 17.08 | A | C |
| ATOM | 682 | CB | THR | 232 | 115.287 | 31.347 | -8.194 | 1.00 | 20.70 | A | C |
| ATOM | 683 | OG1 | THR | 232 | 114.714 | 30.041 | -8.279 | 1.00 | 19.21 | A | O |
| ATOM | 684 | CG2 | THR | 232 | 114.191 | 32.370 | -8.358 | 1.00 | 14.24 | A | C |
| ATOM | 685 | C | THR | 232 | 116.859 | 32.937 | -9.264 | 1.00 | 17.71 | A | C |
| ATOM | 686 | O | THR | 232 | 116.390 | 33.801 | -10.010 | 1.00 | 17.88 | A | O |
| ATOM | 687 | N | ALA | 233 | 117.815 | 33.187 | -8.379 | 1.00 | 19.66 | A | N |
| ATOM | 688 | CA | ALA | 233 | 118.395 | 34.517 | -8.270 | 1.00 | 22.31 | A | C |
| ATOM | 689 | CB | ALA | 233 | 119.364 | 34.580 | -7.099 | 1.00 | 15.15 | A | C |
| ATOM | 690 | C | ALA | 233 | 119.125 | 34.796 | -9.575 | 1.00 | 24.62 | A | C |
| ATOM | 691 | O | ALA | 233 | 119.187 | 35.929 | -10.031 | 1.00 | 26.53 | A | O |
| ATOM | 692 | N | ARG | 234 | 119.666 | 33.746 | -10.180 | 1.00 | 30.19 | A | N |
| ATOM | 693 | CA | ARG | 234 | 120.390 | 33.879 | -11.434 | 1.00 | 33.29 | A | C |
| ATOM | 694 | CB | ARG | 234 | 121.241 | 32.637 | -11.693 | 1.00 | 15.32 | A | C |
| ATOM | 695 | CG | ARG | 234 | 122.345 | 32.875 | -12.693 | 1.00 | 15.32 | A | C |
| ATOM | 696 | CD | ARG | 234 | 122.760 | 31.617 | -13.460 | 1.00 | 15.32 | A | C |
| ATOM | 697 | NE | ARG | 234 | 121.839 | 31.311 | -14.554 | 1.00 | 15.32 | A | N |
| ATOM | 698 | CZ | ARG | 234 | 120.875 | 30.405 | -14.481 | 1.00 | 15.32 | A | C |
| ATOM | 699 | NH1 | ARG | 234 | 120.708 | 29.713 | -13.368 | 1.00 | 15.32 | A | N |
| ATOM | 700 | NH2 | ARG | 234 | 120.078 | 30.188 | -15.511 | 1.00 | 15.32 | A | N |
| ATOM | 701 | C | ARG | 234 | 119.446 | 34.083 | -12.619 | 1.00 | 35.42 | A | C |
| ATOM | 702 | O | ARG | 234 | 119.409 | 35.153 | -13.215 | 1.00 | 35.47 | A | O |
| ATOM | 703 | N | LYS | 235 | 118.666 | 33.057 | -12.941 | 1.00 | 67.48 | A | N |
| ATOM | 704 | CA | LYS | 235 | 117.767 | 33.124 | -14.085 | 1.00 | 67.43 | A | C |
| ATOM | 705 | CB | LYS | 235 | 117.204 | 31.730 | -14.397 | 1.00 | 53.18 | A | C |
| ATOM | 706 | CG | LYS | 235 | 115.965 | 31.308 | -13.615 | 1.00 | 54.33 | A | C |
| ATOM | 707 | CD | LYS | 235 | 115.583 | 29.867 | -13.970 | 1.00 | 54.15 | A | C |
| ATOM | 708 | CE | LYS | 235 | 114.146 | 29.517 | -13.590 | 1.00 | 54.95 | A | C |
| ATOM | 709 | NZ | LYS | 235 | 113.873 | 29.660 | -12.135 | 1.00 | 55.71 | A | N |
| ATOM | 710 | C | LYS | 235 | 116.628 | 34.134 | -14.017 | 1.00 | 67.57 | A | C |
| ATOM | 711 | O | LYS | 235 | 116.074 | 34.500 | -15.054 | 1.00 | 67.91 | A | O |
| ATOM | 712 | N | GLU | 236 | 116.277 | 34.596 | -12.822 | 1.00 | 98.68 | A | N |
| ATOM | 713 | CA | GLU | 236 | 115.186 | 35.558 | -12.693 | 1.00 | 100.30 | A | C |
| ATOM | 714 | CB | GLU | 236 | 114.087 | 34.999 | -11.781 | 1.00 | 50.64 | A | C |
| ATOM | 715 | CG | GLU | 236 | 113.008 | 34.192 | -12.510 | 1.00 | 53.41 | A | C |
| ATOM | 716 | CD | GLU | 236 | 112.199 | 33.276 | -11.582 | 1.00 | 55.89 | A | C |
| ATOM | 717 | OE1 | GLU | 236 | 111.660 | 33.760 | -10.565 | 1.00 | 55.98 | A | O |
| ATOM | 718 | OE2 | GLU | 236 | 112.098 | 32.065 | -11.875 | 1.00 | 55.73 | A | O |
| ATOM | 719 | C | GLU | 236 | 115.627 | 36.917 | -12.174 | 1.00 | 98.85 | A | C |
| ATOM | 720 | O | GLU | 236 | 115.638 | 37.900 | -12.912 | 1.00 | 100.28 | A | O |
| ATOM | 721 | N | ALA | 237 | 115.991 | 36.969 | -10.899 | 1.00 | 71.25 | A | N |
| ATOM | 722 | CA | ALA | 237 | 116.405 | 38.218 | -10.276 | 1.00 | 68.72 | A | C |
| ATOM | 723 | CB | ALA | 237 | 117.046 | 37.934 | -8.932 | 1.00 | 56.85 | A | C |
| ATOM | 724 | C | ALA | 237 | 117.349 | 39.046 | -11.139 | 1.00 | 67.56 | A | C |
| ATOM | 725 | O | ALA | 237 | 117.225 | 40.267 | -11.200 | 1.00 | 65.98 | A | O |
| ATOM | 726 | N | PHE | 238 | 118.283 | 38.385 | -11.812 | 1.00 | 41.81 | A | N |
| ATOM | 727 | CA | PHE | 238 | 119.256 | 39.080 | -12.651 | 1.00 | 41.24 | A | C |
| ATOM | 728 | CB | PHE | 238 | 120.606 | 38.369 | -12.591 | 1.00 | 47.57 | A | C |
| ATOM | 729 | CG | PHE | 238 | 121.413 | 38.696 | -11.378 | 1.00 | 46.60 | A | C |
| ATOM | 730 | CD1 | PHE | 238 | 121.686 | 37.725 | -10.419 | 1.00 | 47.83 | A | C |

Fig. 19: A-11

| | | | | | | | | | | | |
|---|---|---|---|---|---|---|---|---|---|---|---|
| ATOM | 731 | CD2 | PHE | 238 | 121.931 | 39.970 | -11.208 | 1.00 | 44.20 | A | C |
| ATOM | 732 | CE1 | PHE | 238 | 122.476 | 38.023 | -9.298 | 1.00 | 45.63 | A | C |
| ATOM | 733 | CE2 | PHE | 238 | 122.719 | 40.282 | -10.094 | 1.00 | 50.51 | A | C |
| ATOM | 734 | CZ | PHE | 238 | 122.993 | 39.305 | -9.137 | 1.00 | 51.93 | A | C |
| ATOM | 735 | C | PHE | 238 | 118.861 | 39.252 | -14.116 | 1.00 | 43.09 | A | C |
| ATOM | 736 | O | PHE | 238 | 119.699 | 39.129 | -15.017 | 1.00 | 43.19 | A | O |
| ATOM | 737 | N | THR | 239 | 117.586 | 39.520 | -14.362 | 1.00 | 28.84 | A | N |
| ATOM | 738 | CA | THR | 239 | 117.117 | 39.744 | -15.724 | 1.00 | 32.78 | A | C |
| ATOM | 739 | CB | THR | 239 | 115.952 | 38.821 | -16.086 | 1.00 | 22.29 | A | C |
| ATOM | 740 | OG1 | THR | 239 | 114.866 | 39.059 | -15.191 | 1.00 | 20.25 | A | O |
| ATOM | 741 | CG2 | THR | 239 | 116.363 | 37.382 | -15.988 | 1.00 | 25.20 | A | C |
| ATOM | 742 | C | THR | 239 | 116.655 | 41.202 | -15.798 | 1.00 | 33.04 | A | C |
| ATOM | 743 | O | THR | 239 | 115.955 | 41.695 | -14.902 | 1.00 | 33.54 | A | O |
| ATOM | 744 | N | GLU | 240 | 117.067 | 41.881 | -16.868 | 1.00 | 73.11 | A | N |
| ATOM | 745 | CA | GLU | 240 | 116.755 | 43.291 | -17.085 | 1.00 | 73.36 | A | C |
| ATOM | 746 | CB | GLU | 240 | 116.995 | 43.654 | -18.549 | 1.00 | 97.49 | A | C |
| ATOM | 747 | CG | GLU | 240 | 117.147 | 45.141 | -18.793 | 1.00 | 102.13 | A | C |
| ATOM | 748 | CD | GLU | 240 | 117.738 | 45.441 | -20.152 | 1.00 | 105.04 | A | C |
| ATOM | 749 | OE1 | GLU | 240 | 118.794 | 44.858 | -20.483 | 1.00 | 105.14 | A | O |
| ATOM | 750 | OE2 | GLU | 240 | 117.151 | 46.263 | -20.885 | 1.00 | 105.11 | A | O |
| ATOM | 751 | C | GLU | 240 | 115.336 | 43.665 | -16.689 | 1.00 | 74.71 | A | C |
| ATOM | 752 | O | GLU | 240 | 115.083 | 44.772 | -16.210 | 1.00 | 75.92 | A | O |
| ATOM | 753 | N | ALA | 241 | 114.417 | 42.730 | -16.885 | 1.00 | 32.59 | A | N |
| ATOM | 754 | CA | ALA | 241 | 113.016 | 42.952 | -16.552 | 1.00 | 33.44 | A | C |
| ATOM | 755 | CB | ALA | 241 | 112.170 | 41.769 | -17.051 | 1.00 | 4.05 | A | C |
| ATOM | 756 | C | ALA | 241 | 112.802 | 43.165 | -15.044 | 1.00 | 32.91 | A | C |
| ATOM | 757 | O | ALA | 241 | 111.809 | 43.759 | -14.622 | 1.00 | 34.37 | A | O |
| ATOM | 758 | N | ARG | 242 | 113.725 | 42.678 | -14.223 | 1.00 | 31.60 | A | N |
| ATOM | 759 | CA | ARG | 242 | 113.585 | 42.851 | -12.786 | 1.00 | 31.34 | A | C |
| ATOM | 760 | CB | ARG | 242 | 113.757 | 41.500 | -12.079 | 1.00 | 27.81 | A | C |
| ATOM | 761 | CG | ARG | 242 | 112.489 | 40.658 | -12.052 | 1.00 | 28.01 | A | C |
| ATOM | 762 | CD | ARG | 242 | 112.669 | 39.440 | -11.160 | 1.00 | 28.87 | A | C |
| ATOM | 763 | NE | ARG | 242 | 111.425 | 39.010 | -10.515 | 1.00 | 30.07 | A | N |
| ATOM | 764 | CZ | ARG | 242 | 110.582 | 38.106 | -11.011 | 1.00 | 29.27 | A | C |
| ATOM | 765 | NH1 | ARG | 242 | 110.846 | 37.525 | -12.176 | 1.00 | 28.32 | A | N |
| ATOM | 766 | NH2 | ARG | 242 | 109.485 | 37.769 | -10.334 | 1.00 | 31.29 | A | N |
| ATOM | 767 | C | ARG | 242 | 114.557 | 43.898 | -12.231 | 1.00 | 32.54 | A | C |
| ATOM | 768 | O | ARG | 242 | 114.824 | 43.954 | -11.026 | 1.00 | 35.55 | A | O |
| ATOM | 769 | N | GLY | 243 | 115.080 | 44.733 | -13.122 | 1.00 | 38.70 | A | N |
| ATOM | 770 | CA | GLY | 243 | 115.996 | 45.775 | -12.706 | 1.00 | 36.85 | A | C |
| ATOM | 771 | C | GLY | 243 | 117.468 | 45.462 | -12.890 | 1.00 | 35.13 | A | C |
| ATOM | 772 | O | GLY | 243 | 118.318 | 46.139 | -12.308 | 1.00 | 34.75 | A | O |
| ATOM | 773 | N | ALA | 244 | 117.792 | 44.447 | -13.683 | 1.00 | 32.25 | A | N |
| ATOM | 774 | CA | ALA | 244 | 119.190 | 44.119 | -13.896 | 1.00 | 30.25 | A | C |
| ATOM | 775 | CB | ALA | 244 | 119.326 | 42.709 | -14.442 | 1.00 | 67.28 | A | C |
| ATOM | 776 | C | ALA | 244 | 119.750 | 45.130 | -14.886 | 1.00 | 32.13 | A | C |
| ATOM | 777 | O | ALA | 244 | 119.437 | 45.088 | -16.068 | 1.00 | 31.59 | A | O |
| ATOM | 778 | N | ARG | 245 | 120.566 | 46.054 | -14.401 | 1.00 | 18.96 | A | N |
| ATOM | 779 | CA | ARG | 245 | 121.154 | 47.074 | -15.258 | 1.00 | 19.79 | A | C |
| ATOM | 780 | CB | ARG | 245 | 121.853 | 48.130 | -14.399 | 1.00 | 36.60 | A | C |
| ATOM | 781 | CG | ARG | 245 | 120.888 | 49.043 | -13.655 | 1.00 | 39.07 | A | C |
| ATOM | 782 | CD | ARG | 245 | 121.614 | 49.991 | -12.741 | 1.00 | 39.28 | A | C |
| ATOM | 783 | NE | ARG | 245 | 122.309 | 49.254 | -11.701 | 1.00 | 33.70 | A | N |
| ATOM | 784 | CZ | ARG | 245 | 122.997 | 49.824 | -10.726 | 1.00 | 33.52 | A | C |
| ATOM | 785 | NH1 | ARG | 245 | 123.084 | 51.145 | -10.662 | 1.00 | 32.72 | A | N |
| ATOM | 786 | NH2 | ARG | 245 | 123.590 | 49.075 | -9.810 | 1.00 | 30.81 | A | N |
| ATOM | 787 | C | ARG | 245 | 122.131 | 46.493 | -16.266 | 1.00 | 18.16 | A | C |
| ATOM | 788 | O | ARG | 245 | 123.003 | 45.710 | -15.911 | 1.00 | 14.27 | A | O |
| ATOM | 789 | N | ARG | 246 | 121.985 | 46.896 | -17.525 | 1.00 | 55.16 | A | N |
| ATOM | 790 | CA | ARG | 246 | 122.848 | 46.429 | -18.607 | 1.00 | 57.95 | A | C |
| ATOM | 791 | CB | ARG | 246 | 122.447 | 47.078 | -19.928 | 1.00 | 115.62 | A | C |
| ATOM | 792 | CG | ARG | 246 | 123.405 | 46.764 | -21.067 | 1.00 | 120.98 | A | C |
| ATOM | 793 | CD | ARG | 246 | 123.057 | 47.546 | -22.318 | 1.00 | 126.90 | A | C |
| ATOM | 794 | NE | ARG | 246 | 121.637 | 47.444 | -22.641 | 1.00 | 129.81 | A | N |
| ATOM | 795 | CZ | ARG | 246 | 120.981 | 46.298 | -22.804 | 1.00 | 132.92 | A | C |
| ATOM | 796 | NH1 | ARG | 246 | 121.615 | 45.138 | -22.676 | 1.00 | 132.61 | A | N |
| ATOM | 797 | NH2 | ARG | 246 | 119.685 | 46.314 | -23.094 | 1.00 | 133.70 | A | N |
| ATOM | 798 | C | ARG | 246 | 124.313 | 46.736 | -18.364 | 1.00 | 55.77 | A | C |
| ATOM | 799 | O | ARG | 246 | 124.671 | 47.879 | -18.092 | 1.00 | 58.40 | A | O |
| ATOM | 800 | N | GLY | 247 | 125.151 | 45.711 | -18.475 | 1.00 | 47.75 | A | N |
| ATOM | 801 | CA | GLY | 247 | 126.587 | 45.878 | -18.302 | 1.00 | 50.33 | A | C |
| ATOM | 802 | C | GLY | 247 | 127.097 | 46.294 | -16.934 | 1.00 | 50.40 | A | C |
| ATOM | 803 | O | GLY | 247 | 128.129 | 46.958 | -16.824 | 1.00 | 53.36 | A | O |

Fig. 19: A-12

| | | | | | | | | | | | |
|---|---|---|---|---|---|---|---|---|---|---|---|
| ATOM | 804 | N | VAL | 248 | 126.382 | 45.911 | -15.887 | 1.00 | 40.38 | A | N |
| ATOM | 805 | CA | VAL | 248 | 126.790 | 46.248 | -14.535 | 1.00 | 38.39 | A | C |
| ATOM | 806 | CB | VAL | 248 | 125.653 | 46.928 | -13.780 | 1.00 | 41.70 | A | C |
| ATOM | 807 | CG1 | VAL | 248 | 126.049 | 47.136 | -12.331 | 1.00 | 39.35 | A | C |
| ATOM | 808 | CG2 | VAL | 248 | 125.331 | 48.250 | -14.436 | 1.00 | 33.47 | A | C |
| ATOM | 809 | C | VAL | 248 | 127.173 | 44.970 | -13.807 | 1.00 | 41.41 | A | C |
| ATOM | 810 | O | VAL | 248 | 126.530 | 43.936 | -13.993 | 1.00 | 45.46 | A | O |
| ATOM | 811 | N | LYS | 249 | 128.208 | 45.036 | -12.975 | 1.00 | 30.45 | A | N |
| ATOM | 812 | CA | LYS | 249 | 128.645 | 43.852 | -12.250 | 1.00 | 31.36 | A | C |
| ATOM | 813 | CB | LYS | 249 | 129.799 | 44.186 | -11.299 | 1.00 | 85.59 | A | C |
| ATOM | 814 | CG | LYS | 249 | 130.426 | 42.940 | -10.690 | 1.00 | 91.11 | A | C |
| ATOM | 815 | CD | LYS | 249 | 130.844 | 41.943 | -11.782 | 1.00 | 92.18 | A | C |
| ATOM | 816 | CE | LYS | 249 | 131.040 | 40.539 | -11.224 | 1.00 | 94.54 | A | C |
| ATOM | 817 | NZ | LYS | 249 | 131.548 | 39.546 | -12.218 | 1.00 | 97.36 | A | N |
| ATOM | 818 | C | LYS | 249 | 127.503 | 43.190 | -11.473 | 1.00 | 30.02 | A | C |
| ATOM | 819 | O | LYS | 249 | 126.706 | 43.862 | -10.815 | 1.00 | 29.84 | A | O |
| ATOM | 820 | N | LYS | 250 | 127.432 | 41.864 | -11.559 | 1.00 | 29.51 | A | N |
| ATOM | 821 | CA | LYS | 250 | 126.396 | 41.110 | -10.879 | 1.00 | 29.16 | A | C |
| ATOM | 822 | CB | LYS | 250 | 125.763 | 40.134 | -11.871 | 1.00 | 45.59 | A | C |
| ATOM | 823 | CG | LYS | 250 | 125.050 | 40.864 | -12.996 | 1.00 | 44.19 | A | C |
| ATOM | 824 | CD | LYS | 250 | 124.892 | 40.022 | -14.263 | 1.00 | 45.74 | A | C |
| ATOM | 825 | CE | LYS | 250 | 123.827 | 38.928 | -14.135 | 1.00 | 44.90 | A | C |
| ATOM | 826 | NZ | LYS | 250 | 123.513 | 38.274 | -15.453 | 1.00 | 46.72 | A | N |
| ATOM | 827 | C | LYS | 250 | 126.979 | 40.391 | -9.663 | 1.00 | 28.51 | A | C |
| ATOM | 828 | O | LYS | 250 | 127.849 | 39.541 | -9.804 | 1.00 | 28.19 | A | O |
| ATOM | 829 | N | VAL | 251 | 126.493 | 40.754 | -8.474 | 1.00 | 23.05 | A | N |
| ATOM | 830 | CA | VAL | 251 | 126.954 | 40.173 | -7.219 | 1.00 | 22.96 | A | C |
| ATOM | 831 | CB | VAL | 251 | 127.504 | 41.263 | -6.307 | 1.00 | 28.85 | A | C |
| ATOM | 832 | CG1 | VAL | 251 | 127.901 | 40.676 | -4.959 | 1.00 | 27.00 | A | C |
| ATOM | 833 | CG2 | VAL | 251 | 128.678 | 41.928 | -6.974 | 1.00 | 30.06 | A | C |
| ATOM | 834 | C | VAL | 251 | 125.863 | 39.421 | -6.451 | 1.00 | 21.44 | A | C |
| ATOM | 835 | O | VAL | 251 | 124.778 | 39.945 | -6.232 | 1.00 | 17.44 | A | O |
| ATOM | 836 | N | MET | 252 | 126.168 | 38.199 | -6.023 | 1.00 | 19.32 | A | N |
| ATOM | 837 | CA | MET | 252 | 125.212 | 37.383 | -5.278 | 1.00 | 20.30 | A | C |
| ATOM | 838 | CB | MET | 252 | 124.949 | 36.073 | -6.024 | 1.00 | 19.49 | A | C |
| ATOM | 839 | CG | MET | 252 | 123.850 | 35.212 | -5.425 | 1.00 | 18.18 | A | C |
| ATOM | 840 | SD | MET | 252 | 123.556 | 33.701 | -6.379 | 1.00 | 22.23 | A | S |
| ATOM | 841 | CE | MET | 252 | 123.009 | 34.366 | -7.960 | 1.00 | 13.54 | A | C |
| ATOM | 842 | C | MET | 252 | 125.730 | 37.072 | -3.875 | 1.00 | 19.32 | A | C |
| ATOM | 843 | O | MET | 252 | 126.880 | 36.675 | -3.704 | 1.00 | 21.69 | A | O |
| ATOM | 844 | N | VAL | 253 | 124.886 | 37.261 | -2.869 | 1.00 | 11.70 | A | N |
| ATOM | 845 | CA | VAL | 253 | 125.286 | 36.971 | -1.505 | 1.00 | 12.85 | A | C |
| ATOM | 846 | CB | VAL | 253 | 125.173 | 38.221 | -0.593 | 1.00 | 5.67 | A | C |
| ATOM | 847 | CG1 | VAL | 253 | 125.508 | 37.856 | 0.842 | 1.00 | 7.09 | A | C |
| ATOM | 848 | CG2 | VAL | 253 | 126.118 | 39.310 | -1.079 | 1.00 | 5.31 | A | C |
| ATOM | 849 | C | VAL | 253 | 124.370 | 35.881 | -0.974 | 1.00 | 12.42 | A | C |
| ATOM | 850 | O | VAL | 253 | 123.166 | 36.093 | -0.870 | 1.00 | 10.86 | A | O |
| ATOM | 851 | N | ILE | 254 | 124.936 | 34.716 | -0.649 | 1.00 | 26.88 | A | N |
| ATOM | 852 | CA | ILE | 254 | 124.142 | 33.597 | -0.126 | 1.00 | 23.78 | A | C |
| ATOM | 853 | CB | ILE | 254 | 124.457 | 32.266 | -0.847 | 1.00 | 10.72 | A | C |
| ATOM | 854 | CG2 | ILE | 254 | 123.584 | 31.171 | -0.294 | 1.00 | 7.19 | A | C |
| ATOM | 855 | CG1 | ILE | 254 | 124.220 | 32.397 | -2.352 | 1.00 | 9.30 | A | C |
| ATOM | 856 | CD1 | ILE | 254 | 125.307 | 33.140 | -3.078 | 1.00 | 8.93 | A | C |
| ATOM | 857 | C | ILE | 254 | 124.379 | 33.370 | 1.359 | 1.00 | 21.87 | A | C |
| ATOM | 858 | O | ILE | 254 | 125.508 | 33.431 | 1.833 | 1.00 | 23.74 | A | O |
| ATOM | 859 | N | VAL | 255 | 123.300 | 33.105 | 2.084 | 1.00 | 38.19 | A | N |
| ATOM | 860 | CA | VAL | 255 | 123.379 | 32.858 | 3.516 | 1.00 | 36.93 | A | C |
| ATOM | 861 | CB | VAL | 255 | 122.733 | 33.994 | 4.328 | 1.00 | 13.80 | A | C |
| ATOM | 862 | CG1 | VAL | 255 | 123.224 | 33.949 | 5.753 | 1.00 | 12.25 | A | C |
| ATOM | 863 | CG2 | VAL | 255 | 123.056 | 35.325 | 3.713 | 1.00 | 14.44 | A | C |
| ATOM | 864 | C | VAL | 255 | 122.592 | 31.594 | 3.798 | 1.00 | 34.68 | A | C |
| ATOM | 865 | O | VAL | 255 | 121.431 | 31.491 | 3.403 | 1.00 | 36.68 | A | O |
| ATOM | 866 | N | THR | 256 | 123.210 | 30.632 | 4.474 | 1.00 | 19.22 | A | N |
| ATOM | 867 | CA | THR | 256 | 122.514 | 29.387 | 4.798 | 1.00 | 20.04 | A | C |
| ATOM | 868 | CB | THR | 256 | 122.477 | 28.457 | 3.566 | 1.00 | 10.08 | A | C |
| ATOM | 869 | OG1 | THR | 256 | 122.032 | 27.147 | 3.952 | 1.00 | 6.12 | A | O |
| ATOM | 870 | CG2 | THR | 256 | 123.851 | 28.387 | 2.926 | 1.00 | 8.93 | A | C |
| ATOM | 871 | C | THR | 256 | 123.128 | 28.650 | 5.995 | 1.00 | 23.52 | A | C |
| ATOM | 872 | O | THR | 256 | 124.303 | 28.831 | 6.310 | 1.00 | 19.68 | A | O |
| ATOM | 873 | N | ASP | 257 | 122.323 | 27.829 | 6.663 | 1.00 | 46.58 | A | N |
| ATOM | 874 | CA | ASP | 257 | 122.794 | 27.097 | 7.830 | 1.00 | 46.96 | A | C |
| ATOM | 875 | CB | ASP | 257 | 122.069 | 27.585 | 9.091 | 1.00 | 21.89 | A | C |
| ATOM | 876 | CG | ASP | 257 | 120.655 | 27.009 | 9.225 | 1.00 | 27.25 | A | C |

Fig. 19: A-13

| | | | | | | | | | | | |
|---|---|---|---|---|---|---|---|---|---|---|---|
| ATOM | 877 | OD1 | ASP | 257 | 120.089 | 26.573 | 8.191 | 1.00 | 27.72 | A | O |
| ATOM | 878 | OD2 | ASP | 257 | 120.110 | 27.006 | 10.362 | 1.00 | 32.52 | A | O |
| ATOM | 879 | C | ASP | 257 | 122.599 | 25.596 | 7.693 | 1.00 | 43.55 | A | C |
| ATOM | 880 | O | ASP | 257 | 122.525 | 24.883 | 8.695 | 1.00 | 42.79 | A | O |
| ATOM | 881 | N | GLY | 258 | 122.510 | 25.106 | 6.461 | 1.00 | 42.38 | A | N |
| ATOM | 882 | CA | GLY | 258 | 122.330 | 23.678 | 6.283 | 1.00 | 44.80 | A | C |
| ATOM | 883 | C | GLY | 258 | 122.618 | 23.150 | 4.896 | 1.00 | 48.62 | A | C |
| ATOM | 884 | O | GLY | 258 | 122.523 | 23.871 | 3.903 | 1.00 | 44.34 | A | O |
| ATOM | 885 | N | GLU | 259 | 122.984 | 21.876 | 4.832 | 1.00 | 88.78 | A | N |
| ATOM | 886 | CA | GLU | 259 | 123.265 | 21.230 | 3.562 | 1.00 | 90.66 | A | C |
| ATOM | 887 | CB | GLU | 259 | 123.650 | 19.770 | 3.782 | 1.00 | 87.02 | A | C |
| ATOM | 888 | CG | GLU | 259 | 124.983 | 19.588 | 4.461 | 1.00 | 94.80 | A | C |
| ATOM | 889 | CD | GLU | 259 | 125.130 | 18.214 | 5.070 | 1.00 | 98.61 | A | C |
| ATOM | 890 | OE1 | GLU | 259 | 126.256 | 17.861 | 5.481 | 1.00 | 105.36 | A | O |
| ATOM | 891 | OE2 | GLU | 259 | 124.115 | 17.490 | 5.147 | 1.00 | 98.63 | A | O |
| ATOM | 892 | C | GLU | 259 | 122.004 | 21.298 | 2.727 | 1.00 | 89.52 | A | C |
| ATOM | 893 | O | GLU | 259 | 120.927 | 20.906 | 3.174 | 1.00 | 86.69 | A | O |
| ATOM | 894 | N | SER | 260 | 122.140 | 21.815 | 1.517 | 1.00 | 31.72 | A | N |
| ATOM | 895 | CA | SER | 260 | 121.007 | 21.922 | 0.615 | 1.00 | 34.88 | A | C |
| ATOM | 896 | CB | SER | 260 | 121.435 | 22.606 | -0.685 | 1.00 | 104.64 | A | C |
| ATOM | 897 | OG | SER | 260 | 122.467 | 21.872 | -1.325 | 1.00 | 105.15 | A | O |
| ATOM | 898 | C | SER | 260 | 120.489 | 20.526 | 0.304 | 1.00 | 34.78 | A | C |
| ATOM | 899 | O | SER | 260 | 121.257 | 19.571 | 0.315 | 1.00 | 30.81 | A | O |
| ATOM | 900 | N | HIS | 261 | 119.192 | 20.409 | 0.039 | 1.00 | 119.42 | A | N |
| ATOM | 901 | CA | HIS | 261 | 118.609 | 19.114 | -0.284 | 1.00 | 123.77 | A | C |
| ATOM | 902 | CB | HIS | 261 | 117.107 | 19.116 | 0.020 | 1.00 | 89.56 | A | C |
| ATOM | 903 | CG | HIS | 261 | 116.789 | 19.030 | 1.482 | 1.00 | 92.76 | A | C |
| ATOM | 904 | CD2 | HIS | 261 | 116.610 | 19.997 | 2.413 | 1.00 | 91.87 | A | C |
| ATOM | 905 | ND1 | HIS | 261 | 116.648 | 17.830 | 2.147 | 1.00 | 94.24 | A | N |
| ATOM | 906 | CE1 | HIS | 261 | 116.393 | 18.065 | 3.422 | 1.00 | 94.31 | A | C |
| ATOM | 907 | NE2 | HIS | 261 | 116.365 | 19.372 | 3.610 | 1.00 | 91.58 | A | N |
| ATOM | 908 | C | HIS | 261 | 118.866 | 18.815 | -1.754 | 1.00 | 124.83 | A | C |
| ATOM | 909 | O | HIS | 261 | 118.732 | 17.676 | -2.203 | 1.00 | 122.05 | A | O |
| ATOM | 910 | N | ASP | 262 | 119.251 | 19.850 | -2.495 | 1.00 | 94.20 | A | N |
| ATOM | 911 | CA | ASP | 262 | 119.556 | 19.709 | -3.913 | 1.00 | 99.17 | A | C |
| ATOM | 912 | CB | ASP | 262 | 118.838 | 20.798 | -4.732 | 1.00 | 77.35 | A | C |
| ATOM | 913 | CG | ASP | 262 | 118.558 | 22.065 | -3.929 | 1.00 | 77.35 | A | C |
| ATOM | 914 | OD1 | ASP | 262 | 119.382 | 22.429 | -3.067 | 1.00 | 77.35 | A | O |
| ATOM | 915 | OD2 | ASP | 262 | 117.515 | 22.708 | -4.179 | 1.00 | 77.35 | A | O |
| ATOM | 916 | C | ASP | 262 | 121.065 | 19.758 | -4.191 | 1.00 | 99.22 | A | C |
| ATOM | 917 | O | ASP | 262 | 121.510 | 20.456 | -5.104 | 1.00 | 99.08 | A | O |
| ATOM | 918 | N | ASN | 263 | 121.842 | 19.009 | -3.406 | 1.00 | 48.33 | A | N |
| ATOM | 919 | CA | ASN | 263 | 123.300 | 18.956 | -3.558 | 1.00 | 49.50 | A | C |
| ATOM | 920 | CB | ASN | 263 | 123.896 | 17.820 | -2.719 | 1.00 | 78.20 | A | C |
| ATOM | 921 | CG | ASN | 263 | 123.359 | 17.781 | -1.303 | 1.00 | 82.57 | A | C |
| ATOM | 922 | OD1 | ASN | 263 | 123.578 | 18.703 | -0.511 | 1.00 | 84.07 | A | O |
| ATOM | 923 | ND2 | ASN | 263 | 122.651 | 16.702 | -0.974 | 1.00 | 77.07 | A | N |
| ATOM | 924 | C | ASN | 263 | 123.657 | 18.684 | -5.012 | 1.00 | 50.14 | A | C |
| ATOM | 925 | O | ASN | 263 | 124.574 | 19.286 | -5.572 | 1.00 | 49.04 | A | O |
| ATOM | 926 | N | TYR | 264 | 122.915 | 17.754 | -5.601 | 1.00 | 83.05 | A | N |
| ATOM | 927 | CA | TYR | 264 | 123.112 | 17.330 | -6.976 | 1.00 | 80.90 | A | C |
| ATOM | 928 | CB | TYR | 264 | 121.905 | 16.512 | -7.431 | 1.00 | 165.37 | A | C |
| ATOM | 929 | CG | TYR | 264 | 121.684 | 15.297 | -6.568 | 1.00 | 165.37 | A | C |
| ATOM | 930 | CD1 | TYR | 264 | 121.294 | 15.427 | -5.234 | 1.00 | 165.37 | A | C |
| ATOM | 931 | CE1 | TYR | 264 | 121.137 | 14.312 | -4.419 | 1.00 | 165.37 | A | C |
| ATOM | 932 | CD2 | TYR | 264 | 121.909 | 14.016 | -7.067 | 1.00 | 165.37 | A | C |
| ATOM | 933 | CE2 | TYR | 264 | 121.753 | 12.892 | -6.262 | 1.00 | 165.37 | A | C |
| ATOM | 934 | CZ | TYR | 264 | 121.369 | 13.048 | -4.939 | 1.00 | 165.37 | A | C |
| ATOM | 935 | OH | TYR | 264 | 121.224 | 11.940 | -4.139 | 1.00 | 165.37 | A | O |
| ATOM | 936 | C | TYR | 264 | 123.396 | 18.439 | -7.977 | 1.00 | 79.55 | A | C |
| ATOM | 937 | O | TYR | 264 | 124.509 | 18.536 | -8.498 | 1.00 | 76.68 | A | O |
| ATOM | 938 | N | ARG | 265 | 122.406 | 19.283 | -8.245 | 1.00 | 83.26 | A | N |
| ATOM | 939 | CA | ARG | 265 | 122.605 | 20.340 | -9.224 | 1.00 | 82.16 | A | C |
| ATOM | 940 | CB | ARG | 265 | 121.297 | 20.636 | -9.957 | 1.00 | 36.62 | A | C |
| ATOM | 941 | CG | ARG | 265 | 120.182 | 21.225 | -9.142 | 1.00 | 37.07 | A | C |
| ATOM | 942 | CD | ARG | 265 | 119.267 | 21.953 | -10.110 | 1.00 | 38.90 | A | C |
| ATOM | 943 | NE | ARG | 265 | 118.140 | 22.620 | -9.464 | 1.00 | 44.29 | A | N |
| ATOM | 944 | CZ | ARG | 265 | 117.562 | 23.714 | -9.947 | 1.00 | 44.46 | A | C |
| ATOM | 945 | NH1 | ARG | 265 | 118.016 | 24.257 | -11.071 | 1.00 | 49.09 | A | N |
| ATOM | 946 | NH2 | ARG | 265 | 116.528 | 24.258 | -9.321 | 1.00 | 48.43 | A | N |
| ATOM | 947 | C | ARG | 265 | 123.211 | 21.644 | -8.720 | 1.00 | 81.41 | A | C |
| ATOM | 948 | O | ARG | 265 | 123.137 | 22.668 | -9.396 | 1.00 | 82.72 | A | O |
| ATOM | 949 | N | LEU | 266 | 123.819 | 21.614 | -7.543 | 1.00 | 27.19 | A | N |

Fig. 19: A-14

| | | | | | | | | | | | |
|---|---|---|---|---|---|---|---|---|---|---|---|
| ATOM | 950 | CA | LEU | 266 | 124.435 | 22.815 | -7.003 | 1.00 | 28.76 | A | C |
| ATOM | 951 | CB | LEU | 266 | 124.798 | 22.601 | -5.539 | 1.00 | 4.24 | A | C |
| ATOM | 952 | CG | LEU | 266 | 125.336 | 23.820 | -4.797 | 1.00 | 3.45 | A | C |
| ATOM | 953 | CD1 | LEU | 266 | 124.393 | 24.999 | -4.976 | 1.00 | 5.79 | A | C |
| ATOM | 954 | CD2 | LEU | 266 | 125.502 | 23.466 | -3.320 | 1.00 | 1.87 | A | C |
| ATOM | 955 | C | LEU | 266 | 125.684 | 23.084 | -7.828 | 1.00 | 31.58 | A | C |
| ATOM | 956 | O | LEU | 266 | 126.086 | 24.226 | -8.022 | 1.00 | 31.46 | A | O |
| ATOM | 957 | N | LYS | 267 | 126.286 | 22.007 | -8.317 | 1.00 | 45.65 | A | N |
| ATOM | 958 | CA | LYS | 267 | 127.479 | 22.088 | -9.149 | 1.00 | 47.96 | A | C |
| ATOM | 959 | CB | LYS | 267 | 127.949 | 20.673 | -9.497 | 1.00 | 72.30 | A | C |
| ATOM | 960 | CG | LYS | 267 | 129.239 | 20.583 | -10.298 | 1.00 | 72.30 | A | C |
| ATOM | 961 | CD | LYS | 267 | 130.428 | 20.277 | -9.403 | 1.00 | 72.30 | A | C |
| ATOM | 962 | CE | LYS | 267 | 131.649 | 19.894 | -10.230 | 1.00 | 72.30 | A | C |
| ATOM | 963 | NZ | LYS | 267 | 132.793 | 19.452 | -9.381 | 1.00 | 72.30 | A | N |
| ATOM | 964 | C | LYS | 267 | 127.103 | 22.842 | -10.427 | 1.00 | 47.45 | A | C |
| ATOM | 965 | O | LYS | 267 | 127.763 | 23.810 | -10.809 | 1.00 | 46.97 | A | O |
| ATOM | 966 | N | GLN | 268 | 126.032 | 22.389 | -11.074 | 1.00 | 32.65 | A | N |
| ATOM | 967 | CA | GLN | 268 | 125.553 | 22.999 | -12.303 | 1.00 | 31.62 | A | C |
| ATOM | 968 | CB | GLN | 268 | 124.292 | 22.295 | -12.798 | 1.00 | 88.56 | A | C |
| ATOM | 969 | CG | GLN | 268 | 124.449 | 20.845 | -13.182 | 1.00 | 88.56 | A | C |
| ATOM | 970 | CD | GLN | 268 | 123.119 | 20.227 | -13.576 | 1.00 | 88.56 | A | C |
| ATOM | 971 | OE1 | GLN | 268 | 123.059 | 19.078 | -14.010 | 1.00 | 88.56 | A | O |
| ATOM | 972 | NE2 | GLN | 268 | 122.041 | 20.992 | -13.423 | 1.00 | 88.56 | A | N |
| ATOM | 973 | C | GLN | 268 | 125.221 | 24.474 | -12.100 | 1.00 | 27.37 | A | C |
| ATOM | 974 | O | GLN | 268 | 125.678 | 25.332 | -12.851 | 1.00 | 28.55 | A | O |
| ATOM | 975 | N | VAL | 269 | 124.410 | 24.767 | -11.089 | 1.00 | 11.19 | A | N |
| ATOM | 976 | CA | VAL | 269 | 124.007 | 26.140 | -10.830 | 1.00 | 8.94 | A | C |
| ATOM | 977 | CB | VAL | 269 | 123.088 | 26.223 | -9.598 | 1.00 | 22.95 | A | C |
| ATOM | 978 | CG1 | VAL | 269 | 122.650 | 27.667 | -9.374 | 1.00 | 18.60 | A | C |
| ATOM | 979 | CG2 | VAL | 269 | 121.872 | 25.334 | -9.801 | 1.00 | 20.81 | A | C |
| ATOM | 980 | C | VAL | 269 | 125.198 | 27.076 | -10.649 | 1.00 | 8.53 | A | C |
| ATOM | 981 | O | VAL | 269 | 125.286 | 28.093 | -11.318 | 1.00 | 11.37 | A | O |
| ATOM | 982 | N | ILE | 270 | 126.114 | 26.744 | -9.746 | 1.00 | 5.57 | A | N |
| ATOM | 983 | CA | ILE | 270 | 127.291 | 27.585 | -9.535 | 1.00 | 6.19 | A | C |
| ATOM | 984 | CB | ILE | 270 | 128.281 | 26.944 | -8.533 | 1.00 | 12.81 | A | C |
| ATOM | 985 | CG2 | ILE | 270 | 129.592 | 27.731 | -8.504 | 1.00 | 7.43 | A | C |
| ATOM | 986 | CG1 | ILE | 270 | 127.671 | 26.926 | -7.135 | 1.00 | 10.37 | A | C |
| ATOM | 987 | CD1 | ILE | 270 | 127.367 | 28.317 | -6.591 | 1.00 | 11.49 | A | C |
| ATOM | 988 | C | ILE | 270 | 128.001 | 27.775 | -10.870 | 1.00 | 10.06 | A | C |
| ATOM | 989 | O | ILE | 270 | 128.549 | 28.838 | -11.140 | 1.00 | 8.84 | A | O |
| ATOM | 990 | N | GLN | 271 | 127.981 | 26.729 | -11.696 | 1.00 | 7.96 | A | N |
| ATOM | 991 | CA | GLN | 271 | 128.605 | 26.751 | -13.011 | 1.00 | 10.02 | A | C |
| ATOM | 992 | CB | GLN | 271 | 128.434 | 25.394 | -13.698 | 1.00 | 84.89 | A | C |
| ATOM | 993 | CG | GLN | 271 | 129.267 | 25.214 | -14.947 | 1.00 | 86.79 | A | C |
| ATOM | 994 | CD | GLN | 271 | 130.744 | 25.366 | -14.665 | 1.00 | 89.29 | A | C |
| ATOM | 995 | OE1 | GLN | 271 | 131.244 | 26.477 | -14.506 | 1.00 | 89.62 | A | O |
| ATOM | 996 | NE2 | GLN | 271 | 131.451 | 24.243 | -14.583 | 1.00 | 90.86 | A | N |
| ATOM | 997 | C | GLN | 271 | 127.962 | 27.842 | -13.860 | 1.00 | 12.48 | A | C |
| ATOM | 998 | O | GLN | 271 | 128.644 | 28.733 | -14.348 | 1.00 | 15.17 | A | O |
| ATOM | 999 | N | ASP | 272 | 126.648 | 27.770 | -14.031 | 1.00 | 33.57 | A | N |
| ATOM | 1000 | CA | ASP | 272 | 125.929 | 28.758 | -14.818 | 1.00 | 34.85 | A | C |
| ATOM | 1001 | CB | ASP | 272 | 124.430 | 28.459 | -14.786 | 1.00 | 74.39 | A | C |
| ATOM | 1002 | CG | ASP | 272 | 124.084 | 27.142 | -15.454 | 1.00 | 76.01 | A | C |
| ATOM | 1003 | OD1 | ASP | 272 | 123.000 | 26.589 | -15.163 | 1.00 | 78.08 | A | O |
| ATOM | 1004 | OD2 | ASP | 272 | 124.893 | 26.665 | -16.278 | 1.00 | 82.27 | A | O |
| ATOM | 1005 | C | ASP | 272 | 126.194 | 30.163 | -14.283 | 1.00 | 35.65 | A | C |
| ATOM | 1006 | O | ASP | 272 | 126.190 | 31.131 | -15.042 | 1.00 | 33.10 | A | O |
| ATOM | 1007 | N | CYS | 273 | 126.426 | 30.280 | -12.978 | 1.00 | 42.88 | A | N |
| ATOM | 1008 | CA | CYS | 273 | 126.698 | 31.582 | -12.387 | 1.00 | 41.31 | A | C |
| ATOM | 1009 | CB | CYS | 273 | 126.630 | 31.516 | -10.862 | 1.00 | 24.14 | A | C |
| ATOM | 1010 | SG | CYS | 273 | 124.940 | 31.489 | -10.191 | 1.00 | 22.24 | A | S |
| ATOM | 1011 | C | CYS | 273 | 128.059 | 32.090 | -12.826 | 1.00 | 41.68 | A | C |
| ATOM | 1012 | O | CYS | 273 | 128.244 | 33.288 | -13.008 | 1.00 | 35.99 | A | O |
| ATOM | 1013 | N | GLU | 274 | 129.010 | 31.178 | -12.994 | 1.00 | 20.07 | A | N |
| ATOM | 1014 | CA | GLU | 274 | 130.364 | 31.531 | -13.440 | 1.00 | 22.87 | A | C |
| ATOM | 1015 | CB | GLU | 274 | 131.317 | 30.338 | -13.298 | 1.00 | 39.18 | A | C |
| ATOM | 1016 | CG | GLU | 274 | 132.090 | 30.309 | -11.989 | 1.00 | 44.30 | A | C |
| ATOM | 1017 | CD | GLU | 274 | 133.041 | 31.490 | -11.836 | 1.00 | 49.41 | A | C |
| ATOM | 1018 | OE1 | GLU | 274 | 133.622 | 31.659 | -10.740 | 1.00 | 51.28 | A | O |
| ATOM | 1019 | OE2 | GLU | 274 | 133.212 | 32.251 | -12.812 | 1.00 | 53.97 | A | O |
| ATOM | 1020 | C | GLU | 274 | 130.345 | 31.984 | -14.893 | 1.00 | 25.29 | A | C |
| ATOM | 1021 | O | GLU | 274 | 131.031 | 32.931 | -15.266 | 1.00 | 27.49 | A | O |
| ATOM | 1022 | N | ASP | 275 | 129.550 | 31.298 | -15.707 | 1.00 | 41.03 | A | N |

Fig. 19: A-15

| | | | | | | | | | | | |
|---|---|---|---|---|---|---|---|---|---|---|---|
| ATOM | 1023 | CA | ASP | 275 | 129.421 | 31.625 | -17.119 | 1.00 | 39.77 | A | C |
| ATOM | 1024 | CB | ASP | 275 | 128.538 | 30.594 | -17.822 | 1.00 | 63.42 | A | C |
| ATOM | 1025 | CG | ASP | 275 | 129.106 | 29.203 | -17.757 | 1.00 | 64.69 | A | C |
| ATOM | 1026 | OD1 | ASP | 275 | 129.987 | 28.959 | -16.906 | 1.00 | 68.39 | A | O |
| ATOM | 1027 | OD2 | ASP | 275 | 128.657 | 28.352 | -18.551 | 1.00 | 66.35 | A | O |
| ATOM | 1028 | C | ASP | 275 | 128.789 | 32.996 | -17.295 | 1.00 | 38.76 | A | C |
| ATOM | 1029 | O | ASP | 275 | 128.883 | 33.595 | -18.367 | 1.00 | 34.31 | A | O |
| ATOM | 1030 | N | GLU | 276 | 128.137 | 33.485 | -16.247 | 1.00 | 28.36 | A | N |
| ATOM | 1031 | CA | GLU | 276 | 127.479 | 34.771 | -16.328 | 1.00 | 28.01 | A | C |
| ATOM | 1032 | CB | GLU | 276 | 126.019 | 34.617 | -15.913 | 1.00 | 53.33 | A | C |
| ATOM | 1033 | CG | GLU | 276 | 125.310 | 33.520 | -16.700 | 1.00 | 53.20 | A | C |
| ATOM | 1034 | CD | GLU | 276 | 123.807 | 33.493 | -16.487 | 1.00 | 54.30 | A | C |
| ATOM | 1035 | OE1 | GLU | 276 | 123.150 | 32.629 | -17.102 | 1.00 | 55.01 | A | O |
| ATOM | 1036 | OE2 | GLU | 276 | 123.280 | 34.330 | -15.717 | 1.00 | 51.24 | A | O |
| ATOM | 1037 | C | GLU | 276 | 128.172 | 35.841 | -15.504 | 1.00 | 26.84 | A | C |
| ATOM | 1038 | O | GLU | 276 | 127.621 | 36.919 | -15.288 | 1.00 | 27.95 | A | O |
| ATOM | 1039 | N | ASN | 277 | 129.382 | 35.535 | -15.050 | 1.00 | 28.50 | A | N |
| ATOM | 1040 | CA | ASN | 277 | 130.185 | 36.472 | -14.268 | 1.00 | 28.47 | A | C |
| ATOM | 1041 | CB | ASN | 277 | 130.607 | 37.655 | -15.140 | 1.00 | 86.35 | A | C |
| ATOM | 1042 | CG | ASN | 277 | 131.230 | 37.218 | -16.439 | 1.00 | 91.27 | A | C |
| ATOM | 1043 | OD1 | ASN | 277 | 132.263 | 36.548 | -16.451 | 1.00 | 91.09 | A | O |
| ATOM | 1044 | ND2 | ASN | 277 | 130.601 | 37.589 | -17.550 | 1.00 | 90.23 | A | N |
| ATOM | 1045 | C | ASN | 277 | 129.493 | 37.014 | -13.018 | 1.00 | 24.82 | A | C |
| ATOM | 1046 | O | ASN | 277 | 129.476 | 38.226 | -12.790 | 1.00 | 25.80 | A | O |
| ATOM | 1047 | N | ILE | 278 | 128.925 | 36.127 | -12.207 | 1.00 | 15.37 | A | N |
| ATOM | 1048 | CA | ILE | 278 | 128.261 | 36.560 | -10.989 | 1.00 | 15.82 | A | C |
| ATOM | 1049 | CB | ILE | 278 | 126.963 | 35.773 | -10.747 | 1.00 | 17.43 | A | C |
| ATOM | 1050 | CG2 | ILE | 278 | 126.304 | 36.243 | -9.454 | 1.00 | 18.82 | A | C |
| ATOM | 1051 | CG1 | ILE | 278 | 126.016 | 35.949 | -11.932 | 1.00 | 14.88 | A | C |
| ATOM | 1052 | CD1 | ILE | 278 | 124.742 | 35.153 | -11.796 | 1.00 | 17.16 | A | C |
| ATOM | 1053 | C | ILE | 278 | 129.168 | 36.345 | -9.780 | 1.00 | 16.42 | A | C |
| ATOM | 1054 | O | ILE | 278 | 129.363 | 35.212 | -9.354 | 1.00 | 16.76 | A | O |
| ATOM | 1055 | N | GLN | 279 | 129.737 | 37.426 | -9.244 | 1.00 | 26.25 | A | N |
| ATOM | 1056 | CA | GLN | 279 | 130.578 | 37.335 | -8.053 | 1.00 | 25.85 | A | C |
| ATOM | 1057 | CB | GLN | 279 | 131.035 | 38.716 | -7.605 | 1.00 | 41.76 | A | C |
| ATOM | 1058 | CG | GLN | 279 | 131.959 | 39.382 | -8.574 | 1.00 | 47.54 | A | C |
| ATOM | 1059 | CD | GLN | 279 | 133.158 | 38.524 | -8.894 | 1.00 | 51.46 | A | C |
| ATOM | 1060 | OE1 | GLN | 279 | 133.992 | 38.255 | -8.023 | 1.00 | 45.70 | A | O |
| ATOM | 1061 | NE2 | GLN | 279 | 133.252 | 38.078 | -10.146 | 1.00 | 51.05 | A | N |
| ATOM | 1062 | C | GLN | 279 | 129.716 | 36.736 | -6.958 | 1.00 | 23.72 | A | C |
| ATOM | 1063 | O | GLN | 279 | 128.609 | 37.216 | -6.692 | 1.00 | 20.64 | A | O |
| ATOM | 1064 | N | ARG | 280 | 130.214 | 35.697 | -6.310 | 1.00 | 16.06 | A | N |
| ATOM | 1065 | CA | ARG | 280 | 129.440 | 35.054 | -5.258 | 1.00 | 17.58 | A | C |
| ATOM | 1066 | CB | ARG | 280 | 129.107 | 33.620 | -5.661 | 1.00 | 19.51 | A | C |
| ATOM | 1067 | CG | ARG | 280 | 128.413 | 33.488 | -6.997 | 1.00 | 18.14 | A | C |
| ATOM | 1068 | CD | ARG | 280 | 128.274 | 32.021 | -7.371 | 1.00 | 17.81 | A | C |
| ATOM | 1069 | NE | ARG | 280 | 129.576 | 31.365 | -7.441 | 1.00 | 14.86 | A | N |
| ATOM | 1070 | CZ | ARG | 280 | 130.427 | 31.489 | -8.452 | 1.00 | 18.77 | A | C |
| ATOM | 1071 | NH1 | ARG | 280 | 130.131 | 32.241 | -9.493 | 1.00 | 21.69 | A | N |
| ATOM | 1072 | NH2 | ARG | 280 | 131.579 | 30.846 | -8.422 | 1.00 | 23.71 | A | N |
| ATOM | 1073 | C | ARG | 280 | 130.123 | 35.037 | -3.892 | 1.00 | 17.24 | A | C |
| ATOM | 1074 | O | ARG | 280 | 131.269 | 34.592 | -3.750 | 1.00 | 16.97 | A | O |
| ATOM | 1075 | N | PHE | 281 | 129.406 | 35.539 | -2.894 | 1.00 | 21.33 | A | N |
| ATOM | 1076 | CA | PHE | 281 | 129.889 | 35.538 | -1.527 | 1.00 | 23.32 | A | C |
| ATOM | 1077 | CB | PHE | 281 | 129.848 | 36.933 | -0.924 | 1.00 | 12.67 | A | C |
| ATOM | 1078 | CG | PHE | 281 | 130.754 | 37.900 | -1.603 | 1.00 | 15.70 | A | C |
| ATOM | 1079 | CD1 | PHE | 281 | 130.419 | 38.434 | -2.837 | 1.00 | 19.55 | A | C |
| ATOM | 1080 | CD2 | PHE | 281 | 131.968 | 38.250 | -1.024 | 1.00 | 17.43 | A | C |
| ATOM | 1081 | CE1 | PHE | 281 | 131.281 | 39.305 | -3.487 | 1.00 | 19.61 | A | C |
| ATOM | 1082 | CE2 | PHE | 281 | 132.842 | 39.120 | -1.665 | 1.00 | 15.16 | A | C |
| ATOM | 1083 | CZ | PHE | 281 | 132.498 | 39.650 | -2.900 | 1.00 | 16.59 | A | C |
| ATOM | 1084 | C | PHE | 281 | 128.925 | 34.646 | -0.785 | 1.00 | 24.03 | A | C |
| ATOM | 1085 | O | PHE | 281 | 127.710 | 34.867 | -0.821 | 1.00 | 26.40 | A | O |
| ATOM | 1086 | N | SER | 282 | 129.449 | 33.613 | -0.141 | 1.00 | 13.47 | A | N |
| ATOM | 1087 | CA | SER | 282 | 128.594 | 32.705 | 0.602 | 1.00 | 15.32 | A | C |
| ATOM | 1088 | CB | SER | 282 | 128.746 | 31.272 | 0.084 | 1.00 | 11.38 | A | C |
| ATOM | 1089 | OG | SER | 282 | 130.081 | 30.816 | 0.216 | 1.00 | 7.93 | A | O |
| ATOM | 1090 | C | SER | 282 | 128.947 | 32.782 | 2.069 | 1.00 | 17.20 | A | C |
| ATOM | 1091 | O | SER | 282 | 130.066 | 33.135 | 2.435 | 1.00 | 21.06 | A | O |
| ATOM | 1092 | N | ILE | 283 | 127.969 | 32.477 | 2.908 | 1.00 | 24.08 | A | N |
| ATOM | 1093 | CA | ILE | 283 | 128.164 | 32.504 | 4.343 | 1.00 | 22.00 | A | C |
| ATOM | 1094 | CB | ILE | 283 | 127.517 | 33.733 | 4.968 | 1.00 | 17.91 | A | C |
| ATOM | 1095 | CG2 | ILE | 283 | 127.843 | 33.791 | 6.442 | 1.00 | 18.72 | A | C |

Fig. 19: A-16

| | | | | | | | | | | | |
|---|---|---|---|---|---|---|---|---|---|---|---|
| ATOM | 1096 | CG1 | ILE | 283 | 128.045 | 34.986 | 4.281 | 1.00 | 14.38 | A | C |
| ATOM | 1097 | CD1 | ILE | 283 | 127.103 | 36.171 | 4.383 | 1.00 | 17.94 | A | C |
| ATOM | 1098 | C | ILE | 283 | 127.510 | 31.273 | 4.912 | 1.00 | 21.07 | A | C |
| ATOM | 1099 | O | ILE | 283 | 126.394 | 30.917 | 4.536 | 1.00 | 20.93 | A | O |
| ATOM | 1100 | N | ALA | 284 | 128.204 | 30.618 | 5.823 | 1.00 | 29.93 | A | N |
| ATOM | 1101 | CA | ALA | 284 | 127.663 | 29.421 | 6.412 | 1.00 | 29.95 | A | C |
| ATOM | 1102 | CB | ALA | 284 | 128.548 | 28.253 | 6.070 | 1.00 | 1.87 | A | C |
| ATOM | 1103 | C | ALA | 284 | 127.507 | 29.536 | 7.920 | 1.00 | 28.08 | A | C |
| ATOM | 1104 | O | ALA | 284 | 128.482 | 29.740 | 8.641 | 1.00 | 26.74 | A | O |
| ATOM | 1105 | N | ILE | 285 | 126.270 | 29.422 | 8.389 | 1.00 | 31.23 | A | N |
| ATOM | 1106 | CA | ILE | 285 | 125.997 | 29.457 | 9.817 | 1.00 | 25.43 | A | C |
| ATOM | 1107 | CB | ILE | 285 | 124.529 | 29.859 | 10.107 | 1.00 | 43.54 | A | C |
| ATOM | 1108 | CG2 | ILE | 285 | 124.187 | 29.569 | 11.555 | 1.00 | 38.36 | A | C |
| ATOM | 1109 | CG1 | ILE | 285 | 124.306 | 31.344 | 9.791 | 1.00 | 38.87 | A | C |
| ATOM | 1110 | CD1 | ILE | 285 | 124.206 | 31.670 | 8.315 | 1.00 | 40.01 | A | C |
| ATOM | 1111 | C | ILE | 285 | 126.227 | 28.022 | 10.296 | 1.00 | 28.75 | A | C |
| ATOM | 1112 | O | ILE | 285 | 125.523 | 27.106 | 9.872 | 1.00 | 30.49 | A | O |
| ATOM | 1113 | N | LEU | 286 | 127.205 | 27.818 | 11.169 | 1.00 | 38.23 | A | N |
| ATOM | 1114 | CA | LEU | 286 | 127.497 | 26.471 | 11.649 | 1.00 | 38.71 | A | C |
| ATOM | 1115 | CB | LEU | 286 | 128.999 | 26.313 | 11.876 | 1.00 | 50.51 | A | C |
| ATOM | 1116 | CG | LEU | 286 | 129.917 | 26.722 | 10.727 | 1.00 | 53.33 | A | C |
| ATOM | 1117 | CD1 | LEU | 286 | 131.340 | 26.363 | 11.105 | 1.00 | 55.89 | A | C |
| ATOM | 1118 | CD2 | LEU | 286 | 129.513 | 26.019 | 9.441 | 1.00 | 55.00 | A | C |
| ATOM | 1119 | C | LEU | 286 | 126.760 | 26.069 | 12.923 | 1.00 | 39.16 | A | C |
| ATOM | 1120 | O | LEU | 286 | 127.068 | 25.036 | 13.517 | 1.00 | 40.00 | A | O |
| ATOM | 1121 | N | GLY | 287 | 125.789 | 26.875 | 13.339 | 1.00 | 72.80 | A | N |
| ATOM | 1122 | CA | GLY | 287 | 125.042 | 26.579 | 14.551 | 1.00 | 71.58 | A | C |
| ATOM | 1123 | C | GLY | 287 | 124.586 | 25.139 | 14.700 | 1.00 | 69.16 | A | C |
| ATOM | 1124 | O | GLY | 287 | 125.056 | 24.419 | 15.583 | 1.00 | 73.26 | A | O |
| ATOM | 1125 | N | THR | 296 | 131.112 | 19.210 | 10.542 | 1.00 | 87.02 | A | N |
| ATOM | 1126 | CA | THR | 296 | 130.609 | 20.333 | 9.766 | 1.00 | 87.06 | A | C |
| ATOM | 1127 | CB | THR | 296 | 130.702 | 21.652 | 10.554 | 1.00 | 100.17 | A | C |
| ATOM | 1128 | OG1 | THR | 296 | 132.071 | 21.903 | 10.895 | 1.00 | 105.23 | A | O |
| ATOM | 1129 | CG2 | THR | 296 | 129.861 | 21.592 | 11.817 | 1.00 | 100.04 | A | C |
| ATOM | 1130 | C | THR | 296 | 131.387 | 20.535 | 8.479 | 1.00 | 88.04 | A | C |
| ATOM | 1131 | O | THR | 296 | 130.985 | 21.331 | 7.631 | 1.00 | 86.85 | A | O |
| ATOM | 1132 | N | GLU | 297 | 132.497 | 19.825 | 8.322 | 1.00 | 78.34 | A | N |
| ATOM | 1133 | CA | GLU | 297 | 133.304 | 20.020 | 7.128 | 1.00 | 81.80 | A | C |
| ATOM | 1134 | CB | GLU | 297 | 134.577 | 19.171 | 7.169 | 1.00 | 125.47 | A | C |
| ATOM | 1135 | CG | GLU | 297 | 134.403 | 17.709 | 6.851 | 1.00 | 132.50 | A | C |
| ATOM | 1136 | CD | GLU | 297 | 135.690 | 17.103 | 6.342 | 1.00 | 133.75 | A | C |
| ATOM | 1137 | OE1 | GLU | 297 | 135.709 | 15.886 | 6.067 | 1.00 | 135.24 | A | O |
| ATOM | 1138 | OE2 | GLU | 297 | 136.682 | 17.853 | 6.212 | 1.00 | 137.19 | A | O |
| ATOM | 1139 | C | GLU | 297 | 132.550 | 19.770 | 5.832 | 1.00 | 79.84 | A | C |
| ATOM | 1140 | O | GLU | 297 | 132.581 | 20.609 | 4.931 | 1.00 | 79.34 | A | O |
| ATOM | 1141 | N | LYS | 298 | 131.865 | 18.638 | 5.728 | 1.00 | 42.69 | A | N |
| ATOM | 1142 | CA | LYS | 298 | 131.125 | 18.352 | 4.505 | 1.00 | 42.69 | A | C |
| ATOM | 1143 | CB | LYS | 298 | 130.281 | 17.087 | 4.678 | 1.00 | 102.63 | A | C |
| ATOM | 1144 | CG | LYS | 298 | 129.695 | 16.562 | 3.376 | 1.00 | 111.34 | A | C |
| ATOM | 1145 | CD | LYS | 298 | 129.117 | 15.166 | 3.545 | 1.00 | 113.06 | A | C |
| ATOM | 1146 | CE | LYS | 298 | 130.167 | 14.187 | 4.057 | 1.00 | 116.88 | A | C |
| ATOM | 1147 | NZ | LYS | 298 | 131.378 | 14.159 | 3.195 | 1.00 | 121.20 | A | N |
| ATOM | 1148 | C | LYS | 298 | 130.228 | 19.547 | 4.143 | 1.00 | 40.29 | A | C |
| ATOM | 1149 | O | LYS | 298 | 130.032 | 19.853 | 2.964 | 1.00 | 41.17 | A | O |
| ATOM | 1150 | N | PHE | 299 | 129.700 | 20.218 | 5.167 | 1.00 | 38.43 | A | N |
| ATOM | 1151 | CA | PHE | 299 | 128.839 | 21.380 | 4.978 | 1.00 | 36.67 | A | C |
| ATOM | 1152 | CB | PHE | 299 | 128.100 | 21.712 | 6.283 | 1.00 | 55.97 | A | C |
| ATOM | 1153 | CG | PHE | 299 | 127.256 | 22.967 | 6.209 | 1.00 | 48.41 | A | C |
| ATOM | 1154 | CD1 | PHE | 299 | 126.319 | 23.146 | 5.186 | 1.00 | 44.86 | A | C |
| ATOM | 1155 | CD2 | PHE | 299 | 127.400 | 23.970 | 7.160 | 1.00 | 46.14 | A | C |
| ATOM | 1156 | CE1 | PHE | 299 | 125.545 | 24.307 | 5.117 | 1.00 | 44.27 | A | C |
| ATOM | 1157 | CE2 | PHE | 299 | 126.627 | 25.132 | 7.095 | 1.00 | 40.55 | A | C |
| ATOM | 1158 | CZ | PHE | 299 | 125.701 | 25.299 | 6.073 | 1.00 | 39.06 | A | C |
| ATOM | 1159 | C | PHE | 299 | 129.684 | 22.573 | 4.544 | 1.00 | 37.02 | A | C |
| ATOM | 1160 | O | PHE | 299 | 129.439 | 23.190 | 3.504 | 1.00 | 32.83 | A | O |
| ATOM | 1161 | N | VAL | 300 | 130.682 | 22.896 | 5.352 | 1.00 | 13.94 | A | N |
| ATOM | 1162 | CA | VAL | 300 | 131.551 | 24.010 | 5.034 | 1.00 | 18.89 | A | C |
| ATOM | 1163 | CB | VAL | 300 | 132.752 | 24.068 | 5.993 | 1.00 | 40.51 | A | C |
| ATOM | 1164 | CG1 | VAL | 300 | 133.769 | 25.076 | 5.493 | 1.00 | 44.08 | A | C |
| ATOM | 1165 | CG2 | VAL | 300 | 132.282 | 24.451 | 7.382 | 1.00 | 44.52 | A | C |
| ATOM | 1166 | C | VAL | 300 | 132.061 | 23.893 | 3.607 | 1.00 | 17.53 | A | C |
| ATOM | 1167 | O | VAL | 300 | 132.177 | 24.889 | 2.906 | 1.00 | 18.03 | A | O |
| ATOM | 1168 | N | GLU | 301 | 132.365 | 22.679 | 3.164 | 1.00 | 18.30 | A | N |

Fig. 19: A-17

| | | | | | | | | | | | |
|---|---|---|---|---|---|---|---|---|---|---|---|
| ATOM | 1169 | CA | GLU | 301 | 132.866 | 22.513 | 1.808 | 1.00 | 18.96 | A | C |
| ATOM | 1170 | CB | GLU | 301 | 133.407 | 21.094 | 1.605 | 1.00 | 40.16 | A | C |
| ATOM | 1171 | CG | GLU | 301 | 134.058 | 20.854 | 0.243 | 1.00 | 42.43 | A | C |
| ATOM | 1172 | CD | GLU | 301 | 135.049 | 21.943 | -0.155 | 1.00 | 48.24 | A | C |
| ATOM | 1173 | OE1 | GLU | 301 | 135.956 | 22.267 | 0.645 | 1.00 | 47.79 | A | O |
| ATOM | 1174 | OE2 | GLU | 301 | 134.918 | 22.469 | -1.282 | 1.00 | 50.51 | A | O |
| ATOM | 1175 | C | GLU | 301 | 131.770 | 22.832 | 0.791 | 1.00 | 17.53 | A | C |
| ATOM | 1176 | O | GLU | 301 | 132.034 | 23.458 | -0.242 | 1.00 | 15.61 | A | O |
| ATOM | 1177 | N | GLU | 302 | 130.541 | 22.420 | 1.097 | 1.00 | 32.12 | A | N |
| ATOM | 1178 | CA | GLU | 302 | 129.412 | 22.667 | 0.210 | 1.00 | 31.93 | A | C |
| ATOM | 1179 | CB | GLU | 302 | 128.127 | 22.084 | 0.801 | 1.00 | 76.04 | A | C |
| ATOM | 1180 | CG | GLU | 302 | 126.894 | 22.274 | -0.071 | 1.00 | 75.79 | A | C |
| ATOM | 1181 | CD | GLU | 302 | 125.659 | 21.594 | 0.501 | 1.00 | 72.72 | A | C |
| ATOM | 1182 | OE1 | GLU | 302 | 125.651 | 20.349 | 0.584 | 1.00 | 72.70 | A | O |
| ATOM | 1183 | OE2 | GLU | 302 | 124.698 | 22.302 | 0.872 | 1.00 | 77.14 | A | O |
| ATOM | 1184 | C | GLU | 302 | 129.237 | 24.158 | -0.033 | 1.00 | 35.00 | A | C |
| ATOM | 1185 | O | GLU | 302 | 129.040 | 24.580 | -1.170 | 1.00 | 34.26 | A | O |
| ATOM | 1186 | N | ILE | 303 | 129.334 | 24.953 | 1.031 | 1.00 | 23.69 | A | N |
| ATOM | 1187 | CA | ILE | 303 | 129.171 | 26.405 | 0.936 | 1.00 | 23.74 | A | C |
| ATOM | 1188 | CB | ILE | 303 | 128.933 | 27.019 | 2.326 | 1.00 | 28.42 | A | C |
| ATOM | 1189 | CG2 | ILE | 303 | 128.556 | 28.480 | 2.199 | 1.00 | 23.60 | A | C |
| ATOM | 1190 | CG1 | ILE | 303 | 127.823 | 26.245 | 3.046 | 1.00 | 26.02 | A | C |
| ATOM | 1191 | CD1 | ILE | 303 | 126.599 | 25.926 | 2.183 | 1.00 | 22.48 | A | C |
| ATOM | 1192 | C | ILE | 303 | 130.340 | 27.129 | 0.267 | 1.00 | 25.77 | A | C |
| ATOM | 1193 | O | ILE | 303 | 130.133 | 28.036 | -0.553 | 1.00 | 28.26 | A | O |
| ATOM | 1194 | N | LYS | 304 | 131.564 | 26.740 | 0.612 | 1.00 | 28.18 | A | N |
| ATOM | 1195 | CA | LYS | 304 | 132.733 | 27.363 | 0.003 | 1.00 | 28.98 | A | C |
| ATOM | 1196 | CB | LYS | 304 | 134.018 | 26.713 | 0.501 | 1.00 | 31.11 | A | C |
| ATOM | 1197 | CG | LYS | 304 | 134.415 | 27.051 | 1.915 | 1.00 | 37.78 | A | C |
| ATOM | 1198 | CD | LYS | 304 | 135.810 | 26.502 | 2.190 | 1.00 | 39.31 | A | C |
| ATOM | 1199 | CE | LYS | 304 | 136.298 | 26.803 | 3.599 | 1.00 | 42.04 | A | C |
| ATOM | 1200 | NZ | LYS | 304 | 137.673 | 26.262 | 3.857 | 1.00 | 44.22 | A | N |
| ATOM | 1201 | C | LYS | 304 | 132.665 | 27.210 | -1.512 | 1.00 | 25.07 | A | C |
| ATOM | 1202 | O | LYS | 304 | 133.033 | 28.118 | -2.252 | 1.00 | 29.15 | A | O |
| ATOM | 1203 | N | SER | 305 | 132.195 | 26.054 | -1.965 | 1.00 | 30.32 | A | N |
| ATOM | 1204 | CA | SER | 305 | 132.100 | 25.785 | -3.386 | 1.00 | 27.48 | A | C |
| ATOM | 1205 | CB | SER | 305 | 131.702 | 24.329 | -3.635 | 1.00 | 18.09 | A | C |
| ATOM | 1206 | OG | SER | 305 | 130.352 | 24.088 | -3.293 | 1.00 | 14.77 | A | O |
| ATOM | 1207 | C | SER | 305 | 131.094 | 26.709 | -4.044 | 1.00 | 28.00 | A | C |
| ATOM | 1208 | O | SER | 305 | 131.137 | 26.917 | -5.263 | 1.00 | 30.57 | A | O |
| ATOM | 1209 | N | ILE | 306 | 130.181 | 27.258 | -3.247 | 1.00 | 37.08 | A | N |
| ATOM | 1210 | CA | ILE | 306 | 129.180 | 28.176 | -3.783 | 1.00 | 33.83 | A | C |
| ATOM | 1211 | CB | ILE | 306 | 127.990 | 28.319 | -2.831 | 1.00 | 15.00 | A | C |
| ATOM | 1212 | CG2 | ILE | 306 | 127.190 | 29.565 | -3.167 | 1.00 | 15.73 | A | C |
| ATOM | 1213 | CG1 | ILE | 306 | 127.118 | 27.069 | -2.929 | 1.00 | 17.63 | A | C |
| ATOM | 1214 | CD1 | ILE | 306 | 125.993 | 27.029 | -1.916 | 1.00 | 15.34 | A | C |
| ATOM | 1215 | C | ILE | 306 | 129.812 | 29.544 | -4.008 | 1.00 | 31.59 | A | C |
| ATOM | 1216 | O | ILE | 306 | 129.361 | 30.333 | -4.851 | 1.00 | 32.12 | A | O |
| ATOM | 1217 | N | ALA | 307 | 130.874 | 29.805 | -3.251 | 1.00 | 20.26 | A | N |
| ATOM | 1218 | CA | ALA | 307 | 131.584 | 31.062 | -3.349 | 1.00 | 22.45 | A | C |
| ATOM | 1219 | CB | ALA | 307 | 132.444 | 31.260 | -2.118 | 1.00 | 5.65 | A | C |
| ATOM | 1220 | C | ALA | 307 | 132.441 | 31.113 | -4.611 | 1.00 | 22.11 | A | C |
| ATOM | 1221 | O | ALA | 307 | 132.622 | 30.103 | -5.302 | 1.00 | 21.10 | A | O |
| ATOM | 1222 | N | SER | 308 | 132.953 | 32.307 | -4.906 | 1.00 | 24.29 | A | N |
| ATOM | 1223 | CA | SER | 308 | 133.796 | 32.533 | -6.072 | 1.00 | 27.22 | A | C |
| ATOM | 1224 | CB | SER | 308 | 133.489 | 33.899 | -6.700 | 1.00 | 15.61 | A | C |
| ATOM | 1225 | OG | SER | 308 | 132.299 | 33.860 | -7.460 | 1.00 | 19.00 | A | O |
| ATOM | 1226 | C | SER | 308 | 135.264 | 32.482 | -5.690 | 1.00 | 30.87 | A | C |
| ATOM | 1227 | O | SER | 308 | 135.625 | 32.797 | -4.555 | 1.00 | 28.21 | A | O |
| ATOM | 1228 | N | GLU | 309 | 136.103 | 32.069 | -6.640 | 1.00 | 26.43 | A | N |
| ATOM | 1229 | CA | GLU | 309 | 137.542 | 32.008 | -6.418 | 1.00 | 29.92 | A | C |
| ATOM | 1230 | CB | GLU | 309 | 138.224 | 31.266 | -7.569 | 1.00 | 73.14 | A | C |
| ATOM | 1231 | CG | GLU | 309 | 137.811 | 29.809 | -7.737 | 1.00 | 78.51 | A | C |
| ATOM | 1232 | CD | GLU | 309 | 138.181 | 28.950 | -6.541 | 1.00 | 81.27 | A | C |
| ATOM | 1233 | OE1 | GLU | 309 | 138.103 | 27.708 | -6.651 | 1.00 | 83.60 | A | O |
| ATOM | 1234 | OE2 | GLU | 309 | 138.544 | 29.514 | -5.487 | 1.00 | 85.42 | A | O |
| ATOM | 1235 | C | GLU | 309 | 138.009 | 33.461 | -6.396 | 1.00 | 30.67 | A | C |
| ATOM | 1236 | O | GLU | 309 | 137.580 | 34.257 | -7.230 | 1.00 | 32.32 | A | O |
| ATOM | 1237 | N | PRO | 310 | 138.882 | 33.834 | -5.442 | 1.00 | 19.51 | A | N |
| ATOM | 1238 | CD | PRO | 310 | 139.395 | 35.217 | -5.381 | 1.00 | 49.07 | A | C |
| ATOM | 1239 | CA | PRO | 310 | 139.483 | 33.029 | -4.377 | 1.00 | 19.70 | A | C |
| ATOM | 1240 | CB | PRO | 310 | 140.703 | 33.851 | -3.982 | 1.00 | 50.90 | A | C |
| ATOM | 1241 | CG | PRO | 310 | 140.182 | 35.231 | -4.065 | 1.00 | 50.46 | A | C |

Fig. 19: A-18

| | | | | | | | | | | | |
|---|---|---|---|---|---|---|---|---|---|---|---|
| ATOM | 1242 | C | PRO | 310 | 138.569 | 32.751 | -3.178 | 1.00 | 20.19 | A | C |
| ATOM | 1243 | O | PRO | 310 | 138.229 | 33.654 | -2.394 | 1.00 | 16.98 | A | O |
| ATOM | 1244 | N | THR | 311 | 138.197 | 31.483 | -3.043 | 1.00 | 25.93 | A | N |
| ATOM | 1245 | CA | THR | 311 | 137.352 | 31.013 | -1.957 | 1.00 | 26.80 | A | C |
| ATOM | 1246 | CB | THR | 311 | 137.618 | 29.521 | -1.695 | 1.00 | 73.61 | A | C |
| ATOM | 1247 | OG1 | THR | 311 | 137.053 | 29.145 | -0.434 | 1.00 | 77.77 | A | O |
| ATOM | 1248 | CG2 | THR | 311 | 139.118 | 29.244 | -1.696 | 1.00 | 76.69 | A | C |
| ATOM | 1249 | C | THR | 311 | 137.521 | 31.781 | -0.643 | 1.00 | 28.67 | A | C |
| ATOM | 1250 | O | THR | 311 | 136.535 | 32.173 | -0.025 | 1.00 | 29.84 | A | O |
| ATOM | 1251 | N | GLU | 312 | 138.759 | 32.009 | -0.223 | 1.00 | 47.89 | A | N |
| ATOM | 1252 | CA | GLU | 312 | 139.007 | 32.713 | 1.029 | 1.00 | 46.51 | A | C |
| ATOM | 1253 | CB | GLU | 312 | 140.506 | 32.751 | 1.340 | 1.00 | 98.24 | A | C |
| ATOM | 1254 | CG | GLU | 312 | 141.354 | 33.411 | 0.268 | 1.00 | 100.00 | A | C |
| ATOM | 1255 | CD | GLU | 312 | 142.621 | 34.031 | 0.825 | 1.00 | 99.11 | A | C |
| ATOM | 1256 | OE1 | GLU | 312 | 143.491 | 34.431 | 0.024 | 1.00 | 102.46 | A | O |
| ATOM | 1257 | OE2 | GLU | 312 | 142.742 | 34.130 | 2.065 | 1.00 | 99.98 | A | O |
| ATOM | 1258 | C | GLU | 312 | 138.453 | 34.134 | 1.092 | 1.00 | 45.13 | A | C |
| ATOM | 1259 | O | GLU | 312 | 137.997 | 34.576 | 2.147 | 1.00 | 45.09 | A | O |
| ATOM | 1260 | N | LYS | 313 | 138.490 | 34.856 | -0.021 | 1.00 | 49.11 | A | N |
| ATOM | 1261 | CA | LYS | 313 | 137.990 | 36.226 | -0.024 | 1.00 | 48.31 | A | C |
| ATOM | 1262 | CB | LYS | 313 | 138.797 | 37.091 | -1.000 | 1.00 | 91.02 | A | C |
| ATOM | 1263 | CG | LYS | 313 | 140.171 | 37.508 | -0.486 | 1.00 | 90.90 | A | C |
| ATOM | 1264 | CD | LYS | 313 | 140.081 | 38.565 | 0.620 | 1.00 | 87.20 | A | C |
| ATOM | 1265 | CE | LYS | 313 | 139.966 | 39.982 | 0.066 | 1.00 | 89.24 | A | C |
| ATOM | 1266 | NZ | LYS | 313 | 138.804 | 40.159 | -0.842 | 1.00 | 93.72 | A | N |
| ATOM | 1267 | C | LYS | 313 | 136.511 | 36.307 | -0.374 | 1.00 | 49.46 | A | C |
| ATOM | 1268 | O | LYS | 313 | 135.973 | 37.397 | -0.580 | 1.00 | 51.78 | A | O |
| ATOM | 1269 | N | HIS | 314 | 135.849 | 35.159 | -0.427 | 1.00 | 27.67 | A | N |
| ATOM | 1270 | CA | HIS | 314 | 134.437 | 35.137 | -0.775 | 1.00 | 28.52 | A | C |
| ATOM | 1271 | CB | HIS | 314 | 134.274 | 34.652 | -2.212 | 1.00 | 32.51 | A | C |
| ATOM | 1272 | CG | HIS | 314 | 134.872 | 35.574 | -3.224 | 1.00 | 29.37 | A | C |
| ATOM | 1273 | CD2 | HIS | 314 | 136.073 | 35.552 | -3.849 | 1.00 | 28.84 | A | C |
| ATOM | 1274 | ND1 | HIS | 314 | 134.220 | 36.697 | -3.683 | 1.00 | 28.95 | A | N |
| ATOM | 1275 | CE1 | HIS | 314 | 134.992 | 37.326 | -4.551 | 1.00 | 28.24 | A | C |
| ATOM | 1276 | NE2 | HIS | 314 | 136.122 | 36.652 | -4.669 | 1.00 | 28.63 | A | N |
| ATOM | 1277 | C | HIS | 314 | 133.587 | 34.277 | 0.141 | 1.00 | 28.65 | A | C |
| ATOM | 1278 | O | HIS | 314 | 132.366 | 34.238 | -0.008 | 1.00 | 32.05 | A | O |
| ATOM | 1279 | N | PHE | 315 | 134.230 | 33.591 | 1.081 | 1.00 | 32.99 | A | N |
| ATOM | 1280 | CA | PHE | 315 | 133.519 | 32.723 | 2.013 | 1.00 | 32.79 | A | C |
| ATOM | 1281 | CB | PHE | 315 | 134.045 | 31.294 | 1.878 | 1.00 | 35.38 | A | C |
| ATOM | 1282 | CG | PHE | 315 | 133.476 | 30.339 | 2.884 | 1.00 | 30.36 | A | C |
| ATOM | 1283 | CD1 | PHE | 315 | 132.123 | 30.026 | 2.877 | 1.00 | 32.20 | A | C |
| ATOM | 1284 | CD2 | PHE | 315 | 134.298 | 29.749 | 3.839 | 1.00 | 28.44 | A | C |
| ATOM | 1285 | CE1 | PHE | 315 | 131.592 | 29.144 | 3.800 | 1.00 | 27.15 | A | C |
| ATOM | 1286 | CE2 | PHE | 315 | 133.783 | 28.866 | 4.769 | 1.00 | 29.14 | A | C |
| ATOM | 1287 | CZ | PHE | 315 | 132.421 | 28.560 | 4.749 | 1.00 | 30.81 | A | C |
| ATOM | 1288 | C | PHE | 315 | 133.640 | 33.198 | 3.466 | 1.00 | 33.51 | A | C |
| ATOM | 1289 | O | PHE | 315 | 134.706 | 33.643 | 3.896 | 1.00 | 34.91 | A | O |
| ATOM | 1290 | N | PHE | 316 | 132.539 | 33.104 | 4.210 | 1.00 | 26.09 | A | N |
| ATOM | 1291 | CA | PHE | 316 | 132.513 | 33.516 | 5.610 | 1.00 | 23.14 | A | C |
| ATOM | 1292 | CB | PHE | 316 | 131.707 | 34.803 | 5.780 | 1.00 | 27.51 | A | C |
| ATOM | 1293 | CG | PHE | 316 | 132.343 | 36.008 | 5.155 | 1.00 | 31.13 | A | C |
| ATOM | 1294 | CD1 | PHE | 316 | 132.125 | 36.312 | 3.822 | 1.00 | 26.72 | A | C |
| ATOM | 1295 | CD2 | PHE | 316 | 133.182 | 36.827 | 5.903 | 1.00 | 27.98 | A | C |
| ATOM | 1296 | CE1 | PHE | 316 | 132.737 | 37.420 | 3.237 | 1.00 | 29.29 | A | C |
| ATOM | 1297 | CE2 | PHE | 316 | 133.799 | 37.931 | 5.334 | 1.00 | 31.09 | A | C |
| ATOM | 1298 | CZ | PHE | 316 | 133.577 | 38.230 | 3.998 | 1.00 | 31.32 | A | C |
| ATOM | 1299 | C | PHE | 316 | 131.909 | 32.438 | 6.497 | 1.00 | 21.07 | A | C |
| ATOM | 1300 | O | PHE | 316 | 130.901 | 31.831 | 6.153 | 1.00 | 20.31 | A | O |
| ATOM | 1301 | N | ASN | 317 | 132.533 | 32.220 | 7.647 | 1.00 | 37.16 | A | N |
| ATOM | 1302 | CA | ASN | 317 | 132.093 | 31.214 | 8.599 | 1.00 | 38.38 | A | C |
| ATOM | 1303 | CB | ASN | 317 | 133.288 | 30.385 | 9.047 | 1.00 | 74.28 | A | C |
| ATOM | 1304 | CG | ASN | 317 | 133.055 | 28.919 | 8.888 | 1.00 | 77.27 | A | C |
| ATOM | 1305 | OD1 | ASN | 317 | 131.954 | 28.433 | 9.138 | 1.00 | 79.20 | A | O |
| ATOM | 1306 | ND2 | ASN | 317 | 134.088 | 28.190 | 8.478 | 1.00 | 75.53 | A | N |
| ATOM | 1307 | C | ASN | 317 | 131.487 | 31.893 | 9.817 | 1.00 | 39.34 | A | C |
| ATOM | 1308 | O | ASN | 317 | 132.001 | 32.902 | 10.285 | 1.00 | 40.20 | A | O |
| ATOM | 1309 | N | VAL | 318 | 130.398 | 31.348 | 10.336 | 1.00 | 30.64 | A | N |
| ATOM | 1310 | CA | VAL | 318 | 129.763 | 31.924 | 11.521 | 1.00 | 29.27 | A | C |
| ATOM | 1311 | CB | VAL | 318 | 128.531 | 32.778 | 11.144 | 1.00 | 70.89 | A | C |
| ATOM | 1312 | CG1 | VAL | 318 | 127.896 | 33.349 | 12.386 | 1.00 | 71.02 | A | C |
| ATOM | 1313 | CG2 | VAL | 318 | 128.942 | 33.899 | 10.223 | 1.00 | 70.87 | A | C |
| ATOM | 1314 | C | VAL | 318 | 129.331 | 30.808 | 12.482 | 1.00 | 24.42 | A | C |

Fig. 19: A-19

| | | | | | | | | | | | |
|---|---|---|---|---|---|---|---|---|---|---|---|
| ATOM | 1315 | O | VAL | 318 | 128.872 | 29.744 | 12.053 | 1.00 | 25.09 | A | O |
| ATOM | 1316 | N | SER | 319 | 129.482 | 31.045 | 13.779 | 1.00 | 32.47 | A | N |
| ATOM | 1317 | CA | SER | 319 | 129.108 | 30.035 | 14.752 | 1.00 | 31.73 | A | C |
| ATOM | 1318 | CB | SER | 319 | 129.669 | 30.384 | 16.134 | 1.00 | 29.19 | A | C |
| ATOM | 1319 | OG | SER | 319 | 129.289 | 31.687 | 16.538 | 1.00 | 41.14 | A | O |
| ATOM | 1320 | C | SER | 319 | 127.600 | 29.840 | 14.831 | 1.00 | 30.33 | A | C |
| ATOM | 1321 | O | SER | 319 | 127.132 | 28.716 | 14.963 | 1.00 | 28.40 | A | O |
| ATOM | 1322 | N | ASP | 320 | 126.839 | 30.926 | 14.741 | 1.00 | 32.33 | A | N |
| ATOM | 1323 | CA | ASP | 320 | 125.382 | 30.846 | 14.816 | 1.00 | 32.31 | A | C |
| ATOM | 1324 | CB | ASP | 320 | 124.934 | 30.632 | 16.275 | 1.00 | 63.91 | A | C |
| ATOM | 1325 | CG | ASP | 320 | 125.369 | 31.760 | 17.209 | 1.00 | 62.36 | A | C |
| ATOM | 1326 | OD1 | ASP | 320 | 126.586 | 31.992 | 17.364 | 1.00 | 61.04 | A | O |
| ATOM | 1327 | OD2 | ASP | 320 | 124.486 | 32.412 | 17.801 | 1.00 | 62.91 | A | O |
| ATOM | 1328 | C | ASP | 320 | 124.698 | 32.088 | 14.237 | 1.00 | 30.68 | A | C |
| ATOM | 1329 | O | ASP | 320 | 125.367 | 33.072 | 13.905 | 1.00 | 30.46 | A | O |
| ATOM | 1330 | N | GLU | 321 | 123.371 | 32.042 | 14.110 | 1.00 | 35.58 | A | N |
| ATOM | 1331 | CA | GLU | 321 | 122.614 | 33.173 | 13.569 | 1.00 | 36.56 | A | C |
| ATOM | 1332 | CB | GLU | 321 | 121.126 | 33.029 | 13.889 | 1.00 | 84.00 | A | C |
| ATOM | 1333 | CG | GLU | 321 | 120.285 | 32.398 | 12.796 | 1.00 | 77.84 | A | C |
| ATOM | 1334 | CD | GLU | 321 | 120.602 | 30.938 | 12.569 | 1.00 | 77.59 | A | C |
| ATOM | 1335 | OE1 | GLU | 321 | 120.595 | 30.164 | 13.549 | 1.00 | 79.02 | A | O |
| ATOM | 1336 | OE2 | GLU | 321 | 120.849 | 30.565 | 11.404 | 1.00 | 81.63 | A | O |
| ATOM | 1337 | C | GLU | 321 | 123.101 | 34.500 | 14.134 | 1.00 | 40.55 | A | C |
| ATOM | 1338 | O | GLU | 321 | 123.278 | 35.475 | 13.397 | 1.00 | 37.31 | A | O |
| ATOM | 1339 | N | LEU | 322 | 123.323 | 34.519 | 15.447 | 1.00 | 25.97 | A | N |
| ATOM | 1340 | CA | LEU | 322 | 123.769 | 35.717 | 16.155 | 1.00 | 28.66 | A | C |
| ATOM | 1341 | CB | LEU | 322 | 123.925 | 35.407 | 17.648 | 1.00 | 49.06 | A | C |
| ATOM | 1342 | CG | LEU | 322 | 122.646 | 35.281 | 18.477 | 1.00 | 47.69 | A | C |
| ATOM | 1343 | CD1 | LEU | 322 | 121.935 | 36.625 | 18.486 | 1.00 | 49.43 | A | C |
| ATOM | 1344 | CD2 | LEU | 322 | 121.745 | 34.194 | 17.917 | 1.00 | 52.74 | A | C |
| ATOM | 1345 | C | LEU | 322 | 125.052 | 36.368 | 15.644 | 1.00 | 30.25 | A | C |
| ATOM | 1346 | O | LEU | 322 | 125.106 | 37.580 | 15.459 | 1.00 | 33.60 | A | O |
| ATOM | 1347 | N | ALA | 323 | 126.080 | 35.558 | 15.424 | 1.00 | 27.12 | A | N |
| ATOM | 1348 | CA | ALA | 323 | 127.358 | 36.071 | 14.965 | 1.00 | 27.55 | A | C |
| ATOM | 1349 | CB | ALA | 323 | 128.420 | 34.994 | 15.112 | 1.00 | 20.92 | A | C |
| ATOM | 1350 | C | ALA | 323 | 127.368 | 36.631 | 13.539 | 1.00 | 27.96 | A | C |
| ATOM | 1351 | O | ALA | 323 | 128.363 | 37.227 | 13.120 | 1.00 | 27.98 | A | O |
| ATOM | 1352 | N | LEU | 324 | 126.280 | 36.451 | 12.794 | 1.00 | 44.60 | A | N |
| ATOM | 1353 | CA | LEU | 324 | 126.231 | 36.961 | 11.427 | 1.00 | 43.08 | A | C |
| ATOM | 1354 | CB | LEU | 324 | 124.807 | 36.875 | 10.867 | 1.00 | 12.96 | A | C |
| ATOM | 1355 | CG | LEU | 324 | 124.398 | 35.546 | 10.215 | 1.00 | 11.69 | A | C |
| ATOM | 1356 | CD1 | LEU | 324 | 122.900 | 35.547 | 9.935 | 1.00 | 10.83 | A | C |
| ATOM | 1357 | CD2 | LEU | 324 | 125.197 | 35.331 | 8.938 | 1.00 | 9.62 | A | C |
| ATOM | 1358 | C | LEU | 324 | 126.734 | 38.400 | 11.346 | 1.00 | 46.61 | A | C |
| ATOM | 1359 | O | LEU | 324 | 127.545 | 38.735 | 10.484 | 1.00 | 43.15 | A | O |
| ATOM | 1360 | N | VAL | 325 | 126.257 | 39.244 | 12.252 | 1.00 | 37.14 | A | N |
| ATOM | 1361 | CA | VAL | 325 | 126.657 | 40.645 | 12.297 | 1.00 | 40.67 | A | C |
| ATOM | 1362 | CB | VAL | 325 | 126.111 | 41.328 | 13.549 | 1.00 | 15.02 | A | C |
| ATOM | 1363 | CG1 | VAL | 325 | 124.613 | 41.517 | 13.425 | 1.00 | 15.13 | A | C |
| ATOM | 1364 | CG2 | VAL | 325 | 126.453 | 40.503 | 14.773 | 1.00 | 18.41 | A | C |
| ATOM | 1365 | C | VAL | 325 | 128.168 | 40.840 | 12.304 | 1.00 | 43.49 | A | C |
| ATOM | 1366 | O | VAL | 325 | 128.706 | 41.663 | 11.560 | 1.00 | 45.55 | A | O |
| ATOM | 1367 | N | THR | 326 | 128.844 | 40.088 | 13.161 | 1.00 | 37.74 | A | N |
| ATOM | 1368 | CA | THR | 326 | 130.289 | 40.164 | 13.286 | 1.00 | 39.15 | A | C |
| ATOM | 1369 | CB | THR | 326 | 130.768 | 39.218 | 14.391 | 1.00 | 28.63 | A | C |
| ATOM | 1370 | OG1 | THR | 326 | 130.648 | 37.863 | 13.944 | 1.00 | 30.54 | A | O |
| ATOM | 1371 | CG2 | THR | 326 | 129.911 | 39.398 | 15.643 | 1.00 | 31.00 | A | C |
| ATOM | 1372 | C | THR | 326 | 130.996 | 39.790 | 11.985 | 1.00 | 39.16 | A | C |
| ATOM | 1373 | O | THR | 326 | 132.105 | 39.268 | 12.005 | 1.00 | 37.98 | A | O |
| ATOM | 1374 | N | ILE | 327 | 130.358 | 40.065 | 10.854 | 1.00 | 29.50 | A | N |
| ATOM | 1375 | CA | ILE | 327 | 130.922 | 39.739 | 9.552 | 1.00 | 29.69 | A | C |
| ATOM | 1376 | CB | ILE | 327 | 130.407 | 38.343 | 9.098 | 1.00 | 36.77 | A | C |
| ATOM | 1377 | CG2 | ILE | 327 | 129.867 | 38.372 | 7.679 | 1.00 | 37.54 | A | C |
| ATOM | 1378 | CG1 | ILE | 327 | 131.539 | 37.335 | 9.199 | 1.00 | 37.13 | A | C |
| ATOM | 1379 | CD1 | ILE | 327 | 131.100 | 35.928 | 8.903 | 1.00 | 36.80 | A | C |
| ATOM | 1380 | C | ILE | 327 | 130.572 | 40.816 | 8.520 | 1.00 | 30.20 | A | C |
| ATOM | 1381 | O | ILE | 327 | 131.284 | 41.008 | 7.530 | 1.00 | 30.45 | A | O |
| ATOM | 1382 | N | VAL | 328 | 129.478 | 41.527 | 8.766 | 1.00 | 25.26 | A | N |
| ATOM | 1383 | CA | VAL | 328 | 129.040 | 42.565 | 7.851 | 1.00 | 27.40 | A | C |
| ATOM | 1384 | CB | VAL | 328 | 127.851 | 43.363 | 8.436 | 1.00 | 56.37 | A | C |
| ATOM | 1385 | CG1 | VAL | 328 | 126.752 | 42.408 | 8.838 | 1.00 | 58.32 | A | C |
| ATOM | 1386 | CG2 | VAL | 328 | 128.301 | 44.197 | 9.626 | 1.00 | 57.64 | A | C |
| ATOM | 1387 | C | VAL | 328 | 130.159 | 43.539 | 7.485 | 1.00 | 27.32 | A | C |

Fig. 19: A-20

| | | | | | | | | | | | |
|---|---|---|---|---|---|---|---|---|---|---|---|
| ATOM | 1388 | O | VAL | 328 | 130.220 | 44.017 | 6.355 | 1.00 | 26.60 | A | O |
| ATOM | 1389 | N | LYS | 329 | 131.047 | 43.837 | 8.426 | 1.00 | 32.39 | A | N |
| ATOM | 1390 | CA | LYS | 329 | 132.121 | 44.773 | 8.124 | 1.00 | 31.60 | A | C |
| ATOM | 1391 | CB | LYS | 329 | 132.949 | 45.076 | 9.378 | 1.00 | 67.11 | A | C |
| ATOM | 1392 | CG | LYS | 329 | 133.861 | 46.291 | 9.242 | 1.00 | 68.66 | A | C |
| ATOM | 1393 | CD | LYS | 329 | 134.737 | 46.454 | 10.474 | 1.00 | 70.98 | A | C |
| ATOM | 1394 | CE | LYS | 329 | 135.540 | 47.746 | 10.437 | 1.00 | 74.02 | A | C |
| ATOM | 1395 | NZ | LYS | 329 | 134.660 | 48.952 | 10.496 | 1.00 | 77.70 | A | N |
| ATOM | 1396 | C | LYS | 329 | 133.014 | 44.194 | 7.036 | 1.00 | 29.77 | A | C |
| ATOM | 1397 | O | LYS | 329 | 133.205 | 44.802 | 5.978 | 1.00 | 30.98 | A | O |
| ATOM | 1398 | N | ALA | 330 | 133.551 | 43.008 | 7.293 | 1.00 | 29.12 | A | N |
| ATOM | 1399 | CA | ALA | 330 | 134.425 | 42.365 | 6.331 | 1.00 | 29.15 | A | C |
| ATOM | 1400 | CB | ALA | 330 | 134.997 | 41.091 | 6.922 | 1.00 | 30.19 | A | C |
| ATOM | 1401 | C | ALA | 330 | 133.681 | 42.056 | 5.043 | 1.00 | 30.30 | A | C |
| ATOM | 1402 | O | ALA | 330 | 134.207 | 42.269 | 3.955 | 1.00 | 30.20 | A | O |
| ATOM | 1403 | N | LEU | 331 | 132.457 | 41.551 | 5.168 | 1.00 | 22.22 | A | N |
| ATOM | 1404 | CA | LEU | 331 | 131.661 | 41.206 | 3.994 | 1.00 | 19.86 | A | C |
| ATOM | 1405 | CB | LEU | 331 | 130.284 | 40.667 | 4.403 | 1.00 | 36.97 | A | C |
| ATOM | 1406 | CG | LEU | 331 | 129.567 | 39.761 | 3.389 | 1.00 | 33.39 | A | C |
| ATOM | 1407 | CD1 | LEU | 331 | 128.110 | 39.600 | 3.787 | 1.00 | 35.02 | A | C |
| ATOM | 1408 | CD2 | LEU | 331 | 129.658 | 40.343 | 1.996 | 1.00 | 29.08 | A | C |
| ATOM | 1409 | C | LEU | 331 | 131.483 | 42.467 | 3.162 | 1.00 | 19.89 | A | C |
| ATOM | 1410 | O | LEU | 331 | 131.741 | 42.468 | 1.961 | 1.00 | 19.24 | A | O |
| ATOM | 1411 | N | GLY | 332 | 131.045 | 43.535 | 3.830 | 1.00 | 15.82 | A | N |
| ATOM | 1412 | CA | GLY | 332 | 130.824 | 44.811 | 3.179 | 1.00 | 16.92 | A | C |
| ATOM | 1413 | C | GLY | 332 | 132.024 | 45.309 | 2.402 | 1.00 | 17.18 | A | C |
| ATOM | 1414 | O | GLY | 332 | 131.911 | 45.651 | 1.224 | 1.00 | 21.05 | A | O |
| ATOM | 1415 | N | GLU | 333 | 133.185 | 45.347 | 3.045 | 1.00 | 34.74 | A | N |
| ATOM | 1416 | CA | GLU | 333 | 134.369 | 45.831 | 2.362 | 1.00 | 32.80 | A | C |
| ATOM | 1417 | CB | GLU | 333 | 135.472 | 46.165 | 3.371 | 1.00 | 75.29 | A | C |
| ATOM | 1418 | CG | GLU | 333 | 136.139 | 44.968 | 4.005 | 1.00 | 73.66 | A | C |
| ATOM | 1419 | CD | GLU | 333 | 137.251 | 45.363 | 4.959 | 1.00 | 73.68 | A | C |
| ATOM | 1420 | OE1 | GLU | 333 | 137.953 | 44.459 | 5.456 | 1.00 | 75.73 | A | O |
| ATOM | 1421 | OE2 | GLU | 333 | 137.421 | 46.575 | 5.215 | 1.00 | 67.80 | A | O |
| ATOM | 1422 | C | GLU | 333 | 134.888 | 44.841 | 1.322 | 1.00 | 31.78 | A | C |
| ATOM | 1423 | O | GLU | 333 | 135.370 | 45.236 | 0.261 | 1.00 | 31.40 | A | O |
| ATOM | 1424 | N | ARG | 334 | 134.781 | 43.552 | 1.610 | 1.00 | 50.02 | A | N |
| ATOM | 1425 | CA | ARG | 334 | 135.275 | 42.563 | 0.669 | 1.00 | 53.40 | A | C |
| ATOM | 1426 | CB | ARG | 334 | 135.064 | 41.152 | 1.215 | 1.00 | 83.27 | A | C |
| ATOM | 1427 | CG | ARG | 334 | 136.000 | 40.123 | 0.607 | 1.00 | 82.56 | A | C |
| ATOM | 1428 | CD | ARG | 334 | 136.564 | 39.198 | 1.677 | 1.00 | 81.32 | A | C |
| ATOM | 1429 | NE | ARG | 334 | 137.441 | 39.901 | 2.612 | 1.00 | 76.87 | A | N |
| ATOM | 1430 | CZ | ARG | 334 | 137.888 | 39.383 | 3.753 | 1.00 | 80.96 | A | C |
| ATOM | 1431 | NH1 | ARG | 334 | 137.537 | 38.148 | 4.108 | 1.00 | 77.70 | A | N |
| ATOM | 1432 | NH2 | ARG | 334 | 138.686 | 40.097 | 4.539 | 1.00 | 87.10 | A | N |
| ATOM | 1433 | C | ARG | 334 | 134.556 | 42.757 | -0.654 | 1.00 | 54.70 | A | C |
| ATOM | 1434 | O | ARG | 334 | 135.170 | 42.716 | -1.716 | 1.00 | 51.62 | A | O |
| ATOM | 1435 | N | ILE | 335 | 133.253 | 42.988 | -0.591 | 1.00 | 36.48 | A | N |
| ATOM | 1436 | CA | ILE | 335 | 132.473 | 43.214 | -1.803 | 1.00 | 36.41 | A | C |
| ATOM | 1437 | CB | ILE | 335 | 130.940 | 42.967 | -1.539 | 1.00 | 33.09 | A | C |
| ATOM | 1438 | CG2 | ILE | 335 | 130.524 | 43.522 | -0.203 | 1.00 | 35.87 | A | C |
| ATOM | 1439 | CG1 | ILE | 335 | 130.094 | 43.611 | -2.630 | 1.00 | 34.31 | A | C |
| ATOM | 1440 | CD1 | ILE | 335 | 128.612 | 43.520 | -2.368 | 1.00 | 37.10 | A | C |
| ATOM | 1441 | C | ILE | 335 | 132.742 | 44.663 | -2.215 | 1.00 | 34.70 | A | C |
| ATOM | 1442 | O | ILE | 335 | 132.421 | 45.092 | -3.326 | 1.00 | 37.30 | A | O |
| ATOM | 1443 | N | PHE | 336 | 133.392 | 45.377 | -1.299 | 1.00 | 108.43 | A | N |
| ATOM | 1444 | CA | PHE | 336 | 133.744 | 46.789 | -1.419 | 1.00 | 108.06 | A | C |
| ATOM | 1445 | CB | PHE | 336 | 135.092 | 46.989 | -2.157 | 1.00 | 57.00 | A | C |
| ATOM | 1446 | CG | PHE | 336 | 135.114 | 46.540 | -3.601 | 1.00 | 53.32 | A | C |
| ATOM | 1447 | CD1 | PHE | 336 | 134.135 | 46.941 | -4.508 | 1.00 | 52.74 | A | C |
| ATOM | 1448 | CD2 | PHE | 336 | 136.178 | 45.779 | -4.073 | 1.00 | 51.27 | A | C |
| ATOM | 1449 | CE1 | PHE | 336 | 134.219 | 46.589 | -5.868 | 1.00 | 43.07 | A | C |
| ATOM | 1450 | CE2 | PHE | 336 | 136.271 | 45.426 | -5.422 | 1.00 | 45.63 | A | C |
| ATOM | 1451 | CZ | PHE | 336 | 135.292 | 45.832 | -6.319 | 1.00 | 46.09 | A | C |
| ATOM | 1452 | C | PHE | 336 | 132.662 | 47.670 | -2.020 | 1.00 | 108.09 | A | C |
| ATOM | 1453 | O | PHE | 336 | 131.623 | 47.131 | -2.453 | 1.00 | 87.71 | A | O |
| ATOM | 1454 | OXT | PHE | 336 | 132.864 | 48.902 | -2.024 | 1.00 | 40.49 | A | O |
| ATOM | 1455 | CB | GLU | 1 | 119.537 | 12.185 | 27.786 | 1.00 | 88.08 | H | C |
| ATOM | 1456 | CG | GLU | 1 | 118.650 | 11.120 | 28.419 | 1.00 | 88.08 | H | C |
| ATOM | 1457 | CD | GLU | 1 | 119.399 | 10.237 | 29.409 | 1.00 | 88.08 | H | C |
| ATOM | 1458 | OE1 | GLU | 1 | 120.127 | 10.777 | 30.271 | 1.00 | 88.08 | H | O |
| ATOM | 1459 | OE2 | GLU | 1 | 119.251 | 8.998 | 29.324 | 1.00 | 88.08 | H | O |
| ATOM | 1460 | C | GLU | 1 | 118.366 | 14.360 | 28.176 | 1.00 | 62.78 | H | C |

Fig. 19: A-21

| | | | | | | | | | | |
|---|---|---|---|---|---|---|---|---|---|---|
| ATOM | 1461 | O | GLU | 1 | 117.763 | 15.033 | 29.012 | 1.00 | 62.78 | H | O |
| ATOM | 1462 | N | GLU | 1 | 119.687 | 13.262 | 30.016 | 1.00 | 62.78 | H | N |
| ATOM | 1463 | CA | GLU | 1 | 119.580 | 13.515 | 28.553 | 1.00 | 62.78 | H | C |
| ATOM | 1464 | N | VAL | 2 | 118.019 | 14.312 | 26.896 | 1.00 | 44.26 | H | N |
| ATOM | 1465 | CA | VAL | 2 | 116.896 | 15.064 | 26.359 | 1.00 | 44.26 | H | C |
| ATOM | 1466 | CB | VAL | 2 | 117.154 | 15.460 | 24.909 | 1.00 | 15.14 | H | C |
| ATOM | 1467 | CG1 | VAL | 2 | 118.610 | 15.840 | 24.732 | 1.00 | 15.14 | H | C |
| ATOM | 1468 | CG2 | VAL | 2 | 116.807 | 14.309 | 23.997 | 1.00 | 15.14 | H | C |
| ATOM | 1469 | C | VAL | 2 | 115.677 | 14.174 | 26.353 | 1.00 | 44.26 | H | C |
| ATOM | 1470 | O | VAL | 2 | 115.803 | 12.951 | 26.347 | 1.00 | 44.26 | H | O |
| ATOM | 1471 | N | GLN | 3 | 114.497 | 14.780 | 26.340 | 1.00 | 25.45 | H | N |
| ATOM | 1472 | CA | GLN | 3 | 113.280 | 13.984 | 26.288 | 1.00 | 25.45 | H | C |
| ATOM | 1473 | CB | GLN | 3 | 113.191 | 13.046 | 27.494 | 1.00 | 105.15 | H | C |
| ATOM | 1474 | CG | GLN | 3 | 113.307 | 13.707 | 28.841 | 1.00 | 105.15 | H | C |
| ATOM | 1475 | CD | GLN | 3 | 113.015 | 12.733 | 29.961 | 1.00 | 105.15 | H | C |
| ATOM | 1476 | OE1 | GLN | 3 | 113.554 | 11.623 | 29.990 | 1.00 | 105.15 | H | O |
| ATOM | 1477 | NE2 | GLN | 3 | 112.157 | 13.139 | 30.892 | 1.00 | 105.15 | H | N |
| ATOM | 1478 | C | GLN | 3 | 111.961 | 14.708 | 26.119 | 1.00 | 25.45 | H | C |
| ATOM | 1479 | O | GLN | 3 | 111.809 | 15.887 | 26.438 | 1.00 | 25.45 | H | O |
| ATOM | 1480 | N | LEU | 4 | 111.009 | 13.959 | 25.588 | 1.00 | 27.88 | H | N |
| ATOM | 1481 | CA | LEU | 4 | 109.668 | 14.446 | 25.339 | 1.00 | 27.88 | H | C |
| ATOM | 1482 | CB | LEU | 4 | 109.347 | 14.369 | 23.842 | 1.00 | 33.14 | H | C |
| ATOM | 1483 | CG | LEU | 4 | 110.367 | 14.924 | 22.847 | 1.00 | 33.14 | H | C |
| ATOM | 1484 | CD1 | LEU | 4 | 109.821 | 14.772 | 21.438 | 1.00 | 33.14 | H | C |
| ATOM | 1485 | CD2 | LEU | 4 | 110.646 | 16.385 | 23.155 | 1.00 | 33.14 | H | C |
| ATOM | 1486 | C | LEU | 4 | 108.755 | 13.507 | 26.095 | 1.00 | 27.88 | H | C |
| ATOM | 1487 | O | LEU | 4 | 108.871 | 12.282 | 25.960 | 1.00 | 27.88 | H | O |
| ATOM | 1488 | N | VAL | 5 | 107.858 | 14.061 | 26.901 | 1.00 | 26.47 | H | N |
| ATOM | 1489 | CA | VAL | 5 | 106.942 | 13.215 | 27.656 | 1.00 | 26.47 | H | C |
| ATOM | 1490 | CB | VAL | 5 | 107.176 | 13.329 | 29.197 | 1.00 | 25.39 | H | C |
| ATOM | 1491 | CG1 | VAL | 5 | 107.281 | 14.772 | 29.606 | 1.00 | 25.39 | H | C |
| ATOM | 1492 | CG2 | VAL | 5 | 106.046 | 12.654 | 29.947 | 1.00 | 25.39 | H | C |
| ATOM | 1493 | C | VAL | 5 | 105.520 | 13.578 | 27.297 | 1.00 | 26.47 | H | C |
| ATOM | 1494 | O | VAL | 5 | 105.031 | 14.664 | 27.635 | 1.00 | 26.47 | H | O |
| ATOM | 1495 | N | GLU | 6 | 104.868 | 12.650 | 26.601 | 1.00 | 23.78 | H | N |
| ATOM | 1496 | CA | GLU | 6 | 103.495 | 12.835 | 26.133 | 1.00 | 23.78 | H | C |
| ATOM | 1497 | CB | GLU | 6 | 103.258 | 11.995 | 24.885 | 1.00 | 29.58 | H | C |
| ATOM | 1498 | CG | GLU | 6 | 104.409 | 12.017 | 23.933 | 1.00 | 29.58 | H | C |
| ATOM | 1499 | CD | GLU | 6 | 104.188 | 11.109 | 22.756 | 1.00 | 29.58 | H | C |
| ATOM | 1500 | OE1 | GLU | 6 | 105.194 | 10.664 | 22.168 | 1.00 | 29.58 | H | O |
| ATOM | 1501 | OE2 | GLU | 6 | 103.013 | 10.846 | 22.413 | 1.00 | 29.58 | H | O |
| ATOM | 1502 | C | GLU | 6 | 102.429 | 12.485 | 27.155 | 1.00 | 23.78 | H | C |
| ATOM | 1503 | O | GLU | 6 | 102.680 | 11.740 | 28.101 | 1.00 | 23.78 | H | O |
| ATOM | 1504 | N | SER | 7 | 101.242 | 13.047 | 26.937 | 1.00 | 26.30 | H | N |
| ATOM | 1505 | CA | SER | 7 | 100.061 | 12.823 | 27.766 | 1.00 | 26.30 | H | C |
| ATOM | 1506 | CB | SER | 7 | 100.177 | 13.535 | 29.102 | 1.00 | 32.56 | H | C |
| ATOM | 1507 | OG | SER | 7 | 100.574 | 14.871 | 28.906 | 1.00 | 32.56 | H | O |
| ATOM | 1508 | C | SER | 7 | 98.886 | 13.381 | 26.998 | 1.00 | 26.30 | H | C |
| ATOM | 1509 | O | SER | 7 | 99.060 | 14.248 | 26.136 | 1.00 | 26.30 | H | O |
| ATOM | 1510 | N | GLY | 8 | 97.693 | 12.872 | 27.287 | 1.00 | 41.74 | H | N |
| ATOM | 1511 | CA | GLY | 8 | 96.514 | 13.360 | 26.598 | 1.00 | 41.74 | H | C |
| ATOM | 1512 | C | GLY | 8 | 95.807 | 12.321 | 25.752 | 1.00 | 41.74 | H | C |
| ATOM | 1513 | O | GLY | 8 | 94.745 | 12.603 | 25.201 | 1.00 | 41.74 | H | O |
| ATOM | 1514 | N | GLY | 9 | 96.383 | 11.127 | 25.637 | 1.00 | 47.50 | H | N |
| ATOM | 1515 | CA | GLY | 9 | 95.751 | 10.079 | 24.851 | 1.00 | 47.50 | H | C |
| ATOM | 1516 | C | GLY | 9 | 94.431 | 9.601 | 25.446 | 1.00 | 47.50 | H | C |
| ATOM | 1517 | O | GLY | 9 | 94.038 | 10.020 | 26.536 | 1.00 | 47.50 | H | O |
| ATOM | 1518 | N | GLY | 10 | 93.732 | 8.723 | 24.735 | 1.00 | 16.50 | H | N |
| ATOM | 1519 | CA | GLY | 10 | 92.469 | 8.225 | 25.244 | 1.00 | 16.50 | H | C |
| ATOM | 1520 | C | GLY | 10 | 91.485 | 7.806 | 24.169 | 1.00 | 16.50 | H | C |
| ATOM | 1521 | O | GLY | 10 | 91.830 | 7.701 | 22.990 | 1.00 | 16.50 | H | O |
| ATOM | 1522 | N | LEU | 11 | 90.251 | 7.559 | 24.595 | 1.00 | 37.61 | H | N |
| ATOM | 1523 | CA | LEU | 11 | 89.175 | 7.137 | 23.710 | 1.00 | 37.61 | H | C |
| ATOM | 1524 | CB | LEU | 11 | 88.388 | 6.003 | 24.365 | 1.00 | 18.32 | H | C |
| ATOM | 1525 | CG | LEU | 11 | 86.959 | 5.715 | 23.885 | 1.00 | 18.32 | H | C |
| ATOM | 1526 | CD1 | LEU | 11 | 86.962 | 5.148 | 22.463 | 1.00 | 18.32 | H | C |
| ATOM | 1527 | CD2 | LEU | 11 | 86.313 | 4.729 | 24.856 | 1.00 | 18.32 | H | C |
| ATOM | 1528 | C | LEU | 11 | 88.235 | 8.292 | 23.436 | 1.00 | 37.61 | H | C |
| ATOM | 1529 | O | LEU | 11 | 87.769 | 8.943 | 24.365 | 1.00 | 37.61 | H | O |
| ATOM | 1530 | N | VAL | 12 | 87.961 | 8.550 | 22.165 | 1.00 | 31.23 | H | N |
| ATOM | 1531 | CA | VAL | 12 | 87.048 | 9.624 | 21.792 | 1.00 | 31.23 | H | C |
| ATOM | 1532 | CB | VAL | 12 | 87.794 | 10.800 | 21.144 | 1.00 | 52.64 | H | C |
| ATOM | 1533 | CG1 | VAL | 12 | 88.609 | 11.532 | 22.192 | 1.00 | 52.64 | H | C |

Fig. 19: A-22

| | | | | | | | | | | | |
|---|---|---|---|---|---|---|---|---|---|---|---|
| ATOM | 1534 | CG2 | VAL | 12 | 88.699 | 10.290 | 20.039 | 1.00 | 52.64 | H | C |
| ATOM | 1535 | C | VAL | 12 | 86.062 | 9.045 | 20.794 | 1.00 | 31.23 | H | C |
| ATOM | 1536 | O | VAL | 12 | 86.365 | 8.057 | 20.138 | 1.00 | 31.23 | H | O |
| ATOM | 1537 | N | GLN | 13 | 84.882 | 9.640 | 20.681 | 1.00 | 27.32 | H | N |
| ATOM | 1538 | CA | GLN | 13 | 83.894 | 9.126 | 19.741 | 1.00 | 27.32 | H | C |
| ATOM | 1539 | CB | GLN | 13 | 82.493 | 9.391 | 20.270 | 1.00 | 92.40 | H | C |
| ATOM | 1540 | CG | GLN | 13 | 82.206 | 8.652 | 21.553 | 1.00 | 92.40 | H | C |
| ATOM | 1541 | CD | GLN | 13 | 80.808 | 8.906 | 22.056 | 1.00 | 92.40 | H | C |
| ATOM | 1542 | OE1 | GLN | 13 | 79.836 | 8.766 | 21.310 | 1.00 | 92.40 | H | O |
| ATOM | 1543 | NE2 | GLN | 13 | 80.693 | 9.276 | 23.329 | 1.00 | 92.40 | H | N |
| ATOM | 1544 | C | GLN | 13 | 84.063 | 9.747 | 18.356 | 1.00 | 27.32 | H | C |
| ATOM | 1545 | O | GLN | 13 | 84.400 | 10.924 | 18.227 | 1.00 | 27.32 | H | O |
| ATOM | 1546 | N | PRO | 14 | 83.834 | 8.955 | 17.298 | 1.00 | 39.48 | H | N |
| ATOM | 1547 | CD | PRO | 14 | 83.418 | 7.539 | 17.302 | 1.00 | 31.44 | H | C |
| ATOM | 1548 | CA | PRO | 14 | 83.971 | 9.452 | 15.929 | 1.00 | 39.48 | H | C |
| ATOM | 1549 | CB | PRO | 14 | 83.219 | 8.406 | 15.118 | 1.00 | 31.44 | H | C |
| ATOM | 1550 | CG | PRO | 14 | 83.584 | 7.145 | 15.837 | 1.00 | 31.44 | H | C |
| ATOM | 1551 | C | PRO | 14 | 83.401 | 10.849 | 15.766 | 1.00 | 39.48 | H | C |
| ATOM | 1552 | O | PRO | 14 | 82.235 | 11.076 | 16.053 | 1.00 | 39.48 | H | O |
| ATOM | 1553 | N | GLY | 15 | 84.233 | 11.784 | 15.319 | 1.00 | 28.44 | H | N |
| ATOM | 1554 | CA | GLY | 15 | 83.788 | 13.154 | 15.130 | 1.00 | 28.44 | H | C |
| ATOM | 1555 | C | GLY | 15 | 84.048 | 14.065 | 16.323 | 1.00 | 28.44 | H | C |
| ATOM | 1556 | O | GLY | 15 | 83.759 | 15.265 | 16.269 | 1.00 | 28.44 | H | O |
| ATOM | 1557 | N | GLY | 16 | 84.588 | 13.496 | 17.401 | 1.00 | 22.09 | H | N |
| ATOM | 1558 | CA | GLY | 16 | 84.880 | 14.266 | 18.601 | 1.00 | 22.09 | H | C |
| ATOM | 1559 | C | GLY | 16 | 86.286 | 14.826 | 18.571 | 1.00 | 22.09 | H | C |
| ATOM | 1560 | O | GLY | 16 | 86.900 | 14.912 | 17.507 | 1.00 | 22.09 | H | O |
| ATOM | 1561 | N | SER | 17 | 86.819 | 15.202 | 19.726 | 1.00 | 31.69 | H | N |
| ATOM | 1562 | CA | SER | 17 | 88.161 | 15.762 | 19.749 | 1.00 | 31.69 | H | C |
| ATOM | 1563 | CB | SER | 17 | 88.085 | 17.272 | 19.592 | 1.00 | 54.23 | H | C |
| ATOM | 1564 | OG | SER | 17 | 87.308 | 17.829 | 20.625 | 1.00 | 54.23 | H | O |
| ATOM | 1565 | C | SER | 17 | 88.953 | 15.416 | 21.000 | 1.00 | 31.69 | H | C |
| ATOM | 1566 | O | SER | 17 | 88.427 | 14.824 | 21.944 | 1.00 | 31.69 | H | O |
| ATOM | 1567 | N | LEU | 18 | 90.227 | 15.794 | 20.995 | 1.00 | 31.76 | H | N |
| ATOM | 1568 | CA | LEU | 18 | 91.132 | 15.515 | 22.105 | 1.00 | 31.76 | H | C |
| ATOM | 1569 | CB | LEU | 18 | 91.452 | 14.019 | 22.124 | 1.00 | 63.56 | H | C |
| ATOM | 1570 | CG | LEU | 18 | 92.462 | 13.465 | 23.124 | 1.00 | 63.56 | H | C |
| ATOM | 1571 | CD1 | LEU | 18 | 92.121 | 13.932 | 24.536 | 1.00 | 63.56 | H | C |
| ATOM | 1572 | CD2 | LEU | 18 | 92.462 | 11.942 | 23.017 | 1.00 | 63.56 | H | C |
| ATOM | 1573 | C | LEU | 18 | 92.407 | 16.334 | 21.899 | 1.00 | 31.76 | H | C |
| ATOM | 1574 | O | LEU | 18 | 92.622 | 16.884 | 20.815 | 1.00 | 31.76 | H | O |
| ATOM | 1575 | N | ARG | 19 | 93.243 | 16.443 | 22.928 | 1.00 | 39.26 | H | N |
| ATOM | 1576 | CA | ARG | 19 | 94.475 | 17.207 | 22.781 | 1.00 | 39.26 | H | C |
| ATOM | 1577 | CB | ARG | 19 | 94.303 | 18.650 | 23.258 | 1.00 | 32.50 | H | C |
| ATOM | 1578 | CG | ARG | 19 | 95.571 | 19.474 | 23.063 | 1.00 | 32.50 | H | C |
| ATOM | 1579 | CD | ARG | 19 | 95.481 | 20.862 | 23.667 | 1.00 | 32.50 | H | C |
| ATOM | 1580 | NE | ARG | 19 | 95.387 | 20.846 | 25.125 | 1.00 | 32.50 | H | N |
| ATOM | 1581 | CZ | ARG | 19 | 95.262 | 21.936 | 25.879 | 1.00 | 32.50 | H | C |
| ATOM | 1582 | NH1 | ARG | 19 | 95.220 | 23.138 | 25.322 | 1.00 | 32.50 | H | N |
| ATOM | 1583 | NH2 | ARG | 19 | 95.162 | 21.824 | 27.193 | 1.00 | 32.50 | H | N |
| ATOM | 1584 | C | ARG | 19 | 95.668 | 16.606 | 23.500 | 1.00 | 39.26 | H | C |
| ATOM | 1585 | O | ARG | 19 | 95.687 | 16.469 | 24.732 | 1.00 | 39.26 | H | O |
| ATOM | 1586 | N | LEU | 20 | 96.677 | 16.266 | 22.709 | 1.00 | 36.74 | H | N |
| ATOM | 1587 | CA | LEU | 20 | 97.896 | 15.695 | 23.241 | 1.00 | 36.74 | H | C |
| ATOM | 1588 | CB | LEU | 20 | 98.534 | 14.737 | 22.222 | 1.00 | 31.69 | H | C |
| ATOM | 1589 | CG | LEU | 20 | 97.601 | 13.846 | 21.390 | 1.00 | 31.69 | H | C |
| ATOM | 1590 | CD1 | LEU | 20 | 98.426 | 12.870 | 20.555 | 1.00 | 31.69 | H | C |
| ATOM | 1591 | CD2 | LEU | 20 | 96.659 | 13.093 | 22.292 | 1.00 | 31.69 | H | C |
| ATOM | 1592 | C | LEU | 20 | 98.854 | 16.838 | 23.533 | 1.00 | 36.74 | H | C |
| ATOM | 1593 | O | LEU | 20 | 98.866 | 17.856 | 22.840 | 1.00 | 36.74 | H | O |
| ATOM | 1594 | N | SER | 21 | 99.638 | 16.664 | 24.584 | 1.00 | 25.68 | H | N |
| ATOM | 1595 | CA | SER | 21 | 100.635 | 17.640 | 24.974 | 1.00 | 25.68 | H | C |
| ATOM | 1596 | CB | SER | 21 | 100.273 | 18.278 | 26.307 | 1.00 | 13.03 | H | C |
| ATOM | 1597 | OG | SER | 21 | 99.718 | 17.320 | 27.175 | 1.00 | 13.03 | H | O |
| ATOM | 1598 | C | SER | 21 | 101.901 | 16.838 | 25.099 | 1.00 | 25.68 | H | C |
| ATOM | 1599 | O | SER | 21 | 101.851 | 15.635 | 25.336 | 1.00 | 25.68 | H | O |
| ATOM | 1600 | N | CYS | 22 | 103.036 | 17.498 | 24.931 | 1.00 | 22.18 | H | N |
| ATOM | 1601 | CA | CYS | 22 | 104.321 | 16.822 | 25.008 | 1.00 | 22.18 | H | C |
| ATOM | 1602 | C | CYS | 22 | 105.255 | 17.765 | 25.713 | 1.00 | 22.18 | H | C |
| ATOM | 1603 | O | CYS | 22 | 105.491 | 18.863 | 25.229 | 1.00 | 22.18 | H | O |
| ATOM | 1604 | CB | CYS | 22 | 104.804 | 16.543 | 23.603 | 1.00 | 57.35 | H | C |
| ATOM | 1605 | SG | CYS | 22 | 106.473 | 15.867 | 23.383 | 1.00 | 57.35 | H | S |
| ATOM | 1606 | N | ALA | 23 | 105.769 | 17.349 | 26.867 | 1.00 | 26.87 | H | N |

Fig. 19: A-23

| | | | | | | | | | | | |
|---|---|---|---|---|---|---|---|---|---|---|---|
| ATOM | 1607 | CA | ALA | 23 | 106.669 | 18.191 | 27.654 | 1.00 | 26.87 | H | C |
| ATOM | 1608 | CB | ALA | 23 | 106.470 | 17.937 | 29.141 | 1.00 | 9.84 | H | C |
| ATOM | 1609 | C | ALA | 23 | 108.125 | 17.989 | 27.284 | 1.00 | 26.87 | H | C |
| ATOM | 1610 | O | ALA | 23 | 108.683 | 16.899 | 27.437 | 1.00 | 26.87 | H | O |
| ATOM | 1611 | N | ALA | 24 | 108.738 | 19.058 | 26.800 | 1.00 | 13.29 | H | N |
| ATOM | 1612 | CA | ALA | 24 | 110.124 | 18.988 | 26.409 | 1.00 | 13.29 | H | C |
| ATOM | 1613 | CB | ALA | 24 | 110.357 | 19.851 | 25.183 | 1.00 | 45.62 | H | C |
| ATOM | 1614 | C | ALA | 24 | 111.023 | 19.432 | 27.552 | 1.00 | 13.29 | H | C |
| ATOM | 1615 | O | ALA | 24 | 110.664 | 20.304 | 28.356 | 1.00 | 13.29 | H | O |
| ATOM | 1616 | N | SER | 25 | 112.194 | 18.819 | 27.617 | 1.00 | 22.11 | H | N |
| ATOM | 1617 | CA | SER | 25 | 113.168 | 19.152 | 28.634 | 1.00 | 22.11 | H | C |
| ATOM | 1618 | CB | SER | 25 | 112.731 | 18.582 | 29.982 | 1.00 | 51.20 | H | C |
| ATOM | 1619 | OG | SER | 25 | 112.401 | 17.214 | 29.862 | 1.00 | 51.20 | H | O |
| ATOM | 1620 | C | SER | 25 | 114.526 | 18.591 | 28.232 | 1.00 | 22.11 | H | C |
| ATOM | 1621 | O | SER | 25 | 114.614 | 17.539 | 27.590 | 1.00 | 22.11 | H | O |
| ATOM | 1622 | N | GLY | 26 | 115.582 | 19.306 | 28.591 | 1.00 | 10.76 | H | N |
| ATOM | 1623 | CA | GLY | 26 | 116.914 | 18.844 | 28.263 | 1.00 | 10.76 | H | C |
| ATOM | 1624 | C | GLY | 26 | 117.553 | 19.585 | 27.107 | 1.00 | 10.76 | H | C |
| ATOM | 1625 | O | GLY | 26 | 118.728 | 19.367 | 26.809 | 1.00 | 10.76 | H | O |
| ATOM | 1626 | N | PHE | 27 | 116.794 | 20.458 | 26.448 | 1.00 | 18.08 | H | N |
| ATOM | 1627 | CA | PHE | 27 | 117.325 | 21.207 | 25.318 | 1.00 | 18.08 | H | C |
| ATOM | 1628 | CB | PHE | 27 | 117.241 | 20.373 | 24.031 | 1.00 | 16.53 | H | C |
| ATOM | 1629 | CG | PHE | 27 | 115.842 | 19.974 | 23.651 | 1.00 | 16.53 | H | C |
| ATOM | 1630 | CD1 | PHE | 27 | 115.089 | 19.140 | 24.476 | 1.00 | 16.53 | H | C |
| ATOM | 1631 | CD2 | PHE | 27 | 115.269 | 20.448 | 22.476 | 1.00 | 16.53 | H | C |
| ATOM | 1632 | CE1 | PHE | 27 | 113.770 | 18.782 | 24.137 | 1.00 | 16.53 | H | C |
| ATOM | 1633 | CE2 | PHE | 27 | 113.958 | 20.101 | 22.125 | 1.00 | 16.53 | H | C |
| ATOM | 1634 | CZ | PHE | 27 | 113.203 | 19.268 | 22.954 | 1.00 | 16.53 | H | C |
| ATOM | 1635 | C | PHE | 27 | 116.592 | 22.528 | 25.135 | 1.00 | 18.08 | H | C |
| ATOM | 1636 | O | PHE | 27 | 115.566 | 22.780 | 25.763 | 1.00 | 18.08 | H | O |
| ATOM | 1637 | N | THR | 28 | 117.139 | 23.377 | 24.276 | 1.00 | 42.88 | H | N |
| ATOM | 1638 | CA | THR | 28 | 116.544 | 24.672 | 24.017 | 1.00 | 42.88 | H | C |
| ATOM | 1639 | CB | THR | 28 | 117.575 | 25.604 | 23.381 | 1.00 | 53.65 | H | C |
| ATOM | 1640 | OG1 | THR | 28 | 118.841 | 25.399 | 24.018 | 1.00 | 53.65 | H | O |
| ATOM | 1641 | CG2 | THR | 28 | 117.168 | 27.056 | 23.561 | 1.00 | 53.65 | H | C |
| ATOM | 1642 | C | THR | 28 | 115.369 | 24.463 | 23.074 | 1.00 | 42.88 | H | C |
| ATOM | 1643 | O | THR | 28 | 115.484 | 24.666 | 21.868 | 1.00 | 42.88 | H | O |
| ATOM | 1644 | N | PHE | 29 | 114.239 | 24.051 | 23.644 | 1.00 | 29.92 | H | N |
| ATOM | 1645 | CA | PHE | 29 | 113.004 | 23.772 | 22.901 | 1.00 | 29.92 | H | C |
| ATOM | 1646 | CB | PHE | 29 | 111.855 | 23.614 | 23.906 | 1.00 | 3.95 | H | C |
| ATOM | 1647 | CG | PHE | 29 | 110.503 | 23.347 | 23.276 | 1.00 | 3.95 | H | C |
| ATOM | 1648 | CD1 | PHE | 29 | 110.208 | 22.102 | 22.696 | 1.00 | 3.95 | H | C |
| ATOM | 1649 | CD2 | PHE | 29 | 109.504 | 24.336 | 23.283 | 1.00 | 3.95 | H | C |
| ATOM | 1650 | CE1 | PHE | 29 | 108.939 | 21.852 | 22.139 | 1.00 | 3.95 | H | C |
| ATOM | 1651 | CE2 | PHE | 29 | 108.234 | 24.092 | 22.727 | 1.00 | 3.95 | H | C |
| ATOM | 1652 | CZ | PHE | 29 | 107.953 | 22.860 | 22.160 | 1.00 | 3.95 | H | C |
| ATOM | 1653 | C | PHE | 29 | 112.611 | 24.777 | 21.797 | 1.00 | 29.92 | H | C |
| ATOM | 1654 | O | PHE | 29 | 112.390 | 24.389 | 20.647 | 1.00 | 29.92 | H | O |
| ATOM | 1655 | N | SER | 30 | 112.539 | 26.058 | 22.144 | 1.00 | 32.50 | H | N |
| ATOM | 1656 | CA | SER | 30 | 112.139 | 27.105 | 21.199 | 1.00 | 32.50 | H | C |
| ATOM | 1657 | CB | SER | 30 | 112.335 | 28.473 | 21.852 | 1.00 | 67.50 | H | C |
| ATOM | 1658 | OG | SER | 30 | 113.644 | 28.591 | 22.372 | 1.00 | 67.50 | H | O |
| ATOM | 1659 | C | SER | 30 | 112.799 | 27.107 | 19.812 | 1.00 | 32.50 | H | C |
| ATOM | 1660 | O | SER | 30 | 112.191 | 27.504 | 18.816 | 1.00 | 32.50 | H | O |
| ATOM | 1661 | N | ARG | 31 | 114.037 | 26.649 | 19.751 | 1.00 | 18.89 | H | N |
| ATOM | 1662 | CA | ARG | 31 | 114.801 | 26.636 | 18.515 | 1.00 | 18.89 | H | C |
| ATOM | 1663 | CB | ARG | 31 | 116.292 | 26.604 | 18.886 | 1.00 | 48.17 | H | C |
| ATOM | 1664 | CG | ARG | 31 | 117.217 | 25.955 | 17.887 | 1.00 | 48.17 | H | C |
| ATOM | 1665 | CD | ARG | 31 | 118.650 | 26.425 | 18.112 | 1.00 | 48.17 | H | C |
| ATOM | 1666 | NE | ARG | 31 | 119.135 | 26.203 | 19.476 | 1.00 | 48.17 | H | N |
| ATOM | 1667 | CZ | ARG | 31 | 120.228 | 26.777 | 19.980 | 1.00 | 48.17 | H | C |
| ATOM | 1668 | NH1 | ARG | 31 | 120.950 | 27.608 | 19.238 | 1.00 | 48.17 | H | N |
| ATOM | 1669 | NH2 | ARG | 31 | 120.604 | 26.524 | 21.226 | 1.00 | 48.17 | H | N |
| ATOM | 1670 | C | ARG | 31 | 114.463 | 25.523 | 17.521 | 1.00 | 18.89 | H | C |
| ATOM | 1671 | O | ARG | 31 | 114.520 | 25.723 | 16.313 | 1.00 | 18.89 | H | O |
| ATOM | 1672 | N | TYR | 32 | 114.095 | 24.353 | 18.027 | 1.00 | 15.47 | H | N |
| ATOM | 1673 | CA | TYR | 32 | 113.791 | 23.200 | 17.179 | 1.00 | 15.47 | H | C |
| ATOM | 1674 | CB | TYR | 32 | 113.949 | 21.922 | 17.996 | 1.00 | 6.03 | H | C |
| ATOM | 1675 | CG | TYR | 32 | 115.367 | 21.653 | 18.426 | 1.00 | 6.03 | H | C |
| ATOM | 1676 | CD1 | TYR | 32 | 115.934 | 22.336 | 19.500 | 1.00 | 6.03 | H | C |
| ATOM | 1677 | CE1 | TYR | 32 | 117.249 | 22.097 | 19.889 | 1.00 | 6.03 | H | C |
| ATOM | 1678 | CD2 | TYR | 32 | 116.153 | 20.722 | 17.747 | 1.00 | 6.03 | H | C |
| ATOM | 1679 | CE2 | TYR | 32 | 117.467 | 20.477 | 18.122 | 1.00 | 6.03 | H | C |

Fig. 19: A-24

| | | | | | | | | | | | |
|---|---|---|---|---|---|---|---|---|---|---|---|
| ATOM | 1680 | CZ | TYR | 32 | 118.013 | 21.165 | 19.198 | 1.00 | 6.03 | H | C |
| ATOM | 1681 | OH | TYR | 32 | 119.317 | 20.907 | 19.597 | 1.00 | 6.03 | H | O |
| ATOM | 1682 | C | TYR | 32 | 112.426 | 23.184 | 16.534 | 1.00 | 15.47 | H | C |
| ATOM | 1683 | O | TYR | 32 | 111.480 | 23.748 | 17.058 | 1.00 | 15.47 | H | O |
| ATOM | 1684 | N | THR | 33 | 112.309 | 22.545 | 15.382 | 1.00 | 10.91 | H | N |
| ATOM | 1685 | CA | THR | 33 | 110.988 | 22.451 | 14.792 | 1.00 | 10.91 | H | C |
| ATOM | 1686 | CB | THR | 33 | 111.032 | 22.556 | 13.230 | 1.00 | 11.96 | H | C |
| ATOM | 1687 | OG1 | THR | 33 | 111.079 | 21.259 | 12.639 | 1.00 | 11.96 | H | O |
| ATOM | 1688 | CG2 | THR | 33 | 112.251 | 23.338 | 12.786 | 1.00 | 11.96 | H | C |
| ATOM | 1689 | C | THR | 33 | 110.501 | 21.082 | 15.303 | 1.00 | 10.91 | H | C |
| ATOM | 1690 | O | THR | 33 | 111.188 | 20.061 | 15.157 | 1.00 | 10.91 | H | O |
| ATOM | 1691 | N | MET | 34 | 109.348 | 21.070 | 15.960 | 1.00 | 21.14 | H | N |
| ATOM | 1692 | CA | MET | 34 | 108.815 | 19.835 | 16.518 | 1.00 | 21.14 | H | C |
| ATOM | 1693 | CB | MET | 34 | 108.188 | 20.094 | 17.888 | 1.00 | 16.88 | H | C |
| ATOM | 1694 | CG | MET | 34 | 109.035 | 20.899 | 18.847 | 1.00 | 16.88 | H | C |
| ATOM | 1695 | SD | MET | 34 | 110.603 | 20.131 | 19.122 | 1.00 | 16.88 | H | S |
| ATOM | 1696 | CE | MET | 34 | 110.155 | 18.770 | 20.240 | 1.00 | 16.88 | H | C |
| ATOM | 1697 | C | MET | 34 | 107.760 | 19.218 | 15.614 | 1.00 | 21.14 | H | C |
| ATOM | 1698 | O | MET | 34 | 107.160 | 19.905 | 14.781 | 1.00 | 21.14 | H | O |
| ATOM | 1699 | N | SER | 35 | 107.519 | 17.925 | 15.802 | 1.00 | 15.88 | H | N |
| ATOM | 1700 | CA | SER | 35 | 106.533 | 17.232 | 14.997 | 1.00 | 15.88 | H | C |
| ATOM | 1701 | CB | SER | 35 | 107.205 | 16.581 | 13.794 | 1.00 | 13.53 | H | C |
| ATOM | 1702 | OG | SER | 35 | 107.895 | 17.550 | 13.034 | 1.00 | 13.53 | H | O |
| ATOM | 1703 | C | SER | 35 | 105.767 | 16.168 | 15.763 | 1.00 | 15.88 | H | C |
| ATOM | 1704 | O | SER | 35 | 106.058 | 15.867 | 16.926 | 1.00 | 15.88 | H | O |
| ATOM | 1705 | N | TRP | 36 | 104.765 | 15.617 | 15.087 | 1.00 | 13.73 | H | N |
| ATOM | 1706 | CA | TRP | 36 | 103.948 | 14.556 | 15.626 | 1.00 | 13.73 | H | C |
| ATOM | 1707 | CB | TRP | 36 | 102.510 | 15.023 | 15.849 | 1.00 | 20.04 | H | C |
| ATOM | 1708 | CG | TRP | 36 | 102.337 | 15.903 | 17.039 | 1.00 | 20.04 | H | C |
| ATOM | 1709 | CD2 | TRP | 36 | 102.259 | 15.489 | 18.406 | 1.00 | 20.04 | H | C |
| ATOM | 1710 | CE2 | TRP | 36 | 102.112 | 16.654 | 19.186 | 1.00 | 20.04 | H | C |
| ATOM | 1711 | CE3 | TRP | 36 | 102.301 | 14.248 | 19.046 | 1.00 | 20.04 | H | C |
| ATOM | 1712 | CD1 | TRP | 36 | 102.236 | 17.255 | 17.045 | 1.00 | 20.04 | H | C |
| ATOM | 1713 | NE1 | TRP | 36 | 102.100 | 17.716 | 18.329 | 1.00 | 20.04 | H | N |
| ATOM | 1714 | CZ2 | TRP | 36 | 102.004 | 16.622 | 20.576 | 1.00 | 20.04 | H | C |
| ATOM | 1715 | CZ3 | TRP | 36 | 102.192 | 14.211 | 20.442 | 1.00 | 20.04 | H | C |
| ATOM | 1716 | CH2 | TRP | 36 | 102.044 | 15.396 | 21.190 | 1.00 | 20.04 | H | C |
| ATOM | 1717 | C | TRP | 36 | 103.978 | 13.470 | 14.565 | 1.00 | 13.73 | H | C |
| ATOM | 1718 | O | TRP | 36 | 103.879 | 13.769 | 13.373 | 1.00 | 13.73 | H | O |
| ATOM | 1719 | N | VAL | 37 | 104.138 | 12.221 | 15.006 | 1.00 | 21.09 | H | N |
| ATOM | 1720 | CA | VAL | 37 | 104.179 | 11.054 | 14.125 | 1.00 | 21.09 | H | C |
| ATOM | 1721 | CB | VAL | 37 | 105.622 | 10.464 | 14.053 | 1.00 | 6.36 | H | C |
| ATOM | 1722 | CG1 | VAL | 37 | 105.591 | 9.017 | 13.642 | 1.00 | 6.36 | H | C |
| ATOM | 1723 | CG2 | VAL | 37 | 106.461 | 11.253 | 13.057 | 1.00 | 6.36 | H | C |
| ATOM | 1724 | C | VAL | 37 | 103.229 | 10.041 | 14.748 | 1.00 | 21.09 | H | C |
| ATOM | 1725 | O | VAL | 37 | 103.144 | 9.940 | 15.963 | 1.00 | 21.09 | H | O |
| ATOM | 1726 | N | ARG | 38 | 102.508 | 9.294 | 13.929 | 1.00 | 17.98 | H | N |
| ATOM | 1727 | CA | ARG | 38 | 101.562 | 8.309 | 14.454 | 1.00 | 17.98 | H | C |
| ATOM | 1728 | CB | ARG | 38 | 100.133 | 8.697 | 14.058 | 1.00 | 13.99 | H | C |
| ATOM | 1729 | CG | ARG | 38 | 100.106 | 9.210 | 12.633 | 1.00 | 13.99 | H | C |
| ATOM | 1730 | CD | ARG | 38 | 98.899 | 8.817 | 11.839 | 1.00 | 13.99 | H | C |
| ATOM | 1731 | NE | ARG | 38 | 97.664 | 9.434 | 12.289 | 1.00 | 13.99 | H | N |
| ATOM | 1732 | CZ | ARG | 38 | 96.652 | 9.707 | 11.470 | 1.00 | 13.99 | H | C |
| ATOM | 1733 | NH1 | ARG | 38 | 96.744 | 9.432 | 10.171 | 1.00 | 13.99 | H | N |
| ATOM | 1734 | NH2 | ARG | 38 | 95.533 | 10.224 | 11.960 | 1.00 | 13.99 | H | N |
| ATOM | 1735 | C | ARG | 38 | 101.856 | 6.925 | 13.895 | 1.00 | 17.98 | H | C |
| ATOM | 1736 | O | ARG | 38 | 102.468 | 6.785 | 12.840 | 1.00 | 17.98 | H | O |
| ATOM | 1737 | N | GLN | 39 | 101.386 | 5.909 | 14.604 | 1.00 | 17.63 | H | N |
| ATOM | 1738 | CA | GLN | 39 | 101.560 | 4.521 | 14.200 | 1.00 | 17.63 | H | C |
| ATOM | 1739 | CB | GLN | 39 | 102.659 | 3.866 | 15.051 | 1.00 | 12.11 | H | C |
| ATOM | 1740 | CG | GLN | 39 | 102.976 | 2.424 | 14.712 | 1.00 | 12.11 | H | C |
| ATOM | 1741 | CD | GLN | 39 | 104.396 | 2.025 | 15.134 | 1.00 | 12.11 | H | C |
| ATOM | 1742 | OE1 | GLN | 39 | 104.811 | 2.262 | 16.272 | 1.00 | 12.11 | H | O |
| ATOM | 1743 | NE2 | GLN | 39 | 105.143 | 1.414 | 14.212 | 1.00 | 12.11 | H | N |
| ATOM | 1744 | C | GLN | 39 | 100.206 | 3.847 | 14.429 | 1.00 | 17.63 | H | C |
| ATOM | 1745 | O | GLN | 39 | 99.712 | 3.770 | 15.562 | 1.00 | 17.63 | H | O |
| ATOM | 1746 | N | ALA | 40 | 99.590 | 3.399 | 13.344 | 1.00 | 55.11 | H | N |
| ATOM | 1747 | CA | ALA | 40 | 98.300 | 2.737 | 13.436 | 1.00 | 55.11 | H | C |
| ATOM | 1748 | CB | ALA | 40 | 97.605 | 2.754 | 12.088 | 1.00 | 43.12 | H | C |
| ATOM | 1749 | C | ALA | 40 | 98.536 | 1.302 | 13.881 | 1.00 | 55.11 | H | C |
| ATOM | 1750 | O | ALA | 40 | 99.626 | 0.762 | 13.687 | 1.00 | 55.11 | H | O |
| ATOM | 1751 | N | PRO | 41 | 97.517 | 0.670 | 14.491 | 1.00 | 55.83 | H | N |
| ATOM | 1752 | CD | PRO | 41 | 96.189 | 1.237 | 14.782 | 1.00 | 86.02 | H | C |

Fig. 19: A-25

| | | | | | | | | | | | |
|---|---|---|---|---|---|---|---|---|---|---|---|
| ATOM | 1753 | CA | PRO | 41 | 97.600 | -0.712 | 14.969 | 1.00 | 55.83 | H | C |
| ATOM | 1754 | CB | PRO | 41 | 96.169 | -1.009 | 15.400 | 1.00 | 86.02 | H | C |
| ATOM | 1755 | CG | PRO | 41 | 95.681 | 0.315 | 15.859 | 1.00 | 86.02 | H | C |
| ATOM | 1756 | C | PRO | 41 | 98.057 | -1.624 | 13.838 | 1.00 | 55.83 | H | C |
| ATOM | 1757 | O | PRO | 41 | 97.423 | -1.670 | 12.781 | 1.00 | 55.83 | H | O |
| ATOM | 1758 | N | GLY | 42 | 99.160 | -2.335 | 14.061 | 1.00 | 43.01 | H | N |
| ATOM | 1759 | CA | GLY | 42 | 99.684 | -3.227 | 13.042 | 1.00 | 43.01 | H | C |
| ATOM | 1760 | C | GLY | 42 | 100.227 | -2.529 | 11.800 | 1.00 | 43.01 | H | C |
| ATOM | 1761 | O | GLY | 42 | 100.480 | -3.175 | 10.775 | 1.00 | 43.01 | H | O |
| ATOM | 1762 | N | LYS | 43 | 100.415 | -1.212 | 11.882 | 1.00 | 46.16 | H | N |
| ATOM | 1763 | CA | LYS | 43 | 100.922 | -0.446 | 10.750 | 1.00 | 46.16 | H | C |
| ATOM | 1764 | CB | LYS | 43 | 99.896 | 0.612 | 10.334 | 1.00 | 59.60 | H | C |
| ATOM | 1765 | CG | LYS | 43 | 98.800 | 0.081 | 9.421 | 1.00 | 59.60 | H | C |
| ATOM | 1766 | CD | LYS | 43 | 98.003 | -1.023 | 10.079 | 1.00 | 59.60 | H | C |
| ATOM | 1767 | CE | LYS | 43 | 97.230 | -1.831 | 9.047 | 1.00 | 59.60 | H | C |
| ATOM | 1768 | NZ | LYS | 43 | 98.125 | -2.590 | 8.124 | 1.00 | 59.60 | H | N |
| ATOM | 1769 | C | LYS | 43 | 102.278 | 0.215 | 10.994 | 1.00 | 46.16 | H | C |
| ATOM | 1770 | O | LYS | 43 | 102.889 | 0.060 | 12.063 | 1.00 | 46.16 | H | O |
| ATOM | 1771 | N | GLY | 44 | 102.742 | 0.942 | 9.976 | 1.00 | 50.42 | H | N |
| ATOM | 1772 | CA | GLY | 44 | 104.016 | 1.631 | 10.054 | 1.00 | 50.42 | H | C |
| ATOM | 1773 | C | GLY | 44 | 103.916 | 3.004 | 10.691 | 1.00 | 50.42 | H | C |
| ATOM | 1774 | O | GLY | 44 | 103.001 | 3.281 | 11.462 | 1.00 | 50.42 | H | O |
| ATOM | 1775 | N | LEU | 45 | 104.862 | 3.870 | 10.347 | 1.00 | 25.59 | H | N |
| ATOM | 1776 | CA | LEU | 45 | 104.933 | 5.229 | 10.883 | 1.00 | 25.59 | H | C |
| ATOM | 1777 | CB | LEU | 45 | 106.387 | 5.544 | 11.224 | 1.00 | 8.94 | H | C |
| ATOM | 1778 | CG | LEU | 45 | 107.011 | 4.480 | 12.118 | 1.00 | 8.94 | H | C |
| ATOM | 1779 | CD1 | LEU | 45 | 108.520 | 4.578 | 12.054 | 1.00 | 8.94 | H | C |
| ATOM | 1780 | CD2 | LEU | 45 | 106.481 | 4.638 | 13.541 | 1.00 | 8.94 | H | C |
| ATOM | 1781 | C | LEU | 45 | 104.394 | 6.259 | 9.893 | 1.00 | 25.59 | H | C |
| ATOM | 1782 | O | LEU | 45 | 104.613 | 6.142 | 8.684 | 1.00 | 25.59 | H | O |
| ATOM | 1783 | N | GLU | 46 | 103.698 | 7.268 | 10.411 | 1.00 | 28.67 | H | N |
| ATOM | 1784 | CA | GLU | 46 | 103.111 | 8.308 | 9.569 | 1.00 | 28.67 | H | C |
| ATOM | 1785 | CB | GLU | 46 | 101.617 | 8.045 | 9.370 | 1.00 | 21.38 | H | C |
| ATOM | 1786 | CG | GLU | 46 | 100.977 | 8.902 | 8.304 | 1.00 | 21.38 | H | C |
| ATOM | 1787 | CD | GLU | 46 | 99.555 | 8.471 | 7.972 | 1.00 | 21.38 | H | C |
| ATOM | 1788 | OE1 | GLU | 46 | 98.711 | 8.399 | 8.903 | 1.00 | 21.38 | H | O |
| ATOM | 1789 | OE2 | GLU | 46 | 99.283 | 8.214 | 6.776 | 1.00 | 21.38 | H | O |
| ATOM | 1790 | C | GLU | 46 | 103.304 | 9.698 | 10.152 | 1.00 | 28.67 | H | C |
| ATOM | 1791 | O | GLU | 46 | 102.942 | 9.962 | 11.301 | 1.00 | 28.67 | H | O |
| ATOM | 1792 | N | TRP | 47 | 103.887 | 10.579 | 9.347 | 1.00 | 2.61 | H | N |
| ATOM | 1793 | CA | TRP | 47 | 104.132 | 11.944 | 9.758 | 1.00 | 2.61 | H | C |
| ATOM | 1794 | CB | TRP | 47 | 105.055 | 12.618 | 8.757 | 1.00 | 14.19 | H | C |
| ATOM | 1795 | CG | TRP | 47 | 105.068 | 14.095 | 8.904 | 1.00 | 14.19 | H | C |
| ATOM | 1796 | CD2 | TRP | 47 | 104.446 | 15.035 | 8.036 | 1.00 | 14.19 | H | C |
| ATOM | 1797 | CE2 | TRP | 47 | 104.681 | 16.323 | 8.578 | 1.00 | 14.19 | H | C |
| ATOM | 1798 | CE3 | TRP | 47 | 103.709 | 14.919 | 6.852 | 1.00 | 14.19 | H | C |
| ATOM | 1799 | CD1 | TRP | 47 | 105.644 | 14.824 | 9.914 | 1.00 | 14.19 | H | C |
| ATOM | 1800 | NE1 | TRP | 47 | 105.418 | 16.161 | 9.723 | 1.00 | 14.19 | H | N |
| ATOM | 1801 | CZ2 | TRP | 47 | 104.201 | 17.490 | 7.969 | 1.00 | 14.19 | H | C |
| ATOM | 1802 | CZ3 | TRP | 47 | 103.233 | 16.074 | 6.248 | 1.00 | 14.19 | H | C |
| ATOM | 1803 | CH2 | TRP | 47 | 103.480 | 17.344 | 6.808 | 1.00 | 14.19 | H | C |
| ATOM | 1804 | C | TRP | 47 | 102.791 | 12.673 | 9.802 | 1.00 | 2.61 | H | C |
| ATOM | 1805 | O | TRP | 47 | 102.083 | 12.752 | 8.796 | 1.00 | 2.61 | H | O |
| ATOM | 1806 | N | VAL | 48 | 102.443 | 13.215 | 10.962 | 1.00 | 34.26 | H | N |
| ATOM | 1807 | CA | VAL | 48 | 101.165 | 13.895 | 11.114 | 1.00 | 34.26 | H | C |
| ATOM | 1808 | CB | VAL | 48 | 100.576 | 13.639 | 12.523 | 1.00 | 16.29 | H | C |
| ATOM | 1809 | CG1 | VAL | 48 | 99.137 | 14.148 | 12.623 | 1.00 | 16.29 | H | C |
| ATOM | 1810 | CG2 | VAL | 48 | 100.624 | 12.187 | 12.812 | 1.00 | 16.29 | H | C |
| ATOM | 1811 | C | VAL | 48 | 101.246 | 15.393 | 10.884 | 1.00 | 34.26 | H | C |
| ATOM | 1812 | O | VAL | 48 | 100.563 | 15.932 | 10.015 | 1.00 | 34.26 | H | O |
| ATOM | 1813 | N | ALA | 49 | 102.078 | 16.068 | 11.665 | 1.00 | 19.79 | H | N |
| ATOM | 1814 | CA | ALA | 49 | 102.198 | 17.505 | 11.533 | 1.00 | 19.79 | H | C |
| ATOM | 1815 | CB | ALA | 49 | 101.052 | 18.193 | 12.288 | 1.00 | 1.87 | H | C |
| ATOM | 1816 | C | ALA | 49 | 103.542 | 17.994 | 12.041 | 1.00 | 19.79 | H | C |
| ATOM | 1817 | O | ALA | 49 | 104.295 | 17.244 | 12.645 | 1.00 | 19.79 | H | O |
| ATOM | 1818 | N | THR | 50 | 103.816 | 19.271 | 11.795 | 1.00 | 29.76 | H | N |
| ATOM | 1819 | CA | THR | 50 | 105.067 | 19.906 | 12.184 | 1.00 | 29.76 | H | C |
| ATOM | 1820 | CB | THR | 50 | 106.142 | 19.637 | 11.127 | 1.00 | 20.69 | H | C |
| ATOM | 1821 | OG1 | THR | 50 | 106.390 | 18.232 | 11.065 | 1.00 | 20.69 | H | O |
| ATOM | 1822 | CG2 | THR | 50 | 107.422 | 20.357 | 11.460 | 1.00 | 20.69 | H | C |
| ATOM | 1823 | C | THR | 50 | 104.897 | 21.416 | 12.327 | 1.00 | 29.76 | H | C |
| ATOM | 1824 | O | THR | 50 | 104.113 | 22.035 | 11.616 | 1.00 | 29.76 | H | O |
| ATOM | 1825 | N | ILE | 51 | 105.649 | 21.994 | 13.258 | 1.00 | 20.54 | H | N |

Fig. 19: A-26

| | | | | | | | | | | | |
|---|---|---|---|---|---|---|---|---|---|---|---|
| ATOM | 1826 | CA | ILE | 51 | 105.626 | 23.424 | 13.530 | 1.00 | 20.54 | H | C |
| ATOM | 1827 | CB | ILE | 51 | 104.824 | 23.714 | 14.816 | 1.00 | 27.11 | H | C |
| ATOM | 1828 | CG2 | ILE | 51 | 105.430 | 22.955 | 15.975 | 1.00 | 27.11 | H | C |
| ATOM | 1829 | CG1 | ILE | 51 | 104.805 | 25.217 | 15.108 | 1.00 | 27.11 | H | C |
| ATOM | 1830 | CD1 | ILE | 51 | 104.073 | 25.593 | 16.389 | 1.00 | 27.11 | H | C |
| ATOM | 1831 | C | ILE | 51 | 107.090 | 23.813 | 13.723 | 1.00 | 20.54 | H | C |
| ATOM | 1832 | O | ILE | 51 | 107.781 | 23.208 | 14.533 | 1.00 | 20.54 | H | O |
| ATOM | 1833 | N | SER | 52 | 107.565 | 24.803 | 12.970 | 1.00 | 28.49 | H | N |
| ATOM | 1834 | CA | SER | 52 | 108.962 | 25.234 | 13.047 | 1.00 | 28.49 | H | C |
| ATOM | 1835 | CB | SER | 52 | 109.356 | 26.018 | 11.797 | 1.00 | 35.37 | H | C |
| ATOM | 1836 | OG | SER | 52 | 108.819 | 27.332 | 11.832 | 1.00 | 35.37 | H | O |
| ATOM | 1837 | C | SER | 52 | 109.236 | 26.105 | 14.256 | 1.00 | 28.49 | H | C |
| ATOM | 1838 | O | SER | 52 | 108.316 | 26.461 | 14.994 | 1.00 | 28.49 | H | O |
| ATOM | 1839 | N | GLY | 53 | 110.509 | 26.452 | 14.451 | 1.00 | 16.74 | H | N |
| ATOM | 1840 | CA | GLY | 53 | 110.864 | 27.295 | 15.568 | 1.00 | 16.74 | H | C |
| ATOM | 1841 | C | GLY | 53 | 110.203 | 28.651 | 15.410 | 1.00 | 16.74 | H | C |
| ATOM | 1842 | O | GLY | 53 | 110.093 | 29.412 | 16.369 | 1.00 | 16.74 | H | O |
| ATOM | 1843 | N | GLY | 54 | 109.746 | 28.939 | 14.192 | 1.00 | 26.55 | H | N |
| ATOM | 1844 | CA | GLY | 54 | 109.120 | 30.218 | 13.907 | 1.00 | 26.55 | H | C |
| ATOM | 1845 | C | GLY | 54 | 107.605 | 30.253 | 13.815 | 1.00 | 26.55 | H | C |
| ATOM | 1846 | O | GLY | 54 | 107.020 | 31.317 | 13.607 | 1.00 | 26.55 | H | O |
| ATOM | 1847 | N | GLY | 55 | 106.953 | 29.105 | 13.948 | 1.00 | 34.83 | H | N |
| ATOM | 1848 | CA | GLY | 55 | 105.505 | 29.105 | 13.889 | 1.00 | 34.83 | H | C |
| ATOM | 1849 | C | GLY | 55 | 104.878 | 28.610 | 12.604 | 1.00 | 34.83 | H | C |
| ATOM | 1850 | O | GLY | 55 | 103.657 | 28.663 | 12.458 | 1.00 | 34.83 | H | O |
| ATOM | 1851 | N | HIS | 56 | 105.683 | 28.149 | 11.655 | 1.00 | 20.17 | H | N |
| ATOM | 1852 | CA | HIS | 56 | 105.091 | 27.643 | 10.426 | 1.00 | 20.17 | H | C |
| ATOM | 1853 | CB | HIS | 56 | 106.117 | 27.522 | 9.302 | 1.00 | 75.35 | H | C |
| ATOM | 1854 | CG | HIS | 56 | 106.829 | 28.797 | 8.996 | 1.00 | 75.35 | H | C |
| ATOM | 1855 | CD2 | HIS | 56 | 106.561 | 29.773 | 8.096 | 1.00 | 75.35 | H | C |
| ATOM | 1856 | ND1 | HIS | 56 | 107.959 | 29.201 | 9.677 | 1.00 | 75.35 | H | N |
| ATOM | 1857 | CE1 | HIS | 56 | 108.356 | 30.370 | 9.209 | 1.00 | 75.35 | H | C |
| ATOM | 1858 | NE2 | HIS | 56 | 107.525 | 30.739 | 8.250 | 1.00 | 75.35 | H | N |
| ATOM | 1859 | C | HIS | 56 | 104.585 | 26.266 | 10.774 | 1.00 | 20.17 | H | C |
| ATOM | 1860 | O | HIS | 56 | 105.309 | 25.465 | 11.350 | 1.00 | 20.17 | H | O |
| ATOM | 1861 | N | THR | 57 | 103.331 | 25.994 | 10.458 | 1.00 | 9.30 | H | N |
| ATOM | 1862 | CA | THR | 57 | 102.793 | 24.676 | 10.728 | 1.00 | 9.30 | H | C |
| ATOM | 1863 | CB | THR | 57 | 101.437 | 24.766 | 11.475 | 1.00 | 25.93 | H | C |
| ATOM | 1864 | OG1 | THR | 57 | 100.483 | 25.493 | 10.691 | 1.00 | 25.93 | H | O |
| ATOM | 1865 | CG2 | THR | 57 | 101.624 | 25.460 | 12.821 | 1.00 | 25.93 | H | C |
| ATOM | 1866 | C | THR | 57 | 102.657 | 23.911 | 9.403 | 1.00 | 9.30 | H | C |
| ATOM | 1867 | O | THR | 57 | 102.437 | 24.503 | 8.348 | 1.00 | 9.30 | H | O |
| ATOM | 1868 | N | TYR | 58 | 102.849 | 22.598 | 9.463 | 1.00 | 10.35 | H | N |
| ATOM | 1869 | CA | TYR | 58 | 102.739 | 21.729 | 8.293 | 1.00 | 10.35 | H | C |
| ATOM | 1870 | CB | TYR | 58 | 104.115 | 21.217 | 7.912 | 1.00 | 22.31 | H | C |
| ATOM | 1871 | CG | TYR | 58 | 105.023 | 22.324 | 7.485 | 1.00 | 22.31 | H | C |
| ATOM | 1872 | CD1 | TYR | 58 | 105.051 | 22.744 | 6.167 | 1.00 | 22.31 | H | C |
| ATOM | 1873 | CE1 | TYR | 58 | 105.871 | 23.765 | 5.768 | 1.00 | 22.31 | H | C |
| ATOM | 1874 | CD2 | TYR | 58 | 105.843 | 22.967 | 8.399 | 1.00 | 22.31 | H | C |
| ATOM | 1875 | CE2 | TYR | 58 | 106.667 | 23.997 | 8.007 | 1.00 | 22.31 | H | C |
| ATOM | 1876 | CZ | TYR | 58 | 106.674 | 24.388 | 6.689 | 1.00 | 22.31 | H | C |
| ATOM | 1877 | OH | TYR | 58 | 107.478 | 25.419 | 6.279 | 1.00 | 22.31 | H | O |
| ATOM | 1878 | C | TYR | 58 | 101.812 | 20.565 | 8.635 | 1.00 | 10.35 | H | C |
| ATOM | 1879 | O | TYR | 58 | 101.699 | 20.164 | 9.801 | 1.00 | 10.35 | H | O |
| ATOM | 1880 | N | TYR | 59 | 101.147 | 20.007 | 7.634 | 1.00 | 15.64 | H | N |
| ATOM | 1881 | CA | TYR | 59 | 100.219 | 18.936 | 7.931 | 1.00 | 15.64 | H | C |
| ATOM | 1882 | CB | TYR | 59 | 98.843 | 19.542 | 8.203 | 1.00 | 11.32 | H | C |
| ATOM | 1883 | CG | TYR | 59 | 98.803 | 20.511 | 9.360 | 1.00 | 11.32 | H | C |
| ATOM | 1884 | CD1 | TYR | 59 | 98.625 | 20.058 | 10.661 | 1.00 | 11.32 | H | C |
| ATOM | 1885 | CE1 | TYR | 59 | 98.540 | 20.942 | 11.731 | 1.00 | 11.32 | H | C |
| ATOM | 1886 | CD2 | TYR | 59 | 98.912 | 21.886 | 9.148 | 1.00 | 11.32 | H | C |
| ATOM | 1887 | CE2 | TYR | 59 | 98.835 | 22.783 | 10.208 | 1.00 | 11.32 | H | C |
| ATOM | 1888 | CZ | TYR | 59 | 98.640 | 22.302 | 11.502 | 1.00 | 11.32 | H | C |
| ATOM | 1889 | OH | TYR | 59 | 98.498 | 23.177 | 12.557 | 1.00 | 11.32 | H | O |
| ATOM | 1890 | C | TYR | 59 | 100.071 | 17.883 | 6.856 | 1.00 | 15.64 | H | C |
| ATOM | 1891 | O | TYR | 59 | 100.150 | 18.182 | 5.666 | 1.00 | 15.64 | H | O |
| ATOM | 1892 | N | LEU | 60 | 99.854 | 16.644 | 7.286 | 1.00 | 33.81 | H | N |
| ATOM | 1893 | CA | LEU | 60 | 99.616 | 15.539 | 6.366 | 1.00 | 33.81 | H | C |
| ATOM | 1894 | CB | LEU | 60 | 99.625 | 14.217 | 7.135 | 1.00 | 13.27 | H | C |
| ATOM | 1895 | CG | LEU | 60 | 99.371 | 12.896 | 6.406 | 1.00 | 13.27 | H | C |
| ATOM | 1896 | CD1 | LEU | 60 | 100.681 | 12.371 | 5.800 | 1.00 | 13.27 | H | C |
| ATOM | 1897 | CD2 | LEU | 60 | 98.804 | 11.882 | 7.397 | 1.00 | 13.27 | H | C |
| ATOM | 1898 | C | LEU | 60 | 98.198 | 15.861 | 5.869 | 1.00 | 33.81 | H | C |

Fig. 19: A-27

| | | | | | | | | | | | |
|---|---|---|---|---|---|---|---|---|---|---|---|
| ATOM | 1899 | O | LEU | 60 | 97.329 | 16.255 | 6.659 | 1.00 | 33.81 | H | O |
| ATOM | 1900 | N | ASP | 61 | 97.962 | 15.710 | 4.573 | 1.00 | 24.56 | H | N |
| ATOM | 1901 | CA | ASP | 61 | 96.659 | 16.028 | 3.991 | 1.00 | 24.56 | H | C |
| ATOM | 1902 | CB | ASP | 61 | 96.639 | 15.579 | 2.530 | 1.00 | 55.35 | H | C |
| ATOM | 1903 | CG | ASP | 61 | 97.719 | 16.260 | 1.708 | 1.00 | 55.35 | H | C |
| ATOM | 1904 | OD1 | ASP | 61 | 98.919 | 16.083 | 2.023 | 1.00 | 55.35 | H | O |
| ATOM | 1905 | OD2 | ASP | 61 | 97.374 | 16.981 | 0.754 | 1.00 | 55.35 | H | O |
| ATOM | 1906 | C | ASP | 61 | 95.436 | 15.495 | 4.731 | 1.00 | 24.56 | H | C |
| ATOM | 1907 | O | ASP | 61 | 94.515 | 16.254 | 5.043 | 1.00 | 24.56 | H | O |
| ATOM | 1908 | N | SER | 62 | 95.432 | 14.198 | 5.024 | 1.00 | 20.78 | H | N |
| ATOM | 1909 | CA | SER | 62 | 94.317 | 13.567 | 5.717 | 1.00 | 20.78 | H | C |
| ATOM | 1910 | CB | SER | 62 | 94.630 | 12.085 | 5.955 | 1.00 | 31.68 | H | C |
| ATOM | 1911 | OG | SER | 62 | 95.820 | 11.902 | 6.708 | 1.00 | 31.68 | H | O |
| ATOM | 1912 | C | SER | 62 | 93.882 | 14.216 | 7.044 | 1.00 | 20.78 | H | C |
| ATOM | 1913 | O | SER | 62 | 92.732 | 14.053 | 7.475 | 1.00 | 20.78 | H | O |
| ATOM | 1914 | N | VAL | 63 | 94.779 | 14.949 | 7.695 | 1.00 | 24.27 | H | N |
| ATOM | 1915 | CA | VAL | 63 | 94.439 | 15.567 | 8.968 | 1.00 | 24.27 | H | C |
| ATOM | 1916 | CB | VAL | 63 | 95.478 | 15.202 | 10.049 | 1.00 | 45.54 | H | C |
| ATOM | 1917 | CG1 | VAL | 63 | 95.642 | 13.698 | 10.110 | 1.00 | 45.54 | H | C |
| ATOM | 1918 | CG2 | VAL | 63 | 96.812 | 15.873 | 9.752 | 1.00 | 45.54 | H | C |
| ATOM | 1919 | C | VAL | 63 | 94.374 | 17.083 | 8.839 | 1.00 | 24.27 | H | C |
| ATOM | 1920 | O | VAL | 63 | 94.112 | 17.812 | 9.823 | 1.00 | 24.27 | H | O |
| ATOM | 1921 | N | LYS | 64 | 94.611 | 17.556 | 7.618 | 1.00 | 38.99 | H | N |
| ATOM | 1922 | CA | LYS | 64 | 94.611 | 18.985 | 7.348 | 1.00 | 38.99 | H | C |
| ATOM | 1923 | CB | LYS | 64 | 94.983 | 19.235 | 5.889 | 1.00 | 39.16 | H | C |
| ATOM | 1924 | CG | LYS | 64 | 95.736 | 20.528 | 5.671 | 1.00 | 39.16 | H | C |
| ATOM | 1925 | CD | LYS | 64 | 96.417 | 20.521 | 4.309 | 1.00 | 39.16 | H | C |
| ATOM | 1926 | CE | LYS | 64 | 97.432 | 19.380 | 4.176 | 1.00 | 39.16 | H | C |
| ATOM | 1927 | NZ | LYS | 64 | 98.011 | 19.296 | 2.803 | 1.00 | 39.16 | H | N |
| ATOM | 1928 | C | LYS | 64 | 93.262 | 19.607 | 7.667 | 1.00 | 38.99 | H | C |
| ATOM | 1929 | O | LYS | 64 | 92.240 | 19.212 | 7.121 | 1.00 | 38.99 | H | O |
| ATOM | 1930 | N | GLY | 65 | 93.263 | 20.577 | 8.567 | 1.00 | 28.42 | H | N |
| ATOM | 1931 | CA | GLY | 65 | 92.019 | 21.219 | 8.918 | 1.00 | 28.42 | H | C |
| ATOM | 1932 | C | GLY | 65 | 91.277 | 20.501 | 10.021 | 1.00 | 28.42 | H | C |
| ATOM | 1933 | O | GLY | 65 | 90.271 | 21.005 | 10.509 | 1.00 | 28.42 | H | O |
| ATOM | 1934 | N | ARG | 66 | 91.751 | 19.324 | 10.414 | 1.00 | 48.07 | H | N |
| ATOM | 1935 | CA | ARG | 66 | 91.098 | 18.588 | 11.488 | 1.00 | 48.07 | H | C |
| ATOM | 1936 | CB | ARG | 66 | 90.783 | 17.154 | 11.064 | 1.00 | 36.61 | H | C |
| ATOM | 1937 | CG | ARG | 66 | 89.845 | 17.052 | 9.887 | 1.00 | 36.61 | H | C |
| ATOM | 1938 | CD | ARG | 66 | 89.484 | 15.608 | 9.571 | 1.00 | 36.61 | H | C |
| ATOM | 1939 | NE | ARG | 66 | 90.654 | 14.750 | 9.346 | 1.00 | 36.61 | H | N |
| ATOM | 1940 | CZ | ARG | 66 | 91.133 | 13.877 | 10.236 | 1.00 | 36.61 | H | C |
| ATOM | 1941 | NH1 | ARG | 66 | 90.545 | 13.739 | 11.421 | 1.00 | 36.61 | H | N |
| ATOM | 1942 | NH2 | ARG | 66 | 92.203 | 13.144 | 9.944 | 1.00 | 36.61 | H | N |
| ATOM | 1943 | C | ARG | 66 | 92.018 | 18.568 | 12.687 | 1.00 | 48.07 | H | C |
| ATOM | 1944 | O | ARG | 66 | 91.584 | 18.312 | 13.808 | 1.00 | 48.07 | H | O |
| ATOM | 1945 | N | PHE | 67 | 93.296 | 18.839 | 12.438 | 1.00 | 31.81 | H | N |
| ATOM | 1946 | CA | PHE | 67 | 94.304 | 18.854 | 13.490 | 1.00 | 31.81 | H | C |
| ATOM | 1947 | CB | PHE | 67 | 95.372 | 17.802 | 13.211 | 1.00 | 34.94 | H | C |
| ATOM | 1948 | CG | PHE | 67 | 94.937 | 16.394 | 13.444 | 1.00 | 34.94 | H | C |
| ATOM | 1949 | CD1 | PHE | 67 | 93.763 | 15.907 | 12.902 | 1.00 | 34.94 | H | C |
| ATOM | 1950 | CD2 | PHE | 67 | 95.748 | 15.530 | 14.158 | 1.00 | 34.94 | H | C |
| ATOM | 1951 | CE1 | PHE | 67 | 93.400 | 14.564 | 13.063 | 1.00 | 34.94 | H | C |
| ATOM | 1952 | CE2 | PHE | 67 | 95.400 | 14.192 | 14.326 | 1.00 | 34.94 | H | C |
| ATOM | 1953 | CZ | PHE | 67 | 94.222 | 13.706 | 13.777 | 1.00 | 34.94 | H | C |
| ATOM | 1954 | C | PHE | 67 | 94.989 | 20.209 | 13.520 | 1.00 | 31.81 | H | C |
| ATOM | 1955 | O | PHE | 67 | 95.054 | 20.899 | 12.501 | 1.00 | 31.81 | H | O |
| ATOM | 1956 | N | THR | 68 | 95.511 | 20.587 | 14.683 | 1.00 | 27.20 | H | N |
| ATOM | 1957 | CA | THR | 68 | 96.233 | 21.851 | 14.804 | 1.00 | 27.20 | H | C |
| ATOM | 1958 | CB | THR | 68 | 95.344 | 22.998 | 15.384 | 1.00 | 14.56 | H | C |
| ATOM | 1959 | OG1 | THR | 68 | 94.400 | 23.434 | 14.399 | 1.00 | 14.56 | H | O |
| ATOM | 1960 | CG2 | THR | 68 | 96.196 | 24.192 | 15.758 | 1.00 | 14.56 | H | C |
| ATOM | 1961 | C | THR | 68 | 97.466 | 21.680 | 15.689 | 1.00 | 27.20 | H | C |
| ATOM | 1962 | O | THR | 68 | 97.355 | 21.393 | 16.882 | 1.00 | 27.20 | H | O |
| ATOM | 1963 | N | ILE | 69 | 98.643 | 21.847 | 15.099 | 1.00 | 22.74 | H | N |
| ATOM | 1964 | CA | ILE | 69 | 99.869 | 21.718 | 15.861 | 1.00 | 22.74 | H | C |
| ATOM | 1965 | CB | ILE | 69 | 100.991 | 21.084 | 15.020 | 1.00 | 13.28 | H | C |
| ATOM | 1966 | CG2 | ILE | 69 | 101.417 | 22.022 | 13.933 | 1.00 | 13.28 | H | C |
| ATOM | 1967 | CG1 | ILE | 69 | 102.188 | 20.736 | 15.908 | 1.00 | 13.28 | H | C |
| ATOM | 1968 | CD1 | ILE | 69 | 103.226 | 19.848 | 15.206 | 1.00 | 13.28 | H | C |
| ATOM | 1969 | C | ILE | 69 | 100.287 | 23.096 | 16.336 | 1.00 | 22.74 | H | C |
| ATOM | 1970 | O | ILE | 69 | 100.282 | 24.065 | 15.578 | 1.00 | 22.74 | H | O |
| ATOM | 1971 | N | SER | 70 | 100.632 | 23.188 | 17.608 | 1.00 | 15.22 | H | N |

Fig. 19: A-28

| | | | | | | | | | | | |
|---|---|---|---|---|---|---|---|---|---|---|---|
| ATOM | 1972 | CA | SER | 70 | 101.032 | 24.460 | 18.183 | 1.00 | 15.22 | H | C |
| ATOM | 1973 | CB | SER | 70 | 99.834 | 25.147 | 18.851 | 1.00 | 3.12 | H | C |
| ATOM | 1974 | CG | SER | 70 | 99.588 | 24.606 | 20.144 | 1.00 | 3.12 | H | O |
| ATOM | 1975 | C | SER | 70 | 102.088 | 24.203 | 19.235 | 1.00 | 15.22 | H | C |
| ATOM | 1976 | O | SER | 70 | 102.392 | 23.053 | 19.557 | 1.00 | 15.22 | H | O |
| ATOM | 1977 | N | ARG | 71 | 102.636 | 25.281 | 19.780 | 1.00 | 42.13 | H | N |
| ATOM | 1978 | CA | ARG | 71 | 103.640 | 25.158 | 20.813 | 1.00 | 42.13 | H | C |
| ATOM | 1979 | CB | ARG | 71 | 105.039 | 25.089 | 20.210 | 1.00 | 12.52 | H | C |
| ATOM | 1980 | CG | ARG | 71 | 105.417 | 26.296 | 19.388 | 1.00 | 12.52 | H | C |
| ATOM | 1981 | CD | ARG | 71 | 106.906 | 26.507 | 19.436 | 1.00 | 12.52 | H | C |
| ATOM | 1982 | NE | ARG | 71 | 107.644 | 25.627 | 18.540 | 1.00 | 12.52 | H | N |
| ATOM | 1983 | CZ | ARG | 71 | 108.844 | 25.114 | 18.816 | 1.00 | 12.52 | H | C |
| ATOM | 1984 | NH1 | ARG | 71 | 109.444 | 25.380 | 19.970 | 1.00 | 12.52 | H | N |
| ATOM | 1985 | NH2 | ARG | 71 | 109.456 | 24.354 | 17.924 | 1.00 | 12.52 | H | N |
| ATOM | 1986 | C | ARG | 71 | 103.568 | 26.341 | 21.739 | 1.00 | 42.13 | H | C |
| ATOM | 1987 | O | ARG | 71 | 103.115 | 27.416 | 21.352 | 1.00 | 42.13 | H | O |
| ATOM | 1988 | N | ASP | 72 | 104.003 | 26.131 | 22.973 | 1.00 | 26.38 | H | N |
| ATOM | 1989 | CA | ASP | 72 | 104.034 | 27.197 | 23.954 | 1.00 | 26.38 | H | C |
| ATOM | 1990 | CB | ASP | 72 | 102.949 | 27.026 | 25.007 | 1.00 | 47.03 | H | C |
| ATOM | 1991 | CG | ASP | 72 | 103.003 | 28.108 | 26.050 | 1.00 | 47.03 | H | C |
| ATOM | 1992 | OD1 | ASP | 72 | 102.157 | 28.112 | 26.964 | 1.00 | 47.03 | H | O |
| ATOM | 1993 | OD2 | ASP | 72 | 103.907 | 28.959 | 25.953 | 1.00 | 47.03 | H | O |
| ATOM | 1994 | C | ASP | 72 | 105.402 | 27.159 | 24.607 | 1.00 | 26.38 | H | C |
| ATOM | 1995 | O | ASP | 72 | 105.618 | 26.508 | 25.633 | 1.00 | 26.38 | H | O |
| ATOM | 1996 | N | ASN | 73 | 106.325 | 27.868 | 23.979 | 1.00 | 50.64 | H | N |
| ATOM | 1997 | CA | ASN | 73 | 107.692 | 27.939 | 24.441 | 1.00 | 50.64 | H | C |
| ATOM | 1998 | CB | ASN | 73 | 108.522 | 28.747 | 23.446 | 1.00 | 30.24 | H | C |
| ATOM | 1999 | CG | ASN | 73 | 108.584 | 28.091 | 22.086 | 1.00 | 30.24 | H | C |
| ATOM | 2000 | OD1 | ASN | 73 | 109.170 | 28.625 | 21.149 | 1.00 | 30.24 | H | O |
| ATOM | 2001 | ND2 | ASN | 73 | 107.984 | 26.917 | 21.974 | 1.00 | 30.24 | H | N |
| ATOM | 2002 | C | ASN | 73 | 107.827 | 28.516 | 25.841 | 1.00 | 50.64 | H | C |
| ATOM | 2003 | O | ASN | 73 | 108.898 | 28.436 | 26.438 | 1.00 | 50.64 | H | O |
| ATOM | 2004 | N | SER | 74 | 106.758 | 29.097 | 26.376 | 1.00 | 33.75 | H | N |
| ATOM | 2005 | CA | SER | 74 | 106.848 | 29.644 | 27.723 | 1.00 | 33.75 | H | C |
| ATOM | 2006 | CB | SER | 74 | 105.593 | 30.429 | 28.093 | 1.00 | 48.57 | H | C |
| ATOM | 2007 | OG | SER | 74 | 104.534 | 29.556 | 28.444 | 1.00 | 48.57 | H | O |
| ATOM | 2008 | C | SER | 74 | 106.979 | 28.456 | 28.653 | 1.00 | 33.75 | H | C |
| ATOM | 2009 | O | SER | 74 | 107.681 | 28.530 | 29.660 | 1.00 | 33.75 | H | O |
| ATOM | 2010 | N | LYS | 75 | 106.312 | 27.354 | 28.302 | 1.00 | 39.57 | H | N |
| ATOM | 2011 | CA | LYS | 75 | 106.352 | 26.142 | 29.119 | 1.00 | 39.57 | H | C |
| ATOM | 2012 | CB | LYS | 75 | 104.973 | 25.889 | 29.732 | 1.00 | 42.48 | H | C |
| ATOM | 2013 | CG | LYS | 75 | 103.842 | 25.924 | 28.731 | 1.00 | 42.48 | H | C |
| ATOM | 2014 | CD | LYS | 75 | 102.482 | 25.985 | 29.418 | 1.00 | 42.48 | H | C |
| ATOM | 2015 | CE | LYS | 75 | 102.156 | 27.393 | 29.918 | 1.00 | 42.48 | H | C |
| ATOM | 2016 | NZ | LYS | 75 | 103.090 | 27.928 | 30.963 | 1.00 | 42.48 | H | N |
| ATOM | 2017 | C | LYS | 75 | 106.843 | 24.894 | 28.380 | 1.00 | 39.57 | H | C |
| ATOM | 2018 | O | LYS | 75 | 106.497 | 23.767 | 28.744 | 1.00 | 39.57 | H | O |
| ATOM | 2019 | N | ASN | 76 | 107.660 | 25.110 | 27.353 | 1.00 | 44.84 | H | N |
| ATOM | 2020 | CA | ASN | 76 | 108.245 | 24.043 | 26.539 | 1.00 | 44.84 | H | C |
| ATOM | 2021 | CB | ASN | 76 | 109.572 | 23.608 | 27.139 | 1.00 | 31.30 | H | C |
| ATOM | 2022 | CG | ASN | 76 | 110.528 | 24.766 | 27.312 | 1.00 | 31.30 | H | C |
| ATOM | 2023 | OD1 | ASN | 76 | 111.666 | 24.593 | 27.739 | 1.00 | 31.30 | H | O |
| ATOM | 2024 | ND2 | ASN | 76 | 110.067 | 25.965 | 26.979 | 1.00 | 31.30 | H | N |
| ATOM | 2025 | C | ASN | 76 | 107.362 | 22.827 | 26.322 | 1.00 | 44.84 | H | C |
| ATOM | 2026 | O | ASN | 76 | 107.793 | 21.681 | 26.479 | 1.00 | 44.84 | H | O |
| ATOM | 2027 | N | THR | 77 | 106.121 | 23.090 | 25.941 | 1.00 | 30.42 | H | N |
| ATOM | 2028 | CA | THR | 77 | 105.181 | 22.032 | 25.686 | 1.00 | 30.42 | H | C |
| ATOM | 2029 | CB | THR | 77 | 103.989 | 22.131 | 26.628 | 1.00 | 46.49 | H | C |
| ATOM | 2030 | OG1 | THR | 77 | 104.446 | 21.977 | 27.974 | 1.00 | 46.49 | H | O |
| ATOM | 2031 | CG2 | THR | 77 | 102.975 | 21.045 | 26.319 | 1.00 | 46.49 | H | C |
| ATOM | 2032 | C | THR | 77 | 104.708 | 22.182 | 24.254 | 1.00 | 30.42 | H | C |
| ATOM | 2033 | O | THR | 77 | 104.488 | 23.291 | 23.786 | 1.00 | 30.42 | H | O |
| ATOM | 2034 | N | LEU | 78 | 104.583 | 21.056 | 23.563 | 1.00 | 20.66 | H | N |
| ATOM | 2035 | CA | LEU | 78 | 104.135 | 21.017 | 22.185 | 1.00 | 20.66 | H | C |
| ATOM | 2036 | CB | LEU | 78 | 104.978 | 20.024 | 21.394 | 1.00 | 19.59 | H | C |
| ATOM | 2037 | CG | LEU | 78 | 104.550 | 19.758 | 19.953 | 1.00 | 19.59 | H | C |
| ATOM | 2038 | CD1 | LEU | 78 | 104.575 | 21.055 | 19.166 | 1.00 | 19.59 | H | C |
| ATOM | 2039 | CD2 | LEU | 78 | 105.470 | 18.731 | 19.320 | 1.00 | 19.59 | H | C |
| ATOM | 2040 | C | LEU | 78 | 102.716 | 20.520 | 22.298 | 1.00 | 20.66 | H | C |
| ATOM | 2041 | O | LEU | 78 | 102.368 | 19.921 | 23.312 | 1.00 | 20.66 | H | O |
| ATOM | 2042 | N | TYR | 79 | 101.902 | 20.753 | 21.271 | 1.00 | 30.75 | H | N |
| ATOM | 2043 | CA | TYR | 79 | 100.498 | 20.333 | 21.294 | 1.00 | 30.75 | H | C |
| ATOM | 2044 | CB | TYR | 79 | 99.591 | 21.494 | 21.728 | 1.00 | 47.95 | H | C |

Fig. 19: A-29

| | | | | | | | | | | | |
|---|---|---|---|---|---|---|---|---|---|---|---|
| ATOM | 2045 | CG | TYR | 79 | 99.809 | 22.008 | 23.119 | 1.00 | 47.95 | H | C |
| ATOM | 2046 | CD1 | TYR | 79 | 99.166 | 21.430 | 24.205 | 1.00 | 47.95 | H | C |
| ATOM | 2047 | CE1 | TYR | 79 | 99.357 | 21.916 | 25.491 | 1.00 | 47.95 | H | C |
| ATOM | 2048 | CD2 | TYR | 79 | 100.655 | 23.085 | 23.349 | 1.00 | 47.95 | H | C |
| ATOM | 2049 | CE2 | TYR | 79 | 100.857 | 23.579 | 24.628 | 1.00 | 47.95 | H | C |
| ATOM | 2050 | CZ | TYR | 79 | 100.204 | 22.991 | 25.695 | 1.00 | 47.95 | H | C |
| ATOM | 2051 | OH | TYR | 79 | 100.404 | 23.493 | 26.958 | 1.00 | 47.95 | H | O |
| ATOM | 2052 | C | TYR | 79 | 99.966 | 19.863 | 19.950 | 1.00 | 30.75 | H | C |
| ATOM | 2053 | O | TYR | 79 | 100.418 | 20.316 | 18.898 | 1.00 | 30.75 | H | O |
| ATOM | 2054 | N | LEU | 80 | 98.981 | 18.969 | 20.003 | 1.00 | 19.83 | H | N |
| ATOM | 2055 | CA | LEU | 80 | 98.308 | 18.472 | 18.811 | 1.00 | 19.83 | H | C |
| ATOM | 2056 | CB | LEU | 80 | 98.776 | 17.070 | 18.397 | 1.00 | 5.08 | H | C |
| ATOM | 2057 | CG | LEU | 80 | 98.132 | 16.598 | 17.076 | 1.00 | 5.08 | H | C |
| ATOM | 2058 | CD1 | LEU | 80 | 98.706 | 17.386 | 15.914 | 1.00 | 5.08 | H | C |
| ATOM | 2059 | CD2 | LEU | 80 | 98.352 | 15.111 | 16.874 | 1.00 | 5.08 | H | C |
| ATOM | 2060 | C | LEU | 80 | 96.838 | 18.411 | 19.182 | 1.00 | 19.83 | H | C |
| ATOM | 2061 | O | LEU | 80 | 96.398 | 17.503 | 19.879 | 1.00 | 19.83 | H | O |
| ATOM | 2062 | N | GLN | 81 | 96.091 | 19.412 | 18.742 | 1.00 | 24.43 | H | N |
| ATOM | 2063 | CA | GLN | 81 | 94.671 | 19.463 | 19.004 | 1.00 | 24.43 | H | C |
| ATOM | 2064 | CB | GLN | 81 | 94.169 | 20.911 | 18.966 | 1.00 | 60.73 | H | C |
| ATOM | 2065 | CG | GLN | 81 | 92.710 | 21.093 | 19.399 | 1.00 | 60.73 | H | C |
| ATOM | 2066 | CD | GLN | 81 | 92.505 | 20.974 | 20.911 | 1.00 | 60.73 | H | C |
| ATOM | 2067 | OE1 | GLN | 81 | 92.981 | 21.810 | 21.691 | 1.00 | 60.73 | H | O |
| ATOM | 2068 | NE2 | GLN | 81 | 91.787 | 19.935 | 21.328 | 1.00 | 60.73 | H | N |
| ATOM | 2069 | C | GLN | 81 | 94.064 | 18.672 | 17.867 | 1.00 | 24.43 | H | C |
| ATOM | 2070 | O | GLN | 81 | 94.376 | 18.921 | 16.698 | 1.00 | 24.43 | H | O |
| ATOM | 2071 | N | MET | 82 | 93.205 | 17.718 | 18.210 | 1.00 | 35.69 | H | N |
| ATOM | 2072 | CA | MET | 82 | 92.559 | 16.878 | 17.211 | 1.00 | 35.69 | H | C |
| ATOM | 2073 | CB | MET | 82 | 92.989 | 15.424 | 17.383 | 1.00 | 24.95 | H | C |
| ATOM | 2074 | CG | MET | 82 | 94.481 | 15.209 | 17.363 | 1.00 | 24.95 | H | C |
| ATOM | 2075 | SD | MET | 82 | 94.896 | 13.491 | 17.609 | 1.00 | 24.95 | H | S |
| ATOM | 2076 | CE | MET | 82 | 94.985 | 13.427 | 19.373 | 1.00 | 24.95 | H | C |
| ATOM | 2077 | C | MET | 82 | 91.051 | 16.957 | 17.316 | 1.00 | 35.69 | H | C |
| ATOM | 2078 | O | MET | 82 | 90.479 | 16.599 | 18.338 | 1.00 | 35.69 | H | O |
| ATOM | 2079 | N | ASN | 83 | 90.414 | 17.416 | 16.247 | 1.00 | 28.29 | H | N |
| ATOM | 2080 | CA | ASN | 83 | 88.968 | 17.536 | 16.204 | 1.00 | 28.29 | H | C |
| ATOM | 2081 | CB | ASN | 83 | 88.550 | 18.989 | 15.985 | 1.00 | 66.28 | H | C |
| ATOM | 2082 | CG | ASN | 83 | 89.274 | 19.943 | 16.899 | 1.00 | 66.28 | H | C |
| ATOM | 2083 | OD1 | ASN | 83 | 89.213 | 19.819 | 18.121 | 1.00 | 66.28 | H | O |
| ATOM | 2084 | ND2 | ASN | 83 | 89.970 | 20.910 | 16.309 | 1.00 | 66.28 | H | N |
| ATOM | 2085 | C | ASN | 83 | 88.502 | 16.728 | 15.025 | 1.00 | 28.29 | H | C |
| ATOM | 2086 | O | ASN | 83 | 89.306 | 16.348 | 14.185 | 1.00 | 28.29 | H | O |
| ATOM | 2087 | N | SER | 84 | 87.199 | 16.486 | 14.954 | 1.00 | 57.41 | H | N |
| ATOM | 2088 | CA | SER | 84 | 86.618 | 15.739 | 13.847 | 1.00 | 57.41 | H | C |
| ATOM | 2089 | CB | SER | 84 | 86.648 | 16.584 | 12.574 | 1.00 | 29.12 | H | C |
| ATOM | 2090 | OG | SER | 84 | 86.027 | 17.836 | 12.786 | 1.00 | 29.12 | H | O |
| ATOM | 2091 | C | SER | 84 | 87.374 | 14.450 | 13.603 | 1.00 | 57.41 | H | C |
| ATOM | 2092 | O | SER | 84 | 87.642 | 14.085 | 12.456 | 1.00 | 57.41 | H | O |
| ATOM | 2093 | N | LEU | 85 | 87.725 | 13.769 | 14.687 | 1.00 | 32.34 | H | N |
| ATOM | 2094 | CA | LEU | 85 | 88.452 | 12.513 | 14.595 | 1.00 | 32.34 | H | C |
| ATOM | 2095 | CB | LEU | 85 | 88.818 | 12.009 | 15.990 | 1.00 | 15.22 | H | C |
| ATOM | 2096 | CG | LEU | 85 | 89.913 | 12.880 | 16.600 | 1.00 | 15.22 | H | C |
| ATOM | 2097 | CD1 | LEU | 85 | 90.082 | 12.594 | 18.078 | 1.00 | 15.22 | H | C |
| ATOM | 2098 | CD2 | LEU | 85 | 91.204 | 12.636 | 15.828 | 1.00 | 15.22 | H | C |
| ATOM | 2099 | C | LEU | 85 | 87.641 | 11.460 | 13.877 | 1.00 | 32.34 | H | C |
| ATOM | 2100 | O | LEU | 85 | 86.434 | 11.369 | 14.050 | 1.00 | 32.34 | H | O |
| ATOM | 2101 | N | ARG | 86 | 88.319 | 10.680 | 13.049 | 1.00 | 24.27 | H | N |
| ATOM | 2102 | CA | ARG | 86 | 87.686 | 9.604 | 12.316 | 1.00 | 24.27 | H | C |
| ATOM | 2103 | CB | ARG | 86 | 87.858 | 9.801 | 10.815 | 1.00 | 51.87 | H | C |
| ATOM | 2104 | CG | ARG | 86 | 87.146 | 11.026 | 10.286 | 1.00 | 51.87 | H | C |
| ATOM | 2105 | CD | ARG | 86 | 86.864 | 10.887 | 8.808 | 1.00 | 51.87 | H | C |
| ATOM | 2106 | NE | ARG | 86 | 87.237 | 12.088 | 8.076 | 1.00 | 51.87 | H | N |
| ATOM | 2107 | CZ | ARG | 86 | 88.470 | 12.581 | 8.043 | 1.00 | 51.87 | H | C |
| ATOM | 2108 | NH1 | ARG | 86 | 89.444 | 11.967 | 8.707 | 1.00 | 51.87 | H | N |
| ATOM | 2109 | NH2 | ARG | 86 | 88.733 | 13.676 | 7.334 | 1.00 | 51.87 | H | N |
| ATOM | 2110 | C | ARG | 86 | 88.387 | 8.343 | 12.769 | 1.00 | 24.27 | H | C |
| ATOM | 2111 | O | ARG | 86 | 89.367 | 8.416 | 13.514 | 1.00 | 24.27 | H | O |
| ATOM | 2112 | N | ALA | 87 | 87.894 | 7.191 | 12.335 | 1.00 | 40.98 | H | N |
| ATOM | 2113 | CA | ALA | 87 | 88.499 | 5.928 | 12.733 | 1.00 | 40.98 | H | C |
| ATOM | 2114 | CB | ALA | 87 | 87.678 | 4.763 | 12.196 | 1.00 | 28.01 | H | C |
| ATOM | 2115 | C | ALA | 87 | 89.937 | 5.833 | 12.242 | 1.00 | 40.98 | H | C |
| ATOM | 2116 | O | ALA | 87 | 90.824 | 5.425 | 12.989 | 1.00 | 40.98 | H | O |
| ATOM | 2117 | N | GLU | 88 | 90.169 | 6.222 | 10.993 | 1.00 | 32.24 | H | N |

Fig. 19: A-30

| | | | | | | | | | | | |
|---|---|---|---|---|---|---|---|---|---|---|---|
| ATOM | 2118 | CA | GLU | 88 | 91.511 | 6.157 | 10.433 | 1.00 | 32.24 | H | C |
| ATOM | 2119 | CB | GLU | 88 | 91.583 | 6.890 | 9.094 | 1.00 | 72.38 | H | C |
| ATOM | 2120 | CG | GLU | 88 | 90.432 | 6.614 | 8.169 | 1.00 | 72.38 | H | C |
| ATOM | 2121 | CD | GLU | 88 | 89.327 | 7.623 | 8.336 | 1.00 | 72.38 | H | C |
| ATOM | 2122 | OE1 | GLU | 88 | 89.529 | 8.792 | 7.937 | 1.00 | 72.38 | H | O |
| ATOM | 2123 | OE2 | GLU | 88 | 88.265 | 7.246 | 8.874 | 1.00 | 72.38 | H | O |
| ATOM | 2124 | C | GLU | 88 | 92.529 | 6.780 | 11.372 | 1.00 | 32.24 | H | C |
| ATOM | 2125 | O | GLU | 88 | 93.691 | 6.370 | 11.417 | 1.00 | 32.24 | H | O |
| ATOM | 2126 | N | ASP | 89 | 92.080 | 7.772 | 12.128 | 1.00 | 18.63 | H | N |
| ATOM | 2127 | CA | ASP | 89 | 92.935 | 8.497 | 13.054 | 1.00 | 18.63 | H | C |
| ATOM | 2128 | CB | ASP | 89 | 92.212 | 9.764 | 13.507 | 1.00 | 29.25 | H | C |
| ATOM | 2129 | CG | ASP | 89 | 92.073 | 10.775 | 12.392 | 1.00 | 29.25 | H | C |
| ATOM | 2130 | OD1 | ASP | 89 | 91.297 | 11.732 | 12.553 | 1.00 | 29.25 | H | O |
| ATOM | 2131 | OD2 | ASP | 89 | 92.748 | 10.622 | 11.355 | 1.00 | 29.25 | H | O |
| ATOM | 2132 | C | ASP | 89 | 93.434 | 7.724 | 14.268 | 1.00 | 18.63 | H | C |
| ATOM | 2133 | O | ASP | 89 | 94.391 | 8.149 | 14.922 | 1.00 | 18.63 | H | O |
| ATOM | 2134 | N | THR | 90 | 92.817 | 6.588 | 14.575 | 1.00 | 29.66 | H | N |
| ATOM | 2135 | CA | THR | 90 | 93.261 | 5.845 | 15.749 | 1.00 | 29.66 | H | C |
| ATOM | 2136 | CB | THR | 90 | 92.303 | 4.668 | 16.113 | 1.00 | 30.61 | H | C |
| ATOM | 2137 | OG1 | THR | 90 | 92.601 | 3.537 | 15.293 | 1.00 | 30.61 | H | O |
| ATOM | 2138 | CG2 | THR | 90 | 90.828 | 5.072 | 15.903 | 1.00 | 30.61 | H | C |
| ATOM | 2139 | C | THR | 90 | 94.664 | 5.311 | 15.527 | 1.00 | 29.66 | H | C |
| ATOM | 2140 | O | THR | 90 | 94.961 | 4.727 | 14.492 | 1.00 | 29.66 | H | O |
| ATOM | 2141 | N | ALA | 91 | 95.532 | 5.553 | 16.499 | 1.00 | 11.25 | H | N |
| ATOM | 2142 | CA | ALA | 91 | 96.918 | 5.094 | 16.451 | 1.00 | 11.25 | H | C |
| ATOM | 2143 | CB | ALA | 91 | 97.629 | 5.690 | 15.259 | 1.00 | 1.87 | H | C |
| ATOM | 2144 | C | ALA | 91 | 97.611 | 5.536 | 17.729 | 1.00 | 11.25 | H | C |
| ATOM | 2145 | O | ALA | 91 | 96.972 | 6.044 | 18.646 | 1.00 | 11.25 | H | O |
| ATOM | 2146 | N | VAL | 92 | 98.915 | 5.312 | 17.797 | 1.00 | 22.44 | H | N |
| ATOM | 2147 | CA | VAL | 92 | 99.694 | 5.755 | 18.947 | 1.00 | 22.44 | H | C |
| ATOM | 2148 | CB | VAL | 92 | 100.654 | 4.665 | 19.465 | 1.00 | 21.44 | H | C |
| ATOM | 2149 | CG1 | VAL | 92 | 101.306 | 3.966 | 18.298 | 1.00 | 21.44 | H | C |
| ATOM | 2150 | CG2 | VAL | 92 | 101.716 | 5.284 | 20.346 | 1.00 | 21.44 | H | C |
| ATOM | 2151 | C | VAL | 92 | 100.482 | 6.913 | 18.363 | 1.00 | 22.44 | H | C |
| ATOM | 2152 | O | VAL | 92 | 101.107 | 6.771 | 17.310 | 1.00 | 22.44 | H | O |
| ATOM | 2153 | N | TYR | 93 | 100.413 | 8.066 | 19.019 | 1.00 | 21.58 | H | N |
| ATOM | 2154 | CA | TYR | 93 | 101.105 | 9.261 | 18.538 | 1.00 | 21.58 | H | C |
| ATOM | 2155 | CB | TYR | 93 | 100.161 | 10.470 | 18.585 | 1.00 | 12.38 | H | C |
| ATOM | 2156 | CG | TYR | 93 | 99.000 | 10.385 | 17.624 | 1.00 | 12.38 | H | C |
| ATOM | 2157 | CD1 | TYR | 93 | 98.023 | 9.399 | 17.759 | 1.00 | 12.38 | H | C |
| ATOM | 2158 | CE1 | TYR | 93 | 96.975 | 9.287 | 16.836 | 1.00 | 12.38 | H | C |
| ATOM | 2159 | CD2 | TYR | 93 | 98.899 | 11.264 | 16.553 | 1.00 | 12.38 | H | C |
| ATOM | 2160 | CE2 | TYR | 93 | 97.863 | 11.165 | 15.634 | 1.00 | 12.38 | H | C |
| ATOM | 2161 | CZ | TYR | 93 | 96.908 | 10.173 | 15.773 | 1.00 | 12.38 | H | C |
| ATOM | 2162 | OH | TYR | 93 | 95.915 | 10.043 | 14.827 | 1.00 | 12.38 | H | O |
| ATOM | 2163 | C | TYR | 93 | 102.384 | 9.577 | 19.312 | 1.00 | 21.58 | H | C |
| ATOM | 2164 | O | TYR | 93 | 102.466 | 9.401 | 20.531 | 1.00 | 21.58 | H | O |
| ATOM | 2165 | N | TYR | 94 | 103.381 | 10.049 | 18.579 | 1.00 | 19.04 | H | N |
| ATOM | 2166 | CA | TYR | 94 | 104.668 | 10.409 | 19.151 | 1.00 | 19.04 | H | C |
| ATOM | 2167 | CB | TYR | 94 | 105.789 | 9.576 | 18.533 | 1.00 | 29.80 | H | C |
| ATOM | 2168 | CG | TYR | 94 | 105.548 | 8.101 | 18.431 | 1.00 | 29.80 | H | C |
| ATOM | 2169 | CD1 | TYR | 94 | 105.948 | 7.237 | 19.454 | 1.00 | 29.80 | H | C |
| ATOM | 2170 | CE1 | TYR | 94 | 105.768 | 5.876 | 19.345 | 1.00 | 29.80 | H | C |
| ATOM | 2171 | CD2 | TYR | 94 | 104.958 | 7.563 | 17.298 | 1.00 | 29.80 | H | C |
| ATOM | 2172 | CE2 | TYR | 94 | 104.773 | 6.204 | 17.177 | 1.00 | 29.80 | H | C |
| ATOM | 2173 | CZ | TYR | 94 | 105.179 | 5.363 | 18.202 | 1.00 | 29.80 | H | C |
| ATOM | 2174 | OH | TYR | 94 | 104.996 | 4.007 | 18.071 | 1.00 | 29.80 | H | O |
| ATOM | 2175 | C | TYR | 94 | 104.991 | 11.853 | 18.805 | 1.00 | 19.04 | H | C |
| ATOM | 2176 | O | TYR | 94 | 104.867 | 12.244 | 17.642 | 1.00 | 19.04 | H | O |
| ATOM | 2177 | N | CYS | 95 | 105.383 | 12.654 | 19.791 | 1.00 | 25.07 | H | N |
| ATOM | 2178 | CA | CYS | 95 | 105.806 | 14.000 | 19.466 | 1.00 | 25.07 | H | C |
| ATOM | 2179 | C | CYS | 95 | 107.228 | 13.689 | 19.096 | 1.00 | 25.07 | H | C |
| ATOM | 2180 | O | CYS | 95 | 107.716 | 12.584 | 19.342 | 1.00 | 25.07 | H | O |
| ATOM | 2181 | CB | CYS | 95 | 105.784 | 14.942 | 20.647 | 1.00 | 46.53 | H | C |
| ATOM | 2182 | SG | CYS | 95 | 106.112 | 14.206 | 22.267 | 1.00 | 46.53 | H | S |
| ATOM | 2183 | N | THR | 96 | 107.931 | 14.657 | 18.549 | 1.00 | 31.61 | H | N |
| ATOM | 2184 | CA | THR | 96 | 109.253 | 14.331 | 18.115 | 1.00 | 31.61 | H | C |
| ATOM | 2185 | CB | THR | 96 | 109.088 | 13.445 | 16.861 | 1.00 | 32.15 | H | C |
| ATOM | 2186 | OG1 | THR | 96 | 110.331 | 12.862 | 16.494 | 1.00 | 32.15 | H | O |
| ATOM | 2187 | CG2 | THR | 96 | 108.554 | 14.260 | 15.708 | 1.00 | 32.15 | H | C |
| ATOM | 2188 | C | THR | 96 | 110.045 | 15.591 | 17.830 | 1.00 | 31.61 | H | C |
| ATOM | 2189 | O | THR | 96 | 109.530 | 16.548 | 17.260 | 1.00 | 31.61 | H | O |
| ATOM | 2190 | N | ARG | 97 | 111.292 | 15.610 | 18.270 | 1.00 | 26.02 | H | N |

Fig. 19: A-31

| | | | | | | | | | | | |
|---|---|---|---|---|---|---|---|---|---|---|---|
| ATOM | 2191 | CA | ARG | 97 | 112.135 | 16.759 | 17.996 | 1.00 | 26.02 | H | C |
| ATOM | 2192 | CB | ARG | 97 | 113.220 | 16.959 | 19.053 | 1.00 | 22.53 | H | C |
| ATOM | 2193 | CG | ARG | 97 | 114.076 | 18.184 | 18.766 | 1.00 | 22.53 | H | C |
| ATOM | 2194 | CD | ARG | 97 | 115.204 | 18.345 | 19.764 | 1.00 | 22.53 | H | C |
| ATOM | 2195 | NE | ARG | 97 | 116.357 | 17.532 | 19.411 | 1.00 | 22.53 | H | N |
| ATOM | 2196 | CZ | ARG | 97 | 117.494 | 17.509 | 20.099 | 1.00 | 22.53 | H | C |
| ATOM | 2197 | NH1 | ARG | 97 | 117.635 | 18.257 | 21.183 | 1.00 | 22.53 | H | N |
| ATOM | 2198 | NH2 | ARG | 97 | 118.494 | 16.739 | 19.704 | 1.00 | 22.53 | H | N |
| ATOM | 2199 | C | ARG | 97 | 112.799 | 16.473 | 16.665 | 1.00 | 26.02 | H | C |
| ATOM | 2200 | O | ARG | 97 | 113.145 | 15.322 | 16.357 | 1.00 | 26.02 | H | O |
| ATOM | 2201 | N | GLY | 98 | 112.980 | 17.528 | 15.882 | 1.00 | 13.43 | H | N |
| ATOM | 2202 | CA | GLY | 98 | 113.586 | 17.367 | 14.582 | 1.00 | 13.43 | H | C |
| ATOM | 2203 | C | GLY | 98 | 114.947 | 17.995 | 14.496 | 1.00 | 13.43 | H | C |
| ATOM | 2204 | O | GLY | 98 | 115.308 | 18.850 | 15.281 | 1.00 | 13.43 | H | O |
| ATOM | 2205 | N | PHE | 99 | 115.719 | 17.537 | 13.534 | 1.00 | 20.13 | H | N |
| ATOM | 2206 | CA | PHE | 99 | 117.038 | 18.065 | 13.315 | 1.00 | 20.13 | H | C |
| ATOM | 2207 | CB | PHE | 99 | 118.018 | 16.902 | 13.211 | 1.00 | 25.23 | H | C |
| ATOM | 2208 | CG | PHE | 99 | 119.338 | 17.271 | 12.628 | 1.00 | 25.23 | H | C |
| ATOM | 2209 | CD1 | PHE | 99 | 119.587 | 17.079 | 11.279 | 1.00 | 25.23 | H | C |
| ATOM | 2210 | CD2 | PHE | 99 | 120.326 | 17.828 | 13.420 | 1.00 | 25.23 | H | C |
| ATOM | 2211 | CE1 | PHE | 99 | 120.804 | 17.437 | 10.721 | 1.00 | 25.23 | H | C |
| ATOM | 2212 | CE2 | PHE | 99 | 121.543 | 18.191 | 12.875 | 1.00 | 25.23 | H | C |
| ATOM | 2213 | CZ | PHE | 99 | 121.784 | 17.994 | 11.517 | 1.00 | 25.23 | H | C |
| ATOM | 2214 | C | PHE | 99 | 116.887 | 18.819 | 11.996 | 1.00 | 20.13 | H | C |
| ATOM | 2215 | O | PHE | 99 | 115.950 | 18.551 | 11.241 | 1.00 | 20.13 | H | O |
| ATOM | 2216 | N | GLY | 100 | 117.768 | 19.774 | 11.719 | 1.00 | 15.08 | H | N |
| ATOM | 2217 | CA | GLY | 100 | 117.655 | 20.513 | 10.469 | 1.00 | 15.08 | H | C |
| ATOM | 2218 | C | GLY | 100 | 116.285 | 21.139 | 10.274 | 1.00 | 15.08 | H | C |
| ATOM | 2219 | O | GLY | 100 | 115.682 | 21.636 | 11.216 | 1.00 | 15.08 | H | O |
| ATOM | 2220 | N | ASP | 101 | 115.779 | 21.128 | 9.050 | 1.00 | 7.89 | H | N |
| ATOM | 2221 | CA | ASP | 101 | 114.462 | 21.692 | 8.812 | 1.00 | 7.89 | H | C |
| ATOM | 2222 | CB | ASP | 101 | 114.195 | 21.848 | 7.302 | 1.00 | 13.13 | H | C |
| ATOM | 2223 | CG | ASP | 101 | 115.328 | 22.587 | 6.564 | 1.00 | 13.13 | H | C |
| ATOM | 2224 | OD1 | ASP | 101 | 115.921 | 23.558 | 7.105 | 1.00 | 13.13 | H | O |
| ATOM | 2225 | OD2 | ASP | 101 | 115.616 | 22.190 | 5.417 | 1.00 | 13.13 | H | O |
| ATOM | 2226 | C | ASP | 101 | 113.406 | 20.785 | 9.460 | 1.00 | 7.89 | H | C |
| ATOM | 2227 | O | ASP | 101 | 112.222 | 20.844 | 9.124 | 1.00 | 7.89 | H | O |
| ATOM | 2228 | N | GLY | 102 | 113.854 | 19.924 | 10.374 | 1.00 | 22.31 | H | N |
| ATOM | 2229 | CA | GLY | 102 | 112.952 | 19.043 | 11.100 | 1.00 | 22.31 | H | C |
| ATOM | 2230 | C | GLY | 102 | 112.588 | 17.674 | 10.562 | 1.00 | 22.31 | H | C |
| ATOM | 2231 | O | GLY | 102 | 111.927 | 16.915 | 11.263 | 1.00 | 22.31 | H | O |
| ATOM | 2232 | N | GLY | 103 | 113.001 | 17.347 | 9.343 | 1.00 | 25.09 | H | N |
| ATOM | 2233 | CA | GLY | 103 | 112.662 | 16.054 | 8.772 | 1.00 | 25.09 | H | C |
| ATOM | 2234 | C | GLY | 103 | 113.342 | 14.844 | 9.403 | 1.00 | 25.09 | H | C |
| ATOM | 2235 | O | GLY | 103 | 112.948 | 13.703 | 9.156 | 1.00 | 25.09 | H | O |
| ATOM | 2236 | N | TYR | 104 | 114.376 | 15.071 | 10.202 | 1.00 | 22.52 | H | N |
| ATOM | 2237 | CA | TYR | 104 | 115.070 | 13.961 | 10.844 | 1.00 | 22.52 | H | C |
| ATOM | 2238 | CB | TYR | 104 | 116.578 | 14.114 | 10.715 | 1.00 | 15.87 | H | C |
| ATOM | 2239 | CG | TYR | 104 | 117.342 | 13.175 | 11.599 | 1.00 | 15.87 | H | C |
| ATOM | 2240 | CD1 | TYR | 104 | 118.507 | 13.600 | 12.233 | 1.00 | 15.87 | H | C |
| ATOM | 2241 | CE1 | TYR | 104 | 119.198 | 12.776 | 13.100 | 1.00 | 15.87 | H | C |
| ATOM | 2242 | CD2 | TYR | 104 | 116.884 | 11.880 | 11.844 | 1.00 | 15.87 | H | C |
| ATOM | 2243 | CE2 | TYR | 104 | 117.575 | 11.034 | 12.713 | 1.00 | 15.87 | H | C |
| ATOM | 2244 | CZ | TYR | 104 | 118.734 | 11.498 | 13.343 | 1.00 | 15.87 | H | C |
| ATOM | 2245 | OH | TYR | 104 | 119.417 | 10.713 | 14.239 | 1.00 | 15.87 | H | O |
| ATOM | 2246 | C | TYR | 104 | 114.665 | 13.991 | 12.296 | 1.00 | 22.52 | H | C |
| ATOM | 2247 | O | TYR | 104 | 114.933 | 14.956 | 13.001 | 1.00 | 22.52 | H | O |
| ATOM | 2248 | N | PHE | 105 | 114.036 | 12.909 | 12.733 | 1.00 | 16.00 | H | N |
| ATOM | 2249 | CA | PHE | 105 | 113.501 | 12.806 | 14.073 | 1.00 | 16.00 | H | C |
| ATOM | 2250 | CB | PHE | 105 | 112.292 | 11.890 | 14.031 | 1.00 | 16.01 | H | C |
| ATOM | 2251 | CG | PHE | 105 | 111.269 | 12.327 | 13.020 | 1.00 | 16.01 | H | C |
| ATOM | 2252 | CD1 | PHE | 105 | 110.782 | 13.627 | 13.038 | 1.00 | 16.01 | H | C |
| ATOM | 2253 | CD2 | PHE | 105 | 110.827 | 11.459 | 12.023 | 1.00 | 16.01 | H | C |
| ATOM | 2254 | CE1 | PHE | 105 | 109.880 | 14.059 | 12.091 | 1.00 | 16.01 | H | C |
| ATOM | 2255 | CE2 | PHE | 105 | 109.918 | 11.885 | 11.067 | 1.00 | 16.01 | H | C |
| ATOM | 2256 | CZ | PHE | 105 | 109.443 | 13.190 | 11.101 | 1.00 | 16.01 | H | C |
| ATOM | 2257 | C | PHE | 105 | 114.442 | 12.433 | 15.179 | 1.00 | 16.00 | H | C |
| ATOM | 2258 | O | PHE | 105 | 114.543 | 11.283 | 15.595 | 1.00 | 16.00 | H | O |
| ATOM | 2259 | N | ASP | 106 | 115.105 | 13.481 | 15.642 | 1.00 | 29.40 | H | N |
| ATOM | 2260 | CA | ASP | 106 | 116.089 | 13.519 | 16.714 | 1.00 | 29.40 | H | C |
| ATOM | 2261 | CB | ASP | 106 | 116.251 | 14.976 | 17.117 | 1.00 | 39.43 | H | C |
| ATOM | 2262 | CG | ASP | 106 | 117.656 | 15.400 | 17.133 | 1.00 | 39.43 | H | C |
| ATOM | 2263 | OD1 | ASP | 106 | 118.492 | 14.528 | 17.433 | 1.00 | 39.43 | H | O |

Fig. 19: A-32

| | | | | | | | | | | |
|---|---|---|---|---|---|---|---|---|---|---|
| ATOM | 2264 | OD2 | ASP | 106 | 117.922 | 16.591 | 16.859 | 1.00 | 39.43 | H | O |
| ATOM | 2265 | C | ASP | 106 | 115.797 | 12.728 | 17.993 | 1.00 | 29.40 | H | C |
| ATOM | 2266 | O | ASP | 106 | 116.567 | 11.861 | 18.396 | 1.00 | 29.40 | H | O |
| ATOM | 2267 | N | VAL | 107 | 114.687 | 13.094 | 18.635 | 1.00 | 7.69 | H | N |
| ATOM | 2268 | CA | VAL | 107 | 114.248 | 12.533 | 19.906 | 1.00 | 7.69 | H | C |
| ATOM | 2269 | CB | VAL | 107 | 114.402 | 13.600 | 21.026 | 1.00 | 10.61 | H | C |
| ATOM | 2270 | CG1 | VAL | 107 | 113.985 | 13.045 | 22.374 | 1.00 | 10.61 | H | C |
| ATOM | 2271 | CG2 | VAL | 107 | 115.838 | 14.116 | 21.048 | 1.00 | 10.61 | H | C |
| ATOM | 2272 | C | VAL | 107 | 112.778 | 12.199 | 19.765 | 1.00 | 7.69 | H | C |
| ATOM | 2273 | O | VAL | 107 | 112.107 | 12.835 | 18.970 | 1.00 | 7.69 | H | O |
| ATOM | 2274 | N | TRP | 108 | 112.285 | 11.224 | 20.540 | 1.00 | 26.84 | H | N |
| ATOM | 2275 | CA | TRP | 108 | 110.871 | 10.795 | 20.510 | 1.00 | 26.84 | H | C |
| ATOM | 2276 | CB | TRP | 108 | 110.729 | 9.405 | 19.868 | 1.00 | 1.87 | H | C |
| ATOM | 2277 | CG | TRP | 108 | 111.201 | 9.329 | 18.468 | 1.00 | 1.87 | H | C |
| ATOM | 2278 | CD2 | TRP | 108 | 110.431 | 8.950 | 17.328 | 1.00 | 1.87 | H | C |
| ATOM | 2279 | CE2 | TRP | 108 | 111.287 | 9.020 | 16.201 | 1.00 | 1.87 | H | C |
| ATOM | 2280 | CE3 | TRP | 108 | 109.102 | 8.557 | 17.142 | 1.00 | 1.87 | H | C |
| ATOM | 2281 | CD1 | TRP | 108 | 112.460 | 9.606 | 18.008 | 1.00 | 1.87 | H | C |
| ATOM | 2282 | NE1 | TRP | 108 | 112.520 | 9.422 | 16.648 | 1.00 | 1.87 | H | N |
| ATOM | 2283 | CZ2 | TRP | 108 | 110.854 | 8.710 | 14.904 | 1.00 | 1.87 | H | C |
| ATOM | 2284 | CZ3 | TRP | 108 | 108.667 | 8.244 | 15.836 | 1.00 | 1.87 | H | C |
| ATOM | 2285 | CH2 | TRP | 108 | 109.547 | 8.325 | 14.742 | 1.00 | 1.87 | H | C |
| ATOM | 2286 | C | TRP | 108 | 110.204 | 10.724 | 21.881 | 1.00 | 26.84 | H | C |
| ATOM | 2287 | O | TRP | 108 | 110.859 | 10.503 | 22.899 | 1.00 | 26.84 | H | O |
| ATOM | 2288 | N | GLY | 109 | 108.889 | 10.907 | 21.889 | 1.00 | 15.55 | H | N |
| ATOM | 2289 | CA | GLY | 109 | 108.134 | 10.811 | 23.125 | 1.00 | 15.55 | H | C |
| ATOM | 2290 | C | GLY | 109 | 107.896 | 9.331 | 23.386 | 1.00 | 15.55 | H | C |
| ATOM | 2291 | O | GLY | 109 | 108.170 | 8.502 | 22.511 | 1.00 | 15.55 | H | O |
| ATOM | 2292 | N | GLN | 110 | 107.393 | 8.971 | 24.563 | 1.00 | 21.92 | H | N |
| ATOM | 2293 | CA | GLN | 110 | 107.161 | 7.554 | 24.852 | 1.00 | 21.92 | H | C |
| ATOM | 2294 | CB | GLN | 110 | 106.800 | 7.338 | 26.325 | 1.00 | 44.26 | H | C |
| ATOM | 2295 | CG | GLN | 110 | 105.404 | 7.798 | 26.703 | 1.00 | 44.26 | H | C |
| ATOM | 2296 | CD | GLN | 110 | 105.321 | 9.283 | 26.957 | 1.00 | 44.26 | H | C |
| ATOM | 2297 | OE1 | GLN | 110 | 105.573 | 10.102 | 26.071 | 1.00 | 44.26 | H | O |
| ATOM | 2298 | NE2 | GLN | 110 | 104.967 | 9.642 | 28.181 | 1.00 | 44.26 | H | N |
| ATOM | 2299 | C | GLN | 110 | 106.051 | 6.979 | 23.973 | 1.00 | 21.92 | H | C |
| ATOM | 2300 | O | GLN | 110 | 106.054 | 5.798 | 23.651 | 1.00 | 21.92 | H | O |
| ATOM | 2301 | N | GLY | 111 | 105.114 | 7.824 | 23.574 | 1.00 | 22.63 | H | N |
| ATOM | 2302 | CA | GLY | 111 | 104.014 | 7.361 | 22.761 | 1.00 | 22.63 | H | C |
| ATOM | 2303 | C | GLY | 111 | 102.758 | 7.463 | 23.597 | 1.00 | 22.63 | H | C |
| ATOM | 2304 | O | GLY | 111 | 102.834 | 7.414 | 24.827 | 1.00 | 22.63 | H | O |
| ATOM | 2305 | N | THR | 112 | 101.611 | 7.619 | 22.938 | 1.00 | 17.52 | H | N |
| ATOM | 2306 | CA | THR | 112 | 100.333 | 7.740 | 23.630 | 1.00 | 17.52 | H | C |
| ATOM | 2307 | CB | THR | 112 | 100.058 | 9.211 | 24.030 | 1.00 | 34.98 | H | C |
| ATOM | 2308 | OG1 | THR | 112 | 98.958 | 9.261 | 24.939 | 1.00 | 34.98 | H | O |
| ATOM | 2309 | CG2 | THR | 112 | 99.734 | 10.055 | 22.809 | 1.00 | 34.98 | H | C |
| ATOM | 2310 | C | THR | 112 | 99.228 | 7.203 | 22.717 | 1.00 | 17.52 | H | C |
| ATOM | 2311 | O | THR | 112 | 99.133 | 7.559 | 21.533 | 1.00 | 17.52 | H | O |
| ATOM | 2312 | N | LEU | 113 | 98.396 | 6.340 | 23.292 | 1.00 | 32.82 | H | N |
| ATOM | 2313 | CA | LEU | 113 | 97.318 | 5.668 | 22.576 | 1.00 | 32.82 | H | C |
| ATOM | 2314 | CB | LEU | 113 | 96.953 | 4.374 | 23.328 | 1.00 | 26.98 | H | C |
| ATOM | 2315 | CG | LEU | 113 | 95.842 | 3.431 | 22.856 | 1.00 | 26.98 | H | C |
| ATOM | 2316 | CD1 | LEU | 113 | 94.455 | 4.057 | 23.105 | 1.00 | 26.98 | H | C |
| ATOM | 2317 | CD2 | LEU | 113 | 96.055 | 3.115 | 21.392 | 1.00 | 26.98 | H | C |
| ATOM | 2318 | C | LEU | 113 | 96.073 | 6.498 | 22.354 | 1.00 | 32.82 | H | C |
| ATOM | 2319 | O | LEU | 113 | 95.448 | 6.964 | 23.299 | 1.00 | 32.82 | H | O |
| ATOM | 2320 | N | VAL | 114 | 95.708 | 6.671 | 21.094 | 1.00 | 38.48 | H | N |
| ATOM | 2321 | CA | VAL | 114 | 94.506 | 7.419 | 20.767 | 1.00 | 38.48 | H | C |
| ATOM | 2322 | CB | VAL | 114 | 94.809 | 8.658 | 19.870 | 1.00 | 53.69 | H | C |
| ATOM | 2323 | CG1 | VAL | 114 | 93.518 | 9.420 | 19.571 | 1.00 | 53.69 | H | C |
| ATOM | 2324 | CG2 | VAL | 114 | 95.798 | 9.575 | 20.562 | 1.00 | 53.69 | H | C |
| ATOM | 2325 | C | VAL | 114 | 93.557 | 6.484 | 20.022 | 1.00 | 38.48 | H | C |
| ATOM | 2326 | O | VAL | 114 | 93.859 | 6.003 | 18.928 | 1.00 | 38.48 | H | O |
| ATOM | 2327 | N | THR | 115 | 92.411 | 6.216 | 20.629 | 1.00 | 29.76 | H | N |
| ATOM | 2328 | CA | THR | 115 | 91.414 | 5.356 | 20.012 | 1.00 | 29.76 | H | C |
| ATOM | 2329 | CB | THR | 115 | 91.081 | 4.125 | 20.916 | 1.00 | 30.84 | H | C |
| ATOM | 2330 | OG1 | THR | 115 | 92.292 | 3.453 | 21.300 | 1.00 | 30.84 | H | O |
| ATOM | 2331 | CG2 | THR | 115 | 90.180 | 3.151 | 20.170 | 1.00 | 30.84 | H | C |
| ATOM | 2332 | C | THR | 115 | 90.133 | 6.164 | 19.803 | 1.00 | 29.76 | H | C |
| ATOM | 2333 | O | THR | 115 | 89.700 | 6.905 | 20.694 | 1.00 | 29.76 | H | O |
| ATOM | 2334 | N | VAL | 116 | 89.543 | 6.056 | 18.619 | 1.00 | 38.29 | H | N |
| ATOM | 2335 | CA | VAL | 116 | 88.289 | 6.747 | 18.371 | 1.00 | 38.29 | H | C |
| ATOM | 2336 | CB | VAL | 116 | 88.395 | 7.822 | 17.240 | 1.00 | 10.28 | H | C |

Fig. 19: A-33

| | | | | | | | | | | | |
|---|---|---|---|---|---|---|---|---|---|---|---|
| ATOM | 2337 | CG1 | VAL | 116 | 89.861 | 8.088 | 16.922 | 1.00 | 10.28 | H | C |
| ATOM | 2338 | CG2 | VAL | 116 | 87.575 | 7.415 | 15.994 | 1.00 | 10.28 | H | C |
| ATOM | 2339 | C | VAL | 116 | 87.303 | 5.656 | 17.996 | 1.00 | 38.29 | H | C |
| ATOM | 2340 | O | VAL | 116 | 87.545 | 4.888 | 17.063 | 1.00 | 38.29 | H | O |
| ATOM | 2341 | N | SER | 117 | 86.207 | 5.579 | 18.746 | 1.00 | 41.53 | H | N |
| ATOM | 2342 | CA | SER | 117 | 85.193 | 4.565 | 18.517 | 1.00 | 41.53 | H | C |
| ATOM | 2343 | CB | SER | 117 | 85.768 | 3.182 | 18.851 | 1.00 | 61.62 | H | C |
| ATOM | 2344 | OG | SER | 117 | 84.788 | 2.165 | 18.751 | 1.00 | 61.62 | H | O |
| ATOM | 2345 | C | SER | 117 | 83.959 | 4.815 | 19.366 | 1.00 | 41.53 | H | C |
| ATOM | 2346 | O | SER | 117 | 84.049 | 5.336 | 20.482 | 1.00 | 41.53 | H | O |
| ATOM | 2347 | N | SER | 118 | 82.808 | 4.431 | 18.828 | 1.00 | 36.79 | H | N |
| ATOM | 2348 | CA | SER | 118 | 81.538 | 4.581 | 19.525 | 1.00 | 36.79 | H | C |
| ATOM | 2349 | CB | SER | 118 | 80.401 | 4.226 | 18.579 | 1.00 | 49.30 | H | C |
| ATOM | 2350 | OG | SER | 118 | 80.598 | 2.919 | 18.069 | 1.00 | 49.30 | H | O |
| ATOM | 2351 | C | SER | 118 | 81.510 | 3.649 | 20.740 | 1.00 | 36.79 | H | C |
| ATOM | 2352 | O | SER | 118 | 80.753 | 3.853 | 21.685 | 1.00 | 35.84 | H | O |
| ATOM | 2353 | N | ALA | 119 | 82.339 | 2.616 | 20.707 | 1.00 | 26.31 | H | N |
| ATOM | 2354 | CA | ALA | 119 | 82.412 | 1.679 | 21.815 | 1.00 | 26.31 | H | C |
| ATOM | 2355 | CB | ALA | 119 | 83.569 | 0.707 | 21.617 | 1.00 | 20.55 | H | C |
| ATOM | 2356 | C | ALA | 119 | 82.611 | 2.461 | 23.100 | 1.00 | 26.31 | H | C |
| ATOM | 2357 | O | ALA | 119 | 83.319 | 3.477 | 23.124 | 1.00 | 26.31 | H | O |
| ATOM | 2358 | N | SER | 120 | 81.988 | 1.975 | 24.166 | 1.00 | 39.08 | H | N |
| ATOM | 2359 | CA | SER | 120 | 82.074 | 2.621 | 25.462 | 1.00 | 39.08 | H | C |
| ATOM | 2360 | CB | SER | 120 | 80.711 | 2.597 | 26.151 | 1.00 | 57.76 | H | C |
| ATOM | 2361 | OG | SER | 120 | 79.720 | 3.179 | 25.329 | 1.00 | 57.76 | H | O |
| ATOM | 2362 | C | SER | 120 | 83.086 | 1.938 | 26.353 | 1.00 | 39.08 | H | C |
| ATOM | 2363 | O | SER | 120 | 83.194 | 0.715 | 26.362 | 1.00 | 39.08 | H | O |
| ATOM | 2364 | N | THR | 121 | 83.837 | 2.734 | 27.100 | 1.00 | 26.62 | H | N |
| ATOM | 2365 | CA | THR | 121 | 84.813 | 2.188 | 28.023 | 1.00 | 25.63 | H | C |
| ATOM | 2366 | CB | THR | 121 | 85.274 | 3.267 | 29.002 | 1.00 | 27.79 | H | C |
| ATOM | 2367 | OG1 | THR | 121 | 85.860 | 4.353 | 28.268 | 1.00 | 32.58 | H | O |
| ATOM | 2368 | CG2 | THR | 121 | 86.273 | 2.691 | 30.007 | 1.00 | 25.52 | H | C |
| ATOM | 2369 | C | THR | 121 | 84.108 | 1.078 | 28.801 | 1.00 | 26.35 | H | C |
| ATOM | 2370 | O | THR | 121 | 82.919 | 1.189 | 29.098 | 1.00 | 29.95 | H | O |
| ATOM | 2371 | N | LYS | 122 | 84.828 | 0.007 | 29.116 | 1.00 | 53.26 | H | N |
| ATOM | 2372 | CA | LYS | 122 | 84.243 | -1.102 | 29.864 | 1.00 | 50.64 | H | C |
| ATOM | 2373 | CB | LYS | 122 | 83.333 | -1.930 | 28.947 | 1.00 | 42.70 | H | C |
| ATOM | 2374 | CG | LYS | 122 | 83.009 | -3.347 | 29.437 | 1.00 | 44.07 | H | C |
| ATOM | 2375 | CD | LYS | 122 | 82.469 | -3.373 | 30.864 | 1.00 | 47.16 | H | C |
| ATOM | 2376 | CE | LYS | 122 | 82.216 | -4.805 | 31.337 | 1.00 | 51.36 | H | C |
| ATOM | 2377 | NZ | LYS | 122 | 81.986 | -4.880 | 32.809 | 1.00 | 50.23 | H | N |
| ATOM | 2378 | C | LYS | 122 | 85.301 | -1.991 | 30.496 | 1.00 | 52.40 | H | C |
| ATOM | 2379 | O | LYS | 122 | 86.154 | -2.548 | 29.809 | 1.00 | 54.02 | H | O |
| ATOM | 2380 | N | GLY | 123 | 85.240 | -2.114 | 31.817 | 1.00 | 42.56 | H | N |
| ATOM | 2381 | CA | GLY | 123 | 86.188 | -2.952 | 32.530 | 1.00 | 42.89 | H | C |
| ATOM | 2382 | C | GLY | 123 | 86.213 | -4.396 | 32.035 | 1.00 | 44.35 | H | C |
| ATOM | 2383 | O | GLY | 123 | 85.222 | -4.907 | 31.503 | 1.00 | 40.33 | H | O |
| ATOM | 2384 | N | PRO | 124 | 87.346 | -5.090 | 32.198 | 1.00 | 44.81 | H | N |
| ATOM | 2385 | CD | PRO | 124 | 88.680 | -4.632 | 32.633 | 1.00 | 21.78 | H | C |
| ATOM | 2386 | CA | PRO | 124 | 87.397 | -6.472 | 31.731 | 1.00 | 46.19 | H | C |
| ATOM | 2387 | CB | PRO | 124 | 88.868 | -6.668 | 31.439 | 1.00 | 22.93 | H | C |
| ATOM | 2388 | CG | PRO | 124 | 89.504 | -5.905 | 32.561 | 1.00 | 22.69 | H | C |
| ATOM | 2389 | C | PRO | 124 | 86.899 | -7.461 | 32.764 | 1.00 | 45.69 | H | C |
| ATOM | 2390 | O | PRO | 124 | 86.854 | -7.170 | 33.961 | 1.00 | 46.94 | H | O |
| ATOM | 2391 | N | SER | 125 | 86.507 | -8.631 | 32.287 | 1.00 | 43.49 | H | N |
| ATOM | 2392 | CA | SER | 125 | 86.053 | -9.678 | 33.176 | 1.00 | 38.23 | H | C |
| ATOM | 2393 | CB | SER | 125 | 84.858 | -10.416 | 32.579 | 1.00 | 23.34 | H | C |
| ATOM | 2394 | OG | SER | 125 | 83.756 | -9.544 | 32.402 | 1.00 | 25.34 | H | O |
| ATOM | 2395 | C | SER | 125 | 87.262 | -10.576 | 33.200 | 1.00 | 33.52 | H | C |
| ATOM | 2396 | O | SER | 125 | 87.738 | -10.972 | 32.139 | 1.00 | 32.91 | H | O |
| ATOM | 2397 | N | VAL | 126 | 87.787 | -10.873 | 34.386 | 1.00 | 23.96 | H | N |
| ATOM | 2398 | CA | VAL | 126 | 88.962 | -11.727 | 34.452 | 1.00 | 20.86 | H | C |
| ATOM | 2399 | CB | VAL | 126 | 90.135 | -11.003 | 35.174 | 1.00 | 22.19 | H | C |
| ATOM | 2400 | CG1 | VAL | 126 | 89.894 | -9.504 | 35.113 | 1.00 | 17.46 | H | C |
| ATOM | 2401 | CG2 | VAL | 126 | 90.331 | -11.507 | 36.597 | 1.00 | 22.90 | H | C |
| ATOM | 2402 | C | VAL | 126 | 88.666 | -13.091 | 35.065 | 1.00 | 20.51 | H | C |
| ATOM | 2403 | O | VAL | 126 | 88.382 | -13.227 | 36.256 | 1.00 | 24.79 | H | O |
| ATOM | 2404 | N | PHE | 127 | 88.713 | -14.105 | 34.213 | 1.00 | 27.15 | H | N |
| ATOM | 2405 | CA | PHE | 127 | 88.443 | -15.464 | 34.625 | 1.00 | 29.56 | H | C |
| ATOM | 2406 | CB | PHE | 127 | 87.628 | -16.167 | 33.544 | 1.00 | 16.06 | H | C |
| ATOM | 2407 | CG | PHE | 127 | 86.392 | -15.419 | 33.141 | 1.00 | 12.41 | H | C |
| ATOM | 2408 | CD1 | PHE | 127 | 85.380 | -15.167 | 34.071 | 1.00 | 11.21 | H | C |
| ATOM | 2409 | CD2 | PHE | 127 | 86.255 | -14.922 | 31.840 | 1.00 | 10.06 | H | C |

Fig. 19: A-34

| | | | | | | | | | | | |
|---|---|---|---|---|---|---|---|---|---|---|---|
| ATOM | 2410 | CE1 | PHE | 127 | 84.254 | -14.428 | 33.721 | 1.00 | 12.93 | H | C |
| ATOM | 2411 | CE2 | PHE | 127 | 85.126 | -14.174 | 31.470 | 1.00 | 6.89 | H | C |
| ATOM | 2412 | CZ | PHE | 127 | 84.125 | -13.925 | 32.413 | 1.00 | 6.94 | H | C |
| ATOM | 2413 | C | PHE | 127 | 89.763 | -16.183 | 34.825 | 1.00 | 31.37 | H | C |
| ATOM | 2414 | O | PHE | 127 | 90.806 | -15.733 | 34.351 | 1.00 | 34.05 | H | O |
| ATOM | 2415 | N | PRO | 128 | 89.743 | -17.310 | 35.540 | 1.00 | 21.35 | H | N |
| ATOM | 2416 | CD | PRO | 128 | 88.681 | -17.812 | 36.434 | 1.00 | 32.37 | H | C |
| ATOM | 2417 | CA | PRO | 128 | 90.996 | -18.039 | 35.752 | 1.00 | 22.25 | H | C |
| ATOM | 2418 | CB | PRO | 128 | 90.823 | -18.577 | 37.161 | 1.00 | 34.03 | H | C |
| ATOM | 2419 | CG | PRO | 128 | 89.358 | -18.983 | 37.130 | 1.00 | 33.18 | H | C |
| ATOM | 2420 | C | PRO | 128 | 91.198 | -19.176 | 34.739 | 1.00 | 21.65 | H | C |
| ATOM | 2421 | O | PRO | 128 | 90.235 | -19.770 | 34.244 | 1.00 | 21.29 | H | O |
| ATOM | 2422 | N | LEU | 129 | 92.457 | -19.457 | 34.432 | 1.00 | 17.17 | H | N |
| ATOM | 2423 | CA | LEU | 129 | 92.811 | -20.557 | 33.545 | 1.00 | 19.61 | H | C |
| ATOM | 2424 | CB | LEU | 129 | 93.683 | -20.061 | 32.396 | 1.00 | 18.81 | H | C |
| ATOM | 2425 | CG | LEU | 129 | 93.086 | -18.872 | 31.635 | 1.00 | 18.17 | H | C |
| ATOM | 2426 | CD1 | LEU | 129 | 94.115 | -18.254 | 30.696 | 1.00 | 16.12 | H | C |
| ATOM | 2427 | CD2 | LEU | 129 | 91.886 | -19.341 | 30.870 | 1.00 | 11.94 | H | C |
| ATOM | 2428 | C | LEU | 129 | 93.601 | -21.457 | 34.497 | 1.00 | 23.45 | H | C |
| ATOM | 2429 | O | LEU | 129 | 94.824 | -21.481 | 34.499 | 1.00 | 25.82 | H | O |
| ATOM | 2430 | N | ALA | 130 | 92.870 | -22.179 | 35.332 | 1.00 | 16.93 | H | N |
| ATOM | 2431 | CA | ALA | 130 | 93.455 | -23.046 | 36.341 | 1.00 | 18.97 | H | C |
| ATOM | 2432 | CB | ALA | 130 | 92.363 | -23.561 | 37.256 | 1.00 | 49.82 | H | C |
| ATOM | 2433 | C | ALA | 130 | 94.280 | -24.219 | 35.846 | 1.00 | 18.88 | H | C |
| ATOM | 2434 | O | ALA | 130 | 93.928 | -24.876 | 34.869 | 1.00 | 20.61 | H | O |
| ATOM | 2435 | N | PRO | 131 | 95.401 | -24.490 | 36.534 | 1.00 | 29.98 | H | N |
| ATOM | 2436 | CD | PRO | 131 | 95.929 | -23.703 | 37.665 | 1.00 | 16.68 | H | C |
| ATOM | 2437 | CA | PRO | 131 | 96.301 | -25.595 | 36.198 | 1.00 | 27.20 | H | C |
| ATOM | 2438 | CB | PRO | 131 | 97.453 | -25.424 | 37.196 | 1.00 | 12.88 | H | C |
| ATOM | 2439 | CG | PRO | 131 | 96.815 | -24.691 | 38.354 | 1.00 | 15.86 | H | C |
| ATOM | 2440 | C | PRO | 131 | 95.534 | -26.897 | 36.405 | 1.00 | 26.68 | H | C |
| ATOM | 2441 | O | PRO | 131 | 94.666 | -26.978 | 37.274 | 1.00 | 27.16 | H | O |
| ATOM | 2442 | N | SER | 132 | 95.838 | -27.912 | 35.607 | 1.00 | 64.88 | H | N |
| ATOM | 2443 | CA | SER | 132 | 95.138 | -29.187 | 35.720 | 1.00 | 67.56 | H | C |
| ATOM | 2444 | CB | SER | 132 | 93.745 | -29.075 | 35.086 | 1.00 | 44.77 | H | C |
| ATOM | 2445 | OG | SER | 132 | 93.824 | -28.747 | 33.704 | 1.00 | 46.53 | H | O |
| ATOM | 2446 | C | SER | 132 | 95.918 | -30.284 | 35.020 | 1.00 | 69.15 | H | C |
| ATOM | 2447 | O | SER | 132 | 97.107 | -30.139 | 34.757 | 1.00 | 69.80 | H | O |
| ATOM | 2448 | N | SER | 133 | 95.247 | -31.391 | 34.732 | 1.00 | 58.75 | H | N |
| ATOM | 2449 | CA | SER | 133 | 95.894 | -32.483 | 34.024 | 1.00 | 61.13 | H | C |
| ATOM | 2450 | CB | SER | 133 | 95.007 | -33.738 | 34.068 | 1.00 | 91.14 | H | C |
| ATOM | 2451 | OG | SER | 133 | 93.668 | -33.456 | 33.684 | 1.00 | 100.88 | H | O |
| ATOM | 2452 | C | SER | 133 | 96.121 | -32.017 | 32.576 | 1.00 | 60.76 | H | C |
| ATOM | 2453 | O | SER | 133 | 97.091 | -32.413 | 31.927 | 1.00 | 61.01 | H | O |
| ATOM | 2454 | N | LYS | 134 | 95.220 | -31.156 | 32.095 | 1.00 | 101.65 | H | N |
| ATOM | 2455 | CA | LYS | 134 | 95.285 | -30.605 | 30.739 | 1.00 | 102.79 | H | C |
| ATOM | 2456 | CB | LYS | 134 | 93.951 | -29.962 | 30.341 | 1.00 | 44.82 | H | C |
| ATOM | 2457 | CG | LYS | 134 | 92.703 | -30.784 | 30.609 | 1.00 | 52.94 | H | C |
| ATOM | 2458 | CD | LYS | 134 | 92.058 | -30.452 | 31.959 | 1.00 | 55.86 | H | C |
| ATOM | 2459 | CE | LYS | 134 | 90.686 | -31.127 | 32.091 | 1.00 | 53.71 | H | C |
| ATOM | 2460 | NZ | LYS | 134 | 89.988 | -30.792 | 33.367 | 1.00 | 52.28 | H | N |
| ATOM | 2461 | C | LYS | 134 | 96.364 | -29.531 | 30.655 | 1.00 | 102.96 | H | C |
| ATOM | 2462 | O | LYS | 134 | 96.932 | -29.284 | 29.589 | 1.00 | 104.03 | H | O |
| ATOM | 2463 | N | SER | 135 | 96.619 | -28.885 | 31.791 | 1.00 | 77.03 | H | N |
| ATOM | 2464 | CA | SER | 135 | 97.611 | -27.818 | 31.896 | 1.00 | 76.76 | H | C |
| ATOM | 2465 | CB | SER | 135 | 97.069 | -26.698 | 32.784 | 1.00 | 81.66 | H | C |
| ATOM | 2466 | OG | SER | 135 | 95.726 | -26.390 | 32.443 | 1.00 | 81.07 | H | O |
| ATOM | 2467 | C | SER | 135 | 98.911 | -28.358 | 32.488 | 1.00 | 71.98 | H | C |
| ATOM | 2468 | O | SER | 135 | 99.733 | -27.601 | 33.006 | 1.00 | 72.29 | H | O |
| ATOM | 2469 | N | THR | 136 | 99.075 | -29.676 | 32.418 | 1.00 | 86.02 | H | N |
| ATOM | 2470 | CA | THR | 136 | 100.262 | -30.351 | 32.932 | 1.00 | 86.44 | H | C |
| ATOM | 2471 | CB | THR | 136 | 99.897 | -31.391 | 34.036 | 1.00 | 47.16 | H | C |
| ATOM | 2472 | OG1 | THR | 136 | 99.491 | -30.715 | 35.237 | 1.00 | 47.25 | H | O |
| ATOM | 2473 | CG2 | THR | 136 | 101.096 | -32.281 | 34.354 | 1.00 | 50.70 | H | C |
| ATOM | 2474 | C | THR | 136 | 100.977 | -31.072 | 31.788 | 1.00 | 86.90 | H | C |
| ATOM | 2475 | O | THR | 136 | 100.334 | -31.615 | 30.885 | 1.00 | 85.81 | H | O |
| ATOM | 2476 | N | SER | 137 | 102.309 | -31.059 | 31.836 | 1.00 | 82.54 | H | N |
| ATOM | 2477 | CA | SER | 137 | 103.164 | -31.700 | 30.834 | 1.00 | 82.34 | H | C |
| ATOM | 2478 | CB | SER | 137 | 103.113 | -30.942 | 29.495 | 1.00 | 65.40 | H | C |
| ATOM | 2479 | OG | SER | 137 | 101.863 | -31.097 | 28.841 | 1.00 | 66.87 | H | O |
| ATOM | 2480 | C | SER | 137 | 104.600 | -31.715 | 31.352 | 1.00 | 82.68 | H | C |
| ATOM | 2481 | O | SER | 137 | 105.321 | -30.722 | 31.244 | 1.00 | 84.11 | H | O |
| ATOM | 2482 | N | GLY | 138 | 105.016 | -32.845 | 31.911 | 1.00 | 62.73 | H | N |

Fig. 19: A-35

| | | | | | | | | | | | |
|---|---|---|---|---|---|---|---|---|---|---|---|
| ATOM | 2483 | CA | GLY | 138 | 106.361 | -32.941 | 32.438 | 1.00 | 62.79 | H | C |
| ATOM | 2484 | C | GLY | 138 | 106.394 | -32.371 | 33.840 | 1.00 | 65.01 | H | C |
| ATOM | 2485 | O | GLY | 138 | 105.392 | -32.410 | 34.555 | 1.00 | 65.52 | H | O |
| ATOM | 2486 | N | GLY | 139 | 107.537 | -31.827 | 34.237 | 1.00 | 45.62 | H | N |
| ATOM | 2487 | CA | GLY | 139 | 107.645 | -31.267 | 35.570 | 1.00 | 45.97 | H | C |
| ATOM | 2488 | C | GLY | 139 | 107.037 | -29.884 | 35.680 | 1.00 | 46.52 | H | C |
| ATOM | 2489 | O | GLY | 139 | 107.020 | -29.297 | 36.762 | 1.00 | 50.66 | H | O |
| ATOM | 2490 | N | THR | 140 | 106.527 | -29.365 | 34.568 | 1.00 | 41.37 | H | N |
| ATOM | 2491 | CA | THR | 140 | 105.941 | -28.030 | 34.571 | 1.00 | 35.80 | H | C |
| ATOM | 2492 | CB | THR | 140 | 106.626 | -27.108 | 33.533 | 1.00 | 32.97 | H | C |
| ATOM | 2493 | OG1 | THR | 140 | 105.886 | -27.138 | 32.311 | 1.00 | 30.01 | H | O |
| ATOM | 2494 | CG2 | THR | 140 | 108.052 | -27.574 | 33.250 | 1.00 | 33.92 | H | C |
| ATOM | 2495 | C | THR | 140 | 104.434 | -27.993 | 34.299 | 1.00 | 32.68 | H | C |
| ATOM | 2496 | O | THR | 140 | 103.884 | -28.820 | 33.560 | 1.00 | 31.27 | H | O |
| ATOM | 2497 | N | ALA | 141 | 103.777 | -27.013 | 34.914 | 1.00 | 23.19 | H | N |
| ATOM | 2498 | CA | ALA | 141 | 102.350 | -26.817 | 34.752 | 1.00 | 23.90 | H | C |
| ATOM | 2499 | CB | ALA | 141 | 101.647 | -26.986 | 36.087 | 1.00 | 31.87 | H | C |
| ATOM | 2500 | C | ALA | 141 | 102.121 | -25.408 | 34.206 | 1.00 | 24.06 | H | C |
| ATOM | 2501 | O | ALA | 141 | 102.930 | -24.498 | 34.415 | 1.00 | 28.34 | H | O |
| ATOM | 2502 | N | ALA | 142 | 101.022 | -25.239 | 33.487 | 1.00 | 36.28 | H | N |
| ATOM | 2503 | CA | ALA | 142 | 100.685 | -23.948 | 32.924 | 1.00 | 31.12 | H | C |
| ATOM | 2504 | CB | ALA | 142 | 100.507 | -24.062 | 31.419 | 1.00 | 1.87 | H | C |
| ATOM | 2505 | C | ALA | 142 | 99.389 | -23.519 | 33.588 | 1.00 | 29.11 | H | C |
| ATOM | 2506 | O | ALA | 142 | 98.565 | -24.359 | 33.961 | 1.00 | 33.50 | H | O |
| ATOM | 2507 | N | LEU | 143 | 99.233 | -22.211 | 33.751 | 1.00 | 27.06 | H | N |
| ATOM | 2508 | CA | LEU | 143 | 98.054 | -21.611 | 34.372 | 1.00 | 31.22 | H | C |
| ATOM | 2509 | CB | LEU | 143 | 98.154 | -21.670 | 35.900 | 1.00 | 28.24 | H | C |
| ATOM | 2510 | CG | LEU | 143 | 99.269 | -20.865 | 36.582 | 1.00 | 30.55 | H | C |
| ATOM | 2511 | CD1 | LEU | 143 | 98.702 | -19.526 | 36.991 | 1.00 | 23.14 | H | C |
| ATOM | 2512 | CD2 | LEU | 143 | 99.817 | -21.596 | 37.809 | 1.00 | 37.29 | H | C |
| ATOM | 2513 | C | LEU | 143 | 98.068 | -20.169 | 33.913 | 1.00 | 34.46 | H | C |
| ATOM | 2514 | O | LEU | 143 | 99.069 | -19.700 | 33.364 | 1.00 | 32.14 | H | O |
| ATOM | 2515 | N | GLY | 144 | 96.970 | -19.458 | 34.128 | 1.00 | 25.78 | H | N |
| ATOM | 2516 | CA | GLY | 144 | 96.922 | -18.074 | 33.694 | 1.00 | 28.57 | H | C |
| ATOM | 2517 | C | GLY | 144 | 95.578 | -17.425 | 33.896 | 1.00 | 31.81 | H | C |
| ATOM | 2518 | O | GLY | 144 | 94.693 | -17.985 | 34.543 | 1.00 | 35.57 | H | O |
| ATOM | 2519 | N | CYS | 145 | 95.420 | -16.235 | 33.335 | 1.00 | 24.76 | H | N |
| ATOM | 2520 | CA | CYS | 145 | 94.177 | -15.501 | 33.471 | 1.00 | 23.67 | H | C |
| ATOM | 2521 | C | CYS | 145 | 93.665 | -15.071 | 32.122 | 1.00 | 21.65 | H | C |
| ATOM | 2522 | O | CYS | 145 | 94.437 | -14.868 | 31.188 | 1.00 | 22.23 | H | O |
| ATOM | 2523 | CB | CYS | 145 | 94.385 | -14.273 | 34.363 | 1.00 | 28.67 | H | C |
| ATOM | 2524 | SG | CYS | 145 | 94.354 | -14.658 | 36.141 | 1.00 | 36.96 | H | S |
| ATOM | 2525 | N | LEU | 146 | 92.351 | -14.940 | 32.024 | 1.00 | 43.52 | H | N |
| ATOM | 2526 | CA | LEU | 146 | 91.712 | -14.512 | 30.792 | 1.00 | 43.76 | H | C |
| ATOM | 2527 | CB | LEU | 146 | 90.715 | -15.580 | 30.314 | 1.00 | 38.89 | H | C |
| ATOM | 2528 | CG | LEU | 146 | 89.754 | -15.245 | 29.164 | 1.00 | 28.77 | H | C |
| ATOM | 2529 | CD1 | LEU | 146 | 90.519 | -14.669 | 27.982 | 1.00 | 25.69 | H | C |
| ATOM | 2530 | CD2 | LEU | 146 | 88.989 | -16.489 | 28.755 | 1.00 | 35.84 | H | C |
| ATOM | 2531 | C | LEU | 146 | 90.997 | -13.188 | 31.055 | 1.00 | 45.61 | H | C |
| ATOM | 2532 | O | LEU | 146 | 89.943 | -13.160 | 31.690 | 1.00 | 45.79 | H | O |
| ATOM | 2533 | N | VAL | 147 | 91.609 | -12.098 | 30.593 | 1.00 | 12.91 | H | N |
| ATOM | 2534 | CA | VAL | 147 | 91.069 | -10.732 | 30.716 | 1.00 | 12.94 | H | C |
| ATOM | 2535 | CB | VAL | 147 | 92.231 | -9.696 | 30.638 | 1.00 | 24.21 | H | C |
| ATOM | 2536 | CG1 | VAL | 147 | 91.703 | -8.291 | 30.722 | 1.00 | 25.32 | H | C |
| ATOM | 2537 | CG2 | VAL | 147 | 93.212 | -9.947 | 31.778 | 1.00 | 13.52 | H | C |
| ATOM | 2538 | C | VAL | 147 | 90.101 | -10.563 | 29.532 | 1.00 | 18.31 | H | C |
| ATOM | 2539 | O | VAL | 147 | 90.532 | -10.460 | 28.381 | 1.00 | 18.59 | H | O |
| ATOM | 2540 | N | LYS | 148 | 88.798 | -10.519 | 29.806 | 1.00 | 25.16 | H | N |
| ATOM | 2541 | CA | LYS | 148 | 87.835 | -10.467 | 28.709 | 1.00 | 29.22 | H | C |
| ATOM | 2542 | CB | LYS | 148 | 87.140 | -11.827 | 28.609 | 1.00 | 15.56 | H | C |
| ATOM | 2543 | CG | LYS | 148 | 86.353 | -12.032 | 27.348 | 1.00 | 22.92 | H | C |
| ATOM | 2544 | CD | LYS | 148 | 85.731 | -13.405 | 27.355 | 1.00 | 22.16 | H | C |
| ATOM | 2545 | CE | LYS | 148 | 84.795 | -13.570 | 26.190 | 1.00 | 24.54 | H | C |
| ATOM | 2546 | NZ | LYS | 148 | 85.514 | -13.308 | 24.928 | 1.00 | 22.92 | H | N |
| ATOM | 2547 | C | LYS | 148 | 86.777 | -9.372 | 28.646 | 1.00 | 32.79 | H | C |
| ATOM | 2548 | O | LYS | 148 | 86.332 | -8.844 | 29.664 | 1.00 | 33.18 | H | O |
| ATOM | 2549 | N | ASP | 149 | 86.387 | -9.069 | 27.409 | 1.00 | 55.13 | H | N |
| ATOM | 2550 | CA | ASP | 149 | 85.381 | -8.070 | 27.078 | 1.00 | 53.92 | H | C |
| ATOM | 2551 | CB | ASP | 149 | 83.993 | -8.595 | 27.429 | 1.00 | 38.49 | H | C |
| ATOM | 2552 | CG | ASP | 149 | 83.635 | -9.853 | 26.661 | 1.00 | 42.52 | H | C |
| ATOM | 2553 | OD1 | ASP | 149 | 83.797 | -9.882 | 25.421 | 1.00 | 46.52 | H | O |
| ATOM | 2554 | OD2 | ASP | 149 | 83.181 | -10.817 | 27.305 | 1.00 | 41.08 | H | O |
| ATOM | 2555 | C | ASP | 149 | 85.585 | -6.690 | 27.698 | 1.00 | 56.06 | H | C |

Fig. 19: A-36

| | | | | | | | | | | | |
|---|---|---|---|---|---|---|---|---|---|---|---|
| ATOM | 2556 | O | ASP | 149 | 84.720 | -6.175 | 28.415 | 1.00 | 57.30 | H | O |
| ATOM | 2557 | N | TYR | 150 | 86.734 | -6.091 | 27.399 | 1.00 | 33.00 | H | N |
| ATOM | 2558 | CA | TYR | 150 | 87.072 | -4.770 | 27.897 | 1.00 | 33.34 | H | C |
| ATOM | 2559 | CB | TYR | 150 | 88.306 | -4.844 | 28.797 | 1.00 | 39.19 | H | C |
| ATOM | 2560 | CG | TYR | 150 | 89.622 | -5.155 | 28.097 | 1.00 | 44.75 | H | C |
| ATOM | 2561 | CD1 | TYR | 150 | 90.405 | -4.137 | 27.556 | 1.00 | 44.06 | H | C |
| ATOM | 2562 | CE1 | TYR | 150 | 91.653 | -4.401 | 26.994 | 1.00 | 46.40 | H | C |
| ATOM | 2563 | CD2 | TYR | 150 | 90.121 | -6.457 | 28.046 | 1.00 | 44.23 | H | C |
| ATOM | 2564 | CE2 | TYR | 150 | 91.369 | -6.730 | 27.483 | 1.00 | 43.19 | H | C |
| ATOM | 2565 | CZ | TYR | 150 | 92.130 | -5.694 | 26.963 | 1.00 | 45.07 | H | C |
| ATOM | 2566 | OH | TYR | 150 | 93.376 | -5.942 | 26.431 | 1.00 | 42.66 | H | O |
| ATOM | 2567 | C | TYR | 150 | 87.331 | -3.838 | 26.723 | 1.00 | 34.19 | H | C |
| ATOM | 2568 | O | TYR | 150 | 87.420 | -4.275 | 25.569 | 1.00 | 36.79 | H | O |
| ATOM | 2569 | N | PHE | 151 | 87.450 | -2.549 | 27.034 | 1.00 | 53.36 | H | N |
| ATOM | 2570 | CA | PHE | 151 | 87.686 | -1.522 | 26.034 | 1.00 | 51.06 | H | C |
| ATOM | 2571 | CB | PHE | 151 | 86.520 | -1.506 | 25.038 | 1.00 | 22.52 | H | C |
| ATOM | 2572 | CG | PHE | 151 | 86.663 | -0.500 | 23.923 | 1.00 | 22.34 | H | C |
| ATOM | 2573 | CD1 | PHE | 151 | 86.509 | 0.865 | 24.164 | 1.00 | 21.58 | H | C |
| ATOM | 2574 | CD2 | PHE | 151 | 86.896 | -0.923 | 22.616 | 1.00 | 24.08 | H | C |
| ATOM | 2575 | CE1 | PHE | 151 | 86.576 | 1.789 | 23.117 | 1.00 | 22.62 | H | C |
| ATOM | 2576 | CE2 | PHE | 151 | 86.968 | -0.003 | 21.558 | 1.00 | 25.39 | H | C |
| ATOM | 2577 | CZ | PHE | 151 | 86.805 | 1.351 | 21.809 | 1.00 | 25.56 | H | C |
| ATOM | 2578 | C | PHE | 151 | 87.819 | -0.175 | 26.734 | 1.00 | 48.17 | H | C |
| ATOM | 2579 | O | PHE | 151 | 87.161 | 0.084 | 27.737 | 1.00 | 47.45 | H | O |
| ATOM | 2580 | N | PRO | 152 | 88.712 | 0.685 | 26.232 | 1.00 | 46.09 | H | N |
| ATOM | 2581 | CD | PRO | 152 | 88.959 | 2.055 | 26.730 | 1.00 | 7.14 | H | C |
| ATOM | 2582 | CA | PRO | 152 | 89.554 | 0.388 | 25.065 | 1.00 | 47.66 | H | C |
| ATOM | 2583 | CB | PRO | 152 | 89.773 | 1.765 | 24.464 | 1.00 | 12.39 | H | C |
| ATOM | 2584 | CG | PRO | 152 | 90.017 | 2.594 | 25.730 | 1.00 | 9.55 | H | C |
| ATOM | 2585 | C | PRO | 152 | 90.835 | -0.199 | 25.636 | 1.00 | 47.42 | H | C |
| ATOM | 2586 | O | PRO | 152 | 90.826 | -0.716 | 26.748 | 1.00 | 49.63 | H | O |
| ATOM | 2587 | N | GLU | 153 | 91.933 | -0.128 | 24.894 | 1.00 | 48.37 | H | N |
| ATOM | 2588 | CA | GLU | 153 | 93.200 | -0.620 | 25.422 | 1.00 | 45.01 | H | C |
| ATOM | 2589 | CB | GLU | 153 | 94.232 | -0.788 | 24.308 | 1.00 | 35.76 | H | C |
| ATOM | 2590 | CG | GLU | 153 | 93.983 | -1.951 | 23.370 | 1.00 | 41.71 | H | C |
| ATOM | 2591 | CD | GLU | 153 | 94.465 | -3.279 | 23.920 | 1.00 | 49.73 | H | C |
| ATOM | 2592 | OE1 | GLU | 153 | 94.329 | -4.276 | 23.191 | 1.00 | 53.96 | H | O |
| ATOM | 2593 | OE2 | GLU | 153 | 94.979 | -3.337 | 25.062 | 1.00 | 49.06 | H | O |
| ATOM | 2594 | C | GLU | 153 | 93.667 | 0.487 | 26.355 | 1.00 | 40.62 | H | C |
| ATOM | 2595 | O | GLU | 153 | 93.160 | 1.611 | 26.288 | 1.00 | 43.09 | H | O |
| ATOM | 2596 | N | PRO | 154 | 94.626 | 0.193 | 27.242 | 1.00 | 31.67 | H | N |
| ATOM | 2597 | CD | PRO | 154 | 95.605 | 1.250 | 27.562 | 1.00 | 24.24 | H | C |
| ATOM | 2598 | CA | PRO | 154 | 95.266 | -1.107 | 27.404 | 1.00 | 32.01 | H | C |
| ATOM | 2599 | CB | PRO | 154 | 96.707 | -0.803 | 27.072 | 1.00 | 23.56 | H | C |
| ATOM | 2600 | CG | PRO | 154 | 96.899 | 0.447 | 27.855 | 1.00 | 23.31 | H | C |
| ATOM | 2601 | C | PRO | 154 | 95.127 | -1.577 | 28.846 | 1.00 | 37.33 | H | C |
| ATOM | 2602 | O | PRO | 154 | 94.929 | -0.788 | 29.770 | 1.00 | 40.93 | H | O |
| ATOM | 2603 | N | VAL | 155 | 95.270 | -2.874 | 29.029 | 1.00 | 27.89 | H | N |
| ATOM | 2604 | CA | VAL | 155 | 95.171 | -3.468 | 30.339 | 1.00 | 28.93 | H | C |
| ATOM | 2605 | CB | VAL | 155 | 94.167 | -4.647 | 30.309 | 1.00 | 32.63 | H | C |
| ATOM | 2606 | CG1 | VAL | 155 | 94.624 | -5.699 | 29.306 | 1.00 | 39.44 | H | C |
| ATOM | 2607 | CG2 | VAL | 155 | 94.030 | -5.243 | 31.690 | 1.00 | 38.09 | H | C |
| ATOM | 2608 | C | VAL | 155 | 96.561 | -3.969 | 30.715 | 1.00 | 29.75 | H | C |
| ATOM | 2609 | O | VAL | 155 | 97.319 | -4.427 | 29.856 | 1.00 | 34.58 | H | O |
| ATOM | 2610 | N | THR | 156 | 96.898 | -3.864 | 31.995 | 1.00 | 30.47 | H | N |
| ATOM | 2611 | CA | THR | 156 | 98.195 | -4.322 | 32.482 | 1.00 | 30.67 | H | C |
| ATOM | 2612 | CB | THR | 156 | 98.855 | -3.316 | 33.458 | 1.00 | 37.06 | H | C |
| ATOM | 2613 | OG1 | THR | 156 | 98.554 | -3.699 | 34.810 | 1.00 | 41.96 | H | O |
| ATOM | 2614 | CG2 | THR | 156 | 98.346 | -1.895 | 33.213 | 1.00 | 35.30 | H | C |
| ATOM | 2615 | C | THR | 156 | 97.956 | -5.589 | 33.276 | 1.00 | 28.26 | H | C |
| ATOM | 2616 | O | THR | 156 | 96.915 | -5.736 | 33.906 | 1.00 | 24.33 | H | O |
| ATOM | 2617 | N | VAL | 157 | 98.914 | -6.501 | 33.250 | 1.00 | 20.40 | H | N |
| ATOM | 2618 | CA | VAL | 157 | 98.784 | -7.731 | 34.014 | 1.00 | 23.86 | H | C |
| ATOM | 2619 | CB | VAL | 157 | 98.263 | -8.918 | 33.149 | 1.00 | 6.55 | H | C |
| ATOM | 2620 | CG1 | VAL | 157 | 98.307 | -10.191 | 33.970 | 1.00 | 2.70 | H | C |
| ATOM | 2621 | CG2 | VAL | 157 | 96.817 | -8.649 | 32.662 | 1.00 | 8.40 | H | C |
| ATOM | 2622 | C | VAL | 157 | 100.122 | -8.142 | 34.618 | 1.00 | 25.91 | H | C |
| ATOM | 2623 | O | VAL | 157 | 101.130 | -8.220 | 33.918 | 1.00 | 28.24 | H | O |
| ATOM | 2624 | N | SER | 158 | 100.127 | -8.401 | 35.918 | 1.00 | 37.92 | H | N |
| ATOM | 2625 | CA | SER | 158 | 101.333 | -8.840 | 36.606 | 1.00 | 38.42 | H | C |
| ATOM | 2626 | CB | SER | 158 | 101.852 | -7.738 | 37.521 | 1.00 | 26.79 | H | C |
| ATOM | 2627 | OG | SER | 158 | 101.008 | -7.591 | 38.648 | 1.00 | 29.78 | H | O |
| ATOM | 2628 | C | SER | 158 | 100.947 | -10.064 | 37.439 | 1.00 | 37.35 | H | C |

Fig. 19: A-37

| | | | | | | | | | | | |
|---|---|---|---|---|---|---|---|---|---|---|---|
| ATOM | 2629 | O | SER | 158 | 99.765 | -10.366 | 37.583 | 1.00 | 35.45 | H | O |
| ATOM | 2630 | N | TRP | 159 | 101.926 | -10.772 | 37.989 | 1.00 | 38.23 | H | N |
| ATOM | 2631 | CA | TRP | 159 | 101.604 | -11.945 | 38.790 | 1.00 | 38.96 | H | C |
| ATOM | 2632 | CB | TRP | 159 | 102.060 | -13.224 | 38.074 | 1.00 | 33.06 | H | C |
| ATOM | 2633 | CG | TRP | 159 | 101.197 | -13.555 | 36.899 | 1.00 | 30.80 | H | C |
| ATOM | 2634 | CD2 | TRP | 159 | 100.089 | -14.463 | 36.879 | 1.00 | 31.04 | H | C |
| ATOM | 2635 | CE2 | TRP | 159 | 99.540 | -14.423 | 35.577 | 1.00 | 29.21 | H | C |
| ATOM | 2636 | CE3 | TRP | 159 | 99.507 | -15.307 | 37.836 | 1.00 | 31.84 | H | C |
| ATOM | 2637 | CD1 | TRP | 159 | 101.271 | -13.015 | 35.649 | 1.00 | 26.46 | H | C |
| ATOM | 2638 | NE1 | TRP | 159 | 100.280 | -13.531 | 34.848 | 1.00 | 30.17 | H | N |
| ATOM | 2639 | CZ2 | TRP | 159 | 98.439 | -15.196 | 35.204 | 1.00 | 33.73 | H | C |
| ATOM | 2640 | CZ3 | TRP | 159 | 98.407 | -16.079 | 37.465 | 1.00 | 33.56 | H | C |
| ATOM | 2641 | CH2 | TRP | 159 | 97.887 | -16.018 | 36.158 | 1.00 | 34.95 | H | C |
| ATOM | 2642 | C | TRP | 159 | 102.166 | -11.908 | 40.203 | 1.00 | 41.53 | H | C |
| ATOM | 2643 | O | TRP | 159 | 103.355 | -11.670 | 40.412 | 1.00 | 40.45 | H | O |
| ATOM | 2644 | N | ASN | 160 | 101.295 | -12.163 | 41.170 | 1.00 | 50.63 | H | N |
| ATOM | 2645 | CA | ASN | 160 | 101.699 | -12.153 | 42.557 | 1.00 | 51.18 | H | C |
| ATOM | 2646 | CB | ASN | 160 | 102.753 | -13.230 | 42.814 | 1.00 | 31.23 | H | C |
| ATOM | 2647 | CG | ASN | 160 | 102.145 | -14.619 | 42.946 | 1.00 | 28.65 | H | C |
| ATOM | 2648 | OD1 | ASN | 160 | 100.924 | -14.784 | 42.911 | 1.00 | 22.55 | H | O |
| ATOM | 2649 | ND2 | ASN | 160 | 103.000 | -15.630 | 43.107 | 1.00 | 28.71 | H | N |
| ATOM | 2650 | C | ASN | 160 | 102.245 | -10.777 | 42.891 | 1.00 | 53.56 | H | C |
| ATOM | 2651 | O | ASN | 160 | 103.277 | -10.637 | 43.554 | 1.00 | 51.84 | H | O |
| ATOM | 2652 | N | SER | 161 | 101.548 | -9.758 | 42.397 | 1.00 | 57.36 | H | N |
| ATOM | 2653 | CA | SER | 161 | 101.915 | -8.372 | 42.651 | 1.00 | 58.07 | H | C |
| ATOM | 2654 | CB | SER | 161 | 101.833 | -8.106 | 44.161 | 1.00 | 44.49 | H | C |
| ATOM | 2655 | OG | SER | 161 | 100.611 | -8.586 | 44.713 | 1.00 | 48.26 | H | O |
| ATOM | 2656 | C | SER | 161 | 103.305 | -7.997 | 42.118 | 1.00 | 57.98 | H | C |
| ATOM | 2657 | O | SER | 161 | 103.779 | -6.883 | 42.329 | 1.00 | 58.91 | H | O |
| ATOM | 2658 | N | GLY | 162 | 103.957 | -8.927 | 41.431 | 1.00 | 43.40 | H | N |
| ATOM | 2659 | CA | GLY | 162 | 105.271 | -8.641 | 40.886 | 1.00 | 41.61 | H | C |
| ATOM | 2660 | C | GLY | 162 | 106.343 | -9.670 | 41.195 | 1.00 | 41.13 | H | C |
| ATOM | 2661 | O | GLY | 162 | 107.340 | -9.756 | 40.475 | 1.00 | 41.89 | H | O |
| ATOM | 2662 | N | ALA | 163 | 106.144 | -10.460 | 42.248 | 1.00 | 32.79 | H | N |
| ATOM | 2663 | CA | ALA | 163 | 107.135 | -11.462 | 42.644 | 1.00 | 33.15 | H | C |
| ATOM | 2664 | CB | ALA | 163 | 106.845 | -11.956 | 44.065 | 1.00 | 7.75 | H | C |
| ATOM | 2665 | C | ALA | 163 | 107.265 | -12.651 | 41.702 | 1.00 | 33.69 | H | C |
| ATOM | 2666 | O | ALA | 163 | 108.154 | -13.473 | 41.868 | 1.00 | 36.52 | H | O |
| ATOM | 2667 | N | LEU | 164 | 106.378 | -12.750 | 40.722 | 1.00 | 33.04 | H | N |
| ATOM | 2668 | CA | LEU | 164 | 106.412 | -13.847 | 39.755 | 1.00 | 28.09 | H | C |
| ATOM | 2669 | CB | LEU | 164 | 105.146 | -14.701 | 39.869 | 1.00 | 29.67 | H | C |
| ATOM | 2670 | CG | LEU | 164 | 105.008 | -15.851 | 38.870 | 1.00 | 27.43 | H | C |
| ATOM | 2671 | CD1 | LEU | 164 | 105.976 | -16.963 | 39.215 | 1.00 | 24.01 | H | C |
| ATOM | 2672 | CD2 | LEU | 164 | 103.605 | -16.370 | 38.903 | 1.00 | 22.28 | H | C |
| ATOM | 2673 | C | LEU | 164 | 106.483 | -13.227 | 38.370 | 1.00 | 26.00 | H | C |
| ATOM | 2674 | O | LEU | 164 | 105.492 | -12.663 | 37.893 | 1.00 | 20.06 | H | O |
| ATOM | 2675 | N | THR | 165 | 107.656 | -13.326 | 37.740 | 1.00 | 28.49 | H | N |
| ATOM | 2676 | CA | THR | 165 | 107.893 | -12.758 | 36.410 | 1.00 | 32.54 | H | C |
| ATOM | 2677 | CB | THR | 165 | 108.927 | -11.613 | 36.462 | 1.00 | 18.33 | H | C |
| ATOM | 2678 | OG1 | THR | 165 | 110.114 | -12.057 | 37.139 | 1.00 | 21.15 | H | O |
| ATOM | 2679 | CG2 | THR | 165 | 108.348 | -10.419 | 37.184 | 1.00 | 20.86 | H | C |
| ATOM | 2680 | C | THR | 165 | 108.394 | -13.770 | 35.397 | 1.00 | 33.42 | H | C |
| ATOM | 2681 | O | THR | 165 | 108.028 | -13.717 | 34.227 | 1.00 | 34.44 | H | O |
| ATOM | 2682 | N | SER | 166 | 109.244 | -14.683 | 35.849 | 1.00 | 63.46 | H | N |
| ATOM | 2683 | CA | SER | 166 | 109.804 | -15.702 | 34.973 | 1.00 | 62.93 | H | C |
| ATOM | 2684 | CB | SER | 166 | 110.901 | -16.472 | 35.710 | 1.00 | 37.10 | H | C |
| ATOM | 2685 | OG | SER | 166 | 111.503 | -17.442 | 34.870 | 1.00 | 42.11 | H | O |
| ATOM | 2686 | C | SER | 166 | 108.748 | -16.678 | 34.458 | 1.00 | 60.85 | H | C |
| ATOM | 2687 | O | SER | 166 | 107.955 | -17.226 | 35.227 | 1.00 | 60.31 | H | O |
| ATOM | 2688 | N | GLY | 167 | 108.744 | -16.895 | 33.148 | 1.00 | 58.61 | H | N |
| ATOM | 2689 | CA | GLY | 167 | 107.784 | -17.812 | 32.566 | 1.00 | 55.44 | H | C |
| ATOM | 2690 | C | GLY | 167 | 106.425 | -17.181 | 32.332 | 1.00 | 49.55 | H | C |
| ATOM | 2691 | O | GLY | 167 | 105.462 | -17.878 | 32.010 | 1.00 | 51.52 | H | O |
| ATOM | 2692 | N | VAL | 168 | 106.340 | -15.864 | 32.491 | 1.00 | 12.32 | H | N |
| ATOM | 2693 | CA | VAL | 168 | 105.081 | -15.183 | 32.280 | 1.00 | 12.04 | H | C |
| ATOM | 2694 | CB | VAL | 168 | 104.933 | -13.970 | 33.190 | 1.00 | 2.74 | H | C |
| ATOM | 2695 | CG1 | VAL | 168 | 103.590 | -13.273 | 32.906 | 1.00 | 2.74 | H | C |
| ATOM | 2696 | CG2 | VAL | 168 | 105.070 | -14.398 | 34.630 | 1.00 | 2.83 | H | C |
| ATOM | 2697 | C | VAL | 168 | 104.965 | -14.687 | 30.852 | 1.00 | 11.82 | H | C |
| ATOM | 2698 | O | VAL | 168 | 105.894 | -14.087 | 30.319 | 1.00 | 11.28 | H | O |
| ATOM | 2699 | N | HIS | 169 | 103.807 | -14.931 | 30.253 | 1.00 | 28.24 | H | N |
| ATOM | 2700 | CA | HIS | 169 | 103.518 | -14.512 | 28.891 | 1.00 | 24.96 | H | C |
| ATOM | 2701 | CB | HIS | 169 | 103.566 | -15.695 | 27.924 | 1.00 | 1.87 | H | C |

Fig. 19: A-38

| | | | | | | | | | | | |
|---|---|---|---|---|---|---|---|---|---|---|---|
| ATOM | 2702 | CG | HIS | 169 | 104.935 | -16.209 | 27.634 | 1.00 | 1.87 | H | C |
| ATOM | 2703 | CD2 | HIS | 169 | 105.456 | -17.452 | 27.739 | 1.00 | 10.72 | H | C |
| ATOM | 2704 | ND1 | HIS | 169 | 105.935 | -15.415 | 27.114 | 1.00 | 4.04 | H | N |
| ATOM | 2705 | CE1 | HIS | 169 | 107.015 | -16.147 | 26.912 | 1.00 | 11.56 | H | C |
| ATOM | 2706 | NE2 | HIS | 169 | 106.750 | -17.387 | 27.282 | 1.00 | 3.03 | H | N |
| ATOM | 2707 | C | HIS | 169 | 102.106 | -13.934 | 28.818 | 1.00 | 26.88 | H | C |
| ATOM | 2708 | O | HIS | 169 | 101.143 | -14.679 | 28.610 | 1.00 | 27.44 | H | O |
| ATOM | 2709 | N | THR | 170 | 101.960 | -12.628 | 28.995 | 1.00 | 15.52 | H | N |
| ATOM | 2710 | CA | THR | 170 | 100.637 | -12.030 | 28.885 | 1.00 | 14.61 | H | C |
| ATOM | 2711 | CB | THR | 170 | 100.472 | -10.872 | 29.894 | 1.00 | 20.19 | H | C |
| ATOM | 2712 | OG1 | THR | 170 | 99.403 | -10.021 | 29.470 | 1.00 | 14.32 | H | O |
| ATOM | 2713 | CG2 | THR | 170 | 101.760 | -10.096 | 30.042 | 1.00 | 25.14 | H | C |
| ATOM | 2714 | C | THR | 170 | 100.487 | -11.553 | 27.433 | 1.00 | 15.32 | H | C |
| ATOM | 2715 | O | THR | 170 | 101.023 | -10.532 | 27.053 | 1.00 | 11.65 | H | O |
| ATOM | 2716 | N | PHE | 171 | 99.762 | -12.324 | 26.630 | 1.00 | 23.28 | H | N |
| ATOM | 2717 | CA | PHE | 171 | 99.587 | -12.046 | 25.206 | 1.00 | 17.85 | H | C |
| ATOM | 2718 | CB | PHE | 171 | 98.695 | -13.110 | 24.554 | 1.00 | 15.23 | H | C |
| ATOM | 2719 | CG | PHE | 171 | 99.138 | -14.521 | 24.806 | 1.00 | 7.97 | H | C |
| ATOM | 2720 | CD1 | PHE | 171 | 98.731 | -15.195 | 25.955 | 1.00 | 8.65 | H | C |
| ATOM | 2721 | CD2 | PHE | 171 | 99.978 | -15.174 | 23.903 | 1.00 | 7.84 | H | C |
| ATOM | 2722 | CE1 | PHE | 171 | 99.153 | -16.492 | 26.202 | 1.00 | 17.36 | H | C |
| ATOM | 2723 | CE2 | PHE | 171 | 100.407 | -16.473 | 24.144 | 1.00 | 15.22 | H | C |
| ATOM | 2724 | CZ | PHE | 171 | 99.993 | -17.133 | 25.295 | 1.00 | 16.34 | H | C |
| ATOM | 2725 | C | PHE | 171 | 99.032 | -10.692 | 24.793 | 1.00 | 18.20 | H | C |
| ATOM | 2726 | O | PHE | 171 | 98.344 | -10.015 | 25.552 | 1.00 | 23.73 | H | O |
| ATOM | 2727 | N | PRO | 172 | 99.341 | -10.278 | 23.557 | 1.00 | 21.77 | H | N |
| ATOM | 2728 | CD | PRO | 172 | 100.227 | -10.890 | 22.550 | 1.00 | 20.32 | H | C |
| ATOM | 2729 | CA | PRO | 172 | 98.827 | -8.999 | 23.088 | 1.00 | 23.20 | H | C |
| ATOM | 2730 | CB | PRO | 172 | 99.595 | -8.775 | 21.782 | 1.00 | 20.71 | H | C |
| ATOM | 2731 | CG | PRO | 172 | 99.834 | -10.148 | 21.287 | 1.00 | 18.82 | H | C |
| ATOM | 2732 | C | PRO | 172 | 97.339 | -9.235 | 22.876 | 1.00 | 25.11 | H | C |
| ATOM | 2733 | O | PRO | 172 | 96.916 | -10.364 | 22.645 | 1.00 | 23.46 | H | O |
| ATOM | 2734 | N | ALA | 173 | 96.551 | -8.172 | 22.960 | 1.00 | 24.67 | H | N |
| ATOM | 2735 | CA | ALA | 173 | 95.104 | -8.267 | 22.815 | 1.00 | 27.18 | H | C |
| ATOM | 2736 | CB | ALA | 173 | 94.439 | -7.079 | 23.498 | 1.00 | 1.87 | H | C |
| ATOM | 2737 | C | ALA | 173 | 94.604 | -8.379 | 21.391 | 1.00 | 30.18 | H | C |
| ATOM | 2738 | O | ALA | 173 | 95.304 | -8.080 | 20.426 | 1.00 | 32.13 | H | O |
| ATOM | 2739 | N | VAL | 174 | 93.365 | -8.820 | 21.277 | 1.00 | 21.72 | H | N |
| ATOM | 2740 | CA | VAL | 174 | 92.753 | -8.964 | 19.984 | 1.00 | 23.16 | H | C |
| ATOM | 2741 | CB | VAL | 174 | 92.841 | -10.406 | 19.511 | 1.00 | 28.95 | H | C |
| ATOM | 2742 | CG1 | VAL | 174 | 92.103 | -10.566 | 18.201 | 1.00 | 32.21 | H | C |
| ATOM | 2743 | CG2 | VAL | 174 | 94.305 | -10.797 | 19.356 | 1.00 | 26.32 | H | C |
| ATOM | 2744 | C | VAL | 174 | 91.302 | -8.508 | 20.058 | 1.00 | 25.36 | H | C |
| ATOM | 2745 | O | VAL | 174 | 90.611 | -8.718 | 21.069 | 1.00 | 25.35 | H | O |
| ATOM | 2746 | N | LEU | 175 | 90.860 | -7.856 | 18.987 | 1.00 | 41.55 | H | N |
| ATOM | 2747 | CA | LEU | 175 | 89.504 | -7.338 | 18.890 | 1.00 | 40.23 | H | C |
| ATOM | 2748 | CB | LEU | 175 | 89.443 | -6.276 | 17.787 | 1.00 | 23.29 | H | C |
| ATOM | 2749 | CG | LEU | 175 | 88.728 | -4.928 | 17.990 | 1.00 | 20.94 | H | C |
| ATOM | 2750 | CD1 | LEU | 175 | 88.634 | -4.511 | 19.463 | 1.00 | 21.45 | H | C |
| ATOM | 2751 | CD2 | LEU | 175 | 89.518 | -3.900 | 17.186 | 1.00 | 22.78 | H | C |
| ATOM | 2752 | C | LEU | 175 | 88.539 | -8.474 | 18.588 | 1.00 | 42.85 | H | C |
| ATOM | 2753 | O | LEU | 175 | 88.738 | -9.233 | 17.638 | 1.00 | 45.50 | H | O |
| ATOM | 2754 | N | GLN | 176 | 87.500 | -8.592 | 19.407 | 1.00 | 41.11 | H | N |
| ATOM | 2755 | CA | GLN | 176 | 86.514 | -9.645 | 19.228 | 1.00 | 42.33 | H | C |
| ATOM | 2756 | CB | GLN | 176 | 85.852 | -9.990 | 20.564 | 1.00 | 38.15 | H | C |
| ATOM | 2757 | CG | GLN | 176 | 86.817 | -10.276 | 21.703 | 1.00 | 37.93 | H | C |
| ATOM | 2758 | CD | GLN | 176 | 86.109 | -10.801 | 22.939 | 1.00 | 36.82 | H | C |
| ATOM | 2759 | OE1 | GLN | 176 | 85.562 | -11.899 | 22.923 | 1.00 | 36.67 | H | O |
| ATOM | 2760 | NE2 | GLN | 176 | 86.108 | -10.014 | 24.011 | 1.00 | 33.13 | H | N |
| ATOM | 2761 | C | GLN | 176 | 85.439 | -9.207 | 18.245 | 1.00 | 44.39 | H | C |
| ATOM | 2762 | O | GLN | 176 | 85.274 | -8.018 | 17.969 | 1.00 | 34.09 | H | O |
| ATOM | 2763 | N | SER | 177 | 84.708 | -10.182 | 17.718 | 1.00 | 59.83 | H | N |
| ATOM | 2764 | CA | SER | 177 | 83.624 | -9.902 | 16.790 | 1.00 | 58.61 | H | C |
| ATOM | 2765 | CB | SER | 177 | 82.804 | -11.177 | 16.558 | 1.00 | 104.21 | H | C |
| ATOM | 2766 | OG | SER | 177 | 81.708 | -10.945 | 15.689 | 1.00 | 104.01 | H | O |
| ATOM | 2767 | C | SER | 177 | 82.759 | -8.832 | 17.448 | 1.00 | 60.09 | H | C |
| ATOM | 2768 | O | SER | 177 | 82.169 | -7.985 | 16.778 | 1.00 | 62.26 | H | O |
| ATOM | 2769 | N | SER | 178 | 82.722 | -8.877 | 18.778 | 1.00 | 34.26 | H | N |
| ATOM | 2770 | CA | SER | 178 | 81.942 | -7.952 | 19.596 | 1.00 | 32.97 | H | C |
| ATOM | 2771 | CB | SER | 178 | 81.798 | -8.510 | 21.019 | 1.00 | 67.89 | H | C |
| ATOM | 2772 | OG | SER | 178 | 83.057 | -8.636 | 21.663 | 1.00 | 66.22 | H | O |
| ATOM | 2773 | C | SER | 178 | 82.538 | -6.554 | 19.671 | 1.00 | 32.95 | H | C |
| ATOM | 2774 | O | SER | 178 | 81.921 | -5.640 | 20.210 | 1.00 | 35.05 | H | O |

Fig. 19: A-39

| | | | | | | | | | | | |
|---|---|---|---|---|---|---|---|---|---|---|---|
| ATOM | 2775 | N | GLY | 179 | 83.738 | -6.382 | 19.135 | 1.00 | 43.45 | H | N |
| ATOM | 2776 | CA | GLY | 179 | 84.357 | -5.072 | 19.191 | 1.00 | 46.81 | H | C |
| ATOM | 2777 | C | GLY | 179 | 84.972 | -4.821 | 20.552 | 1.00 | 50.21 | H | C |
| ATOM | 2778 | O | GLY | 179 | 85.380 | -3.707 | 20.869 | 1.00 | 50.30 | H | O |
| ATOM | 2779 | N | LEU | 180 | 85.020 | -5.862 | 21.369 | 1.00 | 30.24 | H | N |
| ATOM | 2780 | CA | LEU | 180 | 85.620 | -5.749 | 22.686 | 1.00 | 32.27 | H | C |
| ATOM | 2781 | CB | LEU | 180 | 84.706 | -6.380 | 23.730 | 1.00 | 33.41 | H | C |
| ATOM | 2782 | CG | LEU | 180 | 83.485 | -5.524 | 24.054 | 1.00 | 32.78 | H | C |
| ATOM | 2783 | CD1 | LEU | 180 | 82.513 | -6.292 | 24.902 | 1.00 | 27.00 | H | C |
| ATOM | 2784 | CD2 | LEU | 180 | 83.943 | -4.278 | 24.781 | 1.00 | 32.58 | H | C |
| ATOM | 2785 | C | LEU | 180 | 86.974 | -6.442 | 22.672 | 1.00 | 32.86 | H | C |
| ATOM | 2786 | O | LEU | 180 | 87.135 | -7.488 | 22.054 | 1.00 | 36.18 | H | O |
| ATOM | 2787 | N | TYR | 181 | 87.952 | -5.843 | 23.336 | 1.00 | 31.41 | H | N |
| ATOM | 2788 | CA | TYR | 181 | 89.293 | -6.409 | 23.387 | 1.00 | 32.68 | H | C |
| ATOM | 2789 | CB | TYR | 181 | 90.297 | -5.323 | 23.792 | 1.00 | 57.58 | H | C |
| ATOM | 2790 | CG | TYR | 181 | 90.773 | -4.445 | 22.651 | 1.00 | 56.39 | H | C |
| ATOM | 2791 | CD1 | TYR | 181 | 91.591 | -4.961 | 21.647 | 1.00 | 57.58 | H | C |
| ATOM | 2792 | CE1 | TYR | 181 | 92.063 | -4.155 | 20.605 | 1.00 | 57.08 | H | C |
| ATOM | 2793 | CD2 | TYR | 181 | 90.430 | -3.092 | 22.585 | 1.00 | 56.67 | H | C |
| ATOM | 2794 | CE2 | TYR | 181 | 90.899 | -2.273 | 21.543 | 1.00 | 57.48 | H | C |
| ATOM | 2795 | CZ | TYR | 181 | 91.717 | -2.816 | 20.559 | 1.00 | 58.33 | H | C |
| ATOM | 2796 | OH | TYR | 181 | 92.202 | -2.033 | 19.533 | 1.00 | 62.35 | H | O |
| ATOM | 2797 | C | TYR | 181 | 89.361 | -7.573 | 24.375 | 1.00 | 31.73 | H | C |
| ATOM | 2798 | O | TYR | 181 | 88.581 | -7.638 | 25.324 | 1.00 | 32.08 | H | O |
| ATOM | 2799 | N | SER | 182 | 90.287 | -8.499 | 24.149 | 1.00 | 35.13 | H | N |
| ATOM | 2800 | CA | SER | 182 | 90.446 | -9.642 | 25.045 | 1.00 | 32.04 | H | C |
| ATOM | 2801 | CB | SER | 182 | 89.439 | -10.741 | 24.700 | 1.00 | 65.40 | H | C |
| ATOM | 2802 | OG | SER | 182 | 89.612 | -11.868 | 25.543 | 1.00 | 59.63 | H | O |
| ATOM | 2803 | C | SER | 182 | 91.860 | -10.209 | 24.970 | 1.00 | 33.65 | H | C |
| ATOM | 2804 | O | SER | 182 | 92.494 | -10.187 | 23.906 | 1.00 | 37.13 | H | O |
| ATOM | 2805 | N | LEU | 183 | 92.351 | -10.713 | 26.101 | 1.00 | 28.98 | H | N |
| ATOM | 2806 | CA | LEU | 183 | 93.689 | -11.290 | 26.152 | 1.00 | 24.91 | H | C |
| ATOM | 2807 | CB | LEU | 183 | 94.753 | -10.179 | 26.189 | 1.00 | 31.36 | H | C |
| ATOM | 2808 | CG | LEU | 183 | 94.913 | -9.263 | 27.414 | 1.00 | 23.12 | H | C |
| ATOM | 2809 | CD1 | LEU | 183 | 95.475 | -10.014 | 28.625 | 1.00 | 27.02 | H | C |
| ATOM | 2810 | CD2 | LEU | 183 | 95.849 | -8.148 | 27.036 | 1.00 | 19.84 | H | C |
| ATOM | 2811 | C | LEU | 183 | 93.898 | -12.209 | 27.342 | 1.00 | 24.58 | H | C |
| ATOM | 2812 | O | LEU | 183 | 93.179 | -12.135 | 28.326 | 1.00 | 18.76 | H | O |
| ATOM | 2813 | N | SER | 184 | 94.894 | -13.077 | 27.250 | 1.00 | 26.13 | H | N |
| ATOM | 2814 | CA | SER | 184 | 95.205 | -13.967 | 28.357 | 1.00 | 26.65 | H | C |
| ATOM | 2815 | CB | SER | 184 | 95.000 | -15.445 | 27.968 | 1.00 | 16.60 | H | C |
| ATOM | 2816 | OG | SER | 184 | 93.638 | -15.750 | 27.710 | 1.00 | 22.49 | H | O |
| ATOM | 2817 | C | SER | 184 | 96.660 | -13.752 | 28.784 | 1.00 | 22.47 | H | C |
| ATOM | 2818 | O | SER | 184 | 97.546 | -13.511 | 27.953 | 1.00 | 21.27 | H | O |
| ATOM | 2819 | N | SER | 185 | 96.896 | -13.786 | 30.087 | 1.00 | 27.49 | H | N |
| ATOM | 2820 | CA | SER | 185 | 98.251 | -13.670 | 30.575 | 1.00 | 25.55 | H | C |
| ATOM | 2821 | CB | SER | 185 | 98.389 | -12.634 | 31.678 | 1.00 | 27.24 | H | C |
| ATOM | 2822 | OG | SER | 185 | 99.760 | -12.516 | 32.031 | 1.00 | 25.68 | H | O |
| ATOM | 2823 | C | SER | 185 | 98.460 | -15.060 | 31.123 | 1.00 | 23.97 | H | C |
| ATOM | 2824 | O | SER | 185 | 97.652 | -15.551 | 31.912 | 1.00 | 25.28 | H | O |
| ATOM | 2825 | N | VAL | 186 | 99.533 | -15.699 | 30.679 | 1.00 | 29.81 | H | N |
| ATOM | 2826 | CA | VAL | 186 | 99.830 | -17.060 | 31.064 | 1.00 | 29.28 | H | C |
| ATOM | 2827 | CB | VAL | 186 | 99.717 | -17.966 | 29.831 | 1.00 | 20.56 | H | C |
| ATOM | 2828 | CG1 | VAL | 186 | 100.305 | -19.306 | 30.112 | 1.00 | 20.80 | H | C |
| ATOM | 2829 | CG2 | VAL | 186 | 98.253 | -18.121 | 29.446 | 1.00 | 19.74 | H | C |
| ATOM | 2830 | C | VAL | 186 | 101.204 | -17.193 | 31.664 | 1.00 | 30.42 | H | C |
| ATOM | 2831 | O | VAL | 186 | 102.097 | -16.416 | 31.357 | 1.00 | 31.20 | H | O |
| ATOM | 2832 | N | VAL | 187 | 101.359 | -18.179 | 32.540 | 1.00 | 29.47 | H | N |
| ATOM | 2833 | CA | VAL | 187 | 102.645 | -18.457 | 33.178 | 1.00 | 26.42 | H | C |
| ATOM | 2834 | CB | VAL | 187 | 102.739 | -17.797 | 34.586 | 1.00 | 27.93 | H | C |
| ATOM | 2835 | CG1 | VAL | 187 | 101.681 | -18.385 | 35.507 | 1.00 | 26.86 | H | C |
| ATOM | 2836 | CG2 | VAL | 187 | 104.134 | -17.994 | 35.180 | 1.00 | 26.29 | H | C |
| ATOM | 2837 | C | VAL | 187 | 102.842 | -19.975 | 33.309 | 1.00 | 20.75 | H | C |
| ATOM | 2838 | O | VAL | 187 | 101.882 | -20.743 | 33.316 | 1.00 | 22.47 | H | O |
| ATOM | 2839 | N | THR | 188 | 104.098 | -20.397 | 33.377 | 1.00 | 5.29 | H | N |
| ATOM | 2840 | CA | THR | 188 | 104.441 | -21.807 | 33.539 | 1.00 | 7.86 | H | C |
| ATOM | 2841 | CB | THR | 188 | 105.280 | -22.327 | 32.366 | 1.00 | 35.20 | H | C |
| ATOM | 2842 | OG1 | THR | 188 | 106.425 | -21.487 | 32.194 | 1.00 | 33.26 | H | O |
| ATOM | 2843 | CG2 | THR | 188 | 104.453 | -22.337 | 31.078 | 1.00 | 39.96 | H | C |
| ATOM | 2844 | C | THR | 188 | 105.270 | -21.870 | 34.802 | 1.00 | 13.86 | H | C |
| ATOM | 2845 | O | THR | 188 | 106.194 | -21.077 | 34.975 | 1.00 | 18.45 | H | O |
| ATOM | 2846 | N | VAL | 189 | 104.921 | -22.799 | 35.688 | 1.00 | 28.00 | H | N |
| ATOM | 2847 | CA | VAL | 189 | 105.613 | -22.963 | 36.965 | 1.00 | 25.42 | H | C |

Fig. 19: A-40

| | | | | | | | | | | | |
|---|---|---|---|---|---|---|---|---|---|---|---|
| ATOM | 2848 | CB | VAL | 189 | 104.755 | -22.412 | 38.137 | 1.00 | 24.28 | H | C |
| ATOM | 2849 | CG1 | VAL | 189 | 104.399 | -20.951 | 37.904 | 1.00 | 17.23 | H | C |
| ATOM | 2850 | CG2 | VAL | 189 | 103.478 | -23.234 | 38.270 | 1.00 | 17.84 | H | C |
| ATOM | 2851 | C | VAL | 189 | 105.875 | -24.439 | 37.242 | 1.00 | 32.15 | H | C |
| ATOM | 2852 | O | VAL | 189 | 105.386 | -25.309 | 36.523 | 1.00 | 35.18 | H | O |
| ATOM | 2853 | N | PRO | 190 | 106.671 | -24.738 | 38.280 | 1.00 | 50.39 | H | N |
| ATOM | 2854 | CD | PRO | 190 | 107.545 | -23.823 | 39.036 | 1.00 | 32.03 | H | C |
| ATOM | 2855 | CA | PRO | 190 | 106.962 | -26.133 | 38.624 | 1.00 | 50.40 | H | C |
| ATOM | 2856 | CB | PRO | 190 | 107.911 | -26.001 | 39.814 | 1.00 | 29.50 | H | C |
| ATOM | 2857 | CG | PRO | 190 | 108.651 | -24.746 | 39.514 | 1.00 | 29.72 | H | C |
| ATOM | 2858 | C | PRO | 190 | 105.650 | -26.801 | 39.018 | 1.00 | 50.46 | H | C |
| ATOM | 2859 | O | PRO | 190 | 104.899 | -26.267 | 39.834 | 1.00 | 48.43 | H | O |
| ATOM | 2860 | N | SER | 191 | 105.357 | -27.953 | 38.436 | 1.00 | 54.29 | H | N |
| ATOM | 2861 | CA | SER | 191 | 104.122 | -28.638 | 38.774 | 1.00 | 60.79 | H | C |
| ATOM | 2862 | CB | SER | 191 | 104.111 | -30.036 | 38.157 | 1.00 | 30.49 | H | C |
| ATOM | 2863 | OG | SER | 191 | 104.076 | -29.980 | 36.740 | 1.00 | 31.07 | H | O |
| ATOM | 2864 | C | SER | 191 | 104.009 | -28.730 | 40.297 | 1.00 | 63.91 | H | C |
| ATOM | 2865 | O | SER | 191 | 102.986 | -28.361 | 40.882 | 1.00 | 66.82 | H | O |
| ATOM | 2866 | N | SER | 192 | 105.084 | -29.201 | 40.924 | 1.00 | 39.50 | H | N |
| ATOM | 2867 | CA | SER | 192 | 105.177 | -29.374 | 42.376 | 1.00 | 40.99 | H | C |
| ATOM | 2868 | CB | SER | 192 | 106.602 | -29.776 | 42.739 | 1.00 | 41.75 | H | C |
| ATOM | 2869 | OG | SER | 192 | 107.475 | -28.675 | 42.565 | 1.00 | 41.65 | H | O |
| ATOM | 2870 | C | SER | 192 | 104.795 | -28.150 | 43.220 | 1.00 | 42.26 | H | C |
| ATOM | 2871 | O | SER | 192 | 104.403 | -28.286 | 44.381 | 1.00 | 48.17 | H | O |
| ATOM | 2872 | N | SER | 193 | 104.923 | -26.960 | 42.645 | 1.00 | 20.64 | H | N |
| ATOM | 2873 | CA | SER | 193 | 104.601 | -25.733 | 43.365 | 1.00 | 22.36 | H | C |
| ATOM | 2874 | CB | SER | 193 | 105.396 | -24.567 | 42.771 | 1.00 | 39.90 | H | C |
| ATOM | 2875 | OG | SER | 193 | 104.973 | -24.284 | 41.447 | 1.00 | 36.65 | H | O |
| ATOM | 2876 | C | SER | 193 | 103.097 | -25.380 | 43.392 | 1.00 | 22.92 | H | C |
| ATOM | 2877 | O | SER | 193 | 102.697 | -24.363 | 43.963 | 1.00 | 25.84 | H | O |
| ATOM | 2878 | N | LEU | 194 | 102.268 | -26.218 | 42.776 | 1.00 | 41.78 | H | N |
| ATOM | 2879 | CA | LEU | 194 | 100.827 | -25.974 | 42.741 | 1.00 | 45.87 | H | C |
| ATOM | 2880 | CB | LEU | 194 | 100.172 | -26.850 | 41.677 | 1.00 | 23.80 | H | C |
| ATOM | 2881 | CG | LEU | 194 | 100.533 | -26.605 | 40.216 | 1.00 | 21.31 | H | C |
| ATOM | 2882 | CD1 | LEU | 194 | 99.975 | -27.739 | 39.377 | 1.00 | 19.27 | H | C |
| ATOM | 2883 | CD2 | LEU | 194 | 99.973 | -25.246 | 39.757 | 1.00 | 15.31 | H | C |
| ATOM | 2884 | C | LEU | 194 | 100.177 | -26.276 | 44.080 | 1.00 | 49.01 | H | C |
| ATOM | 2885 | O | LEU | 194 | 99.209 | -25.623 | 44.478 | 1.00 | 48.38 | H | O |
| ATOM | 2886 | N | GLY | 195 | 100.718 | -27.272 | 44.770 | 1.00 | 65.65 | H | N |
| ATOM | 2887 | CA | GLY | 195 | 100.160 | -27.676 | 46.043 | 1.00 | 68.76 | H | C |
| ATOM | 2888 | C | GLY | 195 | 100.625 | -26.877 | 47.235 | 1.00 | 66.22 | H | C |
| ATOM | 2889 | O | GLY | 195 | 100.051 | -26.992 | 48.314 | 1.00 | 68.30 | H | O |
| ATOM | 2890 | N | THR | 196 | 101.659 | -26.067 | 47.053 | 1.00 | 33.26 | H | N |
| ATOM | 2891 | CA | THR | 196 | 102.175 | -25.265 | 48.155 | 1.00 | 32.73 | H | C |
| ATOM | 2892 | CB | THR | 196 | 103.575 | -25.763 | 48.585 | 1.00 | 30.77 | H | C |
| ATOM | 2893 | OG1 | THR | 196 | 104.489 | -25.676 | 47.478 | 1.00 | 28.63 | H | O |
| ATOM | 2894 | CG2 | THR | 196 | 103.488 | -27.213 | 49.071 | 1.00 | 27.23 | H | C |
| ATOM | 2895 | C | THR | 196 | 102.251 | -23.786 | 47.813 | 1.00 | 35.97 | H | C |
| ATOM | 2896 | O | THR | 196 | 102.179 | -22.933 | 48.695 | 1.00 | 36.72 | H | O |
| ATOM | 2897 | N | GLN | 197 | 102.389 | -23.488 | 46.527 | 1.00 | 53.90 | H | N |
| ATOM | 2898 | CA | GLN | 197 | 102.478 | -22.110 | 46.060 | 1.00 | 54.25 | H | C |
| ATOM | 2899 | CB | GLN | 197 | 103.480 | -22.031 | 44.906 | 1.00 | 42.12 | H | C |
| ATOM | 2900 | CG | GLN | 197 | 104.561 | -20.975 | 45.045 | 1.00 | 45.66 | H | C |
| ATOM | 2901 | CD | GLN | 197 | 104.051 | -19.587 | 44.765 | 1.00 | 49.49 | H | C |
| ATOM | 2902 | OE1 | GLN | 197 | 103.257 | -19.032 | 45.528 | 1.00 | 50.05 | H | O |
| ATOM | 2903 | NE2 | GLN | 197 | 104.500 | -19.013 | 43.656 | 1.00 | 49.01 | H | N |
| ATOM | 2904 | C | GLN | 197 | 101.105 | -21.617 | 45.604 | 1.00 | 52.98 | H | C |
| ATOM | 2905 | O | GLN | 197 | 100.314 | -22.382 | 45.050 | 1.00 | 55.53 | H | O |
| ATOM | 2906 | N | THR | 198 | 100.829 | -20.338 | 45.847 | 1.00 | 30.38 | H | N |
| ATOM | 2907 | CA | THR | 198 | 99.559 | -19.719 | 45.470 | 1.00 | 29.29 | H | C |
| ATOM | 2908 | CB | THR | 198 | 98.922 | -18.970 | 46.677 | 1.00 | 45.77 | H | C |
| ATOM | 2909 | OG1 | THR | 198 | 97.546 | -18.682 | 46.404 | 1.00 | 43.55 | H | O |
| ATOM | 2910 | CG2 | THR | 198 | 99.643 | -17.644 | 46.929 | 1.00 | 47.95 | H | C |
| ATOM | 2911 | C | THR | 198 | 99.811 | -18.719 | 44.338 | 1.00 | 27.94 | H | C |
| ATOM | 2912 | O | THR | 198 | 100.722 | -17.891 | 44.413 | 1.00 | 31.22 | H | O |
| ATOM | 2913 | N | TYR | 199 | 99.008 | -18.789 | 43.285 | 1.00 | 40.84 | H | N |
| ATOM | 2914 | CA | TYR | 199 | 99.191 | -17.874 | 42.168 | 1.00 | 31.26 | H | C |
| ATOM | 2915 | CB | TYR | 199 | 99.402 | -18.681 | 40.880 | 1.00 | 39.46 | H | C |
| ATOM | 2916 | CG | TYR | 199 | 100.677 | -19.496 | 40.904 | 1.00 | 33.83 | H | C |
| ATOM | 2917 | CD1 | TYR | 199 | 101.911 | -18.901 | 40.630 | 1.00 | 31.63 | H | C |
| ATOM | 2918 | CE1 | TYR | 199 | 103.107 | -19.626 | 40.735 | 1.00 | 31.28 | H | C |
| ATOM | 2919 | CD2 | TYR | 199 | 100.662 | -20.847 | 41.282 | 1.00 | 32.94 | H | C |
| ATOM | 2920 | CE2 | TYR | 199 | 101.850 | -21.590 | 41.392 | 1.00 | 33.91 | H | C |

Fig. 19: A-41

| | | | | | | | | | | | |
|---|---|---|---|---|---|---|---|---|---|---|---|
| ATOM | 2921 | CZ | TYR | 199 | 103.069 | -20.972 | 41.118 | 1.00 | 33.40 | H | C |
| ATOM | 2922 | OH | TYR | 199 | 104.244 | -21.685 | 41.223 | 1.00 | 37.29 | H | O |
| ATOM | 2923 | C | TYR | 199 | 98.029 | -16.897 | 42.014 | 1.00 | 31.50 | H | C |
| ATOM | 2924 | O | TYR | 199 | 96.876 | -17.302 | 41.913 | 1.00 | 32.18 | H | O |
| ATOM | 2925 | N | ILE | 200 | 98.342 | -15.605 | 42.026 | 1.00 | 38.61 | H | N |
| ATOM | 2926 | CA | ILE | 200 | 97.329 | -14.566 | 41.858 | 1.00 | 39.11 | H | C |
| ATOM | 2927 | CB | ILE | 200 | 97.265 | -13.574 | 43.051 | 1.00 | 27.10 | H | C |
| ATOM | 2928 | CG2 | ILE | 200 | 96.185 | -12.540 | 42.793 | 1.00 | 26.36 | H | C |
| ATOM | 2929 | CG1 | ILE | 200 | 96.978 | -14.301 | 44.363 | 1.00 | 30.59 | H | C |
| ATOM | 2930 | CD1 | ILE | 200 | 98.119 | -15.184 | 44.842 | 1.00 | 36.15 | H | C |
| ATOM | 2931 | C | ILE | 200 | 97.730 | -13.736 | 40.649 | 1.00 | 41.59 | H | C |
| ATOM | 2932 | O | ILE | 200 | 98.916 | -13.517 | 40.415 | 1.00 | 45.01 | H | O |
| ATOM | 2933 | N | CYS | 201 | 96.758 | -13.283 | 39.867 | 1.00 | 30.01 | H | N |
| ATOM | 2934 | CA | CYS | 201 | 97.092 | -12.434 | 38.735 | 1.00 | 27.23 | H | C |
| ATOM | 2935 | C | CYS | 201 | 96.476 | -11.075 | 39.011 | 1.00 | 24.60 | H | C |
| ATOM | 2936 | O | CYS | 201 | 95.307 | -10.967 | 39.386 | 1.00 | 22.36 | H | O |
| ATOM | 2937 | CB | CYS | 201 | 96.577 | -12.997 | 37.394 | 1.00 | 42.80 | H | C |
| ATOM | 2938 | SG | CYS | 201 | 94.784 | -12.909 | 37.090 | 1.00 | 39.16 | H | S |
| ATOM | 2939 | N | ASN | 202 | 97.282 | -10.035 | 38.849 | 1.00 | 26.40 | H | N |
| ATOM | 2940 | CA | ASN | 202 | 96.819 | -8.683 | 39.080 | 1.00 | 32.39 | H | C |
| ATOM | 2941 | CB | ASN | 202 | 97.884 | -7.902 | 39.846 | 1.00 | 36.85 | H | C |
| ATOM | 2942 | CG | ASN | 202 | 98.507 | -8.720 | 40.954 | 1.00 | 39.80 | H | C |
| ATOM | 2943 | OD1 | ASN | 202 | 99.570 | -9.314 | 40.779 | 1.00 | 38.11 | H | O |
| ATOM | 2944 | ND2 | ASN | 202 | 97.837 | -8.776 | 42.097 | 1.00 | 41.02 | H | N |
| ATOM | 2945 | C | ASN | 202 | 96.530 | -8.025 | 37.743 | 1.00 | 36.08 | H | C |
| ATOM | 2946 | O | ASN | 202 | 97.419 | -7.867 | 36.911 | 1.00 | 40.34 | H | O |
| ATOM | 2947 | N | VAL | 203 | 95.273 | -7.668 | 37.533 | 1.00 | 28.99 | H | N |
| ATOM | 2948 | CA | VAL | 203 | 94.868 | -7.017 | 36.295 | 1.00 | 29.18 | H | C |
| ATOM | 2949 | CB | VAL | 203 | 93.691 | -7.781 | 35.624 | 1.00 | 21.70 | H | C |
| ATOM | 2950 | CG1 | VAL | 203 | 93.321 | -7.134 | 34.274 | 1.00 | 17.35 | H | C |
| ATOM | 2951 | CG2 | VAL | 203 | 94.067 | -9.236 | 35.450 | 1.00 | 25.16 | H | C |
| ATOM | 2952 | C | VAL | 203 | 94.443 | -5.580 | 36.615 | 1.00 | 32.31 | H | C |
| ATOM | 2953 | O | VAL | 203 | 93.808 | -5.320 | 37.643 | 1.00 | 27.84 | H | O |
| ATOM | 2954 | N | ASN | 204 | 94.799 | -4.648 | 35.741 | 1.00 | 45.86 | H | N |
| ATOM | 2955 | CA | ASN | 204 | 94.442 | -3.266 | 35.979 | 1.00 | 50.50 | H | C |
| ATOM | 2956 | CB | ASN | 204 | 95.565 | -2.570 | 36.739 | 1.00 | 59.79 | H | C |
| ATOM | 2957 | CG | ASN | 204 | 95.186 | -1.176 | 37.164 | 1.00 | 65.34 | H | C |
| ATOM | 2958 | OD1 | ASN | 204 | 94.801 | -0.347 | 36.338 | 1.00 | 69.10 | H | O |
| ATOM | 2959 | ND2 | ASN | 204 | 95.287 | -0.906 | 38.459 | 1.00 | 65.59 | H | N |
| ATOM | 2960 | C | ASN | 204 | 94.109 | -2.486 | 34.709 | 1.00 | 51.54 | H | C |
| ATOM | 2961 | O | ASN | 204 | 94.985 | -2.164 | 33.905 | 1.00 | 51.77 | H | O |
| ATOM | 2962 | N | HIS | 205 | 92.828 | -2.176 | 34.550 | 1.00 | 30.40 | H | N |
| ATOM | 2963 | CA | HIS | 205 | 92.338 | -1.431 | 33.396 | 1.00 | 29.10 | H | C |
| ATOM | 2964 | CB | HIS | 205 | 90.994 | -1.998 | 32.957 | 1.00 | 20.87 | H | C |
| ATOM | 2965 | CG | HIS | 205 | 90.444 | -1.371 | 31.718 | 1.00 | 25.68 | H | C |
| ATOM | 2966 | CD2 | HIS | 205 | 89.209 | -0.889 | 31.437 | 1.00 | 28.69 | H | C |
| ATOM | 2967 | ND1 | HIS | 205 | 91.165 | -1.282 | 30.548 | 1.00 | 23.44 | H | N |
| ATOM | 2968 | CE1 | HIS | 205 | 90.396 | -0.780 | 29.597 | 1.00 | 25.19 | H | C |
| ATOM | 2969 | NE2 | HIS | 205 | 89.203 | -0.534 | 30.110 | 1.00 | 28.16 | H | N |
| ATOM | 2970 | C | HIS | 205 | 92.157 | 0.022 | 33.793 | 1.00 | 30.12 | H | C |
| ATOM | 2971 | O | HIS | 205 | 91.057 | 0.429 | 34.173 | 1.00 | 28.02 | H | O |
| ATOM | 2972 | N | LYS | 206 | 93.228 | 0.805 | 33.714 | 1.00 | 50.94 | H | N |
| ATOM | 2973 | CA | LYS | 206 | 93.138 | 2.209 | 34.084 | 1.00 | 49.11 | H | C |
| ATOM | 2974 | CB | LYS | 206 | 94.486 | 2.906 | 33.867 | 1.00 | 50.82 | H | C |
| ATOM | 2975 | CG | LYS | 206 | 95.536 | 2.476 | 34.895 | 1.00 | 57.82 | H | C |
| ATOM | 2976 | CD | LYS | 206 | 96.809 | 3.325 | 34.857 | 1.00 | 61.64 | H | C |
| ATOM | 2977 | CE | LYS | 206 | 97.793 | 2.906 | 35.959 | 1.00 | 63.00 | H | C |
| ATOM | 2978 | NZ | LYS | 206 | 99.049 | 3.715 | 35.960 | 1.00 | 66.30 | H | N |
| ATOM | 2979 | C | LYS | 206 | 92.017 | 2.949 | 33.353 | 1.00 | 47.68 | H | C |
| ATOM | 2980 | O | LYS | 206 | 91.318 | 3.765 | 33.955 | 1.00 | 46.73 | H | O |
| ATOM | 2981 | N | PRO | 207 | 91.810 | 2.650 | 32.057 | 1.00 | 33.42 | H | N |
| ATOM | 2982 | CD | PRO | 207 | 92.613 | 1.722 | 31.239 | 1.00 | 21.52 | H | C |
| ATOM | 2983 | CA | PRO | 207 | 90.770 | 3.285 | 31.241 | 1.00 | 34.06 | H | C |
| ATOM | 2984 | CB | PRO | 207 | 90.831 | 2.501 | 29.936 | 1.00 | 21.18 | H | C |
| ATOM | 2985 | CG | PRO | 207 | 92.286 | 2.156 | 29.831 | 1.00 | 24.69 | H | C |
| ATOM | 2986 | C | PRO | 207 | 89.366 | 3.280 | 31.846 | 1.00 | 34.36 | H | C |
| ATOM | 2987 | O | PRO | 207 | 88.452 | 3.927 | 31.311 | 1.00 | 32.31 | H | O |
| ATOM | 2988 | N | SER | 208 | 89.190 | 2.545 | 32.944 | 1.00 | 25.18 | H | N |
| ATOM | 2989 | CA | SER | 208 | 87.893 | 2.481 | 33.628 | 1.00 | 28.11 | H | C |
| ATOM | 2990 | CB | SER | 208 | 87.055 | 1.320 | 33.094 | 1.00 | 29.27 | H | C |
| ATOM | 2991 | OG | SER | 208 | 87.724 | 0.096 | 33.315 | 1.00 | 27.44 | H | O |
| ATOM | 2992 | C | SER | 208 | 88.120 | 2.314 | 35.126 | 1.00 | 31.08 | H | C |
| ATOM | 2993 | O | SER | 208 | 87.266 | 1.789 | 35.846 | 1.00 | 34.78 | H | O |

Fig. 19: A-42

| | | | | | | | | | | | |
|---|---|---|---|---|---|---|---|---|---|---|---|
| ATOM | 2994 | N | ASN | 209 | 89.284 | 2.777 | 35.573 | 1.00 | 68.02 | H | N |
| ATOM | 2995 | CA | ASN | 209 | 89.678 | 2.701 | 36.970 | 1.00 | 70.18 | H | C |
| ATOM | 2996 | CB | ASN | 209 | 89.073 | 3.879 | 37.741 | 1.00 | 49.77 | H | C |
| ATOM | 2997 | CG | ASN | 209 | 89.673 | 4.044 | 39.125 | 1.00 | 56.50 | H | C |
| ATOM | 2998 | OD1 | ASN | 209 | 90.885 | 3.963 | 39.301 | 1.00 | 62.08 | H | O |
| ATOM | 2999 | ND2 | ASN | 209 | 88.824 | 4.290 | 40.114 | 1.00 | 57.03 | H | N |
| ATOM | 3000 | C | ASN | 209 | 89.267 | 1.360 | 37.593 | 1.00 | 68.80 | H | C |
| ATOM | 3001 | O | ASN | 209 | 88.708 | 1.304 | 38.690 | 1.00 | 68.05 | H | O |
| ATOM | 3002 | N | THR | 210 | 89.555 | 0.282 | 36.871 | 1.00 | 35.45 | H | N |
| ATOM | 3003 | CA | THR | 210 | 89.246 | -1.061 | 37.322 | 1.00 | 37.08 | H | C |
| ATOM | 3004 | CB | THR | 210 | 88.640 | -1.883 | 36.201 | 1.00 | 55.80 | H | C |
| ATOM | 3005 | OG1 | THR | 210 | 87.416 | -1.273 | 35.787 | 1.00 | 56.14 | H | O |
| ATOM | 3006 | CG2 | THR | 210 | 88.367 | -3.303 | 36.668 | 1.00 | 57.05 | H | C |
| ATOM | 3007 | C | THR | 210 | 90.538 | -1.719 | 37.762 | 1.00 | 36.35 | H | C |
| ATOM | 3008 | O | THR | 210 | 91.613 | -1.388 | 37.266 | 1.00 | 34.79 | H | O |
| ATOM | 3009 | N | LYS | 211 | 90.426 | -2.655 | 38.692 | 1.00 | 33.96 | H | N |
| ATOM | 3010 | CA | LYS | 211 | 91.588 | -3.352 | 39.207 | 1.00 | 34.09 | H | C |
| ATOM | 3011 | CB | LYS | 211 | 92.366 | -2.422 | 40.154 | 1.00 | 52.60 | H | C |
| ATOM | 3012 | CG | LYS | 211 | 93.360 | -3.095 | 41.117 | 1.00 | 57.40 | H | C |
| ATOM | 3013 | CD | LYS | 211 | 94.338 | -4.040 | 40.416 | 1.00 | 62.07 | H | C |
| ATOM | 3014 | CE | LYS | 211 | 95.636 | -4.228 | 41.216 | 1.00 | 64.56 | H | C |
| ATOM | 3015 | NZ | LYS | 211 | 95.432 | -4.548 | 42.660 | 1.00 | 65.70 | H | N |
| ATOM | 3016 | C | LYS | 211 | 91.147 | -4.609 | 39.935 | 1.00 | 32.12 | H | C |
| ATOM | 3017 | O | LYS | 211 | 90.611 | -4.525 | 41.036 | 1.00 | 32.03 | H | O |
| ATOM | 3018 | N | VAL | 212 | 91.357 | -5.772 | 39.322 | 1.00 | 43.02 | H | N |
| ATOM | 3019 | CA | VAL | 212 | 90.971 | -7.017 | 39.973 | 1.00 | 37.80 | H | C |
| ATOM | 3020 | CB | VAL | 212 | 89.728 | -7.685 | 39.308 | 1.00 | 28.95 | H | C |
| ATOM | 3021 | CG1 | VAL | 212 | 88.671 | -6.639 | 39.021 | 1.00 | 26.33 | H | C |
| ATOM | 3022 | CG2 | VAL | 212 | 90.125 | -8.431 | 38.059 | 1.00 | 26.83 | H | C |
| ATOM | 3023 | C | VAL | 212 | 92.086 | -8.042 | 40.020 | 1.00 | 39.84 | H | C |
| ATOM | 3024 | O | VAL | 212 | 92.832 | -8.224 | 39.057 | 1.00 | 39.92 | H | O |
| ATOM | 3025 | N | ASP | 213 | 92.184 | -8.709 | 41.162 | 1.00 | 52.39 | H | N |
| ATOM | 3026 | CA | ASP | 213 | 93.177 | -9.743 | 41.376 | 1.00 | 49.02 | H | C |
| ATOM | 3027 | CB | ASP | 213 | 93.900 | -9.493 | 42.692 | 1.00 | 46.86 | H | C |
| ATOM | 3028 | CG | ASP | 213 | 94.548 | -8.128 | 42.740 | 1.00 | 52.80 | H | C |
| ATOM | 3029 | OD1 | ASP | 213 | 95.420 | -7.852 | 41.887 | 1.00 | 56.11 | H | O |
| ATOM | 3030 | OD2 | ASP | 213 | 94.182 | -7.329 | 43.626 | 1.00 | 57.38 | H | O |
| ATOM | 3031 | C | ASP | 213 | 92.433 | -11.067 | 41.423 | 1.00 | 46.03 | H | C |
| ATOM | 3032 | O | ASP | 213 | 91.537 | -11.248 | 42.236 | 1.00 | 45.16 | H | O |
| ATOM | 3033 | N | LYS | 214 | 92.796 | -11.993 | 40.548 | 1.00 | 33.42 | H | N |
| ATOM | 3034 | CA | LYS | 214 | 92.124 | -13.282 | 40.502 | 1.00 | 29.46 | H | C |
| ATOM | 3035 | CB | LYS | 214 | 91.732 | -13.602 | 39.055 | 0.00 | 52.86 | H | C |
| ATOM | 3036 | CG | LYS | 214 | 90.422 | -14.370 | 38.875 | 0.00 | 47.62 | H | C |
| ATOM | 3037 | CD | LYS | 214 | 90.398 | -15.699 | 39.614 | 0.00 | 43.68 | H | C |
| ATOM | 3038 | CE | LYS | 214 | 89.852 | -15.541 | 41.024 | 0.00 | 41.24 | H | C |
| ATOM | 3039 | NZ | LYS | 214 | 88.452 | -15.037 | 41.021 | 0.00 | 39.27 | H | N |
| ATOM | 3040 | C | LYS | 214 | 93.027 | -14.377 | 41.047 | 1.00 | 29.68 | H | C |
| ATOM | 3041 | O | LYS | 214 | 94.160 | -14.549 | 40.585 | 1.00 | 27.06 | H | O |
| ATOM | 3042 | N | LYS | 215 | 92.533 | -15.103 | 42.045 | 1.00 | 38.49 | H | N |
| ATOM | 3043 | CA | LYS | 215 | 93.289 | -16.207 | 42.617 | 1.00 | 34.59 | H | C |
| ATOM | 3044 | CB | LYS | 215 | 92.788 | -16.531 | 44.032 | 0.00 | 48.10 | H | C |
| ATOM | 3045 | CG | LYS | 215 | 92.812 | -15.343 | 44.987 | 0.00 | 42.43 | H | C |
| ATOM | 3046 | CD | LYS | 215 | 92.403 | -15.737 | 46.401 | 0.00 | 38.17 | H | C |
| ATOM | 3047 | CE | LYS | 215 | 93.458 | -16.597 | 47.089 | 0.00 | 35.48 | H | C |
| ATOM | 3048 | NZ | LYS | 215 | 93.695 | -17.895 | 46.397 | 0.00 | 33.32 | H | N |
| ATOM | 3049 | C | LYS | 215 | 93.042 | -17.391 | 41.675 | 1.00 | 36.50 | H | C |
| ATOM | 3050 | O | LYS | 215 | 91.901 | -17.770 | 41.413 | 1.00 | 38.63 | H | O |
| ATOM | 3051 | N | VAL | 216 | 94.113 | -17.939 | 41.122 | 1.00 | 32.15 | H | N |
| ATOM | 3052 | CA | VAL | 216 | 93.996 | -19.081 | 40.224 | 1.00 | 32.08 | H | C |
| ATOM | 3053 | CB | VAL | 216 | 94.801 | -18.850 | 38.923 | 1.00 | 21.03 | H | C |
| ATOM | 3054 | CG1 | VAL | 216 | 94.435 | -19.912 | 37.880 | 1.00 | 20.14 | H | C |
| ATOM | 3055 | CG2 | VAL | 216 | 94.482 | -17.480 | 38.375 | 1.00 | 18.92 | H | C |
| ATOM | 3056 | C | VAL | 216 | 94.504 | -20.334 | 40.948 | 1.00 | 33.21 | H | C |
| ATOM | 3057 | O | VAL | 216 | 95.696 | -20.441 | 41.248 | 1.00 | 33.32 | H | O |
| ATOM | 3058 | N | GLU | 217 | 93.586 | -21.269 | 41.219 | 1.00 | 45.06 | H | N |
| ATOM | 3059 | CA | GLU | 217 | 93.871 | -22.508 | 41.949 | 1.00 | 48.19 | H | C |
| ATOM | 3060 | CB | GLU | 217 | 93.065 | -22.532 | 43.250 | 1.00 | 91.11 | H | C |
| ATOM | 3061 | CG | GLU | 217 | 93.114 | -21.248 | 44.065 | 1.00 | 95.99 | H | C |
| ATOM | 3062 | CD | GLU | 217 | 91.872 | -21.005 | 44.901 | 1.00 | 101.94 | H | C |
| ATOM | 3063 | OE1 | GLU | 217 | 90.757 | -21.353 | 44.453 | 1.00 | 105.02 | H | O |
| ATOM | 3064 | OE2 | GLU | 217 | 92.013 | -20.475 | 46.029 | 1.00 | 105.37 | H | O |
| ATOM | 3065 | C | GLU | 217 | 93.426 | -23.720 | 41.109 | 1.00 | 48.96 | H | C |
| ATOM | 3066 | O | GLU | 217 | 92.500 | -23.643 | 40.332 | 1.00 | 51.24 | H | O |

Fig. 19: A-43

| | | | | | | | | | | | |
|---|---|---|---|---|---|---|---|---|---|---|---|
| ATOM | 3067 | N | PRO | 218 | 94.078 | -24.870 | 41.265 | 1.00 | 42.53 | H | N |
| ATOM | 3068 | CD | PRO | 218 | 95.339 | -25.074 | 41.993 | 1.00 | 48.02 | H | C |
| ATOM | 3069 | CA | PRO | 218 | 93.711 | -26.079 | 40.509 | 1.00 | 40.69 | H | C |
| ATOM | 3070 | CB | PRO | 218 | 94.962 | -26.924 | 40.609 | 1.00 | 42.70 | H | C |
| ATOM | 3071 | CG | PRO | 218 | 95.482 | -26.557 | 41.957 | 1.00 | 44.19 | H | C |
| ATOM | 3072 | C | PRO | 218 | 92.544 | -26.782 | 41.183 | 1.00 | 41.85 | H | C |
| ATOM | 3073 | O | PRO | 218 | 92.513 | -26.844 | 42.403 | 1.00 | 45.36 | H | O |
| ATOM | 3074 | N | LYS | 219 | 91.638 | -27.354 | 40.396 | 1.00 | 112.06 | H | N |
| ATOM | 3075 | CA | LYS | 219 | 90.475 | -28.045 | 40.934 | 1.00 | 111.92 | H | C |
| ATOM | 3076 | CB | LYS | 219 | 89.635 | -28.618 | 39.794 | 0.00 | 52.93 | H | C |
| ATOM | 3077 | CG | LYS | 219 | 89.522 | -27.658 | 38.654 | 0.00 | 47.21 | H | C |
| ATOM | 3078 | CD | LYS | 219 | 88.205 | -27.801 | 37.948 | 0.00 | 42.71 | H | C |
| ATOM | 3079 | CE | LYS | 219 | 88.174 | -26.793 | 36.845 | 0.00 | 39.84 | H | C |
| ATOM | 3080 | NZ | LYS | 219 | 86.847 | -26.599 | 36.249 | 0.00 | 37.57 | H | N |
| ATOM | 3081 | C | LYS | 219 | 90.867 | -29.169 | 41.892 | 1.00 | 116.73 | H | C |
| ATOM | 3082 | O | LYS | 219 | 90.330 | -29.223 | 43.021 | 1.00 | 116.18 | H | O |
| ATOM | 3083 | OXT | LYS | 219 | 91.705 | -30.007 | 41.503 | 1.00 | 36.39 | H | O |
| ATOM | 3084 | CB | ILE | 2 | 109.298 | 10.543 | -2.157 | 1.00 | 31.85 | L | C |
| ATOM | 3085 | CG2 | ILE | 2 | 110.285 | 9.382 | -2.130 | 1.00 | 31.85 | L | C |
| ATOM | 3086 | CG1 | ILE | 2 | 109.803 | 11.664 | -3.069 | 1.00 | 31.85 | L | C |
| ATOM | 3087 | CD1 | ILE | 2 | 111.143 | 12.240 | -2.656 | 1.00 | 31.85 | L | C |
| ATOM | 3088 | C | ILE | 2 | 107.518 | 8.858 | -1.778 | 1.00 | 41.66 | L | C |
| ATOM | 3089 | O | ILE | 2 | 107.155 | 9.019 | -0.613 | 1.00 | 41.66 | L | O |
| ATOM | 3090 | N | ILE | 2 | 106.898 | 11.133 | -2.646 | 1.00 | 41.66 | L | N |
| ATOM | 3091 | CA | ILE | 2 | 107.922 | 10.043 | -2.648 | 1.00 | 41.66 | L | C |
| ATOM | 3092 | N | GLN | 3 | 107.597 | 7.665 | -2.361 | 1.00 | 28.81 | L | N |
| ATOM | 3093 | CA | GLN | 3 | 107.244 | 6.433 | -1.669 | 1.00 | 28.81 | L | C |
| ATOM | 3094 | CB | GLN | 3 | 106.206 | 5.677 | -2.484 | 1.00 | 56.92 | L | C |
| ATOM | 3095 | CG | GLN | 3 | 105.708 | 4.412 | -1.837 | 1.00 | 56.92 | L | C |
| ATOM | 3096 | CD | GLN | 3 | 104.579 | 3.778 | -2.622 | 1.00 | 56.92 | L | C |
| ATOM | 3097 | OE1 | GLN | 3 | 104.124 | 2.681 | -2.298 | 1.00 | 56.92 | L | O |
| ATOM | 3098 | NE2 | GLN | 3 | 104.116 | 4.469 | -3.661 | 1.00 | 56.92 | L | N |
| ATOM | 3099 | C | GLN | 3 | 108.482 | 5.557 | -1.428 | 1.00 | 28.81 | L | C |
| ATOM | 3100 | O | GLN | 3 | 109.297 | 5.322 | -2.327 | 1.00 | 28.81 | L | O |
| ATOM | 3101 | N | LEU | 4 | 108.615 | 5.088 | -0.195 | 1.00 | 39.62 | L | N |
| ATOM | 3102 | CA | LEU | 4 | 109.744 | 4.260 | 0.198 | 1.00 | 39.62 | L | C |
| ATOM | 3103 | CB | LEU | 4 | 110.377 | 4.820 | 1.469 | 1.00 | 19.64 | L | C |
| ATOM | 3104 | CG | LEU | 4 | 111.546 | 5.792 | 1.348 | 1.00 | 19.64 | L | C |
| ATOM | 3105 | CD1 | LEU | 4 | 111.407 | 6.643 | 0.092 | 1.00 | 19.64 | L | C |
| ATOM | 3106 | CD2 | LEU | 4 | 111.614 | 6.640 | 2.617 | 1.00 | 19.64 | L | C |
| ATOM | 3107 | C | LEU | 4 | 109.323 | 2.823 | 0.445 | 1.00 | 39.62 | L | C |
| ATOM | 3108 | O | LEU | 4 | 108.470 | 2.548 | 1.289 | 1.00 | 39.62 | L | O |
| ATOM | 3109 | N | THR | 5 | 109.935 | 1.903 | -0.289 | 1.00 | 16.92 | L | N |
| ATOM | 3110 | CA | THR | 5 | 109.634 | 0.485 | -0.152 | 1.00 | 16.92 | L | C |
| ATOM | 3111 | CB | THR | 5 | 108.945 | -0.038 | -1.437 | 1.00 | 21.45 | L | C |
| ATOM | 3112 | OG1 | THR | 5 | 109.307 | -1.402 | -1.651 | 1.00 | 21.45 | L | O |
| ATOM | 3113 | CG2 | THR | 5 | 109.324 | 0.802 | -2.641 | 1.00 | 21.45 | L | C |
| ATOM | 3114 | C | THR | 5 | 110.908 | -0.312 | 0.186 | 1.00 | 16.92 | L | C |
| ATOM | 3115 | O | THR | 5 | 111.849 | -0.382 | -0.601 | 1.00 | 16.92 | L | O |
| ATOM | 3116 | N | GLN | 6 | 110.919 | -0.880 | 1.391 | 1.00 | 17.69 | L | N |
| ATOM | 3117 | CA | GLN | 6 | 112.040 | -1.661 | 1.933 | 1.00 | 17.69 | L | C |
| ATOM | 3118 | CB | GLN | 6 | 112.078 | -1.544 | 3.468 | 1.00 | 15.96 | L | C |
| ATOM | 3119 | CG | GLN | 6 | 111.898 | -0.138 | 4.014 | 1.00 | 15.96 | L | C |
| ATOM | 3120 | CD | GLN | 6 | 112.007 | -0.060 | 5.535 | 1.00 | 15.96 | L | C |
| ATOM | 3121 | OE1 | GLN | 6 | 111.626 | 0.944 | 6.139 | 1.00 | 15.96 | L | O |
| ATOM | 3122 | NE2 | GLN | 6 | 112.541 | -1.115 | 6.158 | 1.00 | 15.96 | L | N |
| ATOM | 3123 | C | GLN | 6 | 111.962 | -3.143 | 1.588 | 1.00 | 17.69 | L | C |
| ATOM | 3124 | O | GLN | 6 | 110.882 | -3.675 | 1.352 | 1.00 | 17.69 | L | O |
| ATOM | 3125 | N | SER | 7 | 113.107 | -3.814 | 1.595 | 1.00 | 44.56 | L | N |
| ATOM | 3126 | CA | SER | 7 | 113.148 | -5.238 | 1.293 | 1.00 | 44.56 | L | C |
| ATOM | 3127 | CB | SER | 7 | 113.109 | -5.470 | -0.214 | 1.00 | 33.18 | L | C |
| ATOM | 3128 | OG | SER | 7 | 114.194 | -4.813 | -0.837 | 1.00 | 33.18 | L | O |
| ATOM | 3129 | C | SER | 7 | 114.394 | -5.898 | 1.855 | 1.00 | 44.56 | L | C |
| ATOM | 3130 | O | SER | 7 | 115.480 | -5.328 | 1.811 | 1.00 | 44.56 | L | O |
| ATOM | 3131 | N | PRO | 8 | 114.246 | -7.107 | 2.415 | 1.00 | 19.10 | L | N |
| ATOM | 3132 | CD | PRO | 8 | 115.292 | -7.921 | 3.063 | 1.00 | 16.76 | L | C |
| ATOM | 3133 | CA | PRO | 8 | 112.945 | -7.771 | 2.494 | 1.00 | 19.10 | L | C |
| ATOM | 3134 | CB | PRO | 8 | 113.303 | -9.161 | 3.004 | 1.00 | 16.76 | L | C |
| ATOM | 3135 | CG | PRO | 8 | 114.481 | -8.882 | 3.905 | 1.00 | 16.76 | L | C |
| ATOM | 3136 | C | PRO | 8 | 112.068 | -7.023 | 3.479 | 1.00 | 19.10 | L | C |
| ATOM | 3137 | O | PRO | 8 | 112.517 | -6.069 | 4.125 | 1.00 | 19.10 | L | O |
| ATOM | 3138 | N | SER | 9 | 110.822 | -7.460 | 3.589 | 1.00 | 12.41 | L | N |
| ATOM | 3139 | CA | SER | 9 | 109.885 | -6.851 | 4.516 | 1.00 | 12.41 | L | C |

Fig. 19: A-44

| | | | | | | | | | | | |
|---|---|---|---|---|---|---|---|---|---|---|---|
| ATOM | 3140 | CB | SER | 9 | 108.466 | -7.059 | 4.023 | 1.00 | 25.43 | L | C |
| ATOM | 3141 | OG | SER | 9 | 108.345 | -6.555 | 2.707 | 1.00 | 25.43 | L | O |
| ATOM | 3142 | C | SER | 9 | 110.083 | -7.558 | 5.837 | 1.00 | 12.41 | L | C |
| ATOM | 3143 | O | SER | 9 | 109.904 | -6.983 | 6.904 | 1.00 | 12.41 | L | O |
| ATOM | 3144 | N | SER | 10 | 110.492 | -8.817 | 5.745 | 1.00 | 33.63 | L | N |
| ATOM | 3145 | CA | SER | 10 | 110.720 | -9.645 | 6.910 | 1.00 | 33.63 | L | C |
| ATOM | 3146 | CB | SER | 10 | 109.490 | -10.517 | 7.144 | 1.00 | 43.13 | L | C |
| ATOM | 3147 | OG | SER | 10 | 109.614 | -11.248 | 8.338 | 1.00 | 43.13 | L | O |
| ATOM | 3148 | C | SER | 10 | 111.942 | -10.504 | 6.624 | 1.00 | 33.63 | L | C |
| ATOM | 3149 | O | SER | 10 | 112.226 | -10.814 | 5.470 | 1.00 | 33.63 | L | O |
| ATOM | 3150 | N | LEU | 11 | 112.677 | -10.880 | 7.666 | 1.00 | 38.19 | L | N |
| ATOM | 3151 | CA | LEU | 11 | 113.867 | -11.709 | 7.484 | 1.00 | 38.19 | L | C |
| ATOM | 3152 | CB | LEU | 11 | 115.020 | -10.880 | 6.894 | 1.00 | 33.64 | L | C |
| ATOM | 3153 | CG | LEU | 11 | 115.721 | -9.849 | 7.793 | 1.00 | 33.64 | L | C |
| ATOM | 3154 | CD1 | LEU | 11 | 116.757 | -10.532 | 8.667 | 1.00 | 33.64 | L | C |
| ATOM | 3155 | CD2 | LEU | 11 | 116.401 | -8.807 | 6.927 | 1.00 | 33.64 | L | C |
| ATOM | 3156 | C | LEU | 11 | 114.319 | -12.335 | 8.792 | 1.00 | 38.19 | L | C |
| ATOM | 3157 | O | LEU | 11 | 114.365 | -11.672 | 9.829 | 1.00 | 38.19 | L | O |
| ATOM | 3158 | N | SER | 12 | 114.661 | -13.616 | 8.736 | 1.00 | 42.98 | L | N |
| ATOM | 3159 | CA | SER | 12 | 115.128 | -14.320 | 9.916 | 1.00 | 42.98 | L | C |
| ATOM | 3160 | CB | SER | 12 | 114.334 | -15.612 | 10.103 | 1.00 | 67.78 | L | C |
| ATOM | 3161 | OG | SER | 12 | 114.474 | -16.092 | 11.426 | 1.00 | 67.78 | L | O |
| ATOM | 3162 | C | SER | 12 | 116.611 | -14.628 | 9.738 | 1.00 | 42.98 | L | C |
| ATOM | 3163 | O | SER | 12 | 117.031 | -15.118 | 8.697 | 1.00 | 42.98 | L | O |
| ATOM | 3164 | N | ALA | 13 | 117.407 | -14.320 | 10.749 | 1.00 | 25.03 | L | N |
| ATOM | 3165 | CA | ALA | 13 | 118.836 | -14.575 | 10.667 | 1.00 | 25.03 | L | C |
| ATOM | 3166 | CB | ALA | 13 | 119.556 | -13.340 | 10.124 | 1.00 | 41.64 | L | C |
| ATOM | 3167 | C | ALA | 13 | 119.390 | -14.952 | 12.037 | 1.00 | 25.03 | L | C |
| ATOM | 3168 | O | ALA | 13 | 118.829 | -14.571 | 13.067 | 1.00 | 25.03 | L | O |
| ATOM | 3169 | N | SER | 14 | 120.493 | -15.701 | 12.045 | 1.00 | 32.48 | L | N |
| ATOM | 3170 | CA | SER | 14 | 121.111 | -16.132 | 13.294 | 1.00 | 32.48 | L | C |
| ATOM | 3171 | CB | SER | 14 | 121.594 | -17.569 | 13.160 | 1.00 | 77.12 | L | C |
| ATOM | 3172 | OG | SER | 14 | 122.348 | -17.721 | 11.975 | 1.00 | 77.12 | L | O |
| ATOM | 3173 | C | SER | 14 | 122.269 | -15.231 | 13.691 | 1.00 | 32.48 | L | C |
| ATOM | 3174 | O | SER | 14 | 122.893 | -14.595 | 12.841 | 1.00 | 32.48 | L | O |
| ATOM | 3175 | N | VAL | 15 | 122.545 | -15.166 | 14.988 | 1.00 | 47.29 | L | N |
| ATOM | 3176 | CA | VAL | 15 | 123.637 | -14.336 | 15.470 | 1.00 | 47.29 | L | C |
| ATOM | 3177 | CB | VAL | 15 | 123.996 | -14.657 | 16.937 | 1.00 | 53.16 | L | C |
| ATOM | 3178 | CG1 | VAL | 15 | 123.121 | -13.847 | 17.881 | 1.00 | 53.16 | L | C |
| ATOM | 3179 | CG2 | VAL | 15 | 123.808 | -16.148 | 17.198 | 1.00 | 53.16 | L | C |
| ATOM | 3180 | C | VAL | 15 | 124.858 | -14.575 | 14.606 | 1.00 | 47.29 | L | C |
| ATOM | 3181 | O | VAL | 15 | 125.164 | -15.712 | 14.250 | 1.00 | 47.29 | L | O |
| ATOM | 3182 | N | GLY | 16 | 125.537 | -13.495 | 14.247 | 1.00 | 32.44 | L | N |
| ATOM | 3183 | CA | GLY | 16 | 126.728 | -13.615 | 13.431 | 1.00 | 32.44 | L | C |
| ATOM | 3184 | C | GLY | 16 | 126.506 | -13.463 | 11.945 | 1.00 | 32.44 | L | C |
| ATOM | 3185 | O | GLY | 16 | 127.467 | -13.306 | 11.191 | 1.00 | 32.44 | L | O |
| ATOM | 3186 | N | ASP | 17 | 125.255 | -13.524 | 11.510 | 1.00 | 32.03 | L | N |
| ATOM | 3187 | CA | ASP | 17 | 124.959 | -13.367 | 10.092 | 1.00 | 32.03 | L | C |
| ATOM | 3188 | CB | ASP | 17 | 123.533 | -13.814 | 9.788 | 1.00 | 55.01 | L | C |
| ATOM | 3189 | CG | ASP | 17 | 123.344 | -15.291 | 9.961 | 1.00 | 55.01 | L | C |
| ATOM | 3190 | OD1 | ASP | 17 | 122.211 | -15.771 | 9.739 | 1.00 | 55.01 | L | O |
| ATOM | 3191 | OD2 | ASP | 17 | 124.331 | -15.965 | 10.320 | 1.00 | 55.01 | L | O |
| ATOM | 3192 | C | ASP | 17 | 125.109 | -11.905 | 9.677 | 1.00 | 32.03 | L | C |
| ATOM | 3193 | O | ASP | 17 | 125.041 | -10.997 | 10.517 | 1.00 | 32.03 | L | O |
| ATOM | 3194 | N | ARG | 18 | 125.324 | -11.680 | 8.385 | 1.00 | 40.86 | L | N |
| ATOM | 3195 | CA | ARG | 18 | 125.447 | -10.325 | 7.875 | 1.00 | 40.86 | L | C |
| ATOM | 3196 | CB | ARG | 18 | 126.587 | -10.231 | 6.865 | 1.00 | 78.37 | L | C |
| ATOM | 3197 | CG | ARG | 18 | 126.790 | -8.842 | 6.293 | 1.00 | 78.37 | L | C |
| ATOM | 3198 | CD | ARG | 18 | 128.223 | -8.662 | 5.812 | 1.00 | 78.37 | L | C |
| ATOM | 3199 | NE | ARG | 18 | 128.413 | -7.408 | 5.087 | 1.00 | 78.37 | L | N |
| ATOM | 3200 | CZ | ARG | 18 | 127.841 | -7.131 | 3.918 | 1.00 | 78.37 | L | C |
| ATOM | 3201 | NH1 | ARG | 18 | 127.042 | -8.021 | 3.336 | 1.00 | 78.37 | L | N |
| ATOM | 3202 | NH2 | ARG | 18 | 128.064 | -5.960 | 3.334 | 1.00 | 78.37 | L | N |
| ATOM | 3203 | C | ARG | 18 | 124.116 | -9.986 | 7.220 | 1.00 | 40.86 | L | C |
| ATOM | 3204 | O | ARG | 18 | 123.690 | -10.656 | 6.284 | 1.00 | 40.86 | L | O |
| ATOM | 3205 | N | VAL | 19 | 123.455 | -8.948 | 7.721 | 1.00 | 26.42 | L | N |
| ATOM | 3206 | CA | VAL | 19 | 122.157 | -8.549 | 7.193 | 1.00 | 26.42 | L | C |
| ATOM | 3207 | CB | VAL | 19 | 121.154 | -8.426 | 8.335 | 1.00 | 32.94 | L | C |
| ATOM | 3208 | CG1 | VAL | 19 | 119.768 | -8.214 | 7.783 | 1.00 | 32.94 | L | C |
| ATOM | 3209 | CG2 | VAL | 19 | 121.204 | -9.678 | 9.194 | 1.00 | 32.94 | L | C |
| ATOM | 3210 | C | VAL | 19 | 122.200 | -7.235 | 6.420 | 1.00 | 26.42 | L | C |
| ATOM | 3211 | O | VAL | 19 | 122.902 | -6.306 | 6.798 | 1.00 | 26.42 | L | O |
| ATOM | 3212 | N | THR | 20 | 121.443 | -7.160 | 5.333 | 1.00 | 42.24 | L | N |

Fig. 19: A-45

| | | | | | | | | | | | |
|---|---|---|---|---|---|---|---|---|---|---|---|
| ATOM | 3213 | CA | THR | 20 | 121.408 | -5.950 | 4.519 | 1.00 | 42.24 | L | C |
| ATOM | 3214 | CB | THR | 20 | 122.310 | -6.097 | 3.289 | 1.00 | 29.90 | L | C |
| ATOM | 3215 | OG1 | THR | 20 | 123.680 | -6.127 | 3.714 | 1.00 | 29.90 | L | O |
| ATOM | 3216 | CG2 | THR | 20 | 122.099 | -4.944 | 2.326 | 1.00 | 29.90 | L | C |
| ATOM | 3217 | C | THR | 20 | 120.008 | -5.582 | 4.050 | 1.00 | 42.24 | L | C |
| ATOM | 3218 | O | THR | 20 | 119.477 | -6.202 | 3.127 | 1.00 | 42.24 | L | O |
| ATOM | 3219 | N | ILE | 21 | 119.418 | -4.568 | 4.683 | 1.00 | 13.95 | L | N |
| ATOM | 3220 | CA | ILE | 21 | 118.077 | -4.114 | 4.326 | 1.00 | 13.95 | L | C |
| ATOM | 3221 | CB | ILE | 21 | 117.349 | -3.486 | 5.541 | 1.00 | 24.11 | L | C |
| ATOM | 3222 | CG2 | ILE | 21 | 115.892 | -3.176 | 5.186 | 1.00 | 24.11 | L | C |
| ATOM | 3223 | CG1 | ILE | 21 | 117.390 | -4.457 | 6.720 | 1.00 | 24.11 | L | C |
| ATOM | 3224 | CD1 | ILE | 21 | 116.709 | -3.936 | 7.960 | 1.00 | 24.11 | L | C |
| ATOM | 3225 | C | ILE | 21 | 118.180 | -3.081 | 3.217 | 1.00 | 13.95 | L | C |
| ATOM | 3226 | O | ILE | 21 | 119.036 | -2.208 | 3.251 | 1.00 | 13.95 | L | O |
| ATOM | 3227 | N | THR | 22 | 117.305 | -3.190 | 2.230 | 1.00 | 27.07 | L | N |
| ATOM | 3228 | CA | THR | 22 | 117.304 | -2.266 | 1.107 | 1.00 | 27.07 | L | C |
| ATOM | 3229 | CB | THR | 22 | 117.335 | -3.022 | -0.239 | 1.00 | 29.03 | L | C |
| ATOM | 3230 | OG1 | THR | 22 | 118.613 | -3.642 | -0.404 | 1.00 | 29.03 | L | O |
| ATOM | 3231 | CG2 | THR | 22 | 117.084 | -2.084 | -1.391 | 1.00 | 29.03 | L | C |
| ATOM | 3232 | C | THR | 22 | 116.067 | -1.385 | 1.123 | 1.00 | 27.07 | L | C |
| ATOM | 3233 | O | THR | 22 | 114.951 | -1.871 | 1.313 | 1.00 | 27.07 | L | O |
| ATOM | 3234 | N | CYS | 23 | 116.281 | -0.089 | 0.916 | 1.00 | 32.83 | L | N |
| ATOM | 3235 | CA | CYS | 23 | 115.203 | 0.896 | 0.882 | 1.00 | 32.83 | L | C |
| ATOM | 3236 | C | CYS | 23 | 115.259 | 1.546 | -0.489 | 1.00 | 32.83 | L | C |
| ATOM | 3237 | O | CYS | 23 | 116.250 | 2.187 | -0.837 | 1.00 | 32.83 | L | O |
| ATOM | 3238 | CB | CYS | 23 | 115.424 | 1.947 | 1.973 | 1.00 | 18.66 | L | C |
| ATOM | 3239 | SG | CYS | 23 | 114.216 | 3.310 | 2.141 | 1.00 | 18.66 | L | S |
| ATOM | 3240 | N | SER | 24 | 114.199 | 1.355 | -1.268 | 1.00 | 11.34 | L | N |
| ATOM | 3241 | CA | SER | 24 | 114.110 | 1.924 | -2.612 | 1.00 | 11.34 | L | C |
| ATOM | 3242 | CB | SER | 24 | 113.696 | 0.853 | -3.614 | 1.00 | 28.67 | L | C |
| ATOM | 3243 | OG | SER | 24 | 114.642 | -0.190 | -3.632 | 1.00 | 28.67 | L | O |
| ATOM | 3244 | C | SER | 24 | 113.096 | 3.058 | -2.641 | 1.00 | 11.34 | L | C |
| ATOM | 3245 | O | SER | 24 | 111.971 | 2.910 | -2.154 | 1.00 | 11.34 | L | O |
| ATOM | 3246 | N | ALA | 25 | 113.496 | 4.186 | -3.217 | 1.00 | 32.05 | L | N |
| ATOM | 3247 | CA | ALA | 25 | 112.617 | 5.343 | -3.286 | 1.00 | 32.05 | L | C |
| ATOM | 3248 | CB | ALA | 25 | 113.312 | 6.567 | -2.707 | 1.00 | 44.86 | L | C |
| ATOM | 3249 | C | ALA | 25 | 112.139 | 5.633 | -4.699 | 1.00 | 32.05 | L | C |
| ATOM | 3250 | O | ALA | 25 | 112.918 | 5.619 | -5.658 | 1.00 | 32.05 | L | O |
| ATOM | 3251 | N | SER | 26 | 110.839 | 5.901 | -4.803 | 1.00 | 26.80 | L | N |
| ATOM | 3252 | CA | SER | 26 | 110.179 | 6.204 | -6.070 | 1.00 | 26.80 | L | C |
| ATOM | 3253 | CB | SER | 26 | 108.717 | 6.572 | -5.814 | 1.00 | 23.33 | L | C |
| ATOM | 3254 | OG | SER | 26 | 108.617 | 7.713 | -4.984 | 1.00 | 23.33 | L | O |
| ATOM | 3255 | C | SER | 26 | 110.866 | 7.338 | -6.813 | 1.00 | 26.80 | L | C |
| ATOM | 3256 | O | SER | 26 | 110.814 | 7.404 | -8.032 | 1.00 | 26.80 | L | O |
| ATOM | 3257 | N | SER | 27 | 111.496 | 8.234 | -6.066 | 1.00 | 22.71 | L | N |
| ATOM | 3258 | CA | SER | 27 | 112.210 | 9.363 | -6.644 | 1.00 | 22.71 | L | C |
| ATOM | 3259 | CB | SER | 27 | 111.439 | 10.661 | -6.406 | 1.00 | 47.74 | L | C |
| ATOM | 3260 | OG | SER | 27 | 110.105 | 10.552 | -6.862 | 1.00 | 47.74 | L | O |
| ATOM | 3261 | C | SER | 27 | 113.547 | 9.438 | -5.934 | 1.00 | 22.71 | L | C |
| ATOM | 3262 | O | SER | 27 | 113.666 | 8.982 | -4.805 | 1.00 | 22.71 | L | O |
| ATOM | 3263 | N | SER | 28 | 114.555 | 10.004 | -6.586 | 1.00 | 37.73 | L | N |
| ATOM | 3264 | CA | SER | 28 | 115.874 | 10.121 | -5.972 | 1.00 | 37.73 | L | C |
| ATOM | 3265 | CB | SER | 28 | 116.890 | 10.583 | -7.010 | 1.00 | 36.75 | L | C |
| ATOM | 3266 | OG | SER | 28 | 116.486 | 11.818 | -7.573 | 1.00 | 36.75 | L | O |
| ATOM | 3267 | C | SER | 28 | 115.846 | 11.106 | -4.804 | 1.00 | 37.73 | L | C |
| ATOM | 3268 | O | SER | 28 | 115.043 | 12.038 | -4.775 | 1.00 | 37.73 | L | O |
| ATOM | 3269 | N | VAL | 29 | 116.726 | 10.890 | -3.838 | 1.00 | 35.34 | L | N |
| ATOM | 3270 | CA | VAL | 29 | 116.807 | 11.753 | -2.669 | 1.00 | 35.34 | L | C |
| ATOM | 3271 | CB | VAL | 29 | 116.002 | 11.154 | -1.484 | 1.00 | 39.96 | L | C |
| ATOM | 3272 | CG1 | VAL | 29 | 114.521 | 11.097 | -1.842 | 1.00 | 39.96 | L | C |
| ATOM | 3273 | CG2 | VAL | 29 | 116.506 | 9.755 | -1.147 | 1.00 | 39.96 | L | C |
| ATOM | 3274 | C | VAL | 29 | 118.277 | 11.895 | -2.289 | 1.00 | 35.34 | L | C |
| ATOM | 3275 | O | VAL | 29 | 119.076 | 11.001 | -2.571 | 1.00 | 35.34 | L | O |
| ATOM | 3276 | N | ASN | 30 | 118.641 | 13.007 | -1.658 | 1.00 | 55.44 | L | N |
| ATOM | 3277 | CA | ASN | 30 | 120.033 | 13.236 | -1.278 | 1.00 | 55.44 | L | C |
| ATOM | 3278 | CB | ASN | 30 | 120.252 | 14.722 | -0.974 | 1.00 | 66.75 | L | C |
| ATOM | 3279 | CG | ASN | 30 | 119.176 | 15.292 | -0.071 | 1.00 | 66.75 | L | C |
| ATOM | 3280 | OD1 | ASN | 30 | 118.006 | 15.359 | -0.453 | 1.00 | 66.75 | L | O |
| ATOM | 3281 | ND2 | ASN | 30 | 119.561 | 15.694 | 1.138 | 1.00 | 66.75 | L | N |
| ATOM | 3282 | C | ASN | 30 | 120.510 | 12.386 | -0.095 | 1.00 | 55.44 | L | C |
| ATOM | 3283 | O | ASN | 30 | 121.705 | 12.099 | 0.033 | 1.00 | 55.44 | L | O |
| ATOM | 3284 | N | HIS | 31 | 119.586 | 11.985 | 0.770 | 1.00 | 34.66 | L | N |
| ATOM | 3285 | CA | HIS | 31 | 119.947 | 11.172 | 1.923 | 1.00 | 34.66 | L | C |

Fig. 19: A-46

| | | | | | | | | | | |
|---|---|---|---|---|---|---|---|---|---|---|
| ATOM | 3286 | CB | HIS | 31 | 120.290 | 12.049 | 3.132 | 1.00 | 51.96 | L | C |
| ATOM | 3287 | CG | HIS | 31 | 121.623 | 12.725 | 3.042 | 1.00 | 51.96 | L | C |
| ATOM | 3288 | CD2 | HIS | 31 | 122.763 | 12.534 | 3.744 | 1.00 | 51.96 | L | C |
| ATOM | 3289 | ND1 | HIS | 31 | 121.879 | 13.763 | 2.172 | 1.00 | 51.96 | L | N |
| ATOM | 3290 | CE1 | HIS | 31 | 123.118 | 14.186 | 2.345 | 1.00 | 51.96 | L | C |
| ATOM | 3291 | NE2 | HIS | 31 | 123.676 | 13.457 | 3.294 | 1.00 | 51.96 | L | N |
| ATOM | 3292 | C | HIS | 31 | 118.811 | 10.241 | 2.316 | 1.00 | 34.66 | L | C |
| ATOM | 3293 | O | HIS | 31 | 117.736 | 10.267 | 1.707 | 1.00 | 34.66 | L | O |
| ATOM | 3294 | N | MET | 32 | 119.070 | 9.415 | 3.332 | 1.00 | 24.85 | L | N |
| ATOM | 3295 | CA | MET | 32 | 118.081 | 8.489 | 3.864 | 1.00 | 24.85 | L | C |
| ATOM | 3296 | CB | MET | 32 | 118.189 | 7.126 | 3.187 | 1.00 | 22.87 | L | C |
| ATOM | 3297 | CG | MET | 32 | 116.961 | 6.226 | 3.394 | 1.00 | 22.87 | L | C |
| ATOM | 3298 | SD | MET | 32 | 115.381 | 6.922 | 2.757 | 1.00 | 22.87 | L | S |
| ATOM | 3299 | CE | MET | 32 | 115.727 | 7.028 | 1.012 | 1.00 | 22.87 | L | C |
| ATOM | 3300 | C | MET | 32 | 118.316 | 8.340 | 5.360 | 1.00 | 24.85 | L | C |
| ATOM | 3301 | O | MET | 32 | 119.454 | 8.377 | 5.831 | 1.00 | 24.85 | L | O |
| ATOM | 3302 | N | PHE | 33 | 117.244 | 8.180 | 6.118 | 1.00 | 7.47 | L | N |
| ATOM | 3303 | CA | PHE | 33 | 117.391 | 8.029 | 7.554 | 1.00 | 7.47 | L | C |
| ATOM | 3304 | CB | PHE | 33 | 116.693 | 9.171 | 8.285 | 1.00 | 11.22 | L | C |
| ATOM | 3305 | CG | PHE | 33 | 117.205 | 10.533 | 7.901 | 1.00 | 11.22 | L | C |
| ATOM | 3306 | CD1 | PHE | 33 | 116.901 | 11.078 | 6.652 | 1.00 | 11.22 | L | C |
| ATOM | 3307 | CD2 | PHE | 33 | 118.017 | 11.259 | 8.776 | 1.00 | 11.22 | L | C |
| ATOM | 3308 | CE1 | PHE | 33 | 117.399 | 12.325 | 6.275 | 1.00 | 11.22 | L | C |
| ATOM | 3309 | CE2 | PHE | 33 | 118.519 | 12.501 | 8.407 | 1.00 | 11.22 | L | C |
| ATOM | 3310 | CZ | PHE | 33 | 118.207 | 13.035 | 7.149 | 1.00 | 11.22 | L | C |
| ATOM | 3311 | C | PHE | 33 | 116.817 | 6.702 | 7.994 | 1.00 | 7.47 | L | C |
| ATOM | 3312 | O | PHE | 33 | 115.959 | 6.150 | 7.320 | 1.00 | 7.47 | L | O |
| ATOM | 3313 | N | TRP | 34 | 117.301 | 6.186 | 9.118 | 1.00 | 15.67 | L | N |
| ATOM | 3314 | CA | TRP | 34 | 116.815 | 4.912 | 9.618 | 1.00 | 15.67 | L | C |
| ATOM | 3315 | CB | TRP | 34 | 117.859 | 3.818 | 9.414 | 1.00 | 16.49 | L | C |
| ATOM | 3316 | CG | TRP | 34 | 118.217 | 3.590 | 7.992 | 1.00 | 16.49 | L | C |
| ATOM | 3317 | CD2 | TRP | 34 | 117.671 | 2.592 | 7.123 | 1.00 | 16.49 | L | C |
| ATOM | 3318 | CE2 | TRP | 34 | 118.315 | 2.732 | 5.872 | 1.00 | 16.49 | L | C |
| ATOM | 3319 | CE3 | TRP | 34 | 116.702 | 1.596 | 7.279 | 1.00 | 16.49 | L | C |
| ATOM | 3320 | CD1 | TRP | 34 | 119.137 | 4.278 | 7.259 | 1.00 | 16.49 | L | C |
| ATOM | 3321 | NE1 | TRP | 34 | 119.205 | 3.767 | 5.984 | 1.00 | 16.49 | L | N |
| ATOM | 3322 | CZ2 | TRP | 34 | 118.024 | 1.914 | 4.782 | 1.00 | 16.49 | L | C |
| ATOM | 3323 | CZ3 | TRP | 34 | 116.409 | 0.780 | 6.194 | 1.00 | 16.49 | L | C |
| ATOM | 3324 | CH2 | TRP | 34 | 117.069 | 0.945 | 4.960 | 1.00 | 16.49 | L | C |
| ATOM | 3325 | C | TRP | 34 | 116.459 | 4.960 | 11.086 | 1.00 | 15.67 | L | C |
| ATOM | 3326 | O | TRP | 34 | 117.149 | 5.593 | 11.882 | 1.00 | 15.67 | L | O |
| ATOM | 3327 | N | TYR | 35 | 115.370 | 4.288 | 11.437 | 1.00 | 19.71 | L | N |
| ATOM | 3328 | CA | TYR | 35 | 114.939 | 4.229 | 12.820 | 1.00 | 19.71 | L | C |
| ATOM | 3329 | CB | TYR | 35 | 113.591 | 4.922 | 13.007 | 1.00 | 25.75 | L | C |
| ATOM | 3330 | CG | TYR | 35 | 113.623 | 6.381 | 12.621 | 1.00 | 25.75 | L | C |
| ATOM | 3331 | CD1 | TYR | 35 | 113.255 | 6.790 | 11.344 | 1.00 | 25.75 | L | C |
| ATOM | 3332 | CE1 | TYR | 35 | 113.310 | 8.124 | 10.980 | 1.00 | 25.75 | L | C |
| ATOM | 3333 | CD2 | TYR | 35 | 114.052 | 7.353 | 13.527 | 1.00 | 25.75 | L | C |
| ATOM | 3334 | CE2 | TYR | 35 | 114.110 | 8.685 | 13.173 | 1.00 | 25.75 | L | C |
| ATOM | 3335 | CZ | TYR | 35 | 113.737 | 9.064 | 11.899 | 1.00 | 25.75 | L | C |
| ATOM | 3336 | OH | TYR | 35 | 113.776 | 10.384 | 11.540 | 1.00 | 25.75 | L | O |
| ATOM | 3337 | C | TYR | 35 | 114.821 | 2.781 | 13.207 | 1.00 | 19.71 | L | C |
| ATOM | 3338 | O | TYR | 35 | 114.508 | 1.937 | 12.373 | 1.00 | 19.71 | L | O |
| ATOM | 3339 | N | GLN | 36 | 115.100 | 2.491 | 14.468 | 1.00 | 30.18 | L | N |
| ATOM | 3340 | CA | GLN | 36 | 114.987 | 1.136 | 14.964 | 1.00 | 30.18 | L | C |
| ATOM | 3341 | CB | GLN | 36 | 116.292 | 0.659 | 15.597 | 1.00 | 33.56 | L | C |
| ATOM | 3342 | CG | GLN | 36 | 116.109 | -0.625 | 16.387 | 1.00 | 33.56 | L | C |
| ATOM | 3343 | CD | GLN | 36 | 117.154 | -0.806 | 17.464 | 1.00 | 33.56 | L | C |
| ATOM | 3344 | OE1 | GLN | 36 | 118.296 | -1.161 | 17.179 | 1.00 | 33.56 | L | O |
| ATOM | 3345 | NE2 | GLN | 36 | 116.770 | -0.550 | 18.716 | 1.00 | 33.56 | L | N |
| ATOM | 3346 | C | GLN | 36 | 113.902 | 1.124 | 16.017 | 1.00 | 30.18 | L | C |
| ATOM | 3347 | O | GLN | 36 | 113.986 | 1.852 | 17.008 | 1.00 | 30.18 | L | O |
| ATOM | 3348 | N | GLN | 37 | 112.877 | 0.311 | 15.803 | 1.00 | 31.84 | L | N |
| ATOM | 3349 | CA | GLN | 37 | 111.811 | 0.209 | 16.778 | 1.00 | 31.84 | L | C |
| ATOM | 3350 | CB | GLN | 37 | 110.467 | 0.599 | 16.162 | 1.00 | 26.28 | L | C |
| ATOM | 3351 | CG | GLN | 37 | 109.335 | 0.494 | 17.165 | 1.00 | 26.28 | L | C |
| ATOM | 3352 | CD | GLN | 37 | 108.003 | 0.979 | 16.632 | 1.00 | 26.28 | L | C |
| ATOM | 3353 | OE1 | GLN | 37 | 107.573 | 0.597 | 15.537 | 1.00 | 26.28 | L | O |
| ATOM | 3354 | NE2 | GLN | 37 | 107.328 | 1.819 | 17.417 | 1.00 | 26.28 | L | N |
| ATOM | 3355 | C | GLN | 37 | 111.729 | -1.201 | 17.360 | 1.00 | 31.84 | L | C |
| ATOM | 3356 | O | GLN | 37 | 111.571 | -2.189 | 16.637 | 1.00 | 31.84 | L | O |
| ATOM | 3357 | N | LYS | 38 | 111.861 | -1.285 | 18.676 | 1.00 | 33.78 | L | N |
| ATOM | 3358 | CA | LYS | 38 | 111.776 | -2.561 | 19.366 | 1.00 | 33.78 | L | C |

Fig. 19: A-47

| | | | | | | | | | | | |
|---|---|---|---|---|---|---|---|---|---|---|---|
| ATOM | 3359 | CB | LYS | 38 | 112.784 | -2.618 | 20.519 | 1.00 | 38.31 | L | C |
| ATOM | 3360 | CG | LYS | 38 | 114.209 | -2.306 | 20.094 | 1.00 | 38.31 | L | C |
| ATOM | 3361 | CD | LYS | 38 | 115.224 | -2.552 | 21.207 | 1.00 | 38.31 | L | C |
| ATOM | 3362 | CE | LYS | 38 | 115.494 | -4.034 | 21.402 | 1.00 | 38.31 | L | C |
| ATOM | 3363 | NZ | LYS | 38 | 115.954 | -4.720 | 20.154 | 1.00 | 38.31 | L | N |
| ATOM | 3364 | C | LYS | 38 | 110.346 | -2.671 | 19.889 | 1.00 | 33.78 | L | C |
| ATOM | 3365 | O | LYS | 38 | 109.770 | -1.690 | 20.354 | 1.00 | 33.78 | L | O |
| ATOM | 3366 | N | PRO | 39 | 109.757 | -3.873 | 19.818 | 1.00 | 36.51 | L | N |
| ATOM | 3367 | CD | PRO | 39 | 110.419 | -5.128 | 19.422 | 1.00 | 56.09 | L | C |
| ATOM | 3368 | CA | PRO | 39 | 108.389 | -4.139 | 20.271 | 1.00 | 36.51 | L | C |
| ATOM | 3369 | CB | PRO | 39 | 108.376 | -5.652 | 20.409 | 1.00 | 56.09 | L | C |
| ATOM | 3370 | CG | PRO | 39 | 109.254 | -6.072 | 19.283 | 1.00 | 56.09 | L | C |
| ATOM | 3371 | C | PRO | 39 | 107.976 | -3.434 | 21.559 | 1.00 | 36.51 | L | C |
| ATOM | 3372 | O | PRO | 39 | 108.664 | -3.523 | 22.573 | 1.00 | 36.51 | L | O |
| ATOM | 3373 | N | GLY | 40 | 106.846 | -2.735 | 21.503 | 1.00 | 29.94 | L | N |
| ATOM | 3374 | CA | GLY | 40 | 106.330 | -2.036 | 22.667 | 1.00 | 29.94 | L | C |
| ATOM | 3375 | C | GLY | 40 | 107.025 | -0.738 | 23.034 | 1.00 | 29.94 | L | C |
| ATOM | 3376 | O | GLY | 40 | 106.669 | -0.119 | 24.037 | 1.00 | 29.94 | L | O |
| ATOM | 3377 | N | LYS | 41 | 108.019 | -0.332 | 22.243 | 1.00 | 32.57 | L | N |
| ATOM | 3378 | CA | LYS | 41 | 108.754 | 0.903 | 22.503 | 1.00 | 32.57 | L | C |
| ATOM | 3379 | CB | LYS | 41 | 110.231 | 0.611 | 22.804 | 1.00 | 82.45 | L | C |
| ATOM | 3380 | CG | LYS | 41 | 110.466 | -0.251 | 24.040 | 1.00 | 82.45 | L | C |
| ATOM | 3381 | CD | LYS | 41 | 111.905 | -0.157 | 24.579 | 1.00 | 82.45 | L | C |
| ATOM | 3382 | CE | LYS | 41 | 112.977 | -0.603 | 23.575 | 1.00 | 82.45 | L | C |
| ATOM | 3383 | NZ | LYS | 41 | 113.257 | 0.396 | 22.496 | 1.00 | 82.45 | L | N |
| ATOM | 3384 | C | LYS | 41 | 108.656 | 1.860 | 21.319 | 1.00 | 32.57 | L | C |
| ATOM | 3385 | O | LYS | 41 | 108.243 | 1.480 | 20.227 | 1.00 | 32.57 | L | O |
| ATOM | 3386 | N | ALA | 42 | 109.029 | 3.112 | 21.547 | 1.00 | 30.66 | L | N |
| ATOM | 3387 | CA | ALA | 42 | 108.990 | 4.126 | 20.502 | 1.00 | 30.66 | L | C |
| ATOM | 3388 | CB | ALA | 42 | 108.980 | 5.513 | 21.129 | 1.00 | 32.87 | L | C |
| ATOM | 3389 | C | ALA | 42 | 110.209 | 3.973 | 19.606 | 1.00 | 30.66 | L | C |
| ATOM | 3390 | O | ALA | 42 | 111.235 | 3.436 | 20.028 | 1.00 | 30.66 | L | O |
| ATOM | 3391 | N | PRO | 43 | 110.112 | 4.435 | 18.351 | 1.00 | 23.79 | L | N |
| ATOM | 3392 | CD | PRO | 43 | 108.939 | 4.976 | 17.647 | 1.00 | 7.10 | L | C |
| ATOM | 3393 | CA | PRO | 43 | 111.248 | 4.323 | 17.440 | 1.00 | 23.79 | L | C |
| ATOM | 3394 | CB | PRO | 43 | 110.727 | 4.980 | 16.170 | 1.00 | 7.10 | L | C |
| ATOM | 3395 | CG | PRO | 43 | 109.275 | 4.677 | 16.212 | 1.00 | 7.10 | L | C |
| ATOM | 3396 | C | PRO | 43 | 112.476 | 5.042 | 18.007 | 1.00 | 23.79 | L | C |
| ATOM | 3397 | O | PRO | 43 | 112.359 | 5.903 | 18.877 | 1.00 | 23.79 | L | O |
| ATOM | 3398 | N | LYS | 44 | 113.652 | 4.678 | 17.514 | 1.00 | 26.42 | L | N |
| ATOM | 3399 | CA | LYS | 44 | 114.888 | 5.283 | 17.972 | 1.00 | 26.42 | L | C |
| ATOM | 3400 | CB | LYS | 44 | 115.656 | 4.289 | 18.843 | 1.00 | 45.11 | L | C |
| ATOM | 3401 | CG | LYS | 44 | 115.840 | 4.724 | 20.288 | 1.00 | 45.11 | L | C |
| ATOM | 3402 | CD | LYS | 44 | 116.535 | 3.651 | 21.131 | 1.00 | 45.11 | L | C |
| ATOM | 3403 | CE | LYS | 44 | 115.656 | 2.400 | 21.338 | 1.00 | 45.11 | L | C |
| ATOM | 3404 | NZ | LYS | 44 | 115.359 | 1.613 | 20.087 | 1.00 | 45.11 | L | N |
| ATOM | 3405 | C | LYS | 44 | 115.741 | 5.673 | 16.767 | 1.00 | 26.42 | L | C |
| ATOM | 3406 | O | LYS | 44 | 115.898 | 4.888 | 15.829 | 1.00 | 26.42 | L | O |
| ATOM | 3407 | N | PRO | 45 | 116.287 | 6.902 | 16.764 | 1.00 | 19.50 | L | N |
| ATOM | 3408 | CD | PRO | 45 | 116.146 | 7.943 | 17.794 | 1.00 | 7.61 | L | C |
| ATOM | 3409 | CA | PRO | 45 | 117.132 | 7.362 | 15.649 | 1.00 | 19.50 | L | C |
| ATOM | 3410 | CB | PRO | 45 | 117.638 | 8.720 | 16.120 | 1.00 | 7.61 | L | C |
| ATOM | 3411 | CG | PRO | 45 | 116.547 | 9.180 | 17.041 | 1.00 | 7.61 | L | C |
| ATOM | 3412 | C | PRO | 45 | 118.273 | 6.367 | 15.542 | 1.00 | 19.50 | L | C |
| ATOM | 3413 | O | PRO | 45 | 118.925 | 6.082 | 16.549 | 1.00 | 19.50 | L | O |
| ATOM | 3414 | N | TRP | 46 | 118.521 | 5.848 | 14.342 | 1.00 | 23.41 | L | N |
| ATOM | 3415 | CA | TRP | 46 | 119.581 | 4.861 | 14.158 | 1.00 | 23.41 | L | C |
| ATOM | 3416 | CB | TRP | 46 | 118.980 | 3.559 | 13.643 | 1.00 | 20.77 | L | C |
| ATOM | 3417 | CG | TRP | 46 | 119.662 | 2.382 | 14.178 | 1.00 | 20.77 | L | C |
| ATOM | 3418 | CD2 | TRP | 46 | 119.738 | 2.007 | 15.554 | 1.00 | 20.77 | L | C |
| ATOM | 3419 | CE2 | TRP | 46 | 120.509 | 0.829 | 15.624 | 1.00 | 20.77 | L | C |
| ATOM | 3420 | CE3 | TRP | 46 | 119.229 | 2.554 | 16.737 | 1.00 | 20.77 | L | C |
| ATOM | 3421 | CD1 | TRP | 46 | 120.365 | 1.446 | 13.481 | 1.00 | 20.77 | L | C |
| ATOM | 3422 | NE1 | TRP | 46 | 120.879 | 0.504 | 14.345 | 1.00 | 20.77 | L | N |
| ATOM | 3423 | CZ2 | TRP | 46 | 120.786 | 0.191 | 16.834 | 1.00 | 20.77 | L | C |
| ATOM | 3424 | CZ3 | TRP | 46 | 119.505 | 1.918 | 17.938 | 1.00 | 20.77 | L | C |
| ATOM | 3425 | CH2 | TRP | 46 | 120.276 | 0.750 | 17.977 | 1.00 | 20.77 | L | C |
| ATOM | 3426 | C | TRP | 46 | 120.691 | 5.302 | 13.209 | 1.00 | 23.41 | L | C |
| ATOM | 3427 | O | TRP | 46 | 121.871 | 5.174 | 13.507 | 1.00 | 23.41 | L | O |
| ATOM | 3428 | N | ILE | 47 | 120.306 | 5.806 | 12.048 | 1.00 | 21.62 | L | N |
| ATOM | 3429 | CA | ILE | 47 | 121.275 | 6.248 | 11.073 | 1.00 | 21.62 | L | C |
| ATOM | 3430 | CB | ILE | 47 | 121.515 | 5.160 | 10.008 | 1.00 | 12.16 | L | C |
| ATOM | 3431 | CG2 | ILE | 47 | 122.473 | 5.668 | 8.929 | 1.00 | 12.16 | L | C |

Fig. 19: A-48

| | | | | | | | | | | |
|---|---|---|---|---|---|---|---|---|---|---|
| ATOM | 3432 | CG1 | ILE | 47 | 122.067 | 3.902 | 10.670 | 1.00 | 12.16 | L | C |
| ATOM | 3433 | CD1 | ILE | 47 | 122.301 | 2.746 | 9.686 | 1.00 | 12.16 | L | C |
| ATOM | 3434 | C | ILE | 47 | 120.694 | 7.482 | 10.408 | 1.00 | 21.62 | L | C |
| ATOM | 3435 | O | ILE | 47 | 119.600 | 7.424 | 9.840 | 1.00 | 21.62 | L | O |
| ATOM | 3436 | N | TYR | 48 | 121.408 | 8.603 | 10.510 | 1.00 | 27.63 | L | N |
| ATOM | 3437 | CA | TYR | 48 | 120.961 | 9.842 | 9.887 | 1.00 | 27.63 | L | C |
| ATOM | 3438 | CB | TYR | 48 | 120.899 | 10.992 | 10.892 | 1.00 | 47.89 | L | C |
| ATOM | 3439 | CG | TYR | 48 | 122.206 | 11.318 | 11.564 | 1.00 | 47.89 | L | C |
| ATOM | 3440 | CD1 | TYR | 48 | 122.762 | 10.454 | 12.502 | 1.00 | 47.89 | L | C |
| ATOM | 3441 | CE1 | TYR | 48 | 123.961 | 10.766 | 13.143 | 1.00 | 47.89 | L | C |
| ATOM | 3442 | CD2 | TYR | 48 | 122.881 | 12.503 | 11.277 | 1.00 | 47.89 | L | C |
| ATOM | 3443 | CE2 | TYR | 48 | 124.078 | 12.827 | 11.907 | 1.00 | 47.89 | L | C |
| ATOM | 3444 | CZ | TYR | 48 | 124.617 | 11.957 | 12.843 | 1.00 | 47.89 | L | C |
| ATOM | 3445 | OH | TYR | 48 | 125.803 | 12.269 | 13.483 | 1.00 | 47.89 | L | O |
| ATOM | 3446 | C | TYR | 48 | 121.922 | 10.181 | 8.766 | 1.00 | 27.63 | L | C |
| ATOM | 3447 | O | TYR | 48 | 122.992 | 9.575 | 8.646 | 1.00 | 27.63 | L | O |
| ATOM | 3448 | N | LEU | 49 | 121.535 | 11.150 | 7.948 | 1.00 | 28.95 | L | N |
| ATOM | 3449 | CA | LEU | 49 | 122.344 | 11.550 | 6.811 | 1.00 | 28.95 | L | C |
| ATOM | 3450 | CB | LEU | 49 | 123.421 | 12.568 | 7.232 | 1.00 | 11.18 | L | C |
| ATOM | 3451 | CG | LEU | 49 | 123.051 | 14.040 | 7.473 | 1.00 | 11.18 | L | C |
| ATOM | 3452 | CD1 | LEU | 49 | 122.174 | 14.552 | 6.344 | 1.00 | 11.18 | L | C |
| ATOM | 3453 | CD2 | LEU | 49 | 122.333 | 14.178 | 8.780 | 1.00 | 11.18 | L | C |
| ATOM | 3454 | C | LEU | 49 | 122.997 | 10.350 | 6.117 | 1.00 | 28.95 | L | C |
| ATOM | 3455 | O | LEU | 49 | 124.204 | 10.323 | 5.920 | 1.00 | 28.95 | L | O |
| ATOM | 3456 | N | THR | 50 | 122.192 | 9.351 | 5.777 | 1.00 | 29.56 | L | N |
| ATOM | 3457 | CA | THR | 50 | 122.666 | 8.165 | 5.072 | 1.00 | 29.56 | L | C |
| ATOM | 3458 | CB | THR | 50 | 123.352 | 8.566 | 3.770 | 1.00 | 23.05 | L | C |
| ATOM | 3459 | OG1 | THR | 50 | 122.490 | 9.434 | 3.040 | 1.00 | 23.05 | L | O |
| ATOM | 3460 | CG2 | THR | 50 | 123.647 | 7.335 | 2.923 | 1.00 | 23.05 | L | C |
| ATOM | 3461 | C | THR | 50 | 123.582 | 7.152 | 5.767 | 1.00 | 29.56 | L | C |
| ATOM | 3462 | O | THR | 50 | 123.229 | 5.976 | 5.888 | 1.00 | 29.56 | L | O |
| ATOM | 3463 | N | SER | 51 | 124.757 | 7.586 | 6.203 | 1.00 | 25.90 | L | N |
| ATOM | 3464 | CA | SER | 51 | 125.697 | 6.670 | 6.839 | 1.00 | 25.90 | L | C |
| ATOM | 3465 | CB | SER | 51 | 126.976 | 6.594 | 6.003 | 1.00 | 41.07 | L | C |
| ATOM | 3466 | OG | SER | 51 | 127.467 | 7.893 | 5.715 | 1.00 | 41.07 | L | O |
| ATOM | 3467 | C | SER | 51 | 126.049 | 6.998 | 8.287 | 1.00 | 25.90 | L | C |
| ATOM | 3468 | O | SER | 51 | 126.578 | 6.160 | 9.015 | 1.00 | 25.90 | L | O |
| ATOM | 3469 | N | ASN | 52 | 125.749 | 8.211 | 8.712 | 1.00 | 36.32 | L | N |
| ATOM | 3470 | CA | ASN | 52 | 126.050 | 8.615 | 10.075 | 1.00 | 36.32 | L | C |
| ATOM | 3471 | CB | ASN | 52 | 125.741 | 10.092 | 10.247 | 1.00 | 35.00 | L | C |
| ATOM | 3472 | CG | ASN | 52 | 126.708 | 10.954 | 9.499 | 1.00 | 35.00 | L | C |
| ATOM | 3473 | OD1 | ASN | 52 | 127.881 | 11.022 | 9.857 | 1.00 | 35.00 | L | O |
| ATOM | 3474 | ND2 | ASN | 52 | 126.236 | 11.608 | 8.439 | 1.00 | 35.00 | L | N |
| ATOM | 3475 | C | ASN | 52 | 125.288 | 7.815 | 11.109 | 1.00 | 36.32 | L | C |
| ATOM | 3476 | O | ASN | 52 | 124.059 | 7.766 | 11.078 | 1.00 | 36.32 | L | O |
| ATOM | 3477 | N | LEU | 53 | 126.018 | 7.190 | 12.027 | 1.00 | 27.25 | L | N |
| ATOM | 3478 | CA | LEU | 53 | 125.387 | 6.408 | 13.080 | 1.00 | 27.25 | L | C |
| ATOM | 3479 | CB | LEU | 53 | 126.355 | 5.366 | 13.631 | 1.00 | 36.82 | L | C |
| ATOM | 3480 | CG | LEU | 53 | 126.949 | 4.324 | 12.682 | 1.00 | 36.82 | L | C |
| ATOM | 3481 | CD1 | LEU | 53 | 127.640 | 3.266 | 13.531 | 1.00 | 36.82 | L | C |
| ATOM | 3482 | CD2 | LEU | 53 | 125.876 | 3.674 | 11.822 | 1.00 | 36.82 | L | C |
| ATOM | 3483 | C | LEU | 53 | 124.938 | 7.312 | 14.219 | 1.00 | 27.25 | L | C |
| ATOM | 3484 | O | LEU | 53 | 125.643 | 8.241 | 14.581 | 1.00 | 27.25 | L | O |
| ATOM | 3485 | N | ALA | 54 | 123.763 | 7.043 | 14.779 | 1.00 | 46.43 | L | N |
| ATOM | 3486 | CA | ALA | 54 | 123.251 | 7.827 | 15.897 | 1.00 | 46.43 | L | C |
| ATOM | 3487 | CB | ALA | 54 | 121.938 | 7.272 | 16.373 | 1.00 | 9.56 | L | C |
| ATOM | 3488 | C | ALA | 54 | 124.267 | 7.728 | 17.008 | 1.00 | 46.43 | L | C |
| ATOM | 3489 | O | ALA | 54 | 125.380 | 7.254 | 16.794 | 1.00 | 46.43 | L | O |
| ATOM | 3490 | N | SER | 55 | 123.891 | 8.140 | 18.208 | 1.00 | 82.41 | L | N |
| ATOM | 3491 | CA | SER | 55 | 124.847 | 8.081 | 19.290 | 1.00 | 82.41 | L | C |
| ATOM | 3492 | CB | SER | 55 | 124.439 | 9.036 | 20.406 | 1.00 | 85.12 | L | C |
| ATOM | 3493 | OG | SER | 55 | 125.561 | 9.342 | 21.215 | 1.00 | 85.12 | L | O |
| ATOM | 3494 | C | SER | 55 | 125.049 | 6.675 | 19.850 | 1.00 | 82.41 | L | C |
| ATOM | 3495 | O | SER | 55 | 126.187 | 6.226 | 20.004 | 1.00 | 82.41 | L | O |
| ATOM | 3496 | N | GLY | 56 | 123.957 | 5.970 | 20.137 | 1.00 | 57.94 | L | N |
| ATOM | 3497 | CA | GLY | 56 | 124.074 | 4.632 | 20.701 | 1.00 | 57.94 | L | C |
| ATOM | 3498 | C | GLY | 56 | 124.408 | 3.486 | 19.758 | 1.00 | 57.94 | L | C |
| ATOM | 3499 | O | GLY | 56 | 125.101 | 2.545 | 20.136 | 1.00 | 57.94 | L | O |
| ATOM | 3500 | N | VAL | 57 | 123.914 | 3.562 | 18.530 | 1.00 | 69.56 | L | N |
| ATOM | 3501 | CA | VAL | 57 | 124.131 | 2.519 | 17.530 | 1.00 | 69.56 | L | C |
| ATOM | 3502 | CB | VAL | 57 | 123.809 | 3.053 | 16.108 | 1.00 | 49.85 | L | C |
| ATOM | 3503 | CG1 | VAL | 57 | 123.682 | 1.898 | 15.128 | 1.00 | 49.85 | L | C |
| ATOM | 3504 | CG2 | VAL | 57 | 122.529 | 3.875 | 16.139 | 1.00 | 49.85 | L | C |

Fig. 19: A-49

| | | | | | | | | | | | |
|---|---|---|---|---|---|---|---|---|---|---|---|
| ATOM | 3505 | C | VAL | 57 | 125.544 | 1.929 | 17.513 | 1.00 | 69.56 | L | C |
| ATOM | 3506 | O | VAL | 57 | 126.515 | 2.637 | 17.244 | 1.00 | 69.56 | L | O |
| ATOM | 3507 | N | PRO | 58 | 125.674 | 0.618 | 17.799 | 1.00 | 24.22 | L | N |
| ATOM | 3508 | CD | PRO | 58 | 124.609 | -0.342 | 18.141 | 1.00 | 44.23 | L | C |
| ATOM | 3509 | CA | PRO | 58 | 126.978 | -0.046 | 17.802 | 1.00 | 24.22 | L | C |
| ATOM | 3510 | CB | PRO | 58 | 126.638 | -1.472 | 18.237 | 1.00 | 44.23 | L | C |
| ATOM | 3511 | CG | PRO | 58 | 125.244 | -1.653 | 17.772 | 1.00 | 44.23 | L | C |
| ATOM | 3512 | C | PRO | 58 | 127.609 | 0.017 | 16.415 | 1.00 | 24.22 | L | C |
| ATOM | 3513 | O | PRO | 58 | 126.903 | -0.083 | 15.400 | 1.00 | 24.22 | L | O |
| ATOM | 3514 | N | SER | 59 | 128.935 | 0.174 | 16.381 | 1.00 | 54.17 | L | N |
| ATOM | 3515 | CA | SER | 59 | 129.691 | 0.295 | 15.134 | 1.00 | 54.17 | L | C |
| ATOM | 3516 | CB | SER | 59 | 131.184 | 0.489 | 15.438 | 1.00 | 118.98 | L | C |
| ATOM | 3517 | OG | SER | 59 | 131.729 | -0.615 | 16.139 | 1.00 | 118.98 | L | O |
| ATOM | 3518 | C | SER | 59 | 129.528 | -0.815 | 14.096 | 1.00 | 54.17 | L | C |
| ATOM | 3519 | O | SER | 59 | 130.015 | -0.672 | 12.970 | 1.00 | 54.17 | L | O |
| ATOM | 3520 | N | ARG | 60 | 128.861 | -1.914 | 14.449 | 1.00 | 62.94 | L | N |
| ATOM | 3521 | CA | ARG | 60 | 128.659 | -2.983 | 13.473 | 1.00 | 62.94 | L | C |
| ATOM | 3522 | CB | ARG | 60 | 128.247 | -4.291 | 14.159 | 1.00 | 67.90 | L | C |
| ATOM | 3523 | CG | ARG | 60 | 127.110 | -4.165 | 15.136 | 1.00 | 67.90 | L | C |
| ATOM | 3524 | CD | ARG | 60 | 126.572 | -5.533 | 15.506 | 1.00 | 67.90 | L | C |
| ATOM | 3525 | NE | ARG | 60 | 125.638 | -5.453 | 16.621 | 1.00 | 67.90 | L | N |
| ATOM | 3526 | CZ | ARG | 60 | 125.978 | -5.050 | 17.840 | 1.00 | 67.90 | L | C |
| ATOM | 3527 | NH1 | ARG | 60 | 127.230 | -4.696 | 18.093 | 1.00 | 67.90 | L | N |
| ATOM | 3528 | NH2 | ARG | 60 | 125.070 | -5.002 | 18.807 | 1.00 | 67.90 | L | N |
| ATOM | 3529 | C | ARG | 60 | 127.596 | -2.555 | 12.459 | 1.00 | 62.94 | L | C |
| ATOM | 3530 | O | ARG | 60 | 127.471 | -3.146 | 11.382 | 1.00 | 62.94 | L | O |
| ATOM | 3531 | N | PHE | 61 | 126.839 | -1.517 | 12.814 | 1.00 | 65.80 | L | N |
| ATOM | 3532 | CA | PHE | 61 | 125.799 | -0.979 | 11.943 | 1.00 | 65.80 | L | C |
| ATOM | 3533 | CB | PHE | 61 | 124.718 | -0.270 | 12.752 | 1.00 | 20.54 | L | C |
| ATOM | 3534 | CG | PHE | 61 | 123.650 | -1.177 | 13.278 | 1.00 | 20.54 | L | C |
| ATOM | 3535 | CD1 | PHE | 61 | 123.613 | -1.519 | 14.628 | 1.00 | 20.54 | L | C |
| ATOM | 3536 | CD2 | PHE | 61 | 122.656 | -1.662 | 12.428 | 1.00 | 20.54 | L | C |
| ATOM | 3537 | CE1 | PHE | 61 | 122.593 | -2.330 | 15.133 | 1.00 | 20.54 | L | C |
| ATOM | 3538 | CE2 | PHE | 61 | 121.627 | -2.476 | 12.914 | 1.00 | 20.54 | L | C |
| ATOM | 3539 | CZ | PHE | 61 | 121.594 | -2.809 | 14.270 | 1.00 | 20.54 | L | C |
| ATOM | 3540 | C | PHE | 61 | 126.389 | 0.019 | 10.964 | 1.00 | 65.80 | L | C |
| ATOM | 3541 | O | PHE | 61 | 127.300 | 0.773 | 11.300 | 1.00 | 65.80 | L | O |
| ATOM | 3542 | N | SER | 62 | 125.851 | 0.030 | 9.754 | 1.00 | 31.43 | L | N |
| ATOM | 3543 | CA | SER | 62 | 126.317 | 0.941 | 8.722 | 1.00 | 31.43 | L | C |
| ATOM | 3544 | CB | SER | 62 | 127.530 | 0.355 | 8.001 | 1.00 | 48.53 | L | C |
| ATOM | 3545 | OG | SER | 62 | 127.212 | -0.890 | 7.412 | 1.00 | 48.53 | L | O |
| ATOM | 3546 | C | SER | 62 | 125.211 | 1.216 | 7.714 | 1.00 | 31.43 | L | C |
| ATOM | 3547 | O | SER | 62 | 124.402 | 0.340 | 7.395 | 1.00 | 31.43 | L | O |
| ATOM | 3548 | N | GLY | 63 | 125.177 | 2.443 | 7.216 | 1.00 | 26.27 | L | N |
| ATOM | 3549 | CA | GLY | 63 | 124.168 | 2.802 | 6.244 | 1.00 | 26.27 | L | C |
| ATOM | 3550 | C | GLY | 63 | 124.870 | 3.245 | 4.988 | 1.00 | 26.27 | L | C |
| ATOM | 3551 | O | GLY | 63 | 126.032 | 3.634 | 5.044 | 1.00 | 26.27 | L | O |
| ATOM | 3552 | N | SER | 64 | 124.177 | 3.201 | 3.860 | 1.00 | 35.51 | L | N |
| ATOM | 3553 | CA | SER | 64 | 124.789 | 3.605 | 2.610 | 1.00 | 35.51 | L | C |
| ATOM | 3554 | CB | SER | 64 | 125.824 | 2.565 | 2.193 | 1.00 | 33.46 | L | C |
| ATOM | 3555 | OG | SER | 64 | 126.422 | 2.920 | 0.964 | 1.00 | 33.46 | L | O |
| ATOM | 3556 | C | SER | 64 | 123.772 | 3.783 | 1.495 | 1.00 | 35.51 | L | C |
| ATOM | 3557 | O | SER | 64 | 122.614 | 3.371 | 1.622 | 1.00 | 35.51 | L | O |
| ATOM | 3558 | N | GLY | 65 | 124.209 | 4.401 | 0.401 | 1.00 | 29.14 | L | N |
| ATOM | 3559 | CA | GLY | 65 | 123.318 | 4.594 | -0.727 | 1.00 | 29.14 | L | C |
| ATOM | 3560 | C | GLY | 65 | 123.334 | 5.963 | -1.370 | 1.00 | 29.14 | L | C |
| ATOM | 3561 | O | GLY | 65 | 124.127 | 6.837 | -1.024 | 1.00 | 29.14 | L | O |
| ATOM | 3562 | N | SER | 66 | 122.439 | 6.137 | -2.329 | 1.00 | 15.93 | L | N |
| ATOM | 3563 | CA | SER | 66 | 122.305 | 7.389 | -3.052 | 1.00 | 15.93 | L | C |
| ATOM | 3564 | CB | SER | 66 | 123.623 | 7.750 | -3.741 | 1.00 | 32.28 | L | C |
| ATOM | 3565 | OG | SER | 66 | 124.127 | 6.657 | -4.482 | 1.00 | 32.28 | L | O |
| ATOM | 3566 | C | SER | 66 | 121.171 | 7.264 | -4.076 | 1.00 | 15.93 | L | C |
| ATOM | 3567 | O | SER | 66 | 120.609 | 6.184 | -4.284 | 1.00 | 15.93 | L | O |
| ATOM | 3568 | N | GLY | 67 | 120.812 | 8.378 | -4.690 | 1.00 | 33.97 | L | N |
| ATOM | 3569 | CA | GLY | 67 | 119.751 | 8.349 | -5.673 | 1.00 | 33.97 | L | C |
| ATOM | 3570 | C | GLY | 67 | 118.469 | 7.706 | -5.194 | 1.00 | 33.97 | L | C |
| ATOM | 3571 | O | GLY | 67 | 117.757 | 8.262 | -4.361 | 1.00 | 33.97 | L | O |
| ATOM | 3572 | N | THR | 68 | 118.182 | 6.521 | -5.715 | 1.00 | 25.46 | L | N |
| ATOM | 3573 | CA | THR | 68 | 116.954 | 5.828 | -5.366 | 1.00 | 25.46 | L | C |
| ATOM | 3574 | CB | THR | 68 | 116.176 | 5.455 | -6.633 | 1.00 | 47.05 | L | C |
| ATOM | 3575 | OG1 | THR | 68 | 117.003 | 4.636 | -7.471 | 1.00 | 47.05 | L | O |
| ATOM | 3576 | CG2 | THR | 68 | 115.772 | 6.704 | -7.395 | 1.00 | 47.05 | L | C |
| ATOM | 3577 | C | THR | 68 | 117.132 | 4.559 | -4.539 | 1.00 | 25.46 | L | C |

Fig. 19: A-50

| | | | | | | | | | | |
|---|---|---|---|---|---|---|---|---|---|---|
| ATOM | 3578 | O | THR | 68 | 116.144 | 3.963 | -4.103 | 1.00 | 25.46 | L | O |
| ATOM | 3579 | N | ASP | 69 | 118.374 | 4.134 | -4.327 | 1.00 | 17.04 | L | N |
| ATOM | 3580 | CA | ASP | 69 | 118.614 | 2.921 | -3.554 | 1.00 | 17.04 | L | C |
| ATOM | 3581 | CB | ASP | 69 | 119.156 | 1.812 | -4.463 | 1.00 | 63.22 | L | C |
| ATOM | 3582 | CG | ASP | 69 | 118.129 | 1.354 | -5.490 | 1.00 | 63.22 | L | C |
| ATOM | 3583 | OD1 | ASP | 69 | 117.087 | 0.791 | -5.083 | 1.00 | 63.22 | L | O |
| ATOM | 3584 | OD2 | ASP | 69 | 118.356 | 1.565 | -6.703 | 1.00 | 63.22 | L | O |
| ATOM | 3585 | C | ASP | 69 | 119.544 | 3.146 | -2.372 | 1.00 | 17.04 | L | C |
| ATOM | 3586 | O | ASP | 69 | 120.684 | 3.567 | -2.535 | 1.00 | 17.04 | L | O |
| ATOM | 3587 | N | TYR | 70 | 119.030 | 2.866 | -1.177 | 1.00 | 19.76 | L | N |
| ATOM | 3588 | CA | TYR | 70 | 119.778 | 3.037 | 0.061 | 1.00 | 19.76 | L | C |
| ATOM | 3589 | CB | TYR | 70 | 119.130 | 4.151 | 0.895 | 1.00 | 24.73 | L | C |
| ATOM | 3590 | CG | TYR | 70 | 119.424 | 5.544 | 0.369 | 1.00 | 24.73 | L | C |
| ATOM | 3591 | CD1 | TYR | 70 | 120.547 | 6.255 | 0.809 | 1.00 | 24.73 | L | C |
| ATOM | 3592 | CE1 | TYR | 70 | 120.865 | 7.511 | 0.281 | 1.00 | 24.73 | L | C |
| ATOM | 3593 | CD2 | TYR | 70 | 118.620 | 6.129 | -0.616 | 1.00 | 24.73 | L | C |
| ATOM | 3594 | CE2 | TYR | 70 | 118.931 | 7.384 | -1.153 | 1.00 | 24.73 | L | C |
| ATOM | 3595 | CZ | TYR | 70 | 120.053 | 8.062 | -0.700 | 1.00 | 24.73 | L | C |
| ATOM | 3596 | OH | TYR | 70 | 120.371 | 9.275 | -1.247 | 1.00 | 24.73 | L | O |
| ATOM | 3597 | C | TYR | 70 | 119.812 | 1.727 | 0.840 | 1.00 | 19.76 | L | C |
| ATOM | 3598 | O | TYR | 70 | 118.997 | 0.828 | 0.599 | 1.00 | 19.76 | L | O |
| ATOM | 3599 | N | THR | 71 | 120.751 | 1.603 | 1.772 | 1.00 | 26.87 | L | N |
| ATOM | 3600 | CA | THR | 71 | 120.837 | 0.366 | 2.535 | 1.00 | 26.87 | L | C |
| ATOM | 3601 | CB | THR | 71 | 121.754 | -0.661 | 1.828 | 1.00 | 34.85 | L | C |
| ATOM | 3602 | OG1 | THR | 71 | 123.107 | -0.192 | 1.860 | 1.00 | 34.85 | L | O |
| ATOM | 3603 | CG2 | THR | 71 | 121.329 | -0.863 | 0.376 | 1.00 | 34.85 | L | C |
| ATOM | 3604 | C | THR | 71 | 121.333 | 0.483 | 3.977 | 1.00 | 26.87 | L | C |
| ATOM | 3605 | O | THR | 71 | 122.160 | 1.335 | 4.306 | 1.00 | 26.87 | L | O |
| ATOM | 3606 | N | LEU | 72 | 120.800 | -0.385 | 4.829 | 1.00 | 24.40 | L | N |
| ATOM | 3607 | CA | LEU | 72 | 121.204 | -0.467 | 6.222 | 1.00 | 24.40 | L | C |
| ATOM | 3608 | CB | LEU | 72 | 119.987 | -0.412 | 7.150 | 1.00 | 25.91 | L | C |
| ATOM | 3609 | CG | LEU | 72 | 120.183 | -0.827 | 8.614 | 1.00 | 25.91 | L | C |
| ATOM | 3610 | CD1 | LEU | 72 | 121.539 | -0.387 | 9.105 | 1.00 | 25.91 | L | C |
| ATOM | 3611 | CD2 | LEU | 72 | 119.097 | -0.207 | 9.470 | 1.00 | 25.91 | L | C |
| ATOM | 3612 | C | LEU | 72 | 121.875 | -1.837 | 6.296 | 1.00 | 24.40 | L | C |
| ATOM | 3613 | O | LEU | 72 | 121.386 | -2.803 | 5.707 | 1.00 | 24.40 | L | O |
| ATOM | 3614 | N | THR | 73 | 123.000 | -1.930 | 6.990 | 1.00 | 38.15 | L | N |
| ATOM | 3615 | CA | THR | 73 | 123.695 | -3.204 | 7.066 | 1.00 | 38.15 | L | C |
| ATOM | 3616 | CB | THR | 73 | 124.907 | -3.217 | 6.110 | 1.00 | 35.63 | L | C |
| ATOM | 3617 | OG1 | THR | 73 | 124.556 | -2.566 | 4.885 | 1.00 | 35.63 | L | O |
| ATOM | 3618 | CG2 | THR | 73 | 125.328 | -4.649 | 5.797 | 1.00 | 35.63 | L | C |
| ATOM | 3619 | C | THR | 73 | 124.189 | -3.542 | 8.467 | 1.00 | 38.15 | L | C |
| ATOM | 3620 | O | THR | 73 | 124.719 | -2.690 | 9.177 | 1.00 | 38.15 | L | O |
| ATOM | 3621 | N | ILE | 74 | 123.997 | -4.791 | 8.866 | 1.00 | 31.55 | L | N |
| ATOM | 3622 | CA | ILE | 74 | 124.467 | -5.246 | 10.158 | 1.00 | 31.55 | L | C |
| ATOM | 3623 | CB | ILE | 74 | 123.342 | -5.884 | 10.988 | 1.00 | 39.02 | L | C |
| ATOM | 3624 | CG2 | ILE | 74 | 123.734 | -5.878 | 12.461 | 1.00 | 39.02 | L | C |
| ATOM | 3625 | CG1 | ILE | 74 | 122.041 | -5.099 | 10.821 | 1.00 | 39.02 | L | C |
| ATOM | 3626 | CD1 | ILE | 74 | 120.870 | -5.663 | 11.635 | 1.00 | 39.02 | L | C |
| ATOM | 3627 | C | ILE | 74 | 125.504 | -6.313 | 9.814 | 1.00 | 31.55 | L | C |
| ATOM | 3628 | O | ILE | 74 | 125.146 | -7.434 | 9.440 | 1.00 | 31.55 | L | O |
| ATOM | 3629 | N | SER | 75 | 126.782 | -5.951 | 9.921 | 1.00 | 48.74 | L | N |
| ATOM | 3630 | CA | SER | 75 | 127.888 | -6.857 | 9.605 | 1.00 | 48.74 | L | C |
| ATOM | 3631 | CB | SER | 75 | 129.209 | -6.106 | 9.727 | 1.00 | 44.70 | L | C |
| ATOM | 3632 | OG | SER | 75 | 129.306 | -5.485 | 10.994 | 1.00 | 44.70 | L | O |
| ATOM | 3633 | C | SER | 75 | 127.940 | -8.129 | 10.456 | 1.00 | 48.74 | L | C |
| ATOM | 3634 | O | SER | 75 | 128.346 | -9.184 | 9.970 | 1.00 | 48.74 | L | O |
| ATOM | 3635 | N | SER | 76 | 127.544 | -8.021 | 11.722 | 1.00 | 53.77 | L | N |
| ATOM | 3636 | CA | SER | 76 | 127.530 | -9.165 | 12.635 | 1.00 | 53.77 | L | C |
| ATOM | 3637 | CB | SER | 76 | 128.773 | -9.166 | 13.521 | 1.00 | 79.21 | L | C |
| ATOM | 3638 | OG | SER | 76 | 128.707 | -10.224 | 14.463 | 1.00 | 79.21 | L | O |
| ATOM | 3639 | C | SER | 76 | 126.288 | -9.102 | 13.515 | 1.00 | 53.77 | L | C |
| ATOM | 3640 | O | SER | 76 | 126.306 | -8.533 | 14.604 | 1.00 | 53.77 | L | O |
| ATOM | 3641 | N | LEU | 77 | 125.211 | -9.704 | 13.036 | 1.00 | 35.38 | L | N |
| ATOM | 3642 | CA | LEU | 77 | 123.946 | -9.691 | 13.756 | 1.00 | 35.38 | L | C |
| ATOM | 3643 | CB | LEU | 77 | 122.955 | -10.639 | 13.085 | 1.00 | 37.68 | L | C |
| ATOM | 3644 | CG | LEU | 77 | 121.514 | -10.154 | 12.995 | 1.00 | 37.68 | L | C |
| ATOM | 3645 | CD1 | LEU | 77 | 120.623 | -11.329 | 12.638 | 1.00 | 37.68 | L | C |
| ATOM | 3646 | CD2 | LEU | 77 | 121.080 | -9.548 | 14.317 | 1.00 | 37.68 | L | C |
| ATOM | 3647 | C | LEU | 77 | 124.096 | -10.080 | 15.215 | 1.00 | 35.38 | L | C |
| ATOM | 3648 | O | LEU | 77 | 124.714 | -11.086 | 15.531 | 1.00 | 35.38 | L | O |
| ATOM | 3649 | N | GLN | 78 | 123.527 | -9.279 | 16.105 | 1.00 | 50.91 | L | N |
| ATOM | 3650 | CA | GLN | 78 | 123.589 | -9.577 | 17.527 | 1.00 | 50.91 | L | C |

Fig. 19: A-51

| | | | | | | | | | | | |
|---|---|---|---|---|---|---|---|---|---|---|---|
| ATOM | 3651 | CB | GLN | 78 | 124.201 | -8.408 | 18.290 | 1.00 | 82.93 | L | C |
| ATOM | 3652 | CG | GLN | 78 | 125.653 | -8.159 | 17.938 | 1.00 | 82.93 | L | C |
| ATOM | 3653 | CD | GLN | 78 | 126.525 | -9.385 | 18.135 | 1.00 | 82.93 | L | C |
| ATOM | 3654 | OE1 | GLN | 78 | 126.509 | -10.007 | 19.200 | 1.00 | 82.93 | L | O |
| ATOM | 3655 | NE2 | GLN | 78 | 127.299 | -9.736 | 17.109 | 1.00 | 82.93 | L | N |
| ATOM | 3656 | C | GLN | 78 | 122.192 | -9.880 | 18.062 | 1.00 | 50.91 | L | C |
| ATOM | 3657 | O | GLN | 78 | 121.197 | -9.411 | 17.519 | 1.00 | 50.91 | L | O |
| ATOM | 3658 | N | PRO | 79 | 122.104 | -10.680 | 19.135 | 1.00 | 74.65 | L | N |
| ATOM | 3659 | CD | PRO | 79 | 123.228 | -11.171 | 19.952 | 1.00 | 43.98 | L | C |
| ATOM | 3660 | CA | PRO | 79 | 120.821 | -11.049 | 19.743 | 1.00 | 74.65 | L | C |
| ATOM | 3661 | CB | PRO | 79 | 121.243 | -11.963 | 20.887 | 1.00 | 43.98 | L | C |
| ATOM | 3662 | CG | PRO | 79 | 122.577 | -11.373 | 21.284 | 1.00 | 43.98 | L | C |
| ATOM | 3663 | C | PRO | 79 | 120.033 | -9.830 | 20.224 | 1.00 | 74.65 | L | C |
| ATOM | 3664 | O | PRO | 79 | 118.855 | -9.922 | 20.577 | 1.00 | 74.65 | L | O |
| ATOM | 3665 | N | GLU | 80 | 120.697 | -8.685 | 20.221 | 1.00 | 42.25 | L | N |
| ATOM | 3666 | CA | GLU | 80 | 120.080 | -7.451 | 20.659 | 1.00 | 42.25 | L | C |
| ATOM | 3667 | CB | GLU | 80 | 121.085 | -6.697 | 21.527 | 1.00 | 40.93 | L | C |
| ATOM | 3668 | CG | GLU | 80 | 122.485 | -6.700 | 20.958 | 1.00 | 40.93 | L | C |
| ATOM | 3669 | CD | GLU | 80 | 123.424 | -5.786 | 21.726 | 1.00 | 40.93 | L | C |
| ATOM | 3670 | OE1 | GLU | 80 | 123.013 | -4.648 | 22.033 | 1.00 | 40.93 | L | O |
| ATOM | 3671 | OE2 | GLU | 80 | 124.572 | -6.197 | 22.009 | 1.00 | 40.93 | L | O |
| ATOM | 3672 | C | GLU | 80 | 119.602 | -6.575 | 19.489 | 1.00 | 42.25 | L | C |
| ATOM | 3673 | O | GLU | 80 | 118.723 | -5.726 | 19.656 | 1.00 | 42.25 | L | O |
| ATOM | 3674 | N | ASP | 81 | 120.189 | -6.787 | 18.312 | 1.00 | 42.48 | L | N |
| ATOM | 3675 | CA | ASP | 81 | 119.835 | -6.037 | 17.108 | 1.00 | 42.48 | L | C |
| ATOM | 3676 | CB | ASP | 81 | 120.867 | -6.254 | 16.005 | 1.00 | 43.12 | L | C |
| ATOM | 3677 | CG | ASP | 81 | 122.262 | -5.914 | 16.441 | 1.00 | 43.12 | L | C |
| ATOM | 3678 | OD1 | ASP | 81 | 122.422 | -5.003 | 17.281 | 1.00 | 43.12 | L | O |
| ATOM | 3679 | OD2 | ASP | 81 | 123.205 | -6.549 | 15.924 | 1.00 | 43.12 | L | O |
| ATOM | 3680 | C | ASP | 81 | 118.495 | -6.488 | 16.564 | 1.00 | 42.48 | L | C |
| ATOM | 3681 | O | ASP | 81 | 118.086 | -6.063 | 15.488 | 1.00 | 42.48 | L | O |
| ATOM | 3682 | N | PHE | 82 | 117.810 | -7.351 | 17.299 | 1.00 | 48.53 | L | N |
| ATOM | 3683 | CA | PHE | 82 | 116.544 | -7.856 | 16.822 | 1.00 | 48.53 | L | C |
| ATOM | 3684 | CB | PHE | 82 | 116.337 | -9.265 | 17.368 | 1.00 | 189.91 | L | C |
| ATOM | 3685 | CG | PHE | 82 | 117.320 | -10.260 | 16.810 | 1.00 | 189.91 | L | C |
| ATOM | 3686 | CD1 | PHE | 82 | 117.227 | -10.676 | 15.485 | 1.00 | 189.91 | L | C |
| ATOM | 3687 | CD2 | PHE | 82 | 118.369 | -10.741 | 17.587 | 1.00 | 189.91 | L | C |
| ATOM | 3688 | CE1 | PHE | 82 | 118.164 | -11.554 | 14.940 | 1.00 | 189.91 | L | C |
| ATOM | 3689 | CE2 | PHE | 82 | 119.311 | -11.622 | 17.048 | 1.00 | 189.91 | L | C |
| ATOM | 3690 | CZ | PHE | 82 | 119.207 | -12.027 | 15.725 | 1.00 | 189.91 | L | C |
| ATOM | 3691 | C | PHE | 82 | 115.359 | -6.953 | 17.094 | 1.00 | 48.53 | L | C |
| ATOM | 3692 | O | PHE | 82 | 114.857 | -6.863 | 18.216 | 1.00 | 48.53 | L | O |
| ATOM | 3693 | N | ALA | 83 | 114.939 | -6.271 | 16.032 | 1.00 | 31.52 | L | N |
| ATOM | 3694 | CA | ALA | 83 | 113.813 | -5.350 | 16.052 | 1.00 | 31.52 | L | C |
| ATOM | 3695 | CB | ALA | 83 | 114.217 | -4.051 | 16.723 | 1.00 | 63.37 | L | C |
| ATOM | 3696 | C | ALA | 83 | 113.398 | -5.090 | 14.605 | 1.00 | 31.52 | L | C |
| ATOM | 3697 | O | ALA | 83 | 113.816 | -5.808 | 13.693 | 1.00 | 31.52 | L | O |
| ATOM | 3698 | N | THR | 84 | 112.565 | -4.075 | 14.395 | 1.00 | 28.09 | L | N |
| ATOM | 3699 | CA | THR | 84 | 112.124 | -3.733 | 13.045 | 1.00 | 28.09 | L | C |
| ATOM | 3700 | CB | THR | 84 | 110.572 | -3.799 | 12.928 | 1.00 | 15.50 | L | C |
| ATOM | 3701 | OG1 | THR | 84 | 110.127 | -3.002 | 11.822 | 1.00 | 15.50 | L | O |
| ATOM | 3702 | CG2 | THR | 84 | 109.922 | -3.332 | 14.207 | 1.00 | 15.50 | L | C |
| ATOM | 3703 | C | THR | 84 | 112.664 | -2.346 | 12.659 | 1.00 | 28.09 | L | C |
| ATOM | 3704 | O | THR | 84 | 112.505 | -1.373 | 13.400 | 1.00 | 28.09 | L | O |
| ATOM | 3705 | N | TYR | 85 | 113.316 | -2.282 | 11.496 | 1.00 | 21.31 | L | N |
| ATOM | 3706 | CA | TYR | 85 | 113.935 | -1.055 | 11.000 | 1.00 | 21.31 | L | C |
| ATOM | 3707 | CB | TYR | 85 | 115.367 | -1.338 | 10.517 | 1.00 | 19.63 | L | C |
| ATOM | 3708 | CG | TYR | 85 | 116.240 | -1.976 | 11.566 | 1.00 | 19.63 | L | C |
| ATOM | 3709 | CD1 | TYR | 85 | 115.988 | -3.279 | 12.021 | 1.00 | 19.63 | L | C |
| ATOM | 3710 | CE1 | TYR | 85 | 116.718 | -3.834 | 13.061 | 1.00 | 19.63 | L | C |
| ATOM | 3711 | CD2 | TYR | 85 | 117.255 | -1.259 | 12.174 | 1.00 | 19.63 | L | C |
| ATOM | 3712 | CE2 | TYR | 85 | 117.990 | -1.807 | 13.217 | 1.00 | 19.63 | L | C |
| ATOM | 3713 | CZ | TYR | 85 | 117.711 | -3.087 | 13.655 | 1.00 | 19.63 | L | C |
| ATOM | 3714 | OH | TYR | 85 | 118.405 | -3.592 | 14.722 | 1.00 | 19.63 | L | O |
| ATOM | 3715 | C | TYR | 85 | 113.173 | -0.365 | 9.882 | 1.00 | 21.31 | L | C |
| ATOM | 3716 | O | TYR | 85 | 112.768 | -0.996 | 8.900 | 1.00 | 21.31 | L | O |
| ATOM | 3717 | N | TYR | 86 | 113.015 | 0.948 | 10.046 | 1.00 | 18.01 | L | N |
| ATOM | 3718 | CA | TYR | 86 | 112.321 | 1.806 | 9.090 | 1.00 | 18.01 | L | C |
| ATOM | 3719 | CB | TYR | 86 | 111.242 | 2.632 | 9.790 | 1.00 | 24.73 | L | C |
| ATOM | 3720 | CG | TYR | 86 | 110.130 | 1.846 | 10.421 | 1.00 | 24.73 | L | C |
| ATOM | 3721 | CD1 | TYR | 86 | 109.020 | 1.459 | 9.679 | 1.00 | 24.73 | L | C |
| ATOM | 3722 | CE1 | TYR | 86 | 107.971 | 0.756 | 10.278 | 1.00 | 24.73 | L | C |
| ATOM | 3723 | CD2 | TYR | 86 | 110.177 | 1.508 | 11.773 | 1.00 | 24.73 | L | C |

Fig. 19: A-52

| | | | | | | | | | | | |
|---|---|---|---|---|---|---|---|---|---|---|---|
| ATOM | 3724 | CE2 | TYR | 86 | 109.140 | 0.804 | 12.378 | 1.00 | 24.73 | L | C |
| ATOM | 3725 | CZ | TYR | 86 | 108.042 | 0.438 | 11.628 | 1.00 | 24.73 | L | C |
| ATOM | 3726 | OH | TYR | 86 | 107.002 | -0.204 | 12.238 | 1.00 | 24.73 | L | O |
| ATOM | 3727 | C | TYR | 86 | 113.280 | 2.798 | 8.465 | 1.00 | 18.01 | L | C |
| ATOM | 3728 | O | TYR | 86 | 114.110 | 3.378 | 9.158 | 1.00 | 18.01 | L | O |
| ATOM | 3729 | N | CYS | 87 | 113.170 | 2.996 | 7.158 | 1.00 | 20.53 | L | N |
| ATOM | 3730 | CA | CYS | 87 | 113.989 | 3.999 | 6.494 | 1.00 | 20.53 | L | C |
| ATOM | 3731 | C | CYS | 87 | 113.021 | 5.156 | 6.335 | 1.00 | 20.53 | L | C |
| ATOM | 3732 | O | CYS | 87 | 111.806 | 4.954 | 6.351 | 1.00 | 20.53 | L | O |
| ATOM | 3733 | CB | CYS | 87 | 114.509 | 3.527 | 5.133 | 1.00 | 17.33 | L | C |
| ATOM | 3734 | SG | CYS | 87 | 113.306 | 2.900 | 3.921 | 1.00 | 17.33 | L | S |
| ATOM | 3735 | N | GLN | 88 | 113.545 | 6.363 | 6.212 | 1.00 | 10.63 | L | N |
| ATOM | 3736 | CA | GLN | 88 | 112.696 | 7.534 | 6.083 | 1.00 | 10.63 | L | C |
| ATOM | 3737 | CB | GLN | 88 | 112.393 | 8.083 | 7.482 | 1.00 | 18.09 | L | C |
| ATOM | 3738 | CG | GLN | 88 | 111.509 | 9.303 | 7.525 | 1.00 | 18.09 | L | C |
| ATOM | 3739 | CD | GLN | 88 | 112.256 | 10.547 | 7.971 | 1.00 | 18.09 | L | C |
| ATOM | 3740 | OE1 | GLN | 88 | 112.946 | 10.539 | 8.987 | 1.00 | 18.09 | L | O |
| ATOM | 3741 | NE2 | GLN | 88 | 112.106 | 11.627 | 7.219 | 1.00 | 18.09 | L | N |
| ATOM | 3742 | C | GLN | 88 | 113.390 | 8.583 | 5.219 | 1.00 | 10.63 | L | C |
| ATOM | 3743 | O | GLN | 88 | 114.626 | 8.680 | 5.198 | 1.00 | 10.63 | L | O |
| ATOM | 3744 | N | GLN | 89 | 112.600 | 9.357 | 4.483 | 1.00 | 11.94 | L | N |
| ATOM | 3745 | CA | GLN | 89 | 113.171 | 10.386 | 3.625 | 1.00 | 11.94 | L | C |
| ATOM | 3746 | CB | GLN | 89 | 112.877 | 10.073 | 2.152 | 1.00 | 25.01 | L | C |
| ATOM | 3747 | CG | GLN | 89 | 111.407 | 10.008 | 1.776 | 1.00 | 25.01 | L | C |
| ATOM | 3748 | CD | GLN | 89 | 110.786 | 11.377 | 1.579 | 1.00 | 25.01 | L | C |
| ATOM | 3749 | OE1 | GLN | 89 | 111.373 | 12.247 | 0.935 | 1.00 | 25.01 | L | O |
| ATOM | 3750 | NE2 | GLN | 89 | 109.591 | 11.571 | 2.119 | 1.00 | 25.01 | L | N |
| ATOM | 3751 | C | GLN | 89 | 112.606 | 11.732 | 4.023 | 1.00 | 11.94 | L | C |
| ATOM | 3752 | O | GLN | 89 | 111.498 | 11.802 | 4.552 | 1.00 | 11.94 | L | O |
| ATOM | 3753 | N | TRP | 90 | 113.375 | 12.794 | 3.792 | 1.00 | 19.62 | L | N |
| ATOM | 3754 | CA | TRP | 90 | 112.948 | 14.144 | 4.145 | 1.00 | 19.62 | L | C |
| ATOM | 3755 | CB | TRP | 90 | 113.773 | 14.667 | 5.336 | 1.00 | 17.27 | L | C |
| ATOM | 3756 | CG | TRP | 90 | 115.220 | 15.018 | 5.023 | 1.00 | 17.27 | L | C |
| ATOM | 3757 | CD2 | TRP | 90 | 116.174 | 15.611 | 5.918 | 1.00 | 17.27 | L | C |
| ATOM | 3758 | CE2 | TRP | 90 | 117.373 | 15.797 | 5.189 | 1.00 | 17.27 | L | C |
| ATOM | 3759 | CE3 | TRP | 90 | 116.132 | 16.005 | 7.267 | 1.00 | 17.27 | L | C |
| ATOM | 3760 | CD1 | TRP | 90 | 115.869 | 14.867 | 3.823 | 1.00 | 17.27 | L | C |
| ATOM | 3761 | NE1 | TRP | 90 | 117.156 | 15.334 | 3.918 | 1.00 | 17.27 | L | N |
| ATOM | 3762 | CZ2 | TRP | 90 | 118.522 | 16.363 | 5.759 | 1.00 | 17.27 | L | C |
| ATOM | 3763 | CZ3 | TRP | 90 | 117.284 | 16.570 | 7.839 | 1.00 | 17.27 | L | C |
| ATOM | 3764 | CH2 | TRP | 90 | 118.462 | 16.741 | 7.080 | 1.00 | 17.27 | L | C |
| ATOM | 3765 | C | TRP | 90 | 113.074 | 15.093 | 2.947 | 1.00 | 19.62 | L | C |
| ATOM | 3766 | O | TRP | 90 | 112.783 | 16.289 | 3.048 | 1.00 | 19.62 | L | O |
| ATOM | 3767 | N | SER | 91 | 113.494 | 14.552 | 1.807 | 1.00 | 12.71 | L | N |
| ATOM | 3768 | CA | SER | 91 | 113.662 | 15.359 | 0.600 | 1.00 | 12.71 | L | C |
| ATOM | 3769 | CB | SER | 91 | 114.504 | 14.587 | -0.414 | 1.00 | 23.55 | L | C |
| ATOM | 3770 | OG | SER | 91 | 115.762 | 14.248 | 0.137 | 1.00 | 23.55 | L | O |
| ATOM | 3771 | C | SER | 91 | 112.344 | 15.800 | -0.054 | 1.00 | 12.71 | L | C |
| ATOM | 3772 | O | SER | 91 | 112.284 | 16.860 | -0.680 | 1.00 | 12.71 | L | O |
| ATOM | 3773 | N | GLY | 92 | 111.297 | 14.986 | 0.096 | 1.00 | 23.24 | L | N |
| ATOM | 3774 | CA | GLY | 92 | 110.008 | 15.310 | -0.493 | 1.00 | 23.24 | L | C |
| ATOM | 3775 | C | GLY | 92 | 108.867 | 15.347 | 0.509 | 1.00 | 23.24 | L | C |
| ATOM | 3776 | O | GLY | 92 | 108.931 | 14.718 | 1.567 | 1.00 | 23.24 | L | O |
| ATOM | 3777 | N | ASN | 93 | 107.811 | 16.078 | 0.169 | 1.00 | 31.94 | L | N |
| ATOM | 3778 | CA | ASN | 93 | 106.663 | 16.206 | 1.048 | 1.00 | 31.94 | L | C |
| ATOM | 3779 | CB | ASN | 93 | 106.307 | 17.670 | 1.203 | 1.00 | 23.71 | L | C |
| ATOM | 3780 | CG | ASN | 93 | 107.400 | 18.448 | 1.896 | 1.00 | 23.71 | L | C |
| ATOM | 3781 | OD1 | ASN | 93 | 107.790 | 19.525 | 1.445 | 1.00 | 23.71 | L | O |
| ATOM | 3782 | ND2 | ASN | 93 | 107.905 | 17.905 | 3.006 | 1.00 | 23.71 | L | N |
| ATOM | 3783 | C | ASN | 93 | 105.478 | 15.454 | 0.507 | 1.00 | 31.94 | L | C |
| ATOM | 3784 | O | ASN | 93 | 105.227 | 15.478 | -0.692 | 1.00 | 31.94 | L | O |
| ATOM | 3785 | N | PRO | 94 | 104.724 | 14.779 | 1.386 | 1.00 | 29.10 | L | N |
| ATOM | 3786 | CD | PRO | 94 | 103.575 | 13.939 | 1.009 | 1.00 | 1.87 | L | C |
| ATOM | 3787 | CA | PRO | 94 | 104.950 | 14.713 | 2.830 | 1.00 | 29.10 | L | C |
| ATOM | 3788 | CB | PRO | 94 | 103.651 | 14.113 | 3.340 | 1.00 | 1.87 | L | C |
| ATOM | 3789 | CG | PRO | 94 | 103.336 | 13.137 | 2.269 | 1.00 | 1.87 | L | C |
| ATOM | 3790 | C | PRO | 94 | 106.131 | 13.823 | 3.167 | 1.00 | 29.10 | L | C |
| ATOM | 3791 | O | PRO | 94 | 106.516 | 12.987 | 2.361 | 1.00 | 29.10 | L | O |
| ATOM | 3792 | N | TRP | 95 | 106.711 | 14.011 | 4.349 | 1.00 | 16.41 | L | N |
| ATOM | 3793 | CA | TRP | 95 | 107.810 | 13.155 | 4.772 | 1.00 | 16.41 | L | C |
| ATOM | 3794 | CB | TRP | 95 | 108.425 | 13.629 | 6.094 | 1.00 | 13.37 | L | C |
| ATOM | 3795 | CG | TRP | 95 | 109.201 | 14.906 | 5.979 | 1.00 | 13.37 | L | C |
| ATOM | 3796 | CD2 | TRP | 95 | 109.284 | 15.950 | 6.954 | 1.00 | 13.37 | L | C |

Fig. 19: A-53

| | | | | | | | | | | | |
|---|---|---|---|---|---|---|---|---|---|---|---|
| ATOM | 3797 | CE2 | TRP | 95 | 110.104 | 16.960 | 6.412 | 1.00 | 13.37 | L | C |
| ATOM | 3798 | CE3 | TRP | 95 | 108.743 | 16.132 | 8.229 | 1.00 | 13.37 | L | C |
| ATOM | 3799 | CD1 | TRP | 95 | 109.963 | 15.312 | 4.917 | 1.00 | 13.37 | L | C |
| ATOM | 3800 | NE1 | TRP | 95 | 110.504 | 16.543 | 5.168 | 1.00 | 13.37 | L | N |
| ATOM | 3801 | CZ2 | TRP | 95 | 110.394 | 18.144 | 7.107 | 1.00 | 13.37 | L | C |
| ATOM | 3802 | CZ3 | TRP | 95 | 109.030 | 17.305 | 8.919 | 1.00 | 13.37 | L | C |
| ATOM | 3803 | CH2 | TRP | 95 | 109.845 | 18.297 | 8.358 | 1.00 | 13.37 | L | C |
| ATOM | 3804 | C | TRP | 95 | 107.226 | 11.751 | 4.942 | 1.00 | 16.41 | L | C |
| ATOM | 3805 | O | TRP | 95 | 106.136 | 11.575 | 5.484 | 1.00 | 16.41 | L | O |
| ATOM | 3806 | N | THR | 96 | 107.956 | 10.748 | 4.481 | 1.00 | 6.71 | L | N |
| ATOM | 3807 | CA | THR | 96 | 107.465 | 9.388 | 4.563 | 1.00 | 6.71 | L | C |
| ATOM | 3808 | CB | THR | 96 | 106.963 | 8.932 | 3.172 | 1.00 | 11.59 | L | C |
| ATOM | 3809 | OG1 | THR | 96 | 108.045 | 8.991 | 2.235 | 1.00 | 11.59 | L | O |
| ATOM | 3810 | CG2 | THR | 96 | 105.859 | 9.852 | 2.674 | 1.00 | 11.59 | L | C |
| ATOM | 3811 | C | THR | 96 | 108.489 | 8.369 | 5.087 | 1.00 | 6.71 | L | C |
| ATOM | 3812 | O | THR | 96 | 109.703 | 8.621 | 5.121 | 1.00 | 6.71 | L | O |
| ATOM | 3813 | N | PHE | 97 | 107.966 | 7.222 | 5.513 | 1.00 | 24.36 | L | N |
| ATOM | 3814 | CA | PHE | 97 | 108.777 | 6.119 | 6.013 | 1.00 | 24.36 | L | C |
| ATOM | 3815 | CB | PHE | 97 | 108.327 | 5.689 | 7.418 | 1.00 | 11.10 | L | C |
| ATOM | 3816 | CG | PHE | 97 | 108.422 | 6.762 | 8.461 | 1.00 | 11.10 | L | C |
| ATOM | 3817 | CD1 | PHE | 97 | 107.541 | 7.831 | 8.460 | 1.00 | 11.10 | L | C |
| ATOM | 3818 | CD2 | PHE | 97 | 109.391 | 6.685 | 9.470 | 1.00 | 11.10 | L | C |
| ATOM | 3819 | CE1 | PHE | 97 | 107.612 | 8.821 | 9.453 | 1.00 | 11.10 | L | C |
| ATOM | 3820 | CE2 | PHE | 97 | 109.475 | 7.665 | 10.468 | 1.00 | 11.10 | L | C |
| ATOM | 3821 | CZ | PHE | 97 | 108.577 | 8.738 | 10.456 | 1.00 | 11.10 | L | C |
| ATOM | 3822 | C | PHE | 97 | 108.532 | 4.950 | 5.062 | 1.00 | 24.36 | L | C |
| ATOM | 3823 | O | PHE | 97 | 107.613 | 4.990 | 4.241 | 1.00 | 24.36 | L | O |
| ATOM | 3824 | N | GLY | 98 | 109.362 | 3.919 | 5.168 | 1.00 | 21.54 | L | N |
| ATOM | 3825 | CA | GLY | 98 | 109.183 | 2.727 | 4.350 | 1.00 | 21.54 | L | C |
| ATOM | 3826 | C | GLY | 98 | 108.266 | 1.849 | 5.184 | 1.00 | 21.54 | L | C |
| ATOM | 3827 | O | GLY | 98 | 107.977 | 2.196 | 6.339 | 1.00 | 21.54 | L | O |
| ATOM | 3828 | N | GLN | 99 | 107.796 | 0.728 | 4.645 | 1.00 | 11.59 | L | N |
| ATOM | 3829 | CA | GLN | 99 | 106.894 | -0.114 | 5.442 | 1.00 | 11.59 | L | C |
| ATOM | 3830 | CB | GLN | 99 | 106.211 | -1.197 | 4.593 | 1.00 | 37.88 | L | C |
| ATOM | 3831 | CG | GLN | 99 | 106.810 | -1.403 | 3.238 | 1.00 | 37.88 | L | C |
| ATOM | 3832 | CD | GLN | 99 | 108.266 | -1.748 | 3.319 | 1.00 | 37.88 | L | C |
| ATOM | 3833 | OE1 | GLN | 99 | 108.638 | -2.821 | 3.796 | 1.00 | 37.88 | L | O |
| ATOM | 3834 | NE2 | GLN | 99 | 109.110 | -0.832 | 2.866 | 1.00 | 37.88 | L | N |
| ATOM | 3835 | C | GLN | 99 | 107.586 | -0.758 | 6.634 | 1.00 | 11.59 | L | C |
| ATOM | 3836 | O | GLN | 99 | 106.943 | -1.317 | 7.508 | 1.00 | 11.59 | L | O |
| ATOM | 3837 | N | GLY | 100 | 108.902 | -0.640 | 6.684 | 1.00 | 24.72 | L | N |
| ATOM | 3838 | CA | GLY | 100 | 109.633 | -1.225 | 7.785 | 1.00 | 24.72 | L | C |
| ATOM | 3839 | C | GLY | 100 | 110.055 | -2.630 | 7.425 | 1.00 | 24.72 | L | C |
| ATOM | 3840 | O | GLY | 100 | 109.402 | -3.279 | 6.606 | 1.00 | 24.72 | L | O |
| ATOM | 3841 | N | THR | 101 | 111.157 | -3.084 | 8.017 | 1.00 | 23.77 | L | N |
| ATOM | 3842 | CA | THR | 101 | 111.685 | -4.424 | 7.780 | 1.00 | 23.77 | L | C |
| ATOM | 3843 | CB | THR | 101 | 113.019 | -4.382 | 7.040 | 1.00 | 10.18 | L | C |
| ATOM | 3844 | OG1 | THR | 101 | 112.790 | -4.076 | 5.659 | 1.00 | 10.18 | L | O |
| ATOM | 3845 | CG2 | THR | 101 | 113.735 | -5.716 | 7.173 | 1.00 | 10.18 | L | C |
| ATOM | 3846 | C | THR | 101 | 111.908 | -5.076 | 9.129 | 1.00 | 23.77 | L | C |
| ATOM | 3847 | O | THR | 101 | 112.689 | -4.582 | 9.942 | 1.00 | 23.77 | L | O |
| ATOM | 3848 | N | LYS | 102 | 111.223 | -6.188 | 9.365 | 1.00 | 19.34 | L | N |
| ATOM | 3849 | CA | LYS | 102 | 111.347 | -6.858 | 10.641 | 1.00 | 19.34 | L | C |
| ATOM | 3850 | CB | LYS | 102 | 110.009 | -7.496 | 11.027 | 1.00 | 36.70 | L | C |
| ATOM | 3851 | CG | LYS | 102 | 109.872 | -7.774 | 12.521 | 1.00 | 36.70 | L | C |
| ATOM | 3852 | CD | LYS | 102 | 108.464 | -8.244 | 12.876 | 1.00 | 36.70 | L | C |
| ATOM | 3853 | CE | LYS | 102 | 108.313 | -8.467 | 14.372 | 1.00 | 36.70 | L | C |
| ATOM | 3854 | NZ | LYS | 102 | 108.632 | -7.218 | 15.120 | 1.00 | 36.70 | L | N |
| ATOM | 3855 | C | LYS | 102 | 112.449 | -7.907 | 10.608 | 1.00 | 19.34 | L | C |
| ATOM | 3856 | O | LYS | 102 | 112.530 | -8.703 | 9.661 | 1.00 | 19.34 | L | O |
| ATOM | 3857 | N | VAL | 103 | 113.304 | -7.894 | 11.634 | 1.00 | 20.01 | L | N |
| ATOM | 3858 | CA | VAL | 103 | 114.378 | -8.868 | 11.714 | 1.00 | 20.01 | L | C |
| ATOM | 3859 | CB | VAL | 103 | 115.793 | -8.188 | 11.567 | 1.00 | 24.69 | L | C |
| ATOM | 3860 | CG1 | VAL | 103 | 115.696 | -6.991 | 10.636 | 1.00 | 24.69 | L | C |
| ATOM | 3861 | CG2 | VAL | 103 | 116.361 | -7.780 | 12.908 | 1.00 | 24.69 | L | C |
| ATOM | 3862 | C | VAL | 103 | 114.280 | -9.654 | 13.031 | 1.00 | 20.01 | L | C |
| ATOM | 3863 | O | VAL | 103 | 114.380 | -9.075 | 14.117 | 1.00 | 20.01 | L | O |
| ATOM | 3864 | N | GLU | 104 | 114.047 | -10.969 | 12.927 | 1.00 | 25.78 | L | N |
| ATOM | 3865 | CA | GLU | 104 | 113.948 | -11.831 | 14.106 | 1.00 | 25.78 | L | C |
| ATOM | 3866 | CB | GLU | 104 | 112.662 | -12.666 | 14.098 | 1.00 | 117.28 | L | C |
| ATOM | 3867 | CG | GLU | 104 | 112.589 | -13.728 | 13.022 | 1.00 | 117.28 | L | C |
| ATOM | 3868 | CD | GLU | 104 | 112.095 | -13.176 | 11.705 | 1.00 | 117.28 | L | C |
| ATOM | 3869 | OE1 | GLU | 104 | 112.047 | -13.942 | 10.717 | 1.00 | 117.28 | L | O |

Fig. 19: A-54

| | | | | | | | | | | | |
|---|---|---|---|---|---|---|---|---|---|---|---|
| ATOM | 3870 | OE2 | GLU | 104 | 111.747 | -11.975 | 11.660 | 1.00 | 117.28 | L | O |
| ATOM | 3871 | C | GLU | 104 | 115.148 | -12.759 | 14.179 | 1.00 | 25.78 | L | C |
| ATOM | 3872 | O | GLU | 104 | 115.852 | -12.955 | 13.185 | 1.00 | 25.78 | L | O |
| ATOM | 3873 | N | ILE | 105 | 115.368 | -13.324 | 15.365 | 1.00 | 16.82 | L | N |
| ATOM | 3874 | CA | ILE | 105 | 116.489 | -14.228 | 15.621 | 1.00 | 16.82 | L | C |
| ATOM | 3875 | CB | ILE | 105 | 116.771 | -14.386 | 17.124 | 1.00 | 41.57 | L | C |
| ATOM | 3876 | CG2 | ILE | 105 | 118.226 | -14.701 | 17.335 | 1.00 | 41.57 | L | C |
| ATOM | 3877 | CG1 | ILE | 105 | 116.372 | -13.111 | 17.873 | 1.00 | 41.57 | L | C |
| ATOM | 3878 | CD1 | ILE | 105 | 116.594 | -13.151 | 19.385 | 1.00 | 41.57 | L | C |
| ATOM | 3879 | C | ILE | 105 | 116.204 | -15.611 | 15.102 | 1.00 | 16.82 | L | C |
| ATOM | 3880 | O | ILE | 105 | 115.251 | -16.250 | 15.543 | 1.00 | 16.82 | L | O |
| ATOM | 3881 | N | LYS | 106 | 117.008 | -16.076 | 14.153 | 1.00 | 39.65 | L | N |
| ATOM | 3882 | CA | LYS | 106 | 116.807 | -17.422 | 13.653 | 1.00 | 39.65 | L | C |
| ATOM | 3883 | CB | LYS | 106 | 117.310 | -17.587 | 12.217 | 1.00 | 48.57 | L | C |
| ATOM | 3884 | CG | LYS | 106 | 116.947 | -18.952 | 11.631 | 1.00 | 48.57 | L | C |
| ATOM | 3885 | CD | LYS | 106 | 117.401 | -19.148 | 10.179 | 1.00 | 48.57 | L | C |
| ATOM | 3886 | CE | LYS | 106 | 117.087 | -20.579 | 9.702 | 1.00 | 48.57 | L | C |
| ATOM | 3887 | NZ | LYS | 106 | 117.672 | -20.948 | 8.369 | 1.00 | 48.57 | L | N |
| ATOM | 3888 | C | LYS | 106 | 117.598 | -18.310 | 14.600 | 1.00 | 39.65 | L | C |
| ATOM | 3889 | O | LYS | 106 | 118.804 | -18.122 | 14.782 | 1.00 | 38.70 | L | O |
| ATOM | 3890 | N | ARG | 107 | 116.894 | -19.242 | 15.235 | 1.00 | 14.86 | L | N |
| ATOM | 3891 | CA | ARG | 107 | 117.492 | -20.178 | 16.174 | 1.00 | 14.86 | L | C |
| ATOM | 3892 | CB | ARG | 107 | 117.158 | -19.771 | 17.605 | 1.00 | 20.96 | L | C |
| ATOM | 3893 | CG | ARG | 107 | 115.687 | -19.532 | 17.832 | 1.00 | 20.96 | L | C |
| ATOM | 3894 | CD | ARG | 107 | 115.296 | -19.930 | 19.239 | 1.00 | 20.96 | L | C |
| ATOM | 3895 | NE | ARG | 107 | 115.615 | -21.335 | 19.502 | 1.00 | 20.96 | L | N |
| ATOM | 3896 | CZ | ARG | 107 | 115.513 | -21.910 | 20.692 | 1.00 | 20.96 | L | C |
| ATOM | 3897 | NH1 | ARG | 107 | 115.096 | -21.206 | 21.732 | 1.00 | 20.96 | L | N |
| ATOM | 3898 | NH2 | ARG | 107 | 115.843 | -23.182 | 20.840 | 1.00 | 20.96 | L | N |
| ATOM | 3899 | C | ARG | 107 | 116.986 | -21.595 | 15.899 | 1.00 | 14.86 | L | C |
| ATOM | 3900 | O | ARG | 107 | 116.062 | -21.796 | 15.107 | 1.00 | 14.86 | L | O |
| ATOM | 3901 | N | THR | 108 | 117.606 | -22.575 | 16.545 | 1.00 | 15.74 | L | N |
| ATOM | 3902 | CA | THR | 108 | 117.220 | -23.963 | 16.354 | 1.00 | 15.74 | L | C |
| ATOM | 3903 | CB | THR | 108 | 118.025 | -24.921 | 17.260 | 1.00 | 26.88 | L | C |
| ATOM | 3904 | OG1 | THR | 108 | 118.232 | -24.320 | 18.548 | 1.00 | 26.88 | L | O |
| ATOM | 3905 | CG2 | THR | 108 | 119.347 | -25.257 | 16.618 | 1.00 | 26.88 | L | C |
| ATOM | 3906 | C | THR | 108 | 115.756 | -24.161 | 16.653 | 1.00 | 15.74 | L | C |
| ATOM | 3907 | O | THR | 108 | 115.179 | -23.450 | 17.481 | 1.00 | 15.74 | L | O |
| ATOM | 3908 | N | VAL | 109 | 115.170 | -25.134 | 15.963 | 1.00 | 14.98 | L | N |
| ATOM | 3909 | CA | VAL | 109 | 113.775 | -25.469 | 16.136 | 1.00 | 12.60 | L | C |
| ATOM | 3910 | CB | VAL | 109 | 113.368 | -26.593 | 15.189 | 1.00 | 15.46 | L | C |
| ATOM | 3911 | CG1 | VAL | 109 | 111.987 | -27.105 | 15.527 | 1.00 | 14.41 | L | C |
| ATOM | 3912 | CG2 | VAL | 109 | 113.383 | -26.074 | 13.789 | 1.00 | 13.59 | L | C |
| ATOM | 3913 | C | VAL | 109 | 113.517 | -25.909 | 17.565 | 1.00 | 13.54 | L | C |
| ATOM | 3914 | O | VAL | 109 | 114.393 | -26.477 | 18.236 | 1.00 | 21.28 | L | O |
| ATOM | 3915 | N | ALA | 110 | 112.313 | -25.637 | 18.036 | 1.00 | 11.81 | L | N |
| ATOM | 3916 | CA | ALA | 110 | 111.953 | -26.001 | 19.383 | 1.00 | 12.99 | L | C |
| ATOM | 3917 | CB | ALA | 110 | 112.312 | -24.878 | 20.330 | 1.00 | 8.30 | L | C |
| ATOM | 3918 | C | ALA | 110 | 110.463 | -26.281 | 19.426 | 1.00 | 13.63 | L | C |
| ATOM | 3919 | O | ALA | 110 | 109.654 | -25.390 | 19.158 | 1.00 | 15.92 | L | O |
| ATOM | 3920 | N | ALA | 111 | 110.112 | -27.525 | 19.758 | 1.00 | 25.70 | L | N |
| ATOM | 3921 | CA | ALA | 111 | 108.715 | -27.951 | 19.838 | 1.00 | 26.75 | L | C |
| ATOM | 3922 | CB | ALA | 111 | 108.641 | -29.446 | 20.087 | 1.00 | 23.32 | L | C |
| ATOM | 3923 | C | ALA | 111 | 107.981 | -27.198 | 20.936 | 1.00 | 25.59 | L | C |
| ATOM | 3924 | O | ALA | 111 | 108.525 | -26.926 | 22.008 | 1.00 | 29.44 | L | O |
| ATOM | 3925 | N | PRO | 112 | 106.720 | -26.857 | 20.686 | 1.00 | 20.76 | L | N |
| ATOM | 3926 | CD | PRO | 112 | 105.901 | -27.063 | 19.477 | 1.00 | 26.01 | L | C |
| ATOM | 3927 | CA | PRO | 112 | 105.975 | -26.125 | 21.707 | 1.00 | 26.81 | L | C |
| ATOM | 3928 | CB | PRO | 112 | 104.938 | -25.381 | 20.882 | 1.00 | 26.37 | L | C |
| ATOM | 3929 | CG | PRO | 112 | 104.550 | -26.457 | 19.876 | 1.00 | 24.71 | L | C |
| ATOM | 3930 | C | PRO | 112 | 105.322 | -27.058 | 22.703 | 1.00 | 30.67 | L | C |
| ATOM | 3931 | O | PRO | 112 | 104.936 | -28.166 | 22.353 | 1.00 | 31.28 | L | O |
| ATOM | 3932 | N | SER | 113 | 105.220 | -26.618 | 23.947 | 1.00 | 12.97 | L | N |
| ATOM | 3933 | CA | SER | 113 | 104.530 | -27.410 | 24.944 | 1.00 | 16.57 | L | C |
| ATOM | 3934 | CB | SER | 113 | 105.027 | -27.079 | 26.334 | 1.00 | 14.96 | L | C |
| ATOM | 3935 | OG | SER | 113 | 106.427 | -27.168 | 26.370 | 1.00 | 27.37 | L | O |
| ATOM | 3936 | C | SER | 113 | 103.099 | -26.913 | 24.815 | 1.00 | 15.10 | L | C |
| ATOM | 3937 | O | SER | 113 | 102.884 | -25.708 | 24.770 | 1.00 | 12.98 | L | O |
| ATOM | 3938 | N | VAL | 114 | 102.111 | -27.792 | 24.731 | 1.00 | 10.23 | L | N |
| ATOM | 3939 | CA | VAL | 114 | 100.766 | -27.258 | 24.630 | 1.00 | 9.98 | L | C |
| ATOM | 3940 | CB | VAL | 114 | 99.989 | -27.808 | 23.413 | 1.00 | 7.82 | L | C |
| ATOM | 3941 | CG1 | VAL | 114 | 100.921 | -27.972 | 22.212 | 1.00 | 4.17 | L | C |
| ATOM | 3942 | CG2 | VAL | 114 | 99.331 | -29.100 | 23.777 | 1.00 | 9.35 | L | C |

Fig. 19: A-55

| | | | | | | | | | | | |
|---|---|---|---|---|---|---|---|---|---|---|---|
| ATOM | 3943 | C | VAL | 114 | 99.992 | -27.558 | 25.899 | 1.00 | 9.84 | L | C |
| ATOM | 3944 | O | VAL | 114 | 100.318 | -28.494 | 26.628 | 1.00 | 12.49 | L | O |
| ATOM | 3945 | N | PHE | 115 | 98.981 | -26.728 | 26.153 | 1.00 | 26.11 | L | N |
| ATOM | 3946 | CA | PHE | 115 | 98.109 | -26.840 | 27.318 | 1.00 | 30.12 | L | C |
| ATOM | 3947 | CB | PHE | 115 | 98.581 | -25.896 | 28.416 | 1.00 | 36.06 | L | C |
| ATOM | 3948 | CG | PHE | 115 | 100.030 | -26.015 | 28.706 | 1.00 | 35.84 | L | C |
| ATOM | 3949 | CD1 | PHE | 115 | 100.505 | -27.040 | 29.513 | 1.00 | 38.16 | L | C |
| ATOM | 3950 | CD2 | PHE | 115 | 100.935 | -25.146 | 28.115 | 1.00 | 34.45 | L | C |
| ATOM | 3951 | CE1 | PHE | 115 | 101.854 | -27.203 | 29.723 | 1.00 | 41.30 | L | C |
| ATOM | 3952 | CE2 | PHE | 115 | 102.287 | -25.302 | 28.319 | 1.00 | 38.56 | L | C |
| ATOM | 3953 | CZ | PHE | 115 | 102.749 | -26.335 | 29.126 | 1.00 | 39.82 | L | C |
| ATOM | 3954 | C | PHE | 115 | 96.727 | -26.410 | 26.873 | 1.00 | 32.06 | L | C |
| ATOM | 3955 | O | PHE | 115 | 96.590 | -25.543 | 26.017 | 1.00 | 32.56 | L | O |
| ATOM | 3956 | N | ILE | 116 | 95.694 | -27.018 | 27.432 | 1.00 | 24.34 | L | N |
| ATOM | 3957 | CA | ILE | 116 | 94.354 | -26.608 | 27.069 | 1.00 | 18.54 | L | C |
| ATOM | 3958 | CB | ILE | 116 | 93.606 | -27.735 | 26.309 | 1.00 | 15.62 | L | C |
| ATOM | 3959 | CG2 | ILE | 116 | 93.239 | -28.855 | 27.249 | 1.00 | 4.34 | L | C |
| ATOM | 3960 | CG1 | ILE | 116 | 92.377 | -27.145 | 25.615 | 1.00 | 12.45 | L | C |
| ATOM | 3961 | CD1 | ILE | 116 | 91.695 | -28.089 | 24.646 | 1.00 | 4.28 | L | C |
| ATOM | 3962 | C | ILE | 116 | 93.661 | -26.233 | 28.371 | 1.00 | 19.64 | L | C |
| ATOM | 3963 | O | ILE | 116 | 93.931 | -26.834 | 29.412 | 1.00 | 19.05 | L | O |
| ATOM | 3964 | N | PHE | 117 | 92.802 | -25.217 | 28.308 | 1.00 | 17.52 | L | N |
| ATOM | 3965 | CA | PHE | 117 | 92.066 | -24.715 | 29.475 | 1.00 | 21.17 | L | C |
| ATOM | 3966 | CB | PHE | 117 | 92.501 | -23.295 | 29.828 | 1.00 | 22.98 | L | C |
| ATOM | 3967 | CG | PHE | 117 | 93.922 | -23.177 | 30.280 | 1.00 | 26.62 | L | C |
| ATOM | 3968 | CD1 | PHE | 117 | 94.293 | -23.562 | 31.559 | 1.00 | 29.31 | L | C |
| ATOM | 3969 | CD2 | PHE | 117 | 94.882 | -22.653 | 29.433 | 1.00 | 28.01 | L | C |
| ATOM | 3970 | CE1 | PHE | 117 | 95.599 | -23.421 | 31.988 | 1.00 | 28.27 | L | C |
| ATOM | 3971 | CE2 | PHE | 117 | 96.186 | -22.511 | 29.854 | 1.00 | 26.58 | L | C |
| ATOM | 3972 | CZ | PHE | 117 | 96.550 | -22.895 | 31.134 | 1.00 | 28.58 | L | C |
| ATOM | 3973 | C | PHE | 117 | 90.585 | -24.642 | 29.194 | 1.00 | 24.71 | L | C |
| ATOM | 3974 | O | PHE | 117 | 90.167 | -23.964 | 28.261 | 1.00 | 29.18 | L | O |
| ATOM | 3975 | N | PRO | 118 | 89.768 | -25.323 | 30.007 | 1.00 | 23.78 | L | N |
| ATOM | 3976 | CD | PRO | 118 | 90.235 | -26.376 | 30.926 | 1.00 | 9.40 | L | C |
| ATOM | 3977 | CA | PRO | 118 | 88.300 | -25.354 | 29.883 | 1.00 | 26.26 | L | C |
| ATOM | 3978 | CB | PRO | 118 | 87.907 | -26.568 | 30.718 | 1.00 | 9.92 | L | C |
| ATOM | 3979 | CG | PRO | 118 | 89.159 | -27.404 | 30.763 | 1.00 | 12.26 | L | C |
| ATOM | 3980 | C | PRO | 118 | 87.660 | -24.081 | 30.455 | 1.00 | 29.72 | L | C |
| ATOM | 3981 | O | PRO | 118 | 88.231 | -23.440 | 31.338 | 1.00 | 31.19 | L | O |
| ATOM | 3982 | N | PRO | 119 | 86.464 | -23.699 | 29.966 | 1.00 | 9.50 | L | N |
| ATOM | 3983 | CD | PRO | 119 | 85.678 | -24.330 | 28.892 | 1.00 | 26.21 | L | C |
| ATOM | 3984 | CA | PRO | 119 | 85.787 | -22.493 | 30.479 | 1.00 | 9.82 | L | C |
| ATOM | 3985 | CB | PRO | 119 | 84.413 | -22.555 | 29.826 | 1.00 | 24.20 | L | C |
| ATOM | 3986 | CG | PRO | 119 | 84.703 | -23.219 | 28.519 | 1.00 | 27.52 | L | C |
| ATOM | 3987 | C | PRO | 119 | 85.682 | -22.566 | 32.001 | 1.00 | 15.21 | L | C |
| ATOM | 3988 | O | PRO | 119 | 85.463 | -23.630 | 32.561 | 1.00 | 17.89 | L | O |
| ATOM | 3989 | N | SER | 120 | 85.843 | -21.435 | 32.665 | 1.00 | 31.09 | L | N |
| ATOM | 3990 | CA | SER | 120 | 85.765 | -21.378 | 34.118 | 1.00 | 35.08 | L | C |
| ATOM | 3991 | CB | SER | 120 | 86.299 | -20.027 | 34.586 | 1.00 | 17.54 | L | C |
| ATOM | 3992 | OG | SER | 120 | 85.709 | -18.983 | 33.832 | 1.00 | 27.86 | L | O |
| ATOM | 3993 | C | SER | 120 | 84.334 | -21.550 | 34.623 | 1.00 | 35.73 | L | C |
| ATOM | 3994 | O | SER | 120 | 83.370 | -21.381 | 33.869 | 1.00 | 35.32 | L | O |
| ATOM | 3995 | N | ASP | 121 | 84.185 | -21.896 | 35.897 | 1.00 | 24.20 | L | N |
| ATOM | 3996 | CA | ASP | 121 | 82.842 | -22.015 | 36.465 | 1.00 | 27.07 | L | C |
| ATOM | 3997 | CB | ASP | 121 | 82.897 | -22.458 | 37.937 | 1.00 | 55.35 | L | C |
| ATOM | 3998 | CG | ASP | 121 | 83.160 | -23.950 | 38.101 | 1.00 | 60.98 | L | C |
| ATOM | 3999 | OD1 | ASP | 121 | 82.573 | -24.736 | 37.331 | 1.00 | 62.35 | L | O |
| ATOM | 4000 | OD2 | ASP | 121 | 83.934 | -24.337 | 39.008 | 1.00 | 63.66 | L | O |
| ATOM | 4001 | C | ASP | 121 | 82.194 | -20.627 | 36.384 | 1.00 | 26.11 | L | C |
| ATOM | 4002 | O | ASP | 121 | 81.053 | -20.474 | 35.941 | 1.00 | 23.12 | L | O |
| ATOM | 4003 | N | GLU | 122 | 82.954 | -19.617 | 36.794 | 1.00 | 48.87 | L | N |
| ATOM | 4004 | CA | GLU | 122 | 82.490 | -18.234 | 36.797 | 1.00 | 47.43 | L | C |
| ATOM | 4005 | CB | GLU | 122 | 83.596 | -17.328 | 37.348 | 1.00 | 56.26 | L | C |
| ATOM | 4006 | CG | GLU | 122 | 83.180 | -15.870 | 37.529 | 1.00 | 59.80 | L | C |
| ATOM | 4007 | CD | GLU | 122 | 84.328 | -14.966 | 37.984 | 1.00 | 63.49 | L | C |
| ATOM | 4008 | OE1 | GLU | 122 | 84.099 | -13.741 | 38.109 | 1.00 | 64.12 | L | O |
| ATOM | 4009 | OE2 | GLU | 122 | 85.453 | -15.472 | 38.213 | 1.00 | 63.98 | L | O |
| ATOM | 4010 | C | GLU | 122 | 82.018 | -17.703 | 35.434 | 1.00 | 47.22 | L | C |
| ATOM | 4011 | O | GLU | 122 | 80.884 | -17.232 | 35.303 | 1.00 | 45.96 | L | O |
| ATOM | 4012 | N | GLN | 123 | 82.881 | -17.774 | 34.424 | 1.00 | 34.52 | L | N |
| ATOM | 4013 | CA | GLN | 123 | 82.523 | -17.273 | 33.102 | 1.00 | 32.32 | L | C |
| ATOM | 4014 | CB | GLN | 123 | 83.643 | -17.511 | 32.097 | 1.00 | 23.68 | L | C |
| ATOM | 4015 | CG | GLN | 123 | 83.286 | -17.000 | 30.723 | 1.00 | 24.85 | L | C |

Fig. 19: A-56

| | | | | | | | | | | | |
|---|---|---|---|---|---|---|---|---|---|---|---|
| ATOM | 4016 | CD | GLN | 123 | 84.089 | -17.644 | 29.635 | 1.00 | 26.94 | L | C |
| ATOM | 4017 | OE1 | GLN | 123 | 83.877 | -17.369 | 28.463 | 1.00 | 23.36 | L | O |
| ATOM | 4018 | NE2 | GLN | 123 | 85.017 | -18.511 | 30.010 | 1.00 | 24.66 | L | N |
| ATOM | 4019 | C | GLN | 123 | 81.256 | -17.909 | 32.565 | 1.00 | 32.32 | L | C |
| ATOM | 4020 | O | GLN | 123 | 80.424 | -17.233 | 31.969 | 1.00 | 29.27 | L | O |
| ATOM | 4021 | N | LEU | 124 | 81.128 | -19.218 | 32.745 | 1.00 | 36.22 | L | N |
| ATOM | 4022 | CA | LEU | 124 | 79.938 | -19.926 | 32.288 | 1.00 | 37.57 | L | C |
| ATOM | 4023 | CB | LEU | 124 | 80.075 | -21.425 | 32.570 | 1.00 | 20.16 | L | C |
| ATOM | 4024 | CG | LEU | 124 | 80.878 | -22.173 | 31.498 | 1.00 | 19.96 | L | C |
| ATOM | 4025 | CD1 | LEU | 124 | 81.099 | -23.623 | 31.892 | 1.00 | 15.21 | L | C |
| ATOM | 4026 | CD2 | LEU | 124 | 80.123 | -22.085 | 30.176 | 1.00 | 18.53 | L | C |
| ATOM | 4027 | C | LEU | 124 | 78.722 | -19.355 | 33.003 | 1.00 | 41.33 | L | C |
| ATOM | 4028 | O | LEU | 124 | 77.648 | -19.204 | 32.417 | 1.00 | 43.14 | L | O |
| ATOM | 4029 | N | LYS | 125 | 78.912 | -19.022 | 34.274 | 1.00 | 101.23 | L | N |
| ATOM | 4030 | CA | LYS | 125 | 77.856 | -18.441 | 35.090 | 1.00 | 102.45 | L | C |
| ATOM | 4031 | CB | LYS | 125 | 78.355 | -18.285 | 36.534 | 1.00 | 60.11 | L | C |
| ATOM | 4032 | CG | LYS | 125 | 77.286 | -18.376 | 37.612 | 1.00 | 62.95 | L | C |
| ATOM | 4033 | CD | LYS | 125 | 76.737 | -19.797 | 37.713 | 1.00 | 68.67 | L | C |
| ATOM | 4034 | CE | LYS | 125 | 75.726 | -19.942 | 38.847 | 1.00 | 73.14 | L | C |
| ATOM | 4035 | NZ | LYS | 125 | 75.101 | -21.299 | 38.895 | 1.00 | 74.11 | L | N |
| ATOM | 4036 | C | LYS | 125 | 77.545 | -17.065 | 34.494 | 1.00 | 104.22 | L | C |
| ATOM | 4037 | O | LYS | 125 | 77.004 | -16.195 | 35.168 | 1.00 | 105.97 | L | O |
| ATOM | 4038 | N | SER | 126 | 77.892 | -16.880 | 33.222 | 1.00 | 44.02 | L | N |
| ATOM | 4039 | CA | SER | 126 | 77.693 | -15.614 | 32.522 | 1.00 | 43.14 | L | C |
| ATOM | 4040 | CB | SER | 126 | 79.045 | -14.925 | 32.308 | 1.00 | 48.89 | L | C |
| ATOM | 4041 | OG | SER | 126 | 78.953 | -13.915 | 31.324 | 1.00 | 52.18 | L | O |
| ATOM | 4042 | C | SER | 126 | 76.995 | -15.769 | 31.176 | 1.00 | 41.22 | L | C |
| ATOM | 4043 | O | SER | 126 | 76.469 | -14.802 | 30.631 | 1.00 | 40.32 | L | O |
| ATOM | 4044 | N | GLY | 127 | 77.007 | -16.978 | 30.626 | 1.00 | 29.57 | L | N |
| ATOM | 4045 | CA | GLY | 127 | 76.340 | -17.190 | 29.355 | 1.00 | 30.30 | L | C |
| ATOM | 4046 | C | GLY | 127 | 77.266 | -17.332 | 28.168 | 1.00 | 29.68 | L | C |
| ATOM | 4047 | O | GLY | 127 | 76.818 | -17.391 | 27.022 | 1.00 | 30.41 | L | O |
| ATOM | 4048 | N | THR | 128 | 78.564 | -17.375 | 28.432 | 1.00 | 60.53 | L | N |
| ATOM | 4049 | CA | THR | 128 | 79.530 | -17.531 | 27.360 | 1.00 | 57.77 | L | C |
| ATOM | 4050 | CB | THR | 128 | 80.105 | -16.180 | 26.921 | 1.00 | 55.78 | L | C |
| ATOM | 4051 | OG1 | THR | 128 | 79.080 | -15.424 | 26.264 | 1.00 | 56.94 | L | O |
| ATOM | 4052 | CG2 | THR | 128 | 81.259 | -16.381 | 25.960 | 1.00 | 54.81 | L | C |
| ATOM | 4053 | C | THR | 128 | 80.643 | -18.434 | 27.830 | 1.00 | 56.24 | L | C |
| ATOM | 4054 | O | THR | 128 | 80.979 | -18.446 | 29.015 | 1.00 | 51.99 | L | O |
| ATOM | 4055 | N | ALA | 129 | 81.201 | -19.203 | 26.901 | 1.00 | 18.93 | L | N |
| ATOM | 4056 | CA | ALA | 129 | 82.275 | -20.125 | 27.232 | 1.00 | 17.83 | L | C |
| ATOM | 4057 | CB | ALA | 129 | 81.779 | -21.558 | 27.108 | 1.00 | 65.23 | L | C |
| ATOM | 4058 | C | ALA | 129 | 83.512 | -19.937 | 26.374 | 1.00 | 17.59 | L | C |
| ATOM | 4059 | O | ALA | 129 | 83.443 | -19.993 | 25.148 | 1.00 | 23.96 | L | O |
| ATOM | 4060 | N | SER | 130 | 84.652 | -19.729 | 27.020 | 1.00 | 24.31 | L | N |
| ATOM | 4061 | CA | SER | 130 | 85.905 | -19.560 | 26.298 | 1.00 | 19.76 | L | C |
| ATOM | 4062 | CB | SER | 130 | 86.565 | -18.256 | 26.741 | 1.00 | 18.21 | L | C |
| ATOM | 4063 | OG | SER | 130 | 85.724 | -17.142 | 26.477 | 1.00 | 20.32 | L | O |
| ATOM | 4064 | C | SER | 130 | 86.835 | -20.755 | 26.573 | 1.00 | 16.63 | L | C |
| ATOM | 4065 | O | SER | 130 | 87.037 | -21.141 | 27.732 | 1.00 | 19.43 | L | O |
| ATOM | 4066 | N | VAL | 131 | 87.370 | -21.371 | 25.521 | 1.00 | 11.62 | L | N |
| ATOM | 4067 | CA | VAL | 131 | 88.294 | -22.502 | 25.686 | 1.00 | 9.15 | L | C |
| ATOM | 4068 | CB | VAL | 131 | 87.848 | -23.743 | 24.872 | 1.00 | 17.04 | L | C |
| ATOM | 4069 | CG1 | VAL | 131 | 88.738 | -24.927 | 25.196 | 1.00 | 21.32 | L | C |
| ATOM | 4070 | CG2 | VAL | 131 | 86.413 | -24.081 | 25.180 | 1.00 | 16.62 | L | C |
| ATOM | 4071 | C | VAL | 131 | 89.647 | -22.030 | 25.156 | 1.00 | 9.42 | L | C |
| ATOM | 4072 | O | VAL | 131 | 89.731 | -21.557 | 24.025 | 1.00 | 13.02 | L | O |
| ATOM | 4073 | N | VAL | 132 | 90.704 | -22.146 | 25.956 | 1.00 | 21.24 | L | N |
| ATOM | 4074 | CA | VAL | 132 | 92.011 | -21.677 | 25.501 | 1.00 | 16.30 | L | C |
| ATOM | 4075 | CB | VAL | 132 | 92.573 | -20.538 | 26.414 | 1.00 | 43.77 | L | C |
| ATOM | 4076 | CG1 | VAL | 132 | 93.958 | -20.122 | 25.934 | 1.00 | 47.77 | L | C |
| ATOM | 4077 | CG2 | VAL | 132 | 91.645 | -19.324 | 26.393 | 1.00 | 44.24 | L | C |
| ATOM | 4078 | C | VAL | 132 | 93.081 | -22.743 | 25.374 | 1.00 | 17.14 | L | C |
| ATOM | 4079 | O | VAL | 132 | 93.372 | -23.482 | 26.320 | 1.00 | 14.49 | L | O |
| ATOM | 4080 | N | CYS | 133 | 93.662 | -22.793 | 24.178 | 1.00 | 23.86 | L | N |
| ATOM | 4081 | CA | CYS | 133 | 94.737 | -23.713 | 23.822 | 1.00 | 24.13 | L | C |
| ATOM | 4082 | C | CYS | 133 | 96.034 | -22.880 | 23.891 | 1.00 | 24.10 | L | C |
| ATOM | 4083 | O | CYS | 133 | 96.072 | -21.744 | 23.425 | 1.00 | 27.83 | L | O |
| ATOM | 4084 | CB | CYS | 133 | 94.486 | -24.219 | 22.399 | 1.00 | 19.56 | L | C |
| ATOM | 4085 | SG | CYS | 133 | 95.558 | -25.537 | 21.738 | 1.00 | 32.96 | L | S |
| ATOM | 4086 | N | LEU | 134 | 97.085 | -23.432 | 24.482 | 1.00 | 36.02 | L | N |
| ATOM | 4087 | CA | LEU | 134 | 98.343 | -22.709 | 24.591 | 1.00 | 34.35 | L | C |
| ATOM | 4088 | CB | LEU | 134 | 98.658 | -22.383 | 26.058 | 1.00 | 16.71 | L | C |

Fig. 19: A-57

| | | | | | | | | | | | |
|---|---|---|---|---|---|---|---|---|---|---|---|
| ATOM | 4089 | CG | LEU | 134 | 100.079 | -21.843 | 26.376 | 1.00 | 12.52 | L | C |
| ATOM | 4090 | CD1 | LEU | 134 | 100.297 | -20.468 | 25.729 | 1.00 | 9.26 | L | C |
| ATOM | 4091 | CD2 | LEU | 134 | 100.275 | -21.746 | 27.892 | 1.00 | 9.75 | L | C |
| ATOM | 4092 | C | LEU | 134 | 99.532 | -23.457 | 24.001 | 1.00 | 33.88 | L | C |
| ATOM | 4093 | O | LEU | 134 | 99.820 | -24.595 | 24.378 | 1.00 | 33.96 | L | O |
| ATOM | 4094 | N | LEU | 135 | 100.206 | -22.802 | 23.060 | 1.00 | 23.69 | L | N |
| ATOM | 4095 | CA | LEU | 135 | 101.406 | -23.336 | 22.441 | 1.00 | 29.22 | L | C |
| ATOM | 4096 | CB | LEU | 135 | 101.353 | -23.150 | 20.926 | 1.00 | 1.87 | L | C |
| ATOM | 4097 | CG | LEU | 135 | 100.337 | -24.016 | 20.168 | 1.00 | 4.32 | L | C |
| ATOM | 4098 | CD1 | LEU | 135 | 98.962 | -23.751 | 20.672 | 1.00 | 5.12 | L | C |
| ATOM | 4099 | CD2 | LEU | 135 | 100.392 | -23.713 | 18.681 | 1.00 | 3.70 | L | C |
| ATOM | 4100 | C | LEU | 135 | 102.454 | -22.437 | 23.097 | 1.00 | 29.43 | L | C |
| ATOM | 4101 | O | LEU | 135 | 102.401 | -21.216 | 22.977 | 1.00 | 30.81 | L | O |
| ATOM | 4102 | N | ASN | 136 | 103.394 | -23.047 | 23.810 | 1.00 | 17.75 | L | N |
| ATOM | 4103 | CA | ASN | 136 | 104.393 | -22.299 | 24.550 | 1.00 | 20.05 | L | C |
| ATOM | 4104 | CB | ASN | 136 | 104.179 | -22.576 | 26.016 | 1.00 | 15.03 | L | C |
| ATOM | 4105 | CG | ASN | 136 | 104.905 | -21.615 | 26.885 | 1.00 | 19.57 | L | C |
| ATOM | 4106 | OD1 | ASN | 136 | 105.767 | -22.017 | 27.666 | 1.00 | 25.01 | L | O |
| ATOM | 4107 | ND2 | ASN | 136 | 104.569 | -20.327 | 26.769 | 1.00 | 19.54 | L | N |
| ATOM | 4108 | C | ASN | 136 | 105.856 | -22.526 | 24.212 | 1.00 | 18.78 | L | C |
| ATOM | 4109 | O | ASN | 136 | 106.283 | -23.651 | 23.963 | 1.00 | 17.25 | L | O |
| ATOM | 4110 | N | ASN | 137 | 106.619 | -21.436 | 24.240 | 1.00 | 28.11 | L | N |
| ATOM | 4111 | CA | ASN | 137 | 108.053 | -21.425 | 23.950 | 1.00 | 27.19 | L | C |
| ATOM | 4112 | CB | ASN | 137 | 108.869 | -21.844 | 25.173 | 1.00 | 13.82 | L | C |
| ATOM | 4113 | CG | ASN | 137 | 108.594 | -20.986 | 26.387 | 1.00 | 24.17 | L | C |
| ATOM | 4114 | OD1 | ASN | 137 | 108.027 | -19.901 | 26.281 | 1.00 | 19.30 | L | O |
| ATOM | 4115 | ND2 | ASN | 137 | 109.009 | -21.468 | 27.558 | 1.00 | 29.25 | L | N |
| ATOM | 4116 | C | ASN | 137 | 108.486 | -22.292 | 22.783 | 1.00 | 25.42 | L | C |
| ATOM | 4117 | O | ASN | 137 | 109.125 | -23.324 | 22.977 | 1.00 | 28.31 | L | O |
| ATOM | 4118 | N | PHE | 138 | 108.152 | -21.880 | 21.571 | 1.00 | 45.01 | L | N |
| ATOM | 4119 | CA | PHE | 138 | 108.557 | -22.652 | 20.412 | 1.00 | 41.21 | L | C |
| ATOM | 4120 | CB | PHE | 138 | 107.362 | -23.361 | 19.777 | 1.00 | 23.11 | L | C |
| ATOM | 4121 | CG | PHE | 138 | 106.230 | -22.452 | 19.442 | 1.00 | 20.89 | L | C |
| ATOM | 4122 | CD1 | PHE | 138 | 105.342 | -22.043 | 20.433 | 1.00 | 18.63 | L | C |
| ATOM | 4123 | CD2 | PHE | 138 | 106.055 | -21.993 | 18.137 | 1.00 | 19.93 | L | C |
| ATOM | 4124 | CE1 | PHE | 138 | 104.289 | -21.189 | 20.134 | 1.00 | 11.59 | L | C |
| ATOM | 4125 | CE2 | PHE | 138 | 105.010 | -21.138 | 17.818 | 1.00 | 16.52 | L | C |
| ATOM | 4126 | CZ | PHE | 138 | 104.118 | -20.730 | 18.818 | 1.00 | 14.07 | L | C |
| ATOM | 4127 | C | PHE | 138 | 109.248 | -21.794 | 19.369 | 1.00 | 36.81 | L | C |
| ATOM | 4128 | O | PHE | 138 | 109.456 | -20.594 | 19.559 | 1.00 | 35.37 | L | O |
| ATOM | 4129 | N | TYR | 139 | 109.606 | -22.437 | 18.267 | 1.00 | 17.70 | L | N |
| ATOM | 4130 | CA | TYR | 139 | 110.283 | -21.797 | 17.159 | 1.00 | 20.93 | L | C |
| ATOM | 4131 | CB | TYR | 139 | 111.660 | -21.300 | 17.579 | 1.00 | 31:56 | L | C |
| ATOM | 4132 | CG | TYR | 139 | 112.317 | -20.472 | 16.502 | 1.00 | 31.46 | L | C |
| ATOM | 4133 | CD1 | TYR | 139 | 112.207 | -19.083 | 16.502 | 1.00 | 26.49 | L | C |
| ATOM | 4134 | CE1 | TYR | 139 | 112.725 | -18.327 | 15.462 | 1.00 | 25.20 | L | C |
| ATOM | 4135 | CD2 | TYR | 139 | 112.974 | -21.083 | 15.428 | 1.00 | 25.20 | L | C |
| ATOM | 4136 | CE2 | TYR | 139 | 113.490 | -20.336 | 14.386 | 1.00 | 25.20 | L | C |
| ATOM | 4137 | CZ | TYR | 139 | 113.358 | -18.960 | 14.407 | 1.00 | 25.20 | L | C |
| ATOM | 4138 | OH | TYR | 139 | 113.820 | -18.216 | 13.353 | 1.00 | 28.00 | L | O |
| ATOM | 4139 | C | TYR | 139 | 110.447 | -22.917 | 16.166 | 1.00 | 20.32 | L | C |
| ATOM | 4140 | O | TYR | 139 | 110.798 | -24.022 | 16.550 | 1.00 | 25.25 | L | O |
| ATOM | 4141 | N | PRO | 140 | 110.223 | -22.662 | 14.876 | 1.00 | 34.32 | L | N |
| ATOM | 4142 | CD | PRO | 140 | 110.342 | -23.783 | 13.937 | 1.00 | 6.42 | L | C |
| ATOM | 4143 | CA | PRO | 140 | 109.824 | -21.443 | 14.171 | 1.00 | 30.02 | L | C |
| ATOM | 4144 | CB | PRO | 140 | 109.691 | -21.901 | 12.723 | 1.00 | 2.76 | L | C |
| ATOM | 4145 | CG | PRO | 140 | 110.570 | -23.070 | 12.643 | 1.00 | 4.42 | L | C |
| ATOM | 4146 | C | PRO | 140 | 108.502 | -20.939 | 14.685 | 1.00 | 31.53 | L | C |
| ATOM | 4147 | O | PRO | 140 | 107.830 | -21.612 | 15.466 | 1.00 | 29.36 | L | O |
| ATOM | 4148 | N | ARG | 141 | 108.119 | -19.764 | 14.203 | 1.00 | 22.83 | L | N |
| ATOM | 4149 | CA | ARG | 141 | 106.871 | -19.115 | 14.588 | 1.00 | 27.99 | L | C |
| ATOM | 4150 | CB | ARG | 141 | 106.931 | -17.657 | 14.148 | 1.00 | 21.70 | L | C |
| ATOM | 4151 | CG | ARG | 141 | 105.753 | -16.783 | 14.473 | 1.00 | 25.87 | L | C |
| ATOM | 4152 | CD | ARG | 141 | 106.157 | -15.358 | 14.129 | 1.00 | 37.20 | L | C |
| ATOM | 4153 | NE | ARG | 141 | 105.187 | -14.366 | 14.564 | 1.00 | 43.19 | L | N |
| ATOM | 4154 | CZ | ARG | 141 | 104.001 | -14.188 | 13.995 | 1.00 | 43.90 | L | C |
| ATOM | 4155 | NH1 | ARG | 141 | 103.642 | -14.941 | 12.960 | 1.00 | 39.57 | L | N |
| ATOM | 4156 | NH2 | ARG | 141 | 103.173 | -13.262 | 14.464 | 1.00 | 42.44 | L | N |
| ATOM | 4157 | C | ARG | 141 | 105.668 | -19.798 | 13.960 | 1.00 | 30.81 | L | C |
| ATOM | 4158 | O | ARG | 141 | 104.585 | -19.815 | 14.537 | 1.00 | 34.71 | L | O |
| ATOM | 4159 | N | GLU | 142 | 105.860 | -20.365 | 12.776 | 1.00 | 28.20 | L | N |
| ATOM | 4160 | CA | GLU | 142 | 104.756 | -21.013 | 12.091 | 1.00 | 24.33 | L | C |
| ATOM | 4161 | CB | GLU | 142 | 105.171 | -21.552 | 10.725 | 1.00 | 7.98 | L | C |

Fig. 19: A-58

| | | | | | | | | | | | |
|---|---|---|---|---|---|---|---|---|---|---|---|
| ATOM | 4162 | CG | GLU | 142 | 105.741 | -20.523 | 9.781 | 1.00 | 19.00 | L | C |
| ATOM | 4163 | CD | GLU | 142 | 107.096 | -20.051 | 10.217 | 1.00 | 27.12 | L | C |
| ATOM | 4164 | OE1 | GLU | 142 | 107.152 | -18.970 | 10.837 | 1.00 | 31.02 | L | O |
| ATOM | 4165 | OE2 | GLU | 142 | 108.095 | -20.772 | 9.952 | 1.00 | 33.88 | L | O |
| ATOM | 4166 | C | GLU | 142 | 104.154 | -22.151 | 12.878 | 1.00 | 22.94 | L | C |
| ATOM | 4167 | O | GLU | 142 | 104.753 | -23.220 | 13.021 | 1.00 | 26.95 | L | O |
| ATOM | 4168 | N | ALA | 143 | 102.958 | -21.909 | 13.386 | 1.00 | 30.55 | L | N |
| ATOM | 4169 | CA | ALA | 143 | 102.238 | -22.914 | 14.130 | 1.00 | 32.81 | L | C |
| ATOM | 4170 | CB | ALA | 143 | 102.260 | -22.593 | 15.640 | 1.00 | 21.32 | L | C |
| ATOM | 4171 | C | ALA | 143 | 100.819 | -22.862 | 13.579 | 1.00 | 34.94 | L | C |
| ATOM | 4172 | O | ALA | 143 | 100.373 | -21.832 | 13.058 | 1.00 | 38.69 | L | O |
| ATOM | 4173 | N | LYS | 144 | 100.120 | -23.981 | 13.677 | 1.00 | 46.96 | L | N |
| ATOM | 4174 | CA | LYS | 144 | 98.761 | -24.047 | 13.197 | 1.00 | 49.64 | L | C |
| ATOM | 4175 | CB | LYS | 144 | 98.734 | -24.807 | 11.870 | 1.00 | 34.36 | L | C |
| ATOM | 4176 | CG | LYS | 144 | 97.631 | -24.370 | 10.922 | 1.00 | 44.31 | L | C |
| ATOM | 4177 | CD | LYS | 144 | 97.441 | -25.358 | 9.772 | 1.00 | 55.06 | L | C |
| ATOM | 4178 | CE | LYS | 144 | 96.888 | -26.699 | 10.279 | 1.00 | 57.35 | L | C |
| ATOM | 4179 | NZ | LYS | 144 | 96.807 | -27.761 | 9.225 | 1.00 | 58.76 | L | N |
| ATOM | 4180 | C | LYS | 144 | 97.934 | -24.771 | 14.266 | 1.00 | 52.97 | L | C |
| ATOM | 4181 | O | LYS | 144 | 98.340 | -25.822 | 14.775 | 1.00 | 51.55 | L | O |
| ATOM | 4182 | N | VAL | 145 | 96.791 | -24.194 | 14.630 | 1.00 | 15.87 | L | N |
| ATOM | 4183 | CA | VAL | 145 | 95.927 | -24.813 | 15.629 | 1.00 | 21.71 | L | C |
| ATOM | 4184 | CB | VAL | 145 | 95.790 | -23.937 | 16.905 | 1.00 | 8.53 | L | C |
| ATOM | 4185 | CG1 | VAL | 145 | 94.817 | -24.597 | 17.889 | 1.00 | 7.53 | L | C |
| ATOM | 4186 | CG2 | VAL | 145 | 97.151 | -23.769 | 17.570 | 1.00 | 8.28 | L | C |
| ATOM | 4187 | C | VAL | 145 | 94.536 | -25.074 | 15.073 | 1.00 | 25.32 | L | C |
| ATOM | 4188 | O | VAL | 145 | 93.909 | -24.193 | 14.497 | 1.00 | 27.49 | L | O |
| ATOM | 4189 | N | GLN | 146 | 94.055 | -26.296 | 15.231 | 1.00 | 39.17 | L | N |
| ATOM | 4190 | CA | GLN | 146 | 92.729 | -26.611 | 14.743 | 1.00 | 38.70 | L | C |
| ATOM | 4191 | CB | GLN | 146 | 92.798 | -27.679 | 13.653 | 1.00 | 72.09 | L | C |
| ATOM | 4192 | CG | GLN | 146 | 93.678 | -27.281 | 12.482 | 1.00 | 76.00 | L | C |
| ATOM | 4193 | CD | GLN | 146 | 93.630 | -28.276 | 11.339 | 1.00 | 75.94 | L | C |
| ATOM | 4194 | OE1 | GLN | 146 | 92.616 | -28.399 | 10.654 | 1.00 | 76.92 | L | O |
| ATOM | 4195 | NE2 | GLN | 146 | 94.730 | -28.997 | 11.130 | 1.00 | 77.33 | L | N |
| ATOM | 4196 | C | GLN | 146 | 91.880 | -27.094 | 15.904 | 1.00 | 37.70 | L | C |
| ATOM | 4197 | O | GLN | 146 | 92.302 | -27.965 | 16.667 | 1.00 | 34.46 | L | O |
| ATOM | 4198 | N | TRP | 147 | 90.699 | -26.498 | 16.048 | 1.00 | 30.86 | L | N |
| ATOM | 4199 | CA | TRP | 147 | 89.777 | -26.878 | 17.102 | 1.00 | 30.91 | L | C |
| ATOM | 4200 | CB | TRP | 147 | 88.947 | -25.687 | 17.556 | 1.00 | 36.68 | L | C |
| ATOM | 4201 | CG | TRP | 147 | 89.689 | -24.788 | 18.432 | 1.00 | 34.29 | L | C |
| ATOM | 4202 | CD2 | TRP | 147 | 89.927 | -24.969 | 19.825 | 1.00 | 32.37 | L | C |
| ATOM | 4203 | CE2 | TRP | 147 | 90.723 | -23.885 | 20.258 | 1.00 | 33.31 | L | C |
| ATOM | 4204 | CE3 | TRP | 147 | 89.552 | -25.943 | 20.752 | 1.00 | 31.13 | L | C |
| ATOM | 4205 | CD1 | TRP | 147 | 90.326 | -23.641 | 18.077 | 1.00 | 36.68 | L | C |
| ATOM | 4206 | NE1 | TRP | 147 | 90.951 | -23.086 | 19.168 | 1.00 | 33.41 | L | N |
| ATOM | 4207 | CZ2 | TRP | 147 | 91.150 | -23.747 | 21.587 | 1.00 | 31.66 | L | C |
| ATOM | 4208 | CZ3 | TRP | 147 | 89.977 | -25.808 | 22.073 | 1.00 | 33.39 | L | C |
| ATOM | 4209 | CH2 | TRP | 147 | 90.767 | -24.716 | 22.476 | 1.00 | 33.58 | L | C |
| ATOM | 4210 | C | TRP | 147 | 88.844 | -27.963 | 16.611 | 1.00 | 33.36 | L | C |
| ATOM | 4211 | O | TRP | 147 | 88.440 | -27.968 | 15.453 | 1.00 | 34.42 | L | O |
| ATOM | 4212 | N | LYS | 148 | 88.495 | -28.877 | 17.501 | 1.00 | 28.86 | L | N |
| ATOM | 4213 | CA | LYS | 148 | 87.609 | -29.958 | 17.147 | 1.00 | 29.96 | L | C |
| ATOM | 4214 | CB | LYS | 148 | 88.431 | -31.196 | 16.787 | 1.00 | 35.94 | L | C |
| ATOM | 4215 | CG | LYS | 148 | 88.353 | -31.585 | 15.320 | 1.00 | 39.31 | L | C |
| ATOM | 4216 | CD | LYS | 148 | 89.726 | -31.865 | 14.715 | 1.00 | 45.24 | L | C |
| ATOM | 4217 | CE | LYS | 148 | 90.421 | -33.078 | 15.337 | 1.00 | 45.54 | L | C |
| ATOM | 4218 | NZ | LYS | 148 | 91.826 | -33.267 | 14.818 | 1.00 | 44.96 | L | N |
| ATOM | 4219 | C | LYS | 148 | 86.712 | -30.227 | 18.340 | 1.00 | 32.40 | L | C |
| ATOM | 4220 | O | LYS | 148 | 87.197 | -30.505 | 19.438 | 1.00 | 31.51 | L | O |
| ATOM | 4221 | N | VAL | 149 | 85.404 | -30.124 | 18.118 | 1.00 | 22.85 | L | N |
| ATOM | 4222 | CA | VAL | 149 | 84.406 | -30.352 | 19.161 | 1.00 | 20.04 | L | C |
| ATOM | 4223 | CB | VAL | 149 | 83.453 | -29.167 | 19.269 | 1.00 | 1.90 | L | C |
| ATOM | 4224 | CG1 | VAL | 149 | 82.408 | -29.440 | 20.364 | 1.00 | 1.90 | L | C |
| ATOM | 4225 | CG2 | VAL | 149 | 84.242 | -27.899 | 19.563 | 1.00 | 1.90 | L | C |
| ATOM | 4226 | C | VAL | 149 | 83.580 | -31.605 | 18.862 | 1.00 | 23.24 | L | C |
| ATOM | 4227 | O | VAL | 149 | 82.835 | -31.642 | 17.883 | 1.00 | 24.43 | L | O |
| ATOM | 4228 | N | ASP | 150 | 83.679 | -32.611 | 19.731 | 1.00 | 18.00 | L | N |
| ATOM | 4229 | CA | ASP | 150 | 82.974 | -33.863 | 19.502 | 1.00 | 21.30 | L | C |
| ATOM | 4230 | CB | ASP | 150 | 81.464 | -33.661 | 19.459 | 1.00 | 45.33 | L | C |
| ATOM | 4231 | CG | ASP | 150 | 80.862 | -33.543 | 20.840 | 1.00 | 50.39 | L | C |
| ATOM | 4232 | OD1 | ASP | 150 | 81.334 | -34.248 | 21.760 | 1.00 | 51.76 | L | O |
| ATOM | 4233 | OD2 | ASP | 150 | 79.910 | -32.756 | 21.007 | 1.00 | 53.67 | L | O |
| ATOM | 4234 | C | ASP | 150 | 83.487 | -34.293 | 18.152 | 1.00 | 22.51 | L | C |

Fig. 19: A-59

| | | | | | | | | | | | |
|---|---|---|---|---|---|---|---|---|---|---|---|
| ATOM | 4235 | O | ASP | 150 | 82.737 | -34.683 | 17.268 | 1.00 | 23.76 | L | O |
| ATOM | 4236 | N | ASN | 151 | 84.800 | -34.161 | 18.007 | 1.00 | 36.79 | L | N |
| ATOM | 4237 | CA | ASN | 151 | 85.493 | -34.524 | 16.789 | 1.00 | 39.62 | L | C |
| ATOM | 4238 | CB | ASN | 151 | 85.425 | -36.041 | 16.614 | 1.00 | 29.22 | L | C |
| ATOM | 4239 | CG | ASN | 151 | 86.220 | -36.776 | 17.683 | 1.00 | 38.58 | L | C |
| ATOM | 4240 | OD1 | ASN | 151 | 87.450 | -36.736 | 17.686 | 1.00 | 42.16 | L | O |
| ATOM | 4241 | ND2 | ASN | 151 | 85.522 | -37.430 | 18.608 | 1.00 | 39.63 | L | N |
| ATOM | 4242 | C | ASN | 151 | 84.985 | -33.778 | 15.557 | 1.00 | 37.90 | L | C |
| ATOM | 4243 | O | ASN | 151 | 85.224 | -34.183 | 14.425 | 1.00 | 41.98 | L | O |
| ATOM | 4244 | N | ALA | 152 | 84.293 | -32.672 | 15.793 | 1.00 | 26.76 | L | N |
| ATOM | 4245 | CA | ALA | 152 | 83.802 | -31.838 | 14.703 | 1.00 | 29.16 | L | C |
| ATOM | 4246 | CB | ALA | 152 | 82.421 | -31.261 | 15.034 | 1.00 | 1.87 | L | C |
| ATOM | 4247 | C | ALA | 152 | 84.801 | -30.698 | 14.501 | 1.00 | 30.47 | L | C |
| ATOM | 4248 | O | ALA | 152 | 84.940 | -29.813 | 15.355 | 1.00 | 32.16 | L | O |
| ATOM | 4249 | N | LEU | 153 | 85.502 | -30.724 | 13.375 | 1.00 | 37.66 | L | N |
| ATOM | 4250 | CA | LEU | 153 | 86.470 | -29.684 | 13.073 | 1.00 | 38.47 | L | C |
| ATOM | 4251 | CB | LEU | 153 | 87.021 | -29.896 | 11.656 | 1.00 | 33.69 | L | C |
| ATOM | 4252 | CG | LEU | 153 | 87.944 | -28.864 | 11.005 | 1.00 | 36.76 | L | C |
| ATOM | 4253 | CD1 | LEU | 153 | 87.112 | -27.705 | 10.466 | 1.00 | 35.54 | L | C |
| ATOM | 4254 | CD2 | LEU | 153 | 88.999 | -28.394 | 12.004 | 1.00 | 35.80 | L | C |
| ATOM | 4255 | C | LEU | 153 | 85.796 | -28.315 | 13.206 | 1.00 | 37.05 | L | C |
| ATOM | 4256 | O | LEU | 153 | 84.632 | -28.150 | 12.870 | 1.00 | 37.53 | L | O |
| ATOM | 4257 | N | GLN | 154 | 86.524 | -27.342 | 13.732 | 1.00 | 42.87 | L | N |
| ATOM | 4258 | CA | GLN | 154 | 85.984 | -26.006 | 13.885 | 1.00 | 41.76 | L | C |
| ATOM | 4259 | CB | GLN | 154 | 86.346 | -25.438 | 15.255 | 1.00 | 24.84 | L | C |
| ATOM | 4260 | CG | GLN | 154 | 85.653 | -26.133 | 16.403 | 1.00 | 25.94 | L | C |
| ATOM | 4261 | CD | GLN | 154 | 84.146 | -26.162 | 16.225 | 1.00 | 28.42 | L | C |
| ATOM | 4262 | OE1 | GLN | 154 | 83.495 | -25.115 | 16.127 | 1.00 | 30.98 | L | O |
| ATOM | 4263 | NE2 | GLN | 154 | 83.584 | -27.365 | 16.176 | 1.00 | 27.76 | L | N |
| ATOM | 4264 | C | GLN | 154 | 86.574 | -25.139 | 12.793 | 1.00 | 40.20 | L | C |
| ATOM | 4265 | O | GLN | 154 | 87.702 | -25.363 | 12.350 | 1.00 | 39.24 | L | O |
| ATOM | 4266 | N | SER | 155 | 85.813 | -24.146 | 12.359 | 1.00 | 42.27 | L | N |
| ATOM | 4267 | CA | SER | 155 | 86.269 | -23.257 | 11.306 | 1.00 | 44.34 | L | C |
| ATOM | 4268 | CB | SER | 155 | 85.770 | -23.768 | 9.952 | 1.00 | 47.84 | L | C |
| ATOM | 4269 | OG | SER | 155 | 86.319 | -23.035 | 8.872 | 1.00 | 49.98 | L | O |
| ATOM | 4270 | C | SER | 155 | 85.693 | -21.888 | 11.600 | 1.00 | 40.94 | L | C |
| ATOM | 4271 | O | SER | 155 | 86.208 | -20.864 | 11.160 | 1.00 | 39.18 | L | O |
| ATOM | 4272 | N | GLY | 156 | 84.621 | -21.877 | 12.374 | 1.00 | 21.85 | L | N |
| ATOM | 4273 | CA | GLY | 156 | 83.986 | -20.619 | 12.702 | 1.00 | 22.33 | L | C |
| ATOM | 4274 | C | GLY | 156 | 84.732 | -19.585 | 13.544 | 1.00 | 22.19 | L | C |
| ATOM | 4275 | O | GLY | 156 | 85.518 | -18.793 | 13.032 | 1.00 | 19.16 | L | O |
| ATOM | 4276 | N | ASN | 157 | 84.484 | -19.595 | 14.850 | 1.00 | 39.06 | L | N |
| ATOM | 4277 | CA | ASN | 157 | 85.088 | -18.595 | 15.697 | 1.00 | 40.50 | L | C |
| ATOM | 4278 | CB | ASN | 157 | 83.992 | -17.700 | 16.281 | 1.00 | 106.22 | L | C |
| ATOM | 4279 | CG | ASN | 157 | 83.201 | -16.977 | 15.200 | 1.00 | 109.22 | L | C |
| ATOM | 4280 | OD1 | ASN | 157 | 83.779 | -16.402 | 14.277 | 1.00 | 109.54 | L | O |
| ATOM | 4281 | ND2 | ASN | 157 | 81.874 | -16.999 | 15.313 | 1.00 | 114.95 | L | N |
| ATOM | 4282 | C | ASN | 157 | 86.059 | -18.997 | 16.790 | 1.00 | 41.01 | L | C |
| ATOM | 4283 | O | ASN | 157 | 85.713 | -19.566 | 17.827 | 1.00 | 40.41 | L | O |
| ATOM | 4284 | N | SER | 158 | 87.299 | -18.635 | 16.520 | 1.00 | 42.44 | L | N |
| ATOM | 4285 | CA | SER | 158 | 88.409 | -18.862 | 17.405 | 1.00 | 35.84 | L | C |
| ATOM | 4286 | CB | SER | 158 | 89.078 | -20.173 | 17.047 | 1.00 | 10.55 | L | C |
| ATOM | 4287 | OG | SER | 158 | 89.643 | -20.069 | 15.757 | 1.00 | 10.12 | L | O |
| ATOM | 4288 | C | SER | 158 | 89.326 | -17.691 | 17.059 | 1.00 | 34.29 | L | C |
| ATOM | 4289 | O | SER | 158 | 89.197 | -17.092 | 15.992 | 1.00 | 32.27 | L | O |
| ATOM | 4290 | N | GLN | 159 | 90.238 | -17.345 | 17.952 | 1.00 | 34.35 | L | N |
| ATOM | 4291 | CA | GLN | 159 | 91.133 | -16.250 | 17.652 | 1.00 | 31.73 | L | C |
| ATOM | 4292 | CB | GLN | 159 | 90.538 | -14.932 | 18.130 | 1.00 | 20.18 | L | C |
| ATOM | 4293 | CG | GLN | 159 | 89.399 | -14.413 | 17.266 | 1.00 | 21.46 | L | C |
| ATOM | 4294 | CD | GLN | 159 | 89.053 | -12.981 | 17.608 | 1.00 | 25.67 | L | C |
| ATOM | 4295 | OE1 | GLN | 159 | 88.796 | -12.658 | 18.762 | 1.00 | 28.88 | L | O |
| ATOM | 4296 | NE2 | GLN | 159 | 89.051 | -12.114 | 16.606 | 1.00 | 25.13 | L | N |
| ATOM | 4297 | C | GLN | 159 | 92.502 | -16.452 | 18.255 | 1.00 | 29.74 | L | C |
| ATOM | 4298 | O | GLN | 159 | 92.647 | -16.711 | 19.449 | 1.00 | 28.24 | L | O |
| ATOM | 4299 | N | GLU | 160 | 93.514 | -16.327 | 17.414 | 1.00 | 31.36 | L | N |
| ATOM | 4300 | CA | GLU | 160 | 94.872 | -16.510 | 17.865 | 1.00 | 24.49 | L | C |
| ATOM | 4301 | CB | GLU | 160 | 95.646 | -17.316 | 16.834 | 1.00 | 58.94 | L | C |
| ATOM | 4302 | CG | GLU | 160 | 94.977 | -18.617 | 16.476 | 1.00 | 59.06 | L | C |
| ATOM | 4303 | CD | GLU | 160 | 95.890 | -19.506 | 15.678 | 1.00 | 67.10 | L | C |
| ATOM | 4304 | OE1 | GLU | 160 | 95.463 | -20.619 | 15.285 | 1.00 | 71.37 | L | O |
| ATOM | 4305 | OE2 | GLU | 160 | 97.043 | -19.078 | 15.452 | 1.00 | 65.02 | L | O |
| ATOM | 4306 | C | GLU | 160 | 95.591 | -15.199 | 18.140 | 1.00 | 20.89 | L | C |
| ATOM | 4307 | O | GLU | 160 | 95.211 | -14.141 | 17.654 | 1.00 | 14.39 | L | O |

Fig. 19: A-60

| | | | | | | | | | | |
|---|---|---|---|---|---|---|---|---|---|---|
| ATOM | 4308 | N | SER | 161 | 96.639 | -15.293 | 18.941 | 1.00 | 19.35 | L | N |
| ATOM | 4309 | CA | SER | 161 | 97.456 | -14.151 | 19.310 | 1.00 | 16.36 | L | C |
| ATOM | 4310 | CB | SER | 161 | 96.953 | -13.486 | 20.597 | 1.00 | 26.12 | L | C |
| ATOM | 4311 | OG | SER | 161 | 97.935 | -12.623 | 21.157 | 1.00 | 26.54 | L | O |
| ATOM | 4312 | C | SER | 161 | 98.811 | -14.751 | 19.556 | 1.00 | 11.36 | L | C |
| ATOM | 4313 | O | SER | 161 | 98.934 | -15.799 | 20.191 | 1.00 | 11.86 | L | O |
| ATOM | 4314 | N | VAL | 162 | 99.833 | -14.086 | 19.053 | 1.00 | 21.19 | L | N |
| ATOM | 4315 | CA | VAL | 162 | 101.170 | -14.592 | 19.215 | 1.00 | 22.81 | L | C |
| ATOM | 4316 | CB | VAL | 162 | 101.764 | -14.965 | 17.832 | 1.00 | 29.37 | L | C |
| ATOM | 4317 | CG1 | VAL | 162 | 101.449 | -13.865 | 16.834 | 1.00 | 33.68 | L | C |
| ATOM | 4318 | CG2 | VAL | 162 | 103.270 | -15.178 | 17.933 | 1.00 | 33.85 | L | C |
| ATOM | 4319 | C | VAL | 162 | 101.997 | -13.524 | 19.877 | 1.00 | 25.31 | L | C |
| ATOM | 4320 | O | VAL | 162 | 101.835 | -12.349 | 19.566 | 1.00 | 32.55 | L | O |
| ATOM | 4321 | N | THR | 163 | 102.861 | -13.928 | 20.805 | 1.00 | 22.97 | L | N |
| ATOM | 4322 | CA | THR | 163 | 103.735 | -12.975 | 21.475 | 1.00 | 21.36 | L | C |
| ATOM | 4323 | CB | THR | 163 | 104.424 | -13.567 | 22.719 | 1.00 | 4.31 | L | C |
| ATOM | 4324 | OG1 | THR | 163 | 105.214 | -14.705 | 22.342 | 1.00 | 10.67 | L | O |
| ATOM | 4325 | CG2 | THR | 163 | 103.411 | -13.966 | 23.748 | 1.00 | 4.70 | L | C |
| ATOM | 4326 | C | THR | 163 | 104.842 | -12.550 | 20.520 | 1.00 | 20.43 | L | C |
| ATOM | 4327 | O | THR | 163 | 104.880 | -12.951 | 19.350 | 1.00 | 20.01 | L | O |
| ATOM | 4328 | N | GLU | 164 | 105.741 | -11.722 | 21.022 | 1.00 | 16.64 | L | N |
| ATOM | 4329 | CA | GLU | 164 | 106.844 | -11.283 | 20.211 | 1.00 | 24.33 | L | C |
| ATOM | 4330 | CB | GLU | 164 | 107.182 | -9.828 | 20.515 | 1.00 | 53.60 | L | C |
| ATOM | 4331 | CG | GLU | 164 | 107.982 | -9.187 | 19.415 | 1.00 | 64.34 | L | C |
| ATOM | 4332 | CD | GLU | 164 | 107.202 | -9.144 | 18.126 | 1.00 | 70.19 | L | C |
| ATOM | 4333 | OE1 | GLU | 164 | 106.337 | -8.252 | 17.994 | 1.00 | 69.97 | L | O |
| ATOM | 4334 | OE2 | GLU | 164 | 107.442 | -10.011 | 17.257 | 1.00 | 73.61 | L | O |
| ATOM | 4335 | C | GLU | 164 | 107.989 | -12.190 | 20.635 | 1.00 | 22.81 | L | C |
| ATOM | 4336 | O | GLU | 164 | 107.990 | -12.697 | 21.765 | 1.00 | 25.48 | L | O |
| ATOM | 4337 | N | GLN | 165 | 108.948 | -12.407 | 19.734 | 1.00 | 26.35 | L | N |
| ATOM | 4338 | CA | GLN | 165 | 110.100 | -13.261 | 20.018 | 1.00 | 31.24 | L | C |
| ATOM | 4339 | CB | GLN | 165 | 111.181 | -13.024 | 18.967 | 1.00 | 24.53 | L | C |
| ATOM | 4340 | CG | GLN | 165 | 111.927 | -14.274 | 18.584 | 1.00 | 20.02 | L | C |
| ATOM | 4341 | CD | GLN | 165 | 112.911 | -14.054 | 17.454 | 1.00 | 22.62 | L | C |
| ATOM | 4342 | OE1 | GLN | 165 | 113.487 | -15.005 | 16.930 | 1.00 | 23.83 | L | O |
| ATOM | 4343 | NE2 | GLN | 165 | 113.118 | -12.794 | 17.080 | 1.00 | 19.11 | L | N |
| ATOM | 4344 | C | GLN | 165 | 110.633 | -12.941 | 21.412 | 1.00 | 35.11 | L | C |
| ATOM | 4345 | O | GLN | 165 | 110.857 | -11.783 | 21.739 | 1.00 | 31.98 | L | O |
| ATOM | 4346 | N | ASP | 166 | 110.826 | -13.963 | 22.236 | 1.00 | 20.85 | L | N |
| ATOM | 4347 | CA | ASP | 166 | 111.311 | -13.741 | 23.592 | 1.00 | 27.22 | L | C |
| ATOM | 4348 | CB | ASP | 166 | 111.206 | -15.030 | 24.402 | 1.00 | 40.40 | L | C |
| ATOM | 4349 | CG | ASP | 166 | 111.513 | -14.813 | 25.872 | 1.00 | 48.39 | L | C |
| ATOM | 4350 | OD1 | ASP | 166 | 112.706 | -14.808 | 26.246 | 1.00 | 51.89 | L | O |
| ATOM | 4351 | OD2 | ASP | 166 | 110.555 | -14.631 | 26.655 | 1.00 | 52.06 | L | O |
| ATOM | 4352 | C | ASP | 166 | 112.741 | -13.205 | 23.656 | 1.00 | 29.80 | L | C |
| ATOM | 4353 | O | ASP | 166 | 113.659 | -13.787 | 23.079 | 1.00 | 33.62 | L | O |
| ATOM | 4354 | N | SER | 167 | 112.923 | -12.098 | 24.371 | 1.00 | 40.62 | L | N |
| ATOM | 4355 | CA | SER | 167 | 114.238 | -11.463 | 24.521 | 1.00 | 38.35 | L | C |
| ATOM | 4356 | CB | SER | 167 | 114.089 | -10.092 | 25.191 | 1.00 | 42.38 | L | C |
| ATOM | 4357 | OG | SER | 167 | 113.564 | -10.221 | 26.499 | 1.00 | 53.10 | L | O |
| ATOM | 4358 | C | SER | 167 | 115.229 | -12.312 | 25.325 | 1.00 | 40.21 | L | C |
| ATOM | 4359 | O | SER | 167 | 116.373 | -11.913 | 25.544 | 1.00 | 45.86 | L | O |
| ATOM | 4360 | N | LYS | 168 | 114.777 | -13.475 | 25.782 | 1.00 | 39.00 | L | N |
| ATOM | 4361 | CA | LYS | 168 | 115.637 | -14.383 | 26.527 | 1.00 | 40.59 | L | C |
| ATOM | 4362 | CB | LYS | 168 | 114.968 | -14.809 | 27.837 | 1.00 | 73.78 | L | C |
| ATOM | 4363 | CG | LYS | 168 | 115.002 | -13.726 | 28.916 | 1.00 | 80.02 | L | C |
| ATOM | 4364 | CD | LYS | 168 | 114.141 | -12.523 | 28.554 | 1.00 | 89.23 | L | C |
| ATOM | 4365 | CE | LYS | 168 | 112.663 | -12.805 | 28.778 | 1.00 | 96.32 | L | C |
| ATOM | 4366 | NZ | LYS | 168 | 112.355 | -13.017 | 30.222 | 1.00 | 95.77 | L | N |
| ATOM | 4367 | C | LYS | 168 | 115.959 | -15.597 | 25.650 | 1.00 | 39.39 | L | C |
| ATOM | 4368 | O | LYS | 168 | 117.046 | -15.671 | 25.077 | 1.00 | 43.53 | L | O |
| ATOM | 4369 | N | ASP | 169 | 115.011 | -16.522 | 25.506 | 1.00 | 18.93 | L | N |
| ATOM | 4370 | CA | ASP | 169 | 115.240 | -17.716 | 24.686 | 1.00 | 15.08 | L | C |
| ATOM | 4371 | CB | ASP | 169 | 114.476 | -18.913 | 25.262 | 1.00 | 29.81 | L | C |
| ATOM | 4372 | CG | ASP | 169 | 112.992 | -18.648 | 25.407 | 1.00 | 32.60 | L | C |
| ATOM | 4373 | OD1 | ASP | 169 | 112.397 | -18.049 | 24.488 | 1.00 | 27.93 | L | O |
| ATOM | 4374 | OD2 | ASP | 169 | 112.415 | -19.054 | 26.441 | 1.00 | 29.85 | L | O |
| ATOM | 4375 | C | ASP | 169 | 114.914 | -17.596 | 23.193 | 1.00 | 15.61 | L | C |
| ATOM | 4376 | O | ASP | 169 | 115.038 | -18.571 | 22.459 | 1.00 | 9.73 | L | O |
| ATOM | 4377 | N | SER | 170 | 114.490 | -16.418 | 22.747 | 1.00 | 28.98 | L | N |
| ATOM | 4378 | CA | SER | 170 | 114.170 | -16.202 | 21.331 | 1.00 | 26.94 | L | C |
| ATOM | 4379 | CB | SER | 170 | 115.401 | -16.487 | 20.433 | 1.00 | 15.64 | L | C |
| ATOM | 4380 | OG | SER | 170 | 116.466 | -15.560 | 20.636 | 1.00 | 17.90 | L | O |

Fig. 19: A-61

| | | | | | | | | | | | |
|---|---|---|---|---|---|---|---|---|---|---|---|
| ATOM | 4381 | C | SER | 170 | 112.995 | -17.042 | 20.825 | 1.00 | 25.42 | L | C |
| ATOM | 4382 | O | SER | 170 | 112.916 | -17.345 | 19.636 | 1.00 | 25.18 | L | O |
| ATOM | 4383 | N | THR | 171 | 112.071 | -17.411 | 21.702 | 1.00 | 22.07 | L | N |
| ATOM | 4384 | CA | THR | 171 | 110.946 | -18.222 | 21.247 | 1.00 | 22.16 | L | C |
| ATOM | 4385 | CB | THR | 171 | 110.658 | -19.406 | 22.212 | 1.00 | 16.53 | L | C |
| ATOM | 4386 | OG1 | THR | 171 | 110.127 | -18.911 | 23.452 | 1.00 | 18.93 | L | O |
| ATOM | 4387 | CG2 | THR | 171 | 111.939 | -20.191 | 22.471 | 1.00 | 18.13 | L | C |
| ATOM | 4388 | C | THR | 171 | 109.657 | -17.437 | 21.064 | 1.00 | 26.03 | L | C |
| ATOM | 4389 | O | THR | 171 | 109.601 | -16.235 | 21.327 | 1.00 | 31.48 | L | O |
| ATOM | 4390 | N | TYR | 172 | 108.633 | -18.147 | 20.596 | 1.00 | 7.82 | L | N |
| ATOM | 4391 | CA | TYR | 172 | 107.297 | -17.600 | 20.373 | 1.00 | 6.45 | L | C |
| ATOM | 4392 | CB | TYR | 172 | 106.934 | -17.706 | 18.894 | 1.00 | 43.65 | L | C |
| ATOM | 4393 | CG | TYR | 172 | 107.809 | -16.890 | 17.974 | 1.00 | 37.38 | L | C |
| ATOM | 4394 | CD1 | TYR | 172 | 107.652 | -15.507 | 17.865 | 1.00 | 32.97 | L | C |
| ATOM | 4395 | CE1 | TYR | 172 | 108.438 | -14.759 | 16.977 | 1.00 | 32.97 | L | C |
| ATOM | 4396 | CD2 | TYR | 172 | 108.776 | -17.508 | 17.181 | 1.00 | 37.97 | L | C |
| ATOM | 4397 | CE2 | TYR | 172 | 109.565 | -16.774 | 16.296 | 1.00 | 34.76 | L | C |
| ATOM | 4398 | CZ | TYR | 172 | 109.391 | -15.405 | 16.194 | 1.00 | 32.97 | L | C |
| ATOM | 4399 | OH | TYR | 172 | 110.163 | -14.703 | 15.294 | 1.00 | 32.97 | L | O |
| ATOM | 4400 | C | TYR | 172 | 106.255 | -18.364 | 21.212 | 1.00 | 6.45 | L | C |
| ATOM | 4401 | O | TYR | 172 | 106.431 | -19.539 | 21.528 | 1.00 | 9.78 | L | O |
| ATOM | 4402 | N | SER | 173 | 105.183 | -17.687 | 21.600 | 1.00 | 23.67 | L | N |
| ATOM | 4403 | CA | SER | 173 | 104.123 | -18.323 | 22.370 | 1.00 | 25.48 | L | C |
| ATOM | 4404 | CB | SER | 173 | 104.165 | -17.902 | 23.834 | 1.00 | 31.18 | L | C |
| ATOM | 4405 | OG | SER | 173 | 105.281 | -18.492 | 24.468 | 1.00 | 25.15 | L | O |
| ATOM | 4406 | C | SER | 173 | 102.836 | -17.886 | 21.728 | 1.00 | 26.94 | L | C |
| ATOM | 4407 | O | SER | 173 | 102.611 | -16.699 | 21.473 | 1.00 | 27.36 | L | O |
| ATOM | 4408 | N | LEU | 174 | 101.980 | -18.857 | 21.474 | 1.00 | 22.39 | L | N |
| ATOM | 4409 | CA | LEU | 174 | 100.734 | -18.593 | 20.791 | 1.00 | 25.49 | L | C |
| ATOM | 4410 | CB | LEU | 174 | 100.836 | -19.238 | 19.399 | 1.00 | 22.33 | L | C |
| ATOM | 4411 | CG | LEU | 174 | 99.682 | -19.165 | 18.422 | 1.00 | 13.39 | L | C |
| ATOM | 4412 | CD1 | LEU | 174 | 100.207 | -19.296 | 17.013 | 1.00 | 17.21 | L | C |
| ATOM | 4413 | CD2 | LEU | 174 | 98.663 | -20.257 | 18.769 | 1.00 | 10.23 | L | C |
| ATOM | 4414 | C | LEU | 174 | 99.510 | -19.075 | 21.562 | 1.00 | 27.64 | L | C |
| ATOM | 4415 | O | LEU | 174 | 99.542 | -20.111 | 22.229 | 1.00 | 30.82 | L | O |
| ATOM | 4416 | N | SER | 175 | 98.433 | -18.306 | 21.470 | 1.00 | 22.56 | L | N |
| ATOM | 4417 | CA | SER | 175 | 97.200 | -18.651 | 22.162 | 1.00 | 25.61 | L | C |
| ATOM | 4418 | CB | SER | 175 | 96.913 | -17.644 | 23.292 | 1.00 | 28.99 | L | C |
| ATOM | 4419 | OG | SER | 175 | 96.487 | -16.378 | 22.794 | 1.00 | 32.45 | L | O |
| ATOM | 4420 | C | SER | 175 | 96.009 | -18.693 | 21.214 | 1.00 | 29.48 | L | C |
| ATOM | 4421 | O | SER | 175 | 95.733 | -17.718 | 20.511 | 1.00 | 30.81 | L | O |
| ATOM | 4422 | N | SER | 176 | 95.316 | -19.829 | 21.181 | 1.00 | 31.99 | L | N |
| ATOM | 4423 | CA | SER | 176 | 94.125 | -19.957 | 20.346 | 1.00 | 32.77 | L | C |
| ATOM | 4424 | CB | SER | 176 | 94.154 | -21.247 | 19.514 | 1.00 | 10.71 | L | C |
| ATOM | 4425 | OG | SER | 176 | 93.247 | -21.176 | 18.421 | 1.00 | 10.34 | L | O |
| ATOM | 4426 | C | SER | 176 | 92.985 | -19.991 | 21.352 | 1.00 | 29.41 | L | C |
| ATOM | 4427 | O | SER | 176 | 93.042 | -20.712 | 22.350 | 1.00 | 29.56 | L | O |
| ATOM | 4428 | N | THR | 177 | 91.963 | -19.183 | 21.118 | 1.00 | 38.41 | L | N |
| ATOM | 4429 | CA | THR | 177 | 90.846 | -19.136 | 22.042 | 1.00 | 37.60 | L | C |
| ATOM | 4430 | CB | THR | 177 | 90.742 | -17.741 | 22.706 | 1.00 | 7.23 | L | C |
| ATOM | 4431 | OG1 | THR | 177 | 92.000 | -17.399 | 23.318 | 1.00 | 10.12 | L | O |
| ATOM | 4432 | CG2 | THR | 177 | 89.631 | -17.728 | 23.773 | 1.00 | 2.94 | L | C |
| ATOM | 4433 | C | THR | 177 | 89.551 | -19.455 | 21.311 | 1.00 | 35.94 | L | C |
| ATOM | 4434 | O | THR | 177 | 89.133 | -18.709 | 20.425 | 1.00 | 37.02 | L | O |
| ATOM | 4435 | N | LEU | 178 | 88.941 | -20.584 | 21.669 | 1.00 | 33.89 | L | N |
| ATOM | 4436 | CA | LEU | 178 | 87.682 | -21.015 | 21.072 | 1.00 | 32.44 | L | C |
| ATOM | 4437 | CB | LEU | 178 | 87.587 | -22.542 | 21.069 | 1.00 | 26.21 | L | C |
| ATOM | 4438 | CG | LEU | 178 | 86.291 | -23.170 | 20.539 | 1.00 | 27.24 | L | C |
| ATOM | 4439 | CD1 | LEU | 178 | 86.077 | -22.824 | 19.070 | 1.00 | 27.77 | L | C |
| ATOM | 4440 | CD2 | LEU | 178 | 86.367 | -24.683 | 20.730 | 1.00 | 15.35 | L | C |
| ATOM | 4441 | C | LEU | 178 | 86.552 | -20.412 | 21.901 | 1.00 | 32.70 | L | C |
| ATOM | 4442 | O | LEU | 178 | 86.476 | -20.589 | 23.120 | 1.00 | 29.14 | L | O |
| ATOM | 4443 | N | THR | 179 | 85.669 | -19.683 | 21.244 | 1.00 | 21.74 | L | N |
| ATOM | 4444 | CA | THR | 179 | 84.598 | -19.059 | 21.983 | 1.00 | 27.65 | L | C |
| ATOM | 4445 | CB | THR | 179 | 84.804 | -17.547 | 22.031 | 1.00 | 33.66 | L | C |
| ATOM | 4446 | OG1 | THR | 179 | 83.651 | -16.929 | 22.608 | 1.00 | 34.46 | L | O |
| ATOM | 4447 | CG2 | THR | 179 | 85.056 | -17.005 | 20.633 | 1.00 | 33.07 | L | C |
| ATOM | 4448 | C | THR | 179 | 83.223 | -19.377 | 21.430 | 1.00 | 32.00 | L | C |
| ATOM | 4449 | O | THR | 179 | 82.928 | -19.104 | 20.271 | 1.00 | 32.92 | L | O |
| ATOM | 4450 | N | LEU | 180 | 82.398 | -19.981 | 22.278 | 1.00 | 32.07 | L | N |
| ATOM | 4451 | CA | LEU | 180 | 81.035 | -20.349 | 21.922 | 1.00 | 33.73 | L | C |
| ATOM | 4452 | CB | LEU | 180 | 80.936 | -21.831 | 21.528 | 1.00 | 30.85 | L | C |
| ATOM | 4453 | CG | LEU | 180 | 82.059 | -22.804 | 21.881 | 1.00 | 33.56 | L | C |

Fig. 19: A-62

| | | | | | | | | | | | |
|---|---|---|---|---|---|---|---|---|---|---|---|
| ATOM | 4454 | CD1 | LEU | 180 | 82.518 | -22.589 | 23.309 | 1.00 | 36.03 | L | C |
| ATOM | 4455 | CD2 | LEU | 180 | 81.552 | -24.220 | 21.697 | 1.00 | 34.15 | L | C |
| ATOM | 4456 | C | LEU | 180 | 80.093 | -20.062 | 23.084 | 1.00 | 37.58 | L | C |
| ATOM | 4457 | O | LEU | 180 | 80.526 | -19.899 | 24.229 | 1.00 | 37.41 | L | O |
| ATOM | 4458 | N | SER | 181 | 78.801 | -20.000 | 22.772 | 1.00 | 28.10 | L | N |
| ATOM | 4459 | CA | SER | 181 | 77.778 | -19.711 | 23.770 | 1.00 | 31.26 | L | C |
| ATOM | 4460 | CB | SER | 181 | 76.433 | -19.537 | 23.087 | 1.00 | 22.13 | L | C |
| ATOM | 4461 | OG | SER | 181 | 76.019 | -20.764 | 22.513 | 1.00 | 25.39 | L | O |
| ATOM | 4462 | C | SER | 181 | 77.655 | -20.802 | 24.815 | 1.00 | 33.74 | L | C |
| ATOM | 4463 | O | SER | 181 | 77.917 | -21.978 | 24.533 | 1.00 | 33.98 | L | O |
| ATOM | 4464 | N | LYS | 182 | 77.247 | -20.402 | 26.019 | 1.00 | 29.35 | L | N |
| ATOM | 4465 | CA | LYS | 182 | 77.060 | -21.339 | 27.120 | 1.00 | 30.58 | L | C |
| ATOM | 4466 | CB | LYS | 182 | 76.375 | -20.647 | 28.307 | 1.00 | 27.86 | L | C |
| ATOM | 4467 | CG | LYS | 182 | 76.341 | -21.446 | 29.627 | 1.00 | 29.57 | L | C |
| ATOM | 4468 | CD | LYS | 182 | 74.912 | -21.752 | 30.107 | 1.00 | 31.50 | L | C |
| ATOM | 4469 | CE | LYS | 182 | 74.863 | -22.027 | 31.619 | 1.00 | 34.15 | L | C |
| ATOM | 4470 | NZ | LYS | 182 | 73.622 | -22.756 | 32.099 | 1.00 | 38.40 | L | N |
| ATOM | 4471 | C | LYS | 182 | 76.167 | -22.438 | 26.573 | 1.00 | 28.49 | L | C |
| ATOM | 4472 | O | LYS | 182 | 76.358 | -23.618 | 26.878 | 1.00 | 20.36 | L | O |
| ATOM | 4473 | N | ALA | 183 | 75.206 | -22.030 | 25.743 | 1.00 | 42.67 | L | N |
| ATOM | 4474 | CA | ALA | 183 | 74.252 | -22.937 | 25.108 | 1.00 | 43.14 | L | C |
| ATOM | 4475 | CB | ALA | 183 | 73.319 | -22.150 | 24.203 | 1.00 | 20.20 | L | C |
| ATOM | 4476 | C | ALA | 183 | 74.929 | -24.053 | 24.313 | 1.00 | 42.26 | L | C |
| ATOM | 4477 | O | ALA | 183 | 74.645 | -25.229 | 24.531 | 1.00 | 43.50 | L | O |
| ATOM | 4478 | N | ASP | 184 | 75.820 | -23.691 | 23.395 | 1.00 | 37.65 | L | N |
| ATOM | 4479 | CA | ASP | 184 | 76.523 | -24.692 | 22.587 | 1.00 | 39.98 | L | C |
| ATOM | 4480 | CB | ASP | 184 | 77.271 | -24.023 | 21.434 | 1.00 | 60.24 | L | C |
| ATOM | 4481 | CG | ASP | 184 | 76.362 | -23.219 | 20.545 | 1.00 | 66.97 | L | C |
| ATOM | 4482 | OD1 | ASP | 184 | 75.360 | -23.784 | 20.055 | 1.00 | 70.29 | L | O |
| ATOM | 4483 | OD2 | ASP | 184 | 76.653 | -22.023 | 20.335 | 1.00 | 70.50 | L | O |
| ATOM | 4484 | C | ASP | 184 | 77.519 | -25.525 | 23.395 | 1.00 | 38.91 | L | C |
| ATOM | 4485 | O | ASP | 184 | 77.531 | -26.753 | 23.308 | 1.00 | 36.50 | L | O |
| ATOM | 4486 | N | TYR | 185 | 78.362 | -24.849 | 24.167 | 1.00 | 50.74 | L | N |
| ATOM | 4487 | CA | TYR | 185 | 79.352 | -25.544 | 24.972 | 1.00 | 51.74 | L | C |
| ATOM | 4488 | CB | TYR | 185 | 80.011 | -24.589 | 25.965 | 1.00 | 23.76 | L | C |
| ATOM | 4489 | CG | TYR | 185 | 81.104 | -25.256 | 26.771 | 1.00 | 21.08 | L | C |
| ATOM | 4490 | CD1 | TYR | 185 | 82.328 | -25.552 | 26.192 | 1.00 | 16.43 | L | C |
| ATOM | 4491 | CE1 | TYR | 185 | 83.332 | -26.186 | 26.915 | 1.00 | 15.99 | L | C |
| ATOM | 4492 | CD2 | TYR | 185 | 80.905 | -25.613 | 28.104 | 1.00 | 17.64 | L | C |
| ATOM | 4493 | CE2 | TYR | 185 | 81.902 | -26.244 | 28.839 | 1.00 | 14.97 | L | C |
| ATOM | 4494 | CZ | TYR | 185 | 83.118 | -26.526 | 28.235 | 1.00 | 14.93 | L | C |
| ATOM | 4495 | OH | TYR | 185 | 84.141 | -27.119 | 28.944 | 1.00 | 16.56 | L | O |
| ATOM | 4496 | C | TYR | 185 | 78.729 | -26.695 | 25.756 | 1.00 | 52.88 | L | C |
| ATOM | 4497 | O | TYR | 185 | 79.364 | -27.728 | 25.978 | 1.00 | 52.42 | L | O |
| ATOM | 4498 | N | GLU | 186 | 77.484 | -26.505 | 26.177 | 1.00 | 52.93 | L | N |
| ATOM | 4499 | CA | GLU | 186 | 76.787 | -27.509 | 26.965 | 1.00 | 54.71 | L | C |
| ATOM | 4500 | CB | GLU | 186 | 75.643 | -26.870 | 27.748 | 1.00 | 28.62 | L | C |
| ATOM | 4501 | CG | GLU | 186 | 76.067 | -26.060 | 28.955 | 1.00 | 35.11 | L | C |
| ATOM | 4502 | CD | GLU | 186 | 74.876 | -25.493 | 29.702 | 1.00 | 38.66 | L | C |
| ATOM | 4503 | OE1 | GLU | 186 | 75.089 | -24.850 | 30.746 | 1.00 | 41.21 | L | O |
| ATOM | 4504 | OE2 | GLU | 186 | 73.725 | -25.689 | 29.245 | 1.00 | 36.89 | L | O |
| ATOM | 4505 | C | GLU | 186 | 76.242 | -28.694 | 26.190 | 1.00 | 52.40 | L | C |
| ATOM | 4506 | O | GLU | 186 | 76.029 | -29.755 | 26.769 | 1.00 | 48.88 | L | O |
| ATOM | 4507 | N | LYS | 187 | 76.004 | -28.538 | 24.895 | 1.00 | 35.74 | L | N |
| ATOM | 4508 | CA | LYS | 187 | 75.472 | -29.662 | 24.147 | 1.00 | 37.64 | L | C |
| ATOM | 4509 | CB | LYS | 187 | 74.507 | -29.173 | 23.057 | 1.00 | 53.22 | L | C |
| ATOM | 4510 | CG | LYS | 187 | 75.138 | -28.512 | 21.849 | 1.00 | 54.27 | L | C |
| ATOM | 4511 | CD | LYS | 187 | 74.055 | -27.941 | 20.930 | 1.00 | 53.80 | L | C |
| ATOM | 4512 | CE | LYS | 187 | 74.665 | -27.203 | 19.740 | 1.00 | 49.76 | L | C |
| ATOM | 4513 | NZ | LYS | 187 | 73.707 | -26.272 | 19.069 | 1.00 | 48.24 | L | N |
| ATOM | 4514 | C | LYS | 187 | 76.568 | -30.553 | 23.549 | 1.00 | 36.73 | L | C |
| ATOM | 4515 | O | LYS | 187 | 76.287 | -31.436 | 22.732 | 1.00 | 37.96 | L | O |
| ATOM | 4516 | N | HIS | 188 | 77.813 | -30.339 | 23.972 | 1.00 | 23.77 | L | N |
| ATOM | 4517 | CA | HIS | 188 | 78.934 | -31.124 | 23.468 | 1.00 | 21.36 | L | C |
| ATOM | 4518 | CB | HIS | 188 | 79.811 | -30.257 | 22.562 | 1.00 | 41.13 | L | C |
| ATOM | 4519 | CG | HIS | 188 | 79.099 | -29.774 | 21.338 | 1.00 | 42.53 | L | C |
| ATOM | 4520 | CD2 | HIS | 188 | 78.800 | -28.524 | 20.913 | 1.00 | 44.25 | L | C |
| ATOM | 4521 | ND1 | HIS | 188 | 78.562 | -30.633 | 20.405 | 1.00 | 41.45 | L | N |
| ATOM | 4522 | CE1 | HIS | 188 | 77.961 | -29.935 | 19.458 | 1.00 | 45.45 | L | C |
| ATOM | 4523 | NE2 | HIS | 188 | 78.090 | -28.652 | 19.743 | 1.00 | 43.75 | L | N |
| ATOM | 4524 | C | HIS | 188 | 79.743 | -31.715 | 24.610 | 1.00 | 19.53 | L | C |
| ATOM | 4525 | O | HIS | 188 | 79.648 | -31.253 | 25.751 | 1.00 | 19.70 | L | O |
| ATOM | 4526 | N | LYS | 189 | 80.521 | -32.747 | 24.294 | 1.00 | 33.83 | L | N |

Fig. 19: A-63

| | | | | | | | | | | | |
|---|---|---|---|---|---|---|---|---|---|---|---|
| ATOM | 4527 | CA | LYS | 189 | 81.334 | -33.445 | 25.281 | 1.00 | 33.86 | L | C |
| ATOM | 4528 | CB | LYS | 189 | 81.136 | -34.957 | 25.152 | 1.00 | 43.10 | L | C |
| ATOM | 4529 | CG | LYS | 189 | 79.898 | -35.516 | 25.815 | 1.00 | 47.03 | L | C |
| ATOM | 4530 | CD | LYS | 189 | 79.974 | -37.041 | 25.887 | 1.00 | 53.76 | L | C |
| ATOM | 4531 | CE | LYS | 189 | 79.997 | -37.680 | 24.505 | 1.00 | 59.30 | L | C |
| ATOM | 4532 | NZ | LYS | 189 | 78.694 | -37.545 | 23.794 | 1.00 | 59.64 | L | N |
| ATOM | 4533 | C | LYS | 189 | 82.831 | -33.155 | 25.201 | 1.00 | 33.18 | L | C |
| ATOM | 4534 | O | LYS | 189 | 83.435 | -32.657 | 26.155 | 1.00 | 36.85 | L | O |
| ATOM | 4535 | N | VAL | 190 | 83.435 | -33.482 | 24.069 | 1.00 | 39.67 | L | N |
| ATOM | 4536 | CA | VAL | 190 | 84.860 | -33.260 | 23.916 | 1.00 | 35.33 | L | C |
| ATOM | 4537 | CB | VAL | 190 | 85.516 | -34.439 | 23.214 | 1.00 | 33.71 | L | C |
| ATOM | 4538 | CG1 | VAL | 190 | 85.356 | -35.648 | 24.059 | 1.00 | 26.86 | L | C |
| ATOM | 4539 | CG2 | VAL | 190 | 84.880 | -34.657 | 21.855 | 1.00 | 36.79 | L | C |
| ATOM | 4540 | C | VAL | 190 | 85.249 | -31.992 | 23.170 | 1.00 | 35.17 | L | C |
| ATOM | 4541 | O | VAL | 190 | 84.656 | -31.641 | 22.141 | 1.00 | 36.62 | L | O |
| ATOM | 4542 | N | TYR | 191 | 86.256 | -31.319 | 23.718 | 1.00 | 27.65 | L | N |
| ATOM | 4543 | CA | TYR | 191 | 86.811 | -30.105 | 23.152 | 1.00 | 26.85 | L | C |
| ATOM | 4544 | CB | TYR | 191 | 86.554 | -28.934 | 24.095 | 1.00 | 16.61 | L | C |
| ATOM | 4545 | CG | TYR | 191 | 85.109 | -28.475 | 24.056 | 1.00 | 23.44 | L | C |
| ATOM | 4546 | CD1 | TYR | 191 | 84.654 | -27.650 | 23.030 | 1.00 | 27.57 | L | C |
| ATOM | 4547 | CE1 | TYR | 191 | 83.322 | -27.300 | 22.929 | 1.00 | 29.06 | L | C |
| ATOM | 4548 | CD2 | TYR | 191 | 84.178 | -28.937 | 24.991 | 1.00 | 24.37 | L | C |
| ATOM | 4549 | CE2 | TYR | 191 | 82.838 | -28.592 | 24.894 | 1.00 | 25.88 | L | C |
| ATOM | 4550 | CZ | TYR | 191 | 82.419 | -27.773 | 23.859 | 1.00 | 28.22 | L | C |
| ATOM | 4551 | OH | TYR | 191 | 81.097 | -27.419 | 23.745 | 1.00 | 30.91 | L | O |
| ATOM | 4552 | C | TYR | 191 | 88.295 | -30.381 | 23.010 | 1.00 | 28.07 | L | C |
| ATOM | 4553 | O | TYR | 191 | 88.946 | -30.821 | 23.960 | 1.00 | 29.13 | L | O |
| ATOM | 4554 | N | ALA | 192 | 88.837 | -30.159 | 21.822 | 1.00 | 17.93 | L | N |
| ATOM | 4555 | CA | ALA | 192 | 90.246 | -30.425 | 21.621 | 1.00 | 13.94 | L | C |
| ATOM | 4556 | CB | ALA | 192 | 90.424 | -31.850 | 21.160 | 1.00 | 12.32 | L | C |
| ATOM | 4557 | C | ALA | 192 | 90.921 | -29.489 | 20.640 | 1.00 | 14.27 | L | C |
| ATOM | 4558 | O | ALA | 192 | 90.271 | -28.885 | 19.784 | 1.00 | 14.89 | L | O |
| ATOM | 4559 | N | CYS | 193 | 92.234 | -29.362 | 20.787 | 1.00 | 20.91 | L | N |
| ATOM | 4560 | CA | CYS | 193 | 93.015 | -28.544 | 19.883 | 1.00 | 19.50 | L | C |
| ATOM | 4561 | C | CYS | 193 | 94.268 | -29.301 | 19.502 | 1.00 | 17.29 | L | C |
| ATOM | 4562 | O | CYS | 193 | 95.057 | -29.729 | 20.352 | 1.00 | 15.43 | L | O |
| ATOM | 4563 | CB | CYS | 193 | 93.361 | -27.183 | 20.490 | 1.00 | 44.80 | L | C |
| ATOM | 4564 | SG | CYS | 193 | 94.412 | -27.194 | 21.962 | 1.00 | 52.58 | L | S |
| ATOM | 4565 | N | GLU | 194 | 94.411 | -29.480 | 18.195 | 1.00 | 24.90 | L | N |
| ATOM | 4566 | CA | GLU | 194 | 95.522 | -30.193 | 17.600 | 1.00 | 25.90 | L | C |
| ATOM | 4567 | CB | GLU | 194 | 95.004 | -30.956 | 16.384 | 1.00 | 66.26 | L | C |
| ATOM | 4568 | CG | GLU | 194 | 95.979 | -31.887 | 15.718 | 1.00 | 77.97 | L | C |
| ATOM | 4569 | CD | GLU | 194 | 95.392 | -32.479 | 14.461 | 1.00 | 83.25 | L | C |
| ATOM | 4570 | OE1 | GLU | 194 | 95.276 | -31.738 | 13.462 | 1.00 | 80.00 | L | O |
| ATOM | 4571 | OE2 | GLU | 194 | 95.028 | -33.674 | 14.477 | 1.00 | 89.05 | L | O |
| ATOM | 4572 | C | GLU | 194 | 96.546 | -29.158 | 17.175 | 1.00 | 25.27 | L | C |
| ATOM | 4573 | O | GLU | 194 | 96.204 | -28.171 | 16.538 | 1.00 | 23.30 | L | O |
| ATOM | 4574 | N | VAL | 195 | 97.798 | -29.373 | 17.537 | 1.00 | 38.95 | L | N |
| ATOM | 4575 | CA | VAL | 195 | 98.850 | -28.443 | 17.168 | 1.00 | 34.83 | L | C |
| ATOM | 4576 | CB | VAL | 195 | 99.715 | -28.048 | 18.403 | 1.00 | 15.18 | L | C |
| ATOM | 4577 | CG1 | VAL | 195 | 100.911 | -27.210 | 17.971 | 1.00 | 11.26 | L | C |
| ATOM | 4578 | CG2 | VAL | 195 | 98.869 | -27.268 | 19.395 | 1.00 | 16.15 | L | C |
| ATOM | 4579 | C | VAL | 195 | 99.730 | -29.115 | 16.126 | 1.00 | 34.14 | L | C |
| ATOM | 4580 | O | VAL | 195 | 99.964 | -30.319 | 16.180 | 1.00 | 32.63 | L | O |
| ATOM | 4581 | N | THR | 196 | 100.190 | -28.340 | 15.157 | 1.00 | 43.12 | L | N |
| ATOM | 4582 | CA | THR | 196 | 101.063 | -28.876 | 14.135 | 1.00 | 42.44 | L | C |
| ATOM | 4583 | CB | THR | 196 | 100.411 | -28.867 | 12.764 | 1.00 | 26.65 | L | C |
| ATOM | 4584 | OG1 | THR | 196 | 99.001 | -28.673 | 12.909 | 1.00 | 36.35 | L | O |
| ATOM | 4585 | CG2 | THR | 196 | 100.671 | -30.180 | 12.067 | 1.00 | 28.65 | L | C |
| ATOM | 4586 | C | THR | 196 | 102.233 | -27.927 | 14.121 | 1.00 | 42.04 | L | C |
| ATOM | 4587 | O | THR | 196 | 102.049 | -26.710 | 14.053 | 1.00 | 37.83 | L | O |
| ATOM | 4588 | N | HIS | 197 | 103.437 | -28.479 | 14.186 | 1.00 | 32.41 | L | N |
| ATOM | 4589 | CA | HIS | 197 | 104.623 | -27.653 | 14.217 | 1.00 | 27.77 | L | C |
| ATOM | 4590 | CB | HIS | 197 | 104.867 | -27.172 | 15.651 | 1.00 | 21.71 | L | C |
| ATOM | 4591 | CG | HIS | 197 | 105.914 | -26.113 | 15.762 | 1.00 | 23.27 | L | C |
| ATOM | 4592 | CD2 | HIS | 197 | 105.817 | -24.761 | 15.753 | 1.00 | 17.64 | L | C |
| ATOM | 4593 | ND1 | HIS | 197 | 107.257 | -26.402 | 15.868 | 1.00 | 25.39 | L | N |
| ATOM | 4594 | CE1 | HIS | 197 | 107.944 | -25.274 | 15.923 | 1.00 | 22.67 | L | C |
| ATOM | 4595 | NE2 | HIS | 197 | 107.093 | -24.264 | 15.854 | 1.00 | 24.76 | L | N |
| ATOM | 4596 | C | HIS | 197 | 105.825 | -28.417 | 13.708 | 1.00 | 24.98 | L | C |
| ATOM | 4597 | O | HIS | 197 | 105.932 | -29.629 | 13.885 | 1.00 | 29.24 | L | O |
| ATOM | 4598 | N | GLN | 198 | 106.728 | -27.687 | 13.070 | 1.00 | 28.46 | L | N |
| ATOM | 4599 | CA | GLN | 198 | 107.944 | -28.252 | 12.515 | 1.00 | 26.49 | L | C |

Fig. 19: A-64

| | | | | | | | | | | | |
|---|---|---|---|---|---|---|---|---|---|---|---|
| ATOM | 4600 | CB | GLN | 198 | 108.840 | -27.114 | 12.048 | 1.00 | 34.42 | L | C |
| ATOM | 4601 | CG | GLN | 198 | 110.091 | -27.549 | 11.333 | 1.00 | 36.17 | L | C |
| ATOM | 4602 | CD | GLN | 198 | 110.868 | -26.365 | 10.821 | 1.00 | 48.65 | L | C |
| ATOM | 4603 | OE1 | GLN | 198 | 110.286 | -25.414 | 10.299 | 1.00 | 57.22 | L | O |
| ATOM | 4604 | NE2 | GLN | 198 | 112.185 | -26.414 | 10.956 | 1.00 | 51.65 | L | N |
| ATOM | 4605 | C | GLN | 198 | 108.681 | -29.107 | 13.541 | 1.00 | 29.43 | L | C |
| ATOM | 4606 | O | GLN | 198 | 109.331 | -30.088 | 13.182 | 1.00 | 31.15 | L | O |
| ATOM | 4607 | N | GLY | 199 | 108.568 | -28.728 | 14.815 | 1.00 | 31.39 | L | N |
| ATOM | 4608 | CA | GLY | 199 | 109.234 | -29.452 | 15.887 | 1.00 | 36.65 | L | C |
| ATOM | 4609 | C | GLY | 199 | 108.465 | -30.636 | 16.444 | 1.00 | 39.08 | L | C |
| ATOM | 4610 | O | GLY | 199 | 108.880 | -31.244 | 17.425 | 1.00 | 43.81 | L | O |
| ATOM | 4611 | N | LEU | 200 | 107.339 | -30.961 | 15.823 | 1.00 | 25.48 | L | N |
| ATOM | 4612 | CA | LEU | 200 | 106.510 | -32.087 | 16.247 | 1.00 | 22.67 | L | C |
| ATOM | 4613 | CB | LEU | 200 | 105.094 | -31.597 | 16.570 | 1.00 | 31.49 | L | C |
| ATOM | 4614 | CG | LEU | 200 | 104.868 | -31.002 | 17.964 | 1.00 | 34.60 | L | C |
| ATOM | 4615 | CD1 | LEU | 200 | 106.036 | -30.149 | 18.361 | 1.00 | 37.97 | L | C |
| ATOM | 4616 | CD2 | LEU | 200 | 103.592 | -30.188 | 17.967 | 1.00 | 34.28 | L | C |
| ATOM | 4617 | C | LEU | 200 | 106.463 | -33.152 | 15.144 | 1.00 | 23.29 | L | C |
| ATOM | 4618 | O | LEU | 200 | 106.089 | -32.869 | 14.003 | 1.00 | 24.15 | L | O |
| ATOM | 4619 | N | SER | 201 | 106.860 | -34.372 | 15.499 | 1.00 | 21.11 | L | N |
| ATOM | 4620 | CA | SER | 201 | 106.886 | -35.503 | 14.570 | 1.00 | 24.08 | L | C |
| ATOM | 4621 | CB | SER | 201 | 107.367 | -36.747 | 15.311 | 1.00 | 27.13 | L | C |
| ATOM | 4622 | OG | SER | 201 | 106.702 | -36.875 | 16.561 | 1.00 | 28.99 | L | O |
| ATOM | 4623 | C | SER | 201 | 105.510 | -35.761 | 13.957 | 1.00 | 24.14 | L | C |
| ATOM | 4624 | O | SER | 201 | 105.392 | -36.267 | 12.835 | 1.00 | 25.49 | L | O |
| ATOM | 4625 | N | SER | 202 | 104.476 | -35.405 | 14.717 | 1.00 | 17.09 | L | N |
| ATOM | 4626 | CA | SER | 202 | 103.086 | -35.562 | 14.302 | 1.00 | 21.15 | L | C |
| ATOM | 4627 | CB | SER | 202 | 102.636 | -37.010 | 14.522 | 1.00 | 43.22 | L | C |
| ATOM | 4628 | OG | SER | 202 | 103.011 | -37.462 | 15.810 | 1.00 | 46.12 | L | O |
| ATOM | 4629 | C | SER | 202 | 102.265 | -34.603 | 15.155 | 1.00 | 21.60 | L | C |
| ATOM | 4630 | O | SER | 202 | 102.656 | -34.296 | 16.282 | 1.00 | 27.36 | L | O |
| ATOM | 4631 | N | PRO | 203 | 101.119 | -34.121 | 14.636 | 1.00 | 22.94 | L | N |
| ATOM | 4632 | CD | PRO | 203 | 100.457 | -34.478 | 13.368 | 1.00 | 32.35 | L | C |
| ATOM | 4633 | CA | PRO | 203 | 100.290 | -33.187 | 15.407 | 1.00 | 18.89 | L | C |
| ATOM | 4634 | CB | PRO | 203 | 98.971 | -33.177 | 14.643 | 1.00 | 26.47 | L | C |
| ATOM | 4635 | CG | PRO | 203 | 99.416 | -33.370 | 13.223 | 1.00 | 29.48 | L | C |
| ATOM | 4636 | C | PRO | 203 | 100.128 | -33.646 | 16.836 | 1.00 | 18.90 | L | C |
| ATOM | 4637 | O | PRO | 203 | 100.178 | -34.842 | 17.100 | 1.00 | 21.86 | L | O |
| ATOM | 4638 | N | VAL | 204 | 99.980 | -32.693 | 17.753 | 1.00 | 28.11 | L | N |
| ATOM | 4639 | CA | VAL | 204 | 99.794 | -32.996 | 19.172 | 1.00 | 29.99 | L | C |
| ATOM | 4640 | CB | VAL | 204 | 100.759 | -32.201 | 20.081 | 1.00 | 20.42 | L | C |
| ATOM | 4641 | CG1 | VAL | 204 | 100.254 | -32.204 | 21.512 | 1.00 | 20.30 | L | C |
| ATOM | 4642 | CG2 | VAL | 204 | 102.141 | -32.819 | 20.036 | 1.00 | 15.23 | L | C |
| ATOM | 4643 | C | VAL | 204 | 98.393 | -32.574 | 19.514 | 1.00 | 33.93 | L | C |
| ATOM | 4644 | O | VAL | 204 | 97.887 | -31.601 | 18.963 | 1.00 | 35.36 | L | O |
| ATOM | 4645 | N | THR | 205 | 97.755 | -33.293 | 20.422 | 1.00 | 45.34 | L | N |
| ATOM | 4646 | CA | THR | 205 | 96.402 | -32.933 | 20.787 | 1.00 | 46.97 | L | C |
| ATOM | 4647 | CB | THR | 205 | 95.386 | -33.896 | 20.137 | 1.00 | 14.48 | L | C |
| ATOM | 4648 | OG1 | THR | 205 | 95.275 | -33.587 | 18.747 | 1.00 | 10.44 | L | O |
| ATOM | 4649 | CG2 | THR | 205 | 94.013 | -33.761 | 20.769 | 1.00 | 11.16 | L | C |
| ATOM | 4650 | C | THR | 205 | 96.169 | -32.886 | 22.280 | 1.00 | 47.18 | L | C |
| ATOM | 4651 | O | THR | 205 | 96.596 | -33.763 | 23.032 | 1.00 | 49.19 | L | O |
| ATOM | 4652 | N | LYS | 206 | 95.513 | -31.822 | 22.709 | 1.00 | 22.09 | L | N |
| ATOM | 4653 | CA | LYS | 206 | 95.167 | -31.681 | 24.108 | 1.00 | 26.52 | L | C |
| ATOM | 4654 | CB | LYS | 206 | 95.791 | -30.422 | 24.710 | 1.00 | 41.08 | L | C |
| ATOM | 4655 | CG | LYS | 206 | 97.208 | -30.641 | 25.215 | 1.00 | 44.88 | L | C |
| ATOM | 4656 | CD | LYS | 206 | 97.269 | -31.688 | 26.312 | 1.00 | 47.36 | L | C |
| ATOM | 4657 | CE | LYS | 206 | 98.654 | -31.760 | 26.957 | 1.00 | 49.27 | L | C |
| ATOM | 4658 | NZ | LYS | 206 | 99.723 | -32.144 | 25.997 | 1.00 | 50.40 | L | N |
| ATOM | 4659 | C | LYS | 206 | 93.653 | -31.602 | 24.100 | 1.00 | 29.29 | L | C |
| ATOM | 4660 | O | LYS | 206 | 93.063 | -30.939 | 23.246 | 1.00 | 34.45 | L | O |
| ATOM | 4661 | N | SER | 207 | 93.026 | -32.304 | 25.033 | 1.00 | 32.39 | L | N |
| ATOM | 4662 | CA | SER | 207 | 91.578 | -32.324 | 25.083 | 1.00 | 29.18 | L | C |
| ATOM | 4663 | CB | SER | 207 | 91.046 | -33.364 | 24.080 | 1.00 | 31.23 | L | C |
| ATOM | 4664 | OG | SER | 207 | 91.613 | -34.655 | 24.294 | 1.00 | 31.62 | L | O |
| ATOM | 4665 | C | SER | 207 | 91.039 | -32.624 | 26.476 | 1.00 | 28.78 | L | C |
| ATOM | 4666 | O | SER | 207 | 91.798 | -32.938 | 27.397 | 1.00 | 29.47 | L | O |
| ATOM | 4667 | N | PHE | 208 | 89.719 | -32.517 | 26.606 | 1.00 | 33.89 | L | N |
| ATOM | 4668 | CA | PHE | 208 | 89.013 | -32.777 | 27.852 | 1.00 | 39.79 | L | C |
| ATOM | 4669 | CB | PHE | 208 | 89.217 | -31.615 | 28.842 | 1.00 | 17.06 | L | C |
| ATOM | 4670 | CG | PHE | 208 | 88.662 | -30.300 | 28.353 | 1.00 | 14.11 | L | C |
| ATOM | 4671 | CD1 | PHE | 208 | 89.409 | -29.482 | 27.499 | 1.00 | 18.84 | L | C |
| ATOM | 4672 | CD2 | PHE | 208 | 87.376 | -29.906 | 28.690 | 1.00 | 11.57 | L | C |

Fig. 19: A-65

| | | | | | | | | | | |
|---|---|---|---|---|---|---|---|---|---|---|
| ATOM | 4673 | CE1 | PHE | 208 | 88.879 | -28.298 | 26.990 | 1.00 | 19.93 | L | C |
| ATOM | 4674 | CE2 | PHE | 208 | 86.846 | -28.729 | 28.182 | 1.00 | 14.34 | L | C |
| ATOM | 4675 | CZ | PHE | 208 | 87.602 | -27.925 | 27.330 | 1.00 | 20.99 | L | C |
| ATOM | 4676 | C | PHE | 208 | 87.536 | -32.873 | 27.472 | 1.00 | 45.59 | L | C |
| ATOM | 4677 | O | PHE | 208 | 87.168 | -32.576 | 26.335 | 1.00 | 47.78 | L | O |
| ATOM | 4678 | N | ASN | 209 | 86.703 | -33.293 | 28.420 | 1.00 | 24.67 | L | N |
| ATOM | 4679 | CA | ASN | 209 | 85.257 | -33.398 | 28.213 | 1.00 | 28.33 | L | C |
| ATOM | 4680 | CB | ASN | 209 | 84.751 | -34.785 | 28.623 | 1.00 | 27.05 | L | C |
| ATOM | 4681 | CG | ASN | 209 | 85.664 | -35.913 | 28.172 | 1.00 | 33.97 | L | C |
| ATOM | 4682 | OD1 | ASN | 209 | 85.777 | -36.941 | 28.841 | 1.00 | 34.19 | L | O |
| ATOM | 4683 | ND2 | ASN | 209 | 86.304 | -35.732 | 27.031 | 1.00 | 37.01 | L | N |
| ATOM | 4684 | C | ASN | 209 | 84.630 | -32.370 | 29.160 | 1.00 | 29.95 | L | C |
| ATOM | 4685 | O | ASN | 209 | 85.203 | -32.108 | 30.218 | 1.00 | 31.18 | L | O |
| ATOM | 4686 | N | ARG | 210 | 83.473 | -31.800 | 28.805 | 1.00 | 15.88 | L | N |
| ATOM | 4687 | CA | ARG | 210 | 82.810 | -30.829 | 29.687 | 1.00 | 19.72 | L | C |
| ATOM | 4688 | CB | ARG | 210 | 81.337 | -30.721 | 29.371 | 1.00 | 31.19 | L | C |
| ATOM | 4689 | CG | ARG | 210 | 81.027 | -29.666 | 28.361 | 1.00 | 32.77 | L | C |
| ATOM | 4690 | CD | ARG | 210 | 79.655 | -29.104 | 28.627 | 1.00 | 36.35 | L | C |
| ATOM | 4691 | NE | ARG | 210 | 78.656 | -30.166 | 28.633 | 1.00 | 41.72 | L | N |
| ATOM | 4692 | CZ | ARG | 210 | 77.502 | -30.095 | 29.282 | 1.00 | 45.49 | L | C |
| ATOM | 4693 | NH1 | ARG | 210 | 77.204 | -29.008 | 29.981 | 1.00 | 46.04 | L | N |
| ATOM | 4694 | NH2 | ARG | 210 | 76.655 | -31.112 | 29.232 | 1.00 | 47.73 | L | N |
| ATOM | 4695 | C | ARG | 210 | 82.964 | -31.252 | 31.137 | 1.00 | 22.05 | L | C |
| ATOM | 4696 | O | ARG | 210 | 82.962 | -32.440 | 31.428 | 1.00 | 23.93 | L | O |
| ATOM | 4697 | N | GLY | 211 | 83.096 | -30.291 | 32.048 | 1.00 | 53.99 | L | N |
| ATOM | 4698 | CA | GLY | 211 | 83.297 | -30.638 | 33.447 | 1.00 | 53.99 | L | C |
| ATOM | 4699 | C | GLY | 211 | 84.740 | -31.088 | 33.630 | 1.00 | 53.99 | L | C |
| ATOM | 4700 | O | GLY | 211 | 85.665 | -30.312 | 33.387 | 1.00 | 53.99 | L | O |
| ATOM | 4701 | N | GLU | 212 | 84.942 | -32.336 | 34.046 | 1.00 | 80.95 | L | N |
| ATOM | 4702 | CA | GLU | 212 | 86.287 | -32.890 | 34.236 | 1.00 | 80.95 | L | C |
| ATOM | 4703 | CB | GLU | 212 | 86.995 | -33.004 | 32.871 | 1.00 | 34.07 | L | C |
| ATOM | 4704 | CG | GLU | 212 | 88.259 | -33.888 | 32.849 | 1.00 | 34.07 | L | C |
| ATOM | 4705 | CD | GLU | 212 | 88.691 | -34.311 | 31.435 | 1.00 | 34.07 | L | C |
| ATOM | 4706 | OE1 | GLU | 212 | 89.803 | -34.863 | 31.296 | 1.00 | 34.07 | L | O |
| ATOM | 4707 | OE2 | GLU | 212 | 87.923 | -34.113 | 30.468 | 1.00 | 34.07 | L | O |
| ATOM | 4708 | C | GLU | 212 | 87.134 | -32.080 | 35.227 | 1.00 | 80.95 | L | C |
| ATOM | 4709 | O | GLU | 212 | 86.690 | -31.043 | 35.732 | 1.00 | 80.95 | L | O |
| ATOM | 4710 | N | CYS | 213 | 88.341 | -32.566 | 35.516 | 1.00 | 81.74 | L | N |
| ATOM | 4711 | CA | CYS | 213 | 89.243 | -31.893 | 36.450 | 1.00 | 81.74 | L | C |
| ATOM | 4712 | CB | CYS | 213 | 88.990 | -32.374 | 37.883 | 1.00 | 54.42 | L | C |
| ATOM | 4713 | SG | CYS | 213 | 87.479 | -31.701 | 38.656 | 1.00 | 54.42 | L | S |
| ATOM | 4714 | C | CYS | 213 | 90.715 | -32.123 | 36.095 | 1.00 | 81.74 | L | C |
| ATOM | 4715 | O | CYS | 213 | 90.996 | -32.758 | 35.051 | 1.00 | 81.74 | L | O |
| ATOM | 4716 | OXT | CYS | 213 | 91.581 | -31.647 | 36.863 | 1.00 | 72.88 | L | O |
| ATOM | 4717 | MN | MN | 400 | 117.831 | 24.682 | 6.345 | 1.00 | 34.24 | M | |
| ATOM | 4718 | CB | THR | 145 | 114.226 | 73.843 | 15.327 | 1.00 | 72.71 | B | C |
| ATOM | 4719 | OG1 | THR | 145 | 113.673 | 74.174 | 16.611 | 1.00 | 72.71 | B | O |
| ATOM | 4720 | CG2 | THR | 145 | 114.208 | 75.069 | 14.426 | 1.00 | 72.71 | B | C |
| ATOM | 4721 | C | THR | 145 | 113.665 | 71.399 | 15.485 | 1.00 | 109.74 | B | C |
| ATOM | 4722 | O | THR | 145 | 113.590 | 70.290 | 14.948 | 1.00 | 110.14 | B | O |
| ATOM | 4723 | N | THR | 145 | 111.957 | 72.996 | 14.632 | 1.00 | 108.12 | B | N |
| ATOM | 4724 | CA | THR | 145 | 113.414 | 72.677 | 14.686 | 1.00 | 107.72 | B | C |
| ATOM | 4725 | N | GLN | 146 | 113.963 | 71.561 | 16.769 | 1.00 | 79.22 | B | N |
| ATOM | 4726 | CA | GLN | 146 | 114.224 | 70.425 | 17.633 | 1.00 | 77.37 | B | C |
| ATOM | 4727 | CB | GLN | 146 | 115.554 | 70.620 | 18.378 | 1.00 | 80.28 | B | C |
| ATOM | 4728 | CG | GLN | 146 | 115.640 | 71.886 | 19.208 | 1.00 | 80.28 | B | C |
| ATOM | 4729 | CD | GLN | 146 | 116.952 | 72.001 | 19.955 | 1.00 | 80.28 | B | C |
| ATOM | 4730 | OE1 | GLN | 146 | 117.150 | 72.929 | 20.742 | 1.00 | 80.28 | B | O |
| ATOM | 4731 | NE2 | GLN | 146 | 117.858 | 71.059 | 19.712 | 1.00 | 80.28 | B | N |
| ATOM | 4732 | C | GLN | 146 | 113.077 | 70.200 | 18.620 | 1.00 | 77.79 | B | C |
| ATOM | 4733 | O | GLN | 146 | 112.818 | 71.018 | 19.511 | 1.00 | 79.65 | B | O |
| ATOM | 4734 | N | LEU | 147 | 112.383 | 69.081 | 18.432 | 1.00 | 43.47 | B | N |
| ATOM | 4735 | CA | LEU | 147 | 111.265 | 68.710 | 19.288 | 1.00 | 42.60 | B | C |
| ATOM | 4736 | CB | LEU | 147 | 109.936 | 68.755 | 18.525 | 1.00 | 51.95 | B | C |
| ATOM | 4737 | CG | LEU | 147 | 109.450 | 69.952 | 17.707 | 1.00 | 52.14 | B | C |
| ATOM | 4738 | CD1 | LEU | 147 | 110.464 | 70.296 | 16.632 | 1.00 | 47.35 | B | C |
| ATOM | 4739 | CD2 | LEU | 147 | 108.114 | 69.607 | 17.060 | 1.00 | 51.99 | B | C |
| ATOM | 4740 | C | LEU | 147 | 111.461 | 67.281 | 19.756 | 1.00 | 41.58 | B | C |
| ATOM | 4741 | O | LEU | 147 | 112.077 | 66.470 | 19.058 | 1.00 | 42.88 | B | O |
| ATOM | 4742 | N | ASP | 148 | 110.944 | 66.988 | 20.945 | 1.00 | 31.29 | B | N |
| ATOM | 4743 | CA | ASP | 148 | 110.974 | 65.640 | 21.493 | 1.00 | 28.75 | B | C |
| ATOM | 4744 | CB | ASP | 148 | 111.394 | 65.642 | 22.960 | 1.00 | 32.78 | B | C |
| ATOM | 4745 | CG | ASP | 148 | 112.897 | 65.718 | 23.133 | 1.00 | 32.40 | B | C |

Fig. 19: A-66

| | | | | | | | | | | | |
|---|---|---|---|---|---|---|---|---|---|---|---|
| ATOM | 4746 | OD1 | ASP | 148 | 113.366 | 65.715 | 24.290 | 1.00 | 31.51 | B | O |
| ATOM | 4747 | OD2 | ASP | 148 | 113.616 | 65.777 | 22.116 | 1.00 | 30.58 | B | O |
| ATOM | 4748 | C | ASP | 148 | 109.526 | 65.181 | 21.358 | 1.00 | 25.13 | B | C |
| ATOM | 4749 | O | ASP | 148 | 108.664 | 65.583 | 22.128 | 1.00 | 24.43 | B | O |
| ATOM | 4750 | N | ILE | 149 | 109.260 | 64.368 | 20.345 | 1.00 | 21.33 | B | N |
| ATOM | 4751 | CA | ILE | 149 | 107.918 | 63.885 | 20.105 | 1.00 | 20.27 | B | C |
| ATOM | 4752 | CB | ILE | 149 | 107.610 | 63.880 | 18.605 | 1.00 | 13.57 | B | C |
| ATOM | 4753 | CG2 | ILE | 149 | 106.140 | 63.573 | 18.378 | 1.00 | 8.58 | B | C |
| ATOM | 4754 | CG1 | ILE | 149 | 107.932 | 65.234 | 17.998 | 1.00 | 9.29 | B | C |
| ATOM | 4755 | CD1 | ILE | 149 | 107.697 | 65.263 | 16.508 | 1.00 | 12.04 | B | C |
| ATOM | 4756 | C | ILE | 149 | 107.723 | 62.464 | 20.629 | 1.00 | 21.92 | B | C |
| ATOM | 4757 | O | ILE | 149 | 108.507 | 61.563 | 20.315 | 1.00 | 22.32 | B | O |
| ATOM | 4758 | N | VAL | 150 | 106.680 | 62.271 | 21.433 | 1.00 | 32.56 | B | N |
| ATOM | 4759 | CA | VAL | 150 | 106.357 | 60.950 | 21.956 | 1.00 | 34.12 | B | C |
| ATOM | 4760 | CB | VAL | 150 | 106.256 | 60.940 | 23.492 | 1.00 | 12.90 | B | C |
| ATOM | 4761 | CG1 | VAL | 150 | 105.775 | 59.579 | 23.967 | 1.00 | 15.09 | B | C |
| ATOM | 4762 | CG2 | VAL | 150 | 107.620 | 61.256 | 24.110 | 1.00 | 14.71 | B | C |
| ATOM | 4763 | C | VAL | 150 | 105.001 | 60.604 | 21.381 | 1.00 | 31.68 | B | C |
| ATOM | 4764 | O | VAL | 150 | 104.057 | 61.380 | 21.523 | 1.00 | 29.83 | B | O |
| ATOM | 4765 | N | ILE | 151 | 104.904 | 59.459 | 20.714 | 1.00 | 36.82 | B | N |
| ATOM | 4766 | CA | ILE | 151 | 103.640 | 59.037 | 20.115 | 1.00 | 35.62 | B | C |
| ATOM | 4767 | CB | ILE | 151 | 103.862 | 58.436 | 18.709 | 1.00 | 31.63 | B | C |
| ATOM | 4768 | CG2 | ILE | 151 | 102.537 | 58.084 | 18.081 | 1.00 | 27.99 | B | C |
| ATOM | 4769 | CG1 | ILE | 151 | 104.582 | 59.454 | 17.817 | 1.00 | 30.05 | B | C |
| ATOM | 4770 | CD1 | ILE | 151 | 104.981 | 58.916 | 16.457 | 1.00 | 32.03 | B | C |
| ATOM | 4771 | C | ILE | 151 | 102.978 | 58.008 | 21.016 | 1.00 | 33.74 | B | C |
| ATOM | 4772 | O | ILE | 151 | 103.593 | 57.013 | 21.394 | 1.00 | 33.98 | B | O |
| ATOM | 4773 | N | VAL | 152 | 101.725 | 58.254 | 21.368 | 1.00 | 29.85 | B | N |
| ATOM | 4774 | CA | VAL | 152 | 100.996 | 57.347 | 22.243 | 1.00 | 30.70 | B | C |
| ATOM | 4775 | CB | VAL | 152 | 100.279 | 58.127 | 23.344 | 1.00 | 30.57 | B | C |
| ATOM | 4776 | CG1 | VAL | 152 | 99.721 | 57.170 | 24.385 | 1.00 | 29.70 | B | C |
| ATOM | 4777 | CG2 | VAL | 152 | 101.245 | 59.134 | 23.962 | 1.00 | 27.01 | B | C |
| ATOM | 4778 | C | VAL | 152 | 99.966 | 56.560 | 21.451 | 1.00 | 28.60 | B | C |
| ATOM | 4779 | O | VAL | 152 | 98.867 | 57.044 | 21.194 | 1.00 | 22.20 | B | O |
| ATOM | 4780 | N | LEU | 153 | 100.324 | 55.336 | 21.083 | 1.00 | 26.94 | B | N |
| ATOM | 4781 | CA | LEU | 153 | 99.451 | 54.479 | 20.289 | 1.00 | 27.05 | B | C |
| ATOM | 4782 | CB | LEU | 153 | 100.312 | 53.600 | 19.370 | 1.00 | 31.93 | B | C |
| ATOM | 4783 | CG | LEU | 153 | 100.518 | 54.010 | 17.910 | 1.00 | 33.71 | B | C |
| ATOM | 4784 | CD1 | LEU | 153 | 100.287 | 55.490 | 17.732 | 1.00 | 34.22 | B | C |
| ATOM | 4785 | CD2 | LEU | 153 | 101.914 | 53.616 | 17.481 | 1.00 | 36.25 | B | C |
| ATOM | 4786 | C | LEU | 153 | 98.475 | 53.597 | 21.058 | 1.00 | 28.11 | B | C |
| ATOM | 4787 | O | LEU | 153 | 98.837 | 52.930 | 22.035 | 1.00 | 27.11 | B | O |
| ATOM | 4788 | N | ASP | 154 | 97.228 | 53.602 | 20.604 | 1.00 | 33.48 | B | N |
| ATOM | 4789 | CA | ASP | 154 | 96.199 | 52.768 | 21.204 | 1.00 | 32.96 | B | C |
| ATOM | 4790 | CB | ASP | 154 | 94.809 | 53.341 | 20.911 | 1.00 | 34.05 | B | C |
| ATOM | 4791 | CG | ASP | 154 | 93.686 | 52.502 | 21.505 | 1.00 | 33.25 | B | C |
| ATOM | 4792 | OD1 | ASP | 154 | 93.959 | 51.385 | 21.985 | 1.00 | 36.76 | B | O |
| ATOM | 4793 | OD2 | ASP | 154 | 92.523 | 52.960 | 21.489 | 1.00 | 29.57 | B | O |
| ATOM | 4794 | C | ASP | 154 | 96.362 | 51.412 | 20.515 | 1.00 | 36.30 | B | C |
| ATOM | 4795 | O | ASP | 154 | 96.349 | 51.326 | 19.285 | 1.00 | 32.62 | B | O |
| ATOM | 4796 | N | GLY | 155 | 96.539 | 50.361 | 21.303 | 1.00 | 16.68 | B | N |
| ATOM | 4797 | CA | GLY | 155 | 96.700 | 49.039 | 20.732 | 1.00 | 18.75 | B | C |
| ATOM | 4798 | C | GLY | 155 | 95.706 | 48.058 | 21.321 | 1.00 | 20.01 | B | C |
| ATOM | 4799 | O | GLY | 155 | 95.856 | 46.845 | 21.177 | 1.00 | 22.50 | B | O |
| ATOM | 4800 | N | SER | 156 | 94.692 | 48.595 | 21.992 | 1.00 | 30.46 | B | N |
| ATOM | 4801 | CA | SER | 156 | 93.653 | 47.780 | 22.612 | 1.00 | 35.04 | B | C |
| ATOM | 4802 | CB | SER | 156 | 92.616 | 48.670 | 23.302 | 1.00 | 22.70 | B | C |
| ATOM | 4803 | OG | SER | 156 | 91.999 | 49.542 | 22.372 | 1.00 | 25.62 | B | O |
| ATOM | 4804 | C | SER | 156 | 92.962 | 46.891 | 21.584 | 1.00 | 32.03 | B | C |
| ATOM | 4805 | O | SER | 156 | 93.057 | 47.122 | 20.379 | 1.00 | 35.21 | B | O |
| ATOM | 4806 | N | ASN | 157 | 92.257 | 45.879 | 22.074 | 1.00 | 34.08 | B | N |
| ATOM | 4807 | CA | ASN | 157 | 91.565 | 44.927 | 21.216 | 1.00 | 31.16 | B | C |
| ATOM | 4808 | CB | ASN | 157 | 90.632 | 44.046 | 22.047 | 1.00 | 34.61 | B | C |
| ATOM | 4809 | CG | ASN | 157 | 91.378 | 42.971 | 22.811 | 1.00 | 36.10 | B | C |
| ATOM | 4810 | OD1 | ASN | 157 | 90.795 | 42.270 | 23.638 | 1.00 | 33.17 | B | O |
| ATOM | 4811 | ND2 | ASN | 157 | 92.672 | 42.832 | 22.536 | 1.00 | 33.38 | B | N |
| ATOM | 4812 | C | ASN | 157 | 90.783 | 45.529 | 20.069 | 1.00 | 29.13 | B | C |
| ATOM | 4813 | O | ASN | 157 | 90.806 | 45.003 | 18.956 | 1.00 | 27.11 | B | O |
| ATOM | 4814 | N | SER | 158 | 90.094 | 46.631 | 20.339 | 1.00 | 20.01 | B | N |
| ATOM | 4815 | CA | SER | 158 | 89.275 | 47.285 | 19.324 | 1.00 | 18.22 | B | C |
| ATOM | 4816 | CB | SER | 158 | 88.506 | 48.464 | 19.936 | 1.00 | 15.08 | B | C |
| ATOM | 4817 | OG | SER | 158 | 89.356 | 49.363 | 20.616 | 1.00 | 17.79 | B | O |
| ATOM | 4818 | C | SER | 158 | 90.035 | 47.739 | 18.087 | 1.00 | 18.99 | B | C |

Fig. 19: A-67

| | | | | | | | | | | | |
|---|---|---|---|---|---|---|---|---|---|---|---|
| ATOM | 4819 | O | SER | 158 | 89.527 | 47.602 | 16.984 | 1.00 | 16.16 | B | O |
| ATOM | 4820 | N | ILE | 159 | 91.245 | 48.269 | 18.257 | 1.00 | 19.55 | B | N |
| ATOM | 4821 | CA | ILE | 159 | 92.033 | 48.722 | 17.110 | 1.00 | 24.15 | B | C |
| ATOM | 4822 | CB | ILE | 159 | 93.423 | 49.203 | 17.541 | 1.00 | 21.45 | B | C |
| ATOM | 4823 | CG2 | ILE | 159 | 94.256 | 49.546 | 16.307 | 1.00 | 21.36 | B | C |
| ATOM | 4824 | CG1 | ILE | 159 | 93.293 | 50.411 | 18.471 | 1.00 | 26.23 | B | C |
| ATOM | 4825 | CD1 | ILE | 159 | 92.779 | 51.664 | 17.787 | 1.00 | 31.39 | B | C |
| ATOM | 4826 | C | ILE | 159 | 92.204 | 47.597 | 16.089 | 1.00 | 28.46 | B | C |
| ATOM | 4827 | O | ILE | 159 | 92.638 | 46.502 | 16.434 | 1.00 | 27.87 | B | O |
| ATOM | 4828 | N | TYR | 160 | 91.863 | 47.876 | 14.832 | 1.00 | 56.09 | B | N |
| ATOM | 4829 | CA | TYR | 160 | 91.959 | 46.886 | 13.756 | 1.00 | 58.22 | B | C |
| ATOM | 4830 | CB | TYR | 160 | 90.931 | 45.768 | 13.980 | 1.00 | 40.50 | B | C |
| ATOM | 4831 | CG | TYR | 160 | 90.932 | 44.654 | 12.939 | 1.00 | 37.26 | B | C |
| ATOM | 4832 | CD1 | TYR | 160 | 91.606 | 43.449 | 13.172 | 1.00 | 39.68 | B | C |
| ATOM | 4833 | CE1 | TYR | 160 | 91.602 | 42.423 | 12.225 | 1.00 | 37.28 | B | C |
| ATOM | 4834 | CD2 | TYR | 160 | 90.254 | 44.803 | 11.722 | 1.00 | 34.91 | B | C |
| ATOM | 4835 | CE2 | TYR | 160 | 90.251 | 43.782 | 10.770 | 1.00 | 38.62 | B | C |
| ATOM | 4836 | CZ | TYR | 160 | 90.926 | 42.598 | 11.030 | 1.00 | 37.97 | B | C |
| ATOM | 4837 | OH | TYR | 160 | 90.922 | 41.597 | 10.095 | 1.00 | 42.97 | B | O |
| ATOM | 4838 | C | TYR | 160 | 91.696 | 47.533 | 12.400 | 1.00 | 59.94 | B | C |
| ATOM | 4839 | O | TYR | 160 | 90.730 | 48.276 | 12.232 | 1.00 | 65.86 | B | O |
| ATOM | 4840 | N | PRO | 161 | 92.548 | 47.241 | 11.407 | 1.00 | 26.83 | B | N |
| ATOM | 4841 | CD | PRO | 161 | 92.182 | 47.499 | 10.002 | 1.00 | 24.03 | B | C |
| ATOM | 4842 | CA | PRO | 161 | 93.721 | 46.362 | 11.479 | 1.00 | 25.11 | B | C |
| ATOM | 4843 | CB | PRO | 161 | 93.784 | 45.785 | 10.075 | 1.00 | 28.41 | B | C |
| ATOM | 4844 | CG | PRO | 161 | 93.364 | 46.960 | 9.239 | 1.00 | 31.57 | B | C |
| ATOM | 4845 | C | PRO | 161 | 95.008 | 47.109 | 11.857 | 1.00 | 23.77 | B | C |
| ATOM | 4846 | O | PRO | 161 | 95.234 | 48.238 | 11.413 | 1.00 | 23.09 | B | O |
| ATOM | 4847 | N | TRP | 162 | 95.856 | 46.463 | 12.654 | 1.00 | 23.22 | B | N |
| ATOM | 4848 | CA | TRP | 162 | 97.108 | 47.062 | 13.111 | 1.00 | 24.29 | B | C |
| ATOM | 4849 | CB | TRP | 162 | 97.922 | 46.022 | 13.878 | 1.00 | 29.42 | B | C |
| ATOM | 4850 | CG | TRP | 162 | 99.067 | 46.586 | 14.670 | 1.00 | 29.94 | B | C |
| ATOM | 4851 | CD2 | TRP | 162 | 99.004 | 47.603 | 15.676 | 1.00 | 24.78 | B | C |
| ATOM | 4852 | CE2 | TRP | 162 | 100.308 | 47.769 | 16.185 | 1.00 | 28.33 | B | C |
| ATOM | 4853 | CE3 | TRP | 162 | 97.973 | 48.389 | 16.201 | 1.00 | 24.19 | B | C |
| ATOM | 4854 | CD1 | TRP | 162 | 100.369 | 46.192 | 14.611 | 1.00 | 29.13 | B | C |
| ATOM | 4855 | NE1 | TRP | 162 | 101.123 | 46.898 | 15.516 | 1.00 | 31.00 | B | N |
| ATOM | 4856 | CZ2 | TRP | 162 | 100.607 | 48.687 | 17.195 | 1.00 | 26.87 | B | C |
| ATOM | 4857 | CZ3 | TRP | 162 | 98.274 | 49.303 | 17.208 | 1.00 | 22.52 | B | C |
| ATOM | 4858 | CH2 | TRP | 162 | 99.580 | 49.441 | 17.691 | 1.00 | 27.43 | B | C |
| ATOM | 4859 | C | TRP | 162 | 97.961 | 47.663 | 11.988 | 1.00 | 26.07 | B | C |
| ATOM | 4860 | O | TRP | 162 | 98.554 | 48.734 | 12.161 | 1.00 | 25.22 | B | O |
| ATOM | 4861 | N | GLU | 163 | 98.010 | 46.979 | 10.843 | 1.00 | 39.64 | B | N |
| ATOM | 4862 | CA | GLU | 163 | 98.797 | 47.432 | 9.693 | 1.00 | 41.42 | B | C |
| ATOM | 4863 | CB | GLU | 163 | 98.585 | 46.509 | 8.485 | 1.00 | 121.98 | B | C |
| ATOM | 4864 | CG | GLU | 163 | 97.219 | 46.612 | 7.826 | 1.00 | 128.29 | B | C |
| ATOM | 4865 | CD | GLU | 163 | 97.206 | 46.043 | 6.418 | 1.00 | 130.43 | B | C |
| ATOM | 4866 | OE1 | GLU | 163 | 97.894 | 46.611 | 5.541 | 1.00 | 132.14 | B | O |
| ATOM | 4867 | OE2 | GLU | 163 | 96.512 | 45.029 | 6.187 | 1.00 | 129.39 | B | O |
| ATOM | 4868 | C | GLU | 163 | 98.491 | 48.867 | 9.280 | 1.00 | 41.08 | B | C |
| ATOM | 4869 | O | GLU | 163 | 99.390 | 49.609 | 8.881 | 1.00 | 37.25 | B | O |
| ATOM | 4870 | N | SER | 164 | 97.225 | 49.262 | 9.368 | 1.00 | 24.58 | B | N |
| ATOM | 4871 | CA | SER | 164 | 96.850 | 50.620 | 8.989 | 1.00 | 21.77 | B | C |
| ATOM | 4872 | CB | SER | 164 | 95.320 | 50.772 | 8.984 | 1.00 | 53.34 | B | C |
| ATOM | 4873 | OG | SER | 164 | 94.722 | 49.950 | 7.992 | 1.00 | 59.23 | B | O |
| ATOM | 4874 | C | SER | 164 | 97.484 | 51.619 | 9.956 | 1.00 | 22.53 | B | C |
| ATOM | 4875 | O | SER | 164 | 97.993 | 52.661 | 9.536 | 1.00 | 25.73 | B | O |
| ATOM | 4876 | N | VAL | 165 | 97.451 | 51.286 | 11.247 | 1.00 | 28.47 | B | N |
| ATOM | 4877 | CA | VAL | 165 | 98.027 | 52.137 | 12.280 | 1.00 | 27.86 | B | C |
| ATOM | 4878 | CB | VAL | 165 | 97.841 | 51.525 | 13.680 | 1.00 | 11.01 | B | C |
| ATOM | 4879 | CG1 | VAL | 165 | 98.722 | 52.245 | 14.697 | 1.00 | 12.40 | B | C |
| ATOM | 4880 | CG2 | VAL | 165 | 96.376 | 51.622 | 14.089 | 1.00 | 14.01 | B | C |
| ATOM | 4881 | C | VAL | 165 | 99.509 | 52.334 | 12.028 | 1.00 | 29.02 | B | C |
| ATOM | 4882 | O | VAL | 165 | 100.032 | 53.444 | 12.137 | 1.00 | 30.84 | B | O |
| ATOM | 4883 | N | ILE | 166 | 100.184 | 51.248 | 11.678 | 1.00 | 20.94 | B | N |
| ATOM | 4884 | CA | ILE | 166 | 101.613 | 51.305 | 11.400 | 1.00 | 20.26 | B | C |
| ATOM | 4885 | CB | ILE | 166 | 102.211 | 49.894 | 11.330 | 1.00 | 40.92 | B | C |
| ATOM | 4886 | CG2 | ILE | 166 | 103.697 | 49.962 | 10.986 | 1.00 | 40.13 | B | C |
| ATOM | 4887 | CG1 | ILE | 166 | 102.017 | 49.214 | 12.687 | 1.00 | 40.78 | B | C |
| ATOM | 4888 | CD1 | ILE | 166 | 102.580 | 47.823 | 12.762 | 1.00 | 37.18 | B | C |
| ATOM | 4889 | C | ILE | 166 | 101.920 | 52.073 | 10.121 | 1.00 | 19.71 | B | C |
| ATOM | 4890 | O | ILE | 166 | 102.909 | 52.792 | 10.059 | 1.00 | 21.46 | B | O |
| ATOM | 4891 | N | ALA | 167 | 101.076 | 51.927 | 9.106 | 1.00 | 22.08 | B | N |

Fig. 19: A-68

| | | | | | | | | | | | |
|---|---|---|---|---|---|---|---|---|---|---|---|
| ATOM | 4892 | CA | ALA | 167 | 101.271 | 52.670 | 7.866 | 1.00 | 22.68 | B | C |
| ATOM | 4893 | CB | ALA | 167 | 100.207 | 52.309 | 6.859 | 1.00 | 1.87 | B | C |
| ATOM | 4894 | C | ALA | 167 | 101.165 | 54.150 | 8.224 | 1.00 | 23.89 | B | C |
| ATOM | 4895 | O | ALA | 167 | 101.881 | 54.989 | 7.684 | 1.00 | 20.49 | B | O |
| ATOM | 4896 | N | PHE | 168 | 100.261 | 54.458 | 9.147 | 1.00 | 25.99 | B | N |
| ATOM | 4897 | CA | PHE | 168 | 100.083 | 55.823 | 9.583 | 1.00 | 24.51 | B | C |
| ATOM | 4898 | CB | PHE | 168 | 98.964 | 55.902 | 10.623 | 1.00 | 28.51 | B | C |
| ATOM | 4899 | CG | PHE | 168 | 98.962 | 57.185 | 11.406 | 1.00 | 27.01 | B | C |
| ATOM | 4900 | CD1 | PHE | 168 | 99.549 | 57.240 | 12.671 | 1.00 | 28.61 | B | C |
| ATOM | 4901 | CD2 | PHE | 168 | 98.409 | 58.341 | 10.872 | 1.00 | 25.32 | B | C |
| ATOM | 4902 | CE1 | PHE | 168 | 99.587 | 58.424 | 13.392 | 1.00 | 27.09 | B | C |
| ATOM | 4903 | CE2 | PHE | 168 | 98.442 | 59.529 | 11.587 | 1.00 | 27.14 | B | C |
| ATOM | 4904 | CZ | PHE | 168 | 99.034 | 59.570 | 12.853 | 1.00 | 29.63 | B | C |
| ATOM | 4905 | C | PHE | 168 | 101.397 | 56.325 | 10.178 | 1.00 | 25.37 | B | C |
| ATOM | 4906 | O | PHE | 168 | 101.832 | 57.446 | 9.908 | 1.00 | 21.81 | B | O |
| ATOM | 4907 | N | LEU | 169 | 102.030 | 55.488 | 10.990 | 1.00 | 25.37 | B | N |
| ATOM | 4908 | CA | LEU | 169 | 103.286 | 55.867 | 11.611 | 1.00 | 27.96 | B | C |
| ATOM | 4909 | CB | LEU | 169 | 103.749 | 54.790 | 12.585 | 1.00 | 24.35 | B | C |
| ATOM | 4910 | CG | LEU | 169 | 103.127 | 54.723 | 13.977 | 1.00 | 23.51 | B | C |
| ATOM | 4911 | CD1 | LEU | 169 | 103.983 | 53.810 | 14.831 | 1.00 | 19.97 | B | C |
| ATOM | 4912 | CD2 | LEU | 169 | 103.079 | 56.105 | 14.609 | 1.00 | 20.37 | B | C |
| ATOM | 4913 | C | LEU | 169 | 104.357 | 56.081 | 10.555 | 1.00 | 30.26 | B | C |
| ATOM | 4914 | O | LEU | 169 | 105.055 | 57.095 | 10.555 | 1.00 | 31.69 | B | O |
| ATOM | 4915 | N | ASN | 170 | 104.488 | 55.115 | 9.655 | 1.00 | 28.40 | B | N |
| ATOM | 4916 | CA | ASN | 170 | 105.470 | 55.208 | 8.591 | 1.00 | 25.53 | B | C |
| ATOM | 4917 | CB | ASN | 170 | 105.243 | 54.077 | 7.580 | 1.00 | 72.75 | B | C |
| ATOM | 4918 | CG | ASN | 170 | 106.484 | 53.768 | 6.747 | 1.00 | 76.17 | B | C |
| ATOM | 4919 | OD1 | ASN | 170 | 106.703 | 54.346 | 5.680 | 1.00 | 71.70 | B | O |
| ATOM | 4920 | ND2 | ASN | 170 | 107.307 | 52.854 | 7.242 | 1.00 | 74.08 | B | N |
| ATOM | 4921 | C | ASN | 170 | 105.335 | 56.578 | 7.913 | 1.00 | 25.54 | B | C |
| ATOM | 4922 | O | ASN | 170 | 106.242 | 57.408 | 7.992 | 1.00 | 25.75 | B | O |
| ATOM | 4923 | N | ASP | 171 | 104.189 | 56.819 | 7.275 | 1.00 | 35.44 | B | N |
| ATOM | 4924 | CA | ASP | 171 | 103.940 | 58.079 | 6.581 | 1.00 | 37.56 | B | C |
| ATOM | 4925 | CB | ASP | 171 | 102.467 | 58.179 | 6.168 | 1.00 | 72.00 | B | C |
| ATOM | 4926 | CG | ASP | 171 | 102.163 | 57.427 | 4.880 | 1.00 | 79.65 | B | C |
| ATOM | 4927 | OD1 | ASP | 171 | 102.448 | 56.213 | 4.805 | 1.00 | 81.87 | B | O |
| ATOM | 4928 | OD2 | ASP | 171 | 101.635 | 58.055 | 3.937 | 1.00 | 81.51 | B | O |
| ATOM | 4929 | C | ASP | 171 | 104.309 | 59.289 | 7.418 | 1.00 | 39.05 | B | C |
| ATOM | 4930 | O | ASP | 171 | 104.975 | 60.202 | 6.937 | 1.00 | 37.77 | B | O |
| ATOM | 4931 | N | LEU | 172 | 103.881 | 59.289 | 8.674 | 1.00 | 36.54 | B | N |
| ATOM | 4932 | CA | LEU | 172 | 104.152 | 60.403 | 9.570 | 1.00 | 37.22 | B | C |
| ATOM | 4933 | CB | LEU | 172 | 103.410 | 60.204 | 10.891 | 1.00 | 36.27 | B | C |
| ATOM | 4934 | CG | LEU | 172 | 102.901 | 61.423 | 11.674 | 1.00 | 35.76 | B | C |
| ATOM | 4935 | CD1 | LEU | 172 | 103.145 | 61.178 | 13.158 | 1.00 | 33.36 | B | C |
| ATOM | 4936 | CD2 | LEU | 172 | 103.593 | 62.706 | 11.237 | 1.00 | 33.93 | B | C |
| ATOM | 4937 | C | LEU | 172 | 105.642 | 60.561 | 9.849 | 1.00 | 37.56 | B | C |
| ATOM | 4938 | O | LEU | 172 | 106.212 | 61.628 | 9.627 | 1.00 | 37.55 | B | O |
| ATOM | 4939 | N | LEU | 173 | 106.269 | 59.493 | 10.337 | 1.00 | 40.49 | B | N |
| ATOM | 4940 | CA | LEU | 173 | 107.692 | 59.520 | 10.669 | 1.00 | 43.24 | B | C |
| ATOM | 4941 | CB | LEU | 173 | 108.115 | 58.215 | 11.364 | 1.00 | 18.13 | B | C |
| ATOM | 4942 | CG | LEU | 173 | 107.801 | 57.866 | 12.826 | 1.00 | 19.48 | B | C |
| ATOM | 4943 | CD1 | LEU | 173 | 108.033 | 59.060 | 13.729 | 1.00 | 23.00 | B | C |
| ATOM | 4944 | CD2 | LEU | 173 | 106.380 | 57.395 | 12.943 | 1.00 | 20.03 | B | C |
| ATOM | 4945 | C | LEU | 173 | 108.650 | 59.772 | 9.503 | 1.00 | 44.67 | B | C |
| ATOM | 4946 | O | LEU | 173 | 109.601 | 60.537 | 9.642 | 1.00 | 41.39 | B | O |
| ATOM | 4947 | N | LYS | 174 | 108.409 | 59.135 | 8.360 | 1.00 | 37.56 | B | N |
| ATOM | 4948 | CA | LYS | 174 | 109.304 | 59.291 | 7.221 | 1.00 | 37.78 | B | C |
| ATOM | 4949 | CB | LYS | 174 | 108.836 | 58.421 | 6.047 | 1.00 | 42.14 | B | C |
| ATOM | 4950 | CG | LYS | 174 | 107.739 | 58.988 | 5.169 | 1.00 | 42.47 | B | C |
| ATOM | 4951 | CD | LYS | 174 | 107.472 | 58.022 | 4.008 | 1.00 | 41.72 | B | C |
| ATOM | 4952 | CE | LYS | 174 | 106.689 | 58.660 | 2.852 | 1.00 | 36.97 | B | C |
| ATOM | 4953 | NZ | LYS | 174 | 105.297 | 59.097 | 3.187 | 1.00 | 33.44 | B | N |
| ATOM | 4954 | C | LYS | 174 | 109.511 | 60.738 | 6.774 | 1.00 | 36.14 | B | C |
| ATOM | 4955 | O | LYS | 174 | 110.571 | 61.078 | 6.245 | 1.00 | 37.01 | B | O |
| ATOM | 4956 | N | ARG | 175 | 108.514 | 61.589 | 7.004 | 1.00 | 41.42 | B | N |
| ATOM | 4957 | CA | ARG | 175 | 108.587 | 63.006 | 6.635 | 1.00 | 43.65 | B | C |
| ATOM | 4958 | CB | ARG | 175 | 107.182 | 63.634 | 6.654 | 1.00 | 108.28 | B | C |
| ATOM | 4959 | CG | ARG | 175 | 106.189 | 63.149 | 5.589 | 1.00 | 115.21 | B | C |
| ATOM | 4960 | CD | ARG | 175 | 104.762 | 63.613 | 5.939 | 1.00 | 119.49 | B | C |
| ATOM | 4961 | NE | ARG | 175 | 103.895 | 63.818 | 4.775 | 1.00 | 124.39 | B | N |
| ATOM | 4962 | CZ | ARG | 175 | 103.454 | 62.856 | 3.969 | 1.00 | 127.97 | B | C |
| ATOM | 4963 | NH1 | ARG | 175 | 103.793 | 61.593 | 4.182 | 1.00 | 128.17 | B | N |
| ATOM | 4964 | NH2 | ARG | 175 | 102.666 | 63.162 | 2.945 | 1.00 | 128.87 | B | N |

Fig. 19: A-69

| | | | | | | | | | | | |
|---|---|---|---|---|---|---|---|---|---|---|---|
| ATOM | 4965 | C | ARG | 175 | 109.471 | 63.798 | 7.611 | 1.00 | 41.18 | B | C |
| ATOM | 4966 | O | ARG | 175 | 109.696 | 64.986 | 7.411 | 1.00 | 41.02 | B | O |
| ATOM | 4967 | N | MET | 176 | 109.970 | 63.145 | 8.660 | 1.00 | 47.15 | B | N |
| ATOM | 4968 | CA | MET | 176 | 110.777 | 63.821 | 9.678 | 1.00 | 43.63 | B | C |
| ATOM | 4969 | CB | MET | 176 | 110.320 | 63.383 | 11.065 | 1.00 | 33.29 | B | C |
| ATOM | 4970 | CG | MET | 176 | 108.969 | 63.920 | 11.456 | 1.00 | 30.19 | B | C |
| ATOM | 4971 | SD | MET | 176 | 108.444 | 63.366 | 13.073 | 1.00 | 34.33 | B | S |
| ATOM | 4972 | CE | MET | 176 | 107.041 | 62.339 | 12.619 | 1.00 | 27.84 | B | C |
| ATOM | 4973 | C | MET | 176 | 112.284 | 63.663 | 9.611 | 1.00 | 47.14 | B | C |
| ATOM | 4974 | O | MET | 176 | 112.795 | 62.707 | 9.037 | 1.00 | 47.21 | B | O |
| ATOM | 4975 | N | ASP | 177 | 112.991 | 64.617 | 10.213 | 1.00 | 51.06 | B | N |
| ATOM | 4976 | CA | ASP | 177 | 114.451 | 64.590 | 10.276 | 1.00 | 53.55 | B | C |
| ATOM | 4977 | CB | ASP | 177 | 115.047 | 65.944 | 9.881 | 1.00 | 101.95 | B | C |
| ATOM | 4978 | CG | ASP | 177 | 115.065 | 66.158 | 8.381 | 1.00 | 104.90 | B | C |
| ATOM | 4979 | OD1 | ASP | 177 | 115.635 | 67.174 | 7.934 | 1.00 | 104.57 | B | O |
| ATOM | 4980 | OD2 | ASP | 177 | 114.511 | 65.310 | 7.647 | 1.00 | 106.55 | B | O |
| ATOM | 4981 | C | ASP | 177 | 114.851 | 64.249 | 11.706 | 1.00 | 53.47 | B | C |
| ATOM | 4982 | O | ASP | 177 | 115.107 | 65.133 | 12.519 | 1.00 | 53.19 | B | O |
| ATOM | 4983 | N | ILE | 178 | 114.888 | 62.954 | 12.003 | 1.00 | 55.91 | B | N |
| ATOM | 4984 | CA | ILE | 178 | 115.236 | 62.465 | 13.331 | 1.00 | 56.05 | B | C |
| ATOM | 4985 | CB | ILE | 178 | 114.719 | 61.004 | 13.543 | 1.00 | 33.37 | B | C |
| ATOM | 4986 | CG2 | ILE | 178 | 115.323 | 60.410 | 14.790 | 1.00 | 31.65 | B | C |
| ATOM | 4987 | CG1 | ILE | 178 | 113.191 | 60.985 | 13.665 | 1.00 | 34.43 | B | C |
| ATOM | 4988 | CD1 | ILE | 178 | 112.464 | 60.671 | 12.376 | 1.00 | 36.27 | B | C |
| ATOM | 4989 | C | ILE | 178 | 116.743 | 62.502 | 13.583 | 1.00 | 55.19 | B | C |
| ATOM | 4990 | O | ILE | 178 | 117.543 | 62.224 | 12.686 | 1.00 | 57.18 | B | O |
| ATOM | 4991 | N | GLY | 179 | 117.117 | 62.846 | 14.812 | 1.00 | 23.09 | B | N |
| ATOM | 4992 | CA | GLY | 179 | 118.521 | 62.912 | 15.178 | 1.00 | 22.81 | B | C |
| ATOM | 4993 | C | GLY | 179 | 118.736 | 63.508 | 16.560 | 1.00 | 23.57 | B | C |
| ATOM | 4994 | O | GLY | 179 | 117.931 | 64.325 | 17.012 | 1.00 | 21.72 | B | O |
| ATOM | 4995 | N | PRO | 180 | 119.815 | 63.113 | 17.265 | 1.00 | 39.73 | B | N |
| ATOM | 4996 | CD | PRO | 180 | 120.782 | 62.068 | 16.873 | 1.00 | 73.51 | B | C |
| ATOM | 4997 | CA | PRO | 180 | 120.124 | 63.620 | 18.606 | 1.00 | 40.79 | B | C |
| ATOM | 4998 | CB | PRO | 180 | 121.542 | 63.113 | 18.840 | 1.00 | 72.35 | B | C |
| ATOM | 4999 | CG | PRO | 180 | 121.502 | 61.776 | 18.184 | 1.00 | 74.74 | B | C |
| ATOM | 5000 | C | PRO | 180 | 120.019 | 65.135 | 18.697 | 1.00 | 42.57 | B | C |
| ATOM | 5001 | O | PRO | 180 | 119.718 | 65.680 | 19.761 | 1.00 | 43.21 | B | O |
| ATOM | 5002 | N | LYS | 181 | 120.268 | 65.810 | 17.578 | 1.00 | 56.97 | B | N |
| ATOM | 5003 | CA | LYS | 181 | 120.186 | 67.265 | 17.534 | 1.00 | 57.39 | B | C |
| ATOM | 5004 | CB | LYS | 181 | 121.522 | 67.867 | 17.092 | 1.00 | 83.43 | B | C |
| ATOM | 5005 | CG | LYS | 181 | 122.677 | 67.613 | 18.052 | 1.00 | 84.03 | B | C |
| ATOM | 5006 | CD | LYS | 181 | 122.430 | 68.205 | 19.442 | 1.00 | 82.89 | B | C |
| ATOM | 5007 | CE | LYS | 181 | 123.580 | 67.868 | 20.394 | 1.00 | 85.41 | B | C |
| ATOM | 5008 | NZ | LYS | 181 | 123.351 | 68.348 | 21.790 | 1.00 | 84.98 | B | N |
| ATOM | 5009 | C | LYS | 181 | 119.070 | 67.736 | 16.597 | 1.00 | 56.74 | B | C |
| ATOM | 5010 | O | LYS | 181 | 118.973 | 68.917 | 16.274 | 1.00 | 55.06 | B | O |
| ATOM | 5011 | N | GLN | 182 | 118.225 | 66.804 | 16.167 | 1.00 | 33.36 | B | N |
| ATOM | 5012 | CA | GLN | 182 | 117.112 | 67.117 | 15.279 | 1.00 | 32.02 | B | C |
| ATOM | 5013 | CB | GLN | 182 | 117.152 | 66.219 | 14.044 | 1.00 | 74.94 | B | C |
| ATOM | 5014 | CG | GLN | 182 | 118.512 | 66.050 | 13.424 | 1.00 | 76.22 | B | C |
| ATOM | 5015 | CD | GLN | 182 | 119.037 | 67.334 | 12.850 | 1.00 | 77.84 | B | C |
| ATOM | 5016 | OE1 | GLN | 182 | 119.266 | 68.305 | 13.573 | 1.00 | 78.68 | B | O |
| ATOM | 5017 | NE2 | GLN | 182 | 119.230 | 67.356 | 11.537 | 1.00 | 79.20 | B | N |
| ATOM | 5018 | C | GLN | 182 | 115.831 | 66.826 | 16.046 | 1.00 | 30.93 | B | C |
| ATOM | 5019 | O | GLN | 182 | 115.638 | 67.278 | 17.173 | 1.00 | 35.26 | B | O |
| ATOM | 5020 | N | THR | 183 | 114.961 | 66.046 | 15.419 | 1.00 | 29.87 | B | N |
| ATOM | 5021 | CA | THR | 183 | 113.706 | 65.648 | 16.025 | 1.00 | 26.79 | B | C |
| ATOM | 5022 | CB | THR | 183 | 112.612 | 65.493 | 14.962 | 1.00 | 31.40 | B | C |
| ATOM | 5023 | OG1 | THR | 183 | 112.484 | 66.721 | 14.231 | 1.00 | 27.85 | B | O |
| ATOM | 5024 | CG2 | THR | 183 | 111.285 | 65.127 | 15.610 | 1.00 | 29.08 | B | C |
| ATOM | 5025 | C | THR | 183 | 113.957 | 64.288 | 16.666 | 1.00 | 26.45 | B | C |
| ATOM | 5026 | O | THR | 183 | 114.624 | 63.428 | 16.077 | 1.00 | 24.98 | B | O |
| ATOM | 5027 | N | GLN | 184 | 113.464 | 64.102 | 17.883 | 1.00 | 44.27 | B | N |
| ATOM | 5028 | CA | GLN | 184 | 113.619 | 62.822 | 18.546 | 1.00 | 39.92 | B | C |
| ATOM | 5029 | CB | GLN | 184 | 114.254 | 62.981 | 19.920 | 1.00 | 33.99 | B | C |
| ATOM | 5030 | CG | GLN | 184 | 115.752 | 63.197 | 19.878 | 1.00 | 33.74 | B | C |
| ATOM | 5031 | CD | GLN | 184 | 116.427 | 62.766 | 21.163 | 1.00 | 33.21 | B | C |
| ATOM | 5032 | OE1 | GLN | 184 | 116.097 | 63.258 | 22.244 | 1.00 | 28.91 | B | O |
| ATOM | 5033 | NE2 | GLN | 184 | 117.375 | 61.835 | 21.053 | 1.00 | 31.51 | B | N |
| ATOM | 5034 | C | GLN | 184 | 112.227 | 62.240 | 18.670 | 1.00 | 40.30 | B | C |
| ATOM | 5035 | O | GLN | 184 | 111.249 | 62.978 | 18.834 | 1.00 | 37.69 | B | O |
| ATOM | 5036 | N | VAL | 185 | 112.131 | 60.918 | 18.574 | 1.00 | 24.17 | B | N |
| ATOM | 5037 | CA | VAL | 185 | 110.837 | 60.255 | 18.649 | 1.00 | 22.54 | B | C |

Fig. 19: A-70

| | | | | | | | | | | | |
|---|---|---|---|---|---|---|---|---|---|---|---|
| ATOM | 5038 | CB | VAL | 185 | 110.345 | 59.858 | 17.235 | 1.00 | 12.44 | B | C |
| ATOM | 5039 | CG1 | VAL | 185 | 109.105 | 58.990 | 17.335 | 1.00 | 12.43 | B | C |
| ATOM | 5040 | CG2 | VAL | 185 | 110.052 | 61.103 | 16.425 | 1.00 | 1.87 | B | C |
| ATOM | 5041 | C | VAL | 185 | 110.840 | 59.025 | 19.536 | 1.00 | 23.13 | B | C |
| ATOM | 5042 | O | VAL | 185 | 111.756 | 58.206 | 19.510 | 1.00 | 20.28 | B | O |
| ATOM | 5043 | N | GLY | 186 | 109.789 | 58.914 | 20.328 | 1.00 | 27.91 | B | N |
| ATOM | 5044 | CA | GLY | 186 | 109.630 | 57.782 | 21.213 | 1.00 | 29.54 | B | C |
| ATOM | 5045 | C | GLY | 186 | 108.200 | 57.319 | 21.045 | 1.00 | 27.52 | B | C |
| ATOM | 5046 | O | GLY | 186 | 107.308 | 58.138 | 20.839 | 1.00 | 32.88 | B | O |
| ATOM | 5047 | N | ILE | 187 | 107.970 | 56.017 | 21.105 | 1.00 | 20.77 | B | N |
| ATOM | 5048 | CA | ILE | 187 | 106.617 | 55.519 | 20.958 | 1.00 | 19.36 | B | C |
| ATOM | 5049 | CB | ILE | 187 | 106.460 | 54.729 | 19.642 | 1.00 | 17.70 | B | C |
| ATOM | 5050 | CG2 | ILE | 187 | 105.081 | 54.079 | 19.577 | 1.00 | 15.03 | B | C |
| ATOM | 5051 | CG1 | ILE | 187 | 106.639 | 55.676 | 18.454 | 1.00 | 18.22 | B | C |
| ATOM | 5052 | CD1 | ILE | 187 | 106.437 | 55.033 | 17.100 | 1.00 | 19.27 | B | C |
| ATOM | 5053 | C | ILE | 187 | 106.160 | 54.674 | 22.143 | 1.00 | 18.65 | B | C |
| ATOM | 5054 | O | ILE | 187 | 106.852 | 53.763 | 22.590 | 1.00 | 17.55 | B | O |
| ATOM | 5055 | N | VAL | 188 | 104.984 | 55.015 | 22.649 | 1.00 | 23.72 | B | N |
| ATOM | 5056 | CA | VAL | 188 | 104.370 | 54.332 | 23.774 | 1.00 | 23.39 | B | C |
| ATOM | 5057 | CB | VAL | 188 | 104.053 | 55.333 | 24.911 | 1.00 | 24.28 | B | C |
| ATOM | 5058 | CG1 | VAL | 188 | 103.055 | 54.728 | 25.896 | 1.00 | 19.55 | B | C |
| ATOM | 5059 | CG2 | VAL | 188 | 105.320 | 55.715 | 25.625 | 1.00 | 24.70 | B | C |
| ATOM | 5060 | C | VAL | 188 | 103.055 | 53.702 | 23.303 | 1.00 | 21.93 | B | C |
| ATOM | 5061 | O | VAL | 188 | 102.274 | 54.341 | 22.591 | 1.00 | 21.34 | B | O |
| ATOM | 5062 | N | GLN | 189 | 102.815 | 52.453 | 23.686 | 1.00 | 21.90 | B | N |
| ATOM | 5063 | CA | GLN | 189 | 101.580 | 51.785 | 23.312 | 1.00 | 21.58 | B | C |
| ATOM | 5064 | CB | GLN | 189 | 101.857 | 50.545 | 22.463 | 1.00 | 19.75 | B | C |
| ATOM | 5065 | CG | GLN | 189 | 100.577 | 49.784 | 22.128 | 1.00 | 17.26 | B | C |
| ATOM | 5066 | CD | GLN | 189 | 100.819 | 48.495 | 21.377 | 1.00 | 17.97 | B | C |
| ATOM | 5067 | OE1 | GLN | 189 | 99.930 | 47.647 | 21.283 | 1.00 | 19.19 | B | O |
| ATOM | 5068 | NE2 | GLN | 189 | 102.022 | 48.340 | 20.831 | 1.00 | 19.01 | B | N |
| ATOM | 5069 | C | GLN | 189 | 100.820 | 51.386 | 24.572 | 1.00 | 18.57 | B | C |
| ATOM | 5070 | O | GLN | 189 | 101.423 | 50.980 | 25.567 | 1.00 | 16.93 | B | O |
| ATOM | 5071 | N | TYR | 190 | 99.494 | 51.500 | 24.524 | 1.00 | 20.56 | B | N |
| ATOM | 5072 | CA | TYR | 190 | 98.671 | 51.159 | 25.680 | 1.00 | 24.08 | B | C |
| ATOM | 5073 | CB | TYR | 190 | 98.255 | 52.432 | 26.418 | 1.00 | 22.72 | B | C |
| ATOM | 5074 | CG | TYR | 190 | 97.213 | 53.255 | 25.687 | 1.00 | 17.37 | B | C |
| ATOM | 5075 | CD1 | TYR | 190 | 95.849 | 53.072 | 25.929 | 1.00 | 15.48 | B | C |
| ATOM | 5076 | CE1 | TYR | 190 | 94.882 | 53.820 | 25.244 | 1.00 | 17.37 | B | C |
| ATOM | 5077 | CD2 | TYR | 190 | 97.586 | 54.207 | 24.739 | 1.00 | 13.48 | B | C |
| ATOM | 5078 | CE2 | TYR | 190 | 96.624 | 54.957 | 24.051 | 1.00 | 14.90 | B | C |
| ATOM | 5079 | CZ | TYR | 190 | 95.279 | 54.760 | 24.311 | 1.00 | 15.79 | B | C |
| ATOM | 5080 | OH | TYR | 190 | 94.340 | 55.527 | 23.663 | 1.00 | 14.38 | B | O |
| ATOM | 5081 | C | TYR | 190 | 97.428 | 50.342 | 25.344 | 1.00 | 25.93 | B | C |
| ATOM | 5082 | O | TYR | 190 | 97.000 | 50.260 | 24.195 | 1.00 | 26.01 | B | O |
| ATOM | 5083 | N | GLY | 191 | 96.860 | 49.746 | 26.385 | 1.00 | 24.69 | B | N |
| ATOM | 5084 | CA | GLY | 191 | 95.675 | 48.920 | 26.270 | 1.00 | 22.44 | B | C |
| ATOM | 5085 | C | GLY | 191 | 95.277 | 48.649 | 27.701 | 1.00 | 23.88 | B | C |
| ATOM | 5086 | O | GLY | 191 | 94.720 | 49.532 | 28.348 | 1.00 | 27.26 | B | O |
| ATOM | 5087 | N | GLU | 192 | 95.572 | 47.446 | 28.197 | 1.00 | 23.59 | B | N |
| ATOM | 5088 | CA | GLU | 192 | 95.284 | 47.084 | 29.584 | 1.00 | 25.60 | B | C |
| ATOM | 5089 | CB | GLU | 192 | 95.232 | 45.574 | 29.758 | 1.00 | 40.14 | B | C |
| ATOM | 5090 | CG | GLU | 192 | 94.135 | 44.871 | 29.002 | 1.00 | 40.52 | B | C |
| ATOM | 5091 | CD | GLU | 192 | 94.134 | 43.382 | 29.273 | 1.00 | 40.71 | B | C |
| ATOM | 5092 | OE1 | GLU | 192 | 93.230 | 42.690 | 28.759 | 1.00 | 43.60 | B | O |
| ATOM | 5093 | OE2 | GLU | 192 | 95.038 | 42.906 | 29.999 | 1.00 | 38.58 | B | O |
| ATOM | 5094 | C | GLU | 192 | 96.465 | 47.608 | 30.390 | 1.00 | 25.41 | B | C |
| ATOM | 5095 | O | GLU | 192 | 96.325 | 48.027 | 31.536 | 1.00 | 26.78 | B | O |
| ATOM | 5096 | N | ASN | 193 | 97.637 | 47.569 | 29.770 | 1.00 | 17.36 | B | N |
| ATOM | 5097 | CA | ASN | 193 | 98.862 | 48.041 | 30.395 | 1.00 | 18.57 | B | C |
| ATOM | 5098 | CB | ASN | 193 | 99.814 | 46.877 | 30.653 | 1.00 | 57.60 | B | C |
| ATOM | 5099 | CG | ASN | 193 | 99.159 | 45.755 | 31.418 | 1.00 | 60.77 | B | C |
| ATOM | 5100 | OD1 | ASN | 193 | 98.225 | 45.115 | 30.933 | 1.00 | 64.88 | B | O |
| ATOM | 5101 | ND2 | ASN | 193 | 99.644 | 45.509 | 32.626 | 1.00 | 62.88 | B | N |
| ATOM | 5102 | C | ASN | 193 | 99.510 | 49.007 | 29.425 | 1.00 | 16.75 | B | C |
| ATOM | 5103 | O | ASN | 193 | 98.917 | 49.360 | 28.413 | 1.00 | 17.75 | B | O |
| ATOM | 5104 | N | VAL | 194 | 100.735 | 49.418 | 29.728 | 1.00 | 23.63 | B | N |
| ATOM | 5105 | CA | VAL | 194 | 101.454 | 50.346 | 28.866 | 1.00 | 25.97 | B | C |
| ATOM | 5106 | CB | VAL | 194 | 101.516 | 51.750 | 29.490 | 1.00 | 24.85 | B | C |
| ATOM | 5107 | CG1 | VAL | 194 | 102.014 | 52.745 | 28.459 | 1.00 | 25.88 | B | C |
| ATOM | 5108 | CG2 | VAL | 194 | 100.153 | 52.147 | 30.032 | 1.00 | 22.12 | B | C |
| ATOM | 5109 | C | VAL | 194 | 102.887 | 49.864 | 28.661 | 1.00 | 23.74 | B | C |
| ATOM | 5110 | O | VAL | 194 | 103.535 | 49.384 | 29.597 | 1.00 | 21.86 | B | O |

Fig. 19: A-71

| | | | | | | | | | | | |
|---|---|---|---|---|---|---|---|---|---|---|---|
| ATOM | 5111 | N | THR | 195 | 103.397 | 49.986 | 27.444 | 1.00 | 25.03 | B | N |
| ATOM | 5112 | CA | THR | 195 | 104.758 | 49.552 | 27.197 | 1.00 | 26.21 | B | C |
| ATOM | 5113 | CB | THR | 195 | 104.797 | 48.182 | 26.450 | 1.00 | 38.61 | B | C |
| ATOM | 5114 | OG1 | THR | 195 | 104.420 | 48.360 | 25.081 | 1.00 | 42.62 | B | O |
| ATOM | 5115 | CG2 | THR | 195 | 103.828 | 47.195 | 27.087 | 1.00 | 40.24 | B | C |
| ATOM | 5116 | C | THR | 195 | 105.511 | 50.599 | 26.391 | 1.00 | 27.05 | B | C |
| ATOM | 5117 | O | THR | 195 | 104.944 | 51.254 | 25.514 | 1.00 | 29.64 | B | O |
| ATOM | 5118 | N | HIS | 196 | 106.791 | 50.765 | 26.716 | 1.00 | 33.64 | B | N |
| ATOM | 5119 | CA | HIS | 196 | 107.656 | 51.713 | 26.029 | 1.00 | 33.74 | B | C |
| ATOM | 5120 | CB | HIS | 196 | 108.815 | 52.119 | 26.942 | 1.00 | 34.91 | B | C |
| ATOM | 5121 | CG | HIS | 196 | 108.417 | 53.011 | 28.079 | 1.00 | 31.41 | B | C |
| ATOM | 5122 | CD2 | HIS | 196 | 108.084 | 52.725 | 29.360 | 1.00 | 32.04 | B | C |
| ATOM | 5123 | ND1 | HIS | 196 | 108.322 | 54.382 | 27.955 | 1.00 | 30.06 | B | N |
| ATOM | 5124 | CE1 | HIS | 196 | 107.949 | 54.901 | 29.111 | 1.00 | 26.78 | B | C |
| ATOM | 5125 | NE2 | HIS | 196 | 107.797 | 53.918 | 29.979 | 1.00 | 24.99 | B | N |
| ATOM | 5126 | C | HIS | 196 | 108.219 | 51.017 | 24.806 | 1.00 | 33.60 | B | C |
| ATOM | 5127 | O | HIS | 196 | 109.201 | 50.289 | 24.932 | 1.00 | 32.26 | B | O |
| ATOM | 5128 | N | GLU | 197 | 107.609 | 51.216 | 23.636 | 1.00 | 34.73 | B | N |
| ATOM | 5129 | CA | GLU | 197 | 108.123 | 50.583 | 22.417 | 1.00 | 32.06 | B | C |
| ATOM | 5130 | CB | GLU | 197 | 107.313 | 50.999 | 21.193 | 1.00 | 45.57 | B | C |
| ATOM | 5131 | CG | GLU | 197 | 105.913 | 50.386 | 21.130 | 1.00 | 45.91 | B | C |
| ATOM | 5132 | CD | GLU | 197 | 105.911 | 48.876 | 21.303 | 1.00 | 44.98 | B | C |
| ATOM | 5133 | OE1 | GLU | 197 | 106.869 | 48.228 | 20.834 | 1.00 | 43.56 | B | O |
| ATOM | 5134 | OE2 | GLU | 197 | 104.949 | 48.331 | 21.892 | 1.00 | 46.64 | B | O |
| ATOM | 5135 | C | GLU | 197 | 109.595 | 50.958 | 22.245 | 1.00 | 29.53 | B | C |
| ATOM | 5136 | O | GLU | 197 | 110.447 | 50.081 | 22.151 | 1.00 | 34.73 | B | O |
| ATOM | 5137 | N | PHE | 198 | 109.898 | 52.254 | 22.203 | 1.00 | 32.40 | B | N |
| ATOM | 5138 | CA | PHE | 198 | 111.293 | 52.691 | 22.126 | 1.00 | 34.20 | B | C |
| ATOM | 5139 | CB | PHE | 198 | 111.881 | 52.501 | 20.714 | 1.00 | 23.77 | B | C |
| ATOM | 5140 | CG | PHE | 198 | 111.239 | 53.331 | 19.636 | 1.00 | 22.02 | B | C |
| ATOM | 5141 | CD1 | PHE | 198 | 111.379 | 54.711 | 19.614 | 1.00 | 28.16 | B | C |
| ATOM | 5142 | CD2 | PHE | 198 | 110.539 | 52.715 | 18.597 | 1.00 | 16.76 | B | C |
| ATOM | 5143 | CE1 | PHE | 198 | 110.837 | 55.468 | 18.571 | 1.00 | 24.19 | B | C |
| ATOM | 5144 | CE2 | PHE | 198 | 109.990 | 53.460 | 17.548 | 1.00 | 22.67 | B | C |
| ATOM | 5145 | CZ | PHE | 198 | 110.140 | 54.838 | 17.536 | 1.00 | 26.47 | B | C |
| ATOM | 5146 | C | PHE | 198 | 111.471 | 54.120 | 22.642 | 1.00 | 36.88 | B | C |
| ATOM | 5147 | O | PHE | 198 | 110.631 | 54.973 | 22.398 | 1.00 | 38.17 | B | O |
| ATOM | 5148 | N | ASN | 199 | 112.552 | 54.366 | 23.386 | 1.00 | 21.75 | B | N |
| ATOM | 5149 | CA | ASN | 199 | 112.810 | 55.686 | 23.971 | 1.00 | 22.04 | B | C |
| ATOM | 5150 | CB | ASN | 199 | 113.924 | 55.613 | 25.007 | 1.00 | 33.57 | B | C |
| ATOM | 5151 | CG | ASN | 199 | 113.636 | 54.633 | 26.105 | 1.00 | 34.83 | B | C |
| ATOM | 5152 | OD1 | ASN | 199 | 112.614 | 54.717 | 26.785 | 1.00 | 36.36 | B | O |
| ATOM | 5153 | ND2 | ASN | 199 | 114.549 | 53.688 | 26.295 | 1.00 | 33.71 | B | N |
| ATOM | 5154 | C | ASN | 199 | 113.159 | 56.792 | 22.996 | 1.00 | 24.50 | B | C |
| ATOM | 5155 | O | ASN | 199 | 113.569 | 56.546 | 21.862 | 1.00 | 22.31 | B | O |
| ATOM | 5156 | N | LEU | 200 | 113.004 | 58.023 | 23.473 | 1.00 | 27.41 | B | N |
| ATOM | 5157 | CA | LEU | 200 | 113.286 | 59.215 | 22.685 | 1.00 | 29.37 | B | C |
| ATOM | 5158 | CB | LEU | 200 | 113.094 | 60.467 | 23.542 | 1.00 | 22.93 | B | C |
| ATOM | 5159 | CG | LEU | 200 | 111.694 | 61.088 | 23.545 | 1.00 | 20.78 | B | C |
| ATOM | 5160 | CD1 | LEU | 200 | 111.613 | 62.208 | 24.578 | 1.00 | 25.90 | B | C |
| ATOM | 5161 | CD2 | LEU | 200 | 111.375 | 61.607 | 22.140 | 1.00 | 21.95 | B | C |
| ATOM | 5162 | C | LEU | 200 | 114.685 | 59.223 | 22.104 | 1.00 | 29.77 | B | C |
| ATOM | 5163 | O | LEU | 200 | 114.899 | 59.698 | 20.992 | 1.00 | 30.79 | B | O |
| ATOM | 5164 | N | ASN | 201 | 115.635 | 58.685 | 22.856 | 1.00 | 32.06 | B | N |
| ATOM | 5165 | CA | ASN | 201 | 117.027 | 58.660 | 22.426 | 1.00 | 33.91 | B | C |
| ATOM | 5166 | CB | ASN | 201 | 117.920 | 59.105 | 23.578 | 1.00 | 34.75 | B | C |
| ATOM | 5167 | CG | ASN | 201 | 117.838 | 58.168 | 24.769 | 1.00 | 37.03 | B | C |
| ATOM | 5168 | OD1 | ASN | 201 | 118.389 | 58.443 | 25.832 | 1.00 | 37.17 | B | O |
| ATOM | 5169 | ND2 | ASN | 201 | 117.147 | 57.052 | 24.592 | 1.00 | 34.87 | B | N |
| ATOM | 5170 | C | ASN | 201 | 117.517 | 57.309 | 21.936 | 1.00 | 33.96 | B | C |
| ATOM | 5171 | O | ASN | 201 | 118.723 | 57.111 | 21.825 | 1.00 | 29.86 | B | O |
| ATOM | 5172 | N | LYS | 202 | 116.603 | 56.382 | 21.653 | 1.00 | 35.80 | B | N |
| ATOM | 5173 | CA | LYS | 202 | 116.990 | 55.051 | 21.183 | 1.00 | 35.92 | B | C |
| ATOM | 5174 | CB | LYS | 202 | 115.786 | 54.107 | 21.160 | 1.00 | 34.30 | B | C |
| ATOM | 5175 | CG | LYS | 202 | 116.107 | 52.652 | 20.788 | 1.00 | 35.84 | B | C |
| ATOM | 5176 | CD | LYS | 202 | 116.841 | 51.929 | 21.898 | 1.00 | 37.75 | B | C |
| ATOM | 5177 | CE | LYS | 202 | 116.185 | 52.179 | 23.273 | 1.00 | 43.50 | B | C |
| ATOM | 5178 | NZ | LYS | 202 | 114.729 | 51.801 | 23.388 | 1.00 | 42.52 | B | N |
| ATOM | 5179 | C | LYS | 202 | 117.617 | 55.071 | 19.800 | 1.00 | 34.79 | B | C |
| ATOM | 5180 | O | LYS | 202 | 118.667 | 54.472 | 19.589 | 1.00 | 32.07 | B | O |
| ATOM | 5181 | N | TYR | 203 | 116.977 | 55.747 | 18.852 | 1.00 | 23.81 | B | N |
| ATOM | 5182 | CA | TYR | 203 | 117.509 | 55.815 | 17.491 | 1.00 | 23.49 | B | C |
| ATOM | 5183 | CB | TYR | 203 | 116.466 | 55.300 | 16.499 | 1.00 | 32.41 | B | C |

Fig. 19: A-72

| | | | | | | | | | | | |
|---|---|---|---|---|---|---|---|---|---|---|---|
| ATOM | 5184 | CG | TYR | 203 | 115.907 | 53.951 | 16.886 | 1.00 | 31.08 | B | C |
| ATOM | 5185 | CD1 | TYR | 203 | 114.665 | 53.844 | 17.509 | 1.00 | 31.69 | B | C |
| ATOM | 5186 | CE1 | TYR | 203 | 114.179 | 52.613 | 17.930 | 1.00 | 28.16 | B | C |
| ATOM | 5187 | CD2 | TYR | 203 | 116.649 | 52.784 | 16.689 | 1.00 | 33.97 | B | C |
| ATOM | 5188 | CE2 | TYR | 203 | 116.173 | 51.550 | 17.109 | 1.00 | 36.72 | B | C |
| ATOM | 5189 | CZ | TYR | 203 | 114.940 | 51.474 | 17.730 | 1.00 | 36.34 | B | C |
| ATOM | 5190 | OH | TYR | 203 | 114.466 | 50.262 | 18.169 | 1.00 | 41.34 | B | O |
| ATOM | 5191 | C | TYR | 203 | 117.957 | 57.230 | 17.114 | 1.00 | 24.13 | B | C |
| ATOM | 5192 | O | TYR | 203 | 117.268 | 58.211 | 17.387 | 1.00 | 22.30 | B | O |
| ATOM | 5193 | N | SER | 204 | 119.122 | 57.323 | 16.484 | 1.00 | 32.64 | B | N |
| ATOM | 5194 | CA | SER | 204 | 119.693 | 58.608 | 16.089 | 1.00 | 34.49 | B | C |
| ATOM | 5195 | CB | SER | 204 | 121.199 | 58.588 | 16.320 | 1.00 | 50.27 | B | C |
| ATOM | 5196 | OG | SER | 204 | 121.780 | 57.499 | 15.621 | 1.00 | 52.10 | B | O |
| ATOM | 5197 | C | SER | 204 | 119.432 | 58.924 | 14.632 | 1.00 | 37.07 | B | C |
| ATOM | 5198 | O | SER | 204 | 119.922 | 59.919 | 14.118 | 1.00 | 37.58 | B | O |
| ATOM | 5199 | N | SER | 205 | 118.657 | 58.082 | 13.966 | 1.00 | 56.25 | B | N |
| ATOM | 5200 | CA | SER | 205 | 118.379 | 58.289 | 12.558 | 1.00 | 55.91 | B | C |
| ATOM | 5201 | CB | SER | 205 | 119.256 | 57.357 | 11.734 | 1.00 | 30.45 | B | C |
| ATOM | 5202 | OG | SER | 205 | 118.818 | 57.302 | 10.393 | 1.00 | 35.94 | B | O |
| ATOM | 5203 | C | SER | 205 | 116.918 | 58.067 | 12.195 | 1.00 | 54.04 | B | C |
| ATOM | 5204 | O | SER | 205 | 116.208 | 57.320 | 12.866 | 1.00 | 50.30 | B | O |
| ATOM | 5205 | N | THR | 206 | 116.477 | 58.718 | 11.122 | 1.00 | 22.26 | B | N |
| ATOM | 5206 | CA | THR | 206 | 115.105 | 58.589 | 10.661 | 1.00 | 23.61 | B | C |
| ATOM | 5207 | CB | THR | 206 | 114.799 | 59.611 | 9.560 | 1.00 | 36.04 | B | C |
| ATOM | 5208 | OG1 | THR | 206 | 114.968 | 60.935 | 10.086 | 1.00 | 34.85 | B | O |
| ATOM | 5209 | CG2 | THR | 206 | 113.364 | 59.438 | 9.047 | 1.00 | 34.41 | B | C |
| ATOM | 5210 | C | THR | 206 | 114.780 | 57.188 | 10.144 | 1.00 | 24.20 | B | C |
| ATOM | 5211 | O | THR | 206 | 113.676 | 56.683 | 10.363 | 1.00 | 26.99 | B | O |
| ATOM | 5212 | N | GLU | 207 | 115.719 | 56.554 | 9.447 | 1.00 | 31.43 | B | N |
| ATOM | 5213 | CA | GLU | 207 | 115.444 | 55.210 | 8.964 | 1.00 | 30.59 | B | C |
| ATOM | 5214 | CB | GLU | 207 | 116.448 | 54.791 | 7.893 | 1.00 | 74.76 | B | C |
| ATOM | 5215 | CG | GLU | 207 | 117.897 | 54.985 | 8.248 | 1.00 | 75.48 | B | C |
| ATOM | 5216 | CD | GLU | 207 | 118.817 | 54.402 | 7.189 | 1.00 | 76.89 | B | C |
| ATOM | 5217 | OE1 | GLU | 207 | 118.595 | 54.668 | 5.982 | 1.00 | 76.12 | B | O |
| ATOM | 5218 | OE2 | GLU | 207 | 119.765 | 53.679 | 7.565 | 1.00 | 75.79 | B | O |
| ATOM | 5219 | C | GLU | 207 | 115.462 | 54.237 | 10.141 | 1.00 | 31.09 | B | C |
| ATOM | 5220 | O | GLU | 207 | 114.647 | 53.315 | 10.194 | 1.00 | 31.04 | B | O |
| ATOM | 5221 | N | GLU | 208 | 116.373 | 54.449 | 11.093 | 1.00 | 40.73 | B | N |
| ATOM | 5222 | CA | GLU | 208 | 116.441 | 53.584 | 12.267 | 1.00 | 42.46 | B | C |
| ATOM | 5223 | CB | GLU | 208 | 117.542 | 54.038 | 13.230 | 1.00 | 57.02 | B | C |
| ATOM | 5224 | CG | GLU | 208 | 118.951 | 53.899 | 12.682 | 1.00 | 54.49 | B | C |
| ATOM | 5225 | CD | GLU | 208 | 120.022 | 54.254 | 13.703 | 1.00 | 54.01 | B | C |
| ATOM | 5226 | OE1 | GLU | 208 | 121.217 | 54.253 | 13.333 | 1.00 | 59.78 | B | O |
| ATOM | 5227 | OE2 | GLU | 208 | 119.669 | 54.533 | 14.873 | 1.00 | 52.73 | B | O |
| ATOM | 5228 | C | GLU | 208 | 115.100 | 53.611 | 12.991 | 1.00 | 43.16 | B | C |
| ATOM | 5229 | O | GLU | 208 | 114.637 | 52.584 | 13.489 | 1.00 | 44.16 | B | O |
| ATOM | 5230 | N | VAL | 209 | 114.478 | 54.787 | 13.046 | 1.00 | 30.06 | B | N |
| ATOM | 5231 | CA | VAL | 209 | 113.190 | 54.922 | 13.709 | 1.00 | 28.98 | B | C |
| ATOM | 5232 | CB | VAL | 209 | 112.879 | 56.399 | 14.058 | 1.00 | 17.77 | B | C |
| ATOM | 5233 | CG1 | VAL | 209 | 111.379 | 56.612 | 14.232 | 1.00 | 18.10 | B | C |
| ATOM | 5234 | CG2 | VAL | 209 | 113.575 | 56.762 | 15.349 | 1.00 | 18.79 | B | C |
| ATOM | 5235 | C | VAL | 209 | 112.098 | 54.359 | 12.820 | 1.00 | 27.00 | B | C |
| ATOM | 5236 | O | VAL | 209 | 111.198 | 53.660 | 13.296 | 1.00 | 25.96 | B | O |
| ATOM | 5237 | N | LEU | 210 | 112.187 | 54.655 | 11.529 | 1.00 | 33.19 | B | N |
| ATOM | 5238 | CA | LEU | 210 | 111.207 | 54.164 | 10.570 | 1.00 | 33.52 | B | C |
| ATOM | 5239 | CB | LEU | 210 | 111.557 | 54.643 | 9.168 | 1.00 | 15.67 | B | C |
| ATOM | 5240 | CG | LEU | 210 | 110.629 | 55.672 | 8.535 | 1.00 | 15.91 | B | C |
| ATOM | 5241 | CD1 | LEU | 210 | 111.182 | 55.981 | 7.171 | 1.00 | 12.46 | B | C |
| ATOM | 5242 | CD2 | LEU | 210 | 109.191 | 55.157 | 8.437 | 1.00 | 9.36 | B | C |
| ATOM | 5243 | C | LEU | 210 | 111.152 | 52.639 | 10.571 | 1.00 | 31.78 | B | C |
| ATOM | 5244 | O | LEU | 210 | 110.090 | 52.042 | 10.382 | 1.00 | 32.55 | B | O |
| ATOM | 5245 | N | VAL | 211 | 112.307 | 52.017 | 10.779 | 1.00 | 24.37 | B | N |
| ATOM | 5246 | CA | VAL | 211 | 112.404 | 50.569 | 10.809 | 1.00 | 24.13 | B | C |
| ATOM | 5247 | CB | VAL | 211 | 113.852 | 50.123 | 10.575 | 1.00 | 20.01 | B | C |
| ATOM | 5248 | CG1 | VAL | 211 | 114.002 | 48.647 | 10.897 | 1.00 | 22.19 | B | C |
| ATOM | 5249 | CG2 | VAL | 211 | 114.239 | 50.405 | 9.118 | 1.00 | 20.62 | B | C |
| ATOM | 5250 | C | VAL | 211 | 111.913 | 49.997 | 12.129 | 1.00 | 23.38 | B | C |
| ATOM | 5251 | O | VAL | 211 | 111.260 | 48.958 | 12.164 | 1.00 | 24.06 | B | O |
| ATOM | 5252 | N | ALA | 212 | 112.230 | 50.674 | 13.221 | 1.00 | 40.83 | B | N |
| ATOM | 5253 | CA | ALA | 212 | 111.803 | 50.203 | 14.526 | 1.00 | 39.81 | B | C |
| ATOM | 5254 | CB | ALA | 212 | 112.489 | 51.000 | 15.612 | 1.00 | 28.52 | B | C |
| ATOM | 5255 | C | ALA | 212 | 110.295 | 50.339 | 14.650 | 1.00 | 37.62 | B | C |
| ATOM | 5256 | O | ALA | 212 | 109.626 | 49.493 | 15.256 | 1.00 | 37.56 | B | O |

Fig. 19: A-73

| | | | | | | | | | | | |
|---|---|---|---|---|---|---|---|---|---|---|---|
| ATOM | 5257 | N | ALA | 213 | 109.759 | 51.408 | 14.069 | 1.00 | 31.97 | B | N |
| ATOM | 5258 | CA | ALA | 213 | 108.324 | 51.658 | 14.122 | 1.00 | 33.14 | B | C |
| ATOM | 5259 | CB | ALA | 213 | 107.999 | 52.998 | 13.459 | 1.00 | 19.99 | B | C |
| ATOM | 5260 | C | ALA | 213 | 107.530 | 50.535 | 13.458 | 1.00 | 31.94 | B | C |
| ATOM | 5261 | O | ALA | 213 | 106.556 | 50.029 | 14.025 | 1.00 | 29.57 | B | O |
| ATOM | 5262 | N | ASN | 214 | 107.954 | 50.142 | 12.258 | 1.00 | 35.89 | B | N |
| ATOM | 5263 | CA | ASN | 214 | 107.264 | 49.091 | 11.524 | 1.00 | 39.76 | B | C |
| ATOM | 5264 | CB | ASN | 214 | 107.804 | 48.970 | 10.100 | 1.00 | 79.46 | B | C |
| ATOM | 5265 | CG | ASN | 214 | 107.278 | 50.049 | 9.190 | 1.00 | 81.19 | B | C |
| ATOM | 5266 | OD1 | ASN | 214 | 107.668 | 51.210 | 9.296 | 1.00 | 83.12 | B | O |
| ATOM | 5267 | ND2 | ASN | 214 | 106.379 | 49.676 | 8.289 | 1.00 | 81.61 | B | N |
| ATOM | 5268 | C | ASN | 214 | 107.348 | 47.738 | 12.207 | 1.00 | 42.15 | B | C |
| ATOM | 5269 | O | ASN | 214 | 106.583 | 46.829 | 11.891 | 1.00 | 42.87 | B | O |
| ATOM | 5270 | N | LYS | 215 | 108.271 | 47.596 | 13.148 | 1.00 | 30.37 | B | N |
| ATOM | 5271 | CA | LYS | 215 | 108.418 | 46.326 | 13.856 | 1.00 | 30.81 | B | C |
| ATOM | 5272 | CB | LYS | 215 | 109.892 | 46.059 | 14.209 | 1.00 | 46.54 | B | C |
| ATOM | 5273 | CG | LYS | 215 | 110.791 | 45.922 | 12.978 | 1.00 | 54.12 | B | C |
| ATOM | 5274 | CD | LYS | 215 | 112.062 | 45.124 | 13.256 | 1.00 | 57.66 | B | C |
| ATOM | 5275 | CE | LYS | 215 | 112.950 | 45.778 | 14.311 | 1.00 | 61.12 | B | C |
| ATOM | 5276 | NZ | LYS | 215 | 114.249 | 45.057 | 14.483 | 1.00 | 62.11 | B | N |
| ATOM | 5277 | C | LYS | 215 | 107.560 | 46.274 | 15.113 | 1.00 | 28.94 | B | C |
| ATOM | 5278 | O | LYS | 215 | 107.568 | 45.277 | 15.832 | 1.00 | 30.16 | B | O |
| ATOM | 5279 | N | ILE | 216 | 106.809 | 47.341 | 15.377 | 1.00 | 44.32 | B | N |
| ATOM | 5280 | CA | ILE | 216 | 105.945 | 47.362 | 16.553 | 1.00 | 41.14 | B | C |
| ATOM | 5281 | CB | ILE | 216 | 105.443 | 48.776 | 16.874 | 1.00 | 15.33 | B | C |
| ATOM | 5282 | CG2 | ILE | 216 | 104.492 | 48.730 | 18.038 | 1.00 | 12.11 | B | C |
| ATOM | 5283 | CG1 | ILE | 216 | 106.616 | 49.674 | 17.243 | 1.00 | 12.01 | B | C |
| ATOM | 5284 | CD1 | ILE | 216 | 106.191 | 51.073 | 17.602 | 1.00 | 10.70 | B | C |
| ATOM | 5285 | C | ILE | 216 | 104.740 | 46.447 | 16.369 | 1.00 | 39.58 | B | C |
| ATOM | 5286 | O | ILE | 216 | 104.035 | 46.498 | 15.361 | 1.00 | 40.28 | B | O |
| ATOM | 5287 | N | VAL | 217 | 104.524 | 45.611 | 17.372 | 1.00 | 36.13 | B | N |
| ATOM | 5288 | CA | VAL | 217 | 103.436 | 44.647 | 17.392 | 1.00 | 37.90 | B | C |
| ATOM | 5289 | CB | VAL | 217 | 103.949 | 43.284 | 17.887 | 1.00 | 59.95 | B | C |
| ATOM | 5290 | CG1 | VAL | 217 | 102.793 | 42.367 | 18.217 | 1.00 | 59.95 | B | C |
| ATOM | 5291 | CG2 | VAL | 217 | 104.837 | 42.666 | 16.829 | 1.00 | 59.95 | B | C |
| ATOM | 5292 | C | VAL | 217 | 102.316 | 45.111 | 18.311 | 1.00 | 39.06 | B | C |
| ATOM | 5293 | O | VAL | 217 | 102.565 | 45.725 | 19.352 | 1.00 | 38.52 | B | O |
| ATOM | 5294 | N | GLN | 218 | 101.084 | 44.809 | 17.914 | 1.00 | 32.14 | B | N |
| ATOM | 5295 | CA | GLN | 218 | 99.907 | 45.181 | 18.687 | 1.00 | 32.80 | B | C |
| ATOM | 5296 | CB | GLN | 218 | 98.646 | 44.976 | 17.850 | 1.00 | 28.44 | B | C |
| ATOM | 5297 | CG | GLN | 218 | 97.378 | 45.433 | 18.528 | 1.00 | 28.44 | B | C |
| ATOM | 5298 | CD | GLN | 218 | 96.153 | 45.273 | 17.644 | 1.00 | 28.44 | B | C |
| ATOM | 5299 | OE1 | GLN | 218 | 95.096 | 45.843 | 17.928 | 1.00 | 28.44 | B | O |
| ATOM | 5300 | NE2 | GLN | 218 | 96.283 | 44.490 | 16.571 | 1.00 | 28.44 | B | N |
| ATOM | 5301 | C | GLN | 218 | 99.856 | 44.288 | 19.913 | 1.00 | 32.25 | B | C |
| ATOM | 5302 | O | GLN | 218 | 99.948 | 43.079 | 19.792 | 1.00 | 36.00 | B | O |
| ATOM | 5303 | N | ARG | 219 | 99.709 | 44.883 | 21.091 | 1.00 | 14.17 | B | N |
| ATOM | 5304 | CA | ARG | 219 | 99.664 | 44.114 | 22.330 | 1.00 | 13.82 | B | C |
| ATOM | 5305 | CB | ARG | 219 | 100.490 | 44.828 | 23.394 | 1.00 | 43.11 | B | C |
| ATOM | 5306 | CG | ARG | 219 | 101.627 | 45.640 | 22.823 | 1.00 | 43.11 | B | C |
| ATOM | 5307 | CD | ARG | 219 | 102.594 | 46.039 | 23.901 | 1.00 | 43.11 | B | C |
| ATOM | 5308 | NE | ARG | 219 | 103.597 | 45.007 | 24.124 | 1.00 | 43.11 | B | N |
| ATOM | 5309 | CZ | ARG | 219 | 104.694 | 44.867 | 23.384 | 1.00 | 43.11 | B | C |
| ATOM | 5310 | NH1 | ARG | 219 | 104.921 | 45.705 | 22.369 | 1.00 | 43.11 | B | N |
| ATOM | 5311 | NH2 | ARG | 219 | 105.566 | 43.900 | 23.661 | 1.00 | 43.11 | B | N |
| ATOM | 5312 | C | ARG | 219 | 98.221 | 43.910 | 22.821 | 1.00 | 15.03 | B | C |
| ATOM | 5313 | O | ARG | 219 | 97.976 | 43.309 | 23.871 | 1.00 | 15.04 | B | O |
| ATOM | 5314 | N | GLY | 220 | 97.269 | 44.423 | 22.048 | 1.00 | 30.91 | B | N |
| ATOM | 5315 | CA | GLY | 220 | 95.868 | 44.283 | 22.402 | 1.00 | 30.52 | B | C |
| ATOM | 5316 | C | GLY | 220 | 95.495 | 44.884 | 23.742 | 1.00 | 30.19 | B | C |
| ATOM | 5317 | O | GLY | 220 | 96.246 | 45.674 | 24.327 | 1.00 | 28.53 | B | O |
| ATOM | 5318 | N | GLY | 221 | 94.316 | 44.511 | 24.222 | 1.00 | 22.15 | B | N |
| ATOM | 5319 | CA | GLY | 221 | 93.852 | 45.009 | 25.500 | 1.00 | 20.72 | B | C |
| ATOM | 5320 | C | GLY | 221 | 92.348 | 44.902 | 25.652 | 1.00 | 21.14 | B | C |
| ATOM | 5321 | O | GLY | 221 | 91.598 | 45.328 | 24.776 | 1.00 | 17.94 | B | O |
| ATOM | 5322 | N | ARG | 222 | 91.897 | 44.327 | 26.760 | 1.00 | 28.36 | B | N |
| ATOM | 5323 | CA | ARG | 222 | 90.467 | 44.199 | 27.011 | 1.00 | 29.07 | B | C |
| ATOM | 5324 | CB | ARG | 222 | 90.204 | 43.114 | 28.053 | 1.00 | 26.86 | B | C |
| ATOM | 5325 | CG | ARG | 222 | 90.365 | 41.713 | 27.491 | 1.00 | 26.86 | B | C |
| ATOM | 5326 | CD | ARG | 222 | 90.427 | 40.663 | 28.578 | 1.00 | 26.86 | B | C |
| ATOM | 5327 | NE | ARG | 222 | 91.679 | 40.734 | 29.316 | 1.00 | 26.86 | B | N |
| ATOM | 5328 | CZ | ARG | 222 | 92.021 | 39.885 | 30.274 | 1.00 | 26.86 | B | C |
| ATOM | 5329 | NH1 | ARG | 222 | 91.201 | 38.895 | 30.612 | 1.00 | 26.86 | B | N |

Fig. 19: A-74

| | | | | | | | | | | | |
|---|---|---|---|---|---|---|---|---|---|---|---|
| ATOM | 5330 | NH2 | ARG | 222 | 93.184 | 40.027 | 30.893 | 1.00 | 26.86 | B | N |
| ATOM | 5331 | C | ARG | 222 | 89.899 | 45.529 | 27.482 | 1.00 | 29.12 | B | C |
| ATOM | 5332 | O | ARG | 222 | 88.686 | 45.686 | 27.599 | 1.00 | 29.89 | B | O |
| ATOM | 5333 | N | GLN | 223 | 90.792 | 46.477 | 27.756 | 1.00 | 34.74 | B | N |
| ATOM | 5334 | CA | GLN | 223 | 90.423 | 47.826 | 28.182 | 1.00 | 33.03 | B | C |
| ATOM | 5335 | CB | GLN | 223 | 90.700 | 48.050 | 29.677 | 1.00 | 36.16 | B | C |
| ATOM | 5336 | CG | GLN | 223 | 89.723 | 47.394 | 30.641 | 1.00 | 37.60 | B | C |
| ATOM | 5337 | CD | GLN | 223 | 90.065 | 45.957 | 30.915 | 1.00 | 38.01 | B | C |
| ATOM | 5338 | OE1 | GLN | 223 | 91.209 | 45.635 | 31.230 | 1.00 | 38.41 | B | O |
| ATOM | 5339 | NE2 | GLN | 223 | 89.075 | 45.080 | 30.811 | 1.00 | 38.45 | B | N |
| ATOM | 5340 | C | GLN | 223 | 91.221 | 48.849 | 27.372 | 1.00 | 33.77 | B | C |
| ATOM | 5341 | O | GLN | 223 | 92.122 | 48.487 | 26.619 | 1.00 | 33.25 | B | O |
| ATOM | 5342 | N | THR | 224 | 90.893 | 50.126 | 27.535 | 1.00 | 56.95 | B | N |
| ATOM | 5343 | CA | THR | 224 | 91.572 | 51.197 | 26.820 | 1.00 | 54.83 | B | C |
| ATOM | 5344 | CB | THR | 224 | 90.628 | 51.834 | 25.793 | 1.00 | 7.14 | B | C |
| ATOM | 5345 | OG1 | THR | 224 | 90.118 | 50.811 | 24.930 | 1.00 | 7.13 | B | O |
| ATOM | 5346 | CG2 | THR | 224 | 91.357 | 52.895 | 24.965 | 1.00 | 4.73 | B | C |
| ATOM | 5347 | C | THR | 224 | 92.002 | 52.252 | 27.829 | 1.00 | 51.84 | B | C |
| ATOM | 5348 | O | THR | 224 | 91.290 | 53.221 | 28.067 | 1.00 | 48.33 | B | O |
| ATOM | 5349 | N | MET | 225 | 93.175 | 52.061 | 28.419 | 1.00 | 27.08 | B | N |
| ATOM | 5350 | CA | MET | 225 | 93.679 | 52.980 | 29.426 | 1.00 | 27.97 | B | C |
| ATOM | 5351 | CB | MET | 225 | 94.712 | 52.269 | 30.301 | 1.00 | 32.79 | B | C |
| ATOM | 5352 | CG | MET | 225 | 94.280 | 50.904 | 30.804 | 1.00 | 30.22 | B | C |
| ATOM | 5353 | SD | MET | 225 | 92.971 | 50.963 | 31.995 | 1.00 | 37.96 | B | S |
| ATOM | 5354 | CE | MET | 225 | 93.153 | 49.343 | 32.760 | 1.00 | 34.54 | B | C |
| ATOM | 5355 | C | MET | 225 | 94.304 | 54.237 | 28.846 | 1.00 | 29.00 | B | C |
| ATOM | 5356 | O | MET | 225 | 95.442 | 54.561 | 29.180 | 1.00 | 30.46 | B | O |
| ATOM | 5357 | N | THR | 226 | 93.571 | 54.953 | 27.997 | 1.00 | 32.08 | B | N |
| ATOM | 5358 | CA | THR | 226 | 94.102 | 56.178 | 27.393 | 1.00 | 31.55 | B | C |
| ATOM | 5359 | CB | THR | 226 | 93.013 | 56.963 | 26.655 | 1.00 | 28.80 | B | C |
| ATOM | 5360 | OG1 | THR | 226 | 92.395 | 56.132 | 25.665 | 1.00 | 30.82 | B | O |
| ATOM | 5361 | CG2 | THR | 226 | 93.620 | 58.170 | 25.976 | 1.00 | 26.52 | B | C |
| ATOM | 5362 | C | THR | 226 | 94.735 | 57.104 | 28.438 | 1.00 | 30.15 | B | C |
| ATOM | 5363 | O | THR | 226 | 95.804 | 57.672 | 28.216 | 1.00 | 24.84 | B | O |
| ATOM | 5364 | N | ALA | 227 | 94.075 | 57.249 | 29.581 | 1.00 | 17.95 | B | N |
| ATOM | 5365 | CA | ALA | 227 | 94.594 | 58.094 | 30.645 | 1.00 | 16.89 | B | C |
| ATOM | 5366 | CB | ALA | 227 | 93.655 | 58.069 | 31.829 | 1.00 | 18.36 | B | C |
| ATOM | 5367 | C | ALA | 227 | 95.975 | 57.633 | 31.076 | 1.00 | 17.55 | B | C |
| ATOM | 5368 | O | ALA | 227 | 96.898 | 58.439 | 31.199 | 1.00 | 18.35 | B | O |
| ATOM | 5369 | N | LEU | 228 | 96.111 | 56.331 | 31.307 | 1.00 | 19.16 | B | N |
| ATOM | 5370 | CA | LEU | 228 | 97.384 | 55.752 | 31.728 | 1.00 | 17.60 | B | C |
| ATOM | 5371 | CB | LEU | 228 | 97.206 | 54.252 | 32.017 | 1.00 | 6.84 | B | C |
| ATOM | 5372 | CG | LEU | 228 | 98.453 | 53.498 | 32.483 | 1.00 | 14.73 | B | C |
| ATOM | 5373 | CD1 | LEU | 228 | 99.020 | 54.157 | 33.734 | 1.00 | 12.32 | B | C |
| ATOM | 5374 | CD2 | LEU | 228 | 98.097 | 52.064 | 32.732 | 1.00 | 11.78 | B | C |
| ATOM | 5375 | C | LEU | 228 | 98.463 | 55.955 | 30.662 | 1.00 | 16.78 | B | C |
| ATOM | 5376 | O | LEU | 228 | 99.605 | 56.321 | 30.971 | 1.00 | 19.76 | B | O |
| ATOM | 5377 | N | GLY | 229 | 98.094 | 55.713 | 29.408 | 1.00 | 21.79 | B | N |
| ATOM | 5378 | CA | GLY | 229 | 99.033 | 55.877 | 28.318 | 1.00 | 24.15 | B | C |
| ATOM | 5379 | C | GLY | 229 | 99.620 | 57.267 | 28.293 | 1.00 | 26.71 | B | C |
| ATOM | 5380 | O | GLY | 229 | 100.843 | 57.422 | 28.296 | 1.00 | 27.30 | B | O |
| ATOM | 5381 | N | ILE | 230 | 98.756 | 58.281 | 28.280 | 1.00 | 20.54 | B | N |
| ATOM | 5382 | CA | ILE | 230 | 99.216 | 59.666 | 28.259 | 1.00 | 21.87 | B | C |
| ATOM | 5383 | CB | ILE | 230 | 98.039 | 60.677 | 28.160 | 1.00 | 18.79 | B | C |
| ATOM | 5384 | CG2 | ILE | 230 | 98.595 | 62.090 | 28.034 | 1.00 | 18.79 | B | C |
| ATOM | 5385 | CG1 | ILE | 230 | 97.174 | 60.370 | 26.933 | 1.00 | 18.79 | B | C |
| ATOM | 5386 | CD1 | ILE | 230 | 95.945 | 61.225 | 26.807 | 1.00 | 18.79 | B | C |
| ATOM | 5387 | C | ILE | 230 | 100.042 | 60.007 | 29.505 | 1.00 | 22.13 | B | C |
| ATOM | 5388 | O | ILE | 230 | 101.101 | 60.634 | 29.402 | 1.00 | 20.06 | B | O |
| ATOM | 5389 | N | ASP | 231 | 99.566 | 59.595 | 30.677 | 1.00 | 30.92 | B | N |
| ATOM | 5390 | CA | ASP | 231 | 100.286 | 59.876 | 31.916 | 1.00 | 29.32 | B | C |
| ATOM | 5391 | CB | ASP | 231 | 99.494 | 59.354 | 33.116 | 1.00 | 27.91 | B | C |
| ATOM | 5392 | CG | ASP | 231 | 99.993 | 59.917 | 34.442 | 1.00 | 34.91 | B | C |
| ATOM | 5393 | OD1 | ASP | 231 | 99.939 | 61.155 | 34.644 | 1.00 | 33.67 | B | O |
| ATOM | 5394 | OD2 | ASP | 231 | 100.432 | 59.112 | 35.288 | 1.00 | 38.45 | B | O |
| ATOM | 5395 | C | ASP | 231 | 101.676 | 59.231 | 31.884 | 1.00 | 30.30 | B | C |
| ATOM | 5396 | O | ASP | 231 | 102.669 | 59.838 | 32.318 | 1.00 | 27.52 | B | O |
| ATOM | 5397 | N | THR | 232 | 101.741 | 58.007 | 31.361 | 1.00 | 43.37 | B | N |
| ATOM | 5398 | CA | THR | 232 | 102.998 | 57.276 | 31.260 | 1.00 | 42.16 | B | C |
| ATOM | 5399 | CB | THR | 232 | 102.768 | 55.830 | 30.801 | 1.00 | 59.43 | B | C |
| ATOM | 5400 | OG1 | THR | 232 | 101.963 | 55.148 | 31.771 | 1.00 | 57.94 | B | O |
| ATOM | 5401 | CG2 | THR | 232 | 104.097 | 55.098 | 30.645 | 1.00 | 52.97 | B | C |
| ATOM | 5402 | C | THR | 232 | 103.939 | 57.959 | 30.274 | 1.00 | 42.79 | B | C |

Fig. 19: A-75

| | | | | | | | | | | | |
|---|---|---|---|---|---|---|---|---|---|---|---|
| ATOM | 5403 | O | THR | 232 | 105.153 | 58.050 | 30.509 | 1.00 | 42.96 | B | O |
| ATOM | 5404 | N | ALA | 233 | 103.383 | 58.427 | 29.161 | 1.00 | 22.02 | B | N |
| ATOM | 5405 | CA | ALA | 233 | 104.202 | 59.116 | 28.179 | 1.00 | 24.67 | B | C |
| ATOM | 5406 | CB | ALA | 233 | 103.373 | 59.472 | 26.961 | 1.00 | 49.88 | B | C |
| ATOM | 5407 | C | ALA | 233 | 104.752 | 60.385 | 28.836 | 1.00 | 26.98 | B | C |
| ATOM | 5408 | O | ALA | 233 | 105.862 | 60.834 | 28.532 | 1.00 | 28.89 | B | O |
| ATOM | 5409 | N | ARG | 234 | 103.967 | 60.947 | 29.751 | 1.00 | 50.27 | B | N |
| ATOM | 5410 | CA | ARG | 234 | 104.361 | 62.165 | 30.431 | 1.00 | 53.37 | B | C |
| ATOM | 5411 | CB | ARG | 234 | 103.146 | 62.842 | 31.077 | 1.00 | 50.29 | B | C |
| ATOM | 5412 | CG | ARG | 234 | 103.377 | 64.312 | 31.390 | 1.00 | 50.29 | B | C |
| ATOM | 5413 | CD | ARG | 234 | 102.536 | 64.816 | 32.561 | 1.00 | 50.29 | B | C |
| ATOM | 5414 | NE | ARG | 234 | 103.103 | 64.432 | 33.852 | 1.00 | 50.29 | B | N |
| ATOM | 5415 | CZ | ARG | 234 | 102.668 | 63.418 | 34.592 | 1.00 | 50.29 | B | C |
| ATOM | 5416 | NH1 | ARG | 234 | 101.650 | 62.682 | 34.172 | 1.00 | 50.29 | B | N |
| ATOM | 5417 | NH2 | ARG | 234 | 103.258 | 63.135 | 35.744 | 1.00 | 50.29 | B | N |
| ATOM | 5418 | C | ARG | 234 | 105.406 | 61.904 | 31.498 | 1.00 | 55.50 | B | C |
| ATOM | 5419 | O | ARG | 234 | 106.556 | 62.316 | 31.368 | 1.00 | 55.55 | B | O |
| ATOM | 5420 | N | LYS | 235 | 105.009 | 61.196 | 32.547 | 1.00 | 27.28 | B | N |
| ATOM | 5421 | CA | LYS | 235 | 105.914 | 60.939 | 33.660 | 1.00 | 27.23 | B | C |
| ATOM | 5422 | CB | LYS | 235 | 105.129 | 60.356 | 34.848 | 1.00 | 39.45 | B | C |
| ATOM | 5423 | CG | LYS | 235 | 104.888 | 58.857 | 34.831 | 1.00 | 40.60 | B | C |
| ATOM | 5424 | CD | LYS | 235 | 104.027 | 58.450 | 36.030 | 1.00 | 40.42 | B | C |
| ATOM | 5425 | CE | LYS | 235 | 104.119 | 56.955 | 36.346 | 1.00 | 41.22 | B | C |
| ATOM | 5426 | NZ | LYS | 235 | 103.715 | 56.073 | 35.205 | 1.00 | 41.98 | B | N |
| ATOM | 5427 | C | LYS | 235 | 107.149 | 60.078 | 33.375 | 1.00 | 27.37 | B | C |
| ATOM | 5428 | O | LYS | 235 | 108.112 | 60.118 | 34.130 | 1.00 | 27.71 | B | O |
| ATOM | 5429 | N | GLU | 236 | 107.133 | 59.313 | 32.290 | 1.00 | 28.33 | B | N |
| ATOM | 5430 | CA | GLU | 236 | 108.264 | 58.454 | 31.964 | 1.00 | 29.95 | B | C |
| ATOM | 5431 | CB | GLU | 236 | 107.803 | 56.992 | 31.884 | 1.00 | 47.54 | B | C |
| ATOM | 5432 | CG | GLU | 236 | 107.861 | 56.249 | 33.216 | 1.00 | 50.31 | B | C |
| ATOM | 5433 | CD | GLU | 236 | 107.031 | 54.965 | 33.245 | 1.00 | 52.79 | B | C |
| ATOM | 5434 | OE1 | GLU | 236 | 107.194 | 54.118 | 32.342 | 1.00 | 52.88 | B | O |
| ATOM | 5435 | OE2 | GLU | 236 | 106.219 | 54.797 | 34.184 | 1.00 | 52.63 | B | O |
| ATOM | 5436 | C | GLU | 236 | 108.966 | 58.840 | 30.670 | 1.00 | 28.50 | B | C |
| ATOM | 5437 | O | GLU | 236 | 110.092 | 59.336 | 30.684 | 1.00 | 29.93 | B | O |
| ATOM | 5438 | N | ALA | 237 | 108.287 | 58.617 | 29.552 | 1.00 | 22.73 | B | N |
| ATOM | 5439 | CA | ALA | 237 | 108.860 | 58.901 | 28.248 | 1.00 | 20.20 | B | C |
| ATOM | 5440 | CB | ALA | 237 | 107.783 | 58.831 | 27.180 | 1.00 | 41.37 | B | C |
| ATOM | 5441 | C | ALA | 237 | 109.562 | 60.233 | 28.187 | 1.00 | 19.04 | B | C |
| ATOM | 5442 | O | ALA | 237 | 110.636 | 60.344 | 27.589 | 1.00 | 17.46 | B | O |
| ATOM | 5443 | N | PHE | 238 | 108.962 | 61.242 | 28.810 | 1.00 | 29.57 | B | N |
| ATOM | 5444 | CA | PHE | 238 | 109.530 | 62.580 | 28.795 | 1.00 | 29.00 | B | C |
| ATOM | 5445 | CB | PHE | 238 | 108.419 | 63.620 | 28.752 | 1.00 | 35.30 | B | C |
| ATOM | 5446 | CG | PHE | 238 | 107.856 | 63.854 | 27.381 | 1.00 | 34.33 | B | C |
| ATOM | 5447 | CD1 | PHE | 238 | 106.531 | 63.532 | 27.101 | 1.00 | 35.56 | B | C |
| ATOM | 5448 | CD2 | PHE | 238 | 108.635 | 64.429 | 26.380 | 1.00 | 31.93 | B | C |
| ATOM | 5449 | CE1 | PHE | 238 | 105.985 | 63.780 | 25.841 | 1.00 | 33.36 | B | C |
| ATOM | 5450 | CE2 | PHE | 238 | 108.106 | 64.682 | 25.124 | 1.00 | 38.24 | B | C |
| ATOM | 5451 | CZ | PHE | 238 | 106.778 | 64.359 | 24.850 | 1.00 | 39.66 | B | C |
| ATOM | 5452 | C | PHE | 238 | 110.468 | 62.908 | 29.943 | 1.00 | 30.85 | B | C |
| ATOM | 5453 | O | PHE | 238 | 110.433 | 64.012 | 30.479 | 1.00 | 30.95 | B | O |
| ATOM | 5454 | N | THR | 239 | 111.303 | 61.951 | 30.325 | 1.00 | 29.27 | B | N |
| ATOM | 5455 | CA | THR | 239 | 112.266 | 62.182 | 31.391 | 1.00 | 33.21 | B | C |
| ATOM | 5456 | CB | THR | 239 | 112.113 | 61.150 | 32.520 | 1.00 | 23.55 | B | C |
| ATOM | 5457 | OG1 | THR | 239 | 112.276 | 59.840 | 31.989 | 1.00 | 21.51 | B | O |
| ATOM | 5458 | CG2 | THR | 239 | 110.745 | 61.242 | 33.153 | 1.00 | 26.46 | B | C |
| ATOM | 5459 | C | THR | 239 | 113.660 | 62.084 | 30.770 | 1.00 | 33.47 | B | C |
| ATOM | 5460 | O | THR | 239 | 113.930 | 61.177 | 29.980 | 1.00 | 33.97 | B | O |
| ATOM | 5461 | N | GLU | 240 | 114.531 | 63.030 | 31.117 | 1.00 | 17.24 | B | N |
| ATOM | 5462 | CA | GLU | 240 | 115.890 | 63.085 | 30.580 | 1.00 | 17.49 | B | C |
| ATOM | 5463 | CB | GLU | 240 | 116.748 | 64.003 | 31.444 | 1.00 | 74.12 | B | C |
| ATOM | 5464 | CG | GLU | 240 | 118.007 | 64.483 | 30.758 | 1.00 | 78.76 | B | C |
| ATOM | 5465 | CD | GLU | 240 | 118.634 | 65.654 | 31.479 | 1.00 | 81.67 | B | C |
| ATOM | 5466 | OE1 | GLU | 240 | 117.904 | 66.627 | 31.774 | 1.00 | 81.77 | B | O |
| ATOM | 5467 | OE2 | GLU | 240 | 119.853 | 65.605 | 31.746 | 1.00 | 81.74 | B | O |
| ATOM | 5468 | C | GLU | 240 | 116.555 | 61.712 | 30.465 | 1.00 | 18.84 | B | C |
| ATOM | 5469 | O | GLU | 240 | 117.323 | 61.444 | 29.530 | 1.00 | 20.05 | B | O |
| ATOM | 5470 | N | ALA | 241 | 116.234 | 60.839 | 31.415 | 1.00 | 54.75 | B | N |
| ATOM | 5471 | CA | ALA | 241 | 116.784 | 59.491 | 31.446 | 1.00 | 55.60 | B | C |
| ATOM | 5472 | CB | ALA | 241 | 116.331 | 58.783 | 32.723 | 1.00 | 26.00 | B | C |
| ATOM | 5473 | C | ALA | 241 | 116.387 | 58.678 | 30.212 | 1.00 | 55.07 | B | C |
| ATOM | 5474 | O | ALA | 241 | 117.093 | 57.751 | 29.823 | 1.00 | 56.53 | B | O |
| ATOM | 5475 | N | ARG | 242 | 115.259 | 59.024 | 29.598 | 1.00 | 25.17 | B | N |

Fig. 19: A-76

| | | | | | | | | | | | |
|---|---|---|---|---|---|---|---|---|---|---|---|
| ATOM | 5476 | CA | ARG | 242 | 114.805 | 58.305 | 28.417 | 1.00 | 24.91 | B | C |
| ATOM | 5477 | CB | ARG | 242 | 113.337 | 57.917 | 28.570 | 1.00 | 45.62 | B | C |
| ATOM | 5478 | CG | ARG | 242 | 113.136 | 56.644 | 29.392 | 1.00 | 45.82 | B | C |
| ATOM | 5479 | CD | ARG | 242 | 111.684 | 56.188 | 29.334 | 1.00 | 46.68 | B | C |
| ATOM | 5480 | NE | ARG | 242 | 111.525 | 54.733 | 29.424 | 1.00 | 47.88 | B | N |
| ATOM | 5481 | CZ | ARG | 242 | 111.348 | 54.055 | 30.557 | 1.00 | 47.08 | B | C |
| ATOM | 5482 | NH1 | ARG | 242 | 111.307 | 54.695 | 31.721 | 1.00 | 46.13 | B | N |
| ATOM | 5483 | NH2 | ARG | 242 | 111.187 | 52.738 | 30.526 | 1.00 | 49.10 | B | N |
| ATOM | 5484 | C | ARG | 242 | 115.039 | 59.088 | 27.120 | 1.00 | 26.11 | B | C |
| ATOM | 5485 | O | ARG | 242 | 114.450 | 58.796 | 26.076 | 1.00 | 29.12 | B | O |
| ATOM | 5486 | N | GLY | 243 | 115.919 | 60.079 | 27.194 | 1.00 | 41.48 | B | N |
| ATOM | 5487 | CA | GLY | 243 | 116.226 | 60.863 | 26.014 | 1.00 | 39.63 | B | C |
| ATOM | 5488 | C | GLY | 243 | 115.497 | 62.187 | 25.893 | 1.00 | 37.91 | B | C |
| ATOM | 5489 | O | GLY | 243 | 115.454 | 62.774 | 24.810 | 1.00 | 37.53 | B | O |
| ATOM | 5490 | N | ALA | 244 | 114.913 | 62.665 | 26.986 | 1.00 | 32.61 | B | N |
| ATOM | 5491 | CA | ALA | 244 | 114.209 | 63.941 | 26.939 | 1.00 | 30.61 | B | C |
| ATOM | 5492 | CB | ALA | 244 | 113.253 | 64.074 | 28.124 | 1.00 | 2.29 | B | C |
| ATOM | 5493 | C | ALA | 244 | 115.262 | 65.033 | 26.984 | 1.00 | 32.49 | B | C |
| ATOM | 5494 | O | ALA | 244 | 115.867 | 65.266 | 28.021 | 1.00 | 31.95 | B | O |
| ATOM | 5495 | N | ARG | 245 | 115.491 | 65.690 | 25.854 | 1.00 | 46.10 | B | N |
| ATOM | 5496 | CA | ARG | 245 | 116.482 | 66.760 | 25.768 | 1.00 | 46.93 | B | C |
| ATOM | 5497 | CB | ARG | 245 | 116.690 | 67.163 | 24.309 | 1.00 | 24.44 | B | C |
| ATOM | 5498 | CG | ARG | 245 | 117.460 | 66.126 | 23.503 | 1.00 | 26.91 | B | C |
| ATOM | 5499 | CD | ARG | 245 | 117.553 | 66.517 | 22.054 | 1.00 | 27.12 | B | C |
| ATOM | 5500 | NE | ARG | 245 | 116.229 | 66.560 | 21.457 | 1.00 | 21.54 | B | N |
| ATOM | 5501 | CZ | ARG | 245 | 115.999 | 66.826 | 20.179 | 1.00 | 21.36 | B | C |
| ATOM | 5502 | NH1 | ARG | 245 | 117.016 | 67.074 | 19.370 | 1.00 | 20.56 | B | N |
| ATOM | 5503 | NH2 | ARG | 245 | 114.756 | 66.834 | 19.708 | 1.00 | 18.65 | B | N |
| ATOM | 5504 | C | ARG | 245 | 116.101 | 67.986 | 26.585 | 1.00 | 45.30 | B | C |
| ATOM | 5505 | O | ARG | 245 | 114.975 | 68.480 | 26.496 | 1.00 | 41.41 | B | O |
| ATOM | 5506 | N | ARG | 246 | 117.051 | 68.476 | 27.376 | 1.00 | 48.54 | B | N |
| ATOM | 5507 | CA | ARG | 246 | 116.830 | 69.640 | 28.229 | 1.00 | 51.33 | B | C |
| ATOM | 5508 | CB | ARG | 246 | 118.096 | 69.982 | 29.012 | 1.00 | 83.48 | B | C |
| ATOM | 5509 | CG | ARG | 246 | 117.975 | 71.269 | 29.811 | 1.00 | 88.84 | B | C |
| ATOM | 5510 | CD | ARG | 246 | 119.295 | 71.647 | 30.449 | 1.00 | 94.76 | B | C |
| ATOM | 5511 | NE | ARG | 246 | 119.896 | 70.525 | 31.165 | 1.00 | 97.67 | B | N |
| ATOM | 5512 | CZ | ARG | 246 | 119.288 | 69.828 | 32.123 | 1.00 | 100.78 | B | C |
| ATOM | 5513 | NH1 | ARG | 246 | 118.047 | 70.132 | 32.491 | 1.00 | 100.47 | B | N |
| ATOM | 5514 | NH2 | ARG | 246 | 119.923 | 68.825 | 32.717 | 1.00 | 101.56 | B | N |
| ATOM | 5515 | C | ARG | 246 | 116.415 | 70.871 | 27.448 | 1.00 | 49.15 | B | C |
| ATOM | 5516 | O | ARG | 246 | 117.082 | 71.246 | 26.489 | 1.00 | 51.78 | B | O |
| ATOM | 5517 | N | GLY | 247 | 115.311 | 71.489 | 27.868 | 1.00 | 46.59 | B | N |
| ATOM | 5518 | CA | GLY | 247 | 114.825 | 72.705 | 27.233 | 1.00 | 49.17 | B | C |
| ATOM | 5519 | C | GLY | 247 | 114.381 | 72.609 | 25.787 | 1.00 | 49.24 | B | C |
| ATOM | 5520 | O | GLY | 247 | 114.531 | 73.560 | 25.019 | 1.00 | 52.20 | B | O |
| ATOM | 5521 | N | VAL | 248 | 113.836 | 71.462 | 25.407 | 1.00 | 57.57 | B | N |
| ATOM | 5522 | CA | VAL | 248 | 113.357 | 71.266 | 24.049 | 1.00 | 55.58 | B | C |
| ATOM | 5523 | CB | VAL | 248 | 114.012 | 70.043 | 23.407 | 1.00 | 22.85 | B | C |
| ATOM | 5524 | CG1 | VAL | 248 | 113.384 | 69.765 | 22.056 | 1.00 | 20.50 | B | C |
| ATOM | 5525 | CG2 | VAL | 248 | 115.499 | 70.287 | 23.266 | 1.00 | 14.62 | B | C |
| ATOM | 5526 | C | VAL | 248 | 111.855 | 71.056 | 24.094 | 1.00 | 58.60 | B | C |
| ATOM | 5527 | O | VAL | 248 | 111.343 | 70.403 | 25.005 | 1.00 | 62.65 | B | O |
| ATOM | 5528 | N | LYS | 249 | 111.147 | 71.607 | 23.115 | 1.00 | 37.34 | B | N |
| ATOM | 5529 | CA | LYS | 249 | 109.698 | 71.464 | 23.086 | 1.00 | 38.25 | B | C |
| ATOM | 5530 | CB | LYS | 249 | 109.115 | 72.122 | 21.832 | 1.00 | 57.29 | B | C |
| ATOM | 5531 | CG | LYS | 249 | 107.594 | 72.204 | 21.869 | 1.00 | 62.81 | B | C |
| ATOM | 5532 | CD | LYS | 249 | 107.103 | 72.892 | 23.155 | 1.00 | 63.88 | B | C |
| ATOM | 5533 | CE | LYS | 249 | 105.634 | 72.579 | 23.450 | 1.00 | 66.24 | B | C |
| ATOM | 5534 | NZ | LYS | 249 | 105.067 | 73.292 | 24.636 | 1.00 | 69.06 | B | N |
| ATOM | 5535 | C | LYS | 249 | 109.244 | 69.998 | 23.173 | 1.00 | 36.91 | B | C |
| ATOM | 5536 | O | LYS | 249 | 109.790 | 69.112 | 22.505 | 1.00 | 36.73 | B | O |
| ATOM | 5537 | N | LYS | 250 | 108.238 | 69.755 | 24.009 | 1.00 | 33.42 | B | N |
| ATOM | 5538 | CA | LYS | 250 | 107.706 | 68.419 | 24.208 | 1.00 | 33.07 | B | C |
| ATOM | 5539 | CB | LYS | 250 | 107.603 | 68.147 | 25.710 | 1.00 | 46.37 | B | C |
| ATOM | 5540 | CG | LYS | 250 | 108.970 | 68.151 | 26.374 | 1.00 | 44.97 | B | C |
| ATOM | 5541 | CD | LYS | 250 | 108.918 | 68.429 | 27.872 | 1.00 | 46.52 | B | C |
| ATOM | 5542 | CE | LYS | 250 | 108.389 | 67.256 | 28.686 | 1.00 | 45.68 | B | C |
| ATOM | 5543 | NZ | LYS | 250 | 108.578 | 67.474 | 30.157 | 1.00 | 47.50 | B | N |
| ATOM | 5544 | C | LYS | 250 | 106.355 | 68.263 | 23.506 | 1.00 | 32.42 | B | C |
| ATOM | 5545 | O | LYS | 250 | 105.380 | 68.931 | 23.842 | 1.00 | 32.10 | B | O |
| ATOM | 5546 | N | VAL | 251 | 106.320 | 67.372 | 22.519 | 1.00 | 37.83 | B | N |
| ATOM | 5547 | CA | VAL | 251 | 105.121 | 67.115 | 21.730 | 1.00 | 37.74 | B | C |
| ATOM | 5548 | CB | VAL | 251 | 105.403 | 67.373 | 20.248 | 1.00 | 28.71 | B | C |

Fig. 19: A-77

| | | | | | | | | | | | |
|---|---|---|---|---|---|---|---|---|---|---|---|
| ATOM | 5549 | CG1 | VAL | 251 | 104.180 | 67.017 | 19.410 | 1.00 | 26.86 | B | C |
| ATOM | 5550 | CG2 | VAL | 251 | 105.819 | 68.822 | 20.057 | 1.00 | 29.92 | B | C |
| ATOM | 5551 | C | VAL | 251 | 104.591 | 65.689 | 21.866 | 1.00 | 36.22 | B | C |
| ATOM | 5552 | O | VAL | 251 | 105.339 | 64.715 | 21.714 | 1.00 | 32.22 | B | O |
| ATOM | 5553 | N | MET | 252 | 103.289 | 65.572 | 22.122 | 1.00 | 42.57 | B | N |
| ATOM | 5554 | CA | MET | 252 | 102.651 | 64.269 | 22.275 | 1.00 | 43.55 | B | C |
| ATOM | 5555 | CB | MET | 252 | 102.013 | 64.160 | 23.660 | 1.00 | 27.32 | B | C |
| ATOM | 5556 | CG | MET | 252 | 101.440 | 62.787 | 23.998 | 1.00 | 26.01 | B | C |
| ATOM | 5557 | SD | MET | 252 | 100.740 | 62.725 | 25.675 | 1.00 | 30.06 | B | S |
| ATOM | 5558 | CE | MET | 252 | 102.222 | 63.011 | 26.691 | 1.00 | 21.37 | B | C |
| ATOM | 5559 | C | MET | 252 | 101.583 | 64.060 | 21.217 | 1.00 | 42.57 | B | C |
| ATOM | 5560 | O | MET | 252 | 100.761 | 64.937 | 20.982 | 1.00 | 44.94 | B | O |
| ATOM | 5561 | N | VAL | 253 | 101.604 | 62.900 | 20.573 | 1.00 | 21.89 | B | N |
| ATOM | 5562 | CA | VAL | 253 | 100.607 | 62.580 | 19.558 | 1.00 | 23.04 | B | C |
| ATOM | 5563 | CB | VAL | 253 | 101.267 | 62.281 | 18.187 | 1.00 | 9.79 | B | C |
| ATOM | 5564 | CG1 | VAL | 253 | 100.191 | 61.900 | 17.168 | 1.00 | 11.21 | B | C |
| ATOM | 5565 | CG2 | VAL | 253 | 102.044 | 63.490 | 17.701 | 1.00 | 9.43 | B | C |
| ATOM | 5566 | C | VAL | 253 | 99.819 | 61.353 | 20.015 | 1.00 | 22.61 | B | C |
| ATOM | 5567 | O | VAL | 253 | 100.383 | 60.276 | 20.161 | 1.00 | 21.05 | B | O |
| ATOM | 5568 | N | ILE | 254 | 98.522 | 61.516 | 20.252 | 1.00 | 29.50 | B | N |
| ATOM | 5569 | CA | ILE | 254 | 97.692 | 60.403 | 20.701 | 1.00 | 26.40 | B | C |
| ATOM | 5570 | CB | ILE | 254 | 96.820 | 60.777 | 21.925 | 1.00 | 25.01 | B | C |
| ATOM | 5571 | CG2 | ILE | 254 | 96.017 | 59.564 | 22.369 | 1.00 | 21.48 | B | C |
| ATOM | 5572 | CG1 | ILE | 254 | 97.697 | 61.256 | 23.089 | 1.00 | 23.59 | B | C |
| ATOM | 5573 | CD1 | ILE | 254 | 98.231 | 62.661 | 22.921 | 1.00 | 23.22 | B | C |
| ATOM | 5574 | C | ILE | 254 | 96.757 | 59.905 | 19.611 | 1.00 | 24.49 | B | C |
| ATOM | 5575 | O | ILE | 254 | 96.163 | 60.692 | 18.876 | 1.00 | 26.36 | B | O |
| ATOM | 5576 | N | VAL | 255 | 96.628 | 58.587 | 19.516 | 1.00 | 26.63 | B | N |
| ATOM | 5577 | CA | VAL | 255 | 95.758 | 57.981 | 18.521 | 1.00 | 25.37 | B | C |
| ATOM | 5578 | CB | VAL | 255 | 96.553 | 57.259 | 17.428 | 1.00 | 15.78 | B | C |
| ATOM | 5579 | CG1 | VAL | 255 | 95.672 | 57.064 | 16.198 | 1.00 | 14.23 | B | C |
| ATOM | 5580 | CG2 | VAL | 255 | 97.805 | 58.036 | 17.089 | 1.00 | 16.42 | B | C |
| ATOM | 5581 | C | VAL | 255 | 94.907 | 56.947 | 19.221 | 1.00 | 23.12 | B | C |
| ATOM | 5582 | O | VAL | 255 | 95.444 | 56.089 | 19.916 | 1.00 | 25.12 | B | O |
| ATOM | 5583 | N | THR | 256 | 93.591 | 57.012 | 19.036 | 1.00 | 8.41 | B | N |
| ATOM | 5584 | CA | THR | 256 | 92.709 | 56.052 | 19.689 | 1.00 | 8.83 | B | C |
| ATOM | 5585 | CB | THR | 256 | 92.529 | 56.416 | 21.189 | 1.00 | 19.33 | B | C |
| ATOM | 5586 | OG1 | THR | 256 | 91.459 | 55.645 | 21.755 | 1.00 | 15.37 | B | O |
| ATOM | 5587 | CG2 | THR | 256 | 92.255 | 57.908 | 21.344 | 1.00 | 18.18 | B | C |
| ATOM | 5588 | C | THR | 256 | 91.353 | 55.955 | 18.992 | 1.00 | 12.31 | B | C |
| ATOM | 5589 | O | THR | 256 | 90.941 | 56.881 | 18.308 | 1.00 | 8.47 | B | O |
| ATOM | 5590 | N | ASP | 257 | 90.673 | 54.824 | 19.162 | 1.00 | 17.26 | B | N |
| ATOM | 5591 | CA | ASP | 257 | 89.375 | 54.601 | 18.530 | 1.00 | 17.64 | B | C |
| ATOM | 5592 | CB | ASP | 257 | 89.491 | 53.474 | 17.491 | 1.00 | 29.20 | B | C |
| ATOM | 5593 | CG | ASP | 257 | 89.534 | 52.074 | 18.122 | 1.00 | 34.56 | B | C |
| ATOM | 5594 | OD1 | ASP | 257 | 89.894 | 51.957 | 19.313 | 1.00 | 35.03 | B | O |
| ATOM | 5595 | OD2 | ASP | 257 | 89.220 | 51.084 | 17.421 | 1.00 | 39.83 | B | O |
| ATOM | 5596 | C | ASP | 257 | 88.267 | 54.259 | 19.535 | 1.00 | 14.23 | B | C |
| ATOM | 5597 | O | ASP | 257 | 87.243 | 53.660 | 19.169 | 1.00 | 13.47 | B | O |
| ATOM | 5598 | N | GLY | 258 | 88.462 | 54.634 | 20.798 | 1.00 | 26.33 | B | N |
| ATOM | 5599 | CA | GLY | 258 | 87.450 | 54.331 | 21.793 | 1.00 | 28.75 | B | C |
| ATOM | 5600 | C | GLY | 258 | 87.546 | 55.109 | 23.088 | 1.00 | 32.57 | B | C |
| ATOM | 5601 | O | GLY | 258 | 88.615 | 55.601 | 23.476 | 1.00 | 28.29 | B | O |
| ATOM | 5602 | N | GLU | 259 | 86.404 | 55.231 | 23.755 | 1.00 | 39.52 | B | N |
| ATOM | 5603 | CA | GLU | 259 | 86.335 | 55.931 | 25.025 | 1.00 | 41.40 | B | C |
| ATOM | 5604 | CB | GLU | 259 | 84.905 | 55.925 | 25.555 | 1.00 | 36.52 | B | C |
| ATOM | 5605 | CG | GLU | 259 | 83.950 | 56.783 | 24.749 | 1.00 | 44.30 | B | C |
| ATOM | 5606 | CD | GLU | 259 | 82.509 | 56.415 | 24.994 | 1.00 | 48.11 | B | C |
| ATOM | 5607 | OE1 | GLU | 259 | 81.625 | 57.175 | 24.546 | 1.00 | 54.86 | B | O |
| ATOM | 5608 | OE2 | GLU | 259 | 82.262 | 55.360 | 25.626 | 1.00 | 48.13 | B | O |
| ATOM | 5609 | C | GLU | 259 | 87.240 | 55.210 | 26.003 | 1.00 | 40.26 | B | C |
| ATOM | 5610 | O | GLU | 259 | 87.125 | 53.999 | 26.194 | 1.00 | 37.43 | B | O |
| ATOM | 5611 | N | SER | 260 | 88.155 | 55.953 | 26.610 | 1.00 | 34.06 | B | N |
| ATOM | 5612 | CA | SER | 260 | 89.067 | 55.369 | 27.576 | 1.00 | 37.22 | B | C |
| ATOM | 5613 | CB | SER | 260 | 90.041 | 56.432 | 28.083 | 1.00 | 50.00 | B | C |
| ATOM | 5614 | OG | SER | 260 | 89.341 | 57.516 | 28.666 | 1.00 | 50.51 | B | O |
| ATOM | 5615 | C | SER | 260 | 88.261 | 54.814 | 28.740 | 1.00 | 37.12 | B | C |
| ATOM | 5616 | O | SER | 260 | 87.177 | 55.300 | 29.043 | 1.00 | 33.15 | B | O |
| ATOM | 5617 | N | HIS | 261 | 88.781 | 53.787 | 29.392 | 1.00 | 36.47 | B | N |
| ATOM | 5618 | CA | HIS | 261 | 88.084 | 53.212 | 30.527 | 1.00 | 40.82 | B | C |
| ATOM | 5619 | CB | HIS | 261 | 88.509 | 51.755 | 30.728 | 1.00 | 21.13 | B | C |
| ATOM | 5620 | CG | HIS | 261 | 87.908 | 50.809 | 29.732 | 1.00 | 24.33 | B | C |
| ATOM | 5621 | CD2 | HIS | 261 | 88.345 | 50.398 | 28.519 | 1.00 | 23.44 | B | C |

Fig. 19: A-78

| | | | | | | | | | | | |
|---|---|---|---|---|---|---|---|---|---|---|---|
| ATOM | 5622 | ND1 | HIS | 261 | 86.688 | 50.197 | 29.925 | 1.00 | 25.81 | B | N |
| ATOM | 5623 | CE1 | HIS | 261 | 86.400 | 49.448 | 28.876 | 1.00 | 25.88 | B | C |
| ATOM | 5624 | NE2 | HIS | 261 | 87.390 | 49.554 | 28.009 | 1.00 | 23.15 | B | N |
| ATOM | 5625 | C | HIS | 261 | 88.394 | 54.045 | 31.761 | 1.00 | 41.88 | B | C |
| ATOM | 5626 | O | HIS | 261 | 87.711 | 53.940 | 32.779 | 1.00 | 39.10 | B | O |
| ATOM | 5627 | N | ASP | 262 | 89.425 | 54.880 | 31.657 | 1.00 | 49.36 | B | N |
| ATOM | 5628 | CA | ASP | 262 | 89.825 | 55.758 | 32.753 | 1.00 | 54.33 | B | C |
| ATOM | 5629 | CB | ASP | 262 | 91.343 | 55.676 | 32.985 | 1.00 | 33.92 | B | C |
| ATOM | 5630 | CG | ASP | 262 | 92.124 | 55.281 | 31.733 | 1.00 | 33.92 | B | C |
| ATOM | 5631 | OD1 | ASP | 262 | 91.724 | 55.659 | 30.611 | 1.00 | 33.92 | B | O |
| ATOM | 5632 | OD2 | ASP | 262 | 93.162 | 54.600 | 31.875 | 1.00 | 33.92 | B | O |
| ATOM | 5633 | C | ASP | 262 | 89.418 | 57.218 | 32.507 | 1.00 | 54.38 | B | C |
| ATOM | 5634 | O | ASP | 262 | 90.221 | 58.134 | 32.700 | 1.00 | 54.24 | B | O |
| ATOM | 5635 | N | ASN | 263 | 88.171 | 57.424 | 32.085 | 1.00 | 68.10 | B | N |
| ATOM | 5636 | CA | ASN | 263 | 87.646 | 58.765 | 31.813 | 1.00 | 69.27 | B | C |
| ATOM | 5637 | CB | ASN | 263 | 86.123 | 58.734 | 31.630 | 1.00 | 82.52 | B | C |
| ATOM | 5638 | CG | ASN | 263 | 85.660 | 57.631 | 30.707 | 1.00 | 86.89 | B | C |
| ATOM | 5639 | OD1 | ASN | 263 | 85.981 | 57.626 | 29.519 | 1.00 | 88.39 | B | O |
| ATOM | 5640 | ND2 | ASN | 263 | 84.893 | 56.686 | 31.249 | 1.00 | 81.39 | B | N |
| ATOM | 5641 | C | ASN | 263 | 87.948 | 59.670 | 32.998 | 1.00 | 69.91 | B | C |
| ATOM | 5642 | O | ASN | 263 | 88.360 | 60.822 | 32.841 | 1.00 | 68.81 | B | O |
| ATOM | 5643 | N | TYR | 264 | 87.732 | 59.122 | 34.187 | 1.00 | 59.82 | B | N |
| ATOM | 5644 | CA | TYR | 264 | 87.925 | 59.837 | 35.432 | 1.00 | 57.67 | B | C |
| ATOM | 5645 | CB | TYR | 264 | 87.914 | 58.853 | 36.590 | 1.00 | 108.49 | B | C |
| ATOM | 5646 | CG | TYR | 264 | 86.626 | 58.083 | 36.660 | 1.00 | 108.49 | B | C |
| ATOM | 5647 | CD1 | TYR | 264 | 86.284 | 57.171 | 35.663 | 1.00 | 108.49 | B | C |
| ATOM | 5648 | CE1 | TYR | 264 | 85.074 | 56.490 | 35.698 | 1.00 | 108.49 | B | C |
| ATOM | 5649 | CD2 | TYR | 264 | 85.723 | 58.292 | 37.699 | 1.00 | 108.49 | B | C |
| ATOM | 5650 | CE2 | TYR | 264 | 84.509 | 57.615 | 37.744 | 1.00 | 108.49 | B | C |
| ATOM | 5651 | CZ | TYR | 264 | 84.190 | 56.717 | 36.741 | 1.00 | 108.49 | B | C |
| ATOM | 5652 | OH | TYR | 264 | 82.987 | 56.052 | 36.783 | 1.00 | 108.49 | B | O |
| ATOM | 5653 | C | TYR | 264 | 89.156 | 60.710 | 35.512 | 1.00 | 56.32 | B | C |
| ATOM | 5654 | O | TYR | 264 | 89.047 | 61.935 | 35.549 | 1.00 | 53.45 | B | O |
| ATOM | 5655 | N | ARG | 265 | 90.331 | 60.098 | 35.527 | 1.00 | 41.74 | B | N |
| ATOM | 5656 | CA | ARG | 265 | 91.544 | 60.892 | 35.641 | 1.00 | 40.64 | B | C |
| ATOM | 5657 | CB | ARG | 265 | 92.610 | 60.127 | 36.427 | 1.00 | 58.89 | B | C |
| ATOM | 5658 | CG | ARG | 265 | 93.152 | 58.875 | 35.779 | 1.00 | 59.34 | B | C |
| ATOM | 5659 | CD | ARG | 265 | 94.501 | 58.614 | 36.400 | 1.00 | 61.17 | B | C |
| ATOM | 5660 | NE | ARG | 265 | 95.183 | 57.456 | 35.851 | 1.00 | 66.56 | B | N |
| ATOM | 5661 | CZ | ARG | 265 | 96.506 | 57.349 | 35.784 | 1.00 | 66.73 | B | C |
| ATOM | 5662 | NH1 | ARG | 265 | 97.281 | 58.334 | 36.227 | 1.00 | 71.36 | B | N |
| ATOM | 5663 | NH2 | ARG | 265 | 97.059 | 56.256 | 35.280 | 1.00 | 70.70 | B | N |
| ATOM | 5664 | C | ARG | 265 | 92.147 | 61.423 | 34.347 | 1.00 | 39.89 | B | C |
| ATOM | 5665 | O | ARG | 265 | 93.311 | 61.833 | 34.319 | 1.00 | 41.20 | B | O |
| ATOM | 5666 | N | LEU | 266 | 91.360 | 61.433 | 33.278 | 1.00 | 45.12 | B | N |
| ATOM | 5667 | CA | LEU | 266 | 91.855 | 61.947 | 32.007 | 1.00 | 46.69 | B | C |
| ATOM | 5668 | CB | LEU | 266 | 90.885 | 61.580 | 30.886 | 1.00 | 30.69 | B | C |
| ATOM | 5669 | CG | LEU | 266 | 91.357 | 61.919 | 29.480 | 1.00 | 29.90 | B | C |
| ATOM | 5670 | CD1 | LEU | 266 | 92.760 | 61.369 | 29.232 | 1.00 | 32.24 | B | C |
| ATOM | 5671 | CD2 | LEU | 266 | 90.347 | 61.344 | 28.500 | 1.00 | 26.36 | B | C |
| ATOM | 5672 | C | LEU | 266 | 91.989 | 63.466 | 32.139 | 1.00 | 49.51 | B | C |
| ATOM | 5673 | O | LEU | 266 | 92.861 | 64.093 | 31.541 | 1.00 | 49.39 | B | O |
| ATOM | 5674 | N | LYS | 267 | 91.107 | 64.041 | 32.945 | 1.00 | 50.12 | B | N |
| ATOM | 5675 | CA | LYS | 267 | 91.097 | 65.473 | 33.206 | 1.00 | 52.43 | B | C |
| ATOM | 5676 | CB | LYS | 267 | 89.927 | 65.807 | 34.136 | 1.00 | 99.33 | B | C |
| ATOM | 5677 | CG | LYS | 267 | 89.719 | 67.279 | 34.431 | 1.00 | 99.33 | B | C |
| ATOM | 5678 | CD | LYS | 267 | 88.623 | 67.863 | 33.558 | 1.00 | 99.33 | B | C |
| ATOM | 5679 | CE | LYS | 267 | 88.211 | 69.242 | 34.049 | 1.00 | 99.33 | B | C |
| ATOM | 5680 | NZ | LYS | 267 | 87.044 | 69.788 | 33.293 | 1.00 | 99.33 | B | N |
| ATOM | 5681 | C | LYS | 267 | 92.417 | 65.835 | 33.882 | 1.00 | 51.92 | B | C |
| ATOM | 5682 | O | LYS | 267 | 93.126 | 66.738 | 33.440 | 1.00 | 51.44 | B | O |
| ATOM | 5683 | N | GLN | 268 | 92.736 | 65.115 | 34.956 | 1.00 | 36.69 | B | N |
| ATOM | 5684 | CA | GLN | 268 | 93.968 | 65.338 | 35.709 | 1.00 | 35.66 | B | C |
| ATOM | 5685 | CB | GLN | 268 | 94.098 | 64.324 | 36.841 | 1.00 | 127.61 | B | C |
| ATOM | 5686 | CG | GLN | 268 | 93.032 | 64.387 | 37.906 | 1.00 | 127.61 | B | C |
| ATOM | 5687 | CD | GLN | 268 | 93.203 | 63.286 | 38.941 | 1.00 | 127.61 | B | C |
| ATOM | 5688 | OE1 | GLN | 268 | 92.487 | 63.236 | 39.939 | 1.00 | 127.61 | B | O |
| ATOM | 5689 | NE2 | GLN | 268 | 94.158 | 62.392 | 38.702 | 1.00 | 127.61 | B | N |
| ATOM | 5690 | C | GLN | 268 | 95.203 | 65.210 | 34.824 | 1.00 | 31.41 | B | C |
| ATOM | 5691 | O | GLN | 268 | 96.044 | 66.108 | 34.788 | 1.00 | 32.59 | B | O |
| ATOM | 5692 | N | VAL | 269 | 95.308 | 64.085 | 34.114 | 1.00 | 29.89 | B | N |
| ATOM | 5693 | CA | VAL | 269 | 96.457 | 63.831 | 33.256 | 1.00 | 27.64 | B | C |
| ATOM | 5694 | CB | VAL | 269 | 96.321 | 62.467 | 32.516 | 1.00 | 26.10 | B | C |

Fig. 19: A-79

| | | | | | | | | | | | |
|---|---|---|---|---|---|---|---|---|---|---|---|
| ATOM | 5695 | CG1 | VAL | 269 | 97.551 | 62.215 | 31.663 | 1.00 | 21.75 | B | C |
| ATOM | 5696 | CG2 | VAL | 269 | 96.161 | 61.338 | 33.520 | 1.00 | 23.96 | B | C |
| ATOM | 5697 | C | VAL | 269 | 96.683 | 64.956 | 32.246 | 1.00 | 27.23 | B | C |
| ATOM | 5698 | O | VAL | 269 | 97.784 | 65.502 | 32.174 | 1.00 | 30.07 | B | O |
| ATOM | 5699 | N | ILE | 270 | 95.658 | 65.306 | 31.471 | 1.00 | 16.50 | B | N |
| ATOM | 5700 | CA | ILE | 270 | 95.797 | 66.379 | 30.487 | 1.00 | 17.12 | B | C |
| ATOM | 5701 | CB | ILE | 270 | 94.459 | 66.696 | 29.777 | 1.00 | 35.19 | B | C |
| ATOM | 5702 | CG2 | ILE | 270 | 94.594 | 67.973 | 28.937 | 1.00 | 29.81 | B | C |
| ATOM | 5703 | CG1 | ILE | 270 | 94.060 | 65.520 | 28.885 | 1.00 | 32.75 | B | C |
| ATOM | 5704 | CD1 | ILE | 270 | 95.062 | 65.231 | 27.778 | 1.00 | 33.87 | B | C |
| ATOM | 5705 | C | ILE | 270 | 96.275 | 67.631 | 31.210 | 1.00 | 20.99 | B | C |
| ATOM | 5706 | O | ILE | 270 | 97.060 | 68.413 | 30.670 | 1.00 | 19.77 | B | O |
| ATOM | 5707 | N | GLN | 271 | 95.802 | 67.796 | 32.444 | 1.00 | 57.05 | B | N |
| ATOM | 5708 | CA | GLN | 271 | 96.169 | 68.935 | 33.269 | 1.00 | 59.11 | B | C |
| ATOM | 5709 | CB | GLN | 271 | 95.440 | 68.865 | 34.610 | 1.00 | 85.78 | B | C |
| ATOM | 5710 | CG | GLN | 271 | 95.525 | 70.134 | 35.439 | 1.00 | 87.68 | B | C |
| ATOM | 5711 | CD | GLN | 271 | 94.967 | 71.338 | 34.708 | 1.00 | 90.18 | B | C |
| ATOM | 5712 | OE1 | GLN | 271 | 95.614 | 71.898 | 33.822 | 1.00 | 90.51 | B | O |
| ATOM | 5713 | NE2 | GLN | 271 | 93.752 | 71.735 | 35.065 | 1.00 | 91.75 | B | N |
| ATOM | 5714 | C | GLN | 271 | 97.673 | 68.932 | 33.495 | 1.00 | 61.57 | B | C |
| ATOM | 5715 | O | GLN | 271 | 98.359 | 69.896 | 33.172 | 1.00 | 64.26 | B | O |
| ATOM | 5716 | N | ASP | 272 | 98.184 | 67.837 | 34.042 | 1.00 | 39.03 | B | N |
| ATOM | 5717 | CA | ASP | 272 | 99.612 | 67.716 | 34.304 | 1.00 | 40.31 | B | C |
| ATOM | 5718 | CB | ASP | 272 | 99.922 | 66.338 | 34.890 | 1.00 | 54.12 | B | C |
| ATOM | 5719 | CG | ASP | 272 | 99.275 | 66.122 | 36.255 | 1.00 | 55.74 | B | C |
| ATOM | 5720 | OD1 | ASP | 272 | 99.087 | 64.949 | 36.647 | 1.00 | 57.81 | B | O |
| ATOM | 5721 | OD2 | ASP | 272 | 98.961 | 67.123 | 36.939 | 1.00 | 62.00 | B | O |
| ATOM | 5722 | C | ASP | 272 | 100.420 | 67.937 | 33.033 | 1.00 | 41.11 | B | C |
| ATOM | 5723 | O | ASP | 272 | 101.550 | 68.418 | 33.083 | 1.00 | 38.56 | B | O |
| ATOM | 5724 | N | CYS | 273 | 99.843 | 67.587 | 31.891 | 1.00 | 49.56 | B | N |
| ATOM | 5725 | CA | CYS | 273 | 100.538 | 67.776 | 30.629 | 1.00 | 47.99 | B | C |
| ATOM | 5726 | CB | CYS | 273 | 99.824 | 67.028 | 29.503 | 1.00 | 39.07 | B | C |
| ATOM | 5727 | SG | CYS | 273 | 100.050 | 65.235 | 29.538 | 1.00 | 37.17 | B | S |
| ATOM | 5728 | C | CYS | 273 | 100.628 | 69.257 | 30.291 | 1.00 | 48.36 | B | C |
| ATOM | 5729 | O | CYS | 273 | 101.602 | 69.695 | 29.686 | 1.00 | 42.67 | B | O |
| ATOM | 5730 | N | GLU | 274 | 99.609 | 70.022 | 30.682 | 1.00 | 40.12 | B | N |
| ATOM | 5731 | CA | GLU | 274 | 99.584 | 71.467 | 30.425 | 1.00 | 42.92 | B | C |
| ATOM | 5732 | CB | GLU | 274 | 98.187 | 72.055 | 30.703 | 1.00 | 40.77 | B | C |
| ATOM | 5733 | CG | GLU | 274 | 97.285 | 72.151 | 29.470 | 1.00 | 45.89 | B | C |
| ATOM | 5734 | CD | GLU | 274 | 97.830 | 73.108 | 28.405 | 1.00 | 51.00 | B | C |
| ATOM | 5735 | OE1 | GLU | 274 | 97.269 | 73.155 | 27.284 | 1.00 | 52.87 | B | O |
| ATOM | 5736 | OE2 | GLU | 274 | 98.816 | 73.818 | 28.691 | 1.00 | 55.56 | B | O |
| ATOM | 5737 | C | GLU | 274 | 100.615 | 72.172 | 31.293 | 1.00 | 45.34 | B | C |
| ATOM | 5738 | O | GLU | 274 | 101.309 | 73.081 | 30.842 | 1.00 | 47.54 | B | O |
| ATOM | 5739 | N | ASP | 275 | 100.711 | 71.735 | 32.542 | 1.00 | 77.40 | B | N |
| ATOM | 5740 | CA | ASP | 275 | 101.656 | 72.302 | 33.495 | 1.00 | 76.14 | B | C |
| ATOM | 5741 | CB | ASP | 275 | 101.456 | 71.665 | 34.871 | 1.00 | 72.98 | B | C |
| ATOM | 5742 | CG | ASP | 275 | 100.070 | 71.900 | 35.432 | 1.00 | 74.25 | B | C |
| ATOM | 5743 | OD1 | ASP | 275 | 99.160 | 72.258 | 34.656 | 1.00 | 77.95 | B | O |
| ATOM | 5744 | OD2 | ASP | 275 | 99.887 | 71.712 | 36.652 | 1.00 | 75.91 | B | O |
| ATOM | 5745 | C | ASP | 275 | 103.093 | 72.050 | 33.046 | 1.00 | 75.13 | B | C |
| ATOM | 5746 | O | ASP | 275 | 104.021 | 72.707 | 33.512 | 1.00 | 70.68 | B | O |
| ATOM | 5747 | N | GLU | 276 | 103.275 | 71.091 | 32.146 | 1.00 | 44.46 | B | N |
| ATOM | 5748 | CA | GLU | 276 | 104.606 | 70.757 | 31.668 | 1.00 | 44.11 | B | C |
| ATOM | 5749 | CB | GLU | 276 | 104.846 | 69.258 | 31.847 | 1.00 | 54.99 | B | C |
| ATOM | 5750 | CG | GLU | 276 | 104.556 | 68.799 | 33.266 | 1.00 | 54.86 | B | C |
| ATOM | 5751 | CD | GLU | 276 | 105.018 | 67.383 | 33.547 | 1.00 | 55.96 | B | C |
| ATOM | 5752 | OE1 | GLU | 276 | 104.861 | 66.934 | 34.705 | 1.00 | 56.67 | B | O |
| ATOM | 5753 | OE2 | GLU | 276 | 105.538 | 66.724 | 32.616 | 1.00 | 52.90 | B | O |
| ATOM | 5754 | C | GLU | 276 | 104.843 | 71.175 | 30.222 | 1.00 | 42.94 | B | C |
| ATOM | 5755 | O | GLU | 276 | 105.823 | 70.759 | 29.597 | 1.00 | 44.05 | B | O |
| ATOM | 5756 | N | ASN | 277 | 103.938 | 71.997 | 29.700 | 1.00 | 43.81 | B | N |
| ATOM | 5757 | CA | ASN | 277 | 104.043 | 72.505 | 28.338 | 1.00 | 43.78 | B | C |
| ATOM | 5758 | CB | ASN | 277 | 105.229 | 73.464 | 28.233 | 1.00 | 55.27 | B | C |
| ATOM | 5759 | CG | ASN | 277 | 105.219 | 74.514 | 29.311 | 1.00 | 60.19 | B | C |
| ATOM | 5760 | OD1 | ASN | 277 | 104.288 | 75.315 | 29.403 | 1.00 | 60.01 | B | O |
| ATOM | 5761 | ND2 | ASN | 277 | 106.256 | 74.518 | 30.145 | 1.00 | 59.15 | B | N |
| ATOM | 5762 | C | ASN | 277 | 104.188 | 71.428 | 27.261 | 1.00 | 40.13 | B | C |
| ATOM | 5763 | O | ASN | 277 | 105.083 | 71.515 | 26.416 | 1.00 | 41.11 | B | O |
| ATOM | 5764 | N | ILE | 278 | 103.309 | 70.427 | 27.278 | 1.00 | 17.87 | B | N |
| ATOM | 5765 | CA | ILE | 278 | 103.366 | 69.361 | 26.289 | 1.00 | 18.32 | B | C |
| ATOM | 5766 | CB | ILE | 278 | 103.110 | 67.975 | 26.928 | 1.00 | 22.06 | B | C |
| ATOM | 5767 | CG2 | ILE | 278 | 103.120 | 66.897 | 25.854 | 1.00 | 23.45 | B | C |

Fig. 19: A-80

| | | | | | | | | | | | |
|---|---|---|---|---|---|---|---|---|---|---|---|
| ATOM | 5768 | CG1 | ILE | 278 | 104.172 | 67.675 | 27.987 | 1.00 | 19.51 | B | C |
| ATOM | 5769 | CD1 | ILE | 278 | 103.941 | 66.373 | 28.707 | 1.00 | 21.79 | B | C |
| ATOM | 5770 | C | ILE | 278 | 102.316 | 69.579 | 25.213 | 1.00 | 18.92 | B | C |
| ATOM | 5771 | O | ILE | 278 | 101.132 | 69.378 | 25.463 | 1.00 | 19.26 | B | O |
| ATOM | 5772 | N | GLN | 279 | 102.749 | 69.994 | 24.024 | 1.00 | 49.21 | B | N |
| ATOM | 5773 | CA | GLN | 279 | 101.831 | 70.198 | 22.908 | 1.00 | 48.81 | B | C |
| ATOM | 5774 | CB | GLN | 279 | 102.579 | 70.633 | 21.652 | 1.00 | 63.04 | B | C |
| ATOM | 5775 | CG | GLN | 279 | 103.187 | 71.998 | 21.752 | 1.00 | 68.82 | B | C |
| ATOM | 5776 | CD | GLN | 279 | 102.173 | 73.043 | 22.155 | 1.00 | 72.74 | B | C |
| ATOM | 5777 | OE1 | GLN | 279 | 101.233 | 73.328 | 21.410 | 1.00 | 66.98 | B | O |
| ATOM | 5778 | NE2 | GLN | 279 | 102.352 | 73.618 | 23.345 | 1.00 | 72.33 | B | N |
| ATOM | 5779 | C | GLN | 279 | 101.175 | 68.864 | 22.640 | 1.00 | 46.68 | B | C |
| ATOM | 5780 | O | GLN | 279 | 101.861 | 67.859 | 22.467 | 1.00 | 43.60 | B | O |
| ATOM | 5781 | N | ARG | 280 | 99.851 | 68.848 | 22.595 | 1.00 | 28.30 | B | N |
| ATOM | 5782 | CA | ARG | 280 | 99.138 | 67.605 | 22.363 | 1.00 | 29.82 | B | C |
| ATOM | 5783 | CB | ARG | 280 | 98.276 | 67.277 | 23.575 | 1.00 | 38.67 | B | C |
| ATOM | 5784 | CG | ARG | 280 | 99.036 | 67.225 | 24.874 | 1.00 | 37.30 | B | C |
| ATOM | 5785 | CD | ARG | 280 | 98.068 | 67.012 | 26.018 | 1.00 | 36.97 | B | C |
| ATOM | 5786 | NE | ARG | 280 | 97.070 | 68.075 | 26.073 | 1.00 | 34.02 | B | N |
| ATOM | 5787 | CZ | ARG | 280 | 97.288 | 69.298 | 26.557 | 1.00 | 37.93 | B | C |
| ATOM | 5788 | NH1 | ARG | 280 | 98.483 | 69.627 | 27.041 | 1.00 | 40.85 | B | N |
| ATOM | 5789 | NH2 | ARG | 280 | 96.307 | 70.192 | 26.554 | 1.00 | 42.87 | B | N |
| ATOM | 5790 | C | ARG | 280 | 98.264 | 67.579 | 21.111 | 1.00 | 29.48 | B | C |
| ATOM | 5791 | O | ARG | 280 | 97.406 | 68.437 | 20.912 | 1.00 | 29.21 | B | O |
| ATOM | 5792 | N | PHE | 281 | 98.501 | 66.582 | 20.266 | 1.00 | 31.71 | B | N |
| ATOM | 5793 | CA | PHE | 281 | 97.713 | 66.392 | 19.066 | 1.00 | 33.70 | B | C |
| ATOM | 5794 | CB | PHE | 281 | 98.594 | 66.335 | 17.826 | 1.00 | 18.70 | B | C |
| ATOM | 5795 | CG | PHE | 281 | 99.324 | 67.604 | 17.555 | 1.00 | 21.73 | B | C |
| ATOM | 5796 | CD1 | PHE | 281 | 100.438 | 67.950 | 18.308 | 1.00 | 25.58 | B | C |
| ATOM | 5797 | CD2 | PHE | 281 | 98.887 | 68.469 | 16.551 | 1.00 | 23.46 | B | C |
| ATOM | 5798 | CE1 | PHE | 281 | 101.111 | 69.136 | 18.070 | 1.00 | 25.64 | B | C |
| ATOM | 5799 | CE2 | PHE | 281 | 99.554 | 69.665 | 16.301 | 1.00 | 21.19 | B | C |
| ATOM | 5800 | CZ | PHE | 281 | 100.669 | 69.999 | 17.064 | 1.00 | 22.62 | B | C |
| ATOM | 5801 | C | PHE | 281 | 97.025 | 65.060 | 19.266 | 1.00 | 34.41 | B | C |
| ATOM | 5802 | O | PHE | 281 | 97.677 | 64.053 | 19.509 | 1.00 | 36.78 | B | O |
| ATOM | 5803 | N | SER | 282 | 95.704 | 65.061 | 19.202 | 1.00 | 16.00 | B | N |
| ATOM | 5804 | CA | SER | 282 | 94.962 | 63.835 | 19.374 | 1.00 | 17.85 | B | C |
| ATOM | 5805 | CB | SER | 282 | 93.973 | 63.973 | 20.528 | 1.00 | 14.79 | B | C |
| ATOM | 5806 | OG | SER | 282 | 93.036 | 64.997 | 20.286 | 1.00 | 11.34 | B | O |
| ATOM | 5807 | C | SER | 282 | 94.231 | 63.507 | 18.093 | 1.00 | 19.73 | B | C |
| ATOM | 5808 | O | SER | 282 | 93.909 | 64.389 | 17.306 | 1.00 | 23.59 | B | O |
| ATOM | 5809 | N | ILE | 283 | 93.986 | 62.224 | 17.881 | 1.00 | 19.27 | B | N |
| ATOM | 5810 | CA | ILE | 283 | 93.288 | 61.779 | 16.693 | 1.00 | 17.19 | B | C |
| ATOM | 5811 | CB | ILE | 283 | 94.245 | 61.146 | 15.697 | 1.00 | 9.92 | B | C |
| ATOM | 5812 | CG2 | ILE | 283 | 93.501 | 60.806 | 14.425 | 1.00 | 10.73 | B | C |
| ATOM | 5813 | CG1 | ILE | 283 | 95.377 | 62.118 | 15.383 | 1.00 | 6.39 | B | C |
| ATOM | 5814 | CD1 | ILE | 283 | 96.630 | 61.446 | 14.894 | 1.00 | 9.95 | B | C |
| ATOM | 5815 | C | ILE | 283 | 92.278 | 60.748 | 17.127 | 1.00 | 16.26 | B | C |
| ATOM | 5816 | O | ILE | 283 | 92.574 | 59.886 | 17.947 | 1.00 | 16.12 | B | O |
| ATOM | 5817 | N | ALA | 284 | 91.078 | 60.836 | 16.584 | 1.00 | 18.66 | B | N |
| ATOM | 5818 | CA | ALA | 284 | 90.050 | 59.896 | 16.955 | 1.00 | 18.68 | B | C |
| ATOM | 5819 | CB | ALA | 284 | 88.903 | 60.627 | 17.622 | 1.00 | 45.12 | B | C |
| ATOM | 5820 | C | ALA | 284 | 89.542 | 59.107 | 15.759 | 1.00 | 16.81 | B | C |
| ATOM | 5821 | O | ALA | 284 | 89.045 | 59.681 | 14.792 | 1.00 | 15.47 | B | O |
| ATOM | 5822 | N | ILE | 285 | 89.691 | 57.788 | 15.826 | 1.00 | 23.61 | B | N |
| ATOM | 5823 | CA | ILE | 285 | 89.205 | 56.922 | 14.772 | 1.00 | 17.81 | B | C |
| ATOM | 5824 | CB | ILE | 285 | 89.960 | 55.564 | 14.741 | 1.00 | 12.20 | B | C |
| ATOM | 5825 | CG2 | ILE | 285 | 89.210 | 54.576 | 13.862 | 1.00 | 7.02 | B | C |
| ATOM | 5826 | CG1 | ILE | 285 | 91.380 | 55.738 | 14.204 | 1.00 | 7.53 | B | C |
| ATOM | 5827 | CD1 | ILE | 285 | 92.342 | 56.334 | 15.179 | 1.00 | 8.67 | B | C |
| ATOM | 5828 | C | ILE | 285 | 87.745 | 56.678 | 15.148 | 1.00 | 21.13 | B | C |
| ATOM | 5829 | O | ILE | 285 | 87.466 | 56.108 | 16.201 | 1.00 | 22.87 | B | O |
| ATOM | 5830 | N | LEU | 286 | 86.820 | 57.112 | 14.297 | 1.00 | 18.22 | B | N |
| ATOM | 5831 | CA | LEU | 286 | 85.399 | 56.937 | 14.581 | 1.00 | 18.70 | B | C |
| ATOM | 5832 | CB | LEU | 286 | 84.615 | 58.129 | 14.039 | 1.00 | 27.86 | B | C |
| ATOM | 5833 | CG | LEU | 286 | 85.105 | 59.512 | 14.456 | 1.00 | 30.68 | B | C |
| ATOM | 5834 | CD1 | LEU | 286 | 84.112 | 60.536 | 13.961 | 1.00 | 33.24 | B | C |
| ATOM | 5835 | CD2 | LEU | 286 | 85.249 | 59.599 | 15.963 | 1.00 | 32.35 | B | C |
| ATOM | 5836 | C | LEU | 286 | 84.774 | 55.645 | 14.044 | 1.00 | 19.15 | B | C |
| ATOM | 5837 | O | LEU | 286 | 83.552 | 55.458 | 14.122 | 1.00 | 19.99 | B | O |
| ATOM | 5838 | N | GLY | 287 | 85.609 | 54.752 | 13.520 | 1.00 | 37.37 | B | N |
| ATOM | 5839 | CA | GLY | 287 | 85.115 | 53.501 | 12.967 | 1.00 | 36.15 | B | C |
| ATOM | 5840 | C | GLY | 287 | 84.059 | 52.745 | 13.760 | 1.00 | 33.73 | B | C |

Fig. 19: A-81

| | | | | | | | | | | | |
|---|---|---|---|---|---|---|---|---|---|---|---|
| ATOM | 5841 | O | GLY | 287 | 82.899 | 52.681 | 13.367 | 1.00 | 37.83 | B | O |
| ATOM | 5842 | N | HIS | 288 | 84.464 | 52.162 | 14.878 | 1.00 | 34.79 | B | N |
| ATOM | 5843 | CA | HIS | 288 | 83.563 | 51.376 | 15.700 | 1.00 | 32.75 | B | C |
| ATOM | 5844 | CB | HIS | 288 | 84.272 | 51.016 | 16.996 | 1.00 | 68.63 | B | C |
| ATOM | 5845 | CG | HIS | 288 | 85.486 | 50.181 | 16.763 | 1.00 | 70.54 | B | C |
| ATOM | 5846 | CD2 | HIS | 288 | 85.781 | 48.912 | 17.123 | 1.00 | 66.91 | B | C |
| ATOM | 5847 | ND1 | HIS | 288 | 86.520 | 50.600 | 15.955 | 1.00 | 65.20 | B | N |
| ATOM | 5848 | CE1 | HIS | 288 | 87.397 | 49.623 | 15.821 | 1.00 | 65.56 | B | C |
| ATOM | 5849 | NE2 | HIS | 288 | 86.972 | 48.586 | 16.519 | 1.00 | 64.05 | B | N |
| ATOM | 5850 | C | HIS | 288 | 82.214 | 52.006 | 15.968 | 1.00 | 30.23 | B | C |
| ATOM | 5851 | O | HIS | 288 | 81.180 | 51.398 | 15.711 | 1.00 | 29.80 | B | O |
| ATOM | 5852 | N | TYR | 289 | 82.219 | 53.233 | 16.461 | 1.00 | 26.68 | B | N |
| ATOM | 5853 | CA | TYR | 289 | 80.982 | 53.912 | 16.754 | 1.00 | 27.59 | B | C |
| ATOM | 5854 | CB | TYR | 289 | 81.287 | 55.288 | 17.309 | 1.00 | 20.91 | B | C |
| ATOM | 5855 | CG | TYR | 289 | 81.803 | 55.203 | 18.717 | 1.00 | 23.71 | B | C |
| ATOM | 5856 | CD1 | TYR | 289 | 83.163 | 55.293 | 18.997 | 1.00 | 24.30 | B | C |
| ATOM | 5857 | CE1 | TYR | 289 | 83.633 | 55.127 | 20.281 | 1.00 | 27.49 | B | C |
| ATOM | 5858 | CD2 | TYR | 289 | 80.928 | 54.947 | 19.764 | 1.00 | 26.60 | B | C |
| ATOM | 5859 | CE2 | TYR | 289 | 81.381 | 54.776 | 21.047 | 1.00 | 21.41 | B | C |
| ATOM | 5860 | CZ | TYR | 289 | 82.733 | 54.866 | 21.303 | 1.00 | 23.14 | B | C |
| ATOM | 5861 | OH | TYR | 289 | 83.166 | 54.686 | 22.597 | 1.00 | 27.79 | B | O |
| ATOM | 5862 | C | TYR | 289 | 80.039 | 54.015 | 15.572 | 1.00 | 29.36 | B | C |
| ATOM | 5863 | O | TYR | 289 | 78.849 | 53.720 | 15.692 | 1.00 | 28.55 | B | O |
| ATOM | 5864 | N | ASN | 290 | 80.551 | 54.414 | 14.419 | 1.00 | 30.33 | B | N |
| ATOM | 5865 | CA | ASN | 290 | 79.681 | 54.538 | 13.264 | 1.00 | 29.82 | B | C |
| ATOM | 5866 | CB | ASN | 290 | 80.390 | 55.290 | 12.141 | 1.00 | 19.88 | B | C |
| ATOM | 5867 | CG | ASN | 290 | 80.582 | 56.750 | 12.466 | 1.00 | 23.09 | B | C |
| ATOM | 5868 | OD1 | ASN | 290 | 79.681 | 57.395 | 13.005 | 1.00 | 24.51 | B | O |
| ATOM | 5869 | ND2 | ASN | 290 | 81.748 | 57.286 | 12.133 | 1.00 | 26.61 | B | N |
| ATOM | 5870 | C | ASN | 290 | 79.142 | 53.214 | 12.746 | 1.00 | 28.65 | B | C |
| ATOM | 5871 | O | ASN | 290 | 78.008 | 53.153 | 12.264 | 1.00 | 35.25 | B | O |
| ATOM | 5872 | N | ARG | 291 | 79.944 | 52.155 | 12.842 | 1.00 | 46.80 | B | N |
| ATOM | 5873 | CA | ARG | 291 | 79.513 | 50.850 | 12.362 | 1.00 | 46.11 | B | C |
| ATOM | 5874 | CB | ARG | 291 | 80.694 | 49.867 | 12.337 | 1.00 | 45.84 | B | C |
| ATOM | 5875 | CG | ARG | 291 | 81.661 | 50.063 | 11.152 | 1.00 | 50.80 | B | C |
| ATOM | 5876 | CD | ARG | 291 | 82.722 | 48.943 | 11.054 | 1.00 | 54.88 | B | C |
| ATOM | 5877 | NE | ARG | 291 | 83.916 | 49.157 | 11.883 | 1.00 | 47.06 | B | N |
| ATOM | 5878 | CZ | ARG | 291 | 84.884 | 50.030 | 11.603 | 1.00 | 56.55 | B | C |
| ATOM | 5879 | NH1 | ARG | 291 | 84.813 | 50.787 | 10.515 | 1.00 | 55.39 | B | N |
| ATOM | 5880 | NH2 | ARG | 291 | 85.936 | 50.131 | 12.401 | 1.00 | 53.31 | B | N |
| ATOM | 5881 | C | ARG | 291 | 78.367 | 50.296 | 13.207 | 1.00 | 43.91 | B | C |
| ATOM | 5882 | O | ARG | 291 | 77.338 | 49.876 | 12.676 | 1.00 | 47.17 | B | O |
| ATOM | 5883 | N | GLY | 292 | 78.531 | 50.306 | 14.523 | 1.00 | 18.83 | B | N |
| ATOM | 5884 | CA | GLY | 292 | 77.476 | 49.795 | 15.374 | 1.00 | 19.08 | B | C |
| ATOM | 5885 | C | GLY | 292 | 76.427 | 50.857 | 15.628 | 1.00 | 26.45 | B | C |
| ATOM | 5886 | O | GLY | 292 | 75.874 | 50.947 | 16.722 | 1.00 | 32.58 | B | O |
| ATOM | 5887 | N | ASN | 293 | 76.151 | 51.664 | 14.610 | 1.00 | 32.56 | B | N |
| ATOM | 5888 | CA | ASN | 293 | 75.177 | 52.740 | 14.724 | 1.00 | 34.89 | B | C |
| ATOM | 5889 | CB | ASN | 293 | 73.785 | 52.239 | 14.339 | 1.00 | 18.98 | B | C |
| ATOM | 5890 | CG | ASN | 293 | 73.623 | 52.066 | 12.846 | 1.00 | 25.56 | B | C |
| ATOM | 5891 | OD1 | ASN | 293 | 74.249 | 52.776 | 12.063 | 1.00 | 27.19 | B | O |
| ATOM | 5892 | ND2 | ASN | 293 | 72.767 | 51.132 | 12.440 | 1.00 | 26.33 | B | N |
| ATOM | 5893 | C | ASN | 293 | 75.116 | 53.389 | 16.111 | 1.00 | 36.22 | B | C |
| ATOM | 5894 | O | ASN | 293 | 74.054 | 53.448 | 16.722 | 1.00 | 31.70 | B | O |
| ATOM | 5895 | N | LEU | 294 | 76.247 | 53.875 | 16.614 | 1.00 | 40.17 | B | N |
| ATOM | 5896 | CA | LEU | 294 | 76.260 | 54.525 | 17.921 | 1.00 | 39.32 | B | C |
| ATOM | 5897 | CB | LEU | 294 | 77.141 | 53.737 | 18.901 | 1.00 | 27.66 | B | C |
| ATOM | 5898 | CG | LEU | 294 | 76.633 | 52.343 | 19.291 | 1.00 | 26.48 | B | C |
| ATOM | 5899 | CD1 | LEU | 294 | 77.463 | 51.781 | 20.440 | 1.00 | 27.02 | B | C |
| ATOM | 5900 | CD2 | LEU | 294 | 75.175 | 52.437 | 19.714 | 1.00 | 27.39 | B | C |
| ATOM | 5901 | C | LEU | 294 | 76.730 | 55.985 | 17.823 | 1.00 | 41.69 | B | C |
| ATOM | 5902 | O | LEU | 294 | 77.579 | 56.314 | 16.984 | 1.00 | 40.35 | B | O |
| ATOM | 5903 | N | SER | 295 | 76.158 | 56.860 | 18.656 | 1.00 | 29.47 | B | N |
| ATOM | 5904 | CA | SER | 295 | 76.534 | 58.272 | 18.644 | 1.00 | 29.33 | B | C |
| ATOM | 5905 | CB | SER | 295 | 75.802 | 59.063 | 19.740 | 1.00 | 35.11 | B | C |
| ATOM | 5906 | OG | SER | 295 | 76.336 | 60.371 | 19.894 | 1.00 | 41.79 | B | O |
| ATOM | 5907 | C | SER | 295 | 78.022 | 58.329 | 18.890 | 1.00 | 25.45 | B | C |
| ATOM | 5908 | O | SER | 295 | 78.583 | 57.444 | 19.533 | 1.00 | 22.32 | B | O |
| ATOM | 5909 | N | THR | 296 | 78.661 | 59.379 | 18.401 | 1.00 | 28.05 | B | N |
| ATOM | 5910 | CA | THR | 296 | 80.096 | 59.500 | 18.559 | 1.00 | 28.09 | B | C |
| ATOM | 5911 | CB | THR | 296 | 80.786 | 59.452 | 17.191 | 1.00 | 44.94 | B | C |
| ATOM | 5912 | OG1 | THR | 296 | 80.305 | 60.534 | 16.383 | 1.00 | 50.00 | B | O |
| ATOM | 5913 | CG2 | THR | 296 | 80.485 | 58.150 | 16.487 | 1.00 | 44.81 | B | C |

Fig. 19: A-82

| | | | | | | | | | | | |
|---|---|---|---|---|---|---|---|---|---|---|---|
| ATOM | 5914 | C | THR | 296 | 80.519 | 60.792 | 19.227 | 1.00 | 29.07 | B | C |
| ATOM | 5915 | O | THR | 296 | 81.695 | 60.971 | 19.535 | 1.00 | 27.88 | B | O |
| ATOM | 5916 | N | GLU | 297 | 79.581 | 61.705 | 19.451 | 1.00 | 50.64 | B | N |
| ATOM | 5917 | CA | GLU | 297 | 79.970 | 62.978 | 20.038 | 1.00 | 54.10 | B | C |
| ATOM | 5918 | CB | GLU | 297 | 78.781 | 63.943 | 20.111 | 1.00 | 93.12 | B | C |
| ATOM | 5919 | CG | GLU | 297 | 77.787 | 63.695 | 21.213 | 1.00 | 100.15 | B | C |
| ATOM | 5920 | CD | GLU | 297 | 77.036 | 64.960 | 21.569 | 1.00 | 101.40 | B | C |
| ATOM | 5921 | OE1 | GLU | 297 | 76.160 | 64.911 | 22.455 | 1.00 | 104.84 | B | O |
| ATOM | 5922 | OE2 | GLU | 297 | 77.333 | 66.010 | 20.964 | 1.00 | 102.89 | B | O |
| ATOM | 5923 | C | GLU | 297 | 80.639 | 62.849 | 21.399 | 1.00 | 52.14 | B | C |
| ATOM | 5924 | O | GLU | 297 | 81.715 | 63.406 | 21.612 | 1.00 | 51.64 | B | O |
| ATOM | 5925 | N | LYS | 298 | 80.029 | 62.104 | 22.315 | 1.00 | 35.40 | B | N |
| ATOM | 5926 | CA | LYS | 298 | 80.622 | 61.942 | 23.636 | 1.00 | 35.40 | B | C |
| ATOM | 5927 | CB | LYS | 298 | 79.837 | 60.916 | 24.443 | 1.00 | 37.32 | B | C |
| ATOM | 5928 | CG | LYS | 298 | 80.199 | 60.902 | 25.910 | 1.00 | 46.03 | B | C |
| ATOM | 5929 | CD | LYS | 298 | 79.201 | 60.085 | 26.727 | 1.00 | 47.75 | B | C |
| ATOM | 5930 | CE | LYS | 298 | 77.777 | 60.625 | 26.578 | 1.00 | 51.57 | B | C |
| ATOM | 5931 | NZ | LYS | 298 | 77.676 | 62.075 | 26.908 | 1.00 | 55.89 | B | N |
| ATOM | 5932 | C | LYS | 298 | 82.087 | 61.518 | 23.514 | 1.00 | 33.00 | B | C |
| ATOM | 5933 | O | LYS | 298 | 82.939 | 61.933 | 24.310 | 1.00 | 33.88 | B | O |
| ATOM | 5934 | N | PHE | 299 | 82.371 | 60.699 | 22.505 | 1.00 | 29.00 | B | N |
| ATOM | 5935 | CA | PHE | 299 | 83.729 | 60.226 | 22.244 | 1.00 | 27.24 | B | C |
| ATOM | 5936 | CB | PHE | 299 | 83.701 | 59.054 | 21.263 | 1.00 | 39.15 | B | C |
| ATOM | 5937 | CG | PHE | 299 | 85.065 | 58.571 | 20.851 | 1.00 | 31.59 | B | C |
| ATOM | 5938 | CD1 | PHE | 299 | 86.020 | 58.237 | 21.806 | 1.00 | 28.04 | B | C |
| ATOM | 5939 | CD2 | PHE | 299 | 85.396 | 58.435 | 19.505 | 1.00 | 29.32 | B | C |
| ATOM | 5940 | CE1 | PHE | 299 | 87.284 | 57.776 | 21.422 | 1.00 | 27.45 | B | C |
| ATOM | 5941 | CE2 | PHE | 299 | 86.667 | 57.970 | 19.119 | 1.00 | 23.73 | B | C |
| ATOM | 5942 | CZ | PHE | 299 | 87.603 | 57.643 | 20.078 | 1.00 | 22.24 | B | C |
| ATOM | 5943 | C | PHE | 299 | 84.562 | 61.361 | 21.662 | 1.00 | 27.59 | B | C |
| ATOM | 5944 | O | PHE | 299 | 85.625 | 61.702 | 22.183 | 1.00 | 23.40 | B | O |
| ATOM | 5945 | N | VAL | 300 | 84.077 | 61.946 | 20.576 | 1.00 | 13.78 | B | N |
| ATOM | 5946 | CA | VAL | 300 | 84.791 | 63.050 | 19.944 | 1.00 | 18.73 | B | C |
| ATOM | 5947 | CB | VAL | 300 | 83.954 | 63.701 | 18.822 | 1.00 | 24.12 | B | C |
| ATOM | 5948 | CG1 | VAL | 300 | 84.616 | 64.979 | 18.363 | 1.00 | 27.69 | B | C |
| ATOM | 5949 | CG2 | VAL | 300 | 83.814 | 62.731 | 17.646 | 1.00 | 28.13 | B | C |
| ATOM | 5950 | C | VAL | 300 | 85.142 | 64.119 | 20.966 | 1.00 | 17.37 | B | C |
| ATOM | 5951 | O | VAL | 300 | 86.209 | 64.715 | 20.906 | 1.00 | 17.87 | B | O |
| ATOM | 5952 | N | GLU | 301 | 84.248 | 64.359 | 21.914 | 1.00 | 33.19 | B | N |
| ATOM | 5953 | CA | GLU | 301 | 84.520 | 65.377 | 22.915 | 1.00 | 33.85 | B | C |
| ATOM | 5954 | CB | GLU | 301 | 83.255 | 65.707 | 23.706 | 1.00 | 133.49 | B | C |
| ATOM | 5955 | CG | GLU | 301 | 83.426 | 66.851 | 24.703 | 1.00 | 135.76 | B | C |
| ATOM | 5956 | CD | GLU | 301 | 84.115 | 68.077 | 24.108 | 1.00 | 141.57 | B | C |
| ATOM | 5957 | OE1 | GLU | 301 | 83.669 | 68.566 | 23.046 | 1.00 | 141.12 | B | O |
| ATOM | 5958 | OE2 | GLU | 301 | 85.102 | 68.555 | 24.713 | 1.00 | 143.84 | B | O |
| ATOM | 5959 | C | GLU | 301 | 85.634 | 64.925 | 23.847 | 1.00 | 32.42 | B | C |
| ATOM | 5960 | O | GLU | 301 | 86.495 | 65.723 | 24.239 | 1.00 | 30.50 | B | O |
| ATOM | 5961 | N | GLU | 302 | 85.628 | 63.642 | 24.190 | 1.00 | 18.71 | B | N |
| ATOM | 5962 | CA | GLU | 302 | 86.663 | 63.091 | 25.060 | 1.00 | 18.52 | B | C |
| ATOM | 5963 | CB | GLU | 302 | 86.420 | 61.596 | 25.293 | 1.00 | 49.27 | B | C |
| ATOM | 5964 | CG | GLU | 302 | 87.438 | 60.934 | 26.207 | 1.00 | 49.02 | B | C |
| ATOM | 5965 | CD | GLU | 302 | 87.100 | 59.486 | 26.491 | 1.00 | 45.95 | B | C |
| ATOM | 5966 | OE1 | GLU | 302 | 86.051 | 59.237 | 27.118 | 1.00 | 45.93 | B | O |
| ATOM | 5967 | OE2 | GLU | 302 | 87.875 | 58.594 | 26.084 | 1.00 | 50.37 | B | O |
| ATOM | 5968 | C | GLU | 302 | 88.046 | 63.301 | 24.456 | 1.00 | 21.59 | B | C |
| ATOM | 5969 | O | GLU | 302 | 88.964 | 63.720 | 25.150 | 1.00 | 20.85 | B | O |
| ATOM | 5970 | N | ILE | 303 | 88.188 | 63.031 | 23.159 | 1.00 | 30.73 | B | N |
| ATOM | 5971 | CA | ILE | 303 | 89.479 | 63.175 | 22.472 | 1.00 | 30.78 | B | C |
| ATOM | 5972 | CB | ILE | 303 | 89.470 | 62.431 | 21.112 | 1.00 | 21.11 | B | C |
| ATOM | 5973 | CG2 | ILE | 303 | 90.865 | 62.406 | 20.518 | 1.00 | 16.29 | B | C |
| ATOM | 5974 | CG1 | ILE | 303 | 88.932 | 61.003 | 21.306 | 1.00 | 18.71 | B | C |
| ATOM | 5975 | CD1 | ILE | 303 | 89.501 | 60.262 | 22.515 | 1.00 | 15.17 | B | C |
| ATOM | 5976 | C | ILE | 303 | 89.922 | 64.625 | 22.242 | 1.00 | 32.81 | B | C |
| ATOM | 5977 | O | ILE | 303 | 91.097 | 64.955 | 22.415 | 1.00 | 35.30 | B | O |
| ATOM | 5978 | N | LYS | 304 | 88.989 | 65.485 | 21.847 | 1.00 | 41.13 | B | N |
| ATOM | 5979 | CA | LYS | 304 | 89.321 | 66.881 | 21.624 | 1.00 | 41.93 | B | C |
| ATOM | 5980 | CB | LYS | 304 | 88.087 | 67.695 | 21.239 | 1.00 | 34.23 | B | C |
| ATOM | 5981 | CG | LYS | 304 | 87.578 | 67.484 | 19.837 | 1.00 | 40.90 | B | C |
| ATOM | 5982 | CD | LYS | 304 | 86.491 | 68.498 | 19.526 | 1.00 | 42.43 | B | C |
| ATOM | 5983 | CE | LYS | 304 | 85.937 | 68.312 | 18.122 | 1.00 | 45.16 | B | C |
| ATOM | 5984 | NZ | LYS | 304 | 84.893 | 69.323 | 17.799 | 1.00 | 47.34 | B | N |
| ATOM | 5985 | C | LYS | 304 | 89.892 | 67.455 | 22.906 | 1.00 | 38.02 | B | C |
| ATOM | 5986 | O | LYS | 304 | 90.833 | 68.240 | 22.871 | 1.00 | 42.10 | B | O |

Fig. 19: A-83

| | | | | | | | | | | | |
|---|---|---|---|---|---|---|---|---|---|---|---|
| ATOM | 5987 | N | SER | 305 | 89.322 | 67.066 | 24.043 | 1.00 | 21.53 | B | N |
| ATOM | 5988 | CA | SER | 305 | 89.788 | 67.571 | 25.335 | 1.00 | 18.69 | B | C |
| ATOM | 5989 | CB | SER | 305 | 88.872 | 67.096 | 26.460 | 1.00 | 39.18 | B | C |
| ATOM | 5990 | OG | SER | 305 | 89.039 | 65.715 | 26.696 | 1.00 | 35.86 | B | O |
| ATOM | 5991 | C | SER | 305 | 91.223 | 67.134 | 25.622 | 1.00 | 19.21 | B | C |
| ATOM | 5992 | O | SER | 305 | 91.935 | 67.754 | 26.418 | 1.00 | 21.78 | B | O |
| ATOM | 5993 | N | ILE | 306 | 91.652 | 66.063 | 24.969 | 1.00 | 47.39 | B | N |
| ATOM | 5994 | CA | ILE | 306 | 93.005 | 65.582 | 25.158 | 1.00 | 44.14 | B | C |
| ATOM | 5995 | CB | ILE | 306 | 93.129 | 64.131 | 24.682 | 1.00 | 20.56 | B | C |
| ATOM | 5996 | CG2 | ILE | 306 | 94.584 | 63.769 | 24.454 | 1.00 | 21.29 | B | C |
| ATOM | 5997 | CG1 | ILE | 306 | 92.479 | 63.210 | 25.713 | 1.00 | 23.19 | B | C |
| ATOM | 5998 | CD1 | ILE | 306 | 92.459 | 61.762 | 25.302 | 1.00 | 20.90 | B | C |
| ATOM | 5999 | C | ILE | 306 | 93.966 | 66.469 | 24.378 | 1.00 | 41.90 | B | C |
| ATOM | 6000 | O | ILE | 306 | 95.146 | 66.583 | 24.717 | 1.00 | 42.43 | B | O |
| ATOM | 6001 | N | ALA | 307 | 93.445 | 67.103 | 23.334 | 1.00 | 47.34 | B | N |
| ATOM | 6002 | CA | ALA | 307 | 94.247 | 67.979 | 22.497 | 1.00 | 49.53 | B | C |
| ATOM | 6003 | CB | ALA | 307 | 93.538 | 68.236 | 21.181 | 1.00 | 34.34 | B | C |
| ATOM | 6004 | C | ALA | 307 | 94.526 | 69.296 | 23.200 | 1.00 | 49.19 | B | C |
| ATOM | 6005 | O | ALA | 307 | 93.952 | 69.595 | 24.253 | 1.00 | 48.18 | B | O |
| ATOM | 6006 | N | SER | 308 | 95.415 | 70.078 | 22.604 | 1.00 | 31.36 | B | N |
| ATOM | 6007 | CA | SER | 308 | 95.801 | 71.367 | 23.141 | 1.00 | 34.29 | B | C |
| ATOM | 6008 | CB | SER | 308 | 97.299 | 71.580 | 22.943 | 1.00 | 9.08 | B | C |
| ATOM | 6009 | OG | SER | 308 | 98.040 | 70.819 | 23.867 | 1.00 | 12.47 | B | O |
| ATOM | 6010 | C | SER | 308 | 95.054 | 72.489 | 22.446 | 1.00 | 37.94 | B | C |
| ATOM | 6011 | O | SER | 308 | 94.703 | 72.373 | 21.272 | 1.00 | 35.28 | B | O |
| ATOM | 6012 | N | GLU | 309 | 94.813 | 73.575 | 23.178 | 1.00 | 31.30 | B | N |
| ATOM | 6013 | CA | GLU | 309 | 94.137 | 74.735 | 22.614 | 1.00 | 34.79 | B | C |
| ATOM | 6014 | CB | GLU | 309 | 93.786 | 75.736 | 23.721 | 1.00 | 74.37 | B | C |
| ATOM | 6015 | CG | GLU | 309 | 92.834 | 75.203 | 24.787 | 1.00 | 79.74 | B | C |
| ATOM | 6016 | CD | GLU | 309 | 91.461 | 74.845 | 24.234 | 1.00 | 82.50 | B | C |
| ATOM | 6017 | OE1 | GLU | 309 | 90.533 | 74.618 | 25.043 | 1.00 | 84.83 | B | O |
| ATOM | 6018 | OE2 | GLU | 309 | 91.307 | 74.784 | 22.995 | 1.00 | 86.65 | B | O |
| ATOM | 6019 | C | GLU | 309 | 95.138 | 75.359 | 21.642 | 1.00 | 35.54 | B | C |
| ATOM | 6020 | O | GLU | 309 | 96.321 | 75.480 | 21.971 | 1.00 | 37.19 | B | O |
| ATOM | 6021 | N | PRO | 310 | 94.685 | 75.762 | 20.435 | 1.00 | 19.46 | B | N |
| ATOM | 6022 | CD | PRO | 310 | 95.588 | 76.399 | 19.457 | 1.00 | 19.32 | B | C |
| ATOM | 6023 | CA | PRO | 310 | 93.324 | 75.694 | 19.890 | 1.00 | 19.65 | B | C |
| ATOM | 6024 | CB | PRO | 310 | 93.362 | 76.729 | 18.770 | 1.00 | 21.15 | B | C |
| ATOM | 6025 | CG | PRO | 310 | 94.715 | 76.515 | 18.203 | 1.00 | 20.71 | B | C |
| ATOM | 6026 | C | PRO | 310 | 92.884 | 74.312 | 19.384 | 1.00 | 20.14 | B | C |
| ATOM | 6027 | O | PRO | 310 | 93.368 | 73.816 | 18.374 | 1.00 | 16.93 | B | O |
| ATOM | 6028 | N | THR | 311 | 91.945 | 73.714 | 20.101 | 1.00 | 34.98 | B | N |
| ATOM | 6029 | CA | THR | 311 | 91.410 | 72.410 | 19.764 | 1.00 | 35.85 | B | C |
| ATOM | 6030 | CB | THR | 311 | 89.985 | 72.276 | 20.321 | 1.00 | 54.06 | B | C |
| ATOM | 6031 | OG1 | THR | 311 | 89.327 | 71.159 | 19.711 | 1.00 | 58.22 | B | O |
| ATOM | 6032 | CG2 | THR | 311 | 89.195 | 73.556 | 20.052 | 1.00 | 57.14 | B | C |
| ATOM | 6033 | C | THR | 311 | 91.390 | 72.103 | 18.265 | 1.00 | 37.72 | B | C |
| ATOM | 6034 | O | THR | 311 | 91.801 | 71.022 | 17.847 | 1.00 | 38.89 | B | O |
| ATOM | 6035 | N | GLU | 312 | 90.929 | 73.049 | 17.451 | 1.00 | 45.13 | B | N |
| ATOM | 6036 | CA | GLU | 312 | 90.842 | 72.825 | 16.004 | 1.00 | 43.75 | B | C |
| ATOM | 6037 | CB | GLU | 312 | 90.160 | 74.008 | 15.309 | 1.00 | 94.13 | B | C |
| ATOM | 6038 | CG | GLU | 312 | 90.848 | 75.342 | 15.528 | 1.00 | 95.89 | B | C |
| ATOM | 6039 | CD | GLU | 312 | 90.633 | 76.309 | 14.376 | 1.00 | 95.00 | B | C |
| ATOM | 6040 | OE1 | GLU | 312 | 90.998 | 77.496 | 14.516 | 1.00 | 98.35 | B | O |
| ATOM | 6041 | OE2 | GLU | 312 | 90.109 | 75.880 | 13.327 | 1.00 | 95.87 | B | O |
| ATOM | 6042 | C | GLU | 312 | 92.168 | 72.547 | 15.310 | 1.00 | 42.37 | B | C |
| ATOM | 6043 | O | GLU | 312 | 92.219 | 71.771 | 14.367 | 1.00 | 42.33 | B | O |
| ATOM | 6044 | N | LYS | 313 | 93.240 | 73.180 | 15.763 | 1.00 | 62.67 | B | N |
| ATOM | 6045 | CA | LYS | 313 | 94.537 | 72.966 | 15.141 | 1.00 | 61.87 | B | C |
| ATOM | 6046 | CB | LYS | 313 | 95.368 | 74.255 | 15.192 | 1.00 | 80.35 | B | C |
| ATOM | 6047 | CG | LYS | 313 | 94.954 | 75.308 | 14.167 | 1.00 | 80.23 | B | C |
| ATOM | 6048 | CD | LYS | 313 | 95.351 | 74.917 | 12.745 | 1.00 | 76.53 | B | C |
| ATOM | 6049 | CE | LYS | 313 | 96.790 | 75.307 | 12.430 | 1.00 | 78.57 | B | C |
| ATOM | 6050 | NZ | LYS | 313 | 97.781 | 74.730 | 13.383 | 1.00 | 83.05 | B | N |
| ATOM | 6051 | C | LYS | 313 | 95.308 | 71.832 | 15.800 | 1.00 | 63.02 | B | C |
| ATOM | 6052 | O | LYS | 313 | 96.473 | 71.610 | 15.491 | 1.00 | 65.34 | B | O |
| ATOM | 6053 | N | HIS | 314 | 94.656 | 71.103 | 16.697 | 1.00 | 42.28 | B | N |
| ATOM | 6054 | CA | HIS | 314 | 95.326 | 70.011 | 17.391 | 1.00 | 43.13 | B | C |
| ATOM | 6055 | CB | HIS | 314 | 95.631 | 70.426 | 18.828 | 1.00 | 51.27 | B | C |
| ATOM | 6056 | CG | HIS | 314 | 96.611 | 71.551 | 18.938 | 1.00 | 48.13 | B | C |
| ATOM | 6057 | CD2 | HIS | 314 | 96.423 | 72.880 | 19.111 | 1.00 | 47.60 | B | C |
| ATOM | 6058 | ND1 | HIS | 314 | 97.973 | 71.364 | 18.847 | 1.00 | 47.71 | B | N |
| ATOM | 6059 | CE1 | HIS | 314 | 98.582 | 72.530 | 18.960 | 1.00 | 47.00 | B | C |

Fig. 19: A-84

| | | | | | | | | | | | |
|---|---|---|---|---|---|---|---|---|---|---|---|
| ATOM | 6060 | NE2 | HIS | 314 | 97.664 | 73.466 | 19.121 | 1.00 | 47.39 | B | N |
| ATOM | 6061 | C | HIS | 314 | 94.540 | 68.706 | 17.405 | 1.00 | 43.26 | B | C |
| ATOM | 6062 | O | HIS | 314 | 95.034 | 67.690 | 17.896 | 1.00 | 46.66 | B | O |
| ATOM | 6063 | N | PHE | 315 | 93.324 | 68.732 | 16.868 | 1.00 | 55.79 | B | N |
| ATOM | 6064 | CA | PHE | 315 | 92.475 | 67.546 | 16.835 | 1.00 | 55.59 | B | C |
| ATOM | 6065 | CB | PHE | 315 | 91.175 | 67.834 | 17.578 | 1.00 | 29.85 | B | C |
| ATOM | 6066 | CG | PHE | 315 | 90.175 | 66.731 | 17.499 | 1.00 | 24.83 | B | C |
| ATOM | 6067 | CD1 | PHE | 315 | 90.445 | 65.490 | 18.057 | 1.00 | 26.67 | B | C |
| ATOM | 6068 | CD2 | PHE | 315 | 88.944 | 66.942 | 16.890 | 1.00 | 22.91 | B | C |
| ATOM | 6069 | CE1 | PHE | 315 | 89.503 | 64.473 | 18.016 | 1.00 | 21.62 | B | C |
| ATOM | 6070 | CE2 | PHE | 315 | 87.989 | 65.939 | 16.838 | 1.00 | 23.61 | B | C |
| ATOM | 6071 | CZ | PHE | 315 | 88.268 | 64.700 | 17.404 | 1.00 | 25.28 | B | C |
| ATOM | 6072 | C | PHE | 315 | 92.172 | 67.086 | 15.412 | 1.00 | 56.31 | B | C |
| ATOM | 6073 | O | PHE | 315 | 91.948 | 67.903 | 14.516 | 1.00 | 57.71 | B | O |
| ATOM | 6074 | N | PHE | 316 | 92.170 | 65.772 | 15.212 | 1.00 | 44.89 | B | N |
| ATOM | 6075 | CA | PHE | 316 | 91.898 | 65.200 | 13.899 | 1.00 | 41.94 | B | C |
| ATOM | 6076 | CB | PHE | 316 | 93.175 | 64.621 | 13.282 | 1.00 | 20.23 | B | C |
| ATOM | 6077 | CG | PHE | 316 | 94.195 | 65.652 | 12.900 | 1.00 | 23.85 | B | C |
| ATOM | 6078 | CD1 | PHE | 316 | 95.118 | 66.114 | 13.828 | 1.00 | 19.44 | B | C |
| ATOM | 6079 | CD2 | PHE | 316 | 94.229 | 66.165 | 11.605 | 1.00 | 20.70 | B | C |
| ATOM | 6080 | CE1 | PHE | 316 | 96.066 | 67.074 | 13.475 | 1.00 | 22.01 | B | C |
| ATOM | 6081 | CE2 | PHE | 316 | 95.171 | 67.125 | 11.242 | 1.00 | 23.81 | B | C |
| ATOM | 6082 | CZ | PHE | 316 | 96.092 | 67.580 | 12.180 | 1.00 | 24.04 | B | C |
| ATOM | 6083 | C | PHE | 316 | 90.841 | 64.107 | 13.990 | 1.00 | 39.87 | B | C |
| ATOM | 6084 | O | PHE | 316 | 90.845 | 63.302 | 14.910 | 1.00 | 39.11 | B | O |
| ATOM | 6085 | N | ASN | 317 | 89.938 | 64.088 | 13.020 | 1.00 | 36.72 | B | N |
| ATOM | 6086 | CA | ASN | 317 | 88.863 | 63.110 | 12.978 | 1.00 | 37.94 | B | C |
| ATOM | 6087 | CB | ASN | 317 | 87.538 | 63.826 | 12.746 | 1.00 | 58.19 | B | C |
| ATOM | 6088 | CG | ASN | 317 | 86.496 | 63.443 | 13.752 | 1.00 | 61.18 | B | C |
| ATOM | 6089 | OD1 | ASN | 317 | 86.408 | 62.284 | 14.144 | 1.00 | 63.11 | B | O |
| ATOM | 6090 | ND2 | ASN | 317 | 85.688 | 64.411 | 14.176 | 1.00 | 59.44 | B | N |
| ATOM | 6091 | C | ASN | 317 | 89.102 | 62.140 | 11.831 | 1.00 | 38.90 | B | C |
| ATOM | 6092 | O | ASN | 317 | 89.519 | 62.549 | 10.757 | 1.00 | 39.76 | B | O |
| ATOM | 6093 | N | VAL | 318 | 88.840 | 60.858 | 12.045 | 1.00 | 40.86 | B | N |
| ATOM | 6094 | CA | VAL | 318 | 89.027 | 59.872 | 10.981 | 1.00 | 39.49 | B | C |
| ATOM | 6095 | CB | VAL | 318 | 90.348 | 59.096 | 11.156 | 1.00 | 59.32 | B | C |
| ATOM | 6096 | CG1 | VAL | 318 | 90.497 | 58.075 | 10.065 | 1.00 | 59.45 | B | C |
| ATOM | 6097 | CG2 | VAL | 318 | 91.519 | 60.052 | 11.111 | 1.00 | 59.30 | B | C |
| ATOM | 6098 | C | VAL | 318 | 87.861 | 58.894 | 10.987 | 1.00 | 34.64 | B | C |
| ATOM | 6099 | O | VAL | 318 | 87.363 | 58.523 | 12.050 | 1.00 | 35.31 | B | O |
| ATOM | 6100 | N | SER | 319 | 87.417 | 58.482 | 9.803 | 1.00 | 25.74 | B | N |
| ATOM | 6101 | CA | SER | 319 | 86.300 | 57.557 | 9.711 | 1.00 | 25.00 | B | C |
| ATOM | 6102 | CB | SER | 319 | 85.769 | 57.502 | 8.275 | 1.00 | 46.83 | B | C |
| ATOM | 6103 | OG | SER | 319 | 86.801 | 57.222 | 7.348 | 1.00 | 58.78 | B | O |
| ATOM | 6104 | C | SER | 319 | 86.672 | 56.161 | 10.195 | 1.00 | 23.60 | B | C |
| ATOM | 6105 | O | SER | 319 | 85.877 | 55.513 | 10.876 | 1.00 | 21.67 | B | O |
| ATOM | 6106 | N | ASP | 320 | 87.875 | 55.702 | 9.855 | 1.00 | 29.04 | B | N |
| ATOM | 6107 | CA | ASP | 320 | 88.342 | 54.377 | 10.272 | 1.00 | 29.02 | B | C |
| ATOM | 6108 | CB | ASP | 320 | 87.700 | 53.292 | 9.391 | 1.00 | 54.50 | B | C |
| ATOM | 6109 | CG | ASP | 320 | 88.036 | 53.455 | 7.907 | 1.00 | 52.95 | B | C |
| ATOM | 6110 | OD1 | ASP | 320 | 87.708 | 54.505 | 7.318 | 1.00 | 51.63 | B | O |
| ATOM | 6111 | OD2 | ASP | 320 | 88.628 | 52.525 | 7.324 | 1.00 | 53.50 | B | O |
| ATOM | 6112 | C | ASP | 320 | 89.878 | 54.249 | 10.227 | 1.00 | 27.39 | B | C |
| ATOM | 6113 | O | ASP | 320 | 90.574 | 55.142 | 9.734 | 1.00 | 27.17 | B | O |
| ATOM | 6114 | N | GLU | 321 | 90.403 | 53.140 | 10.745 | 1.00 | 32.71 | B | N |
| ATOM | 6115 | CA | GLU | 321 | 91.845 | 52.909 | 10.748 | 1.00 | 33.69 | B | C |
| ATOM | 6116 | CB | GLU | 321 | 92.152 | 51.430 | 11.018 | 1.00 | 76.40 | B | C |
| ATOM | 6117 | CG | GLU | 321 | 92.439 | 51.066 | 12.469 | 1.00 | 70.24 | B | C |
| ATOM | 6118 | CD | GLU | 321 | 91.229 | 51.194 | 13.373 | 1.00 | 69.99 | B | C |
| ATOM | 6119 | OE1 | GLU | 321 | 90.159 | 50.621 | 13.053 | 1.00 | 71.42 | B | O |
| ATOM | 6120 | OE2 | GLU | 321 | 91.357 | 51.862 | 14.418 | 1.00 | 74.03 | B | O |
| ATOM | 6121 | C | GLU | 321 | 92.476 | 53.300 | 9.412 | 1.00 | 37.68 | B | C |
| ATOM | 6122 | O | GLU | 321 | 93.529 | 53.943 | 9.369 | 1.00 | 34.44 | B | O |
| ATOM | 6123 | N | LEU | 322 | 91.820 | 52.905 | 8.323 | 1.00 | 34.24 | B | N |
| ATOM | 6124 | CA | LEU | 322 | 92.310 | 53.175 | 6.971 | 1.00 | 36.93 | B | C |
| ATOM | 6125 | CB | LEU | 322 | 91.345 | 52.598 | 5.937 | 1.00 | 67.00 | B | C |
| ATOM | 6126 | CG | LEU | 322 | 91.361 | 51.081 | 5.743 | 1.00 | 65.63 | B | C |
| ATOM | 6127 | CD1 | LEU | 322 | 92.716 | 50.681 | 5.198 | 1.00 | 67.37 | B | C |
| ATOM | 6128 | CD2 | LEU | 322 | 91.058 | 50.353 | 7.063 | 1.00 | 70.68 | B | C |
| ATOM | 6129 | C | LEU | 322 | 92.566 | 54.632 | 6.643 | 1.00 | 38.52 | B | C |
| ATOM | 6130 | O | LEU | 322 | 93.607 | 54.971 | 6.097 | 1.00 | 41.87 | B | O |
| ATOM | 6131 | N | ALA | 323 | 91.617 | 55.492 | 6.974 | 1.00 | 34.22 | B | N |
| ATOM | 6132 | CA | ALA | 323 | 91.759 | 56.908 | 6.687 | 1.00 | 34.65 | B | C |

Fig. 19: A-85

| | | | | | | | | | | | |
|---|---|---|---|---|---|---|---|---|---|---|---|
| ATOM | 6133 | CB | ALA | 323 | 90.420 | 57.600 | 6.897 | 1.00 | 1.87 | B | C |
| ATOM | 6134 | C | ALA | 323 | 92.859 | 57.644 | 7.476 | 1.00 | 35.06 | B | C |
| ATOM | 6135 | O | ALA | 323 | 93.171 | 58.804 | 7.181 | 1.00 | 35.08 | B | O |
| ATOM | 6136 | N | LEU | 324 | 93.447 | 56.995 | 8.476 | 1.00 | 26.80 | B | N |
| ATOM | 6137 | CA | LEU | 324 | 94.492 | 57.652 | 9.256 | 1.00 | 25.28 | B | C |
| ATOM | 6138 | CB | LEU | 324 | 95.221 | 56.640 | 10.146 | 1.00 | 29.36 | B | C |
| ATOM | 6139 | CG | LEU | 324 | 94.590 | 56.344 | 11.516 | 1.00 | 28.09 | B | C |
| ATOM | 6140 | CD1 | LEU | 324 | 95.288 | 55.158 | 12.170 | 1.00 | 27.23 | B | C |
| ATOM | 6141 | CD2 | LEU | 324 | 94.676 | 57.580 | 12.406 | 1.00 | 26.02 | B | C |
| ATOM | 6142 | C | LEU | 324 | 95.495 | 58.366 | 8.354 | 1.00 | 28.81 | B | C |
| ATOM | 6143 | O | LEU | 324 | 95.822 | 59.521 | 8.588 | 1.00 | 25.35 | B | O |
| ATOM | 6144 | N | VAL | 325 | 95.966 | 57.679 | 7.317 | 1.00 | 52.77 | B | N |
| ATOM | 6145 | CA | VAL | 325 | 96.934 | 58.246 | 6.378 | 1.00 | 56.30 | B | C |
| ATOM | 6146 | CB | VAL | 325 | 97.153 | 57.321 | 5.185 | 1.00 | 36.74 | B | C |
| ATOM | 6147 | CG1 | VAL | 325 | 97.936 | 56.099 | 5.614 | 1.00 | 36.85 | B | C |
| ATOM | 6148 | CG2 | VAL | 325 | 95.810 | 56.923 | 4.599 | 1.00 | 40.13 | B | C |
| ATOM | 6149 | C | VAL | 325 | 96.524 | 59.598 | 5.818 | 1.00 | 59.12 | B | C |
| ATOM | 6150 | O | VAL | 325 | 97.324 | 60.529 | 5.761 | 1.00 | 61.18 | B | O |
| ATOM | 6151 | N | THR | 326 | 95.277 | 59.694 | 5.384 | 1.00 | 40.34 | B | N |
| ATOM | 6152 | CA | THR | 326 | 94.743 | 60.925 | 4.818 | 1.00 | 41.75 | B | C |
| ATOM | 6153 | CB | THR | 326 | 93.298 | 60.706 | 4.344 | 1.00 | 81.94 | B | C |
| ATOM | 6154 | OG1 | THR | 326 | 92.430 | 60.600 | 5.481 | 1.00 | 83.85 | B | O |
| ATOM | 6155 | CG2 | THR | 326 | 93.206 | 59.417 | 3.534 | 1.00 | 84.31 | B | C |
| ATOM | 6156 | C | THR | 326 | 94.744 | 62.070 | 5.836 | 1.00 | 41.76 | B | C |
| ATOM | 6157 | O | THR | 326 | 93.885 | 62.952 | 5.785 | 1.00 | 40.58 | B | O |
| ATOM | 6158 | N | ILE | 327 | 95.705 | 62.052 | 6.755 | 1.00 | 36.65 | B | N |
| ATOM | 6159 | CA | ILE | 327 | 95.812 | 63.075 | 7.792 | 1.00 | 36.84 | B | C |
| ATOM | 6160 | CB | ILE | 327 | 95.078 | 62.604 | 9.085 | 1.00 | 16.25 | B | C |
| ATOM | 6161 | CG2 | ILE | 327 | 95.934 | 62.757 | 10.328 | 1.00 | 17.02 | B | C |
| ATOM | 6162 | CG1 | ILE | 327 | 93.807 | 63.408 | 9.260 | 1.00 | 16.61 | B | C |
| ATOM | 6163 | CD1 | ILE | 327 | 92.943 | 62.878 | 10.372 | 1.00 | 16.28 | B | C |
| ATOM | 6164 | C | ILE | 327 | 97.272 | 63.402 | 8.093 | 1.00 | 37.35 | B | C |
| ATOM | 6165 | O | ILE | 327 | 97.590 | 64.494 | 8.559 | 1.00 | 37.60 | B | O |
| ATOM | 6166 | N | VAL | 328 | 98.158 | 62.455 | 7.804 | 1.00 | 43.89 | B | N |
| ATOM | 6167 | CA | VAL | 328 | 99.575 | 62.643 | 8.060 | 1.00 | 46.03 | B | C |
| ATOM | 6168 | CB | VAL | 328 | 100.407 | 61.469 | 7.510 | 1.00 | 54.81 | B | C |
| ATOM | 6169 | CG1 | VAL | 328 | 99.871 | 60.157 | 8.061 | 1.00 | 56.76 | B | C |
| ATOM | 6170 | CG2 | VAL | 328 | 100.381 | 61.480 | 5.997 | 1.00 | 56.08 | B | C |
| ATOM | 6171 | C | VAL | 328 | 100.121 | 63.943 | 7.481 | 1.00 | 45.95 | B | C |
| ATOM | 6172 | O | VAL | 328 | 100.998 | 64.563 | 8.075 | 1.00 | 45.23 | B | O |
| ATOM | 6173 | N | LYS | 329 | 99.611 | 64.366 | 6.331 | 1.00 | 44.51 | B | N |
| ATOM | 6174 | CA | LYS | 329 | 100.097 | 65.609 | 5.732 | 1.00 | 43.72 | B | C |
| ATOM | 6175 | CB | LYS | 329 | 99.471 | 65.824 | 4.356 | 1.00 | 45.34 | B | C |
| ATOM | 6176 | CG | LYS | 329 | 100.174 | 66.880 | 3.520 | 1.00 | 46.89 | B | C |
| ATOM | 6177 | CD | LYS | 329 | 99.423 | 67.129 | 2.220 | 1.00 | 49.21 | B | C |
| ATOM | 6178 | CE | LYS | 329 | 100.179 | 68.074 | 1.298 | 1.00 | 52.25 | B | C |
| ATOM | 6179 | NZ | LYS | 329 | 101.450 | 67.466 | 0.831 | 1.00 | 55.93 | B | N |
| ATOM | 6180 | C | LYS | 329 | 99.762 | 66.797 | 6.640 | 1.00 | 41.89 | B | C |
| ATOM | 6181 | O | LYS | 329 | 100.640 | 67.552 | 7.056 | 1.00 | 43.10 | B | O |
| ATOM | 6182 | N | ALA | 330 | 98.483 | 66.957 | 6.952 | 1.00 | 14.46 | B | N |
| ATOM | 6183 | CA | ALA | 330 | 98.053 | 68.043 | 7.814 | 1.00 | 14.49 | B | C |
| ATOM | 6184 | CB | ALA | 330 | 96.538 | 68.052 | 7.906 | 1.00 | 26.19 | B | C |
| ATOM | 6185 | C | ALA | 330 | 98.657 | 67.910 | 9.210 | 1.00 | 15.64 | B | C |
| ATOM | 6186 | O | ALA | 330 | 99.090 | 68.896 | 9.796 | 1.00 | 15.54 | B | O |
| ATOM | 6187 | N | LEU | 331 | 98.666 | 66.688 | 9.745 | 1.00 | 29.61 | B | N |
| ATOM | 6188 | CA | LEU | 331 | 99.200 | 66.447 | 11.078 | 1.00 | 27.25 | B | C |
| ATOM | 6189 | CB | LEU | 331 | 99.108 | 64.969 | 11.454 | 1.00 | 20.84 | B | C |
| ATOM | 6190 | CG | LEU | 331 | 99.086 | 64.642 | 12.958 | 1.00 | 17.26 | B | C |
| ATOM | 6191 | CD1 | LEU | 331 | 99.332 | 63.152 | 13.131 | 1.00 | 18.89 | B | C |
| ATOM | 6192 | CD2 | LEU | 331 | 100.130 | 65.436 | 13.722 | 1.00 | 12.95 | B | C |
| ATOM | 6193 | C | LEU | 331 | 100.647 | 66.860 | 11.070 | 1.00 | 27.28 | B | C |
| ATOM | 6194 | O | LEU | 331 | 101.090 | 67.613 | 11.931 | 1.00 | 26.63 | B | O |
| ATOM | 6195 | N | GLY | 332 | 101.374 | 66.358 | 10.079 | 1.00 | 36.12 | B | N |
| ATOM | 6196 | CA | GLY | 332 | 102.784 | 66.666 | 9.949 | 1.00 | 37.22 | B | C |
| ATOM | 6197 | C | GLY | 332 | 103.089 | 68.150 | 9.917 | 1.00 | 37.48 | B | C |
| ATOM | 6198 | O | GLY | 332 | 103.940 | 68.628 | 10.670 | 1.00 | 41.35 | B | O |
| ATOM | 6199 | N | GLU | 333 | 102.398 | 68.892 | 9.058 | 1.00 | 41.72 | B | N |
| ATOM | 6200 | CA | GLU | 333 | 102.653 | 70.317 | 8.967 | 1.00 | 39.78 | B | C |
| ATOM | 6201 | CB | GLU | 333 | 102.052 | 70.889 | 7.683 | 1.00 | 98.89 | B | C |
| ATOM | 6202 | CG | GLU | 333 | 100.546 | 70.988 | 7.678 | 1.00 | 97.26 | B | C |
| ATOM | 6203 | CD | GLU | 333 | 100.018 | 71.598 | 6.400 | 1.00 | 97.28 | B | C |
| ATOM | 6204 | OE1 | GLU | 333 | 98.795 | 71.849 | 6.322 | 1.00 | 99.33 | B | O |
| ATOM | 6205 | OE2 | GLU | 333 | 100.824 | 71.823 | 5.472 | 1.00 | 91.40 | B | O |

Fig. 19: A-86

| | | | | | | | | | | | |
|---|---|---|---|---|---|---|---|---|---|---|---|
| ATOM | 6206 | C | GLU | 333 | 102.120 | 71.069 | 10.179 | 1.00 | 38.76 | B | C |
| ATOM | 6207 | O | GLU | 333 | 102.747 | 72.010 | 10.650 | 1.00 | 38.38 | B | O |
| ATOM | 6208 | N | ARG | 334 | 100.969 | 70.659 | 10.695 | 1.00 | 43.09 | B | N |
| ATOM | 6209 | CA | ARG | 334 | 100.398 | 71.340 | 11.847 | 1.00 | 46.47 | B | C |
| ATOM | 6210 | CB | ARG | 334 | 99.089 | 70.667 | 12.265 | 1.00 | 41.05 | B | C |
| ATOM | 6211 | CG | ARG | 334 | 98.167 | 71.568 | 13.056 | 1.00 | 40.34 | B | C |
| ATOM | 6212 | CD | ARG | 334 | 96.722 | 71.432 | 12.592 | 1.00 | 39.10 | B | C |
| ATOM | 6213 | NE | ARG | 334 | 96.544 | 71.911 | 11.222 | 1.00 | 34.65 | B | N |
| ATOM | 6214 | CZ | ARG | 334 | 95.446 | 71.721 | 10.488 | 1.00 | 38.74 | B | C |
| ATOM | 6215 | NH1 | ARG | 334 | 94.407 | 71.052 | 10.987 | 1.00 | 35.48 | B | N |
| ATOM | 6216 | NH2 | ARG | 334 | 95.388 | 72.197 | 9.246 | 1.00 | 44.88 | B | N |
| ATOM | 6217 | C | ARG | 334 | 101.419 | 71.321 | 12.980 | 1.00 | 47.77 | B | C |
| ATOM | 6218 | O | ARG | 334 | 101.633 | 72.329 | 13.643 | 1.00 | 44.69 | B | O |
| ATOM | 6219 | N | ILE | 335 | 102.060 | 70.177 | 13.192 | 1.00 | 95.68 | B | N |
| ATOM | 6220 | CA | ILE | 335 | 103.084 | 70.066 | 14.227 | 1.00 | 95.61 | B | C |
| ATOM | 6221 | CB | ILE | 335 | 103.349 | 68.565 | 14.599 | 1.00 | 69.44 | B | C |
| ATOM | 6222 | CG2 | ILE | 335 | 103.371 | 67.701 | 13.359 | 1.00 | 72.22 | B | C |
| ATOM | 6223 | CG1 | ILE | 335 | 104.671 | 68.420 | 15.350 | 1.00 | 70.66 | B | C |
| ATOM | 6224 | CD1 | ILE | 335 | 105.043 | 66.983 | 15.628 | 1.00 | 73.45 | B | C |
| ATOM | 6225 | C | ILE | 335 | 104.346 | 70.716 | 13.653 | 1.00 | 93.90 | B | C |
| ATOM | 6226 | O | ILE | 335 | 105.317 | 70.979 | 14.364 | 1.00 | 96.50 | B | O |
| ATOM | 6227 | N | PHE | 336 | 104.273 | 71.011 | 12.356 | 1.00 | 144.26 | B | N |
| ATOM | 6228 | CA | PHE | 336 | 105.347 | 71.604 | 11.560 | 1.00 | 143.89 | B | C |
| ATOM | 6229 | CB | PHE | 336 | 105.336 | 73.156 | 11.625 | 1.00 | 83.50 | B | C |
| ATOM | 6230 | CG | PHE | 336 | 105.600 | 73.748 | 12.992 | 1.00 | 79.82 | B | C |
| ATOM | 6231 | CD1 | PHE | 336 | 106.696 | 73.355 | 13.760 | 1.00 | 79.24 | B | C |
| ATOM | 6232 | CD2 | PHE | 336 | 104.783 | 74.762 | 13.479 | 1.00 | 77.77 | B | C |
| ATOM | 6233 | CE1 | PHE | 336 | 106.973 | 73.966 | 14.988 | 1.00 | 69.57 | B | C |
| ATOM | 6234 | CE2 | PHE | 336 | 105.053 | 75.377 | 14.702 | 1.00 | 72.13 | B | C |
| ATOM | 6235 | CZ | PHE | 336 | 106.152 | 74.977 | 15.457 | 1.00 | 72.59 | B | C |
| ATOM | 6236 | C | PHE | 336 | 106.737 | 71.068 | 11.853 | 1.00 | 143.92 | B | C |
| ATOM | 6237 | O | PHE | 336 | 106.889 | 70.255 | 12.788 | 1.00 | 123.54 | B | O |
| ATOM | 6238 | OXT | PHE | 336 | 107.658 | 71.461 | 11.111 | 1.00 | 66.99 | B | O |
| ATOM | 6239 | CB | GLU | 1 | 68.990 | 38.972 | 10.337 | 1.00 | 143.47 | X | C |
| ATOM | 6240 | CG | GLU | 1 | 68.785 | 37.653 | 11.053 | 1.00 | 143.47 | X | C |
| ATOM | 6241 | CD | GLU | 1 | 68.300 | 36.572 | 10.118 | 1.00 | 143.47 | X | C |
| ATOM | 6242 | OE1 | GLU | 1 | 69.012 | 36.278 | 9.134 | 1.00 | 143.47 | X | O |
| ATOM | 6243 | OE2 | GLU | 1 | 67.209 | 36.019 | 10.363 | 1.00 | 143.47 | X | O |
| ATOM | 6244 | C | GLU | 1 | 71.024 | 39.462 | 11.710 | 1.00 | 74.19 | X | C |
| ATOM | 6245 | O | GLU | 1 | 71.492 | 38.415 | 11.265 | 1.00 | 74.19 | X | O |
| ATOM | 6246 | N | GLU | 1 | 69.921 | 41.257 | 10.328 | 1.00 | 74.19 | X | N |
| ATOM | 6247 | CA | GLU | 1 | 69.711 | 40.037 | 11.162 | 1.00 | 74.19 | X | C |
| ATOM | 6248 | N | VAL | 2 | 71.613 | 40.151 | 12.681 | 1.00 | 55.61 | X | N |
| ATOM | 6249 | CA | VAL | 2 | 72.858 | 39.694 | 13.284 | 1.00 | 55.61 | X | C |
| ATOM | 6250 | CB | VAL | 2 | 73.533 | 40.812 | 14.089 | 1.00 | 66.95 | X | C |
| ATOM | 6251 | CG1 | VAL | 2 | 74.850 | 40.323 | 14.647 | 1.00 | 66.95 | X | C |
| ATOM | 6252 | CG2 | VAL | 2 | 73.752 | 42.021 | 13.210 | 1.00 | 66.95 | X | C |
| ATOM | 6253 | C | VAL | 2 | 72.566 | 38.543 | 14.232 | 1.00 | 55.61 | X | C |
| ATOM | 6254 | O | VAL | 2 | 71.728 | 38.673 | 15.127 | 1.00 | 55.61 | X | O |
| ATOM | 6255 | N | GLN | 3 | 73.258 | 37.421 | 14.045 | 1.00 | 39.72 | X | N |
| ATOM | 6256 | CA | GLN | 3 | 73.044 | 36.261 | 14.908 | 1.00 | 39.72 | X | C |
| ATOM | 6257 | CB | GLN | 3 | 71.807 | 35.502 | 14.455 | 1.00 | 102.66 | X | C |
| ATOM | 6258 | CG | GLN | 3 | 71.852 | 35.144 | 13.002 | 1.00 | 102.66 | X | C |
| ATOM | 6259 | CD | GLN | 3 | 70.688 | 34.291 | 12.604 | 1.00 | 102.66 | X | C |
| ATOM | 6260 | OE1 | GLN | 3 | 69.537 | 34.635 | 12.873 | 1.00 | 102.66 | X | O |
| ATOM | 6261 | NE2 | GLN | 3 | 70.972 | 33.168 | 11.955 | 1.00 | 102.66 | X | N |
| ATOM | 6262 | C | GLN | 3 | 74.213 | 35.288 | 15.002 | 1.00 | 39.72 | X | C |
| ATOM | 6263 | O | GLN | 3 | 75.064 | 35.207 | 14.108 | 1.00 | 39.72 | X | O |
| ATOM | 6264 | N | LEU | 4 | 74.231 | 34.553 | 16.109 | 1.00 | 34.59 | X | N |
| ATOM | 6265 | CA | LEU | 4 | 75.260 | 33.555 | 16.389 | 1.00 | 34.59 | X | C |
| ATOM | 6266 | CB | LEU | 4 | 76.043 | 33.931 | 17.653 | 1.00 | 34.08 | X | C |
| ATOM | 6267 | CG | LEU | 4 | 77.107 | 35.040 | 17.665 | 1.00 | 34.08 | X | C |
| ATOM | 6268 | CD1 | LEU | 4 | 77.119 | 35.820 | 16.353 | 1.00 | 34.08 | X | C |
| ATOM | 6269 | CD2 | LEU | 4 | 76.844 | 35.950 | 18.863 | 1.00 | 34.08 | X | C |
| ATOM | 6270 | C | LEU | 4 | 74.581 | 32.212 | 16.615 | 1.00 | 34.59 | X | C |
| ATOM | 6271 | O | LEU | 4 | 73.737 | 32.080 | 17.503 | 1.00 | 34.59 | X | O |
| ATOM | 6272 | N | VAL | 5 | 74.933 | 31.218 | 15.806 | 1.00 | 36.99 | X | N |
| ATOM | 6273 | CA | VAL | 5 | 74.350 | 29.889 | 15.961 | 1.00 | 36.99 | X | C |
| ATOM | 6274 | CB | VAL | 5 | 73.536 | 29.456 | 14.698 | 1.00 | 37.13 | X | C |
| ATOM | 6275 | CG1 | VAL | 5 | 74.285 | 29.815 | 13.430 | 1.00 | 37.13 | X | C |
| ATOM | 6276 | CG2 | VAL | 5 | 73.264 | 27.963 | 14.744 | 1.00 | 37.13 | X | C |
| ATOM | 6277 | C | VAL | 5 | 75.429 | 28.861 | 16.277 | 1.00 | 36.99 | X | C |
| ATOM | 6278 | O | VAL | 5 | 76.163 | 28.404 | 15.398 | 1.00 | 36.99 | X | O |

Fig. 19: A-87

| | | | | | | | | | | | |
|---|---|---|---|---|---|---|---|---|---|---|---|
| ATOM | 6279 | N | GLU | 6 | 75.519 | 28.517 | 17.555 | 1.00 | 44.32 | X | N |
| ATOM | 6280 | CA | GLU | 6 | 76.499 | 27.550 | 18.020 | 1.00 | 44.32 | X | C |
| ATOM | 6281 | CB | GLU | 6 | 76.924 | 27.884 | 19.457 | 1.00 | 53.96 | X | C |
| ATOM | 6282 | CG | GLU | 6 | 75.844 | 28.531 | 20.292 | 1.00 | 53.96 | X | C |
| ATOM | 6283 | CD | GLU | 6 | 76.340 | 28.943 | 21.659 | 1.00 | 53.96 | X | C |
| ATOM | 6284 | OE1 | GLU | 6 | 75.590 | 29.646 | 22.368 | 1.00 | 53.96 | X | O |
| ATOM | 6285 | OE2 | GLU | 6 | 77.472 | 28.561 | 22.028 | 1.00 | 53.96 | X | O |
| ATOM | 6286 | C | GLU | 6 | 76.029 | 26.095 | 17.930 | 1.00 | 44.32 | X | C |
| ATOM | 6287 | O | GLU | 6 | 74.856 | 25.813 | 17.668 | 1.00 | 44.32 | X | O |
| ATOM | 6288 | N | SER | 7 | 76.980 | 25.185 | 18.135 | 1.00 | 42.31 | X | N |
| ATOM | 6289 | CA | SER | 7 | 76.758 | 23.745 | 18.091 | 1.00 | 42.31 | X | C |
| ATOM | 6290 | CB | SER | 7 | 76.762 | 23.261 | 16.642 | 1.00 | 44.31 | X | C |
| ATOM | 6291 | OG | SER | 7 | 77.832 | 23.845 | 15.922 | 1.00 | 44.31 | X | O |
| ATOM | 6292 | C | SER | 7 | 77.919 | 23.123 | 18.848 | 1.00 | 42.31 | X | C |
| ATOM | 6293 | O | SER | 7 | 78.889 | 23.813 | 19.138 | 1.00 | 42.31 | X | O |
| ATOM | 6294 | N | GLY | 8 | 77.822 | 21.838 | 19.178 | 1.00 | 39.85 | X | N |
| ATOM | 6295 | CA | GLY | 8 | 78.908 | 21.177 | 19.893 | 1.00 | 39.85 | X | C |
| ATOM | 6296 | C | GLY | 8 | 78.569 | 20.747 | 21.313 | 1.00 | 39.85 | X | C |
| ATOM | 6297 | O | GLY | 8 | 79.330 | 20.016 | 21.962 | 1.00 | 39.85 | X | O |
| ATOM | 6298 | N | GLY | 9 | 77.417 | 21.199 | 21.795 | 1.00 | 54.13 | X | N |
| ATOM | 6299 | CA | GLY | 9 | 76.998 | 20.852 | 23.138 | 1.00 | 54.13 | X | C |
| ATOM | 6300 | C | GLY | 9 | 76.467 | 19.439 | 23.283 | 1.00 | 54.13 | X | C |
| ATOM | 6301 | O | GLY | 9 | 75.390 | 19.102 | 22.783 | 1.00 | 54.13 | X | O |
| ATOM | 6302 | N | GLY | 10 | 77.235 | 18.606 | 23.972 | 1.00 | 51.55 | X | N |
| ATOM | 6303 | CA | GLY | 10 | 76.825 | 17.236 | 24.195 | 1.00 | 51.55 | X | C |
| ATOM | 6304 | C | GLY | 10 | 77.359 | 16.807 | 25.544 | 1.00 | 51.55 | X | C |
| ATOM | 6305 | O | GLY | 10 | 77.723 | 17.651 | 26.370 | 1.00 | 51.55 | X | O |
| ATOM | 6306 | N | LEU | 11 | 77.409 | 15.500 | 25.776 | 1.00 | 54.73 | X | N |
| ATOM | 6307 | CA | LEU | 11 | 77.930 | 14.981 | 27.032 | 1.00 | 54.73 | X | C |
| ATOM | 6308 | CB | LEU | 11 | 76.994 | 13.903 | 27.583 | 1.00 | 40.69 | X | C |
| ATOM | 6309 | CG | LEU | 11 | 77.583 | 13.086 | 28.735 | 1.00 | 40.69 | X | C |
| ATOM | 6310 | CD1 | LEU | 11 | 78.170 | 14.011 | 29.795 | 1.00 | 40.69 | X | C |
| ATOM | 6311 | CD2 | LEU | 11 | 76.508 | 12.198 | 29.317 | 1.00 | 40.69 | X | C |
| ATOM | 6312 | C | LEU | 11 | 79.341 | 14.412 | 26.852 | 1.00 | 54.73 | X | C |
| ATOM | 6313 | O | LEU | 11 | 79.664 | 13.853 | 25.806 | 1.00 | 54.73 | X | O |
| ATOM | 6314 | N | VAL | 12 | 80.177 | 14.576 | 27.872 | 1.00 | 43.40 | X | N |
| ATOM | 6315 | CA | VAL | 12 | 81.552 | 14.079 | 27.848 | 1.00 | 43.40 | X | C |
| ATOM | 6316 | CB | VAL | 12 | 82.538 | 15.118 | 27.273 | 1.00 | 57.73 | X | C |
| ATOM | 6317 | CG1 | VAL | 12 | 82.222 | 15.388 | 25.812 | 1.00 | 57.73 | X | C |
| ATOM | 6318 | CG2 | VAL | 12 | 82.473 | 16.404 | 28.086 | 1.00 | 57.73 | X | C |
| ATOM | 6319 | C | VAL | 12 | 81.991 | 13.753 | 29.269 | 1.00 | 43.40 | X | C |
| ATOM | 6320 | O | VAL | 12 | 81.490 | 14.344 | 30.230 | 1.00 | 43.40 | X | O |
| ATOM | 6321 | N | GLN | 13 | 82.931 | 12.821 | 29.403 | 1.00 | 46.11 | X | N |
| ATOM | 6322 | CA | GLN | 13 | 83.404 | 12.420 | 30.720 | 1.00 | 46.11 | X | C |
| ATOM | 6323 | CB | GLN | 13 | 83.873 | 10.965 | 30.676 | 1.00 | 148.60 | X | C |
| ATOM | 6324 | CG | GLN | 13 | 82.843 | 10.015 | 30.094 | 1.00 | 148.60 | X | C |
| ATOM | 6325 | CD | GLN | 13 | 83.232 | 8.560 | 30.263 | 1.00 | 148.60 | X | C |
| ATOM | 6326 | OE1 | GLN | 13 | 84.322 | 8.145 | 29.868 | 1.00 | 148.60 | X | O |
| ATOM | 6327 | NE2 | GLN | 13 | 82.337 | 7.774 | 30.852 | 1.00 | 148.60 | X | N |
| ATOM | 6328 | C | GLN | 13 | 84.532 | 13.311 | 31.234 | 1.00 | 46.11 | X | C |
| ATOM | 6329 | O | GLN | 13 | 85.186 | 14.002 | 30.454 | 1.00 | 46.11 | X | O |
| ATOM | 6330 | N | PRO | 14 | 84.763 | 13.319 | 32.563 | 1.00 | 39.23 | X | N |
| ATOM | 6331 | CD | PRO | 14 | 83.989 | 12.657 | 33.630 | 1.00 | 55.62 | X | C |
| ATOM | 6332 | CA | PRO | 14 | 85.831 | 14.141 | 33.141 | 1.00 | 39.23 | X | C |
| ATOM | 6333 | CB | PRO | 14 | 85.902 | 13.648 | 34.581 | 1.00 | 55.62 | X | C |
| ATOM | 6334 | CG | PRO | 14 | 84.474 | 13.374 | 34.887 | 1.00 | 55.62 | X | C |
| ATOM | 6335 | C | PRO | 14 | 87.122 | 13.905 | 32.392 | 1.00 | 39.23 | X | C |
| ATOM | 6336 | O | PRO | 14 | 87.357 | 12.810 | 31.885 | 1.00 | 39.23 | X | O |
| ATOM | 6337 | N | GLY | 15 | 87.954 | 14.935 | 32.320 | 1.00 | 28.04 | X | N |
| ATOM | 6338 | CA | GLY | 15 | 89.220 | 14.816 | 31.616 | 1.00 | 28.04 | X | C |
| ATOM | 6339 | C | GLY | 15 | 89.037 | 14.807 | 30.109 | 1.00 | 28.04 | X | C |
| ATOM | 6340 | O | GLY | 15 | 89.990 | 14.979 | 29.352 | 1.00 | 28.04 | X | O |
| ATOM | 6341 | N | GLY | 16 | 87.801 | 14.613 | 29.672 | 1.00 | 22.75 | X | N |
| ATOM | 6342 | CA | GLY | 16 | 87.529 | 14.583 | 28.250 | 1.00 | 22.75 | X | C |
| ATOM | 6343 | C | GLY | 16 | 87.705 | 15.912 | 27.539 | 1.00 | 22.75 | X | C |
| ATOM | 6344 | O | GLY | 16 | 87.887 | 16.969 | 28.155 | 1.00 | 22.75 | X | O |
| ATOM | 6345 | N | SER | 17 | 87.633 | 15.845 | 26.217 | 1.00 | 36.95 | X | N |
| ATOM | 6346 | CA | SER | 17 | 87.789 | 17.014 | 25.371 | 1.00 | 36.95 | X | C |
| ATOM | 6347 | CB | SER | 17 | 88.962 | 16.795 | 24.417 | 1.00 | 47.78 | X | C |
| ATOM | 6348 | OG | SER | 17 | 89.203 | 17.952 | 23.645 | 1.00 | 47.78 | X | O |
| ATOM | 6349 | C | SER | 17 | 86.509 | 17.311 | 24.581 | 1.00 | 36.95 | X | C |
| ATOM | 6350 | O | SER | 17 | 85.817 | 16.402 | 24.106 | 1.00 | 36.95 | X | O |
| ATOM | 6351 | N | LEU | 18 | 86.199 | 18.593 | 24.429 | 1.00 | 50.75 | X | N |

Fig. 19: A-88

| | | | | | | | | | | | |
|---|---|---|---|---|---|---|---|---|---|---|---|
| ATOM | 6352 | CA | LEU | 18 | 84.995 | 18.978 | 23.719 | 1.00 | 50.75 | X | C |
| ATOM | 6353 | CB | LEU | 18 | 83.833 | 18.944 | 24.701 | 1.00 | 37.38 | X | C |
| ATOM | 6354 | CG | LEU | 18 | 82.463 | 19.285 | 24.146 | 1.00 | 37.38 | X | C |
| ATOM | 6355 | CD1 | LEU | 18 | 82.177 | 18.476 | 22.874 | 1.00 | 37.38 | X | C |
| ATOM | 6356 | CD2 | LEU | 18 | 81.442 | 19.012 | 25.239 | 1.00 | 37.38 | X | C |
| ATOM | 6357 | C | LEU | 18 | 85.107 | 20.355 | 23.069 | 1.00 | 50.75 | X | C |
| ATOM | 6358 | O | LEU | 18 | 85.530 | 21.313 | 23.714 | 1.00 | 50.75 | X | O |
| ATOM | 6359 | N | ARG | 19 | 84.737 | 20.454 | 21.792 | 1.00 | 27.07 | X | N |
| ATOM | 6360 | CA | ARG | 19 | 84.805 | 21.739 | 21.097 | 1.00 | 27.07 | X | C |
| ATOM | 6361 | CB | ARG | 19 | 85.774 | 21.708 | 19.924 | 1.00 | 43.18 | X | C |
| ATOM | 6362 | CG | ARG | 19 | 85.825 | 23.068 | 19.238 | 1.00 | 43.18 | X | C |
| ATOM | 6363 | CD | ARG | 19 | 86.689 | 23.075 | 18.015 | 1.00 | 43.18 | X | C |
| ATOM | 6364 | NE | ARG | 19 | 86.060 | 22.389 | 16.896 | 1.00 | 43.18 | X | N |
| ATOM | 6365 | CZ | ARG | 19 | 86.564 | 22.371 | 15.666 | 1.00 | 43.18 | X | C |
| ATOM | 6366 | NH1 | ARG | 19 | 87.708 | 23.006 | 15.407 | 1.00 | 43.18 | X | N |
| ATOM | 6367 | NH2 | ARG | 19 | 85.924 | 21.725 | 14.696 | 1.00 | 43.18 | X | N |
| ATOM | 6368 | C | ARG | 19 | 83.501 | 22.302 | 20.558 | 1.00 | 27.07 | X | C |
| ATOM | 6369 | O | ARG | 19 | 82.895 | 21.745 | 19.625 | 1.00 | 27.07 | X | O |
| ATOM | 6370 | N | LEU | 20 | 83.109 | 23.438 | 21.135 | 1.00 | 30.57 | X | N |
| ATOM | 6371 | CA | LEU | 20 | 81.908 | 24.150 | 20.731 | 1.00 | 30.57 | X | C |
| ATOM | 6372 | CB | LEU | 20 | 81.354 | 24.965 | 21.896 | 1.00 | 36.53 | X | C |
| ATOM | 6373 | CG | LEU | 20 | 80.981 | 24.196 | 23.159 | 1.00 | 36.53 | X | C |
| ATOM | 6374 | CD1 | LEU | 20 | 80.415 | 25.142 | 24.218 | 1.00 | 36.53 | X | C |
| ATOM | 6375 | CD2 | LEU | 20 | 79.964 | 23.135 | 22.802 | 1.00 | 36.53 | X | C |
| ATOM | 6376 | C | LEU | 20 | 82.304 | 25.098 | 19.618 | 1.00 | 30.57 | X | C |
| ATOM | 6377 | O | LEU | 20 | 83.313 | 25.784 | 19.723 | 1.00 | 30.57 | X | O |
| ATOM | 6378 | N | SER | 21 | 81.527 | 25.122 | 18.544 | 1.00 | 31.77 | X | N |
| ATOM | 6379 | CA | SER | 21 | 81.789 | 26.024 | 17.426 | 1.00 | 31.77 | X | C |
| ATOM | 6380 | CB | SER | 21 | 81.876 | 25.252 | 16.117 | 1.00 | 32.65 | X | C |
| ATOM | 6381 | OG | SER | 21 | 80.580 | 24.896 | 15.682 | 1.00 | 32.65 | X | O |
| ATOM | 6382 | C | SER | 21 | 80.593 | 26.971 | 17.383 | 1.00 | 31.77 | X | C |
| ATOM | 6383 | O | SER | 21 | 79.591 | 26.738 | 18.057 | 1.00 | 31.77 | X | O |
| ATOM | 6384 | N | CYS | 22 | 80.673 | 28.024 | 16.585 | 1.00 | 49.03 | X | N |
| ATOM | 6385 | CA | CYS | 22 | 79.580 | 28.981 | 16.526 | 1.00 | 49.03 | X | C |
| ATOM | 6386 | C | CYS | 22 | 79.725 | 29.812 | 15.272 | 1.00 | 49.03 | X | C |
| ATOM | 6387 | O | CYS | 22 | 80.743 | 30.484 | 15.096 | 1.00 | 49.03 | X | O |
| ATOM | 6388 | CB | CYS | 22 | 79.643 | 29.849 | 17.788 | 1.00 | 49.62 | X | C |
| ATOM | 6389 | SG | CYS | 22 | 78.993 | 31.555 | 17.774 | 1.00 | 49.62 | X | S |
| ATOM | 6390 | N | ALA | 23 | 78.724 | 29.744 | 14.389 | 1.00 | 43.82 | X | N |
| ATOM | 6391 | CA | ALA | 23 | 78.742 | 30.509 | 13.136 | 1.00 | 43.82 | X | C |
| ATOM | 6392 | CB | ALA | 23 | 78.022 | 29.768 | 12.021 | 1.00 | 1.87 | X | C |
| ATOM | 6393 | C | ALA | 23 | 78.093 | 31.854 | 13.329 | 1.00 | 43.82 | X | C |
| ATOM | 6394 | O | ALA | 23 | 77.118 | 31.999 | 14.070 | 1.00 | 43.82 | X | O |
| ATOM | 6395 | N | ALA | 24 | 78.644 | 32.843 | 12.645 | 1.00 | 28.70 | X | N |
| ATOM | 6396 | CA | ALA | 24 | 78.129 | 34.190 | 12.735 | 1.00 | 28.70 | X | C |
| ATOM | 6397 | CB | ALA | 24 | 79.199 | 35.129 | 13.323 | 1.00 | 18.49 | X | C |
| ATOM | 6398 | C | ALA | 24 | 77.725 | 34.659 | 11.356 | 1.00 | 28.70 | X | C |
| ATOM | 6399 | O | ALA | 24 | 78.213 | 34.160 | 10.345 | 1.00 | 28.70 | X | O |
| ATOM | 6400 | N | SER | 25 | 76.816 | 35.620 | 11.338 | 1.00 | 39.45 | X | N |
| ATOM | 6401 | CA | SER | 25 | 76.338 | 36.218 | 10.108 | 1.00 | 39.45 | X | C |
| ATOM | 6402 | CB | SER | 25 | 75.279 | 35.322 | 9.443 | 1.00 | 48.28 | X | C |
| ATOM | 6403 | OG | SER | 25 | 74.163 | 35.090 | 10.287 | 1.00 | 48.28 | X | O |
| ATOM | 6404 | C | SER | 25 | 75.751 | 37.575 | 10.486 | 1.00 | 39.45 | X | C |
| ATOM | 6405 | O | SER | 25 | 75.425 | 37.819 | 11.656 | 1.00 | 39.45 | X | O |
| ATOM | 6406 | N | GLY | 26 | 75.651 | 38.464 | 9.506 | 1.00 | 15.13 | X | N |
| ATOM | 6407 | CA | GLY | 26 | 75.093 | 39.773 | 9.767 | 1.00 | 15.13 | X | C |
| ATOM | 6408 | C | GLY | 26 | 76.061 | 40.808 | 10.313 | 1.00 | 15.13 | X | C |
| ATOM | 6409 | O | GLY | 26 | 75.650 | 41.692 | 11.070 | 1.00 | 15.13 | X | O |
| ATOM | 6410 | N | PHE | 27 | 77.336 | 40.697 | 9.941 | 1.00 | 51.25 | X | N |
| ATOM | 6411 | CA | PHE | 27 | 78.375 | 41.638 | 10.358 | 1.00 | 51.25 | X | C |
| ATOM | 6412 | CB | PHE | 27 | 78.322 | 41.921 | 11.860 | 1.00 | 33.43 | X | C |
| ATOM | 6413 | CG | PHE | 27 | 78.647 | 40.736 | 12.720 | 1.00 | 33.43 | X | C |
| ATOM | 6414 | CD1 | PHE | 27 | 77.696 | 39.749 | 12.958 | 1.00 | 33.43 | X | C |
| ATOM | 6415 | CD2 | PHE | 27 | 79.891 | 40.629 | 13.337 | 1.00 | 33.43 | X | C |
| ATOM | 6416 | CE1 | PHE | 27 | 77.978 | 38.673 | 13.810 | 1.00 | 33.43 | X | C |
| ATOM | 6417 | CE2 | PHE | 27 | 80.186 | 39.558 | 14.190 | 1.00 | 33.43 | X | C |
| ATOM | 6418 | CZ | PHE | 27 | 79.227 | 38.581 | 14.428 | 1.00 | 33.43 | X | C |
| ATOM | 6419 | C | PHE | 27 | 79.748 | 41.100 | 10.012 | 1.00 | 51.25 | X | C |
| ATOM | 6420 | O | PHE | 27 | 79.966 | 39.894 | 10.027 | 1.00 | 51.25 | X | O |
| ATOM | 6421 | N | THR | 28 | 80.671 | 42.006 | 9.707 | 1.00 | 31.93 | X | N |
| ATOM | 6422 | CA | THR | 28 | 82.031 | 41.637 | 9.348 | 1.00 | 31.93 | X | C |
| ATOM | 6423 | CB | THR | 28 | 82.821 | 42.872 | 8.910 | 1.00 | 48.89 | X | C |
| ATOM | 6424 | OG1 | THR | 28 | 82.126 | 43.520 | 7.836 | 1.00 | 48.89 | X | O |

Fig. 19: A-89

| | | | | | | | | | | | |
|---|---|---|---|---|---|---|---|---|---|---|---|
| ATOM | 6425 | CG2 | THR | 28 | 84.212 | 42.474 | 8.454 | 1.00 | 48.89 | X | C |
| ATOM | 6426 | C | THR | 28 | 82.744 | 40.981 | 10.519 | 1.00 | 31.93 | X | C |
| ATOM | 6427 | O | THR | 28 | 83.431 | 41.640 | 11.286 | 1.00 | 31.93 | X | O |
| ATOM | 6428 | N | PHE | 29 | 82.576 | 39.671 | 10.636 | 1.00 | 37.68 | X | N |
| ATOM | 6429 | CA | PHE | 29 | 83.166 | 38.876 | 11.712 | 1.00 | 37.68 | X | C |
| ATOM | 6430 | CB | PHE | 29 | 83.068 | 37.386 | 11.352 | 1.00 | 38.41 | X | C |
| ATOM | 6431 | CG | PHE | 29 | 83.484 | 36.454 | 12.462 | 1.00 | 38.41 | X | C |
| ATOM | 6432 | CD1 | PHE | 29 | 82.795 | 36.440 | 13.676 | 1.00 | 38.41 | X | C |
| ATOM | 6433 | CD2 | PHE | 29 | 84.570 | 35.587 | 12.296 | 1.00 | 38.41 | X | C |
| ATOM | 6434 | CE1 | PHE | 29 | 83.183 | 35.577 | 14.709 | 1.00 | 38.41 | X | C |
| ATOM | 6435 | CE2 | PHE | 29 | 84.967 | 34.718 | 13.324 | 1.00 | 38.41 | X | C |
| ATOM | 6436 | CZ | PHE | 29 | 84.272 | 34.715 | 14.530 | 1.00 | 38.41 | X | C |
| ATOM | 6437 | C | PHE | 29 | 84.616 | 39.225 | 12.021 | 1.00 | 37.68 | X | C |
| ATOM | 6438 | O | PHE | 29 | 84.958 | 39.552 | 13.160 | 1.00 | 37.68 | X | O |
| ATOM | 6439 | N | SER | 30 | 85.462 | 39.160 | 10.998 | 1.00 | 22.05 | X | N |
| ATOM | 6440 | CA | SER | 30 | 86.890 | 39.421 | 11.157 | 1.00 | 22.05 | X | C |
| ATOM | 6441 | CB | SER | 30 | 87.553 | 39.545 | 9.783 | 1.00 | 37.79 | X | C |
| ATOM | 6442 | OG | SER | 30 | 86.886 | 40.481 | 8.959 | 1.00 | 37.79 | X | O |
| ATOM | 6443 | C | SER | 30 | 87.270 | 40.622 | 12.014 | 1.00 | 22.05 | X | C |
| ATOM | 6444 | O | SER | 30 | 88.326 | 40.634 | 12.639 | 1.00 | 22.05 | X | O |
| ATOM | 6445 | N | ARG | 31 | 86.395 | 41.615 | 12.063 | 1.00 | 29.69 | X | N |
| ATOM | 6446 | CA | ARG | 31 | 86.651 | 42.846 | 12.801 | 1.00 | 29.69 | X | C |
| ATOM | 6447 | CB | ARG | 31 | 85.819 | 43.956 | 12.162 | 1.00 | 51.15 | X | C |
| ATOM | 6448 | CG | ARG | 31 | 86.068 | 45.323 | 12.719 | 1.00 | 51.15 | X | C |
| ATOM | 6449 | CD | ARG | 31 | 84.999 | 46.281 | 12.231 | 1.00 | 51.15 | X | C |
| ATOM | 6450 | NE | ARG | 31 | 84.964 | 46.383 | 10.772 | 1.00 | 51.15 | X | N |
| ATOM | 6451 | CZ | ARG | 31 | 85.899 | 46.974 | 10.038 | 1.00 | 51.15 | X | C |
| ATOM | 6452 | NH1 | ARG | 31 | 86.959 | 47.523 | 10.621 | 1.00 | 51.15 | X | N |
| ATOM | 6453 | NH2 | ARG | 31 | 85.764 | 47.027 | 8.722 | 1.00 | 51.15 | X | N |
| ATOM | 6454 | C | ARG | 31 | 86.425 | 42.833 | 14.329 | 1.00 | 29.69 | X | C |
| ATOM | 6455 | O | ARG | 31 | 87.226 | 43.399 | 15.080 | 1.00 | 29.69 | X | O |
| ATOM | 6456 | N | TYR | 32 | 85.352 | 42.185 | 14.785 | 1.00 | 39.46 | X | N |
| ATOM | 6457 | CA | TYR | 32 | 85.009 | 42.144 | 16.217 | 1.00 | 39.46 | X | C |
| ATOM | 6458 | CB | TYR | 32 | 83.506 | 41.880 | 16.409 | 1.00 | 51.56 | X | C |
| ATOM | 6459 | CG | TYR | 32 | 82.601 | 42.689 | 15.516 | 1.00 | 51.56 | X | C |
| ATOM | 6460 | CD1 | TYR | 32 | 82.540 | 42.437 | 14.148 | 1.00 | 51.56 | X | C |
| ATOM | 6461 | CE1 | TYR | 32 | 81.721 | 43.181 | 13.316 | 1.00 | 51.56 | X | C |
| ATOM | 6462 | CD2 | TYR | 32 | 81.811 | 43.714 | 16.034 | 1.00 | 51.56 | X | C |
| ATOM | 6463 | CE2 | TYR | 32 | 80.985 | 44.467 | 15.209 | 1.00 | 51.56 | X | C |
| ATOM | 6464 | CZ | TYR | 32 | 80.946 | 44.193 | 13.851 | 1.00 | 51.56 | X | C |
| ATOM | 6465 | OH | TYR | 32 | 80.135 | 44.929 | 13.015 | 1.00 | 51.56 | X | O |
| ATOM | 6466 | C | TYR | 32 | 85.761 | 41.108 | 17.037 | 1.00 | 39.46 | X | C |
| ATOM | 6467 | O | TYR | 32 | 86.159 | 40.072 | 16.515 | 1.00 | 39.46 | X | O |
| ATOM | 6468 | N | THR | 33 | 85.943 | 41.386 | 18.328 | 1.00 | 29.44 | X | N |
| ATOM | 6469 | CA | THR | 33 | 86.611 | 40.421 | 19.191 | 1.00 | 29.44 | X | C |
| ATOM | 6470 | CB | THR | 33 | 87.510 | 41.080 | 20.315 | 1.00 | 20.65 | X | C |
| ATOM | 6471 | OG1 | THR | 33 | 86.749 | 41.242 | 21.514 | 1.00 | 20.65 | X | O |
| ATOM | 6472 | CG2 | THR | 33 | 88.072 | 42.437 | 19.866 | 1.00 | 20.65 | X | C |
| ATOM | 6473 | C | THR | 33 | 85.483 | 39.614 | 19.835 | 1.00 | 29.44 | X | C |
| ATOM | 6474 | O | THR | 33 | 84.632 | 40.167 | 20.536 | 1.00 | 29.44 | X | O |
| ATOM | 6475 | N | MET | 34 | 85.484 | 38.307 | 19.568 | 1.00 | 30.35 | X | N |
| ATOM | 6476 | CA | MET | 34 | 84.474 | 37.391 | 20.084 | 1.00 | 30.35 | X | C |
| ATOM | 6477 | CB | MET | 34 | 84.235 | 36.284 | 19.067 | 1.00 | 43.39 | X | C |
| ATOM | 6478 | CG | MET | 34 | 84.070 | 36.798 | 17.652 | 1.00 | 43.39 | X | C |
| ATOM | 6479 | SD | MET | 34 | 82.775 | 38.029 | 17.525 | 1.00 | 43.39 | X | S |
| ATOM | 6480 | CE | MET | 34 | 81.376 | 37.024 | 17.198 | 1.00 | 43.39 | X | C |
| ATOM | 6481 | C | MET | 34 | 84.867 | 36.785 | 21.430 | 1.00 | 30.35 | X | C |
| ATOM | 6482 | O | MET | 34 | 86.049 | 36.761 | 21.790 | 1.00 | 30.35 | X | O |
| ATOM | 6483 | N | SER | 35 | 83.866 | 36.293 | 22.164 | 1.00 | 35.95 | X | N |
| ATOM | 6484 | CA | SER | 35 | 84.073 | 35.701 | 23.487 | 1.00 | 35.95 | X | C |
| ATOM | 6485 | CB | SER | 35 | 83.875 | 36.765 | 24.580 | 1.00 | 34.42 | X | C |
| ATOM | 6486 | OG | SER | 35 | 84.740 | 37.878 | 24.420 | 1.00 | 34.42 | X | O |
| ATOM | 6487 | C | SER | 35 | 83.105 | 34.548 | 23.761 | 1.00 | 35.95 | X | C |
| ATOM | 6488 | O | SER | 35 | 82.191 | 34.290 | 22.978 | 1.00 | 35.95 | X | O |
| ATOM | 6489 | N | TRP | 36 | 83.323 | 33.856 | 24.879 | 1.00 | 43.17 | X | N |
| ATOM | 6490 | CA | TRP | 36 | 82.457 | 32.758 | 25.309 | 1.00 | 43.17 | X | C |
| ATOM | 6491 | CB | TRP | 36 | 83.159 | 31.383 | 25.200 | 1.00 | 32.84 | X | C |
| ATOM | 6492 | CG | TRP | 36 | 83.355 | 30.875 | 23.782 | 1.00 | 32.84 | X | C |
| ATOM | 6493 | CD2 | TRP | 36 | 82.419 | 30.118 | 22.998 | 1.00 | 32.84 | X | C |
| ATOM | 6494 | CE2 | TRP | 36 | 82.982 | 29.957 | 21.711 | 1.00 | 32.84 | X | C |
| ATOM | 6495 | CE3 | TRP | 36 | 81.153 | 29.564 | 23.257 | 1.00 | 32.84 | X | C |
| ATOM | 6496 | CD1 | TRP | 36 | 84.419 | 31.124 | 22.962 | 1.00 | 32.84 | X | C |
| ATOM | 6497 | NE1 | TRP | 36 | 84.201 | 30.579 | 21.716 | 1.00 | 32.84 | X | N |

Fig. 19: A-90

| | | | | | | | | | | | |
|---|---|---|---|---|---|---|---|---|---|---|---|
| ATOM | 6498 | CZ2 | TRP | 36 | 82.324 | 29.267 | 20.681 | 1.00 | 32.84 | X | C |
| ATOM | 6499 | CZ3 | TRP | 36 | 80.495 | 28.877 | 22.228 | 1.00 | 32.84 | X | C |
| ATOM | 6500 | CH2 | TRP | 36 | 81.086 | 28.738 | 20.957 | 1.00 | 32.84 | X | C |
| ATOM | 6501 | C | TRP | 36 | 82.056 | 33.022 | 26.764 | 1.00 | 43.17 | X | C |
| ATOM | 6502 | O | TRP | 36 | 82.908 | 33.298 | 27.615 | 1.00 | 43.17 | X | O |
| ATOM | 6503 | N | VAL | 37 | 80.751 | 32.958 | 27.026 | 1.00 | 29.19 | X | N |
| ATOM | 6504 | CA | VAL | 37 | 80.177 | 33.175 | 28.360 | 1.00 | 29.19 | X | C |
| ATOM | 6505 | CB | VAL | 37 | 79.213 | 34.419 | 28.353 | 1.00 | 8.00 | X | C |
| ATOM | 6506 | CG1 | VAL | 37 | 78.350 | 34.467 | 29.621 | 1.00 | 8.00 | X | C |
| ATOM | 6507 | CG2 | VAL | 37 | 80.026 | 35.689 | 28.240 | 1.00 | 8.00 | X | C |
| ATOM | 6508 | C | VAL | 37 | 79.412 | 31.907 | 28.760 | 1.00 | 29.19 | X | C |
| ATOM | 6509 | O | VAL | 37 | 78.629 | 31.381 | 27.971 | 1.00 | 29.19 | X | O |
| ATOM | 6510 | N | ARG | 38 | 79.651 | 31.415 | 29.974 | 1.00 | 61.80 | X | N |
| ATOM | 6511 | CA | ARG | 38 | 78.992 | 30.198 | 30.454 | 1.00 | 61.80 | X | C |
| ATOM | 6512 | CB | ARG | 38 | 80.036 | 29.167 | 30.899 | 1.00 | 27.50 | X | C |
| ATOM | 6513 | CG | ARG | 38 | 80.926 | 29.688 | 32.011 | 1.00 | 27.50 | X | C |
| ATOM | 6514 | CD | ARG | 38 | 81.370 | 28.603 | 32.965 | 1.00 | 27.50 | X | C |
| ATOM | 6515 | NE | ARG | 38 | 82.222 | 27.579 | 32.364 | 1.00 | 27.50 | X | N |
| ATOM | 6516 | CZ | ARG | 38 | 83.391 | 27.181 | 32.874 | 1.00 | 27.50 | X | C |
| ATOM | 6517 | NH1 | ARG | 38 | 83.862 | 27.725 | 33.992 | 1.00 | 27.50 | X | N |
| ATOM | 6518 | NH2 | ARG | 38 | 84.087 | 26.217 | 32.281 | 1.00 | 27.50 | X | N |
| ATOM | 6519 | C | ARG | 38 | 78.053 | 30.468 | 31.628 | 1.00 | 61.80 | X | C |
| ATOM | 6520 | O | ARG | 38 | 78.104 | 31.528 | 32.245 | 1.00 | 61.80 | X | O |
| ATOM | 6521 | N | GLN | 39 | 77.204 | 29.491 | 31.934 | 1.00 | 39.46 | X | N |
| ATOM | 6522 | CA | GLN | 39 | 76.269 | 29.597 | 33.049 | 1.00 | 39.46 | X | C |
| ATOM | 6523 | CB | GLN | 39 | 74.982 | 30.269 | 32.588 | 1.00 | 44.48 | X | C |
| ATOM | 6524 | CG | GLN | 39 | 73.997 | 30.530 | 33.708 | 1.00 | 44.48 | X | C |
| ATOM | 6525 | CD | GLN | 39 | 72.916 | 31.497 | 33.294 | 1.00 | 44.48 | X | C |
| ATOM | 6526 | OE1 | GLN | 39 | 72.269 | 31.320 | 32.252 | 1.00 | 44.48 | X | O |
| ATOM | 6527 | NE2 | GLN | 39 | 72.709 | 32.532 | 34.106 | 1.00 | 44.48 | X | N |
| ATOM | 6528 | C | GLN | 39 | 75.955 | 28.224 | 33.663 | 1.00 | 39.46 | X | C |
| ATOM | 6529 | O | GLN | 39 | 75.233 | 27.404 | 33.076 | 1.00 | 39.46 | X | O |
| ATOM | 6530 | N | ALA | 40 | 76.514 | 27.984 | 34.846 | 1.00 | 47.11 | X | N |
| ATOM | 6531 | CA | ALA | 40 | 76.324 | 26.727 | 35.558 | 1.00 | 47.11 | X | C |
| ATOM | 6532 | CB | ALA | 40 | 77.241 | 26.678 | 36.773 | 1.00 | 19.87 | X | C |
| ATOM | 6533 | C | ALA | 40 | 74.875 | 26.592 | 35.995 | 1.00 | 47.11 | X | C |
| ATOM | 6534 | O | ALA | 40 | 74.296 | 27.542 | 36.512 | 1.00 | 47.11 | X | O |
| ATOM | 6535 | N | PRO | 41 | 74.271 | 25.403 | 35.802 | 1.00 | 63.91 | X | N |
| ATOM | 6536 | CD | PRO | 41 | 74.879 | 24.157 | 35.299 | 1.00 | 66.56 | X | C |
| ATOM | 6537 | CA | PRO | 41 | 72.875 | 25.168 | 36.187 | 1.00 | 63.91 | X | C |
| ATOM | 6538 | CB | PRO | 41 | 72.793 | 23.649 | 36.244 | 1.00 | 66.56 | X | C |
| ATOM | 6539 | CG | PRO | 41 | 73.667 | 23.254 | 35.115 | 1.00 | 66.56 | X | C |
| ATOM | 6540 | C | PRO | 41 | 72.507 | 25.826 | 37.508 | 1.00 | 63.91 | X | C |
| ATOM | 6541 | O | PRO | 41 | 73.186 | 25.637 | 38.522 | 1.00 | 63.91 | X | O |
| ATOM | 6542 | N | GLY | 42 | 71.432 | 26.608 | 37.478 | 1.00 | 63.56 | X | N |
| ATOM | 6543 | CA | GLY | 42 | 70.979 | 27.297 | 38.671 | 1.00 | 63.56 | X | C |
| ATOM | 6544 | C | GLY | 42 | 71.963 | 28.342 | 39.165 | 1.00 | 63.56 | X | C |
| ATOM | 6545 | O | GLY | 42 | 71.920 | 28.732 | 40.334 | 1.00 | 63.56 | X | O |
| ATOM | 6546 | N | LYS | 43 | 72.846 | 28.793 | 38.276 | 1.00 | 103.79 | X | N |
| ATOM | 6547 | CA | LYS | 43 | 73.852 | 29.802 | 38.607 | 1.00 | 103.79 | X | C |
| ATOM | 6548 | CB | LYS | 43 | 75.248 | 29.168 | 38.641 | 1.00 | 95.84 | X | C |
| ATOM | 6549 | CG | LYS | 43 | 75.752 | 28.830 | 40.037 | 1.00 | 95.84 | X | C |
| ATOM | 6550 | CD | LYS | 43 | 74.840 | 27.853 | 40.755 | 1.00 | 95.84 | X | C |
| ATOM | 6551 | CE | LYS | 43 | 75.225 | 27.734 | 42.222 | 1.00 | 95.84 | X | C |
| ATOM | 6552 | NZ | LYS | 43 | 75.138 | 29.048 | 42.920 | 1.00 | 95.84 | X | N |
| ATOM | 6553 | C | LYS | 43 | 73.848 | 30.984 | 37.634 | 1.00 | 103.79 | X | C |
| ATOM | 6554 | O | LYS | 43 | 73.085 | 31.013 | 36.668 | 1.00 | 103.79 | X | O |
| ATOM | 6555 | N | GLY | 44 | 74.714 | 31.956 | 37.899 | 1.00 | 36.05 | X | N |
| ATOM | 6556 | CA | GLY | 44 | 74.796 | 33.131 | 37.055 | 1.00 | 36.05 | X | C |
| ATOM | 6557 | C | GLY | 44 | 75.710 | 33.025 | 35.845 | 1.00 | 36.05 | X | C |
| ATOM | 6558 | O | GLY | 44 | 76.150 | 31.931 | 35.477 | 1.00 | 36.05 | X | O |
| ATOM | 6559 | N | LEU | 45 | 76.003 | 34.186 | 35.249 | 1.00 | 24.14 | X | N |
| ATOM | 6560 | CA | LEU | 45 | 76.832 | 34.316 | 34.046 | 1.00 | 24.14 | X | C |
| ATOM | 6561 | CB | LEU | 45 | 76.343 | 35.504 | 33.214 | 1.00 | 15.59 | X | C |
| ATOM | 6562 | CG | LEU | 45 | 74.932 | 35.346 | 32.638 | 1.00 | 15.59 | X | C |
| ATOM | 6563 | CD1 | LEU | 45 | 74.470 | 36.606 | 31.917 | 1.00 | 15.59 | X | C |
| ATOM | 6564 | CD2 | LEU | 45 | 74.942 | 34.179 | 31.677 | 1.00 | 15.59 | X | C |
| ATOM | 6565 | C | LEU | 45 | 78.316 | 34.474 | 34.311 | 1.00 | 24.14 | X | C |
| ATOM | 6566 | O | LEU | 45 | 78.732 | 35.324 | 35.095 | 1.00 | 24.14 | X | O |
| ATOM | 6567 | N | GLU | 46 | 79.110 | 33.661 | 33.624 | 1.00 | 56.59 | X | N |
| ATOM | 6568 | CA | GLU | 46 | 80.557 | 33.686 | 33.774 | 1.00 | 56.59 | X | C |
| ATOM | 6569 | CB | GLU | 46 | 81.034 | 32.373 | 34.412 | 1.00 | 46.99 | X | C |
| ATOM | 6570 | CG | GLU | 46 | 82.536 | 32.308 | 34.666 | 1.00 | 46.99 | X | C |

Fig. 19: A-91

| | | | | | | | | | | | |
|---|---|---|---|---|---|---|---|---|---|---|---|
| ATOM | 6571 | CD | GLU | 46 | 82.953 | 31.066 | 35.438 | 1.00 | 46.99 | X | C |
| ATOM | 6572 | OE1 | GLU | 46 | 82.642 | 29.952 | 34.970 | 1.00 | 46.99 | X | O |
| ATOM | 6573 | OE2 | GLU | 46 | 83.594 | 31.201 | 36.508 | 1.00 | 46.99 | X | O |
| ATOM | 6574 | C | GLU | 46 | 81.272 | 33.904 | 32.439 | 1.00 | 56.59 | X | C |
| ATOM | 6575 | O | GLU | 46 | 80.821 | 33.433 | 31.393 | 1.00 | 56.59 | X | O |
| ATOM | 6576 | N | TRP | 47 | 82.385 | 34.632 | 32.489 | 1.00 | 30.60 | X | N |
| ATOM | 6577 | CA | TRP | 47 | 83.188 | 34.910 | 31.300 | 1.00 | 30.60 | X | C |
| ATOM | 6578 | CB | TRP | 47 | 83.889 | 36.273 | 31.426 | 1.00 | 23.41 | X | C |
| ATOM | 6579 | CG | TRP | 47 | 84.944 | 36.481 | 30.385 | 1.00 | 23.41 | X | C |
| ATOM | 6580 | CD2 | TRP | 47 | 86.358 | 36.500 | 30.601 | 1.00 | 23.41 | X | C |
| ATOM | 6581 | CE2 | TRP | 47 | 86.971 | 36.591 | 29.328 | 1.00 | 23.41 | X | C |
| ATOM | 6582 | CE3 | TRP | 47 | 87.170 | 36.441 | 31.746 | 1.00 | 23.41 | X | C |
| ATOM | 6583 | CD1 | TRP | 47 | 84.759 | 36.570 | 29.031 | 1.00 | 23.41 | X | C |
| ATOM | 6584 | NE1 | TRP | 47 | 85.969 | 36.633 | 28.392 | 1.00 | 23.41 | X | N |
| ATOM | 6585 | CZ2 | TRP | 47 | 88.365 | 36.622 | 29.165 | 1.00 | 23.41 | X | C |
| ATOM | 6586 | CZ3 | TRP | 47 | 88.553 | 36.470 | 31.587 | 1.00 | 23.41 | X | C |
| ATOM | 6587 | CH2 | TRP | 47 | 89.137 | 36.560 | 30.304 | 1.00 | 23.41 | X | C |
| ATOM | 6588 | C | TRP | 47 | 84.231 | 33.810 | 31.153 | 1.00 | 30.60 | X | C |
| ATOM | 6589 | O | TRP | 47 | 84.965 | 33.516 | 32.097 | 1.00 | 30.60 | X | O |
| ATOM | 6590 | N | VAL | 48 | 84.317 | 33.219 | 29.967 | 1.00 | 24.17 | X | N |
| ATOM | 6591 | CA | VAL | 48 | 85.270 | 32.128 | 29.755 | 1.00 | 24.17 | X | C |
| ATOM | 6592 | CB | VAL | 48 | 84.589 | 30.924 | 29.011 | 1.00 | 22.03 | X | C |
| ATOM | 6593 | CG1 | VAL | 48 | 85.589 | 29.786 | 28.790 | 1.00 | 22.03 | X | C |
| ATOM | 6594 | CG2 | VAL | 48 | 83.408 | 30.436 | 29.805 | 1.00 | 22.03 | X | C |
| ATOM | 6595 | C | VAL | 48 | 86.550 | 32.490 | 29.006 | 1.00 | 24.17 | X | C |
| ATOM | 6596 | O | VAL | 48 | 87.640 | 32.477 | 29.579 | 1.00 | 24.17 | X | O |
| ATOM | 6597 | N | ALA | 49 | 86.407 | 32.800 | 27.724 | 1.00 | 21.43 | X | N |
| ATOM | 6598 | CA | ALA | 49 | 87.550 | 33.118 | 26.885 | 1.00 | 21.43 | X | C |
| ATOM | 6599 | CB | ALA | 49 | 87.953 | 31.884 | 26.094 | 1.00 | 38.48 | X | C |
| ATOM | 6600 | C | ALA | 49 | 87.228 | 34.257 | 25.934 | 1.00 | 21.43 | X | C |
| ATOM | 6601 | O | ALA | 49 | 86.066 | 34.661 | 25.825 | 1.00 | 21.43 | X | O |
| ATOM | 6602 | N | THR | 50 | 88.257 | 34.745 | 25.235 | 1.00 | 24.70 | X | N |
| ATOM | 6603 | CA | THR | 50 | 88.115 | 35.856 | 24.286 | 1.00 | 24.70 | X | C |
| ATOM | 6604 | CB | THR | 50 | 87.952 | 37.202 | 25.048 | 1.00 | 38.80 | X | C |
| ATOM | 6605 | OG1 | THR | 50 | 86.711 | 37.215 | 25.763 | 1.00 | 38.80 | X | O |
| ATOM | 6606 | CG2 | THR | 50 | 87.981 | 38.369 | 24.087 | 1.00 | 38.80 | X | C |
| ATOM | 6607 | C | THR | 50 | 89.298 | 36.039 | 23.324 | 1.00 | 24.70 | X | C |
| ATOM | 6608 | O | THR | 50 | 90.456 | 35.935 | 23.738 | 1.00 | 24.70 | X | O |
| ATOM | 6609 | N | ILE | 51 | 89.010 | 36.300 | 22.047 | 1.00 | 32.54 | X | N |
| ATOM | 6610 | CA | ILE | 51 | 90.075 | 36.599 | 21.074 | 1.00 | 32.54 | X | C |
| ATOM | 6611 | CB | ILE | 51 | 90.333 | 35.495 | 19.998 | 1.00 | 54.98 | X | C |
| ATOM | 6612 | CG2 | ILE | 51 | 90.567 | 34.178 | 20.661 | 1.00 | 54.98 | X | C |
| ATOM | 6613 | CG1 | ILE | 51 | 89.180 | 35.415 | 18.997 | 1.00 | 54.98 | X | C |
| ATOM | 6614 | CD1 | ILE | 51 | 87.893 | 34.921 | 19.582 | 1.00 | 54.98 | X | C |
| ATOM | 6615 | C | ILE | 51 | 89.674 | 37.865 | 20.335 | 1.00 | 32.54 | X | C |
| ATOM | 6616 | O | ILE | 51 | 88.516 | 38.024 | 19.937 | 1.00 | 32.54 | X | O |
| ATOM | 6617 | N | SER | 52 | 90.628 | 38.774 | 20.167 | 1.00 | 43.61 | X | N |
| ATOM | 6618 | CA | SER | 52 | 90.361 | 40.024 | 19.477 | 1.00 | 43.61 | X | C |
| ATOM | 6619 | CB | SER | 52 | 91.374 | 41.081 | 19.910 | 1.00 | 24.33 | X | C |
| ATOM | 6620 | OG | SER | 52 | 92.684 | 40.702 | 19.528 | 1.00 | 24.33 | X | O |
| ATOM | 6621 | C | SER | 52 | 90.450 | 39.789 | 17.973 | 1.00 | 43.61 | X | C |
| ATOM | 6622 | O | SER | 52 | 90.677 | 38.663 | 17.533 | 1.00 | 43.61 | X | O |
| ATOM | 6623 | N | GLY | 53 | 90.243 | 40.843 | 17.187 | 1.00 | 34.59 | X | N |
| ATOM | 6624 | CA | GLY | 53 | 90.336 | 40.707 | 15.747 | 1.00 | 34.59 | X | C |
| ATOM | 6625 | C | GLY | 53 | 91.800 | 40.559 | 15.381 | 1.00 | 34.59 | X | C |
| ATOM | 6626 | O | GLY | 53 | 92.152 | 40.020 | 14.332 | 1.00 | 34.59 | X | O |
| ATOM | 6627 | N | GLY | 54 | 92.658 | 41.047 | 16.266 | 1.00 | 29.30 | X | N |
| ATOM | 6628 | CA | GLY | 54 | 94.079 | 40.949 | 16.033 | 1.00 | 29.30 | X | C |
| ATOM | 6629 | C | GLY | 54 | 94.555 | 39.550 | 16.359 | 1.00 | 29.30 | X | C |
| ATOM | 6630 | O | GLY | 54 | 95.642 | 39.135 | 15.954 | 1.00 | 29.30 | X | O |
| ATOM | 6631 | N | GLY | 55 | 93.747 | 38.811 | 17.103 | 1.00 | 15.27 | X | N |
| ATOM | 6632 | CA | GLY | 55 | 94.139 | 37.465 | 17.437 | 1.00 | 15.27 | X | C |
| ATOM | 6633 | C | GLY | 55 | 94.596 | 37.254 | 18.867 | 1.00 | 15.27 | X | C |
| ATOM | 6634 | O | GLY | 55 | 94.878 | 36.105 | 19.231 | 1.00 | 15.27 | X | O |
| ATOM | 6635 | N | HIS | 56 | 94.676 | 38.319 | 19.675 | 1.00 | 13.76 | X | N |
| ATOM | 6636 | CA | HIS | 56 | 95.101 | 38.181 | 21.076 | 1.00 | 13.76 | X | C |
| ATOM | 6637 | CB | HIS | 56 | 95.268 | 39.543 | 21.741 | 1.00 | 60.58 | X | C |
| ATOM | 6638 | CG | HIS | 56 | 96.115 | 40.490 | 20.957 | 1.00 | 60.58 | X | C |
| ATOM | 6639 | CD2 | HIS | 56 | 97.417 | 40.838 | 21.087 | 1.00 | 60.58 | X | C |
| ATOM | 6640 | ND1 | HIS | 56 | 95.638 | 41.180 | 19.862 | 1.00 | 60.58 | X | N |
| ATOM | 6641 | CE1 | HIS | 56 | 96.611 | 41.913 | 19.351 | 1.00 | 60.58 | X | C |
| ATOM | 6642 | NE2 | HIS | 56 | 97.701 | 41.724 | 20.075 | 1.00 | 60.58 | X | N |
| ATOM | 6643 | C | HIS | 56 | 94.071 | 37.383 | 21.857 | 1.00 | 13.76 | X | C |

Fig. 19: A-92

| | | | | | | | | | | | |
|---|---|---|---|---|---|---|---|---|---|---|---|
| ATOM | 6644 | O | HIS | 56 | 92.864 | 37.621 | 21.736 | 1.00 | 13.76 | X | O |
| ATOM | 6645 | N | THR | 57 | 94.529 | 36.438 | 22.671 | 1.00 | 20.05 | X | N |
| ATOM | 6646 | CA | THR | 57 | 93.583 | 35.632 | 23.436 | 1.00 | 20.05 | X | C |
| ATOM | 6647 | CB | THR | 57 | 93.759 | 34.123 | 23.096 | 1.00 | 15.53 | X | C |
| ATOM | 6648 | OG1 | THR | 57 | 95.015 | 33.651 | 23.587 | 1.00 | 15.53 | X | O |
| ATOM | 6649 | CG2 | THR | 57 | 93.734 | 33.929 | 21.593 | 1.00 | 15.53 | X | C |
| ATOM | 6650 | C | THR | 57 | 93.655 | 35.876 | 24.952 | 1.00 | 20.05 | X | C |
| ATOM | 6651 | O | THR | 57 | 94.716 | 36.142 | 25.512 | 1.00 | 20.05 | X | O |
| ATOM | 6652 | N | TYR | 58 | 92.500 | 35.808 | 25.603 | 1.00 | 19.06 | X | N |
| ATOM | 6653 | CA | TYR | 58 | 92.410 | 36.037 | 27.040 | 1.00 | 19.06 | X | C |
| ATOM | 6654 | CB | TYR | 58 | 91.829 | 37.428 | 27.304 | 1.00 | 22.48 | X | C |
| ATOM | 6655 | CG | TYR | 58 | 92.614 | 38.542 | 26.661 | 1.00 | 22.48 | X | C |
| ATOM | 6656 | CD1 | TYR | 58 | 93.565 | 39.252 | 27.384 | 1.00 | 22.48 | X | C |
| ATOM | 6657 | CE1 | TYR | 58 | 94.308 | 40.265 | 26.788 | 1.00 | 22.48 | X | C |
| ATOM | 6658 | CD2 | TYR | 58 | 92.423 | 38.871 | 25.316 | 1.00 | 22.48 | X | C |
| ATOM | 6659 | CE2 | TYR | 58 | 93.167 | 39.886 | 24.703 | 1.00 | 22.48 | X | C |
| ATOM | 6660 | CZ | TYR | 58 | 94.105 | 40.580 | 25.447 | 1.00 | 22.48 | X | C |
| ATOM | 6661 | OH | TYR | 58 | 94.828 | 41.611 | 24.876 | 1.00 | 22.48 | X | O |
| ATOM | 6662 | C | TYR | 58 | 91.513 | 34.973 | 27.656 | 1.00 | 19.06 | X | C |
| ATOM | 6663 | O | TYR | 58 | 90.442 | 34.660 | 27.123 | 1.00 | 19.06 | X | O |
| ATOM | 6664 | N | TYR | 59 | 91.945 | 34.437 | 28.792 | 1.00 | 29.06 | X | N |
| ATOM | 6665 | CA | TYR | 59 | 91.199 | 33.378 | 29.456 | 1.00 | 29.06 | X | C |
| ATOM | 6666 | CB | TYR | 59 | 91.988 | 32.080 | 29.371 | 1.00 | 21.37 | X | C |
| ATOM | 6667 | CG | TYR | 59 | 92.252 | 31.641 | 27.969 | 1.00 | 21.37 | X | C |
| ATOM | 6668 | CD1 | TYR | 59 | 91.352 | 30.813 | 27.303 | 1.00 | 21.37 | X | C |
| ATOM | 6669 | CE1 | TYR | 59 | 91.573 | 30.428 | 25.988 | 1.00 | 21.37 | X | C |
| ATOM | 6670 | CD2 | TYR | 59 | 93.382 | 32.076 | 27.286 | 1.00 | 21.37 | X | C |
| ATOM | 6671 | CE2 | TYR | 59 | 93.608 | 31.698 | 25.968 | 1.00 | 21.37 | X | C |
| ATOM | 6672 | CZ | TYR | 59 | 92.697 | 30.874 | 25.330 | 1.00 | 21.37 | X | C |
| ATOM | 6673 | OH | TYR | 59 | 92.897 | 30.495 | 24.027 | 1.00 | 21.37 | X | O |
| ATOM | 6674 | C | TYR | 59 | 90.857 | 33.605 | 30.910 | 1.00 | 29.06 | X | C |
| ATOM | 6675 | O | TYR | 59 | 91.575 | 34.287 | 31.648 | 1.00 | 29.06 | X | O |
| ATOM | 6676 | N | LEU | 60 | 89.745 | 33.002 | 31.308 | 1.00 | 26.45 | X | N |
| ATOM | 6677 | CA | LEU | 60 | 89.309 | 33.048 | 32.689 | 1.00 | 26.45 | X | C |
| ATOM | 6678 | CB | LEU | 60 | 87.927 | 32.397 | 32.826 | 1.00 | 24.21 | X | C |
| ATOM | 6679 | CG | LEU | 60 | 87.411 | 32.193 | 34.252 | 1.00 | 24.21 | X | C |
| ATOM | 6680 | CD1 | LEU | 60 | 87.173 | 33.538 | 34.911 | 1.00 | 24.21 | X | C |
| ATOM | 6681 | CD2 | LEU | 60 | 86.135 | 31.380 | 34.223 | 1.00 | 24.21 | X | C |
| ATOM | 6682 | C | LEU | 60 | 90.382 | 32.189 | 33.360 | 1.00 | 26.45 | X | C |
| ATOM | 6683 | O | LEU | 60 | 90.822 | 31.191 | 32.781 | 1.00 | 26.45 | X | O |
| ATOM | 6684 | N | ASP | 61 | 90.822 | 32.570 | 34.553 | 1.00 | 64.06 | X | N |
| ATOM | 6685 | CA | ASP | 61 | 91.865 | 31.810 | 35.240 | 1.00 | 64.06 | X | C |
| ATOM | 6686 | CB | ASP | 61 | 92.297 | 32.556 | 36.502 | 1.00 | 60.41 | X | C |
| ATOM | 6687 | CG | ASP | 61 | 92.984 | 33.865 | 36.183 | 1.00 | 60.41 | X | C |
| ATOM | 6688 | OD1 | ASP | 61 | 93.262 | 34.650 | 37.114 | 1.00 | 60.41 | X | O |
| ATOM | 6689 | OD2 | ASP | 61 | 93.250 | 34.106 | 34.986 | 1.00 | 60.41 | X | O |
| ATOM | 6690 | C | ASP | 61 | 91.477 | 30.371 | 35.576 | 1.00 | 64.06 | X | C |
| ATOM | 6691 | O | ASP | 61 | 92.337 | 29.503 | 35.701 | 1.00 | 64.06 | X | O |
| ATOM | 6692 | N | SER | 62 | 90.181 | 30.122 | 35.707 | 1.00 | 57.78 | X | N |
| ATOM | 6693 | CA | SER | 62 | 89.681 | 28.791 | 36.028 | 1.00 | 57.78 | X | C |
| ATOM | 6694 | CB | SER | 62 | 88.196 | 28.868 | 36.386 | 1.00 | 42.55 | X | C |
| ATOM | 6695 | OG | SER | 62 | 87.643 | 27.575 | 36.556 | 1.00 | 42.55 | X | O |
| ATOM | 6696 | C | SER | 62 | 89.872 | 27.787 | 34.894 | 1.00 | 57.78 | X | C |
| ATOM | 6697 | O | SER | 62 | 90.000 | 26.590 | 35.142 | 1.00 | 57.78 | X | O |
| ATOM | 6698 | N | VAL | 63 | 89.890 | 28.269 | 33.655 | 1.00 | 47.11 | X | N |
| ATOM | 6699 | CA | VAL | 63 | 90.047 | 27.383 | 32.504 | 1.00 | 47.11 | X | C |
| ATOM | 6700 | CB | VAL | 63 | 88.796 | 27.464 | 31.555 | 1.00 | 39.29 | X | C |
| ATOM | 6701 | CG1 | VAL | 63 | 87.513 | 27.472 | 32.375 | 1.00 | 39.29 | X | C |
| ATOM | 6702 | CG2 | VAL | 63 | 88.863 | 28.700 | 30.679 | 1.00 | 39.29 | X | C |
| ATOM | 6703 | C | VAL | 63 | 91.318 | 27.660 | 31.686 | 1.00 | 47.11 | X | C |
| ATOM | 6704 | O | VAL | 63 | 91.504 | 27.093 | 30.603 | 1.00 | 47.11 | X | O |
| ATOM | 6705 | N | LYS | 64 | 92.200 | 28.511 | 32.208 | 1.00 | 47.01 | X | N |
| ATOM | 6706 | CA | LYS | 64 | 93.424 | 28.843 | 31.483 | 1.00 | 47.01 | X | C |
| ATOM | 6707 | CB | LYS | 64 | 94.116 | 30.063 | 32.107 | 1.00 | 84.46 | X | C |
| ATOM | 6708 | CG | LYS | 64 | 95.038 | 30.797 | 31.135 | 1.00 | 84.46 | X | C |
| ATOM | 6709 | CD | LYS | 64 | 95.670 | 32.025 | 31.766 | 1.00 | 84.46 | X | C |
| ATOM | 6710 | CE | LYS | 64 | 96.370 | 32.907 | 30.725 | 1.00 | 84.46 | X | C |
| ATOM | 6711 | NZ | LYS | 64 | 95.419 | 33.654 | 29.833 | 1.00 | 84.46 | X | N |
| ATOM | 6712 | C | LYS | 64 | 94.388 | 27.666 | 31.441 | 1.00 | 47.01 | X | C |
| ATOM | 6713 | O | LYS | 64 | 94.757 | 27.113 | 32.479 | 1.00 | 47.01 | X | O |
| ATOM | 6714 | N | GLY | 65 | 94.795 | 27.289 | 30.231 | 1.00 | 35.35 | X | N |
| ATOM | 6715 | CA | GLY | 65 | 95.704 | 26.167 | 30.073 | 1.00 | 35.35 | X | C |
| ATOM | 6716 | C | GLY | 65 | 94.953 | 24.919 | 29.652 | 1.00 | 35.35 | X | C |

Fig. 19: A-93

| | | | | | | | | | | | |
|---|---|---|---|---|---|---|---|---|---|---|---|
| ATOM | 6717 | O | GLY | 65 | 95.547 | 23.945 | 29.195 | 1.00 | 35.35 | X | O |
| ATOM | 6718 | N | ARG | 66 | 93.634 | 24.956 | 29.809 | 1.00 | 33.32 | X | N |
| ATOM | 6719 | CA | ARG | 66 | 92.791 | 23.833 | 29.450 | 1.00 | 33.32 | X | C |
| ATOM | 6720 | CB | ARG | 66 | 91.881 | 23.470 | 30.616 | 1.00 | 43.17 | X | C |
| ATOM | 6721 | CG | ARG | 66 | 92.594 | 23.386 | 31.958 | 1.00 | 43.17 | X | C |
| ATOM | 6722 | CD | ARG | 66 | 91.684 | 22.813 | 33.050 | 1.00 | 43.17 | X | C |
| ATOM | 6723 | NE | ARG | 66 | 90.548 | 23.679 | 33.367 | 1.00 | 43.17 | X | N |
| ATOM | 6724 | CZ | ARG | 66 | 89.277 | 23.296 | 33.305 | 1.00 | 43.17 | X | C |
| ATOM | 6725 | NH1 | ARG | 66 | 88.973 | 22.061 | 32.932 | 1.00 | 43.17 | X | N |
| ATOM | 6726 | NH2 | ARG | 66 | 88.309 | 24.144 | 33.630 | 1.00 | 43.17 | X | N |
| ATOM | 6727 | C | ARG | 66 | 91.945 | 24.169 | 28.232 | 1.00 | 33.32 | X | C |
| ATOM | 6728 | O | ARG | 66 | 91.775 | 23.336 | 27.346 | 1.00 | 33.32 | X | O |
| ATOM | 6729 | N | PHE | 67 | 91.411 | 25.389 | 28.191 | 1.00 | 33.69 | X | N |
| ATOM | 6730 | CA | PHE | 67 | 90.567 | 25.834 | 27.074 | 1.00 | 33.69 | X | C |
| ATOM | 6731 | CB | PHE | 67 | 89.444 | 26.750 | 27.587 | 1.00 | 42.44 | X | C |
| ATOM | 6732 | CG | PHE | 67 | 88.346 | 26.030 | 28.330 | 1.00 | 42.44 | X | C |
| ATOM | 6733 | CD1 | PHE | 67 | 88.573 | 24.802 | 28.943 | 1.00 | 42.44 | X | C |
| ATOM | 6734 | CD2 | PHE | 67 | 87.074 | 26.594 | 28.426 | 1.00 | 42.44 | X | C |
| ATOM | 6735 | CE1 | PHE | 67 | 87.547 | 24.145 | 29.637 | 1.00 | 42.44 | X | C |
| ATOM | 6736 | CE2 | PHE | 67 | 86.038 | 25.940 | 29.122 | 1.00 | 42.44 | X | C |
| ATOM | 6737 | CZ | PHE | 67 | 86.278 | 24.717 | 29.724 | 1.00 | 42.44 | X | C |
| ATOM | 6738 | C | PHE | 67 | 91.393 | 26.578 | 26.027 | 1.00 | 33.69 | X | C |
| ATOM | 6739 | O | PHE | 67 | 92.405 | 27.194 | 26.344 | 1.00 | 33.69 | X | O |
| ATOM | 6740 | N | THR | 68 | 90.949 | 26.526 | 24.779 | 1.00 | 56.59 | X | N |
| ATOM | 6741 | CA | THR | 68 | 91.646 | 27.201 | 23.689 | 1.00 | 56.59 | X | C |
| ATOM | 6742 | CB | THR | 68 | 92.454 | 26.193 | 22.846 | 1.00 | 46.98 | X | C |
| ATOM | 6743 | OG1 | THR | 68 | 93.611 | 25.781 | 23.578 | 1.00 | 46.98 | X | O |
| ATOM | 6744 | CG2 | THR | 68 | 92.870 | 26.808 | 21.512 | 1.00 | 46.98 | X | C |
| ATOM | 6745 | C | THR | 68 | 90.661 | 27.913 | 22.768 | 1.00 | 56.59 | X | C |
| ATOM | 6746 | O | THR | 68 | 89.899 | 27.270 | 22.047 | 1.00 | 56.59 | X | O |
| ATOM | 6747 | N | ILE | 69 | 90.672 | 29.239 | 22.781 | 1.00 | 20.15 | X | N |
| ATOM | 6748 | CA | ILE | 69 | 89.760 | 29.975 | 21.918 | 1.00 | 20.15 | X | C |
| ATOM | 6749 | CB | ILE | 69 | 89.287 | 31.289 | 22.607 | 1.00 | 31.46 | X | C |
| ATOM | 6750 | CG2 | ILE | 69 | 90.480 | 32.153 | 22.953 | 1.00 | 31.46 | X | C |
| ATOM | 6751 | CG1 | ILE | 69 | 88.283 | 32.028 | 21.722 | 1.00 | 31.46 | X | C |
| ATOM | 6752 | CD1 | ILE | 69 | 87.574 | 33.159 | 22.446 | 1.00 | 31.46 | X | C |
| ATOM | 6753 | C | ILE | 69 | 90.464 | 30.262 | 20.591 | 1.00 | 20.15 | X | C |
| ATOM | 6754 | O | ILE | 69 | 91.672 | 30.481 | 20.559 | 1.00 | 20.15 | X | O |
| ATOM | 6755 | N | SER | 70 | 89.724 | 30.223 | 19.489 | 1.00 | 21.14 | X | N |
| ATOM | 6756 | CA | SER | 70 | 90.319 | 30.482 | 18.182 | 1.00 | 21.14 | X | C |
| ATOM | 6757 | CB | SER | 70 | 91.105 | 29.263 | 17.693 | 1.00 | 37.41 | X | C |
| ATOM | 6758 | OG | SER | 70 | 90.228 | 28.236 | 17.253 | 1.00 | 37.41 | X | O |
| ATOM | 6759 | C | SER | 70 | 89.242 | 30.824 | 17.163 | 1.00 | 21.14 | X | C |
| ATOM | 6760 | O | SER | 70 | 88.045 | 30.637 | 17.413 | 1.00 | 21.14 | X | O |
| ATOM | 6761 | N | ARG | 71 | 89.673 | 31.322 | 16.009 | 1.00 | 30.73 | X | N |
| ATOM | 6762 | CA | ARG | 71 | 88.734 | 31.687 | 14.966 | 1.00 | 30.73 | X | C |
| ATOM | 6763 | CB | ARG | 71 | 88.369 | 33.178 | 15.073 | 1.00 | 24.51 | X | C |
| ATOM | 6764 | CG | ARG | 71 | 89.546 | 34.139 | 14.901 | 1.00 | 24.51 | X | C |
| ATOM | 6765 | CD | ARG | 71 | 89.071 | 35.503 | 14.453 | 1.00 | 24.51 | X | C |
| ATOM | 6766 | NE | ARG | 71 | 88.464 | 36.278 | 15.534 | 1.00 | 24.51 | X | N |
| ATOM | 6767 | CZ | ARG | 71 | 87.604 | 37.283 | 15.351 | 1.00 | 24.51 | X | C |
| ATOM | 6768 | NH1 | ARG | 71 | 87.229 | 37.643 | 14.131 | 1.00 | 24.51 | X | N |
| ATOM | 6769 | NH2 | ARG | 71 | 87.132 | 37.948 | 16.391 | 1.00 | 24.51 | X | N |
| ATOM | 6770 | C | ARG | 71 | 89.259 | 31.393 | 13.560 | 1.00 | 30.73 | X | C |
| ATOM | 6771 | O | ARG | 71 | 90.464 | 31.415 | 13.301 | 1.00 | 30.73 | X | O |
| ATOM | 6772 | N | ASP | 72 | 88.326 | 31.106 | 12.663 | 1.00 | 55.72 | X | N |
| ATOM | 6773 | CA | ASP | 72 | 88.619 | 30.836 | 11.268 | 1.00 | 55.72 | X | C |
| ATOM | 6774 | CB | ASP | 72 | 88.219 | 29.405 | 10.902 | 1.00 | 83.09 | X | C |
| ATOM | 6775 | CG | ASP | 72 | 88.255 | 29.153 | 9.409 | 1.00 | 83.09 | X | C |
| ATOM | 6776 | OD1 | ASP | 72 | 89.282 | 29.466 | 8.773 | 1.00 | 83.09 | X | O |
| ATOM | 6777 | OD2 | ASP | 72 | 87.256 | 28.637 | 8.870 | 1.00 | 83.09 | X | O |
| ATOM | 6778 | C | ASP | 72 | 87.749 | 31.837 | 10.528 | 1.00 | 55.72 | X | C |
| ATOM | 6779 | O | ASP | 72 | 86.613 | 31.539 | 10.162 | 1.00 | 55.72 | X | O |
| ATOM | 6780 | N | ASN | 73 | 88.284 | 33.036 | 10.340 | 1.00 | 57.89 | X | N |
| ATOM | 6781 | CA | ASN | 73 | 87.552 | 34.098 | 9.673 | 1.00 | 57.89 | X | C |
| ATOM | 6782 | CB | ASN | 73 | 88.426 | 35.345 | 9.558 | 1.00 | 43.96 | X | C |
| ATOM | 6783 | CG | ASN | 73 | 88.777 | 35.928 | 10.912 | 1.00 | 43.96 | X | C |
| ATOM | 6784 | OD1 | ASN | 73 | 88.021 | 35.794 | 11.879 | 1.00 | 43.96 | X | O |
| ATOM | 6785 | ND2 | ASN | 73 | 89.919 | 36.593 | 10.986 | 1.00 | 43.96 | X | N |
| ATOM | 6786 | C | ASN | 73 | 87.020 | 33.715 | 8.306 | 1.00 | 57.89 | X | C |
| ATOM | 6787 | O | ASN | 73 | 85.949 | 34.173 | 7.903 | 1.00 | 57.89 | X | O |
| ATOM | 6788 | N | SER | 74 | 87.756 | 32.870 | 7.594 | 1.00 | 50.09 | X | N |
| ATOM | 6789 | CA | SER | 74 | 87.324 | 32.451 | 6.268 | 1.00 | 50.09 | X | C |

Fig. 19: A-94

| | | | | | | | | | | | |
|---|---|---|---|---|---|---|---|---|---|---|---|
| ATOM | 6790 | CB | SER | 74 | 88.277 | 31.398 | 5.705 | 1.00 | 34.87 | X | C |
| ATOM | 6791 | OG | SER | 74 | 88.179 | 30.197 | 6.441 | 1.00 | 34.87 | X | O |
| ATOM | 6792 | C | SER | 74 | 85.910 | 31.880 | 6.303 | 1.00 | 50.09 | X | C |
| ATOM | 6793 | O | SER | 74 | 85.141 | 32.050 | 5.356 | 1.00 | 50.09 | X | O |
| ATOM | 6794 | N | LYS | 75 | 85.572 | 31.209 | 7.400 | 1.00 | 50.16 | X | N |
| ATOM | 6795 | CA | LYS | 75 | 84.257 | 30.597 | 7.551 | 1.00 | 50.16 | X | C |
| ATOM | 6796 | CB | LYS | 75 | 84.418 | 29.097 | 7.814 | 1.00 | 60.89 | X | C |
| ATOM | 6797 | CG | LYS | 75 | 85.206 | 28.372 | 6.729 | 1.00 | 60.89 | X | C |
| ATOM | 6798 | CD | LYS | 75 | 85.356 | 26.884 | 7.009 | 1.00 | 60.89 | X | C |
| ATOM | 6799 | CE | LYS | 75 | 86.046 | 26.195 | 5.840 | 1.00 | 60.89 | X | C |
| ATOM | 6800 | NZ | LYS | 75 | 85.341 | 26.459 | 4.551 | 1.00 | 60.89 | X | N |
| ATOM | 6801 | C | LYS | 75 | 83.423 | 31.226 | 8.663 | 1.00 | 50.16 | X | C |
| ATOM | 6802 | O | LYS | 75 | 82.470 | 30.618 | 9.142 | 1.00 | 50.16 | X | O |
| ATOM | 6803 | N | ASN | 76 | 83.786 | 32.441 | 9.066 | 1.00 | 54.49 | X | N |
| ATOM | 6804 | CA | ASN | 76 | 83.075 | 33.165 | 10.117 | 1.00 | 54.49 | X | C |
| ATOM | 6805 | CB | ASN | 76 | 81.812 | 33.818 | 9.559 | 1.00 | 41.29 | X | C |
| ATOM | 6806 | CG | ASN | 76 | 82.116 | 34.956 | 8.620 | 1.00 | 41.29 | X | C |
| ATOM | 6807 | OD1 | ASN | 76 | 81.399 | 35.956 | 8.592 | 1.00 | 41.29 | X | O |
| ATOM | 6808 | ND2 | ASN | 76 | 83.181 | 34.812 | 7.839 | 1.00 | 41.29 | X | N |
| ATOM | 6809 | C | ASN | 76 | 82.684 | 32.285 | 11.286 | 1.00 | 54.49 | X | C |
| ATOM | 6810 | O | ASN | 76 | 81.523 | 32.278 | 11.706 | 1.00 | 54.49 | X | O |
| ATOM | 6811 | N | THR | 77 | 83.645 | 31.550 | 11.827 | 1.00 | 48.88 | X | N |
| ATOM | 6812 | CA | THR | 77 | 83.325 | 30.675 | 12.938 | 1.00 | 48.88 | X | C |
| ATOM | 6813 | CB | THR | 77 | 83.321 | 29.215 | 12.481 | 1.00 | 67.62 | X | C |
| ATOM | 6814 | OG1 | THR | 77 | 82.318 | 29.048 | 11.469 | 1.00 | 67.62 | X | O |
| ATOM | 6815 | CG2 | THR | 77 | 83.028 | 28.284 | 13.653 | 1.00 | 67.62 | X | C |
| ATOM | 6816 | C | THR | 77 | 84.245 | 30.817 | 14.132 | 1.00 | 48.88 | X | C |
| ATOM | 6817 | O | THR | 77 | 85.463 | 30.858 | 13.990 | 1.00 | 48.88 | X | O |
| ATOM | 6818 | N | LEU | 78 | 83.641 | 30.900 | 15.313 | 1.00 | 25.08 | X | N |
| ATOM | 6819 | CA | LEU | 78 | 84.387 | 31.014 | 16.562 | 1.00 | 25.08 | X | C |
| ATOM | 6820 | CB | LEU | 78 | 83.739 | 32.047 | 17.488 | 1.00 | 24.57 | X | C |
| ATOM | 6821 | CG | LEU | 78 | 84.362 | 32.022 | 18.881 | 1.00 | 24.57 | X | C |
| ATOM | 6822 | CD1 | LEU | 78 | 85.757 | 32.625 | 18.789 | 1.00 | 24.57 | X | C |
| ATOM | 6823 | CD2 | LEU | 78 | 83.507 | 32.770 | 19.868 | 1.00 | 24.57 | X | C |
| ATOM | 6824 | C | LEU | 78 | 84.370 | 29.653 | 17.250 | 1.00 | 25.08 | X | C |
| ATOM | 6825 | O | LEU | 78 | 83.312 | 29.041 | 17.389 | 1.00 | 25.08 | X | O |
| ATOM | 6826 | N | TYR | 79 | 85.530 | 29.179 | 17.687 | 1.00 | 41.94 | X | N |
| ATOM | 6827 | CA | TYR | 79 | 85.595 | 27.880 | 18.344 | 1.00 | 41.94 | X | C |
| ATOM | 6828 | CB | TYR | 79 | 86.608 | 26.963 | 17.657 | 1.00 | 47.62 | X | C |
| ATOM | 6829 | CG | TYR | 79 | 86.328 | 26.619 | 16.226 | 1.00 | 47.62 | X | C |
| ATOM | 6830 | CD1 | TYR | 79 | 85.264 | 25.794 | 15.887 | 1.00 | 47.62 | X | C |
| ATOM | 6831 | CE1 | TYR | 79 | 85.008 | 25.460 | 14.559 | 1.00 | 47.62 | X | C |
| ATOM | 6832 | CD2 | TYR | 79 | 87.139 | 27.108 | 15.207 | 1.00 | 47.62 | X | C |
| ATOM | 6833 | CE2 | TYR | 79 | 86.896 | 26.784 | 13.878 | 1.00 | 47.62 | X | C |
| ATOM | 6834 | CZ | TYR | 79 | 85.826 | 25.959 | 13.559 | 1.00 | 47.62 | X | C |
| ATOM | 6835 | OH | TYR | 79 | 85.564 | 25.640 | 12.245 | 1.00 | 47.62 | X | O |
| ATOM | 6836 | C | TYR | 79 | 86.043 | 27.991 | 19.779 | 1.00 | 41.94 | X | C |
| ATOM | 6837 | O | TYR | 79 | 86.890 | 28.824 | 20.100 | 1.00 | 41.94 | X | O |
| ATOM | 6838 | N | LEU | 80 | 85.470 | 27.160 | 20.642 | 1.00 | 19.15 | X | N |
| ATOM | 6839 | CA | LEU | 80 | 85.917 | 27.110 | 22.022 | 1.00 | 19.15 | X | C |
| ATOM | 6840 | CB | LEU | 80 | 84.809 | 27.382 | 23.047 | 1.00 | 21.08 | X | C |
| ATOM | 6841 | CG | LEU | 80 | 85.271 | 27.127 | 24.510 | 1.00 | 21.08 | X | C |
| ATOM | 6842 | CD1 | LEU | 80 | 86.500 | 27.981 | 24.840 | 1.00 | 21.08 | X | C |
| ATOM | 6843 | CD2 | LEU | 80 | 84.142 | 27.412 | 25.503 | 1.00 | 21.08 | X | C |
| ATOM | 6844 | C | LEU | 80 | 86.342 | 25.671 | 22.129 | 1.00 | 19.15 | X | C |
| ATOM | 6845 | O | LEU | 80 | 85.517 | 24.769 | 21.941 | 1.00 | 19.15 | X | O |
| ATOM | 6846 | N | GLN | 81 | 87.631 | 25.455 | 22.395 | 1.00 | 31.28 | X | N |
| ATOM | 6847 | CA | GLN | 81 | 88.193 | 24.111 | 22.530 | 1.00 | 31.28 | X | C |
| ATOM | 6848 | CB | GLN | 81 | 89.497 | 24.015 | 21.738 | 1.00 | 68.87 | X | C |
| ATOM | 6849 | CG | GLN | 81 | 90.141 | 22.647 | 21.783 | 1.00 | 68.87 | X | C |
| ATOM | 6850 | CD | GLN | 81 | 89.318 | 21.580 | 21.075 | 1.00 | 68.87 | X | C |
| ATOM | 6851 | OE1 | GLN | 81 | 89.101 | 21.648 | 19.864 | 1.00 | 68.87 | X | O |
| ATOM | 6852 | NE2 | GLN | 81 | 88.857 | 20.588 | 21.831 | 1.00 | 68.87 | X | N |
| ATOM | 6853 | C | GLN | 81 | 88.448 | 23.775 | 24.001 | 1.00 | 31.28 | X | C |
| ATOM | 6854 | O | GLN | 81 | 89.402 | 24.260 | 24.604 | 1.00 | 31.28 | X | O |
| ATOM | 6855 | N | MET | 82 | 87.589 | 22.935 | 24.569 | 1.00 | 32.50 | X | N |
| ATOM | 6856 | CA | MET | 82 | 87.701 | 22.541 | 25.975 | 1.00 | 32.50 | X | C |
| ATOM | 6857 | CB | MET | 82 | 86.297 | 22.429 | 26.589 | 1.00 | 41.50 | X | C |
| ATOM | 6858 | CG | MET | 82 | 85.537 | 23.752 | 26.653 | 1.00 | 41.50 | X | C |
| ATOM | 6859 | SD | MET | 82 | 83.790 | 23.594 | 27.062 | 1.00 | 41.50 | X | S |
| ATOM | 6860 | CE | MET | 82 | 83.088 | 23.391 | 25.452 | 1.00 | 41.50 | X | C |
| ATOM | 6861 | C | MET | 82 | 88.463 | 21.230 | 26.188 | 1.00 | 32.50 | X | C |
| ATOM | 6862 | O | MET | 82 | 88.239 | 20.250 | 25.487 | 1.00 | 32.50 | X | O |

Fig. 19: A-95

| | | | | | | | | | | | |
|---|---|---|---|---|---|---|---|---|---|---|---|
| ATOM | 6863 | N | ASN | 83 | 89.369 | 21.224 | 27.160 | 1.00 | 43.69 | X | N |
| ATOM | 6864 | CA | ASN | 83 | 90.155 | 20.032 | 27.459 | 1.00 | 43.69 | X | C |
| ATOM | 6865 | CB | ASN | 83 | 91.574 | 20.157 | 26.883 | 1.00 | 34.50 | X | C |
| ATOM | 6866 | CG | ASN | 83 | 91.574 | 20.391 | 25.383 | 1.00 | 34.50 | X | C |
| ATOM | 6867 | OD1 | ASN | 83 | 90.920 | 19.670 | 24.636 | 1.00 | 34.50 | X | O |
| ATOM | 6868 | ND2 | ASN | 83 | 92.313 | 21.401 | 24.937 | 1.00 | 34.50 | X | N |
| ATOM | 6869 | C | ASN | 83 | 90.225 | 19.855 | 28.967 | 1.00 | 43.69 | X | C |
| ATOM | 6870 | O | ASN | 83 | 90.054 | 20.822 | 29.705 | 1.00 | 43.69 | X | O |
| ATOM | 6871 | N | SER | 84 | 90.480 | 18.625 | 29.416 | 1.00 | 47.01 | X | N |
| ATOM | 6872 | CA | SER | 84 | 90.560 | 18.322 | 30.843 | 1.00 | 47.01 | X | C |
| ATOM | 6873 | CB | SER | 84 | 91.748 | 19.045 | 31.482 | 1.00 | 36.84 | X | C |
| ATOM | 6874 | OG | SER | 84 | 92.963 | 18.623 | 30.892 | 1.00 | 36.84 | X | O |
| ATOM | 6875 | C | SER | 84 | 89.270 | 18.757 | 31.516 | 1.00 | 47.01 | X | C |
| ATOM | 6876 | O | SER | 84 | 89.272 | 19.261 | 32.644 | 1.00 | 47.01 | X | O |
| ATOM | 6877 | N | LEU | 85 | 88.170 | 18.548 | 30.804 | 1.00 | 35.88 | X | N |
| ATOM | 6878 | CA | LEU | 85 | 86.842 | 18.920 | 31.273 | 1.00 | 35.88 | X | C |
| ATOM | 6879 | CB | LEU | 85 | 85.800 | 18.466 | 30.250 | 1.00 | 45.16 | X | C |
| ATOM | 6880 | CG | LEU | 85 | 85.854 | 19.211 | 28.921 | 1.00 | 45.16 | X | C |
| ATOM | 6881 | CD1 | LEU | 85 | 84.875 | 18.608 | 27.936 | 1.00 | 45.16 | X | C |
| ATOM | 6882 | CD2 | LEU | 85 | 85.536 | 20.672 | 29.178 | 1.00 | 45.16 | X | C |
| ATOM | 6883 | C | LEU | 85 | 86.450 | 18.396 | 32.652 | 1.00 | 35.88 | X | C |
| ATOM | 6884 | O | LEU | 85 | 86.175 | 17.208 | 32.818 | 1.00 | 35.88 | X | O |
| ATOM | 6885 | N | ARG | 86 | 86.415 | 19.290 | 33.636 | 1.00 | 55.90 | X | N |
| ATOM | 6886 | CA | ARG | 86 | 86.022 | 18.907 | 34.985 | 1.00 | 55.90 | X | C |
| ATOM | 6887 | CB | ARG | 86 | 86.606 | 19.864 | 36.023 | 1.00 | 50.18 | X | C |
| ATOM | 6888 | CG | ARG | 86 | 88.108 | 20.015 | 35.994 | 1.00 | 50.18 | X | C |
| ATOM | 6889 | CD | ARG | 86 | 88.620 | 20.357 | 37.385 | 1.00 | 50.18 | X | C |
| ATOM | 6890 | NE | ARG | 86 | 89.970 | 20.904 | 37.355 | 1.00 | 50.18 | X | N |
| ATOM | 6891 | CZ | ARG | 86 | 90.256 | 22.185 | 37.133 | 1.00 | 50.18 | X | C |
| ATOM | 6892 | NH1 | ARG | 86 | 89.280 | 23.066 | 36.926 | 1.00 | 50.18 | X | N |
| ATOM | 6893 | NH2 | ARG | 86 | 91.524 | 22.587 | 37.109 | 1.00 | 50.18 | X | N |
| ATOM | 6894 | C | ARG | 86 | 84.501 | 18.954 | 35.069 | 1.00 | 55.90 | X | C |
| ATOM | 6895 | O | ARG | 86 | 83.818 | 19.086 | 34.055 | 1.00 | 55.90 | X | O |
| ATOM | 6896 | N | ALA | 87 | 83.974 | 18.856 | 36.282 | 1.00 | 39.09 | X | N |
| ATOM | 6897 | CA | ALA | 87 | 82.533 | 18.893 | 36.485 | 1.00 | 39.09 | X | C |
| ATOM | 6898 | CB | ALA | 87 | 82.164 | 18.133 | 37.750 | 1.00 | 69.79 | X | C |
| ATOM | 6899 | C | ALA | 87 | 82.028 | 20.325 | 36.578 | 1.00 | 39.09 | X | C |
| ATOM | 6900 | O | ALA | 87 | 80.885 | 20.607 | 36.219 | 1.00 | 39.09 | X | O |
| ATOM | 6901 | N | GLU | 88 | 82.876 | 21.228 | 37.066 | 1.00 | 49.44 | X | N |
| ATOM | 6902 | CA | GLU | 88 | 82.492 | 22.628 | 37.197 | 1.00 | 49.44 | X | C |
| ATOM | 6903 | CB | GLU | 88 | 83.586 | 23.435 | 37.899 | 1.00 | 57.40 | X | C |
| ATOM | 6904 | CG | GLU | 88 | 84.189 | 22.765 | 39.107 | 1.00 | 57.40 | X | C |
| ATOM | 6905 | CD | GLU | 88 | 85.178 | 21.691 | 38.724 | 1.00 | 57.40 | X | C |
| ATOM | 6906 | OE1 | GLU | 88 | 86.227 | 22.035 | 38.146 | 1.00 | 57.40 | X | O |
| ATOM | 6907 | OE2 | GLU | 88 | 84.906 | 20.504 | 38.993 | 1.00 | 57.40 | X | O |
| ATOM | 6908 | C | GLU | 88 | 82.242 | 23.242 | 35.824 | 1.00 | 49.44 | X | C |
| ATOM | 6909 | O | GLU | 88 | 81.474 | 24.195 | 35.687 | 1.00 | 49.44 | X | O |
| ATOM | 6910 | N | ASP | 89 | 82.892 | 22.698 | 34.803 | 1.00 | 49.12 | X | N |
| ATOM | 6911 | CA | ASP | 89 | 82.720 | 23.229 | 33.464 | 1.00 | 49.12 | X | C |
| ATOM | 6912 | CB | ASP | 89 | 83.818 | 22.698 | 32.549 | 1.00 | 52.75 | X | C |
| ATOM | 6913 | CG | ASP | 89 | 85.194 | 22.903 | 33.124 | 1.00 | 52.75 | X | C |
| ATOM | 6914 | OD1 | ASP | 89 | 85.430 | 23.960 | 33.752 | 1.00 | 52.75 | X | O |
| ATOM | 6915 | OD2 | ASP | 89 | 86.043 | 22.011 | 32.936 | 1.00 | 52.75 | X | O |
| ATOM | 6916 | C | ASP | 89 | 81.348 | 22.914 | 32.871 | 1.00 | 49.12 | X | C |
| ATOM | 6917 | O | ASP | 89 | 80.981 | 23.459 | 31.834 | 1.00 | 49.12 | X | O |
| ATOM | 6918 | N | THR | 90 | 80.590 | 22.034 | 33.517 | 1.00 | 33.14 | X | N |
| ATOM | 6919 | CA | THR | 90 | 79.265 | 21.686 | 33.012 | 1.00 | 33.14 | X | C |
| ATOM | 6920 | CB | THR | 90 | 78.652 | 20.480 | 33.766 | 1.00 | 40.77 | X | C |
| ATOM | 6921 | OG1 | THR | 90 | 78.585 | 20.770 | 35.162 | 1.00 | 40.77 | X | O |
| ATOM | 6922 | CG2 | THR | 90 | 79.498 | 19.257 | 33.590 | 1.00 | 40.77 | X | C |
| ATOM | 6923 | C | THR | 90 | 78.361 | 22.899 | 33.174 | 1.00 | 33.14 | X | C |
| ATOM | 6924 | O | THR | 90 | 78.260 | 23.486 | 34.263 | 1.00 | 33.14 | X | O |
| ATOM | 6925 | N | ALA | 91 | 77.718 | 23.276 | 32.076 | 1.00 | 55.37 | X | N |
| ATOM | 6926 | CA | ALA | 91 | 76.832 | 24.428 | 32.058 | 1.00 | 55.37 | X | C |
| ATOM | 6927 | CB | ALA | 91 | 77.527 | 25.625 | 32.692 | 1.00 | 7.95 | X | C |
| ATOM | 6928 | C | ALA | 91 | 76.504 | 24.732 | 30.609 | 1.00 | 55.37 | X | C |
| ATOM | 6929 | O | ALA | 91 | 77.073 | 24.128 | 29.698 | 1.00 | 55.37 | X | O |
| ATOM | 6930 | N | VAL | 92 | 75.579 | 25.656 | 30.387 | 1.00 | 44.83 | X | N |
| ATOM | 6931 | CA | VAL | 92 | 75.243 | 26.017 | 29.021 | 1.00 | 44.83 | X | C |
| ATOM | 6932 | CB | VAL | 92 | 73.747 | 26.429 | 28.878 | 1.00 | 41.51 | X | C |
| ATOM | 6933 | CG1 | VAL | 92 | 73.210 | 26.967 | 30.198 | 1.00 | 41.51 | X | C |
| ATOM | 6934 | CG2 | VAL | 92 | 73.596 | 27.460 | 27.769 | 1.00 | 41.51 | X | C |
| ATOM | 6935 | C | VAL | 92 | 76.182 | 27.145 | 28.591 | 1.00 | 44.83 | X | C |

Fig. 19: A-96

| | | | | | | | | | | | |
|---|---|---|---|---|---|---|---|---|---|---|---|
| ATOM | 6936 | O | VAL | 92 | 76.446 | 28.085 | 29.354 | 1.00 | 44.83 | X | O |
| ATOM | 6937 | N | TYR | 93 | 76.701 | 27.019 | 27.371 | 1.00 | 51.76 | X | N |
| ATOM | 6938 | CA | TYR | 93 | 77.642 | 27.978 | 26.811 | 1.00 | 51.76 | X | C |
| ATOM | 6939 | CB | TYR | 93 | 78.838 | 27.241 | 26.227 | 1.00 | 15.58 | X | C |
| ATOM | 6940 | CG | TYR | 93 | 79.743 | 26.693 | 27.287 | 1.00 | 15.58 | X | C |
| ATOM | 6941 | CD1 | TYR | 93 | 79.520 | 25.443 | 27.841 | 1.00 | 15.58 | X | C |
| ATOM | 6942 | CE1 | TYR | 93 | 80.339 | 24.959 | 28.860 | 1.00 | 15.58 | X | C |
| ATOM | 6943 | CD2 | TYR | 93 | 80.802 | 27.454 | 27.777 | 1.00 | 15.58 | X | C |
| ATOM | 6944 | CE2 | TYR | 93 | 81.618 | 26.983 | 28.797 | 1.00 | 15.58 | X | C |
| ATOM | 6945 | CZ | TYR | 93 | 81.384 | 25.735 | 29.328 | 1.00 | 15.58 | X | C |
| ATOM | 6946 | OH | TYR | 93 | 82.223 | 25.253 | 30.297 | 1.00 | 15.58 | X | O |
| ATOM | 6947 | C | TYR | 93 | 77.091 | 28.908 | 25.757 | 1.00 | 51.76 | X | C |
| ATOM | 6948 | O | TYR | 93 | 76.223 | 28.534 | 24.972 | 1.00 | 51.76 | X | O |
| ATOM | 6949 | N | TYR | 94 | 77.633 | 30.121 | 25.729 | 1.00 | 29.82 | X | N |
| ATOM | 6950 | CA | TYR | 94 | 77.210 | 31.143 | 24.774 | 1.00 | 29.82 | X | C |
| ATOM | 6951 | CB | TYR | 94 | 76.448 | 32.267 | 25.489 | 1.00 | 45.66 | X | C |
| ATOM | 6952 | CG | TYR | 94 | 75.282 | 31.829 | 26.343 | 1.00 | 45.66 | X | C |
| ATOM | 6953 | CD1 | TYR | 94 | 74.053 | 31.494 | 25.771 | 1.00 | 45.66 | X | C |
| ATOM | 6954 | CE1 | TYR | 94 | 72.979 | 31.108 | 26.564 | 1.00 | 45.66 | X | C |
| ATOM | 6955 | CD2 | TYR | 94 | 75.405 | 31.763 | 27.733 | 1.00 | 45.66 | X | C |
| ATOM | 6956 | CE2 | TYR | 94 | 74.342 | 31.376 | 28.532 | 1.00 | 45.66 | X | C |
| ATOM | 6957 | CZ | TYR | 94 | 73.132 | 31.051 | 27.943 | 1.00 | 45.66 | X | C |
| ATOM | 6958 | OH | TYR | 94 | 72.082 | 30.665 | 28.743 | 1.00 | 45.66 | X | O |
| ATOM | 6959 | C | TYR | 94 | 78.389 | 31.799 | 24.074 | 1.00 | 29.82 | X | C |
| ATOM | 6960 | O | TYR | 94 | 79.360 | 32.174 | 24.727 | 1.00 | 29.82 | X | O |
| ATOM | 6961 | N | CYS | 95 | 78.332 | 31.923 | 22.752 | 1.00 | 22.64 | X | N |
| ATOM | 6962 | CA | CYS | 95 | 79.394 | 32.659 | 22.091 | 1.00 | 22.64 | X | C |
| ATOM | 6963 | C | CYS | 95 | 78.871 | 34.094 | 22.103 | 1.00 | 22.64 | X | C |
| ATOM | 6964 | O | CYS | 95 | 77.656 | 34.337 | 22.170 | 1.00 | 22.64 | X | O |
| ATOM | 6965 | CB | CYS | 95 | 79.660 | 32.185 | 20.660 | 1.00 | 55.79 | X | C |
| ATOM | 6966 | SG | CYS | 95 | 78.222 | 31.748 | 19.650 | 1.00 | 55.79 | X | S |
| ATOM | 6967 | N | THR | 96 | 79.778 | 35.057 | 22.067 | 1.00 | 43.77 | X | N |
| ATOM | 6968 | CA | THR | 96 | 79.337 | 36.435 | 22.107 | 1.00 | 43.77 | X | C |
| ATOM | 6969 | CB | THR | 96 | 79.387 | 36.985 | 23.556 | 1.00 | 38.47 | X | C |
| ATOM | 6970 | OG1 | THR | 96 | 80.723 | 36.865 | 24.069 | 1.00 | 38.47 | X | O |
| ATOM | 6971 | CG2 | THR | 96 | 78.421 | 36.220 | 24.453 | 1.00 | 38.47 | X | C |
| ATOM | 6972 | C | THR | 96 | 80.130 | 37.370 | 21.220 | 1.00 | 43.77 | X | C |
| ATOM | 6973 | O | THR | 96 | 81.328 | 37.174 | 20.987 | 1.00 | 43.77 | X | O |
| ATOM | 6974 | N | ARG | 97 | 79.432 | 38.379 | 20.709 | 1.00 | 52.60 | X | N |
| ATOM | 6975 | CA | ARG | 97 | 80.068 | 39.400 | 19.899 | 1.00 | 52.60 | X | C |
| ATOM | 6976 | CB | ARG | 97 | 79.237 | 39.799 | 18.689 | 1.00 | 26.06 | X | C |
| ATOM | 6977 | CG | ARG | 97 | 80.052 | 40.645 | 17.733 | 1.00 | 26.06 | X | C |
| ATOM | 6978 | CD | ARG | 97 | 79.235 | 41.249 | 16.624 | 1.00 | 26.06 | X | C |
| ATOM | 6979 | NE | ARG | 97 | 78.494 | 42.412 | 17.074 | 1.00 | 26.06 | X | N |
| ATOM | 6980 | CZ | ARG | 97 | 77.853 | 43.231 | 16.255 | 1.00 | 26.06 | X | C |
| ATOM | 6981 | NH1 | ARG | 97 | 77.873 | 43.004 | 14.948 | 1.00 | 26.06 | X | N |
| ATOM | 6982 | NH2 | ARG | 97 | 77.187 | 44.271 | 16.742 | 1.00 | 26.06 | X | N |
| ATOM | 6983 | C | ARG | 97 | 80.142 | 40.590 | 20.820 | 1.00 | 52.60 | X | C |
| ATOM | 6984 | O | ARG | 97 | 79.116 | 41.100 | 21.260 | 1.00 | 52.60 | X | O |
| ATOM | 6985 | N | GLY | 98 | 81.353 | 41.020 | 21.129 | 1.00 | 31.82 | X | N |
| ATOM | 6986 | CA | GLY | 98 | 81.505 | 42.162 | 22.004 | 1.00 | 31.82 | X | C |
| ATOM | 6987 | C | GLY | 98 | 81.635 | 43.450 | 21.225 | 1.00 | 31.82 | X | C |
| ATOM | 6988 | O | GLY | 98 | 81.903 | 43.452 | 20.020 | 1.00 | 31.82 | X | O |
| ATOM | 6989 | N | PHE | 99 | 81.416 | 44.558 | 21.913 | 1.00 | 20.36 | X | N |
| ATOM | 6990 | CA | PHE | 99 | 81.554 | 45.859 | 21.289 | 1.00 | 20.36 | X | C |
| ATOM | 6991 | CB | PHE | 99 | 80.358 | 46.753 | 21.621 | 1.00 | 37.93 | X | C |
| ATOM | 6992 | CG | PHE | 99 | 80.633 | 48.214 | 21.431 | 1.00 | 37.93 | X | C |
| ATOM | 6993 | CD1 | PHE | 99 | 80.968 | 49.015 | 22.517 | 1.00 | 37.93 | X | C |
| ATOM | 6994 | CD2 | PHE | 99 | 80.606 | 48.783 | 20.158 | 1.00 | 37.93 | X | C |
| ATOM | 6995 | CE1 | PHE | 99 | 81.276 | 50.355 | 22.339 | 1.00 | 37.93 | X | C |
| ATOM | 6996 | CE2 | PHE | 99 | 80.913 | 50.127 | 19.967 | 1.00 | 37.93 | X | C |
| ATOM | 6997 | CZ | PHE | 99 | 81.250 | 50.914 | 21.058 | 1.00 | 37.93 | X | C |
| ATOM | 6998 | C | PHE | 99 | 82.836 | 46.468 | 21.835 | 1.00 | 20.36 | X | C |
| ATOM | 6999 | O | PHE | 99 | 83.239 | 46.164 | 22.969 | 1.00 | 20.36 | X | O |
| ATOM | 7000 | N | GLY | 100 | 83.480 | 47.309 | 21.030 | 1.00 | 25.28 | X | N |
| ATOM | 7001 | CA | GLY | 100 | 84.704 | 47.954 | 21.469 | 1.00 | 25.28 | X | C |
| ATOM | 7002 | C | GLY | 100 | 85.850 | 46.983 | 21.672 | 1.00 | 25.28 | X | C |
| ATOM | 7003 | O | GLY | 100 | 86.390 | 46.466 | 20.700 | 1.00 | 25.28 | X | O |
| ATOM | 7004 | N | ASP | 101 | 86.231 | 46.744 | 22.926 | 1.00 | 27.39 | X | N |
| ATOM | 7005 | CA | ASP | 101 | 87.315 | 45.814 | 23.233 | 1.00 | 27.39 | X | C |
| ATOM | 7006 | CB | ASP | 101 | 88.175 | 46.338 | 24.396 | 1.00 | 32.17 | X | C |
| ATOM | 7007 | CG | ASP | 101 | 89.037 | 47.540 | 24.013 | 1.00 | 32.17 | X | C |
| ATOM | 7008 | OD1 | ASP | 101 | 89.287 | 47.744 | 22.812 | 1.00 | 32.17 | X | O |

Fig. 19: A-97

| | | | | | | | | | | |
|---|---|---|---|---|---|---|---|---|---|---|
| ATOM | 7009 | OD2 | ASP | 101 | 89.483 | 48.274 | 24.920 | 1.00 | 32.17 | X | O |
| ATOM | 7010 | C | ASP | 101 | 86.773 | 44.418 | 23.596 | 1.00 | 27.39 | X | C |
| ATOM | 7011 | O | ASP | 101 | 87.549 | 43.518 | 23.929 | 1.00 | 27.39 | X | O |
| ATOM | 7012 | N | GLY | 102 | 85.449 | 44.250 | 23.538 | 1.00 | 18.22 | X | N |
| ATOM | 7013 | CA | GLY | 102 | 84.822 | 42.973 | 23.861 | 1.00 | 18.22 | X | C |
| ATOM | 7014 | C | GLY | 102 | 83.925 | 42.948 | 25.100 | 1.00 | 18.22 | X | C |
| ATOM | 7015 | O | GLY | 102 | 83.031 | 42.113 | 25.198 | 1.00 | 18.22 | X | O |
| ATOM | 7016 | N | GLY | 103 | 84.147 | 43.870 | 26.034 | 1.00 | 34.16 | X | N |
| ATOM | 7017 | CA | GLY | 103 | 83.370 | 43.915 | 27.268 | 1.00 | 34.16 | X | C |
| ATOM | 7018 | C | GLY | 103 | 81.850 | 43.964 | 27.216 | 1.00 | 34.16 | X | C |
| ATOM | 7019 | O | GLY | 103 | 81.182 | 43.416 | 28.087 | 1.00 | 34.16 | X | O |
| ATOM | 7020 | N | TYR | 104 | 81.290 | 44.649 | 26.230 | 1.00 | 25.31 | X | N |
| ATOM | 7021 | CA | TYR | 104 | 79.839 | 44.732 | 26.096 | 1.00 | 25.31 | X | C |
| ATOM | 7022 | CB | TYR | 104 | 79.433 | 46.131 | 25.639 | 1.00 | 26.21 | X | C |
| ATOM | 7023 | CG | TYR | 104 | 77.989 | 46.260 | 25.234 | 1.00 | 26.21 | X | C |
| ATOM | 7024 | CD1 | TYR | 104 | 77.635 | 46.980 | 24.087 | 1.00 | 26.21 | X | C |
| ATOM | 7025 | CE1 | TYR | 104 | 76.309 | 47.079 | 23.677 | 1.00 | 26.21 | X | C |
| ATOM | 7026 | CD2 | TYR | 104 | 76.972 | 45.646 | 25.972 | 1.00 | 26.21 | X | C |
| ATOM | 7027 | CE2 | TYR | 104 | 75.639 | 45.742 | 25.573 | 1.00 | 26.21 | X | C |
| ATOM | 7028 | CZ | TYR | 104 | 75.323 | 46.456 | 24.422 | 1.00 | 26.21 | X | C |
| ATOM | 7029 | OH | TYR | 104 | 74.025 | 46.523 | 23.995 | 1.00 | 26.21 | X | O |
| ATOM | 7030 | C | TYR | 104 | 79.484 | 43.700 | 25.037 | 1.00 | 25.31 | X | C |
| ATOM | 7031 | O | TYR | 104 | 79.905 | 43.810 | 23.886 | 1.00 | 25.31 | X | O |
| ATOM | 7032 | N | PHE | 105 | 78.728 | 42.686 | 25.432 | 1.00 | 17.54 | X | N |
| ATOM | 7033 | CA | PHE | 105 | 78.354 | 41.616 | 24.518 | 1.00 | 17.54 | X | C |
| ATOM | 7034 | CB | PHE | 105 | 78.088 | 40.337 | 25.309 | 1.00 | 20.12 | X | C |
| ATOM | 7035 | CG | PHE | 105 | 79.154 | 40.010 | 26.312 | 1.00 | 20.12 | X | C |
| ATOM | 7036 | CD1 | PHE | 105 | 80.478 | 39.817 | 25.908 | 1.00 | 20.12 | X | C |
| ATOM | 7037 | CD2 | PHE | 105 | 78.832 | 39.891 | 27.661 | 1.00 | 20.12 | X | C |
| ATOM | 7038 | CE1 | PHE | 105 | 81.472 | 39.511 | 26.836 | 1.00 | 20.12 | X | C |
| ATOM | 7039 | CE2 | PHE | 105 | 79.808 | 39.586 | 28.594 | 1.00 | 20.12 | X | C |
| ATOM | 7040 | CZ | PHE | 105 | 81.136 | 39.395 | 28.183 | 1.00 | 20.12 | X | C |
| ATOM | 7041 | C | PHE | 105 | 77.127 | 41.938 | 23.669 | 1.00 | 17.54 | X | C |
| ATOM | 7042 | O | PHE | 105 | 75.989 | 41.689 | 24.080 | 1.00 | 17.54 | X | O |
| ATOM | 7043 | N | ASP | 106 | 77.376 | 42.488 | 22.482 | 1.00 | 46.21 | X | N |
| ATOM | 7044 | CA | ASP | 106 | 76.327 | 42.840 | 21.532 | 1.00 | 46.21 | X | C |
| ATOM | 7045 | CB | ASP | 106 | 76.908 | 43.074 | 20.143 | 1.00 | 54.80 | X | C |
| ATOM | 7046 | CG | ASP | 106 | 77.456 | 44.442 | 19.976 | 1.00 | 54.80 | X | C |
| ATOM | 7047 | OD1 | ASP | 106 | 76.774 | 45.384 | 20.429 | 1.00 | 54.80 | X | O |
| ATOM | 7048 | OD2 | ASP | 106 | 78.552 | 44.576 | 19.387 | 1.00 | 54.80 | X | O |
| ATOM | 7049 | C | ASP | 106 | 75.355 | 41.705 | 21.399 | 1.00 | 46.21 | X | C |
| ATOM | 7050 | O | ASP | 106 | 74.281 | 41.707 | 21.974 | 1.00 | 46.21 | X | O |
| ATOM | 7051 | N | VAL | 107 | 75.769 | 40.732 | 20.603 | 1.00 | 33.04 | X | N |
| ATOM | 7052 | CA | VAL | 107 | 74.979 | 39.559 | 20.312 | 1.00 | 33.04 | X | C |
| ATOM | 7053 | CB | VAL | 107 | 75.180 | 39.152 | 18.858 | 1.00 | 31.62 | X | C |
| ATOM | 7054 | CG1 | VAL | 107 | 74.156 | 38.100 | 18.457 | 1.00 | 31.62 | X | C |
| ATOM | 7055 | CG2 | VAL | 107 | 75.092 | 40.388 | 17.980 | 1.00 | 31.62 | X | C |
| ATOM | 7056 | C | VAL | 107 | 75.322 | 38.379 | 21.197 | 1.00 | 33.04 | X | C |
| ATOM | 7057 | O | VAL | 107 | 76.413 | 38.296 | 21.763 | 1.00 | 33.04 | X | O |
| ATOM | 7058 | N | TRP | 108 | 74.359 | 37.474 | 21.306 | 1.00 | 37.95 | X | N |
| ATOM | 7059 | CA | TRP | 108 | 74.501 | 36.266 | 22.092 | 1.00 | 37.95 | X | C |
| ATOM | 7060 | CB | TRP | 108 | 73.674 | 36.351 | 23.372 | 1.00 | 32.89 | X | C |
| ATOM | 7061 | CG | TRP | 108 | 74.212 | 37.315 | 24.368 | 1.00 | 32.89 | X | C |
| ATOM | 7062 | CD2 | TRP | 108 | 74.712 | 37.004 | 25.668 | 1.00 | 32.89 | X | C |
| ATOM | 7063 | CE2 | TRP | 108 | 75.114 | 38.216 | 26.261 | 1.00 | 32.89 | X | C |
| ATOM | 7064 | CE3 | TRP | 108 | 74.861 | 35.816 | 26.390 | 1.00 | 32.89 | X | C |
| ATOM | 7065 | CD1 | TRP | 108 | 74.327 | 38.664 | 24.225 | 1.00 | 32.89 | X | C |
| ATOM | 7066 | NE1 | TRP | 108 | 74.867 | 39.216 | 25.358 | 1.00 | 32.89 | X | N |
| ATOM | 7067 | CZ2 | TRP | 108 | 75.655 | 38.278 | 27.543 | 1.00 | 32.89 | X | C |
| ATOM | 7068 | CZ3 | TRP | 108 | 75.402 | 35.878 | 27.670 | 1.00 | 32.89 | X | C |
| ATOM | 7069 | CH2 | TRP | 108 | 75.792 | 37.103 | 28.231 | 1.00 | 32.89 | X | C |
| ATOM | 7070 | C | TRP | 108 | 73.984 | 35.119 | 21.260 | 1.00 | 37.95 | X | C |
| ATOM | 7071 | O | TRP | 108 | 73.067 | 35.296 | 20.451 | 1.00 | 37.95 | X | O |
| ATOM | 7072 | N | GLY | 109 | 74.568 | 33.942 | 21.460 | 1.00 | 75.91 | X | N |
| ATOM | 7073 | CA | GLY | 109 | 74.124 | 32.770 | 20.732 | 1.00 | 75.91 | X | C |
| ATOM | 7074 | C | GLY | 109 | 72.791 | 32.307 | 21.288 | 1.00 | 75.91 | X | C |
| ATOM | 7075 | O | GLY | 109 | 71.997 | 33.114 | 21.780 | 1.00 | 75.91 | X | O |
| ATOM | 7076 | N | GLN | 110 | 72.537 | 31.007 | 21.207 | 1.00 | 35.37 | X | N |
| ATOM | 7077 | CA | GLN | 110 | 71.291 | 30.457 | 21.724 | 1.00 | 35.37 | X | C |
| ATOM | 7078 | CB | GLN | 110 | 70.652 | 29.498 | 20.714 | 1.00 | 98.79 | X | C |
| ATOM | 7079 | CG | GLN | 110 | 71.443 | 28.228 | 20.442 | 1.00 | 98.79 | X | C |
| ATOM | 7080 | CD | GLN | 110 | 72.597 | 28.441 | 19.485 | 1.00 | 98.79 | X | C |
| ATOM | 7081 | OE1 | GLN | 110 | 73.318 | 27.502 | 19.152 | 1.00 | 98.79 | X | O |

Fig. 19: A-98

| | | | | | | | | | | | |
|---|---|---|---|---|---|---|---|---|---|---|---|
| ATOM | 7082 | NE2 | GLN | 110 | 72.775 | 29.675 | 19.031 | 1.00 | 98.79 | X | N |
| ATOM | 7083 | C | GLN | 110 | 71.610 | 29.708 | 23.004 | 1.00 | 35.37 | X | C |
| ATOM | 7084 | O | GLN | 110 | 70.793 | 29.626 | 23.918 | 1.00 | 35.37 | X | O |
| ATOM | 7085 | N | GLY | 111 | 72.831 | 29.194 | 23.067 | 1.00 | 45.85 | X | N |
| ATOM | 7086 | CA | GLY | 111 | 73.257 | 28.430 | 24.219 | 1.00 | 45.85 | X | C |
| ATOM | 7087 | C | GLY | 111 | 73.349 | 26.981 | 23.781 | 1.00 | 45.85 | X | C |
| ATOM | 7088 | O | GLY | 111 | 72.596 | 26.540 | 22.913 | 1.00 | 45.85 | X | O |
| ATOM | 7089 | N | THR | 112 | 74.281 | 26.243 | 24.369 | 1.00 | 30.06 | X | N |
| ATOM | 7090 | CA | THR | 112 | 74.480 | 24.840 | 24.040 | 1.00 | 30.06 | X | C |
| ATOM | 7091 | CB | THR | 112 | 75.550 | 24.696 | 22.962 | 1.00 | 24.67 | X | C |
| ATOM | 7092 | OG1 | THR | 112 | 75.636 | 23.327 | 22.562 | 1.00 | 24.67 | X | O |
| ATOM | 7093 | CG2 | THR | 112 | 76.903 | 25.177 | 23.487 | 1.00 | 24.67 | X | C |
| ATOM | 7094 | C | THR | 112 | 74.944 | 24.184 | 25.328 | 1.00 | 30.06 | X | C |
| ATOM | 7095 | O | THR | 112 | 75.883 | 24.658 | 25.960 | 1.00 | 30.06 | X | O |
| ATOM | 7096 | N | LEU | 113 | 74.292 | 23.102 | 25.725 | 1.00 | 42.99 | X | N |
| ATOM | 7097 | CA | LEU | 113 | 74.646 | 22.449 | 26.981 | 1.00 | 42.99 | X | C |
| ATOM | 7098 | CB | LEU | 113 | 73.434 | 21.652 | 27.499 | 1.00 | 32.90 | X | C |
| ATOM | 7099 | CG | LEU | 113 | 73.366 | 21.006 | 28.896 | 1.00 | 32.90 | X | C |
| ATOM | 7100 | CD1 | LEU | 113 | 73.914 | 19.580 | 28.860 | 1.00 | 32.90 | X | C |
| ATOM | 7101 | CD2 | LEU | 113 | 74.109 | 21.884 | 29.889 | 1.00 | 32.90 | X | C |
| ATOM | 7102 | C | LEU | 113 | 75.890 | 21.560 | 26.932 | 1.00 | 42.99 | X | C |
| ATOM | 7103 | O | LEU | 113 | 76.190 | 20.899 | 25.929 | 1.00 | 42.99 | X | O |
| ATOM | 7104 | N | VAL | 114 | 76.621 | 21.561 | 28.037 | 1.00 | 35.21 | X | N |
| ATOM | 7105 | CA | VAL | 114 | 77.815 | 20.754 | 28.141 | 1.00 | 35.21 | X | C |
| ATOM | 7106 | CB | VAL | 114 | 79.070 | 21.592 | 27.837 | 1.00 | 43.74 | X | C |
| ATOM | 7107 | CG1 | VAL | 114 | 80.324 | 20.909 | 28.384 | 1.00 | 43.74 | X | C |
| ATOM | 7108 | CG2 | VAL | 114 | 79.189 | 21.774 | 26.331 | 1.00 | 43.74 | X | C |
| ATOM | 7109 | C | VAL | 114 | 77.906 | 20.141 | 29.529 | 1.00 | 35.21 | X | C |
| ATOM | 7110 | O | VAL | 114 | 78.064 | 20.845 | 30.529 | 1.00 | 35.21 | X | O |
| ATOM | 7111 | N | THR | 115 | 77.788 | 18.819 | 29.575 | 1.00 | 58.81 | X | N |
| ATOM | 7112 | CA | THR | 115 | 77.855 | 18.099 | 30.829 | 1.00 | 58.81 | X | C |
| ATOM | 7113 | CB | THR | 115 | 76.717 | 17.098 | 30.956 | 1.00 | 63.66 | X | C |
| ATOM | 7114 | OG1 | THR | 115 | 75.549 | 17.620 | 30.311 | 1.00 | 63.66 | X | O |
| ATOM | 7115 | CG2 | THR | 115 | 76.412 | 16.849 | 32.422 | 1.00 | 63.66 | X | C |
| ATOM | 7116 | C | THR | 115 | 79.161 | 17.337 | 30.903 | 1.00 | 58.81 | X | C |
| ATOM | 7117 | O | THR | 115 | 79.831 | 17.121 | 29.893 | 1.00 | 58.81 | X | O |
| ATOM | 7118 | N | VAL | 116 | 79.516 | 16.933 | 32.114 | 1.00 | 73.79 | X | N |
| ATOM | 7119 | CA | VAL | 116 | 80.741 | 16.191 | 32.352 | 1.00 | 73.79 | X | C |
| ATOM | 7120 | CB | VAL | 116 | 81.899 | 17.135 | 32.747 | 1.00 | 46.90 | X | C |
| ATOM | 7121 | CG1 | VAL | 116 | 83.172 | 16.339 | 32.941 | 1.00 | 46.90 | X | C |
| ATOM | 7122 | CG2 | VAL | 116 | 82.101 | 18.194 | 31.667 | 1.00 | 46.90 | X | C |
| ATOM | 7123 | C | VAL | 116 | 80.478 | 15.202 | 33.482 | 1.00 | 73.79 | X | C |
| ATOM | 7124 | O | VAL | 116 | 80.382 | 15.584 | 34.649 | 1.00 | 73.79 | X | O |
| ATOM | 7125 | N | SER | 117 | 80.349 | 13.931 | 33.114 | 1.00 | 65.98 | X | N |
| ATOM | 7126 | CA | SER | 117 | 80.088 | 12.858 | 34.066 | 1.00 | 65.98 | X | C |
| ATOM | 7127 | CB | SER | 117 | 78.608 | 12.861 | 34.458 | 1.00 | 62.16 | X | C |
| ATOM | 7128 | OG | SER | 117 | 77.776 | 12.825 | 33.308 | 1.00 | 62.16 | X | O |
| ATOM | 7129 | C | SER | 117 | 80.454 | 11.521 | 33.427 | 1.00 | 65.98 | X | C |
| ATOM | 7130 | O | SER | 117 | 81.498 | 11.396 | 32.789 | 1.00 | 65.98 | X | O |
| ATOM | 7131 | N | SER | 118 | 79.587 | 10.524 | 33.594 | 1.00 | 80.64 | X | N |
| ATOM | 7132 | CA | SER | 118 | 79.828 | 9.208 | 33.014 | 1.00 | 80.64 | X | C |
| ATOM | 7133 | CB | SER | 118 | 80.556 | 8.329 | 34.031 | 1.00 | 66.12 | X | C |
| ATOM | 7134 | OG | SER | 118 | 81.771 | 8.944 | 34.438 | 1.00 | 66.12 | X | O |
| ATOM | 7135 | C | SER | 118 | 78.524 | 8.543 | 32.563 | 1.00 | 80.64 | X | C |
| ATOM | 7136 | O | SER | 118 | 77.445 | 9.021 | 32.973 | 1.00 | 79.69 | X | O |
| ATOM | 7137 | OXT | SER | 118 | 78.594 | 7.553 | 31.804 | 1.00 | 65.17 | X | O |
| ATOM | 7138 | CB | ILE | 2 | 85.629 | 44.767 | 39.417 | 1.00 | 24.34 | Y | C |
| ATOM | 7139 | CG2 | ILE | 2 | 84.329 | 45.456 | 39.830 | 1.00 | 24.34 | Y | C |
| ATOM | 7140 | CG1 | ILE | 2 | 86.754 | 45.793 | 39.275 | 1.00 | 24.34 | Y | C |
| ATOM | 7141 | CD1 | ILE | 2 | 86.473 | 46.861 | 38.237 | 1.00 | 24.34 | Y | C |
| ATOM | 7142 | C | ILE | 2 | 84.812 | 42.776 | 40.634 | 1.00 | 29.24 | Y | C |
| ATOM | 7143 | O | ILE | 2 | 84.508 | 41.962 | 39.756 | 1.00 | 29.24 | Y | O |
| ATOM | 7144 | N | ILE | 2 | 87.254 | 42.972 | 40.068 | 1.00 | 29.24 | Y | N |
| ATOM | 7145 | CA | ILE | 2 | 86.011 | 43.705 | 40.462 | 1.00 | 29.24 | Y | C |
| ATOM | 7146 | N | GLN | 3 | 84.122 | 42.926 | 41.761 | 1.00 | 42.94 | Y | N |
| ATOM | 7147 | CA | GLN | 3 | 82.960 | 42.107 | 42.070 | 1.00 | 42.94 | Y | C |
| ATOM | 7148 | CB | GLN | 3 | 83.156 | 41.435 | 43.434 | 1.00 | 85.86 | Y | C |
| ATOM | 7149 | CG | GLN | 3 | 82.045 | 40.492 | 43.850 | 1.00 | 85.86 | Y | C |
| ATOM | 7150 | CD | GLN | 3 | 82.371 | 39.747 | 45.131 | 1.00 | 85.86 | Y | C |
| ATOM | 7151 | OE1 | GLN | 3 | 81.534 | 39.028 | 45.670 | 1.00 | 85.86 | Y | O |
| ATOM | 7152 | NE2 | GLN | 3 | 83.597 | 39.911 | 45.621 | 1.00 | 85.86 | Y | N |
| ATOM | 7153 | C | GLN | 3 | 81.684 | 42.943 | 42.059 | 1.00 | 42.94 | Y | C |
| ATOM | 7154 | O | GLN | 3 | 81.626 | 44.026 | 42.645 | 1.00 | 42.94 | Y | O |

Fig. 19: A-99

| | | | | | | | | | | | |
|---|---|---|---|---|---|---|---|---|---|---|---|
| ATOM | 7155 | N | LEU | 4 | 80.666 | 42.426 | 41.380 | 1.00 | 33.35 | Y | N |
| ATOM | 7156 | CA | LEU | 4 | 79.378 | 43.098 | 41.269 | 1.00 | 33.35 | Y | C |
| ATOM | 7157 | CB | LEU | 4 | 78.954 | 43.160 | 39.800 | 1.00 | 47.12 | Y | C |
| ATOM | 7158 | CG | LEU | 4 | 79.344 | 44.389 | 38.979 | 1.00 | 47.12 | Y | C |
| ATOM | 7159 | CD1 | LEU | 4 | 80.683 | 44.945 | 39.443 | 1.00 | 47.12 | Y | C |
| ATOM | 7160 | CD2 | LEU | 4 | 79.370 | 44.008 | 37.512 | 1.00 | 47.12 | Y | C |
| ATOM | 7161 | C | LEU | 4 | 78.296 | 42.395 | 42.073 | 1.00 | 33.35 | Y | C |
| ATOM | 7162 | O | LEU | 4 | 78.012 | 41.215 | 41.852 | 1.00 | 33.35 | Y | O |
| ATOM | 7163 | N | THR | 5 | 77.691 | 43.129 | 43.001 | 1.00 | 42.53 | Y | N |
| ATOM | 7164 | CA | THR | 5 | 76.628 | 42.586 | 43.833 | 1.00 | 42.53 | Y | C |
| ATOM | 7165 | CB | THR | 5 | 77.100 | 42.482 | 45.315 | 1.00 | 37.95 | Y | C |
| ATOM | 7166 | OG1 | THR | 5 | 75.992 | 42.697 | 46.196 | 1.00 | 37.95 | Y | O |
| ATOM | 7167 | CG2 | THR | 5 | 78.209 | 43.479 | 45.604 | 1.00 | 37.95 | Y | C |
| ATOM | 7168 | C | THR | 5 | 75.348 | 43.426 | 43.699 | 1.00 | 42.53 | Y | C |
| ATOM | 7169 | O | THR | 5 | 75.306 | 44.593 | 44.089 | 1.00 | 42.53 | Y | O |
| ATOM | 7170 | N | GLN | 6 | 74.318 | 42.806 | 43.119 | 1.00 | 44.79 | Y | N |
| ATOM | 7171 | CA | GLN | 6 | 73.009 | 43.423 | 42.877 | 1.00 | 44.79 | Y | C |
| ATOM | 7172 | CB | GLN | 6 | 72.340 | 42.791 | 41.641 | 1.00 | 23.30 | Y | C |
| ATOM | 7173 | CG | GLN | 6 | 73.239 | 42.643 | 40.421 | 1.00 | 23.30 | Y | C |
| ATOM | 7174 | CD | GLN | 6 | 72.520 | 42.055 | 39.195 | 1.00 | 23.30 | Y | C |
| ATOM | 7175 | OE1 | GLN | 6 | 73.163 | 41.628 | 38.231 | 1.00 | 23.30 | Y | O |
| ATOM | 7176 | NE2 | GLN | 6 | 71.193 | 42.046 | 39.226 | 1.00 | 23.30 | Y | N |
| ATOM | 7177 | C | GLN | 6 | 72.050 | 43.274 | 44.061 | 1.00 | 44.79 | Y | C |
| ATOM | 7178 | O | GLN | 6 | 72.195 | 42.370 | 44.883 | 1.00 | 44.79 | Y | O |
| ATOM | 7179 | N | SER | 7 | 71.057 | 44.156 | 44.128 | 1.00 | 78.31 | Y | N |
| ATOM | 7180 | CA | SER | 7 | 70.069 | 44.113 | 45.201 | 1.00 | 78.31 | Y | C |
| ATOM | 7181 | CB | SER | 7 | 70.640 | 44.715 | 46.480 | 1.00 | 85.46 | Y | C |
| ATOM | 7182 | OG | SER | 7 | 71.028 | 46.058 | 46.262 | 1.00 | 85.46 | Y | O |
| ATOM | 7183 | C | SER | 7 | 68.797 | 44.855 | 44.824 | 1.00 | 78.31 | Y | C |
| ATOM | 7184 | O | SER | 7 | 68.847 | 45.923 | 44.220 | 1.00 | 78.31 | Y | O |
| ATOM | 7185 | N | PRO | 8 | 67.633 | 44.283 | 45.165 | 1.00 | 83.70 | Y | N |
| ATOM | 7186 | CD | PRO | 8 | 66.277 | 44.777 | 44.863 | 1.00 | 54.81 | Y | C |
| ATOM | 7187 | CA | PRO | 8 | 67.571 | 43.000 | 45.865 | 1.00 | 83.70 | Y | C |
| ATOM | 7188 | CB | PRO | 8 | 66.097 | 42.880 | 46.226 | 1.00 | 54.81 | Y | C |
| ATOM | 7189 | CG | PRO | 8 | 65.427 | 43.534 | 45.054 | 1.00 | 54.81 | Y | C |
| ATOM | 7190 | C | PRO | 8 | 68.015 | 41.895 | 44.925 | 1.00 | 83.70 | Y | C |
| ATOM | 7191 | O | PRO | 8 | 68.274 | 42.136 | 43.745 | 1.00 | 83.70 | Y | O |
| ATOM | 7192 | N | SER | 9 | 68.111 | 40.685 | 45.455 | 1.00 | 47.38 | Y | N |
| ATOM | 7193 | CA | SER | 9 | 68.504 | 39.541 | 44.651 | 1.00 | 47.38 | Y | C |
| ATOM | 7194 | CB | SER | 9 | 69.145 | 38.481 | 45.543 | 1.00 | 74.91 | Y | C |
| ATOM | 7195 | OG | SER | 9 | 70.214 | 39.045 | 46.283 | 1.00 | 74.91 | Y | O |
| ATOM | 7196 | C | SER | 9 | 67.232 | 39.002 | 44.025 | 1.00 | 47.38 | Y | C |
| ATOM | 7197 | O | SER | 9 | 67.237 | 38.434 | 42.936 | 1.00 | 47.38 | Y | O |
| ATOM | 7198 | N | SER | 10 | 66.134 | 39.214 | 44.736 | 1.00 | 60.45 | Y | N |
| ATOM | 7199 | CA | SER | 10 | 64.819 | 38.770 | 44.305 | 1.00 | 60.45 | Y | C |
| ATOM | 7200 | CB | SER | 10 | 64.476 | 37.449 | 44.991 | 1.00 | 51.82 | Y | C |
| ATOM | 7201 | OG | SER | 10 | 63.252 | 36.935 | 44.504 | 1.00 | 51.82 | Y | O |
| ATOM | 7202 | C | SER | 10 | 63.797 | 39.840 | 44.691 | 1.00 | 60.45 | Y | C |
| ATOM | 7203 | O | SER | 10 | 63.976 | 40.552 | 45.683 | 1.00 | 60.45 | Y | O |
| ATOM | 7204 | N | LEU | 11 | 62.730 | 39.964 | 43.910 | 1.00 | 65.48 | Y | N |
| ATOM | 7205 | CA | LEU | 11 | 61.710 | 40.964 | 44.206 | 1.00 | 65.48 | Y | C |
| ATOM | 7206 | CB | LEU | 11 | 62.206 | 42.366 | 43.830 | 1.00 | 51.28 | Y | C |
| ATOM | 7207 | CG | LEU | 11 | 62.310 | 42.727 | 42.342 | 1.00 | 51.28 | Y | C |
| ATOM | 7208 | CD1 | LEU | 11 | 60.949 | 43.139 | 41.803 | 1.00 | 51.28 | Y | C |
| ATOM | 7209 | CD2 | LEU | 11 | 63.294 | 43.877 | 42.168 | 1.00 | 51.28 | Y | C |
| ATOM | 7210 | C | LEU | 11 | 60.413 | 40.680 | 43.473 | 1.00 | 65.48 | Y | C |
| ATOM | 7211 | O | LEU | 11 | 60.412 | 40.363 | 42.282 | 1.00 | 65.48 | Y | O |
| ATOM | 7212 | N | SER | 12 | 59.305 | 40.803 | 44.189 | 1.00 | 84.56 | Y | N |
| ATOM | 7213 | CA | SER | 12 | 58.004 | 40.567 | 43.595 | 1.00 | 84.56 | Y | C |
| ATOM | 7214 | CB | SER | 12 | 57.209 | 39.578 | 44.445 | 1.00 | 71.89 | Y | C |
| ATOM | 7215 | OG | SER | 12 | 56.137 | 39.026 | 43.705 | 1.00 | 71.89 | Y | O |
| ATOM | 7216 | C | SER | 12 | 57.273 | 41.902 | 43.507 | 1.00 | 84.56 | Y | C |
| ATOM | 7217 | O | SER | 12 | 57.232 | 42.666 | 44.471 | 1.00 | 84.56 | Y | O |
| ATOM | 7218 | N | ALA | 13 | 56.713 | 42.192 | 42.341 | 1.00 | 109.71 | Y | N |
| ATOM | 7219 | CA | ALA | 13 | 55.997 | 43.442 | 42.152 | 1.00 | 109.71 | Y | C |
| ATOM | 7220 | CB | ALA | 13 | 56.947 | 44.509 | 41.632 | 1.00 | 88.46 | Y | C |
| ATOM | 7221 | C | ALA | 13 | 54.838 | 43.244 | 41.186 | 1.00 | 109.71 | Y | C |
| ATOM | 7222 | O | ALA | 13 | 54.869 | 42.347 | 40.341 | 1.00 | 109.71 | Y | O |
| ATOM | 7223 | N | SER | 14 | 53.816 | 44.084 | 41.315 | 1.00 | 66.55 | Y | N |
| ATOM | 7224 | CA | SER | 14 | 52.632 | 44.000 | 40.461 | 1.00 | 66.55 | Y | C |
| ATOM | 7225 | CB | SER | 14 | 51.370 | 44.265 | 41.290 | 1.00 | 62.23 | Y | C |
| ATOM | 7226 | OG | SER | 14 | 51.506 | 45.449 | 42.059 | 1.00 | 62.23 | Y | O |
| ATOM | 7227 | C | SER | 14 | 52.699 | 44.984 | 39.299 | 1.00 | 66.55 | Y | C |

Fig. 19: A-100

| | | | | | | | | | | | |
|---|---|---|---|---|---|---|---|---|---|---|---|
| ATOM | 7228 | O | SER | 14 | 53.362 | 46.015 | 39.394 | 1.00 | 66.55 | Y | O |
| ATOM | 7229 | N | VAL | 15 | 52.018 | 44.660 | 38.202 | 1.00 | 56.27 | Y | N |
| ATOM | 7230 | CA | VAL | 15 | 52.017 | 45.540 | 37.037 | 1.00 | 56.27 | Y | C |
| ATOM | 7231 | CB | VAL | 15 | 50.922 | 45.156 | 36.016 | 1.00 | 42.35 | Y | C |
| ATOM | 7232 | CG1 | VAL | 15 | 51.449 | 44.089 | 35.066 | 1.00 | 42.35 | Y | C |
| ATOM | 7233 | CG2 | VAL | 15 | 49.679 | 44.644 | 36.750 | 1.00 | 42.35 | Y | C |
| ATOM | 7234 | C | VAL | 15 | 51.773 | 46.964 | 37.492 | 1.00 | 56.27 | Y | C |
| ATOM | 7235 | O | VAL | 15 | 50.948 | 47.208 | 38.369 | 1.00 | 56.27 | Y | O |
| ATOM | 7236 | N | GLY | 16 | 52.509 | 47.903 | 36.911 | 1.00 | 54.44 | Y | N |
| ATOM | 7237 | CA | GLY | 16 | 52.343 | 49.296 | 37.280 | 1.00 | 54.44 | Y | C |
| ATOM | 7238 | C | GLY | 16 | 53.284 | 49.795 | 38.359 | 1.00 | 54.44 | Y | C |
| ATOM | 7239 | O | GLY | 16 | 53.419 | 51.000 | 38.542 | 1.00 | 54.44 | Y | O |
| ATOM | 7240 | N | ASP | 17 | 53.931 | 48.885 | 39.082 | 1.00 | 75.77 | Y | N |
| ATOM | 7241 | CA | ASP | 17 | 54.863 | 49.283 | 40.134 | 1.00 | 75.77 | Y | C |
| ATOM | 7242 | CB | ASP | 17 | 55.212 | 48.091 | 41.034 | 1.00 | 114.73 | Y | C |
| ATOM | 7243 | CG | ASP | 17 | 54.035 | 47.608 | 41.849 | 1.00 | 114.73 | Y | C |
| ATOM | 7244 | OD1 | ASP | 17 | 54.208 | 46.639 | 42.623 | 1.00 | 114.73 | Y | O |
| ATOM | 7245 | OD2 | ASP | 17 | 52.942 | 48.198 | 41.716 | 1.00 | 114.73 | Y | O |
| ATOM | 7246 | C | ASP | 17 | 56.149 | 49.824 | 39.525 | 1.00 | 75.77 | Y | C |
| ATOM | 7247 | O | ASP | 17 | 56.476 | 49.533 | 38.373 | 1.00 | 75.77 | Y | O |
| ATOM | 7248 | N | ARG | 18 | 56.873 | 50.616 | 40.304 | 1.00 | 69.15 | Y | N |
| ATOM | 7249 | CA | ARG | 18 | 58.139 | 51.161 | 39.844 | 1.00 | 69.15 | Y | C |
| ATOM | 7250 | CB | ARG | 18 | 58.263 | 52.634 | 40.225 | 1.00 | 52.23 | Y | C |
| ATOM | 7251 | CG | ARG | 18 | 59.557 | 53.291 | 39.779 | 1.00 | 52.23 | Y | C |
| ATOM | 7252 | CD | ARG | 18 | 59.365 | 54.788 | 39.625 | 1.00 | 52.23 | Y | C |
| ATOM | 7253 | NE | ARG | 18 | 60.622 | 55.478 | 39.370 | 1.00 | 52.23 | Y | N |
| ATOM | 7254 | CZ | ARG | 18 | 61.621 | 55.550 | 40.246 | 1.00 | 52.23 | Y | C |
| ATOM | 7255 | NH1 | ARG | 18 | 61.506 | 54.968 | 41.436 | 1.00 | 52.23 | Y | N |
| ATOM | 7256 | NH2 | ARG | 18 | 62.733 | 56.209 | 39.933 | 1.00 | 52.23 | Y | N |
| ATOM | 7257 | C | ARG | 18 | 59.232 | 50.346 | 40.514 | 1.00 | 69.15 | Y | C |
| ATOM | 7258 | O | ARG | 18 | 59.318 | 50.293 | 41.744 | 1.00 | 69.15 | Y | O |
| ATOM | 7259 | N | VAL | 19 | 60.064 | 49.706 | 39.701 | 1.00 | 58.62 | Y | N |
| ATOM | 7260 | CA | VAL | 19 | 61.132 | 48.871 | 40.221 | 1.00 | 58.62 | Y | C |
| ATOM | 7261 | CB | VAL | 19 | 61.068 | 47.477 | 39.567 | 1.00 | 74.00 | Y | C |
| ATOM | 7262 | CG1 | VAL | 19 | 62.050 | 46.531 | 40.235 | 1.00 | 74.00 | Y | C |
| ATOM | 7263 | CG2 | VAL | 19 | 59.651 | 46.938 | 39.664 | 1.00 | 74.00 | Y | C |
| ATOM | 7264 | C | VAL | 19 | 62.518 | 49.477 | 40.003 | 1.00 | 58.62 | Y | C |
| ATOM | 7265 | O | VAL | 19 | 62.782 | 50.096 | 38.975 | 1.00 | 58.62 | Y | O |
| ATOM | 7266 | N | THR | 20 | 63.399 | 49.297 | 40.978 | 1.00 | 54.75 | Y | N |
| ATOM | 7267 | CA | THR | 20 | 64.753 | 49.815 | 40.878 | 1.00 | 54.75 | Y | C |
| ATOM | 7268 | CB | THR | 20 | 64.883 | 51.148 | 41.639 | 1.00 | 56.43 | Y | C |
| ATOM | 7269 | OG1 | THR | 20 | 64.132 | 52.154 | 40.955 | 1.00 | 56.43 | Y | O |
| ATOM | 7270 | CG2 | THR | 20 | 66.337 | 51.586 | 41.726 | 1.00 | 56.43 | Y | C |
| ATOM | 7271 | C | THR | 20 | 65.806 | 48.834 | 41.401 | 1.00 | 54.75 | Y | C |
| ATOM | 7272 | O | THR | 20 | 65.963 | 48.663 | 42.611 | 1.00 | 54.75 | Y | O |
| ATOM | 7273 | N | ILE | 21 | 66.526 | 48.194 | 40.484 | 1.00 | 38.23 | Y | N |
| ATOM | 7274 | CA | ILE | 21 | 67.572 | 47.250 | 40.855 | 1.00 | 38.23 | Y | C |
| ATOM | 7275 | CB | ILE | 21 | 67.775 | 46.182 | 39.765 | 1.00 | 34.57 | Y | C |
| ATOM | 7276 | CG2 | ILE | 21 | 68.753 | 45.112 | 40.252 | 1.00 | 34.57 | Y | C |
| ATOM | 7277 | CG1 | ILE | 21 | 66.427 | 45.547 | 39.426 | 1.00 | 34.57 | Y | C |
| ATOM | 7278 | CD1 | ILE | 21 | 66.496 | 44.426 | 38.415 | 1.00 | 34.57 | Y | C |
| ATOM | 7279 | C | ILE | 21 | 68.877 | 48.006 | 41.047 | 1.00 | 38.23 | Y | C |
| ATOM | 7280 | O | ILE | 21 | 69.215 | 48.885 | 40.256 | 1.00 | 38.23 | Y | O |
| ATOM | 7281 | N | THR | 22 | 69.610 | 47.660 | 42.100 | 1.00 | 41.70 | Y | N |
| ATOM | 7282 | CA | THR | 22 | 70.880 | 48.312 | 42.396 | 1.00 | 41.70 | Y | C |
| ATOM | 7283 | CB | THR | 22 | 70.919 | 48.826 | 43.856 | 1.00 | 62.77 | Y | C |
| ATOM | 7284 | OG1 | THR | 22 | 69.986 | 49.903 | 44.017 | 1.00 | 62.77 | Y | O |
| ATOM | 7285 | CG2 | THR | 22 | 72.322 | 49.303 | 44.222 | 1.00 | 62.77 | Y | C |
| ATOM | 7286 | C | THR | 22 | 72.052 | 47.370 | 42.199 | 1.00 | 41.70 | Y | C |
| ATOM | 7287 | O | THR | 22 | 72.028 | 46.237 | 42.674 | 1.00 | 41.70 | Y | O |
| ATOM | 7288 | N | CYS | 23 | 73.077 | 47.852 | 41.500 | 1.00 | 52.46 | Y | N |
| ATOM | 7289 | CA | CYS | 23 | 74.289 | 47.076 | 41.247 | 1.00 | 52.46 | Y | C |
| ATOM | 7290 | C | CYS | 23 | 75.446 | 47.833 | 41.875 | 1.00 | 52.46 | Y | C |
| ATOM | 7291 | O | CYS | 23 | 75.749 | 48.957 | 41.476 | 1.00 | 52.46 | Y | O |
| ATOM | 7292 | CB | CYS | 23 | 74.522 | 46.938 | 39.744 | 1.00 | 61.15 | Y | C |
| ATOM | 7293 | SG | CYS | 23 | 75.983 | 45.982 | 39.184 | 1.00 | 61.15 | Y | S |
| ATOM | 7294 | N | SER | 24 | 76.079 | 47.219 | 42.866 | 1.00 | 43.95 | Y | N |
| ATOM | 7295 | CA | SER | 24 | 77.200 | 47.837 | 43.556 | 1.00 | 43.95 | Y | C |
| ATOM | 7296 | CB | SER | 24 | 76.992 | 47.751 | 45.072 | 1.00 | 58.07 | Y | C |
| ATOM | 7297 | OG | SER | 24 | 75.782 | 48.379 | 45.462 | 1.00 | 58.07 | Y | O |
| ATOM | 7298 | C | SER | 24 | 78.495 | 47.138 | 43.177 | 1.00 | 43.95 | Y | C |
| ATOM | 7299 | O | SER | 24 | 78.582 | 45.912 | 43.222 | 1.00 | 43.95 | Y | O |
| ATOM | 7300 | N | ALA | 25 | 79.503 | 47.924 | 42.814 | 1.00 | 35.63 | Y | N |

Fig. 19: A-101

| | | | | | | | | | | | |
|---|---|---|---|---|---|---|---|---|---|---|---|
| ATOM | 7301 | CA | ALA | 25 | 80.796 | 47.373 | 42.427 | 1.00 | 35.63 | Y | C |
| ATOM | 7302 | CB | ALA | 25 | 81.214 | 47.920 | 41.068 | 1.00 | 50.18 | Y | C |
| ATOM | 7303 | C | ALA | 25 | 81.894 | 47.635 | 43.454 | 1.00 | 35.63 | Y | C |
| ATOM | 7304 | O | ALA | 25 | 82.050 | 48.754 | 43.959 | 1.00 | 35.63 | Y | O |
| ATOM | 7305 | N | SER | 26 | 82.650 | 46.579 | 43.742 | 1.00 | 37.44 | Y | N |
| ATOM | 7306 | CA | SER | 26 | 83.746 | 46.616 | 44.697 | 1.00 | 37.44 | Y | C |
| ATOM | 7307 | CB | SER | 26 | 84.492 | 45.280 | 44.672 | 1.00 | 31.41 | Y | C |
| ATOM | 7308 | OG | SER | 26 | 85.018 | 45.005 | 43.381 | 1.00 | 31.41 | Y | O |
| ATOM | 7309 | C | SER | 26 | 84.718 | 47.745 | 44.393 | 1.00 | 37.44 | Y | C |
| ATOM | 7310 | O | SER | 26 | 85.358 | 48.286 | 45.297 | 1.00 | 37.44 | Y | O |
| ATOM | 7311 | N | SER | 27 | 84.835 | 48.088 | 43.116 | 1.00 | 70.39 | Y | N |
| ATOM | 7312 | CA | SER | 27 | 85.726 | 49.157 | 42.687 | 1.00 | 70.39 | Y | C |
| ATOM | 7313 | CB | SER | 27 | 86.941 | 48.581 | 41.954 | 1.00 | 53.81 | Y | C |
| ATOM | 7314 | OG | SER | 27 | 87.574 | 47.567 | 42.716 | 1.00 | 53.81 | Y | O |
| ATOM | 7315 | C | SER | 27 | 84.922 | 50.023 | 41.736 | 1.00 | 70.39 | Y | C |
| ATOM | 7316 | O | SER | 27 | 83.960 | 49.545 | 41.139 | 1.00 | 70.39 | Y | O |
| ATOM | 7317 | N | SER | 28 | 85.306 | 51.290 | 41.595 | 1.00 | 30.73 | Y | N |
| ATOM | 7318 | CA | SER | 28 | 84.598 | 52.194 | 40.695 | 1.00 | 30.73 | Y | C |
| ATOM | 7319 | CB | SER | 28 | 85.060 | 53.628 | 40.920 | 1.00 | 55.81 | Y | C |
| ATOM | 7320 | OG | SER | 28 | 86.448 | 53.723 | 40.688 | 1.00 | 55.81 | Y | O |
| ATOM | 7321 | C | SER | 28 | 84.824 | 51.813 | 39.230 | 1.00 | 30.73 | Y | C |
| ATOM | 7322 | O | SER | 28 | 85.873 | 51.287 | 38.863 | 1.00 | 30.73 | Y | O |
| ATOM | 7323 | N | VAL | 29 | 83.832 | 52.092 | 38.398 | 1.00 | 34.83 | Y | N |
| ATOM | 7324 | CA | VAL | 29 | 83.909 | 51.780 | 36.983 | 1.00 | 34.83 | Y | C |
| ATOM | 7325 | CB | VAL | 29 | 83.173 | 50.443 | 36.682 | 1.00 | 24.96 | Y | C |
| ATOM | 7326 | CG1 | VAL | 29 | 83.891 | 49.286 | 37.382 | 1.00 | 24.96 | Y | C |
| ATOM | 7327 | CG2 | VAL | 29 | 81.717 | 50.518 | 37.153 | 1.00 | 24.96 | Y | C |
| ATOM | 7328 | C | VAL | 29 | 83.267 | 52.929 | 36.208 | 1.00 | 34.83 | Y | C |
| ATOM | 7329 | O | VAL | 29 | 82.397 | 53.621 | 36.738 | 1.00 | 34.83 | Y | O |
| ATOM | 7330 | N | ASN | 30 | 83.689 | 53.134 | 34.963 | 1.00 | 19.83 | Y | N |
| ATOM | 7331 | CA | ASN | 30 | 83.152 | 54.225 | 34.145 | 1.00 | 19.83 | Y | C |
| ATOM | 7332 | CB | ASN | 30 | 84.086 | 54.517 | 32.963 | 1.00 | 44.92 | Y | C |
| ATOM | 7333 | CG | ASN | 30 | 84.524 | 53.261 | 32.254 | 1.00 | 44.92 | Y | C |
| ATOM | 7334 | OD1 | ASN | 30 | 85.235 | 52.431 | 32.832 | 1.00 | 44.92 | Y | O |
| ATOM | 7335 | ND2 | ASN | 30 | 84.097 | 53.099 | 31.001 | 1.00 | 44.92 | Y | N |
| ATOM | 7336 | C | ASN | 30 | 81.740 | 53.976 | 33.634 | 1.00 | 19.83 | Y | C |
| ATOM | 7337 | O | ASN | 30 | 80.998 | 54.926 | 33.381 | 1.00 | 19.83 | Y | O |
| ATOM | 7338 | N | HIS | 31 | 81.367 | 52.708 | 33.475 | 1.00 | 24.55 | Y | N |
| ATOM | 7339 | CA | HIS | 31 | 80.031 | 52.373 | 32.991 | 1.00 | 24.55 | Y | C |
| ATOM | 7340 | CB | HIS | 31 | 80.003 | 52.259 | 31.459 | 1.00 | 41.70 | Y | C |
| ATOM | 7341 | CG | HIS | 31 | 80.061 | 53.572 | 30.737 | 1.00 | 41.70 | Y | C |
| ATOM | 7342 | CD2 | HIS | 31 | 79.124 | 54.233 | 30.016 | 1.00 | 41.70 | Y | C |
| ATOM | 7343 | ND1 | HIS | 31 | 81.196 | 54.351 | 30.692 | 1.00 | 41.70 | Y | N |
| ATOM | 7344 | CE1 | HIS | 31 | 80.958 | 55.435 | 29.973 | 1.00 | 41.70 | Y | C |
| ATOM | 7345 | NE2 | HIS | 31 | 79.708 | 55.387 | 29.551 | 1.00 | 41.70 | Y | N |
| ATOM | 7346 | C | HIS | 31 | 79.548 | 51.058 | 33.567 | 1.00 | 24.55 | Y | C |
| ATOM | 7347 | O | HIS | 31 | 80.274 | 50.392 | 34.305 | 1.00 | 24.55 | Y | O |
| ATOM | 7348 | N | MET | 32 | 78.312 | 50.698 | 33.227 | 1.00 | 16.59 | Y | N |
| ATOM | 7349 | CA | MET | 32 | 77.719 | 49.440 | 33.664 | 1.00 | 16.59 | Y | C |
| ATOM | 7350 | CB | MET | 32 | 76.944 | 49.624 | 34.971 | 1.00 | 29.77 | Y | C |
| ATOM | 7351 | CG | MET | 32 | 76.606 | 48.310 | 35.684 | 1.00 | 29.77 | Y | C |
| ATOM | 7352 | SD | MET | 32 | 78.097 | 47.369 | 36.143 | 1.00 | 29.77 | Y | S |
| ATOM | 7353 | CE | MET | 32 | 78.855 | 48.463 | 37.337 | 1.00 | 29.77 | Y | C |
| ATOM | 7354 | C | MET | 32 | 76.779 | 48.941 | 32.563 | 1.00 | 16.59 | Y | C |
| ATOM | 7355 | O | MET | 32 | 76.138 | 49.734 | 31.871 | 1.00 | 16.59 | Y | O |
| ATOM | 7356 | N | PHE | 33 | 76.706 | 47.629 | 32.383 | 1.00 | 41.04 | Y | N |
| ATOM | 7357 | CA | PHE | 33 | 75.830 | 47.089 | 31.358 | 1.00 | 41.04 | Y | C |
| ATOM | 7358 | CB | PHE | 33 | 76.639 | 46.329 | 30.315 | 1.00 | 16.08 | Y | C |
| ATOM | 7359 | CG | PHE | 33 | 77.695 | 47.161 | 29.657 | 1.00 | 16.08 | Y | C |
| ATOM | 7360 | CD1 | PHE | 33 | 78.846 | 47.528 | 30.354 | 1.00 | 16.08 | Y | C |
| ATOM | 7361 | CD2 | PHE | 33 | 77.524 | 47.609 | 28.350 | 1.00 | 16.08 | Y | C |
| ATOM | 7362 | CE1 | PHE | 33 | 79.810 | 48.328 | 29.763 | 1.00 | 16.08 | Y | C |
| ATOM | 7363 | CE2 | PHE | 33 | 78.484 | 48.414 | 27.745 | 1.00 | 16.08 | Y | C |
| ATOM | 7364 | CZ | PHE | 33 | 79.634 | 48.776 | 28.456 | 1.00 | 16.08 | Y | C |
| ATOM | 7365 | C | PHE | 33 | 74.803 | 46.175 | 31.985 | 1.00 | 41.04 | Y | C |
| ATOM | 7366 | O | PHE | 33 | 75.036 | 45.622 | 33.057 | 1.00 | 41.04 | Y | O |
| ATOM | 7367 | N | TRP | 34 | 73.664 | 46.020 | 31.322 | 1.00 | 26.10 | Y | N |
| ATOM | 7368 | CA | TRP | 34 | 72.604 | 45.168 | 31.843 | 1.00 | 26.10 | Y | C |
| ATOM | 7369 | CB | TRP | 34 | 71.438 | 46.009 | 32.364 | 1.00 | 47.27 | Y | C |
| ATOM | 7370 | CG | TRP | 34 | 71.807 | 46.935 | 33.466 | 1.00 | 47.27 | Y | C |
| ATOM | 7371 | CD2 | TRP | 34 | 71.660 | 46.692 | 34.868 | 1.00 | 47.27 | Y | C |
| ATOM | 7372 | CE2 | TRP | 34 | 72.145 | 47.836 | 35.542 | 1.00 | 47.27 | Y | C |
| ATOM | 7373 | CE3 | TRP | 34 | 71.167 | 45.621 | 35.622 | 1.00 | 47.27 | Y | C |

Fig. 19: A-102

| | | | | | | | | | | | |
|---|---|---|---|---|---|---|---|---|---|---|---|
| ATOM | 7374 | CD1 | TRP | 34 | 72.360 | 48.175 | 33.346 | 1.00 | 47.27 | Y | C |
| ATOM | 7375 | NE1 | TRP | 34 | 72.567 | 48.725 | 34.589 | 1.00 | 47.27 | Y | N |
| ATOM | 7376 | CZ2 | TRP | 34 | 72.150 | 47.939 | 36.940 | 1.00 | 47.27 | Y | C |
| ATOM | 7377 | CZ3 | TRP | 34 | 71.172 | 45.725 | 37.013 | 1.00 | 47.27 | Y | C |
| ATOM | 7378 | CH2 | TRP | 34 | 71.661 | 46.879 | 37.655 | 1.00 | 47.27 | Y | C |
| ATOM | 7379 | C | TRP | 34 | 72.067 | 44.187 | 30.812 | 1.00 | 26.10 | Y | C |
| ATOM | 7380 | O | TRP | 34 | 71.904 | 44.513 | 29.630 | 1.00 | 26.10 | Y | O |
| ATOM | 7381 | N | TYR | 35 | 71.793 | 42.972 | 31.267 | 1.00 | 43.42 | Y | N |
| ATOM | 7382 | CA | TYR | 35 | 71.248 | 41.964 | 30.381 | 1.00 | 43.42 | Y | C |
| ATOM | 7383 | CB | TYR | 35 | 72.230 | 40.808 | 30.189 | 1.00 | 22.29 | Y | C |
| ATOM | 7384 | CG | TYR | 35 | 73.549 | 41.240 | 29.596 | 1.00 | 22.29 | Y | C |
| ATOM | 7385 | CD1 | TYR | 35 | 74.645 | 41.535 | 30.417 | 1.00 | 22.29 | Y | C |
| ATOM | 7386 | CE1 | TYR | 35 | 75.841 | 41.962 | 29.881 | 1.00 | 22.29 | Y | C |
| ATOM | 7387 | CD2 | TYR | 35 | 73.697 | 41.385 | 28.216 | 1.00 | 22.29 | Y | C |
| ATOM | 7388 | CE2 | TYR | 35 | 74.898 | 41.808 | 27.670 | 1.00 | 22.29 | Y | C |
| ATOM | 7389 | CZ | TYR | 35 | 75.960 | 42.094 | 28.510 | 1.00 | 22.29 | Y | C |
| ATOM | 7390 | OH | TYR | 35 | 77.148 | 42.516 | 27.972 | 1.00 | 22.29 | Y | O |
| ATOM | 7391 | C | TYR | 35 | 69.966 | 41.449 | 30.991 | 1.00 | 43.42 | Y | C |
| ATOM | 7392 | O | TYR | 35 | 69.826 | 41.393 | 32.214 | 1.00 | 43.42 | Y | O |
| ATOM | 7393 | N | GLN | 36 | 69.015 | 41.107 | 30.136 | 1.00 | 45.64 | Y | N |
| ATOM | 7394 | CA | GLN | 36 | 67.760 | 40.567 | 30.607 | 1.00 | 45.64 | Y | C |
| ATOM | 7395 | CB | GLN | 36 | 66.574 | 41.346 | 30.054 | 1.00 | 37.71 | Y | C |
| ATOM | 7396 | CG | GLN | 36 | 65.259 | 40.610 | 30.277 | 1.00 | 37.71 | Y | C |
| ATOM | 7397 | CD | GLN | 36 | 64.189 | 41.002 | 29.287 | 1.00 | 37.71 | Y | C |
| ATOM | 7398 | OE1 | GLN | 36 | 63.601 | 42.072 | 29.391 | 1.00 | 37.71 | Y | O |
| ATOM | 7399 | NE2 | GLN | 36 | 63.936 | 40.137 | 28.314 | 1.00 | 37.71 | Y | N |
| ATOM | 7400 | C | GLN | 36 | 67.664 | 39.138 | 30.118 | 1.00 | 45.64 | Y | C |
| ATOM | 7401 | O | GLN | 36 | 67.725 | 38.881 | 28.910 | 1.00 | 45.64 | Y | O |
| ATOM | 7402 | N | GLN | 37 | 67.522 | 38.205 | 31.050 | 1.00 | 50.28 | Y | N |
| ATOM | 7403 | CA | GLN | 37 | 67.390 | 36.809 | 30.670 | 1.00 | 50.28 | Y | C |
| ATOM | 7404 | CB | GLN | 37 | 68.522 | 35.961 | 31.265 | 1.00 | 34.85 | Y | C |
| ATOM | 7405 | CG | GLN | 37 | 68.392 | 34.487 | 30.904 | 1.00 | 34.85 | Y | C |
| ATOM | 7406 | CD | GLN | 37 | 69.543 | 33.645 | 31.388 | 1.00 | 34.85 | Y | C |
| ATOM | 7407 | OE1 | GLN | 37 | 69.925 | 33.699 | 32.565 | 1.00 | 34.85 | Y | O |
| ATOM | 7408 | NE2 | GLN | 37 | 70.098 | 32.842 | 30.484 | 1.00 | 34.85 | Y | N |
| ATOM | 7409 | C | GLN | 37 | 66.042 | 36.248 | 31.108 | 1.00 | 50.28 | Y | C |
| ATOM | 7410 | O | GLN | 37 | 65.690 | 36.272 | 32.293 | 1.00 | 50.28 | Y | O |
| ATOM | 7411 | N | LYS | 38 | 65.284 | 35.763 | 30.133 | 1.00 | 68.24 | Y | N |
| ATOM | 7412 | CA | LYS | 38 | 63.983 | 35.175 | 30.403 | 1.00 | 68.24 | Y | C |
| ATOM | 7413 | CB | LYS | 38 | 62.991 | 35.530 | 29.291 | 1.00 | 55.54 | Y | C |
| ATOM | 7414 | CG | LYS | 38 | 62.893 | 37.031 | 29.023 | 1.00 | 55.54 | Y | C |
| ATOM | 7415 | CD | LYS | 38 | 61.764 | 37.382 | 28.056 | 1.00 | 55.54 | Y | C |
| ATOM | 7416 | CE | LYS | 38 | 60.394 | 37.298 | 28.726 | 1.00 | 55.54 | Y | C |
| ATOM | 7417 | NZ | LYS | 38 | 60.290 | 38.166 | 29.943 | 1.00 | 55.54 | Y | N |
| ATOM | 7418 | C | LYS | 38 | 64.198 | 33.667 | 30.473 | 1.00 | 68.24 | Y | C |
| ATOM | 7419 | O | LYS | 38 | 64.971 | 33.104 | 29.696 | 1.00 | 68.24 | Y | O |
| ATOM | 7420 | N | PRO | 39 | 63.520 | 32.994 | 31.412 | 1.00 | 67.87 | Y | N |
| ATOM | 7421 | CD | PRO | 39 | 62.478 | 33.563 | 32.282 | 1.00 | 58.47 | Y | C |
| ATOM | 7422 | CA | PRO | 39 | 63.621 | 31.546 | 31.614 | 1.00 | 67.87 | Y | C |
| ATOM | 7423 | CB | PRO | 39 | 62.368 | 31.234 | 32.417 | 1.00 | 58.47 | Y | C |
| ATOM | 7424 | CG | PRO | 39 | 62.247 | 32.446 | 33.271 | 1.00 | 58.47 | Y | C |
| ATOM | 7425 | C | PRO | 39 | 63.717 | 30.714 | 30.338 | 1.00 | 67.87 | Y | C |
| ATOM | 7426 | O | PRO | 39 | 62.898 | 30.859 | 29.425 | 1.00 | 67.87 | Y | O |
| ATOM | 7427 | N | GLY | 40 | 64.730 | 29.847 | 30.288 | 1.00 | 54.98 | Y | N |
| ATOM | 7428 | CA | GLY | 40 | 64.925 | 28.977 | 29.137 | 1.00 | 54.98 | Y | C |
| ATOM | 7429 | C | GLY | 40 | 65.488 | 29.625 | 27.882 | 1.00 | 54.98 | Y | C |
| ATOM | 7430 | O | GLY | 40 | 65.625 | 28.957 | 26.855 | 1.00 | 54.98 | Y | O |
| ATOM | 7431 | N | LYS | 41 | 65.801 | 30.918 | 27.955 | 1.00 | 83.28 | Y | N |
| ATOM | 7432 | CA | LYS | 41 | 66.364 | 31.641 | 26.816 | 1.00 | 83.28 | Y | C |
| ATOM | 7433 | CB | LYS | 41 | 65.414 | 32.754 | 26.354 | 1.00 | 72.06 | Y | C |
| ATOM | 7434 | CG | LYS | 41 | 64.045 | 32.271 | 25.882 | 1.00 | 72.06 | Y | C |
| ATOM | 7435 | CD | LYS | 41 | 63.316 | 33.311 | 25.008 | 1.00 | 72.06 | Y | C |
| ATOM | 7436 | CE | LYS | 41 | 63.035 | 34.642 | 25.726 | 1.00 | 72.06 | Y | C |
| ATOM | 7437 | NZ | LYS | 41 | 64.229 | 35.536 | 25.855 | 1.00 | 72.06 | Y | N |
| ATOM | 7438 | C | LYS | 41 | 67.727 | 32.245 | 27.160 | 1.00 | 83.28 | Y | C |
| ATOM | 7439 | O | LYS | 41 | 68.110 | 32.327 | 28.331 | 1.00 | 83.28 | Y | O |
| ATOM | 7440 | N | ALA | 42 | 68.458 | 32.666 | 26.133 | 1.00 | 55.60 | Y | N |
| ATOM | 7441 | CA | ALA | 42 | 69.776 | 33.261 | 26.326 | 1.00 | 55.60 | Y | C |
| ATOM | 7442 | CB | ALA | 42 | 70.561 | 33.194 | 25.041 | 1.00 | 1.87 | Y | C |
| ATOM | 7443 | C | ALA | 42 | 69.623 | 34.707 | 26.754 | 1.00 | 55.60 | Y | C |
| ATOM | 7444 | O | ALA | 42 | 68.607 | 35.337 | 26.462 | 1.00 | 55.60 | Y | O |
| ATOM | 7445 | N | PRO | 43 | 70.628 | 35.259 | 27.455 | 1.00 | 54.21 | Y | N |
| ATOM | 7446 | CD | PRO | 43 | 71.849 | 34.627 | 27.983 | 1.00 | 18.24 | Y | C |

Fig. 19: A-103

| | | | | | | | | | | | |
|---|---|---|---|---|---|---|---|---|---|---|---|
| ATOM | 7447 | CA | PRO | 43 | 70.537 | 36.656 | 27.889 | 1.00 | 54.21 | Y | C |
| ATOM | 7448 | CB | PRO | 43 | 71.875 | 36.890 | 28.594 | 1.00 | 18.24 | Y | C |
| ATOM | 7449 | CG | PRO | 43 | 72.202 | 35.544 | 29.149 | 1.00 | 18.24 | Y | C |
| ATOM | 7450 | C | PRO | 43 | 70.349 | 37.584 | 26.689 | 1.00 | 54.21 | Y | C |
| ATOM | 7451 | O | PRO | 43 | 70.660 | 37.219 | 25.555 | 1.00 | 54.21 | Y | O |
| ATOM | 7452 | N | LYS | 44 | 69.837 | 38.782 | 26.946 | 1.00 | 55.44 | Y | N |
| ATOM | 7453 | CA | LYS | 44 | 69.618 | 39.764 | 25.892 | 1.00 | 55.44 | Y | C |
| ATOM | 7454 | CB | LYS | 44 | 68.120 | 39.894 | 25.601 | 1.00 | 46.11 | Y | C |
| ATOM | 7455 | CG | LYS | 44 | 67.705 | 39.473 | 24.199 | 1.00 | 46.11 | Y | C |
| ATOM | 7456 | CD | LYS | 44 | 66.189 | 39.520 | 24.018 | 1.00 | 46.11 | Y | C |
| ATOM | 7457 | CE | LYS | 44 | 65.457 | 38.464 | 24.865 | 1.00 | 46.11 | Y | C |
| ATOM | 7458 | NZ | LYS | 44 | 65.564 | 38.665 | 26.354 | 1.00 | 46.11 | Y | N |
| ATOM | 7459 | C | LYS | 44 | 70.172 | 41.117 | 26.328 | 1.00 | 55.44 | Y | C |
| ATOM | 7460 | O | LYS | 44 | 69.930 | 41.554 | 27.454 | 1.00 | 55.44 | Y | O |
| ATOM | 7461 | N | PRO | 45 | 70.946 | 41.785 | 25.451 | 1.00 | 21.39 | Y | N |
| ATOM | 7462 | CD | PRO | 45 | 71.303 | 41.365 | 24.085 | 1.00 | 11.37 | Y | C |
| ATOM | 7463 | CA | PRO | 45 | 71.523 | 43.103 | 25.772 | 1.00 | 21.39 | Y | C |
| ATOM | 7464 | CB | PRO | 45 | 72.159 | 43.539 | 24.457 | 1.00 | 11.37 | Y | C |
| ATOM | 7465 | CG | PRO | 45 | 72.485 | 42.234 | 23.795 | 1.00 | 11.37 | Y | C |
| ATOM | 7466 | C | PRO | 45 | 70.361 | 44.010 | 26.138 | 1.00 | 21.39 | Y | C |
| ATOM | 7467 | O | PRO | 45 | 69.407 | 44.103 | 25.383 | 1.00 | 21.39 | Y | O |
| ATOM | 7468 | N | TRP | 46 | 70.434 | 44.676 | 27.281 | 1.00 | 48.64 | Y | N |
| ATOM | 7469 | CA | TRP | 46 | 69.333 | 45.532 | 27.704 | 1.00 | 48.64 | Y | C |
| ATOM | 7470 | CB | TRP | 46 | 68.783 | 45.038 | 29.043 | 1.00 | 23.18 | Y | C |
| ATOM | 7471 | CG | TRP | 46 | 67.316 | 45.220 | 29.143 | 1.00 | 23.18 | Y | C |
| ATOM | 7472 | CD2 | TRP | 46 | 66.330 | 44.620 | 28.299 | 1.00 | 23.18 | Y | C |
| ATOM | 7473 | CE2 | TRP | 46 | 65.070 | 45.075 | 28.739 | 1.00 | 23.18 | Y | C |
| ATOM | 7474 | CE3 | TRP | 46 | 66.391 | 43.736 | 27.206 | 1.00 | 23.18 | Y | C |
| ATOM | 7475 | CD1 | TRP | 46 | 66.637 | 45.997 | 30.038 | 1.00 | 23.18 | Y | C |
| ATOM | 7476 | NE1 | TRP | 46 | 65.282 | 45.914 | 29.803 | 1.00 | 23.18 | Y | N |
| ATOM | 7477 | CZ2 | TRP | 46 | 63.881 | 44.679 | 28.126 | 1.00 | 23.18 | Y | C |
| ATOM | 7478 | CZ3 | TRP | 46 | 65.212 | 43.342 | 26.599 | 1.00 | 23.18 | Y | C |
| ATOM | 7479 | CH2 | TRP | 46 | 63.973 | 43.814 | 27.059 | 1.00 | 23.18 | Y | C |
| ATOM | 7480 | C | TRP | 46 | 69.694 | 47.007 | 27.826 | 1.00 | 48.64 | Y | C |
| ATOM | 7481 | O | TRP | 46 | 68.986 | 47.877 | 27.324 | 1.00 | 48.64 | Y | O |
| ATOM | 7482 | N | ILE | 47 | 70.785 | 47.283 | 28.523 | 1.00 | 42.06 | Y | N |
| ATOM | 7483 | CA | ILE | 47 | 71.238 | 48.644 | 28.717 | 1.00 | 42.06 | Y | C |
| ATOM | 7484 | CB | ILE | 47 | 70.801 | 49.172 | 30.099 | 1.00 | 37.03 | Y | C |
| ATOM | 7485 | CG2 | ILE | 47 | 71.345 | 50.580 | 30.325 | 1.00 | 37.03 | Y | C |
| ATOM | 7486 | CG1 | ILE | 47 | 69.275 | 49.168 | 30.198 | 1.00 | 37.03 | Y | C |
| ATOM | 7487 | CD1 | ILE | 47 | 68.749 | 49.670 | 31.538 | 1.00 | 37.03 | Y | C |
| ATOM | 7488 | C | ILE | 47 | 72.758 | 48.641 | 28.638 | 1.00 | 42.06 | Y | C |
| ATOM | 7489 | O | ILE | 47 | 73.417 | 47.951 | 29.414 | 1.00 | 42.06 | Y | O |
| ATOM | 7490 | N | TYR | 48 | 73.310 | 49.387 | 27.684 | 1.00 | 17.47 | Y | N |
| ATOM | 7491 | CA | TYR | 48 | 74.753 | 49.467 | 27.532 | 1.00 | 17.47 | Y | C |
| ATOM | 7492 | CB | TYR | 48 | 75.189 | 49.145 | 26.106 | 1.00 | 20.64 | Y | C |
| ATOM | 7493 | CG | TYR | 48 | 74.613 | 50.048 | 25.046 | 1.00 | 20.64 | Y | C |
| ATOM | 7494 | CD1 | TYR | 48 | 73.267 | 49.988 | 24.710 | 1.00 | 20.64 | Y | C |
| ATOM | 7495 | CE1 | TYR | 48 | 72.743 | 50.792 | 23.704 | 1.00 | 20.64 | Y | C |
| ATOM | 7496 | CD2 | TYR | 48 | 75.425 | 50.940 | 24.353 | 1.00 | 20.64 | Y | C |
| ATOM | 7497 | CE2 | TYR | 48 | 74.916 | 51.750 | 23.347 | 1.00 | 20.64 | Y | C |
| ATOM | 7498 | CZ | TYR | 48 | 73.573 | 51.671 | 23.028 | 1.00 | 20.64 | Y | C |
| ATOM | 7499 | OH | TYR | 48 | 73.051 | 52.476 | 22.045 | 1.00 | 20.64 | Y | O |
| ATOM | 7500 | C | TYR | 48 | 75.193 | 50.861 | 27.892 | 1.00 | 17.47 | Y | C |
| ATOM | 7501 | O | TYR | 48 | 74.365 | 51.754 | 28.021 | 1.00 | 17.47 | Y | O |
| ATOM | 7502 | N | LEU | 49 | 76.497 | 51.044 | 28.054 | 1.00 | 31.07 | Y | N |
| ATOM | 7503 | CA | LEU | 49 | 77.042 | 52.337 | 28.429 | 1.00 | 31.07 | Y | C |
| ATOM | 7504 | CB | LEU | 49 | 77.200 | 53.247 | 27.205 | 1.00 | 20.44 | Y | C |
| ATOM | 7505 | CG | LEU | 49 | 78.368 | 53.044 | 26.236 | 1.00 | 20.44 | Y | C |
| ATOM | 7506 | CD1 | LEU | 49 | 79.662 | 52.870 | 27.019 | 1.00 | 20.44 | Y | C |
| ATOM | 7507 | CD2 | LEU | 49 | 78.121 | 51.836 | 25.385 | 1.00 | 20.44 | Y | C |
| ATOM | 7508 | C | LEU | 49 | 76.173 | 53.037 | 29.475 | 1.00 | 31.07 | Y | C |
| ATOM | 7509 | O | LEU | 49 | 75.769 | 54.178 | 29.293 | 1.00 | 31.07 | Y | O |
| ATOM | 7510 | N | THR | 50 | 75.861 | 52.329 | 30.555 | 1.00 | 28.24 | Y | N |
| ATOM | 7511 | CA | THR | 50 | 75.083 | 52.870 | 31.670 | 1.00 | 28.24 | Y | C |
| ATOM | 7512 | CB | THR | 50 | 75.754 | 54.128 | 32.230 | 1.00 | 41.62 | Y | C |
| ATOM | 7513 | OG1 | THR | 50 | 77.134 | 53.847 | 32.495 | 1.00 | 41.62 | Y | O |
| ATOM | 7514 | CG2 | THR | 50 | 75.066 | 54.568 | 33.522 | 1.00 | 41.62 | Y | C |
| ATOM | 7515 | C | THR | 50 | 73.605 | 53.187 | 31.485 | 1.00 | 28.24 | Y | C |
| ATOM | 7516 | O | THR | 50 | 72.761 | 52.603 | 32.158 | 1.00 | 28.24 | Y | O |
| ATOM | 7517 | N | SER | 51 | 73.283 | 54.114 | 30.595 | 1.00 | 28.33 | Y | N |
| ATOM | 7518 | CA | SER | 51 | 71.889 | 54.496 | 30.402 | 1.00 | 28.33 | Y | C |
| ATOM | 7519 | CB | SER | 51 | 71.729 | 55.981 | 30.714 | 1.00 | 81.44 | Y | C |

Fig. 19: A-104

| | | | | | | | | | | | |
|---|---|---|---|---|---|---|---|---|---|---|---|
| ATOM | 7520 | OG | SER | 51 | 72.714 | 56.738 | 30.034 | 1.00 | 81.44 | Y | O |
| ATOM | 7521 | C | SER | 51 | 71.312 | 54.190 | 29.019 | 1.00 | 28.33 | Y | C |
| ATOM | 7522 | O | SER | 51 | 70.092 | 54.174 | 28.831 | 1.00 | 28.33 | Y | O |
| ATOM | 7523 | N | ASN | 52 | 72.184 | 53.941 | 28.053 | 1.00 | 27.44 | Y | N |
| ATOM | 7524 | CA | ASN | 52 | 71.736 | 53.648 | 26.704 | 1.00 | 27.44 | Y | C |
| ATOM | 7525 | CB | ASN | 52 | 72.942 | 53.523 | 25.779 | 1.00 | 42.81 | Y | C |
| ATOM | 7526 | CG | ASN | 52 | 73.623 | 54.849 | 25.546 | 1.00 | 42.81 | Y | C |
| ATOM | 7527 | OD1 | ASN | 52 | 73.059 | 55.733 | 24.907 | 1.00 | 42.81 | Y | O |
| ATOM | 7528 | ND2 | ASN | 52 | 74.829 | 55.006 | 26.076 | 1.00 | 42.81 | Y | N |
| ATOM | 7529 | C | ASN | 52 | 70.896 | 52.390 | 26.623 | 1.00 | 27.44 | Y | C |
| ATOM | 7530 | O | ASN | 52 | 71.336 | 51.320 | 27.027 | 1.00 | 27.44 | Y | O |
| ATOM | 7531 | N | LEU | 53 | 69.682 | 52.519 | 26.100 | 1.00 | 46.42 | Y | N |
| ATOM | 7532 | CA | LEU | 53 | 68.805 | 51.367 | 25.954 | 1.00 | 46.42 | Y | C |
| ATOM | 7533 | CB | LEU | 53 | 67.349 | 51.803 | 25.887 | 1.00 | 19.90 | Y | C |
| ATOM | 7534 | CG | LEU | 53 | 66.763 | 52.595 | 27.051 | 1.00 | 19.90 | Y | C |
| ATOM | 7535 | CD1 | LEU | 53 | 65.255 | 52.685 | 26.846 | 1.00 | 19.90 | Y | C |
| ATOM | 7536 | CD2 | LEU | 53 | 67.071 | 51.918 | 28.382 | 1.00 | 19.90 | Y | C |
| ATOM | 7537 | C | LEU | 53 | 69.136 | 50.610 | 24.676 | 1.00 | 46.42 | Y | C |
| ATOM | 7538 | O | LEU | 53 | 69.414 | 51.220 | 23.644 | 1.00 | 46.42 | Y | O |
| ATOM | 7539 | N | ALA | 54 | 69.101 | 49.281 | 24.744 | 1.00 | 35.05 | Y | N |
| ATOM | 7540 | CA | ALA | 54 | 69.378 | 48.447 | 23.583 | 1.00 | 35.05 | Y | C |
| ATOM | 7541 | CB | ALA | 54 | 69.220 | 46.994 | 23.930 | 1.00 | 27.54 | Y | C |
| ATOM | 7542 | C | ALA | 54 | 68.373 | 48.829 | 22.530 | 1.00 | 35.05 | Y | C |
| ATOM | 7543 | O | ALA | 54 | 67.680 | 49.834 | 22.666 | 1.00 | 35.05 | Y | O |
| ATOM | 7544 | N | SER | 55 | 68.259 | 48.026 | 21.486 | 1.00 | 47.40 | Y | N |
| ATOM | 7545 | CA | SER | 55 | 67.319 | 48.376 | 20.443 | 1.00 | 47.40 | Y | C |
| ATOM | 7546 | CB | SER | 55 | 67.689 | 47.681 | 19.140 | 1.00 | 36.06 | Y | C |
| ATOM | 7547 | OG | SER | 55 | 67.083 | 48.359 | 18.051 | 1.00 | 36.06 | Y | O |
| ATOM | 7548 | C | SER | 55 | 65.866 | 48.073 | 20.801 | 1.00 | 47.40 | Y | C |
| ATOM | 7549 | O | SER | 55 | 64.993 | 48.921 | 20.631 | 1.00 | 47.40 | Y | O |
| ATOM | 7550 | N | GLY | 56 | 65.599 | 46.878 | 21.312 | 1.00 | 54.09 | Y | N |
| ATOM | 7551 | CA | GLY | 56 | 64.225 | 46.531 | 21.647 | 1.00 | 54.09 | Y | C |
| ATOM | 7552 | C | GLY | 56 | 63.650 | 47.071 | 22.948 | 1.00 | 54.09 | Y | C |
| ATOM | 7553 | O | GLY | 56 | 62.457 | 47.370 | 23.025 | 1.00 | 54.09 | Y | O |
| ATOM | 7554 | N | VAL | 57 | 64.497 | 47.197 | 23.965 | 1.00 | 63.10 | Y | N |
| ATOM | 7555 | CA | VAL | 57 | 64.082 | 47.667 | 25.282 | 1.00 | 63.10 | Y | C |
| ATOM | 7556 | CB | VAL | 57 | 65.311 | 48.113 | 26.120 | 1.00 | 46.15 | Y | C |
| ATOM | 7557 | CG1 | VAL | 57 | 64.923 | 48.248 | 27.588 | 1.00 | 46.15 | Y | C |
| ATOM | 7558 | CG2 | VAL | 57 | 66.446 | 47.118 | 25.961 | 1.00 | 46.15 | Y | C |
| ATOM | 7559 | C | VAL | 57 | 63.071 | 48.817 | 25.251 | 1.00 | 63.10 | Y | C |
| ATOM | 7560 | O | VAL | 57 | 63.363 | 49.898 | 24.747 | 1.00 | 63.10 | Y | O |
| ATOM | 7561 | N | PRO | 58 | 61.862 | 48.594 | 25.791 | 1.00 | 51.01 | Y | N |
| ATOM | 7562 | CD | PRO | 58 | 61.362 | 47.365 | 26.426 | 1.00 | 31.12 | Y | C |
| ATOM | 7563 | CA | PRO | 58 | 60.834 | 49.639 | 25.815 | 1.00 | 51.01 | Y | C |
| ATOM | 7564 | CB | PRO | 58 | 59.634 | 48.929 | 26.433 | 1.00 | 31.12 | Y | C |
| ATOM | 7565 | CG | PRO | 58 | 60.258 | 47.899 | 27.300 | 1.00 | 31.12 | Y | C |
| ATOM | 7566 | C | PRO | 58 | 61.305 | 50.829 | 26.643 | 1.00 | 51.01 | Y | C |
| ATOM | 7567 | O | PRO | 58 | 61.992 | 50.660 | 27.653 | 1.00 | 51.01 | Y | O |
| ATOM | 7568 | N | SER | 59 | 60.918 | 52.027 | 26.216 | 1.00 | 33.61 | Y | N |
| ATOM | 7569 | CA | SER | 59 | 61.330 | 53.267 | 26.874 | 1.00 | 33.61 | Y | C |
| ATOM | 7570 | CB | SER | 59 | 60.780 | 54.482 | 26.113 | 1.00 | 61.12 | Y | C |
| ATOM | 7571 | OG | SER | 59 | 59.368 | 54.481 | 26.096 | 1.00 | 61.12 | Y | O |
| ATOM | 7572 | C | SER | 59 | 61.023 | 53.411 | 28.359 | 1.00 | 33.61 | Y | C |
| ATOM | 7573 | O | SER | 59 | 61.495 | 54.353 | 28.990 | 1.00 | 33.61 | Y | O |
| ATOM | 7574 | N | ARG | 60 | 60.244 | 52.500 | 28.928 | 1.00 | 39.70 | Y | N |
| ATOM | 7575 | CA | ARG | 60 | 59.963 | 52.599 | 30.359 | 1.00 | 39.70 | Y | C |
| ATOM | 7576 | CB | ARG | 60 | 58.764 | 51.731 | 30.751 | 1.00 | 42.51 | Y | C |
| ATOM | 7577 | CG | ARG | 60 | 58.846 | 50.293 | 30.287 | 1.00 | 42.51 | Y | C |
| ATOM | 7578 | CD | ARG | 60 | 57.798 | 49.425 | 30.971 | 1.00 | 42.51 | Y | C |
| ATOM | 7579 | NE | ARG | 60 | 57.683 | 48.120 | 30.333 | 1.00 | 42.51 | Y | N |
| ATOM | 7580 | CZ | ARG | 60 | 57.277 | 47.939 | 29.079 | 1.00 | 42.51 | Y | C |
| ATOM | 7581 | NH1 | ARG | 60 | 56.943 | 48.979 | 28.324 | 1.00 | 42.51 | Y | N |
| ATOM | 7582 | NH2 | ARG | 60 | 57.210 | 46.718 | 28.569 | 1.00 | 42.51 | Y | N |
| ATOM | 7583 | C | ARG | 60 | 61.202 | 52.180 | 31.158 | 1.00 | 39.70 | Y | C |
| ATOM | 7584 | O | ARG | 60 | 61.311 | 52.451 | 32.357 | 1.00 | 39.70 | Y | O |
| ATOM | 7585 | N | PHE | 61 | 62.136 | 51.522 | 30.480 | 1.00 | 40.60 | Y | N |
| ATOM | 7586 | CA | PHE | 61 | 63.372 | 51.086 | 31.109 | 1.00 | 40.60 | Y | C |
| ATOM | 7587 | CB | PHE | 61 | 63.965 | 49.886 | 30.370 | 1.00 | 38.42 | Y | C |
| ATOM | 7588 | CG | PHE | 61 | 63.416 | 48.563 | 30.811 | 1.00 | 38.42 | Y | C |
| ATOM | 7589 | CD1 | PHE | 61 | 62.493 | 47.881 | 30.028 | 1.00 | 38.42 | Y | C |
| ATOM | 7590 | CD2 | PHE | 61 | 63.830 | 47.997 | 32.010 | 1.00 | 38.42 | Y | C |
| ATOM | 7591 | CE1 | PHE | 61 | 61.990 | 46.652 | 30.434 | 1.00 | 38.42 | Y | C |
| ATOM | 7592 | CE2 | PHE | 61 | 63.332 | 46.770 | 32.423 | 1.00 | 38.42 | Y | C |

Fig. 19: A-105

| | | | | | | | | | | | |
|---|---|---|---|---|---|---|---|---|---|---|---|
| ATOM | 7593 | CZ | PHE | 61 | 62.410 | 46.096 | 31.634 | 1.00 | 38.42 | Y | C |
| ATOM | 7594 | C | PHE | 61 | 64.399 | 52.209 | 31.097 | 1.00 | 40.60 | Y | C |
| ATOM | 7595 | O | PHE | 61 | 64.470 | 52.989 | 30.144 | 1.00 | 40.60 | Y | O |
| ATOM | 7596 | N | SER | 62 | 65.202 | 52.284 | 32.152 | 1.00 | 26.58 | Y | N |
| ATOM | 7597 | CA | SER | 62 | 66.238 | 53.306 | 32.247 | 1.00 | 26.58 | Y | C |
| ATOM | 7598 | CB | SER | 62 | 65.658 | 54.604 | 32.802 | 1.00 | 47.08 | Y | C |
| ATOM | 7599 | OG | SER | 62 | 65.071 | 54.395 | 34.076 | 1.00 | 47.08 | Y | O |
| ATOM | 7600 | C | SER | 62 | 67.376 | 52.828 | 33.145 | 1.00 | 26.58 | Y | C |
| ATOM | 7601 | O | SER | 62 | 67.160 | 52.123 | 34.125 | 1.00 | 26.58 | Y | O |
| ATOM | 7602 | N | GLY | 63 | 68.595 | 53.208 | 32.797 | 1.00 | 30.78 | Y | N |
| ATOM | 7603 | CA | GLY | 63 | 69.738 | 52.810 | 33.591 | 1.00 | 30.78 | Y | C |
| ATOM | 7604 | C | GLY | 63 | 70.426 | 54.067 | 34.056 | 1.00 | 30.78 | Y | C |
| ATOM | 7605 | O | GLY | 63 | 70.266 | 55.122 | 33.442 | 1.00 | 30.78 | Y | O |
| ATOM | 7606 | N | SER | 64 | 71.195 | 53.964 | 35.130 | 1.00 | 54.48 | Y | N |
| ATOM | 7607 | CA | SER | 64 | 71.884 | 55.130 | 35.652 | 1.00 | 54.48 | Y | C |
| ATOM | 7608 | CB | SER | 64 | 70.869 | 56.075 | 36.290 | 1.00 | 25.06 | Y | C |
| ATOM | 7609 | OG | SER | 64 | 71.519 | 57.204 | 36.839 | 1.00 | 25.06 | Y | O |
| ATOM | 7610 | C | SER | 64 | 72.947 | 54.763 | 36.675 | 1.00 | 54.48 | Y | C |
| ATOM | 7611 | O | SER | 64 | 73.000 | 53.632 | 37.154 | 1.00 | 54.48 | Y | O |
| ATOM | 7612 | N | GLY | 65 | 73.793 | 55.732 | 37.007 | 1.00 | 43.76 | Y | N |
| ATOM | 7613 | CA | GLY | 65 | 74.836 | 55.494 | 37.984 | 1.00 | 43.76 | Y | C |
| ATOM | 7614 | C | GLY | 65 | 76.218 | 56.023 | 37.637 | 1.00 | 43.76 | Y | C |
| ATOM | 7615 | O | GLY | 65 | 76.431 | 56.698 | 36.622 | 1.00 | 43.76 | Y | O |
| ATOM | 7616 | N | SER | 66 | 77.167 | 55.703 | 38.508 | 1.00 | 27.01 | Y | N |
| ATOM | 7617 | CA | SER | 66 | 78.546 | 56.110 | 38.339 | 1.00 | 27.01 | Y | C |
| ATOM | 7618 | CB | SER | 66 | 78.641 | 57.635 | 38.286 | 1.00 | 58.01 | Y | C |
| ATOM | 7619 | OG | SER | 66 | 77.927 | 58.229 | 39.355 | 1.00 | 58.01 | Y | O |
| ATOM | 7620 | C | SER | 66 | 79.367 | 55.563 | 39.498 | 1.00 | 27.01 | Y | C |
| ATOM | 7621 | O | SER | 66 | 78.817 | 55.039 | 40.464 | 1.00 | 27.01 | Y | O |
| ATOM | 7622 | N | GLY | 67 | 80.685 | 55.668 | 39.385 | 1.00 | 73.15 | Y | N |
| ATOM | 7623 | CA | GLY | 67 | 81.555 | 55.179 | 40.436 | 1.00 | 73.15 | Y | C |
| ATOM | 7624 | C | GLY | 67 | 81.312 | 53.733 | 40.822 | 1.00 | 73.15 | Y | C |
| ATOM | 7625 | O | GLY | 67 | 81.609 | 52.814 | 40.056 | 1.00 | 73.15 | Y | O |
| ATOM | 7626 | N | THR | 68 | 80.758 | 53.530 | 42.011 | 1.00 | 44.05 | Y | N |
| ATOM | 7627 | CA | THR | 68 | 80.506 | 52.186 | 42.506 | 1.00 | 44.05 | Y | C |
| ATOM | 7628 | CB | THR | 68 | 81.118 | 52.003 | 43.894 | 1.00 | 42.61 | Y | C |
| ATOM | 7629 | OG1 | THR | 68 | 80.524 | 52.945 | 44.793 | 1.00 | 42.61 | Y | O |
| ATOM | 7630 | CG2 | THR | 68 | 82.627 | 52.225 | 43.845 | 1.00 | 42.61 | Y | C |
| ATOM | 7631 | C | THR | 68 | 79.042 | 51.786 | 42.592 | 1.00 | 44.05 | Y | C |
| ATOM | 7632 | O | THR | 68 | 78.743 | 50.632 | 42.879 | 1.00 | 44.05 | Y | O |
| ATOM | 7633 | N | ASP | 69 | 78.128 | 52.720 | 42.352 | 1.00 | 35.15 | Y | N |
| ATOM | 7634 | CA | ASP | 69 | 76.708 | 52.392 | 42.424 | 1.00 | 35.15 | Y | C |
| ATOM | 7635 | CB | ASP | 69 | 76.066 | 53.103 | 43.617 | 1.00 | 108.02 | Y | C |
| ATOM | 7636 | CG | ASP | 69 | 76.592 | 52.591 | 44.946 | 1.00 | 108.02 | Y | C |
| ATOM | 7637 | OD1 | ASP | 69 | 76.357 | 51.406 | 45.268 | 1.00 | 108.02 | Y | O |
| ATOM | 7638 | OD2 | ASP | 69 | 77.249 | 53.370 | 45.667 | 1.00 | 108.02 | Y | O |
| ATOM | 7639 | C | ASP | 69 | 75.942 | 52.705 | 41.139 | 1.00 | 35.15 | Y | C |
| ATOM | 7640 | O | ASP | 69 | 75.884 | 53.850 | 40.693 | 1.00 | 35.15 | Y | O |
| ATOM | 7641 | N | TYR | 70 | 75.359 | 51.664 | 40.551 | 1.00 | 27.55 | Y | N |
| ATOM | 7642 | CA | TYR | 70 | 74.599 | 51.787 | 39.317 | 1.00 | 27.55 | Y | C |
| ATOM | 7643 | CB | TYR | 70 | 75.315 | 51.016 | 38.191 | 1.00 | 25.09 | Y | C |
| ATOM | 7644 | CG | TYR | 70 | 76.543 | 51.737 | 37.662 | 1.00 | 25.09 | Y | C |
| ATOM | 7645 | CD1 | TYR | 70 | 76.447 | 52.637 | 36.596 | 1.00 | 25.09 | Y | C |
| ATOM | 7646 | CE1 | TYR | 70 | 77.562 | 53.365 | 36.158 | 1.00 | 25.09 | Y | C |
| ATOM | 7647 | CD2 | TYR | 70 | 77.787 | 51.577 | 38.275 | 1.00 | 25.09 | Y | C |
| ATOM | 7648 | CE2 | TYR | 70 | 78.906 | 52.299 | 37.848 | 1.00 | 25.09 | Y | C |
| ATOM | 7649 | CZ | TYR | 70 | 78.785 | 53.194 | 36.790 | 1.00 | 25.09 | Y | C |
| ATOM | 7650 | OH | TYR | 70 | 79.873 | 53.933 | 36.382 | 1.00 | 25.09 | Y | O |
| ATOM | 7651 | C | TYR | 70 | 73.184 | 51.267 | 39.523 | 1.00 | 27.55 | Y | C |
| ATOM | 7652 | O | TYR | 70 | 72.920 | 50.545 | 40.488 | 1.00 | 27.55 | Y | O |
| ATOM | 7653 | N | THR | 71 | 72.270 | 51.635 | 38.627 | 1.00 | 38.36 | Y | N |
| ATOM | 7654 | CA | THR | 71 | 70.893 | 51.184 | 38.767 | 1.00 | 38.36 | Y | C |
| ATOM | 7655 | CB | THR | 71 | 70.074 | 52.152 | 39.657 | 1.00 | 44.65 | Y | C |
| ATOM | 7656 | OG1 | THR | 71 | 69.921 | 53.403 | 38.978 | 1.00 | 44.65 | Y | O |
| ATOM | 7657 | CG2 | THR | 71 | 70.770 | 52.394 | 40.989 | 1.00 | 44.65 | Y | C |
| ATOM | 7658 | C | THR | 71 | 70.099 | 50.991 | 37.473 | 1.00 | 38.36 | Y | C |
| ATOM | 7659 | O | THR | 71 | 70.281 | 51.707 | 36.485 | 1.00 | 38.36 | Y | O |
| ATOM | 7660 | N | LEU | 72 | 69.216 | 50.001 | 37.499 | 1.00 | 32.67 | Y | N |
| ATOM | 7661 | CA | LEU | 72 | 68.324 | 49.718 | 36.385 | 1.00 | 32.67 | Y | C |
| ATOM | 7662 | CB | LEU | 72 | 68.392 | 48.238 | 35.985 | 1.00 | 53.11 | Y | C |
| ATOM | 7663 | CG | LEU | 72 | 67.283 | 47.694 | 35.073 | 1.00 | 53.11 | Y | C |
| ATOM | 7664 | CD1 | LEU | 72 | 66.871 | 48.731 | 34.059 | 1.00 | 53.11 | Y | C |
| ATOM | 7665 | CD2 | LEU | 72 | 67.769 | 46.444 | 34.372 | 1.00 | 53.11 | Y | C |

Fig. 19: A-106

| | | | | | | | | | | | |
|---|---|---|---|---|---|---|---|---|---|---|---|
| ATOM | 7666 | C | LEU | 72 | 66.958 | 50.056 | 36.972 | 1.00 | 32.67 | Y | C |
| ATOM | 7667 | O | LEU | 72 | 66.688 | 49.738 | 38.129 | 1.00 | 32.67 | Y | O |
| ATOM | 7668 | N | THR | 73 | 66.106 | 50.715 | 36.195 | 1.00 | 42.60 | Y | N |
| ATOM | 7669 | CA | THR | 73 | 64.795 | 51.100 | 36.700 | 1.00 | 42.60 | Y | C |
| ATOM | 7670 | CB | THR | 73 | 64.780 | 52.597 | 37.094 | 1.00 | 57.15 | Y | C |
| ATOM | 7671 | OG1 | THR | 73 | 66.018 | 52.943 | 37.730 | 1.00 | 57.15 | Y | O |
| ATOM | 7672 | CG2 | THR | 73 | 63.639 | 52.879 | 38.058 | 1.00 | 57.15 | Y | C |
| ATOM | 7673 | C | THR | 73 | 63.665 | 50.854 | 35.708 | 1.00 | 42.60 | Y | C |
| ATOM | 7674 | O | THR | 73 | 63.791 | 51.132 | 34.516 | 1.00 | 42.60 | Y | O |
| ATOM | 7675 | N | ILE | 74 | 62.564 | 50.316 | 36.212 | 1.00 | 51.99 | Y | N |
| ATOM | 7676 | CA | ILE | 74 | 61.396 | 50.068 | 35.386 | 1.00 | 51.99 | Y | C |
| ATOM | 7677 | CB | ILE | 74 | 60.934 | 48.597 | 35.455 | 1.00 | 52.44 | Y | C |
| ATOM | 7678 | CG2 | ILE | 74 | 60.081 | 48.271 | 34.231 | 1.00 | 52.44 | Y | C |
| ATOM | 7679 | CG1 | ILE | 74 | 62.138 | 47.656 | 35.471 | 1.00 | 52.44 | Y | C |
| ATOM | 7680 | CD1 | ILE | 74 | 61.757 | 46.182 | 35.513 | 1.00 | 52.44 | Y | C |
| ATOM | 7681 | C | ILE | 74 | 60.314 | 50.963 | 35.988 | 1.00 | 51.99 | Y | C |
| ATOM | 7682 | O | ILE | 74 | 59.739 | 50.639 | 37.030 | 1.00 | 51.99 | Y | O |
| ATOM | 7683 | N | SER | 75 | 60.058 | 52.094 | 35.335 | 1.00 | 41.67 | Y | N |
| ATOM | 7684 | CA | SER | 75 | 59.069 | 53.066 | 35.801 | 1.00 | 41.67 | Y | C |
| ATOM | 7685 | CB | SER | 75 | 59.090 | 54.291 | 34.889 | 1.00 | 51.63 | Y | C |
| ATOM | 7686 | OG | SER | 75 | 58.934 | 53.909 | 33.535 | 1.00 | 51.63 | Y | O |
| ATOM | 7687 | C | SER | 75 | 57.644 | 52.524 | 35.901 | 1.00 | 41.67 | Y | C |
| ATOM | 7688 | O | SER | 75 | 56.885 | 52.924 | 36.777 | 1.00 | 41.67 | Y | O |
| ATOM | 7689 | N | SER | 76 | 57.280 | 51.627 | 34.993 | 1.00 | 62.86 | Y | N |
| ATOM | 7690 | CA | SER | 76 | 55.950 | 51.032 | 34.996 | 1.00 | 62.86 | Y | C |
| ATOM | 7691 | CB | SER | 76 | 55.045 | 51.724 | 33.980 | 1.00 | 71.45 | Y | C |
| ATOM | 7692 | OG | SER | 76 | 53.779 | 51.086 | 33.932 | 1.00 | 71.45 | Y | O |
| ATOM | 7693 | C | SER | 76 | 56.056 | 49.558 | 34.649 | 1.00 | 62.86 | Y | C |
| ATOM | 7694 | O | SER | 76 | 55.970 | 49.176 | 33.480 | 1.00 | 62.86 | Y | O |
| ATOM | 7695 | N | LEU | 77 | 56.237 | 48.734 | 35.675 | 1.00 | 53.25 | Y | N |
| ATOM | 7696 | CA | LEU | 77 | 56.380 | 47.298 | 35.490 | 1.00 | 53.25 | Y | C |
| ATOM | 7697 | CB | LEU | 77 | 56.342 | 46.596 | 36.841 | 1.00 | 41.03 | Y | C |
| ATOM | 7698 | CG | LEU | 77 | 57.317 | 45.433 | 37.008 | 1.00 | 41.03 | Y | C |
| ATOM | 7699 | CD1 | LEU | 77 | 56.911 | 44.632 | 38.239 | 1.00 | 41.03 | Y | C |
| ATOM | 7700 | CD2 | LEU | 77 | 57.310 | 44.548 | 35.766 | 1.00 | 41.03 | Y | C |
| ATOM | 7701 | C | LEU | 77 | 55.303 | 46.703 | 34.590 | 1.00 | 53.25 | Y | C |
| ATOM | 7702 | O | LEU | 77 | 54.114 | 46.944 | 34.787 | 1.00 | 53.25 | Y | O |
| ATOM | 7703 | N | GLN | 78 | 55.723 | 45.921 | 33.602 | 1.00 | 82.27 | Y | N |
| ATOM | 7704 | CA | GLN | 78 | 54.781 | 45.285 | 32.691 | 1.00 | 82.27 | Y | C |
| ATOM | 7705 | CB | GLN | 78 | 55.094 | 45.667 | 31.243 | 1.00 | 41.92 | Y | C |
| ATOM | 7706 | CG | GLN | 78 | 54.907 | 47.148 | 30.956 | 1.00 | 41.92 | Y | C |
| ATOM | 7707 | CD | GLN | 78 | 53.508 | 47.627 | 31.288 | 1.00 | 41.92 | Y | C |
| ATOM | 7708 | OE1 | GLN | 78 | 52.520 | 47.033 | 30.852 | 1.00 | 41.92 | Y | O |
| ATOM | 7709 | NE2 | GLN | 78 | 53.416 | 48.711 | 32.056 | 1.00 | 41.92 | Y | N |
| ATOM | 7710 | C | GLN | 78 | 54.830 | 43.774 | 32.852 | 1.00 | 82.27 | Y | C |
| ATOM | 7711 | O | GLN | 78 | 55.851 | 43.213 | 33.244 | 1.00 | 82.27 | Y | O |
| ATOM | 7712 | N | PRO | 79 | 53.718 | 43.093 | 32.549 | 1.00 | 81.12 | Y | N |
| ATOM | 7713 | CD | PRO | 79 | 52.505 | 43.636 | 31.915 | 1.00 | 80.96 | Y | C |
| ATOM | 7714 | CA | PRO | 79 | 53.632 | 41.636 | 32.660 | 1.00 | 81.12 | Y | C |
| ATOM | 7715 | CB | PRO | 79 | 52.198 | 41.351 | 32.225 | 1.00 | 80.96 | Y | C |
| ATOM | 7716 | CG | PRO | 79 | 51.949 | 42.426 | 31.213 | 1.00 | 80.96 | Y | C |
| ATOM | 7717 | C | PRO | 79 | 54.663 | 40.914 | 31.792 | 1.00 | 81.12 | Y | C |
| ATOM | 7718 | O | PRO | 79 | 54.865 | 39.708 | 31.914 | 1.00 | 81.12 | Y | O |
| ATOM | 7719 | N | GLU | 80 | 55.316 | 41.670 | 30.921 | 1.00 | 44.20 | Y | N |
| ATOM | 7720 | CA | GLU | 80 | 56.316 | 41.120 | 30.021 | 1.00 | 44.20 | Y | C |
| ATOM | 7721 | CB | GLU | 80 | 56.117 | 41.729 | 28.636 | 1.00 | 102.65 | Y | C |
| ATOM | 7722 | CG | GLU | 80 | 55.853 | 43.217 | 28.678 | 1.00 | 102.65 | Y | C |
| ATOM | 7723 | CD | GLU | 80 | 55.814 | 43.833 | 27.301 | 1.00 | 102.65 | Y | C |
| ATOM | 7724 | OE1 | GLU | 80 | 56.717 | 43.528 | 26.494 | 1.00 | 102.65 | Y | O |
| ATOM | 7725 | OE2 | GLU | 80 | 54.891 | 44.629 | 27.026 | 1.00 | 102.65 | Y | O |
| ATOM | 7726 | C | GLU | 80 | 57.742 | 41.368 | 30.520 | 1.00 | 44.20 | Y | C |
| ATOM | 7727 | O | GLU | 80 | 58.672 | 40.652 | 30.145 | 1.00 | 44.20 | Y | O |
| ATOM | 7728 | N | ASP | 81 | 57.902 | 42.380 | 31.371 | 1.00 | 52.34 | Y | N |
| ATOM | 7729 | CA | ASP | 81 | 59.206 | 42.733 | 31.931 | 1.00 | 52.34 | Y | C |
| ATOM | 7730 | CB | ASP | 81 | 59.167 | 44.111 | 32.593 | 1.00 | 55.47 | Y | C |
| ATOM | 7731 | CG | ASP | 81 | 58.700 | 45.195 | 31.663 | 1.00 | 55.47 | Y | C |
| ATOM | 7732 | OD1 | ASP | 81 | 58.950 | 45.085 | 30.446 | 1.00 | 55.47 | Y | O |
| ATOM | 7733 | OD2 | ASP | 81 | 58.099 | 46.171 | 32.156 | 1.00 | 55.47 | Y | O |
| ATOM | 7734 | C | ASP | 81 | 59.641 | 41.740 | 32.991 | 1.00 | 52.34 | Y | C |
| ATOM | 7735 | O | ASP | 81 | 60.649 | 41.946 | 33.673 | 1.00 | 52.34 | Y | O |
| ATOM | 7736 | N | PHE | 82 | 58.884 | 40.664 | 33.138 | 1.00 | 63.15 | Y | N |
| ATOM | 7737 | CA | PHE | 82 | 59.207 | 39.685 | 34.158 | 1.00 | 63.15 | Y | C |
| ATOM | 7738 | CB | PHE | 82 | 57.917 | 39.041 | 34.647 | 1.00 | 168.46 | Y | C |

Fig. 19: A-107

| | | | | | | | | | | |
|---|---|---|---|---|---|---|---|---|---|---|
| ATOM | 7739 | CG | PHE | 82 | 57.024 | 40.004 | 35.381 | 1.00 | 168.46 | Y | C |
| ATOM | 7740 | CD1 | PHE | 82 | 57.371 | 40.454 | 36.650 | 1.00 | 168.46 | Y | C |
| ATOM | 7741 | CD2 | PHE | 82 | 55.866 | 40.498 | 34.791 | 1.00 | 168.46 | Y | C |
| ATOM | 7742 | CE1 | PHE | 82 | 56.579 | 41.384 | 37.321 | 1.00 | 168.46 | Y | C |
| ATOM | 7743 | CE2 | PHE | 82 | 55.067 | 41.430 | 35.458 | 1.00 | 168.46 | Y | C |
| ATOM | 7744 | CZ | PHE | 82 | 55.425 | 41.872 | 36.724 | 1.00 | 168.46 | Y | C |
| ATOM | 7745 | C | PHE | 82 | 60.238 | 38.657 | 33.742 | 1.00 | 63.15 | Y | C |
| ATOM | 7746 | O | PHE | 82 | 59.960 | 37.733 | 32.979 | 1.00 | 63.15 | Y | O |
| ATOM | 7747 | N | ALA | 83 | 61.447 | 38.867 | 34.256 | 1.00 | 34.42 | Y | N |
| ATOM | 7748 | CA | ALA | 83 | 62.601 | 38.015 | 34.000 | 1.00 | 34.42 | Y | C |
| ATOM | 7749 | CB | ALA | 83 | 63.138 | 38.260 | 32.595 | 1.00 | 53.93 | Y | C |
| ATOM | 7750 | C | ALA | 83 | 63.669 | 38.353 | 35.036 | 1.00 | 34.42 | Y | C |
| ATOM | 7751 | O | ALA | 83 | 63.389 | 39.033 | 36.025 | 1.00 | 34.42 | Y | O |
| ATOM | 7752 | N | THR | 84 | 64.890 | 37.877 | 34.821 | 1.00 | 50.51 | Y | N |
| ATOM | 7753 | CA | THR | 84 | 65.968 | 38.161 | 35.758 | 1.00 | 50.51 | Y | C |
| ATOM | 7754 | CB | THR | 84 | 66.566 | 36.849 | 36.323 | 1.00 | 63.35 | Y | C |
| ATOM | 7755 | OG1 | THR | 84 | 67.888 | 37.096 | 36.819 | 1.00 | 63.35 | Y | O |
| ATOM | 7756 | CG2 | THR | 84 | 66.584 | 35.766 | 35.260 | 1.00 | 63.35 | Y | C |
| ATOM | 7757 | C | THR | 84 | 67.028 | 39.021 | 35.065 | 1.00 | 50.51 | Y | C |
| ATOM | 7758 | O | THR | 84 | 67.474 | 38.708 | 33.959 | 1.00 | 50.51 | Y | O |
| ATOM | 7759 | N | TYR | 85 | 67.401 | 40.119 | 35.723 | 1.00 | 40.66 | Y | N |
| ATOM | 7760 | CA | TYR | 85 | 68.364 | 41.076 | 35.187 | 1.00 | 40.66 | Y | C |
| ATOM | 7761 | CB | TYR | 85 | 67.819 | 42.503 | 35.330 | 1.00 | 42.00 | Y | C |
| ATOM | 7762 | CG | TYR | 85 | 66.476 | 42.693 | 34.668 | 1.00 | 42.00 | Y | C |
| ATOM | 7763 | CD1 | TYR | 85 | 65.330 | 42.084 | 35.185 | 1.00 | 42.00 | Y | C |
| ATOM | 7764 | CE1 | TYR | 85 | 64.110 | 42.163 | 34.521 | 1.00 | 42.00 | Y | C |
| ATOM | 7765 | CD2 | TYR | 85 | 66.363 | 43.401 | 33.472 | 1.00 | 42.00 | Y | C |
| ATOM | 7766 | CE2 | TYR | 85 | 65.148 | 43.486 | 32.800 | 1.00 | 42.00 | Y | C |
| ATOM | 7767 | CZ | TYR | 85 | 64.028 | 42.860 | 33.327 | 1.00 | 42.00 | Y | C |
| ATOM | 7768 | OH | TYR | 85 | 62.841 | 42.889 | 32.633 | 1.00 | 42.00 | Y | O |
| ATOM | 7769 | C | TYR | 85 | 69.746 | 41.012 | 35.816 | 1.00 | 40.66 | Y | C |
| ATOM | 7770 | O | TYR | 85 | 69.891 | 40.982 | 37.042 | 1.00 | 40.66 | Y | O |
| ATOM | 7771 | N | TYR | 86 | 70.756 | 41.016 | 34.949 | 1.00 | 43.34 | Y | N |
| ATOM | 7772 | CA | TYR | 86 | 72.159 | 40.970 | 35.349 | 1.00 | 43.34 | Y | C |
| ATOM | 7773 | CB | TYR | 86 | 72.890 | 39.833 | 34.633 | 1.00 | 34.52 | Y | C |
| ATOM | 7774 | CG | TYR | 86 | 72.406 | 38.441 | 34.941 | 1.00 | 34.52 | Y | C |
| ATOM | 7775 | CD1 | TYR | 86 | 72.902 | 37.731 | 36.040 | 1.00 | 34.52 | Y | C |
| ATOM | 7776 | CE1 | TYR | 86 | 72.472 | 36.433 | 36.303 | 1.00 | 34.52 | Y | C |
| ATOM | 7777 | CD2 | TYR | 86 | 71.466 | 37.820 | 34.118 | 1.00 | 34.52 | Y | C |
| ATOM | 7778 | CE2 | TYR | 86 | 71.031 | 36.530 | 34.375 | 1.00 | 34.52 | Y | C |
| ATOM | 7779 | CZ | TYR | 86 | 71.538 | 35.841 | 35.462 | 1.00 | 34.52 | Y | C |
| ATOM | 7780 | OH | TYR | 86 | 71.124 | 34.549 | 35.683 | 1.00 | 34.52 | Y | O |
| ATOM | 7781 | C | TYR | 86 | 72.873 | 42.259 | 34.957 | 1.00 | 43.34 | Y | C |
| ATOM | 7782 | O | TYR | 86 | 72.662 | 42.780 | 33.851 | 1.00 | 43.34 | Y | O |
| ATOM | 7783 | N | CYS | 87 | 73.706 | 42.773 | 35.862 | 1.00 | 31.05 | Y | N |
| ATOM | 7784 | CA | CYS | 87 | 74.499 | 43.945 | 35.548 | 1.00 | 31.05 | Y | C |
| ATOM | 7785 | C | CYS | 87 | 75.857 | 43.346 | 35.237 | 1.00 | 31.05 | Y | C |
| ATOM | 7786 | O | CYS | 87 | 76.171 | 42.248 | 35.707 | 1.00 | 31.05 | Y | O |
| ATOM | 7787 | CB | CYS | 87 | 74.587 | 44.922 | 36.721 | 1.00 | 63.19 | Y | C |
| ATOM | 7788 | SG | CYS | 87 | 75.151 | 44.318 | 38.354 | 1.00 | 63.19 | Y | S |
| ATOM | 7789 | N | GLN | 88 | 76.653 | 44.040 | 34.431 | 1.00 | 35.54 | Y | N |
| ATOM | 7790 | CA | GLN | 88 | 77.964 | 43.536 | 34.058 | 1.00 | 35.54 | Y | C |
| ATOM | 7791 | CB | GLN | 88 | 77.834 | 42.732 | 32.769 | 1.00 | 42.46 | Y | C |
| ATOM | 7792 | CG | GLN | 88 | 79.114 | 42.125 | 32.259 | 1.00 | 42.46 | Y | C |
| ATOM | 7793 | CD | GLN | 88 | 79.594 | 42.783 | 30.983 | 1.00 | 42.46 | Y | C |
| ATOM | 7794 | OE1 | GLN | 88 | 78.834 | 42.928 | 30.019 | 1.00 | 42.46 | Y | O |
| ATOM | 7795 | NE2 | GLN | 88 | 80.863 | 43.183 | 30.965 | 1.00 | 42.46 | Y | N |
| ATOM | 7796 | C | GLN | 88 | 78.930 | 44.691 | 33.873 | 1.00 | 35.54 | Y | C |
| ATOM | 7797 | O | GLN | 88 | 78.530 | 45.774 | 33.436 | 1.00 | 35.54 | Y | O |
| ATOM | 7798 | N | GLN | 89 | 80.195 | 44.465 | 34.216 | 1.00 | 24.85 | Y | N |
| ATOM | 7799 | CA | GLN | 89 | 81.208 | 45.502 | 34.082 | 1.00 | 24.85 | Y | C |
| ATOM | 7800 | CB | GLN | 89 | 81.794 | 45.851 | 35.458 | 1.00 | 29.69 | Y | C |
| ATOM | 7801 | CG | GLN | 89 | 82.481 | 44.722 | 36.182 | 1.00 | 29.69 | Y | C |
| ATOM | 7802 | CD | GLN | 89 | 83.903 | 44.496 | 35.696 | 1.00 | 29.69 | Y | C |
| ATOM | 7803 | OE1 | GLN | 89 | 84.676 | 45.442 | 35.535 | 1.00 | 29.69 | Y | O |
| ATOM | 7804 | NE2 | GLN | 89 | 84.261 | 43.238 | 35.476 | 1.00 | 29.69 | Y | N |
| ATOM | 7805 | C | GLN | 89 | 82.294 | 45.043 | 33.128 | 1.00 | 24.85 | Y | C |
| ATOM | 7806 | O | GLN | 89 | 82.527 | 43.853 | 32.990 | 1.00 | 24.85 | Y | O |
| ATOM | 7807 | N | TRP | 90 | 82.943 | 45.993 | 32.460 | 1.00 | 39.13 | Y | N |
| ATOM | 7808 | CA | TRP | 90 | 84.008 | 45.672 | 31.510 | 1.00 | 39.13 | Y | C |
| ATOM | 7809 | CB | TRP | 90 | 83.529 | 45.955 | 30.069 | 1.00 | 30.35 | Y | C |
| ATOM | 7810 | CG | TRP | 90 | 83.422 | 47.437 | 29.678 | 1.00 | 30.35 | Y | C |
| ATOM | 7811 | CD2 | TRP | 90 | 83.088 | 47.967 | 28.385 | 1.00 | 30.35 | Y | C |

Fig. 19: A-108

| | | | | | | | | | | | |
|---|---|---|---|---|---|---|---|---|---|---|---|
| ATOM | 7812 | CE2 | TRP | 90 | 83.122 | 49.375 | 28.486 | 1.00 | 30.35 | Y | C |
| ATOM | 7813 | CE3 | TRP | 90 | 82.762 | 47.389 | 27.152 | 1.00 | 30.35 | Y | C |
| ATOM | 7814 | CD1 | TRP | 90 | 83.635 | 48.523 | 30.484 | 1.00 | 30.35 | Y | C |
| ATOM | 7815 | NE1 | TRP | 90 | 83.460 | 49.686 | 29.776 | 1.00 | 30.35 | Y | N |
| ATOM | 7816 | CZ2 | TRP | 90 | 82.840 | 50.217 | 27.398 | 1.00 | 30.35 | Y | C |
| ATOM | 7817 | CZ3 | TRP | 90 | 82.480 | 48.232 | 26.063 | 1.00 | 30.35 | Y | C |
| ATOM | 7818 | CH2 | TRP | 90 | 82.522 | 49.627 | 26.199 | 1.00 | 30.35 | Y | C |
| ATOM | 7819 | C | TRP | 90 | 85.290 | 46.457 | 31.816 | 1.00 | 39.13 | Y | C |
| ATOM | 7820 | O | TRP | 90 | 86.293 | 46.339 | 31.115 | 1.00 | 39.13 | Y | O |
| ATOM | 7821 | N | SER | 91 | 85.251 | 47.254 | 32.876 | 1.00 | 18.51 | Y | N |
| ATOM | 7822 | CA | SER | 91 | 86.395 | 48.067 | 33.257 | 1.00 | 18.51 | Y | C |
| ATOM | 7823 | CB | SER | 91 | 85.948 | 49.152 | 34.237 | 1.00 | 45.24 | Y | C |
| ATOM | 7824 | OG | SER | 91 | 84.909 | 49.937 | 33.686 | 1.00 | 45.24 | Y | O |
| ATOM | 7825 | C | SER | 91 | 87.555 | 47.267 | 33.866 | 1.00 | 18.51 | Y | C |
| ATOM | 7826 | O | SER | 91 | 88.717 | 47.649 | 33.739 | 1.00 | 18.51 | Y | O |
| ATOM | 7827 | N | GLY | 92 | 87.241 | 46.166 | 34.534 | 1.00 | 40.34 | Y | N |
| ATOM | 7828 | CA | GLY | 92 | 88.282 | 45.360 | 35.146 | 1.00 | 40.34 | Y | C |
| ATOM | 7829 | C | GLY | 92 | 88.273 | 43.910 | 34.687 | 1.00 | 40.34 | Y | C |
| ATOM | 7830 | O | GLY | 92 | 87.248 | 43.386 | 34.244 | 1.00 | 40.34 | Y | O |
| ATOM | 7831 | N | ASN | 93 | 89.420 | 43.249 | 34.801 | 1.00 | 37.36 | Y | N |
| ATOM | 7832 | CA | ASN | 93 | 89.544 | 41.863 | 34.380 | 1.00 | 37.36 | Y | C |
| ATOM | 7833 | CB | ASN | 93 | 90.765 | 41.702 | 33.492 | 1.00 | 14.59 | Y | C |
| ATOM | 7834 | CG | ASN | 93 | 90.634 | 42.451 | 32.208 | 1.00 | 14.59 | Y | C |
| ATOM | 7835 | OD1 | ASN | 93 | 91.556 | 43.159 | 31.796 | 1.00 | 14.59 | Y | O |
| ATOM | 7836 | ND2 | ASN | 93 | 89.482 | 42.305 | 31.552 | 1.00 | 14.59 | Y | N |
| ATOM | 7837 | C | ASN | 93 | 89.668 | 40.944 | 35.574 | 1.00 | 37.36 | Y | C |
| ATOM | 7838 | O | ASN | 93 | 90.346 | 41.265 | 36.539 | 1.00 | 37.36 | Y | O |
| ATOM | 7839 | N | PRO | 94 | 89.005 | 39.783 | 35.525 | 1.00 | 28.71 | Y | N |
| ATOM | 7840 | CD | PRO | 94 | 88.990 | 38.808 | 36.629 | 1.00 | 9.29 | Y | C |
| ATOM | 7841 | CA | PRO | 94 | 88.167 | 39.322 | 34.412 | 1.00 | 28.71 | Y | C |
| ATOM | 7842 | CB | PRO | 94 | 87.940 | 37.858 | 34.745 | 1.00 | 9.29 | Y | C |
| ATOM | 7843 | CG | PRO | 94 | 87.823 | 37.904 | 36.251 | 1.00 | 9.29 | Y | C |
| ATOM | 7844 | C | PRO | 94 | 86.845 | 40.076 | 34.372 | 1.00 | 28.71 | Y | C |
| ATOM | 7845 | O | PRO | 94 | 86.418 | 40.640 | 35.384 | 1.00 | 28.71 | Y | O |
| ATOM | 7846 | N | TRP | 95 | 86.200 | 40.084 | 33.206 | 1.00 | 37.86 | Y | N |
| ATOM | 7847 | CA | TRP | 95 | 84.910 | 40.743 | 33.082 | 1.00 | 37.86 | Y | C |
| ATOM | 7848 | CB | TRP | 95 | 84.428 | 40.762 | 31.629 | 1.00 | 24.14 | Y | C |
| ATOM | 7849 | CG | TRP | 95 | 85.220 | 41.665 | 30.744 | 1.00 | 24.14 | Y | C |
| ATOM | 7850 | CD2 | TRP | 95 | 85.537 | 41.458 | 29.359 | 1.00 | 24.14 | Y | C |
| ATOM | 7851 | CE2 | TRP | 95 | 86.285 | 42.575 | 28.929 | 1.00 | 24.14 | Y | C |
| ATOM | 7852 | CE3 | TRP | 95 | 85.264 | 40.437 | 28.440 | 1.00 | 24.14 | Y | C |
| ATOM | 7853 | CD1 | TRP | 95 | 85.770 | 42.867 | 31.085 | 1.00 | 24.14 | Y | C |
| ATOM | 7854 | NE1 | TRP | 95 | 86.411 | 43.419 | 30.000 | 1.00 | 24.14 | Y | N |
| ATOM | 7855 | CZ2 | TRP | 95 | 86.765 | 42.697 | 27.624 | 1.00 | 24.14 | Y | C |
| ATOM | 7856 | CZ3 | TRP | 95 | 85.748 | 40.566 | 27.133 | 1.00 | 24.14 | Y | C |
| ATOM | 7857 | CH2 | TRP | 95 | 86.487 | 41.685 | 26.744 | 1.00 | 24.14 | Y | C |
| ATOM | 7858 | C | TRP | 95 | 83.959 | 39.922 | 33.941 | 1.00 | 37.86 | Y | C |
| ATOM | 7859 | O | TRP | 95 | 83.997 | 38.688 | 33.920 | 1.00 | 37.86 | Y | O |
| ATOM | 7860 | N | THR | 96 | 83.105 | 40.605 | 34.695 | 1.00 | 19.88 | Y | N |
| ATOM | 7861 | CA | THR | 96 | 82.192 | 39.913 | 35.582 | 1.00 | 19.88 | Y | C |
| ATOM | 7862 | CB | THR | 96 | 82.692 | 40.028 | 37.038 | 1.00 | 22.31 | Y | C |
| ATOM | 7863 | OG1 | THR | 96 | 82.747 | 41.408 | 37.404 | 1.00 | 22.31 | Y | O |
| ATOM | 7864 | CG2 | THR | 96 | 84.091 | 39.443 | 37.186 | 1.00 | 22.31 | Y | C |
| ATOM | 7865 | C | THR | 96 | 80.759 | 40.413 | 35.508 | 1.00 | 19.88 | Y | C |
| ATOM | 7866 | O | THR | 96 | 80.500 | 41.491 | 34.998 | 1.00 | 19.88 | Y | O |
| ATOM | 7867 | N | PHE | 97 | 79.839 | 39.596 | 36.015 | 1.00 | 20.15 | Y | N |
| ATOM | 7868 | CA | PHE | 97 | 78.420 | 39.912 | 36.073 | 1.00 | 20.15 | Y | C |
| ATOM | 7869 | CB | PHE | 97 | 77.580 | 38.827 | 35.397 | 1.00 | 25.28 | Y | C |
| ATOM | 7870 | CG | PHE | 97 | 77.890 | 38.613 | 33.946 | 1.00 | 25.28 | Y | C |
| ATOM | 7871 | CD1 | PHE | 97 | 79.062 | 37.994 | 33.554 | 1.00 | 25.28 | Y | C |
| ATOM | 7872 | CD2 | PHE | 97 | 76.979 | 38.990 | 32.969 | 1.00 | 25.28 | Y | C |
| ATOM | 7873 | CE1 | PHE | 97 | 79.322 | 37.750 | 32.204 | 1.00 | 25.28 | Y | C |
| ATOM | 7874 | CE2 | PHE | 97 | 77.234 | 38.748 | 31.611 | 1.00 | 25.28 | Y | C |
| ATOM | 7875 | CZ | PHE | 97 | 78.404 | 38.128 | 31.233 | 1.00 | 25.28 | Y | C |
| ATOM | 7876 | C | PHE | 97 | 78.054 | 39.931 | 37.557 | 1.00 | 20.15 | Y | C |
| ATOM | 7877 | O | PHE | 97 | 78.841 | 39.487 | 38.394 | 1.00 | 20.15 | Y | O |
| ATOM | 7878 | N | GLY | 98 | 76.875 | 40.460 | 37.879 | 1.00 | 30.22 | Y | N |
| ATOM | 7879 | CA | GLY | 98 | 76.412 | 40.488 | 39.256 | 1.00 | 30.22 | Y | C |
| ATOM | 7880 | C | GLY | 98 | 75.676 | 39.178 | 39.406 | 1.00 | 30.22 | Y | C |
| ATOM | 7881 | O | GLY | 98 | 75.506 | 38.478 | 38.405 | 1.00 | 30.22 | Y | O |
| ATOM | 7882 | N | GLN | 99 | 75.235 | 38.819 | 40.608 | 1.00 | 24.51 | Y | N |
| ATOM | 7883 | CA | GLN | 99 | 74.537 | 37.541 | 40.755 | 1.00 | 24.51 | Y | C |
| ATOM | 7884 | CB | GLN | 99 | 74.350 | 37.163 | 42.231 | 1.00 | 60.71 | Y | C |

Fig. 19: A-109

| | | | | | | | | | | | |
|---|---|---|---|---|---|---|---|---|---|---|---|
| ATOM | 7885 | CG | GLN | 99 | 74.599 | 38.274 | 43.209 | 1.00 | 60.71 | Y | C |
| ATOM | 7886 | CD | GLN | 99 | 73.728 | 39.464 | 42.945 | 1.00 | 60.71 | Y | C |
| ATOM | 7887 | OE1 | GLN | 99 | 72.510 | 39.411 | 43.113 | 1.00 | 60.71 | Y | O |
| ATOM | 7888 | NE2 | GLN | 99 | 74.346 | 40.551 | 42.515 | 1.00 | 60.71 | Y | N |
| ATOM | 7889 | C | GLN | 99 | 73.189 | 37.507 | 40.043 | 1.00 | 24.51 | Y | C |
| ATOM | 7890 | O | GLN | 99 | 72.587 | 36.443 | 39.894 | 1.00 | 24.51 | Y | O |
| ATOM | 7891 | N | GLY | 100 | 72.730 | 38.666 | 39.586 | 1.00 | 42.40 | Y | N |
| ATOM | 7892 | CA | GLY | 100 | 71.455 | 38.725 | 38.900 | 1.00 | 42.40 | Y | C |
| ATOM | 7893 | C | GLY | 100 | 70.355 | 39.043 | 39.886 | 1.00 | 42.40 | Y | C |
| ATOM | 7894 | O | GLY | 100 | 70.483 | 38.749 | 41.074 | 1.00 | 42.40 | Y | O |
| ATOM | 7895 | N | THR | 101 | 69.283 | 39.662 | 39.399 | 1.00 | 27.30 | Y | N |
| ATOM | 7896 | CA | THR | 101 | 68.144 | 40.021 | 40.236 | 1.00 | 27.30 | Y | C |
| ATOM | 7897 | CB | THR | 101 | 68.024 | 41.538 | 40.401 | 1.00 | 28.79 | Y | C |
| ATOM | 7898 | OG1 | THR | 101 | 69.008 | 41.995 | 41.336 | 1.00 | 28.79 | Y | O |
| ATOM | 7899 | CG2 | THR | 101 | 66.646 | 41.907 | 40.892 | 1.00 | 28.79 | Y | C |
| ATOM | 7900 | C | THR | 101 | 66.903 | 39.492 | 39.551 | 1.00 | 27.30 | Y | C |
| ATOM | 7901 | O | THR | 101 | 66.619 | 39.845 | 38.408 | 1.00 | 27.30 | Y | O |
| ATOM | 7902 | N | LYS | 102 | 66.166 | 38.635 | 40.240 | 1.00 | 67.88 | Y | N |
| ATOM | 7903 | CA | LYS | 102 | 64.978 | 38.064 | 39.642 | 1.00 | 67.88 | Y | C |
| ATOM | 7904 | CB | LYS | 102 | 64.806 | 36.618 | 40.106 | 1.00 | 117.75 | Y | C |
| ATOM | 7905 | CG | LYS | 102 | 63.920 | 35.785 | 39.198 | 1.00 | 117.75 | Y | C |
| ATOM | 7906 | CD | LYS | 102 | 63.925 | 34.321 | 39.608 | 1.00 | 117.75 | Y | C |
| ATOM | 7907 | CE | LYS | 102 | 63.094 | 33.485 | 38.651 | 1.00 | 117.75 | Y | C |
| ATOM | 7908 | NZ | LYS | 102 | 63.586 | 33.621 | 37.250 | 1.00 | 117.75 | Y | N |
| ATOM | 7909 | C | LYS | 102 | 63.749 | 38.885 | 39.996 | 1.00 | 67.88 | Y | C |
| ATOM | 7910 | O | LYS | 102 | 63.560 | 39.262 | 41.155 | 1.00 | 67.88 | Y | O |
| ATOM | 7911 | N | VAL | 103 | 62.926 | 39.176 | 38.989 | 1.00 | 55.50 | Y | N |
| ATOM | 7912 | CA | VAL | 103 | 61.706 | 39.941 | 39.208 | 1.00 | 55.50 | Y | C |
| ATOM | 7913 | CB | VAL | 103 | 61.779 | 41.349 | 38.510 | 1.00 | 68.46 | Y | C |
| ATOM | 7914 | CG1 | VAL | 103 | 63.207 | 41.865 | 38.530 | 1.00 | 68.46 | Y | C |
| ATOM | 7915 | CG2 | VAL | 103 | 61.258 | 41.290 | 37.084 | 1.00 | 68.46 | Y | C |
| ATOM | 7916 | C | VAL | 103 | 60.489 | 39.141 | 38.709 | 1.00 | 55.50 | Y | C |
| ATOM | 7917 | O | VAL | 103 | 60.378 | 38.828 | 37.517 | 1.00 | 55.50 | Y | O |
| ATOM | 7918 | N | GLU | 104 | 59.597 | 38.779 | 39.633 | 1.00 | 70.95 | Y | N |
| ATOM | 7919 | CA | GLU | 104 | 58.395 | 38.025 | 39.281 | 1.00 | 70.95 | Y | C |
| ATOM | 7920 | CB | GLU | 104 | 58.243 | 36.764 | 40.145 | 1.00 | 145.77 | Y | C |
| ATOM | 7921 | CG | GLU | 104 | 57.957 | 37.019 | 41.616 | 1.00 | 145.77 | Y | C |
| ATOM | 7922 | CD | GLU | 104 | 59.215 | 37.263 | 42.418 | 1.00 | 145.77 | Y | C |
| ATOM | 7923 | OE1 | GLU | 104 | 59.106 | 37.542 | 43.631 | 1.00 | 145.77 | Y | O |
| ATOM | 7924 | OE2 | GLU | 104 | 60.315 | 37.167 | 41.839 | 1.00 | 145.77 | Y | O |
| ATOM | 7925 | C | GLU | 104 | 57.157 | 38.897 | 39.443 | 1.00 | 70.95 | Y | C |
| ATOM | 7926 | O | GLU | 104 | 57.197 | 39.939 | 40.108 | 1.00 | 70.95 | Y | O |
| ATOM | 7927 | N | ILE | 105 | 56.058 | 38.459 | 38.834 | 1.00 | 139.77 | Y | N |
| ATOM | 7928 | CA | ILE | 105 | 54.791 | 39.184 | 38.876 | 1.00 | 139.77 | Y | C |
| ATOM | 7929 | CB | ILE | 105 | 53.838 | 38.730 | 37.757 | 1.00 | 105.35 | Y | C |
| ATOM | 7930 | CG2 | ILE | 105 | 52.923 | 39.875 | 37.373 | 1.00 | 105.35 | Y | C |
| ATOM | 7931 | CG1 | ILE | 105 | 54.633 | 38.232 | 36.553 | 1.00 | 105.35 | Y | C |
| ATOM | 7932 | CD1 | ILE | 105 | 53.775 | 37.746 | 35.397 | 1.00 | 105.35 | Y | C |
| ATOM | 7933 | C | ILE | 105 | 54.047 | 38.952 | 40.180 | 1.00 | 139.77 | Y | C |
| ATOM | 7934 | O | ILE | 105 | 53.763 | 37.810 | 40.533 | 1.00 | 139.77 | Y | O |
| ATOM | 7935 | N | LYS | 106 | 53.706 | 40.031 | 40.880 | 1.00 | 101.75 | Y | N |
| ATOM | 7936 | CA | LYS | 106 | 52.969 | 39.916 | 42.135 | 1.00 | 101.75 | Y | C |
| ATOM | 7937 | CB | LYS | 106 | 53.545 | 40.870 | 43.189 | 1.00 | 95.13 | Y | C |
| ATOM | 7938 | CG | LYS | 106 | 52.954 | 40.690 | 44.584 | 1.00 | 95.13 | Y | C |
| ATOM | 7939 | CD | LYS | 106 | 53.556 | 41.665 | 45.586 | 1.00 | 95.13 | Y | C |
| ATOM | 7940 | CE | LYS | 106 | 52.939 | 41.482 | 46.965 | 1.00 | 95.13 | Y | C |
| ATOM | 7941 | NZ | LYS | 106 | 53.446 | 42.478 | 47.948 | 1.00 | 95.13 | Y | N |
| ATOM | 7942 | C | LYS | 106 | 51.492 | 40.235 | 41.897 | 1.00 | 101.75 | Y | C |
| ATOM | 7943 | O | LYS | 106 | 51.148 | 40.637 | 40.765 | 1.00 | 100.80 | Y | O |
| ATOM | 7944 | OXT | LYS | 106 | 50.694 | 40.080 | 42.844 | 1.00 | 94.18 | Y | O |
| ATOM | 7945 | MN | MN | 400 | 89.864 | 50.249 | 22.621 | 1.00 | 34.24 | N | |

END

ANTIBODIES TO VLA-1

CROSS-REFERENCE TO RELATED APPLICATIONS

This application is a continuation of U.S. application Ser. No. 14/597,262, filed Jan. 15, 2015, which is a divisional application of U.S. application Ser. No. 13/297,124, filed Nov. 15, 2011, which is a continuation of U.S. application Ser. No. 13/017,919, filed Jan. 31, 2011 (which issued as U.S. Pat. No. 8,084,028 on Dec. 27, 2011), which is a continuation application of U.S. application Ser. No. 12/727,965, filed Mar. 19, 2010 (which issued as U.S. Pat. No. 7,910,099 on Mar. 22, 2011), which is a divisional application of U.S. application Ser. No. 12/015,213, filed Jan. 16, 2008 (which issued as U.S. Pat. No. 7,723,073 on May 25, 2010), which is a divisional application of U.S. application Ser. No. 10/474,832, filed Oct. 14, 2003 (which issued as U.S. Pat. No. 7,358,054 on Apr. 15, 2008), which is the National Stage filing under 35 U.S.C. § 371 of International Application No. PCT/US02/11521, filed Apr. 12, 2002, which claims benefit under 35 U.S.C. § 119(e) of U.S. provisional application No. 60/283,794, filed Apr. 13, 2001, and 60/303,689, filed Jul. 6, 2001, the entire contents of each of which are expressly incorporated by reference in their entireties.

FIELD OF THE INVENTION

This invention relates to antibodies to VLA-1 integrin and the use of these antibodies in treating inflammatory diseases and other immunological disorders.

This invention also relates to the crystal structure of the complex between one such antibody and the α1-I domain of VLA-1, and to the use of this structural information for computational drug design.

BACKGROUND OF THE INVENTION

Integrins are a superfamily of cell surface receptors that mediate cell-cell and cell-matrix adhesion. These proteins are known to provide anchorage as well as signals for cellular growth, migration and differentiation during development and tissue repair. They have been implicated in immune and inflammatory processes.

Integrins are heterodimeric proteins composed of two noncovalently linked polypeptide chains, α and β. The amino terminus of each chain forms a globular head that contributes to interchain linking and to ligand binding. The globular heads are connected to the transmembrane segments by stalks. The cytoplasmic tails are usually less than 50 amino acid residues long. Integrin subfamilies were originally defined on the basis of which β subunit was used to form the heterodimers. The β1-containing integrins are also called VLA molecules, referring to "very late activation" antigens. VLA-1 to VLA-6 refer to β1 subfamily members containing α1 to α6 (i.e., CD49a to CD49f), respectively. For general review, see Cellular and Molecular Immunology, eds. Abul K. Abbas et al., W. B. Saunders Company, Philadelphia, Pa., 2000.

Collagen (both types I and IV) and laminin are known ligands of α1β1 integrin (i.e., VLA-1). VLA-1 has been implicated in cell adhesion and migration on collagen (Keely et al., 1995, J. Cell Sci. 108:595-607; and Gotwals et al., 1996, J. Clin. Invest. 97:2469-2477); in promoting contraction and reorganization of collagen matrices, a critical component of wound healing (Gotwals et al., supra; and Chiro, 1991, Cell 67:403-410); and in regulating the expression of genes involved in extracellular matrix remodeling (Riikonen et al., 1995, J. Biol. Chem. 270:1-5; and Langholz et al., 1995, J. Cell Biol. 131:1903-1915). Thus, improper regulation of VLA-1 may result in certain pathological conditions such as fibrosis.

Moreover, it has been suggested that VLA-1 may play a role in T cell/monocyte-driven diseases. Anti-VLA-1 antibodies block T-cell dependent cytokine expression (Miyake et al., 1993, J. Exp. Med. 177:863-868). Expression of VLA-1 is increased in persistently activated, 2 to 4 week old cultured T cells (Hemler et al., 1985, Eur. J. Immunol. 15:502-508). VLA-1 is also expressed on a high percentage of T cells isolated from the synovium of patients with rheumatoid arthritis (Hemler et al., 1986, J. Clin. Invest. 78:692-702).

Several crystal structures of integrin a subunits have been determined, including the structures of the α2-I domain of α2β1 (PDB accession code 1aox; Emsley et al., 1997, J. Biol. Chem. 272:28512-28517); the α1-I domain of rat α1β1 (PDB accession number 1ck4; Nolte et al., 1999, FEBS Lett. 452:379-85; WO 00/20459); the α1 subunit of human α1β1 (PDB accession code 1qc5; Rich et al., 1999, J. Biol. Chem. 274:24906-24913); the αL-I and αM-I domains; and vWF-A3 (Lee et al., 1995, Cell 80:631-635; Lee et al., 1995, Structure 3:1333-1340; Qu et al., 1995, Proc. Natl. Acad. Sci. USA 92:10277-10281; Qu et al., 1996, Structure 4:931-942). The α2β1 structure revealed a helix (i.e., the C-helix) that created a trench or groove on one face of the protein at the metal-ion binding site (Emsley et al., supra). The crystal structure of the α2-I domain complexed to a short collagen-based triple helical peptide revealed that the collagen-based peptide was bound to that trench, where the α2-I amino acids that made intermolecular or metal contacts included Asp151, Asn154, Tyr157, Gln215, Asp219, Leu220, Thr221, Asp254, Glu256, His258, Tyr285, Leu286, Asn289, Leu291, Asn295, and Lys298 (PDB accession code 1dzi; Emsley et al., 2000, Cell 101:47-56; WO 01/73444). The amino acid numbering immediately above is based on PDB accession code 1dzi and herein referred to as "crystal numbering." The crystal structures of the rat and human α1-I domains revealed a similar trench.

SUMMARY OF THE INVENTION

The present invention provides anti-VLA-1 antibodies and methods of using these antibodies to treat a variety of inflammatory and immunological disorders.

Specifically, the invention embraces an antibody that specifically binds to VLA-1 (e.g., human VLA-1). This antibody contains light chain complementarity determining regions ("CDR"s) defined by amino acid residues 24 to 33, 49 to 55, and 88 to 96 of SEQ ID NO:1, and/or heavy chain complementarity determining regions defined by amino acid residues 31 to 35, 50 to 65, and 98 to 107 of SEQ ID NO:2. These CDRs may contain mutations (e.g., deletions, insertions and/or substitutions) in the non-antigen-contacting portions, as determined from the crystal structure disclosed herein, without affecting the VLA-1-binding activity of the antibody. Exemplary mutations are S24N, G92S and D101A in the light chain CDRs, and G55S in the heavy chain CDR2. In one embodiment, the antibody of this invention contains a light chain variable domain sequence of SEQ ID NO:1 and/or a heavy chain variable domain sequence of SEQ ID NO:2.

In a related embodiment, the antibody of this invention contains the same heavy and light chain polypeptide sequences as an antibody produced by hybridoma mAQC2, deposited on Apr. 18, 2001 at the American Type Culture Collection ("ATCC"), 10801 University Boulevard, Manassas, Va. 20110-2209 and having ATCC accession number PTA3273. (All ATCC deposits recited herein were made under the Budapest Treaty). This antibody can be produced by, for example, hybridoma mAQC2, or cells containing nucleic acid sequences isolated from that hybridoma that encode the heavy and light chains of the mAQC2 monoclonal antibody.

In another embodiment, the antibody is a humanized antibody comprising at least one (e.g., 2, 3, 4, or 5) of the following residues in its light chain: Q1, L4, P46, W47 and Y71; or at least one (e.g., 2, 3, 4, 5, 6 or 7) of the following residues in its heavy chain: D1, V12, S28, F29, A49, T93, R94 (Kabat numbering convention). For instance, the antibody comprises Q1, L4 and Y71 in the light chain; and/or (i) F29, A49, T93 and R94, or (ii) A49 and T93, in the heavy chain.

The humanized antibody of this invention may contain a light chain variable domain sequence defined by amino acid residues 1 to 106 of SEQ ID NO:3, and/or a heavy chain variable domain sequence defined by amino acid residues 1 to 118 of SEQ ID NO:4. The humanized antibody may comprise the same heavy and/or light chain polypeptide sequences as an antibody produced by cell line hAQC2 (ATCC accession number PTA3275; deposited on Apr. 18, 2001).

In another embodiment, the humanized antibody of this invention may contain a mutation (e.g., deletion, substitution or addition) at one or more (e.g., 2, 3, 4, 5, 6, 7 or 8) of certain positions in the heavy chain such that an effector function of the antibody (e.g., the ability of the antibody to bind to a Fc receptor or a complement factor) is altered without affecting the antibody's ability to bind to VLA-1 (U.S. Pat. No. 5,648,260). These heavy chain positions include, without limitation, residues 234, 235, 236, 237, 297, 318, 320 and 322 (EU numbering system). The humanized antibody can, for instance, contain the mutations L234A (i.e., replacing leucine at position 234 of an unmodified antibody with alanine) and L235A (EU numbering system) in its heavy chain. In one related embodiment, the antibody comprises the same heavy chain polypeptide sequence as an antibody produced by cell line hsAQC2 (ATCC accession number PTA3356; deposited on May 4, 2001).

In yet another embodiment, the humanized antibody of this invention may contain a mutation (e.g., deletion or substitution) at an amino acid residue that is a site for glycosylation, such that the glycosylation site is eliminated. Such an antibody may be clinically beneficial for having reduced effector functions or other undesired functions while retaining its VLA-1 binding affinity. Mutations of glycosylation sites can also be beneficial for process development (e.g., protein expression and purification). For instance, the heavy chain of the antibody may contain the mutation N297Q (EU numbering system) such that the heavy chain can no longer be glycosylated at this site. In one related embodiment, the humanized antibody may comprise the same heavy chain polypeptide sequence as an antibody produced by cell line haAQC2 (ATCC accession number PTA3274; deposited on Apr. 18, 2001).

In still other embodiments, the heavy and/or light chains of the antibody of this invention contain mutations that increase affinity for binding to VLA-1 and thereby increase potency for treating VLA-1-mediated disorders.

Embraced in this invention are also a composition containing an antibody of the invention and a pharmaceutically acceptable carrier; an isolated nucleic acid containing a coding sequence for SEQ ID NO:1; an isolated nucleic acid containing a coding sequence for SEQ ID NO:2; an isolated nucleic acid containing a coding sequence for the light chain of an antibody produced by hybridoma mAQC2; an isolated nucleic acid containing a coding sequence for the heavy chain of an antibody produced by hybridoma mAQC2; an isolated nucleic acid containing a coding sequence for the light chain of an antibody produced by cell line hAQC2; an isolated nucleic acid containing a coding sequence for the heavy chain of an antibody produced by cell line hAQC2; an isolated nucleic acid containing a coding sequence for the heavy chain of an antibody produced by cell line haAQC2; an isolated nucleic acid containing a coding sequence for the heavy chain of an antibody produced by cell line hsAQC2; an isolated nucleic acid containing a coding sequence for residues 1 to 106 of SEQ ID NO:3; an isolated nucleic acid containing a coding sequence for residues 1 to 118 of SEQ ID NO:4; cells of hybridoma mAQC2; cells from cell line hAQC2; cells from cell line haAQC2; and cells from cell line hsAQC2.

The present invention also provides a method of treating a subject with an immunological disorder mediated by VLA-1, including administering to the subject an effective amount of an antibody of this invention. For instance, this method is used to treat a human subject to palliate, ameliorate, stabilize, reverse, prevent, slow or delay progression of the disorder. Alternatively, this method is used prophylactically to treat a human subject at risk for developing this immunological disorder so as to prevent or delay the onset of the disorder. An "effective amount" of the composition can be administered in one or more dosages.

VLA-1 mediated immunological disorders include, but are not limited to, disorders in which the VLA-1 activity level is elevated in one or more tissues as compared to a normal subject. Examples of such disorders are skin related conditions (e.g., psoriasis, eczema, burns, dermatitis, and abnormal proliferation of hair follicle cells), fibrosis (e.g., kidney or lung fibrosis), allergic rhinitis, respiratory distress syndrome, asthma, bronchitis, tendinitis, bursitis, fever, migraine headaches, gastrointestinal conditions (e.g., inflammatory bowel disease, Crohn's disease, gastritis, irritable bowel syndrome, colitis and colorectal cancer), vascular diseases (e.g., atherosclerosis), periarteritis nodosa, thyroiditis, aplastic anemia, Hodgkin's Disease, rheumatic fever, osteoarthritis, autoimmune diseases (e.g., type I diabetes, myasthenia gravis, rheumatoid arthritis, systemic lupus erythematosus, and multiple sclerosis), sarcoidosis, nephrotic syndrome, renal failure, Bechet's Syndrome, polymyositis, gingivitis, hypersensitivity (e.g., delayed type hypersensitivity or immediate hypersensitivity), graft and transplant rejections, graft versus host disease (GVHD), conjunctivitis, swelling occurring after injury, myocardial ischemia, and endotoxin shock syndrome.

The present invention also provides a method of determining the level of VLA-1 in a tissue (e.g., tissue specimen and body fluid) comprising contacting the tissue (e.g., in vivo or in vitro) with the antibody of the invention, and then detecting the binding of the antibody to the tissue, thereby determining the level of VLA-1 in the tissue.

As used herein, the antibody of this invention can be, for instance, a murine antibody, a humanized antibody, or a chimeric antibody. It can be a whole antibody (i.e., with two full length light chains and two full length heavy chains) of any isotype and subtypes (e.g., IgM, IgD, $IgG_1$, $IgG_2$, $IgG_3$, $IgG_4$, IgE, $IgA_1$, and $IgA_2$; with either kappa or lambda light chain). Alternatively, the antibody of this invention refers to an antigen-binding fragment (e.g., Fab, $F(ab')_2$, and single chain Fv) of a whole antibody.

The present invention further provides crystallizable compositions and crystals of complexes formed by a rat-human chimeric α1-I domain (mutant RΔH) and a hAQC2 Fab fragment, and methods for using such compositions and crystals. This invention also provides the structure coordinates and binding sites of the chimeric domain and the hAQC2 Fab fragment. The atomic coordinates derived from the crystal structure described herein provide a structural basis for the biological activities of hAQC2 as well as a basis for rational design of VLA-1 agonists or antagonists with predicted biological activities (e.g., small molecule compounds or antibodies such as hAQC2 variants).

The crystal structure disclosed herein is the first crystal structure of an α1-I domain of an α1β1 integrin/Fab complex. This structure shows the residues critical for Fab binding by α1-I domain. In addition, the Fab binds in the putative collagen-binding site and inhibits collagen binding. Amino acid residues found in the binding site on the α1-I domain include Asp154, Ser156, Asn157, Ser158, Tyr160, Glu192, Glu218, Arg219, Gly220, Gly221, Arg222, Gln223, Thr224, Asp257, His261, Asn263, Arg291, and Leu294 (crystal numbering). Residues on the Fab fragment found to bind to the α1-I domain include light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering).

This invention also provides a computer for producing a three-dimensional representation of a molecular complex, where the molecular complex is defined by the set of structure coordinates of a complex of a chimeric I domain of an α1β1 integrin RΔH and humanized antibody hAQC2, according to FIG. 19A-1 to A-109; or a homologue of the molecular complex, the homologue having a root mean square deviation from the backbone atoms of the amino acids of not more than 0.65 Å. The computer includes a machine-readable data storage medium including a data storage material encoded with machine-readable data, where the data contains at least a portion of the structure coordinates of the complex according to FIG. 19A-1 to A-109; a working memory for storing instructions for processing the machine-readable data; a central processing unit coupled to the working memory and to the machine-readable data storage medium for processing the machine readable data into the three-dimensional representations; and a display coupled to the central-processing unit for displaying the three-dimensional representation.

This invention further provides a computer for producing a three-dimensional representation of a molecule or molecular complex including a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19A-1 to A-109; or a homologue of the molecule or molecular complex, where the homologue includes a binding site that has a root mean square deviation from the backbone atoms of the hAQC2 amino acids of not more than 1.10 Å. This invention also provides a computer for producing a three-dimensional representation of: a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19A-1 to A-109; a binding site of a homologue that has a root mean square deviation from the backbone atoms of the hAQC2 amino acids of not more than 1.10 Å.

This invention also provides a method for identifying an inhibitor of an I domain of an integrin including the steps of using structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg39, Trp47, Ser52, Gly53, His56, Tyr58, Phe99, Gly100 and Asp101 (crystal numbering), according to FIG. 19A-1 to A-109 or ±a root mean square deviation from the backbone atoms of the hAQC2 amino acids not more than 1.10 Å, to generate a three-dimensional structure of a binding site; employing the three-dimensional structure to design or select a potential antagonist; synthesizing the potential antagonist; and contacting the potential antagonist with hAQC2 to determine the ability of the potential antagonist to interact with hAQC2, where the ability of the potential antagonist to interact with hAQC2 indicates that the potential antagonist is an inhibitor of the I domain. This invention further provides an inhibitor of I domain of integrin identified by this method.

This invention also provides a computer for producing a three-dimensional representation of a molecule or molecular complex including: a binding site defined by structure coordinates of I domain amino acid residues Asp 154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109; or a homologue of the molecule or molecular complex, where the homologue includes a second binding site that has a root mean square deviation from the backbone atoms of the I domain amino acids not more than 0.65 Å. This invention also provides a computer for producing a three-dimensional representation of: a first binding site defined by structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109; or a binding site of a homologue that has a root mean square deviation from the backbone atoms of the I domain amino acids not more than 0.65 Å.

This invention also provides a computer for producing a three-dimensional representation of a molecule or molecular complex including: a binding site defined by structure coordinates of I domain amino acids including at least three of residues Glu192, Gln218, Arg219, Gly220, and Gly221 (crystal numbering), according to FIG. 19A-1 to A-109; or a homologue of the molecule or molecular complex, where the homologue includes a second binding site that has a root mean square deviation from the backbone atoms of the I domain amino acids not more than 1.0 Å. The invention further provides a computer for producing a three-dimensional representation of a binding site defined by structure coordinates of I domain amino acids including at least three of residues Glu192, Gln218, Arg219, Gly220, and Gly221 (crystal numbering), according to FIG. 19A-1 to A-109; or a binding site of a homologue that has a root mean square deviation from the backbone atoms of the I domain amino acids not more than 1.0 Å.

This invention further provides methods for using these three-dimensional representations to design chemical entities that associate with the chimeric domain or the hAQC2 Fab fragment, or portions thereof; and act as potential inhibitors of the chimeric domain or the hAQC2 Fab fragment, or portions thereof. This invention also relates to compositions including chemical entities, such as inhibitors and variants of the chimeric domain or variants of the hAQC2 Fab fragment, where such chemical entities and variants are rationally designed by means of the structure coordinates of the chimeric domain or the hAQC2 Fab fragment, or binding sites. The invention further relates to use of the above-identified chemical entities to treat or prevent conditions associated with inappropriate or abnormal α1β1 activity in a subject.

This invention further provides a method for identifying an inhibitor of an I domain of an integrin including the steps of using the structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain, where the ability of the potential antagonist to interact with the I domain indicates that the potential antagonist is an inhibitor of the I domain.

This invention also provides a method for identifying an inhibitor of an I domain of an integrin including the steps of using the structure coordinates of at least three of I domain amino acids including residues Glu192, Gln218, Arg219, Gly220, and Gly221 (crystal numbering), according to FIG. 19A-1 to A-109, or ±a root mean square deviation from the backbone atoms of the I domain amino acids not more than 0.65 Å, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain of integrin, where the ability of the potential antagonist to interact with the I domain indicates that the potential antagonist is an inhibitor of the I domain. This invention also provides an inhibitor of I domain of integrin identified by this method.

Other features and advantages of the invention will be apparent from the following detailed description, and from the claims.

BRIEF DESCRIPTION OF THE DRAWINGS

FIG. 1A. Flow cytometric analysis of α1 and α2β1 integrin expression on IL-2-activated splenocytes (d 11). Cells were labeled with either anti-α1 mAb, anti-α2 mAb, or non-binding control mAb (grey lines), and followed by FITC-anti-hamster immunoglobulin. FIG. 1B. Effect of anti-α1 and anti-α2 mAbs on leukocyte adhesion to collagen. $10^5$ IL-2 activated splenocytes were treated with indicated mAbs for 15 min before plating onto either type IV or type I collagen-coated wells for 1 h at 37° C. Adhesion was calculated as illustrated in Example 1, and expressed as % adhesion relative to control mAb-treated cells. Adhesion assays were done in triplicate, and at least three independent experiments were performed. One representative experiment is shown.

FIG. 11A. Amino acid sequence of the rat (top; SEQ ID NO:63) and human (below; residues of SEQ ID NO:64, which are different from rat, are shown) α1-I domain. The residues that comprise the MIDAS (metal ion dependent adhesion site) motif are shown in bold. The human amino acids that replaced the corresponding rat residues (RΔH) are shown below the rat sequence in the boxed region. For clarity, residue numbering in the text refers to this figure, unless otherwise designated, e.g., as crystal numbering. FIG. 11B. Increasing concentrations of mAb AJH10 (ATCC No. PTA-3580; deposited under the Budapest Treaty with the American Type Culture Collection, Manassas, Va., USA on Aug. 2, 2001) were bound to plates coated with 30 μg/ml human (circles), rat (triangles) or RΔH (squares) α1-I domain. Data shown is representative of three experiments.

FIG. 12. Amino acid sequence of the human α1-I domain (SEQ ID NO:64).

FIG. 13A. Increasing concentration of mAbs AEF3 (triangles) or AJH10 (circles) were bound to plates coated with 30 μg/ml α1-I domain. FIG. 13B. The α1-I domain was treated with increasing concentrations of mAb AJH10 (diamonds) or mAb BGCS (squares) and bound collagen IV (2 μg/ml) coated plates. FIG. 13C. K562-α1 cell were treated with increasing concentration of mAbs AEF3 (triangles) or AJH10 (circles) and bound to collagen IV (5 μg/ml) coated plates. 45-50% of cells added to each well adhered to collagen IV. Data shown is representative of three independent experiments.

FIG. 15A. Increasing concentrations of the human α1-I domain were bound to plates previously coated with 1 μg/ml collagen I (squares) or collagen IV (circles). Values shown have been corrected for background binding to BSA. FIG. 15B. 2 μg/ml human α1-I domain was mixed with increasing concentration of an anti-human α1-I integrin antibody 5E8D9 (squares) or an anti-human α2-integrin antibody A2IIE10 (circles), and then bound to plates previously coated with 1 μg/ml collagen IV. FIG. 15C. Plates were coated with 1 μg/ml collagen TV or 3% BSA. α1-I domain (2 μg/ml) was subsequently bound to coated plates in the presence of 1 mM $Mn^{2+}$, 1 mM $Mg^{2+}$, or 5 mM EDTA. Data shown is representative of three independent experiments.

FIG. 16A. Inhibition of VLA-1 binding to type IV collagen.

FIG. 16B. Inhibition of α1-I domain binding to type IV collagen.

FIG. 16C. Binding to immobilized α1-I domain.

FIG. 16D. Competition with biotinylated mAQC2 for binding to immobilized α1-I domain.

FIG. 19A-1 to A-109. Atomic structure coordinates for the α1-I domain/Fab complex, as derived by X-ray crystallography from crystals of that complex in Protein Data Bank (PDB) format. The coordinates of the two complexes in the asymmetric unit are listed as follows.

Complex 1:
molecule A=I domain of integrin
molecule H=heavy chain of hAQC2 Fab
molecule L=light chain of hAQC2 Fab
molecule M=$Mn^{+2}$
Complex 2:
molecule B=I domain of integrin
molecule X=heavy chain of hAQC2 Fab
molecule Y=light chain of hAQC2 Fab
molecule M=$Mn^{+2}$ FIG. 20. I domain-Fab complex. A. Ribbon diagram of the I domain-Fab complex. The I domain and the antibody heavy and light chain are labeled. The $Mn^{+2}$ ion is shown as a sphere. B. Close-up of the MIDAS (Metal-Ion-Dependent-Adhesion-Site) site showing the coordination of the metal ion (sphere) by Asp101 (crystal numbering). The protein backbones are shown as ribbons and the side chains in the ball-and-stick representation. The cylinders represent interactions between the metal ion and protein atoms. The thin lines represent H-bonds.

DETAILED DESCRIPTION OF THE INVENTION

Figure 1A:
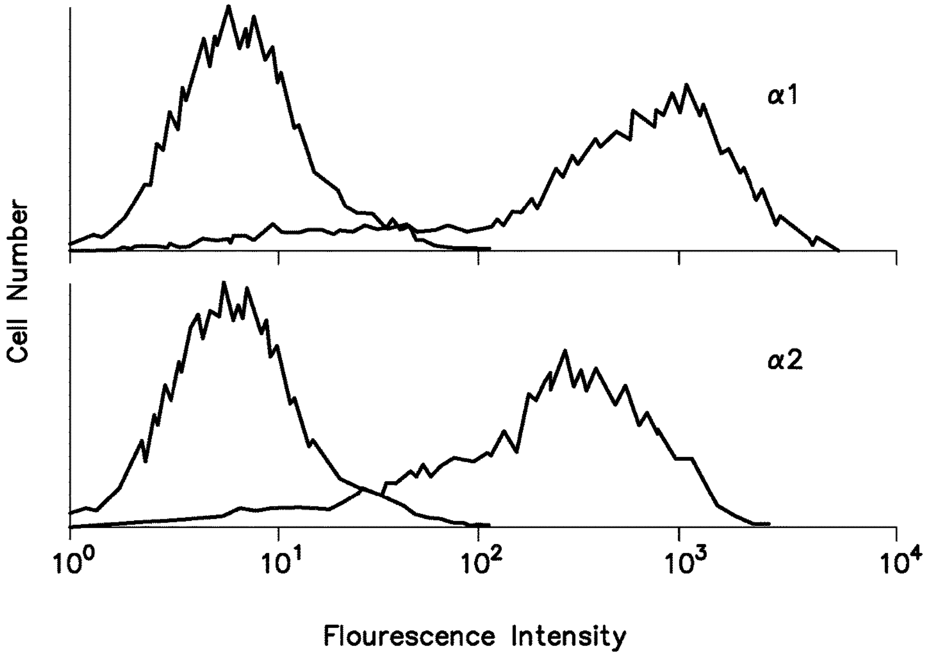
FIG. 1A-B. Collagen-binding integrins α1β1 and α2β1 on activated leukocytes.

It is a discovery of the present invention that an antibody to an integrin (e.g., VLA-1) and fragment thereof, particularly, an α1-integrin subunit, can block the interaction of pro-inflammatory leukocytes with components of the extracellular matrix including, but not limited to collagens, laminin and fibronectin. This discovery illustrates the importance of adhesion molecules of the integrin family, particularly α1β1, in the peripheral tissue environment during conditions related to inflammation. It also extends the role of integrins family and fragments thereof in inflammation beyond leukocyte attachment and extravasation at the endothelial interface by highlighting the importance of the matrix-rich peripheral tissue environment to immune responses and it reveals peripheral tissues as a new point of intervention for adhesion based therapies.

I. Anti-Integrin Antibodies

The methods of the present invention contemplate the use of antibodies to integrins where the integrins contemplated include molecules which comprise a β chain, including but not limited to β1, β2, β3, β4, β5, β6, β7, β8, non-covalently bound to an α chain, including but not limited to α1, α2, α3, α4, α5, α6, α7, α8, α9, α10, αV, αL, αM, αX, αD, αE, αIIb. Examples of the various integrins contemplated for use in the invention include, but are not limited to:

α1β1, α2β1, α3β1, α4β1, α5β1, α6β1, α7β1, α8β1, α9β1, α10β1, αVβ1, αLβ1, αMβ1, αXβ1, αDβ1, αAIIbβ1, αEβ1;

α1β2, α2β2, α3β2, α4β2, α5β2, α6β2, α7β2, α8β2, α9β2, α10β2, αVβ2, αLβ2, αMβ2, αXβ2, αDβ2, αIIbβ2, αEβ2;

α1β3, α2β3, α3β3, α4β3, α5β3, α6β3, α7β3, α8β3, α9β3, α10β3, αVβ3, αLβ3, αMβ3, αXβ3, αDβ3, αIIbβ3, αEβ3;

α1β4, α2β4, α3β4, α4β4, α5β4, α6β4, α7β4, α8β4, α9β4, α10β4, αVβ4, αLβ4, αMβ4, αXβ4, αDβ4, αIIbβ4, αEβ4;

α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5;

α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6;

α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7;

α1β8, α2β8, α3β8, α4β8, α5β8, α6β8, α7β8, α8β8, α9β8, α10β8, αVβ8, αLβ8, αMβ8, αXβ8, αDβ8, αIIbβ8, αEβ8;

The methods of the present invention also contemplate the use of antibodies to integrin fragments including for example antibodies to a β chain alone, including but not limited to β1, β2, β3, β4, β5, β6, β7, β8, as well as an a chain alone, including but not limited to α1, α2, α3, α4, α5, α6, α7, α8, α9, α10, αV, αL, αM, αX, αD, αE, αIIb. In addition, the methods of the present invention further contemplate the use of antibodies to integrin fragments including for example antibodies to the I domain of the α chain, including but not limited to the I domain from α1β1 (Briesewitz et al., 1993, J. Biol. Chem. 268:2989); α2β1 (Takada and Hemler, 1989, J Cell Biol 109:397), αLβ2 (Larson et al., 1989, J Cell Biol 108:703), αMβ2 (Corbi et al., 1988, J Biol Chem 263:12403), αXβ2 (Corbi et al., 1987, EMBO J 6:4023), αDβ2 (Grayson et al., 1988, J Exp Med 188:2187), αEβ7 (Shaw et al., 1994, J Biol Chem 269:6016). In one embodiment, the α1-I domain antigenic determinant includes an amino acid sequence of at least 6 contiguous amino acids, wherein the contiguous sequence is found within the sequence of FIG. 12. In a related embodiment, the contiguous sequence is Val-Gln-Arg-Gly-Gly-Arg (residues 91-96 of SEQ ID NO:64).

Methods for producing integrins for use in the present invention are known to those of skill in the art (see, e.g., Springer et al., 1990, Nature 346:425-434).

Embodiments of the present invention further include anti-integrin polyclonal and monoclonal antibodies. Embodiments of the present invention include a monoclonal antibody such an anti-α1 monoclonal antibody. Antibodies for treatment, in particular for human treatment, include human antibodies, humanized antibodies, chimeric antibodies, and antigen-binding fragments of whole antibodies such as Fab, Fab', F(ab')2 and F(v) antibody fragments. Some antibodies of this invention may also include proteins containing one or more immunoglobulin light chains and/or heavy chains, such as monomers and homo- or heteromultimers (e.g., dimers or trimers) of these chains, where these chains are optionally disulfide-bonded or otherwise cross-linked. These antibodies may be capable of binding to one or more antigens (e.g., α1, α2, α6 or alpha-I domain containing integrin subunits).

An α1β1 function blocking antibody as used herein refers to an antibody that binds to the α1-I domain, for example, residues 91-97 of FIG. 12, and blocks α1β1 function as tested, for example, by their ability to inhibit K562-α1 dependent adhesion to Collagen IV (see Example 15).

The following describes the various methods of making the antibodies of this invention. Methods that are known in the art but not specifically described herein are also within the scope of this invention. For instance, antibodies of this invention can also be identified using phage-displayed antibody libraries, such as those described in Smith, 1985, Science 228:1315-7; U.S. Pat. Nos. 5,565,332, 5,733,743, 6,291,650, and 6,303,313. Additional antibodies of this invention can be made by coupling the heavy chains identified herein with a noncognate light chain, e.g., a light chain identified by phage display technology.

II. Non-Human Hybridoma Antibodies

The monoclonal antibodies of this invention can be generated by well known hybridoma technology. For instance, $\beta_1$-/- animals (e.g., mice, rats or rabbits) can be immunized with purified or crude $\alpha_1\beta_1$ preparations, cells transfected with cDNA constructs encoding $\alpha_1$, $\beta_1$ or both antigens, cells that constitutively express $\alpha_1\beta1$, and the like. The antigen can be delivered as purified protein, protein expressed on cells, protein fragment or peptide thereof, or as naked DNA or viral vectors encoding the protein, protein fragment, or peptide. Sera of the immunized animals are then tested for the presence of anti-$\alpha_1\beta_1$ antibodies. B cells are isolated from animals that test positive, and hybridomas are made with these B cells.

Antibodies secreted by the hybridomas are screened for their ability to bind specifically to VLA-1 (e.g., binding to $\alpha_1$-transfected cells and not to untransfected parent cells) and for any other desired features, e.g., having the desired CDR consensus sequences, inhibiting (or not inhibiting in the case of nonblockers) the binding between collagen and VLA-1.

Hybridoma cells that test positive in the screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e.g., CHO or NSO cells) with the cDNAs, culturing the transfected host cells, and recovering the antibody from the culture medium.

III. Chimeric Antibodies

The monoclonal antibodies of this invention can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art. Human constant regions include those derived from IgG1 and IgG4.

IV. Fully Human Antibodies

The monoclonal antibodies of this invention also include fully human antibodies. They may be prepared using in vitro-primed human splenocytes, as described by Boerner et al., 1991, J. Immunol. 147:8695, or using phage-displayed antibody libraries, as described in, e.g., U.S. Pat. No. 6,300,064.

Alternatively, fully human antibodies may be prepared by repertoire cloning as described by Persson et al., 1991, Proc. Nat. Acad. Sci. USA 88: 2432-2436; and Huang and Stollar, 1991, J. Immunol, Methods 141: 227-236. In addition, U.S. Pat. No. 5,798,230 (Aug. 25, 1998) describes preparation of human monoclonal antibodies from human B cells, wherein human antibody-producing B cells are immortalized by infection with an Epstein-Barr virus, or a derivative thereof, that expresses Epstein Barr virus nuclear antigen 2 (EBNA2), a protein required for immortalization. The EBNA2 function is subsequently shut off, resulting in an increase in antibody production.

Some other methods for producing fully human antibodies involve the use of nonhuman animals that have inactivated endogenous Ig loci and are transgenic for un-rearranged human antibody heavy chain and light chain genes. Such transgenic animals can be immunized with $\alpha_1\beta_1$ and hybridomas are then made from B cells derived therefrom. These methods are described in, e.g., the various GenPharm/Medarex (Palo Alto, Calif.) publications/patents concerning transgenic mice containing human Ig miniloci (e.g., Lonberg U.S. Pat. No. 5,789,650); the various Abgenix (Fremont, Calif.) publications/patents with respect to XENOMICE (e.g., Kucherlapati U.S. Pat. Nos. 6,075,181, 6,150,584 and 6,162,963; Green et al., 1994, Nature Genetics 7:13-21; and Mendez et al., 1997, Nature Genetics 15(2):146-56); and the various Kirin (Japan) publications/patents concerning "transonic" mice (e.g., EP 843 961, and Tomizuka et al., 1997, Nature Genetics 16:133-1443).

V. Humanized Antibodies

The monoclonal antibodies of this invention also include humanized versions of cognate anti-$\alpha_1\beta_1$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer nonhuman components.

The methods for making humanized antibodies are described in, e.g., Winter EP 239 400; Jones et al., 1986, Nature 321:522-525; Riechmann et al., 1988, Nature 332: 323-327 (1988); Verhoeyen et al., 1988, Science 239:1534-1536; Queen et al., 1989, Proc. Nat. Acad. Sci. USA 86:10029; U.S. Pat. No. 6,180,370; and Orlandi et al., 1989, Proc. Natl. Acad. Sci. USA 86:3833. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs encoding the CDRs are transferred to the corresponding regions of a human antibody heavy or light chain variable domain coding sequence by site directed mutagenesis. Then human constant region gene segments of a desired isotype (e.g, γ1 for CH and k for CL) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" (supra) in the framework regions of the acceptor antibody in order to retain the antigen-binding activity of the cognate antibody.

The general approach of making back mutations is known in the art. For instance, Queen et al. (supra), Co et al., 1991, Proc. Nat. Acad. Sci. USA 88:2869-2873, and WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the nonhuman donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, 1991, Biotechnology 9: 266-271. Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

VI. Other Moieties

The monoclonal antibodies of this invention may further include other moieties to effect the desired functions. For instance, the antibodies may include a toxin moiety (e.g., tetanus toxoid or ricin) or a radionuclide (e.g., $^{111}In$ or $^{90}Y$) for killing of cells targeted by the antibodies (see, e.g., U.S. Pat. No. 6,307,026). The antibodies may include a moiety (e.g., biotin, fluorescent moieties, radioactive moieties, histidine tag or other peptide tags) for easy isolation or detection. The antibodies may also include a moiety that can prolong their serum half life, for example, a polyethylene glycol (PEG) moiety, and a member of the immunoglobulin super family or fragment thereof (e.g., a portion of human IgG1 heavy chain constant region such as the hinge, CH2 and CH3 regions).

VII. Crystallizable Compositions and Crystals

Figure 20:
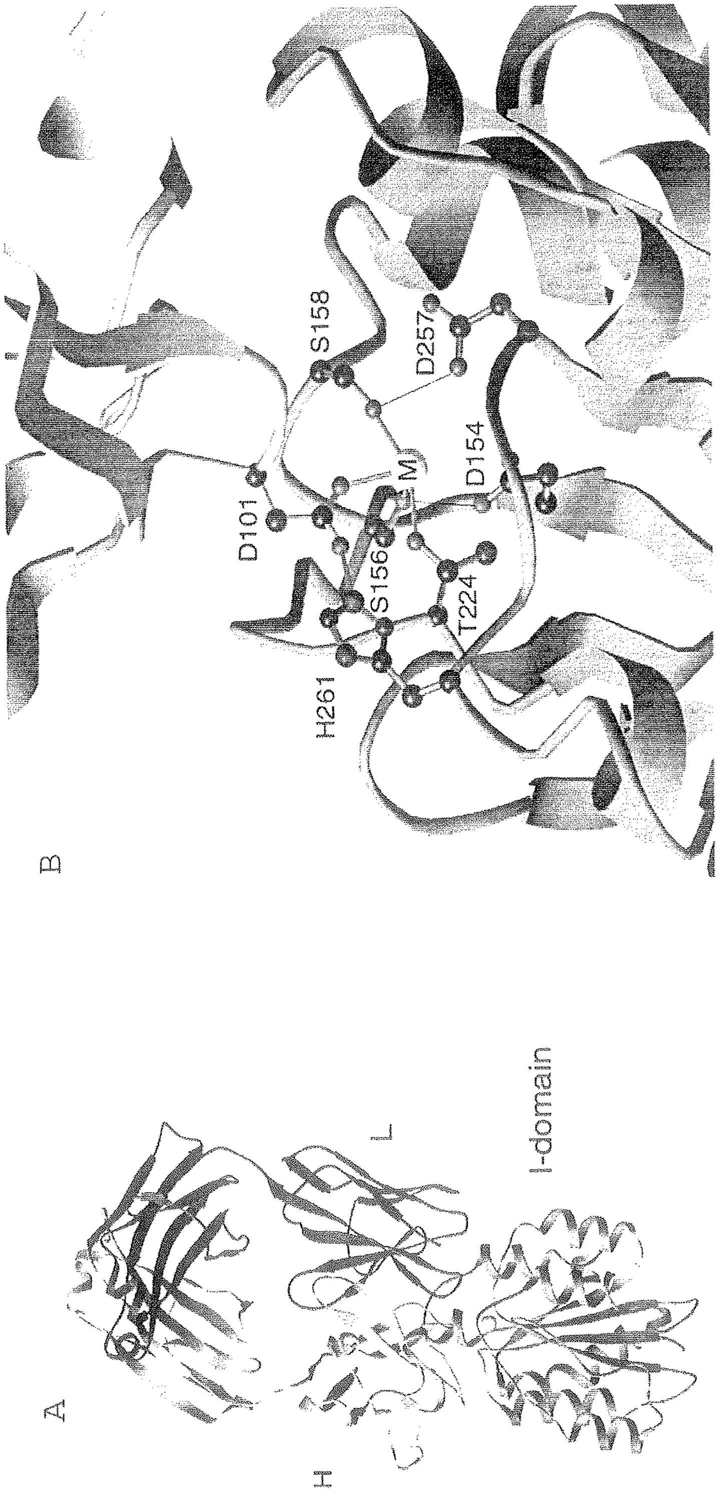
FIG. 20 was made with the software program RIBBONS (Carson, 1991, J. Appl. Cryst, 24:958-961).

This invention also provides a crystallizable composition containing a complex of: (1) a rat-human chimeric α1-I domain (e.g., mutant RΔH), or a portion thereof (e.g., a polypeptide including 135 to 336 amino acids of the rat-human chimeric α1-I domain); and (2) a Fab fragment of hAQC2, or a portion thereof (e.g., a polypeptide including 3 to 213 amino acids of the light chain and/or a polypeptide including 3 to 219 amino acids of the heavy chain). An exemplary complex is shown in FIG. 20. The RΔH α1-I domain can include, e.g., amino acid residues 145 to 336 (crystal numbering) (SEQ ID NO:59, infra) of the rat α1 subunit. The hAQC2 Fab fragments may include light chain amino acid residues 1 to 106 (e.g., 1-213) of SEQ ID NO:3 and heavy chain amino acid residues 1 to 118 (e.g., 1-219) of SEQ ID NO:4. The hAQC2 Fab fragments may be obtained by papain digestion of the whole antibody or made by recombinant methods. The Fab fragments include at least an antigen-binding portion of the variable domains of the light chain and/or the heavy chains of hAQC2.

```
                                         (SEQ ID NO: 59)
145   TQLDIV

151   IVLDGSNSIY PWESVIAFLN DLLKRMDIGP KQTQVGIVQY

191   GENVTHEFNL NKYSSTEEVL VAANKIVQRG GRQTMTALGI

231   DTARKEAFTE ARGARRGVKK VMVIVTDGES HDNYRLKQVI

271   QDCEDENIQR FSIAILGHYN RGNLSTEKFV EEIKSIASEP

311   TEKHPENVSD ELALVTIVKA LGERIF
```

Some crystallizable compositions and crystals of this invention may contain a molecule or molecular complex that is homologous to the α1-I domain and/or the hAQC2 Fab fragment by amino acid sequence or by three-dimensional structure. Examples of homologues include, but are not limited to: the α1-I domain and/or the hAQC2 Fab fragment with mutations, such as conservative substitutions, additions, deletions or a combination thereof. "Conservative substitutions" refer to replacement residues that are physically similar in size, shape, hydrophobicity, charge, and/or chemical properties to the corresponding reference residues. Methods for identifying a "corresponding" amino acid are known in the art and are based upon sequence, structural alignment, its functional position or a combination thereof as compared to the crystal structure solved in the present invention. For example, corresponding amino acids may be identified by superimposing the backbone atoms of the amino acids in the α1-I domain/hAQC2 complex and a α1-I domain and/or hAQC2 homologue using well known software applications, such as QUANTA (Molecular Simulations, Inc., San Diego, Calif. ©1998, 2000). The corresponding amino acids may also be identified using sequence alignment programs such as the "bestfit" program available from the Genetics Computer Group, which uses the local homology algorithm described by Smith and Waterman in Adv. Appl. Math. 2:482 (1981).

Crystallizable compositions of this invention may further include one or more components that promote crystallization and/or is compatible with crystallization conditions. Such components may include, but are not limited to, buffer, salts, precipitating agents and other reagents. One component can be 30% weight/volume Polyethylene Glycol 1500 (PEG1500).

The instant invention also provides methods of making crystals from crystallizable compositions including a complex of α1-I domain and an antigen-binding portion of hAQC2 (e.g., Fab, Fab' or other fragments, supra). Various techniques of crystallization can be used in the claimed invention, including, but not limited to, vapor-diffusion, dialysis, microbatch, batch, and liquid-liquid diffusion. Vapor diffusion methods include, but are not limited too, sitting-drop, hanging-drop and sandwich-drop techniques. Vapor-diffusion methods can use techniques to control the rate of crystallization, such as the addition of oils on the drops or reservoir solution. Crystallization methods can include mixing a reservoir solution containing precipitating agent with an aqueous solution of a complex of α1-I domain and an antigen-binding portion of hAQC2 to produce a crystallizable composition. The mixture or crystallizable composition may then be crystallized using the various above-listed techniques. The crystallizable composition of this invention may be an aqueous solution of a complex of α1-I domain and an antigen-binding portion of hAQC2 containing the complex at a concentration of about 1 to 50 mg per mL, such as a concentration of about 5 to 115 mg per mL (e.g., 11 mg per mL).

VIII. Crystal Structures and Structure Coordinates

This invention further provides the three-dimensional structure of a crystal including a complex of mutant RΔH, and a hAQC2 Fab fragment at 2.8 Å resolution (Example 24, infra). The three-dimensional structures of other related crystals may also be determined using techniques described herein and those known in the art. The three-dimensional structure of this complex is defined by a set of structure coordinates set forth in FIG. 19A-1 to A-109. These structure coordinates are Cartesian atomic coordinates derived from mathematical equations related to the patterns obtained from diffraction of a monochromatic beam of X-rays by the atoms or scattering centers of the crystalline complex of the α1-I domain and the hAQC2 Fab fragment. Diffraction data are first used to calculate an electron density map of the repeating unit of the crystal. The electron density map is then used to establish the positions of individual atoms of the complex.

This invention provides a molecule or a molecular complex defined by all or part of the structure coordinates of all amino acids set forth in FIG. 19A-1 to A-109, as well as a homologue of the molecule or molecular complex, where the homologue has a root mean square deviation from the backbone atoms of these amino acids between 0.00 Å and 0.65 Å, such as between 0.00 Å and 0.60 Å (e.g., between 0.00 Å and 0.50 Å). The term "root mean square deviation" or "r.m.s. deviation" means the square root of the arithmetic mean of the squares of the deviations from the mean. It is a way to express the deviation or variation from a trend or object. For purposes of this invention, the "root mean square deviation" or "r.m.s. positional deviation" defines the variation in the backbone of a protein from the relevant portion of the backbone of the polypeptide as defined by the structure coordinates described herein.

A molecule or a molecular complex of this invention may also include a binding site defined by structure coordinates of at least seven amino acids of the hAQC2 Fab fragment selected from the group including of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19A-1 to A-109; or a homologue of the molecule or molecular complex, where the homologue includes a binding site that has a root mean square deviation from the backbone atoms of one or more of these amino acids between 0.00 Å and 1.10 Å, such as between 0.00 Å and 1.00 Å (e.g., between 0.00 Å and 0.50 Å.). The term "binding site" as used herein, refers to a region of a molecule or molecular complex that, as a result of its shape and charge, favorably associates with another chemical entity. The term "site" includes, but is not limited to, trench, cleft, channel or pocket. For instance, binding sites on the α1-I domain may include a collagen-binding site (Emsley et al., 1997, supra), an antibody-binding site, and an allosteric (or IDAS) binding site (Huth et al., 2000, Proc. Natl. Acad. Sci. U.S.A. 97:5231-5236). The term "chemical entity" includes, but is not limited to, any molecule, molecular complex, compound or fragment thereof. The term "associate with" refers to an association or binding in a condition of proximity between a chemical entity, or portions thereof, and a binding pocket or binding site on a protein. The association may be non-covalent—where the juxtaposition is energetically favored by hydrogen bonding or van der Waals or electrostatic interactions or it may be covalent.

A molecule or molecular complex of this invention can include a binding site defined by structure coordinates of α1-I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109, or a homologue of the molecule or molecular complex, where the homologue includes a binding site that has a root mean square deviation from the backbone atoms of the α1-I domain amino acids between 0.00 Å and 0.92 Å.

A molecule or molecular complex of this invention also may include a binding site defined by structure coordinates of α1-I domain amino acids selected from the group consisting of residues Glu192, Gln218, Arg219, Gly220, and Gly221 (crystal numbering), according to FIG. 19A-1 to A-109; or a homologue of the molecule or molecular complex, where the homologue includes a binding site that has a root mean square deviation from the backbone atoms of the α1-I domain amino acids between 0.00 Å and 0.30 Å.

Those of skill in the art will understand that a set of structure coordinates for a polypeptide is a relative set of points that define a shape in three dimensions. Thus, it is possible that an entirely different set of coordinates that define a similar or identical shape could be generated using mathematical manipulations of the structure coordinates in FIG. 19A-1 to A-109. For example, the structure coordinates could be manipulated by crystallographic permutations of the structure coordinates, fractionalization of the structure coordinates, integer additions or subtractions to sets of the structure coordinates, inversion of the structure coordinates, or any combination thereof. Moreover, slight variations in the individual coordinates will have little effect on overall shape.

Alternatively, modification in the crystal structure due to mutations, such as additions, substitutions, and/or deletions of amino acids, or other changes in any of the polypeptide components (e.g., a hAQC2 Fab fragment or a α1-I domain) that make up the crystal can also account for variations in structure coordinates. If such variations are within an acceptable standard error as compared to the original coordinates, the resulting three-dimensional shape is considered to be the same as that of the unmodified crystal.

It is therefore necessary to determine whether an entity is sufficiently similar to all or parts of the structure described herein as to be considered the same. Such analyses may be carried out using current software applications, such as QUANTA (Accelrys, Inc. and Molecular Simulations, Inc., San Diego, Calif. ©1998, 2000) and O (Jones et al., 1991, Acta Cryst. A47:110-119), and accompanying User Guides. The Molecular Similarity application of QUANTA and the LSQ application of O permit comparisons between different structures, different conformations of the same structure, and different parts of the same structure. The general procedure used in both applications is to input the structures to be compared, define the equivalent atomic positions in these structures, perform a fitting operation, and analyze the results.

When each structure is input into the application, it is given a name. and identified as the fixed structure or a moving structures. Atom equivalency is usually defined by equivalent atoms such as protein backbone atoms (N, Cα, C and O) for all conserved residues between the two structures being compared. The moving structure is translated and rotated to obtain an optimum or least-squares fit with the fixed structure. The root mean square difference of the fit over the specified pairs of equivalent atom is reported by both programs in angstroms.

For the purpose of this invention, any molecular complex that has a root mean square deviation of conserved residue backbone atoms (N, Cα, C, O) between 0.00 Å and 1.50 Å, such as between 0.00 Å and 1.00 Å (e.g., between 0.00 Å and 0.50 Å), when superimposed on the relevant backbone atoms described by structure coordinates listed in FIG. 19A-1 to A-109 are considered identical.

IX. Determining Other Crystal Structures

The structure coordinates set forth in FIG. 19A-1 to A-109 can also be used to aid in obtaining structural information about another crystallized molecular entity, such as another hAQC2 containing amino acid substitutions in one of its CDRs. This may be achieved by any well-known techniques, including molecular replacement, an especially useful method for determining the structures of mutants and homologues of α1-I domain/Fab.

The structure coordinates set forth in FIG. 19A-1 to A-109 can also be used for determining at least a portion of the three-dimensional structure of molecular entities that contain at least some structural features similar to at least a portion of the α1-I domain or the hAQC2 Fab. Therefore, another embodiment of this invention provides a method of utilizing molecular replacement to obtain structural information about a crystallized molecule or molecular complex with unknown structure including the steps of: (a) generating an X-ray diffraction pattern from the crystallized molecule or molecular complex; and (b) applying at least a portion of the structure coordinates set forth in FIG. 19A-1 to A-109 to the X-ray diffraction pattern to generate a three-dimensional electron density map of the molecule or molecular complex with unknown structure.

By using molecular replacement, all or part of the structure coordinates set forth in FIG. 19A-1 to A-109 can be used to determine the unknown structure of a crystallized molecular entity more rapidly and efficiently than attempting to determine such information ab initio. Molecular replacement provides an accurate estimation of the phases for an unknown structure. Phases are a factor in equations used to solve crystal structures that cannot be determined directly. Obtaining accurate values for the phases, by methods other than molecular replacement, can often be a time-consuming process that involves iterative cycles of approximations and refinements and greatly hinders the solution of crystal structures. However, when the crystal structure of a protein containing at least a homologous portion has been solved, the phases from the known structure can often provide a satisfactory estimate of the phases for the unknown structure.

Thus, molecular replacement involves generating a preliminary model of a molecule or molecular complex whose structure coordinates are unknown, by orienting and positioning the relevant portion of the complex according to FIG. 19A-1 to A-109 within the unit cell of the crystal of the unknown molecule or molecular complex, so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, 1985, Meth. Enzymol. 115:55-77; Rossmann, ed., "The Molecular Replacement Method", Int. Sci. Rev. Ser., No. 13, Gordon & Breach, New York, 1972). The structure of any portion of any crystallized molecule or molecular complex that is sufficiently homologous to any portion of the α1-I domain and/or the hAQC2 Fab fragment (according to FIG. 19A-1 to A-109) can be solved by this method.

X. Computer and Storage Medium

To use the structure coordinates of this invention, e.g., those set forth in FIG. 19A-1 to A-109, it is usually necessary to convert the coordinates into a three-dimensional representation or shape. Commercially available graphical software programs including, but not limited to, O (Jones et al., 1991, Acta Cryst. A47:110-119) and ISIGHTII (©Accelrys, Inc. and Molecular Simulations, Inc., San Diego, Calif.) are capable of generating three-dimensional representations of molecules or molecular complexes, or portions thereof, from a set of structure coordinates.

In accordance with the present invention, the structure coordinates of the molecular entities of this invention are stored in a storage medium readable by machine (e.g., a computer). Using a computer and appropriate software, such data may be used for a variety of purposes, such as drug discovery and X-ray crystallographic analysis of other protein crystals.

Accordingly, a machine-readable data storage medium may include a data storage material encoded with machine-readable data including at least a portion of the structure coordinates set forth in FIG. 19A-1 to A-109. The computer may further include instructions to produce three-dimensional representations of the molecular complexes of α1-I domain and the hAQC2 Fab fragment by processing the machine-readable data of this invention. The computer of this invention may also include a display, a graphical interface for displaying, or an input device for moving and manipulating the three-dimensional graphical representation of the structure coordinates.

This invention also provides a computer for determining at least a portion of the structure coordinates corresponding to X-ray diffraction data obtained from a molecular complex of α1β1 integrin and the Fab fragment of hAQC2 antibody, where the computer includes a machine-readable data storage medium including a data storage material encoded with machine-readable data, where the data includes at least a portion of the structure coordinates of the molecular complex of α1-I domain and the hAQC2 Fab fragment according to FIG. 19A-1 to A-109, or X-ray diffraction data obtained from the crystalline molecular complex. The computer further includes instructions for performing a Fourier transform of the machine readable coordinate data, and instructions for processing this machine readable diffraction data into structure coordinates. This computer may further include: a working memory for storing instructions for processing the machine-readable data; a central-processing unit coupled to the working memory and to the machine-readable data; and optionally a graphical interface or display coupled to the central-processing unit for displaying the three-dimensional graphical representation of the structure coordinates of the molecule or molecular complex.

This invention further provides a computer for producing a three-dimensional representation of: a molecule or a molecular complex defined by at least a portion or all of the structure coordinates of all the α1-I domain and the AQC2 Fab fragment amino acids set forth in FIG. 19A-1 to A-109, or a homologue of the molecule or molecular complex, where the homologue has a root mean square deviation from the backbone atoms of the amino acids of between 0.00 Å than 1.50 Å, such as between 0.00 Å and 1.00 Å, (e.g., between 0.00 Å and 0.50 Å). Further in this invention the computer includes: a machine-readable data storage medium including a data storage material encoded with machine-readable data, where the data includes at least a portion or all of the structure coordinates of all of the α1-I domain and the Fab hAQC2 fragment amino acids set forth in FIG. 19A-1 to A-109.

A computer of this invention may also produce a three-dimensional representation of a molecule or molecular complex including a binding site. The binding site may be defined by structure coordinates of at least seven amino acids of: the hAQC2 Fab fragment selected from the group including light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19A-1 to A-109; or a homologue of the molecule or molecular complex, where the homologue includes a binding site that has a root mean square deviation from the backbone atoms of the at least one amino acid of the hAQC2 Fab fragment of between 0.00 Å and 1.10 Å, such as between 0.00 Å and 1.00 Å, (e.g., between 0.00 Å and 0.50 Å). Further, the computer of this invention includes: a machine-readable data storage medium including a data storage material encoded with machine-readable data, where the data includes the structure coordinates of at least seven amino acids of the hAQC2 Fab fragment selected from the group consisting of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19A-1 to A-109.

This invention also provides a computer for producing a three-dimensional representation of: a molecule or molecular complex including a binding site defined by structure coordinates I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109; or a homologue of the molecule or molecular complex, where the homologue includes a binding site that has a root mean square deviation from the backbone atoms of the I domain amino acids between 0.00 Å and 0.92 Å. Further in this invention, the computer includes: a machine-readable data storage medium including a data storage material encoded with machine-readable data, where the data includes the structure coordinates of I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109.

This invention also provides a computer for producing a three-dimensional representation of a molecule or molecular complex including a binding site defined by structure coordinates of I domain amino acids selected from the group consisting of residues Glu192, Gln218, Arg219, Gly220, and Gly221 (crystal numbering), according to FIG. 19A-1 to A-109; or a homologue of the molecule or molecular complex, where the homologue includes a binding site that has a root mean square deviation from the backbone atoms of I domain amino acids between 0.00 Å and 0.30 Å. Further in this invention the computer includes: a machine-readable data storage medium including a data storage material encoded with machine-readable data, where the data includes the structure coordinates I domain amino acids selected from the group consisting of residues Glu192, Gln218, Arg219, Gly220, and Gly221 (crystal numbering), according to FIG. 19A-1 to A-109.

Figure 21:
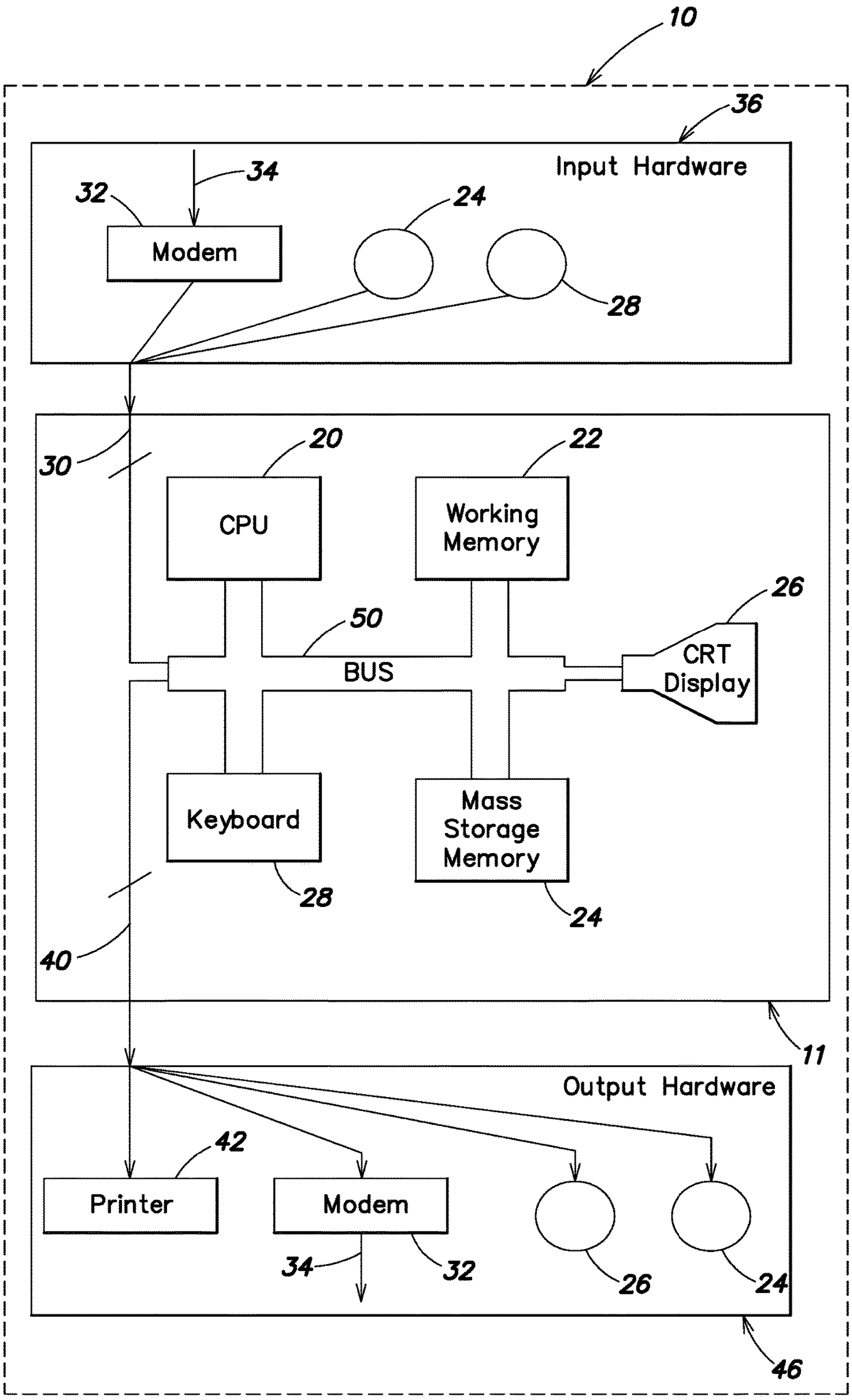
FIG. 21. A diagram of a system used to carry out the instructions encoded by the storage medium of FIGS. 22 and 23.

FIG. 21 demonstrates one such embodiment. System 10 includes a computer 11 including a central-processing unit ("CPU") 20, a working memory 22 which may be, e.g., Ram (random-access memory) or "core" memory, mass storage memory 24 (such as one or more disk or tape drives or CD-ROM or DVD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may include CD-ROM or DVD-ROM drives or tape or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding site of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

Figure 22:
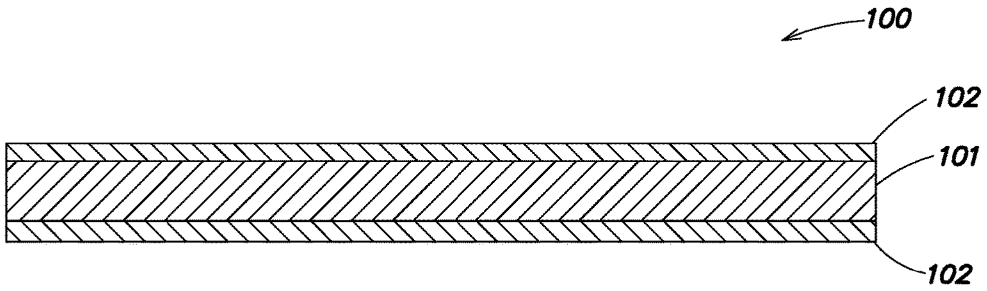
FIG. 22. A cross section of a magnetic storage medium.

FIG. 22 shows a cross-section of a magnetic data storage medium 100 which can be encoded with machine-readable data that can be carried out by a system such as system 10 of FIG. 21. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 11 of FIG. 21.

Figure 23:
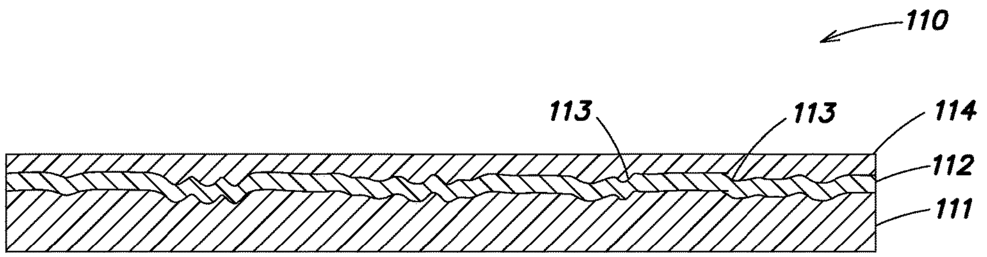
FIG. 23. A cross section of an optically-readable data storage medium.

FIG. 23 shows a cross-section of an optically-readable data storage medium 110 which also can be encoded with such machine-readable data, or a set of instructions, which can be carried out by a system such as system 10 of FIG. 21. Medium 110 can be a conventional compact disk or DVD disk read only memory (CD-ROM or DVD-ROM) or a rewritable medium, such as a magneto-optical disk which is optically readable and magneto-optically writable. Medium 100 has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

XI. Rational Drug Design

The present invention permits the use of structure-based and rational drug design techniques to design, select, and synthesize or isolate chemical entities, such as inhibitors of the α1-I domain and to improve known inhibitors of this domain. These inhibitors may be capable of blocking the collagen-binding site of VLA-1. This invention also permits the use of structure-based and rational drug design techniques to design variants that may act as inhibitors of collagen binding.

The three-dimensional representation of this invention can be used experimentally or computationally to design potential inhibitors, other chemical entities, variants of the Fab fragment or combinations of chemical entities that may bind to and effect the biological functions of the hAQC2 Fab fragment or the chimeric α1-I domain of the current invention.

One skilled in the art can use one of several methods to screen chemical entities for their ability to associate with the complex of the hAQC2 Fab fragment or the chimeric α1-I domain of the current invention and more particularly with a binding site of either the I domain or the Fab fragment. This process may begin by visual inspection of, for example, the binding site for either the I domain or the Fab fragment on the computer screen, based on the coordinates of the complex in FIG. 19A-1 to A-109. Selected chemical entities may then be positioned in a variety of orientations, or docked, within an individual binding site of either the I domain or the Fab fragment. Docking may be accomplished using software such as QUANTA, followed by energy minimization and molecular dynamics with standard molecular mechanics forcefields, such as CHARMM (Molecular Simulations, Inc., Burlington, Mass. ©1994) and AMBER (P. A. Kollman, University of California at San Francisco, ©1994).

Specialized computer programs may also assist in the process of selecting chemical entities. These include, inter alia:

1. GRID (Goodford, P. J., 1985, J. Med. Chem. 28:849-857). GRID is available from Oxford University, Oxford, UK.
2. MCSS (Miranker, A. and M. Karplus, 1991, Proteins: Structure, Function and Genetics 11:29-34). MCSS is available from Molecular Simulations, Burlington, Mass.
3. AUTODOCK (Goodsell, D. S, and A. J. Olsen, 1990, Proteins: Structure, Function, and Genetics 8:195-202). AUTODOCK is available from Scripps Research Institute, La Jolla, Calif.
4. DOCK (Kuntz, I. D. et al., 1982, J. Mol. Biol. 161:269-288). DOCK is available from University of California, San Francisco, Calif.

Once suitable chemical entities have been selected, they can be assembled into a single compound. Assembly may proceed by visual inspection of the relationship of the entities to each other on the three-dimensional image displayed on a computer screen in relation to the structure coordinates of the complex of hAQC2 Fab fragment and the chimeric α1-I domain. This is followed by manual model building using software such as Quanta or Sybyl.

The above-described evaluation process for chemical entities may be performed in a similar fashion for compounds or for variants that may bind the α1-I domain.

Useful programs to aid one of skill in the art in connecting the individual chemical entities include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., 1989, Royal Chem. Soc., 78:182-196). CAVEAT is available from the University of California, Berkeley, Calif.
2. 3D Database systems such as MACCS-3D (MDL Information Systems, San Leandro, Calif.). This area is reviewed in Martin, Y. C., 1992, J. Med. Chem. 35:2145-2154.
3. HOOK (available from Molecular Simulations, Burlington, Mass.).

Instead of proceeding to build an inhibitor or binding compound in a step-wise fashion one chemical entity at a time, as described above, binding compounds may be designed as a whole or "de novo" using either an empty binding site (such as a binding site of the α1-I domain or the hAQC2 Fab fragment) or optionally including some portion(s) of a known α1-I domain or the hAQC2 Fab fragment binding compound. These methods include:

1. LUDI (Bohm, H.-J., 1992, J. Comp. Aid. Molec. Design 6:61-78). LUDI is available from Biosym Technologies, San Diego, Calif.
2. LEGEND (Nishibata, Y. and A. Itai, 1991, Tetrahedron 47:8985). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., 1990, J. Med. Chem. 33:883-894. See also Navia, M. A. and M. A. Murcko, 1992, Curr. Opin. Struct. Biol. 2:202-210.

Once an entity has been designed or selected by the above methods, the efficiency with which that entity may bind to the α1-I domain or the hAQC2 Fab fragment can be tested and optimized by computational evaluation. For example, a compound that has been designed or selected to function as α1-I domain binding compound can traverse a volume not overlapping that occupied by the binding site when it is bound to the chimeric α1-I domain. An effective α1-I domain binding compound can demonstrate a relatively small difference in energy between its bound and free states (i.e., a small deformation energy of binding). Thus, the most efficient α1-I domain binding compound should be designed with a deformation energy of binding of not greater than about 10 kcal/mole, e.g., not greater than 7 kcal/mole. α1-I domain binding compounds may interact with the α1-I domain in more than one conformation that is similar in overall binding energy. In those cases, the deformation energy of binding is taken to be the difference between the energy of the free compound and the average energy of the conformations observed when the compound binds to the protein.

A compound designed or selected as binding to α1-I domain may be further computationally optimized so that in its bound state it would lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the compound and the protein when the compound is bound to α1-I domain, should make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa. ©1992); AMBER, version 4.0 (P. A. Kollman, University of California at San Francisco, ©1994); QUANTA/CHARMM (Molecular Simulations, Inc., Burlington, Mass. 1994); and Insight II/Discover (Biosysm Technologies Inc., San Diego, Calif. ©1994). These programs may be implemented, for instance, using a Silicon Graphics workstation. Other hardware systems and software packages will be known to those skilled in the alt.

One other useful drug design technique enabled by this invention is iterative drug design. Iterative drug design is a method for optimizing associations between a protein and a compound (that compound includes an antibody) by determining and evaluating the three-dimensional structures of successive sets of protein/compound complexes. In iterative drug design, a series of crystals of a protein complexed with entities that bind the protein are obtained and then the three-dimensional structure of each molecular complex is solved. Such an approach provides insight into the associations between the proteins and other entities of each complex. This is accomplished by selecting chemical entities with inhibitory activity, obtaining crystals of these new complexes, solving the three-dimensional structure of the complexes, and comparing the associations between the new complexes and the previously solved complex. Associations within a complex can be optimized by observing how changes in the components of the complex affect associations.

In some cases, iterative drug design is carried out by forming successive complexes and then crystallizing each new complex. Alternatively, a pre-formed protein crystal is soaked in the presence of another chemical entity, thereby forming a complex and obviating the need to crystallize each individual complex.

XII. Pharmaceutical Compositions

The pharmaceutical compositions of this invention contains one or more VLA-1 antagonists of the present invention (e.g., anti-VLA-1 antibodies and the small molecular VLA-1 antagonists identified by the above-described rational drug design methods), or pharmaceutically acceptable derivatives thereof. The compositions may further contain a pharmaceutically acceptable carrier, such as an adjuvant, a vehicle, a buffer, and a stabilizer.

The pharmaceutical compositions of this invention may be given orally, topically, intravenously, subcutaneously, intraperitoneally, intramuscularly, intramedullarily, intraarterially, intra-articularly, intra-synovially, intrasternally, intrathecally, intrahepatically, intraspinally, intracranially as desired, or just locally at sites of inflammation or tumor growth. The pharmaceutical compositions of this invention may also be administered by inhalation through the use of, e.g., a nebulizer, a dry powder inhaler or a metered dose inhaler, or by implantation of an infusion pump or a biocompatible sustained release implant into the subject.

The pharmaceutical compositions may be in the form of a sterile injectable preparation, for example a sterile injectable aqueous or oleaginous suspension. This suspension may be formulated according to techniques known in the art using suitable dispersing, wetting, and suspending agents. If given orally, the pharmaceutical compositions can be administered in form of capsules, tablets, aqueous suspensions or solutions. For topical applications, the pharmaceutical compositions may be formulated in a suitable ointment.

The dosage and dose rate of the VLA-1 antagonists of this invention effective to produce the desired effects will depend on a variety of factors, such as the nature of the disease to be treated, the size of the subject, the goal of the treatment, the specific pharmaceutical composition used, and the judgment of the treating physician. Dosage levels of between about 0.001 and about 100 mg/kg body weight per day, for example between about 0.1 and about 50 mg/kg body weight per day, of the active ingredient compound are useful. For instance, antibody of the invention will be administered at a dose ranging between about 0.01 mg/kg body weight/day and about 20 mg/kg body weight/day, e.g., ranging between about 0.1 mg/kg body weight/day and about 10 mg/kg body weight/day, and at intervals of every one to fourteen days. In another embodiment, the antibody is administered at a dose of about 0.3 to 1 mg/kg body weight when administered intraperitoneally. In yet another embodiment, the antibody is administered at a dose of about 5 to 12.5 mg/kg body weight when administered intravenously. In one embodiment, an antibody composition is administered in an amount effective to provide a plasma level of antibody of at least 1 mg/ml.

XIII. Diseased Conditions and Animal Models

The VLA-1 antagonists of the invention are useful in the treatment, including prevention, of $\alpha_1\beta_1$-mediated diseases such as those enumerated above. The treatments of this invention are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

The efficacy of the VLA-1 antagonists of the invention can be tested in various animal models. For instance, useful psoriasis and arthritis models include those described in WO 00/72881. Kidney fibrosis models include those described in WO 99/61040, the Alport's syndrome kidney model described in Cosgove et al., 2000, Am. J. Path. 157:1649-1659, and the SNF1 mouse model of lupus nephritis described in Kalled et al., 2001, Lupus 10:9-22. Vascular fibrosis models for restenosis include a rat carotid balloon injury model described in Smith et al., 1999, Circ. Res. 84:1212-1222. Lung fibrosis models for idiopathic pulmonary fibrosis and scleroderma-associated pulmonary fibrosis include a bleomycin-induced pulmonary fibrosis model described in Wang et al., 1999, Thorax 54:805-812. Liver cirrhosis models for hepatitis C- or alcohol-induced cirrhosis include the bile duct ligation model described in George et al., 1999, Proc. Natl. Acad. Sci. USA 96:12719-12724 and the CCL4-induced liver fibrosis model described in Shi et al., 1997, Proc. Natl. Acad. Sci. USA 94:10663-10668.

The efficacy of the treatments of this invention may be measured by a number of available diagnostic tools, including physical examination, blood tests, proteinuria measurements, creatinine levels and creatinine clearance, pulmonary function tests, chest X-rays, bronchoscopy, bronchioalveolar lavage, lung biopsy, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

XIV. Diagnostic Methods

The antibodies of this invention can be used to diagnose diseased conditions associated with altered all expression levels. A tissue sample from a subject, such as a tissue biopsy, body fluid sample or lavage (e.g., alveolar lavage), can be tested in an antigen capture assay, ELISA, immunohistochemistry assay, and the like using the antibodies. A tissue sample from a normal individual is used as control.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition (Sambrook et al., Eds.), 1989; Oligonucleotide Synthesis, (M. J. Gait, Ed.), 1984; U.S. Pat. No. 4,683,195 to Mullis et al.; Nucleic Acid Hybridization, (B. D. Hames and S. J. Higgins), 1984; Transcription and Translation, (B. D. Hames and S. J. Higgins), 1984; Culture of Animal Cells (R. I. Freshney, Ed.), 1987; Immobilized Cells and Enzymes, IRL Press, 1986; A Practical Guide to Molecular Cloning (B. Perbal), 1984; Methods in Enzymology, Volumes 154 and 155 (Wu et al., Eds.), Academic Press, New York; Gene Transfer Vectors for Mammalian Cells (J. H. Miller and M. P. Calos, Eds.), 1987; Immunochemical Methods in Cell and Molecular Biology (Mayer and Walker, Eds.), 1987; Handbook of Experiment Immunology, Volumes I-IV (D. M. Weir and C. C. Blackwell, Eds.), 1986; Manipulating the Mouse Embryo, 1986.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word “comprise,” or variations such as “comprises” or “comprising” will be understood to imply the inclusion of a stated integer or group of integers but not the exclusion of any other integer or group of integers.

The following Examples are provided to illustrate the present invention, and should not be construed as limiting thereof.

EXAMPLES

Chemical Reagents

Fluorescein isothiocyanate (FITC) was purchased from Sigma Chemical Co. (St. Louis, Mo.). Croton oil was purchased from ICN Biochemicals (Aurora, Ohio). Whole sheep blood in Alsevers solution was obtained from East Acres Biologicals (Southbridge, Mass.). Type I rat tail collagen and type IV mouse collagen were purchased from Collaborative Research Inc. (Bedford, Mass.) and Gibco (Gaithersburg, Md.), respectively.

Balb/c female mice of 6-8 weeks of age were purchased from Taconic (Germantown, N.Y.) and the α1β1 integrin-deficient mice on a Balb/c background were as previously described (3).

Example 1

Monoclonal Antibodies. Function-blocking mAbs to murine antigens were prepared in an azide-free and low endotoxin format: Ha31/8 (hamster anti-CD49a; integrin oil) (Mendrick et al. 1995. Lab. Invest. 72:367-375), Ha1/29 (hamster anti-CD49b; integrin α2)(β1) (Mendrick et al. 1995. Lab. Invest. 72:367-375; Mendrick, D. L. and D. M. Kelly 1993 Lab. Invest. 69:690-702), hamster group II control mAb Ha4/8 (hamster anti-KLH) (Mendrick, D. L. and D. M. Kelly 1993 Lab. Invest. 69:690-702), and PS/2 (rat anti-CD49d; integrin α4β1 chain) (Miyake et al. 1991 J. Exp. Med. 173:599-607). In addition, the following function-blocking mAbs to murine antigens were purchased as no-azide/low endotoxin preparations from Pharmingen (San Diego, Calif.): HMβ1-1 (hamster anti-CD29; integrin β1 chain) (Noto et al. 1995 Int. Immunol. 7:835-842), Ha2/5 (hamster anti-CD29; integrin β1 chain) (Mendrick, D. L. and D. M. Kelly 1993 Lab. Invest. 69:690-702), 3E2 (hamster anti-CD54, ICAM-1) (Scheynius et al. 1993 J. Immunol. 150:655-663), 5H10-27 (rat anti-CD49e; integrin α5) (Kinashi, T., and T. A. Springer. 1994. Blood Cells. 20:25-44), GoH3 (rat anti-CD49f; integrin α6) (Sonnenberg et al. 1987 J. Biol. Chem. 262:10376-10383), and the rat isotype control mAbs R35-95 (rat IgG2a) and R35-38 (rat IgG2b).

Adhesion Assay. Splenocytes from Balb/c mice were cultured with 20 ng/ml IL-2 for 7-12 d. Adhesion of cells to type I and type TV collagen was as previously described (Gotwals et al. 1996 J. Clin. Invest. 97:2469-2477). Briefly, 96-well Maxisorp plates (Nunc, Napierville, Ill.) were coated with either 10 μg/ml type IV or 5 μg/ml type I collagen and non-specific sites blocked with 1% BSA. IL-2 activated splenocytes were labeled with 2 μM BCECF [2',7'-bis(carboxyethyl)-5(6) carboxyl fluorescein penta acetoxymethylester](Molecular Probes, Eugene, Oreg.) and incubated with 10 μg/ml of indicated mAbs for 15 min. $10^5$ cells in 0.25% BSA in RPMI were then added to coated wells and incubated for 60 min at 37° C. Unbound cells were removed by washing three times with 0.25% BSA in RPMI. Adhesion was quantified using a CytoFluor 2350 fluorescent plate reader (Millipore, Bedford, Mass.). The ratio of bound cells to input cells was measured and percent adhesion relative to control mAb-treated cells (normalized to 100%) calculated. Background values due to cell adhesion on wells coated with BSA alone were subtracted.

Figure 1B:
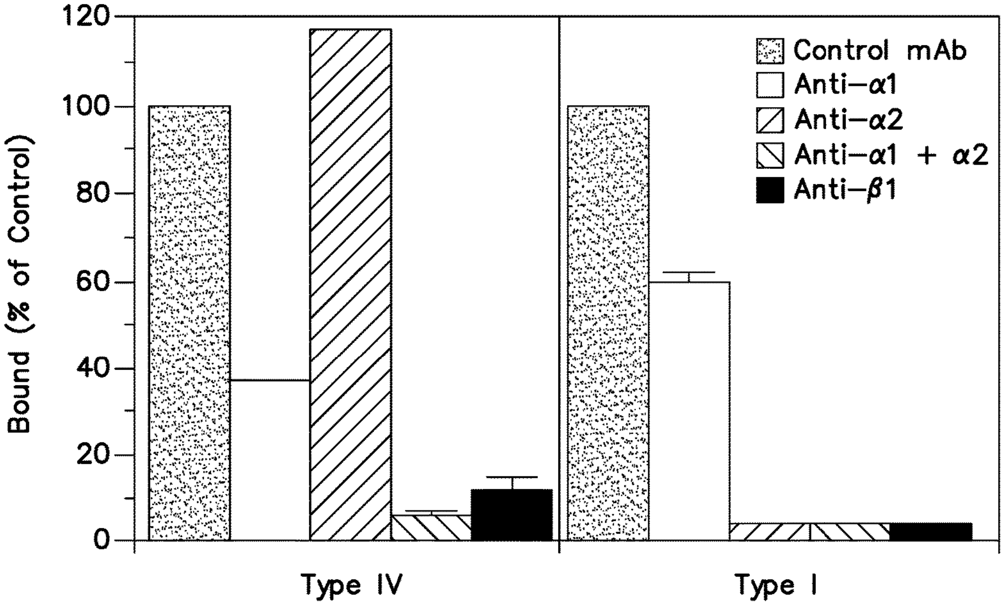

Expression and functional blockade of α1β1 and α2β1 on activated leukocytes. Given the key role leukocytes play in inflammation, we decided to test whether anti-α1 and anti-α2 mAbs were capable of blocking leukocyte adhesion to collagens. In order to obtain leukocytes expressing high levels of both α1 and α2, murine T cells were stimulated in vitro with IL-2 for 7-12 d. These cells expressed high levels of both α1 and α2 (FIG. 1A), and bound well to both collagen type IV and type I-coated surfaces (FIG. 1B). Adhesion to type IV collagen was partially inhibited by anti-α1 mAb alone and was not inhibited by anti-α2 mAb alone. In contrast, adhesion to type I collagen was completely inhibited by anti-α2 mAb and anti-α1 mAb alone showed only partial inhibition. Both anti-β1 mAb and the combination of anti-α1 and anti-α2 mAbs completely inhibited adhesion to types I and IV collagen. Having demonstrated that the α1β1 and α2β1 integrins are expressed on activated T cells and that anti-α1 and α2 mAbs are able to functionally block leukocyte adhesion to collagens, we used these mAbs to investigate the in vivo role of these integrins in animal models of inflammatory disorders.

Example 2

Inhibition of DTH responses by anti-integrin mAbs. SRBC-induced delayed type hypersensitivity (DTH)

responses were adapted from a previously published protocol (Hurtrel et al., 1992, Cell. Immunol. 142:252-263). Briefly, mice were immunized s.c. in the back with 2×10$^7$ SRBC in 100 ul PBS on d 0. The mice were challenged on d 5 by injecting 1×10$^8$ SRBC in 25 ul PBS s.c into the right hind footpad. Footpad thickness was measured with an engineer's caliper (Mitutoyo/MTI, Paramus, N.J.) 20 h after antigen challenge, and the degree of footpad swelling calculated. Results are reported as the mean percent increase footpad thickness ±SEM and calculated as % increase=[1= (Right footpad thickness 20 h after antigen challenge/Uninjected left footpad thickness 20 h after antigen challenge)]×100. To block the effector phase of the SRBC-induced DTH response, therapeutic or control mAb (100 ug), which were prepared according to the methods described in Example 1, was given i.p. 1 h prior to antigen challenge on d 5.

Figure 2:
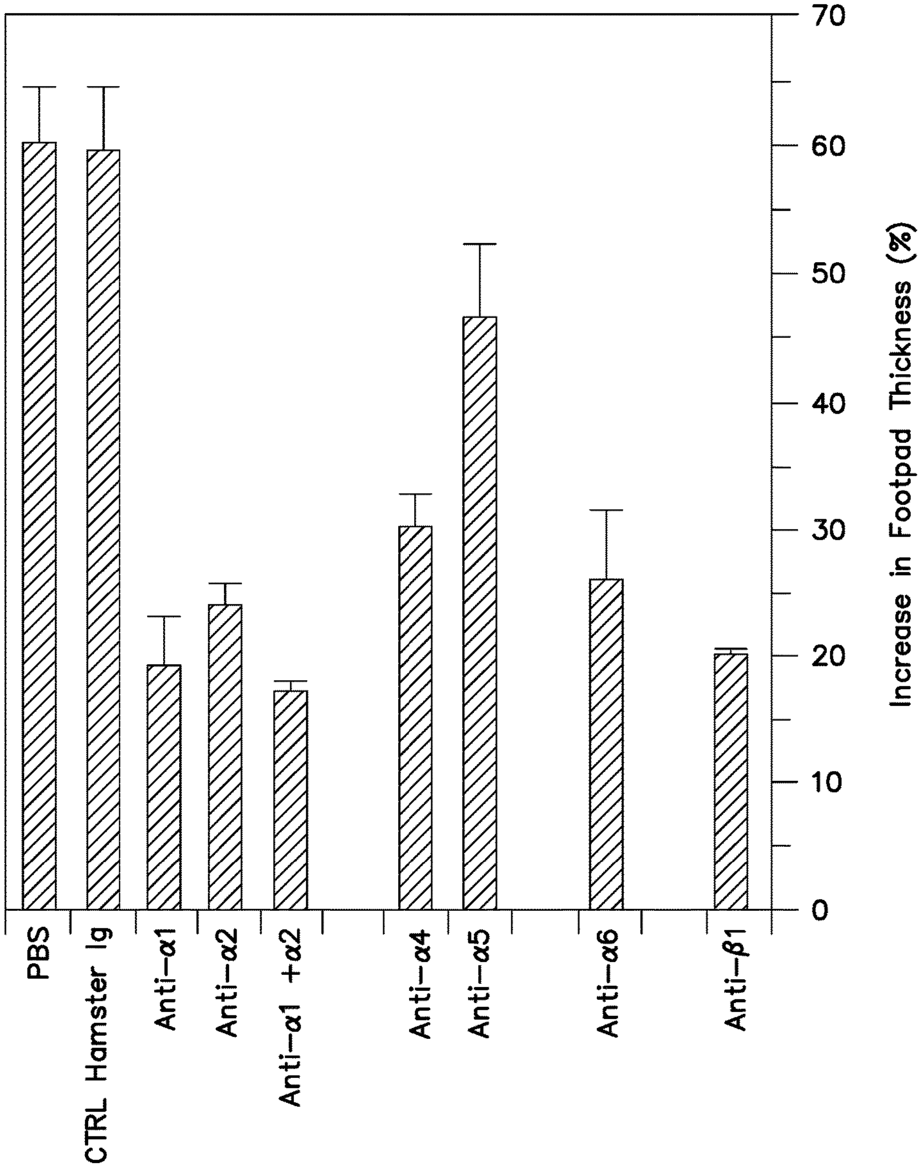
FIG. 2. Effect of anti-integrin mAbs on the effector phase of delayed-type hypersensitivity. SRBC-sensitized mice were injected i.p. with the indicated mAbs 1 h prior to SRBC challenge, Footpad thickness was measured 20 h after antigen challenge, and results shown as % increase in footpad thickness±SEM as illustrated in Example 2. These data represent a summary of eight experiments with n=79 (PBS), 68 (control hamster Ig), 68 (anti-α1), 29 (anti-α2), 18 (anti-α1+anti-α2), 45 (anti-α4), 18 (anti-α5), 20 (anti-α6), and 10 (anti-β1). The mAbs used were: Ha4/8 (control hamster Ig group 2), Ha31/8 (anti-α1), Ha1/29 (anti-α2), PS/2 (anti-α4), 5H10-27 (anti-α5), GoH3 (anti-α6), and HM β1-1 (anti-β1).

SRBC-induced DTH is a well characterized in vivo model of inflammation, and in particular psoriasis, that has been used to demonstrate the importance of a variety of cytokines and adhesion molecules in inflammation (Tedder et al., 1995, J. Exp. Med. 181:2259-2264, Terashita et al., 1996, J Immunol 156:4638-4643). SRBC-sensitized mice received anti-integrin mAbs 1 h prior to footpad antigen challenge and inflammation was assessed 20 h later as measured by increased footpad thickness. PBS and control hamster Ig-treated mice showed a 60-70% increase in footpad thickness 20 h after antigen challenge (FIG. 2). Compared to control hamster Ig treatment, anti-α1 or anti-α2 mAbs resulted in a 68% and 60% inhibition in footpad thickness, respectively. The combination of anti-α1 and α2 mAbs resulted in 71% inhibition, demonstrating little additive effect over anti-α1 or anti-α2 mAbs alone. Treatment with other anti-integrin mAbs was also effective at inhibiting DTH effector response. The degree of inhibition seen with the various mAb treatments was 49% (anti-α4), 23% (anti-α5), and 57% (anti-α6). Lastly, mAb blockade of the common β1 integrin subunit (mAb HMBI-1) inhibited the effector DTH response by 67%.

Example 3

Inhibition of CHS effector responses by anti-integrin mAbs. Contact hypersensitivity (CHS) to FITC was assayed as previously described (Gaspari et al., 1991, In Current Protocols in Immunology. J. E. Coligan, A. M. Kruisbeek, D. H. Margulies, E. M. Shevach, and W. Strober, editors. John Wiley & Sons, New York. Section 4.2:1). Briefly, mice were sensitized by painting 100 ul 0.5% FITC in 1:1 acetone/dibutylphthalate onto the shaved back on d 0.10 d later, animals were challenged by applying 5 ul 0.5% FITC onto both sides of each ear. Ear swelling response was determined by ear thickness measured with an engineer's caliper (Mitutoyo/MTI, Paramus, N.J.) at the time of antigen challenge (d 10) and 24 h later, and the results reported as mean percent increase in baseline ear thickness±SEM. Increase in ear thickness was calculated as % increase=[1= (Ear thickness 24 h after antigen challenge/Ear thickness at the time of antigen challenge)]×100. To block the effector phase of the CHS response, therapeutic or control in mAb (250 ug) was given i.p. 4 h prior to antigen challenge on d 10. Mice that were antigen-sensitized and ear challenged with vehicle only (vehicle control) or mice that were ear challenged without prior sensitization (irritant control) served as negative controls (never exceeded 2% increase in ear thickness).

Figure 3:
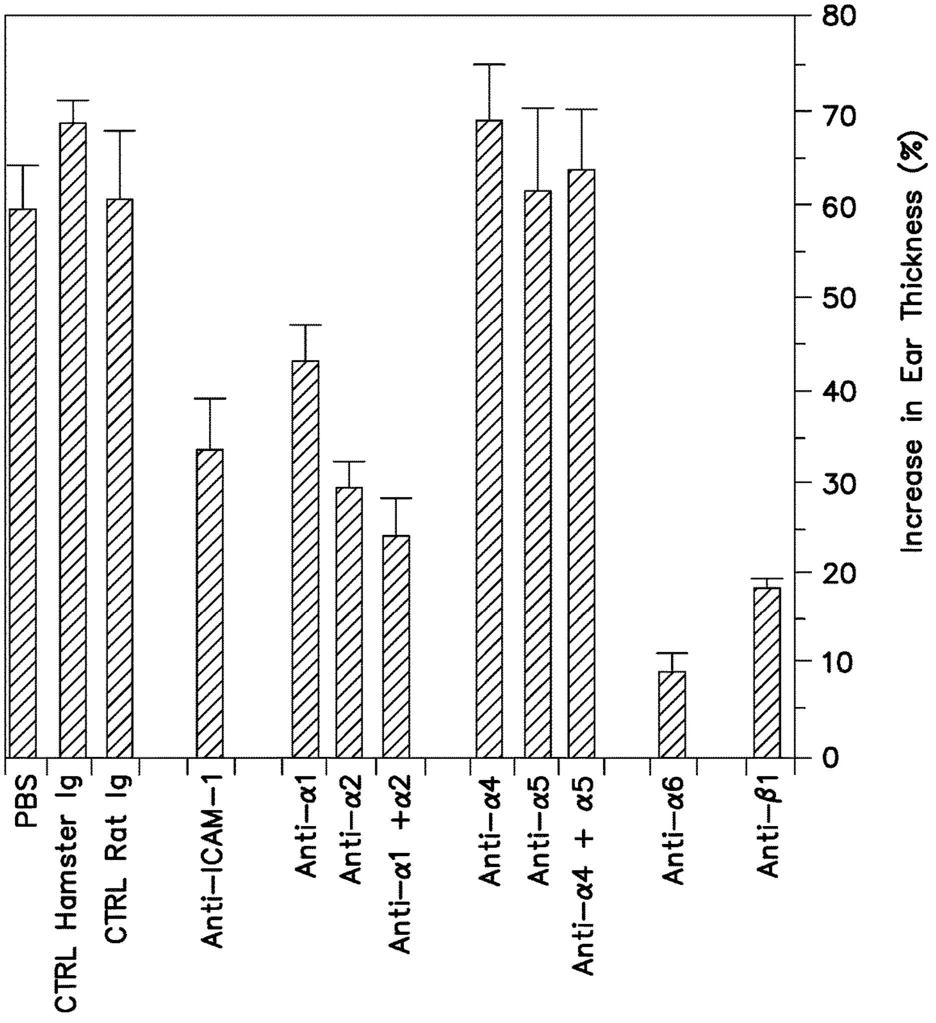
FIG. 3. Effect of anti-integrin mAbs on the effector phase of contact hypersensitivity. FITC-sensitized mice were injected i.p. with the indicated mAbs 4 h prior to FITC challenge. Ear thickness was measured at baseline and 24 h later, and results shown as % increase in ear thickness±SEM as illustrated in Example 3. These data represent a summary of nine experiments with n=74 (PBS), 60 (control hamster Ig), 26 (anti-ICAM-1), 44 (anti-α1), 44 (anti-α2), 38 (anti-α1+anti-α2), 36 (anti-α4), 16 (anti-α5), 26 (anti-α4+anti-α5), 24 (anti-α6), and 22 (anti-β1). The hamster mAbs used were: Ha4/8 (control hamster Ig group 2), Ha31/8 (anti-α1), Ha1/29 (anti-α2), HMβ1-1 (anti-β1), 3E2 (anti-ICAM-1); the rat mAbs used were: R35-95 and R35-38 (control rate IgG2a and rat IgG2b, respectively), PS/2 (anti-α4), 5H10-27 (anti-α5), GoH3 (anti-α6).

Given that CHS is mechanistically distinct from DTH and involves different effector cells, we investigated what effect anti-integrin mAbs had on the effector phase of αbacks, followed 10 d later with FITC challenge to the ear resulting in an inflammatory response the next day. FITC-sensitized mice demonstrated a 60-70% increase in thickness 24 h after antigen challenge (FIG. 3). Consistent with published results (Scheynius et al., J. Immunol. 150:655-663), anti-ICAM-1 mAb treatment resulted in 51% inhibition of ear swelling. Compared to control hamster mAb, treatment of mice with anti-α1 or anti-α2 mAb 4 h prior to antigen challenge resulted in 37% and 57% inhibition in ear swelling, respectively (FIG. 3). The combination of anti-α1 and anti-α2 mAbs resulted in slightly greater inhibition of ear swelling (65%). Treatment with other mAbs to β1 integrins revealed that while anti-α4 and anti-α5 mAbs resulted in no inhibition of FITC-induced CHS effector response when compared to control rat mAb, treatment with anti-α6 mAb resulted in an 86% inhibition of effector responses. Lastly, mAb blockade of the common β1 integrin subunit inhibited CHS effector responses by 74%. Similar CHS results were obtained using different strains of mice (C57/BL6, 129/Sv) and a different sensitizing agent (oxazolone) (data not shown). Similar to the results seen in the SRBC-induced DTH model, histologic analysis of inflamed ears revealed that both edema formation and leukocytic infiltration were inhibited by anti-α1 and anti-α2 mAb treatment.

Consistent with the finding that α1β1 and α2β1 can be expressed on IL-2-activated splenocytes, analysis of lymph nodes from antigen-sensitized mice (FITC or oxazolone) revealed of α1β1 and α2β1 to be expressed exclusively on CD44$^{hi}$ LFA-1$^{hi}$ activated CD4+ and CD8+ T cells (data not shown). Treatment of mice with anti-α1 and anti-α2 mAbs did not result in deletion of these cells, as the numbers of activated T cells in both spleen and lymph nodes seen in response to antigen sensitization in the CHS model was unaffected. In addition, effector cells were not functionally deleted as prolonged treatment of antigen-sensitized mice with anti-α1 and anti-α2 mAbs (d 10-16) did not affect the inflammatory response of mice challenged with antigen at d 20 (data not shown).

Example 4

Figure 4:
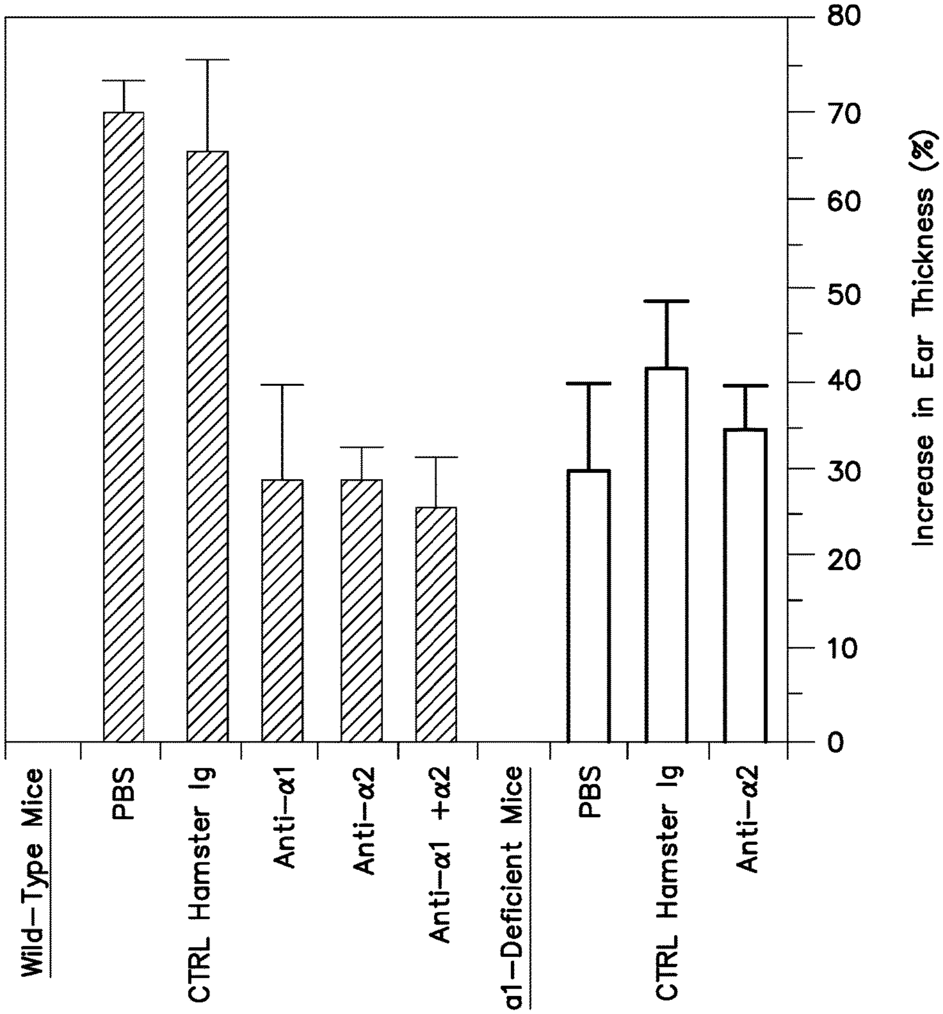
FIG. 4. Contact hypersensitivity responses in α1-deficient mice compared to wild-type mice. FITC-sensitized mice were injected i.p. with indicated mAbs 4 h prior to FITC challenge. Ear thickness was measured at baseline and 24 h later, and results shown as % increase in ear thickness±SEM as illustrated in Example 4. Groups of four to five mice per condition were used, and all experiments were performed a minimum of three times. One representative experiment is shown.

CHS effector responses are decreased in α1β-deficient mice. To exclude the possibility that the inhibitory role of α1β1 in the effector response of FITC-mediated CHS was mAb-mediated, experiments were carried out in wild-type and α1β1 integrin deficient mice (FIG. 4). MAb inhibition of the effector phase in wild-type mice was consistent with previous results with 56% inhibition in ear thickness seen with anti-α1, 56% with anti-α2 and 62% with a combination of anti-α1 and anti-α2. The effector phase of CHS was significantly reduced in untreated α1β1-deficient mice as compared to untreated wild-type mice (30% vs 71% increase in ear thickness, respectively). As expected, the level of ear swelling in untreated α1β1-deficient mice was equivalent to the level of ear swelling seen in anti-α1 mAb-treated wild-type mice. Lastly, mAb blockade of α2β1 in the α1β1-deficient mice resulted in only slightly increased inhibition of ear swelling, consistent with the results seen in wild-type mice treated with a combination of anti-α1 and anti-α2 mAbs.

Example 5

To further exclude the possibility that the inhibitory effect of the anti-integrin mAbs seen in both the DTH and CHS models of inflammation is caused by a general anti-inflammatory effect mediated by the anti-α1 and anti-α2 mAbs, the effect of these mAbs on irritant dermatitis was studied.

To assess irritant dermatitis, mice were painted with 5 ul of 0.8% croton oil in acetone on both sides of each ear. Therapeutic or control antibodies were given 4 h prior to the application of the irritant. Ear swelling was measured 24 h later as described above and compared to ear thickness prior to croton oil application. Results are reported as mean percent increase in baseline ear thickness±SEM as described above. Mice painted with acetone only (vehicle control) served as a negative control.

Figure 5:
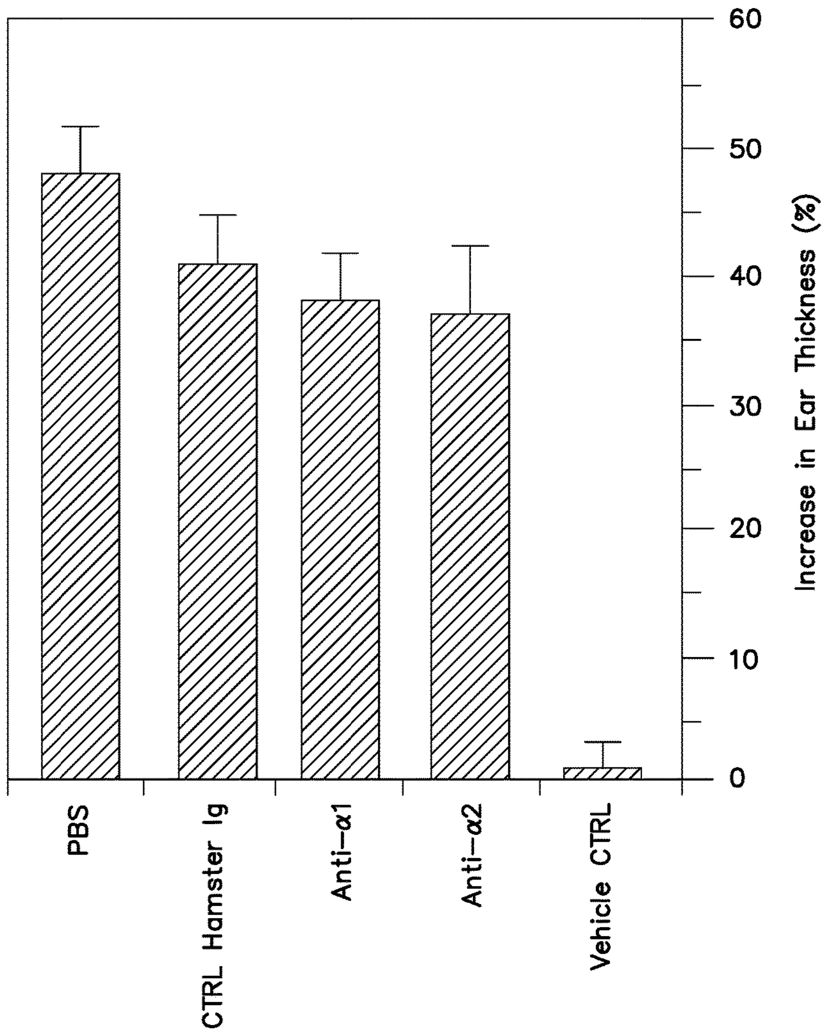
FIG. 5. Effect of anti-α1 and anti-α2 mAbs on croton oil-induced non-specific inflammation. Mice were injected i.p. with indicated mAbs 4 h prior to ear painting with croton oil. Ear thickness was measured at baseline and 24 h later, and results shown as % increase in ear thickness±SEM as illustrated in Example 5. Groups of four to five mice per condition were used, and all experiments were performed a minimum of three times. One representative experiment is shown.

24 h later, ears of mice treated with croton oil showed a significant increase in ear thickness (48%), when compared to mice receiving vehicle only (acetone). Toxic ear swelling caused by croton oil was not significantly affected in mice pretreated with anti-α1 or anti-α2 mAbs when compared to either PBS or control mAb-treated animals (FIG. 5). Histologic examination of the croton oil-treated ears revealed no differences in numbers or types of infiltrating cells or edema formation in mice treated with anti-α1 or anti-α2 mAbs, as compared to control mAb-treated mice or PBS-treated mice (data not shown).

Example 6

Inhibition of arthritis bar α1β1 and α2β1. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, J. Immunol. 148:2103-2108; Terato et al., 1995, Autoimmunity 22:137-147).

Arthrogen-CIA Antibody kits were purchased from Stratagene (La Jolla, Calif.) and arthritis induced using a well established protocol (Terato et al., 1992, J. Immunol. 148:2103-2108; Terato et al., 1995, Autoimmunity 22:137-147). Briefly, arthritis was induced through i.p. injection of a cocktail of 4 anti-collagen type II mAbs (1 mg each) on d 0, followed by i.p. injection of 50 ug LPS on d 3. Over the course of the next 3-4 d, the mice developed swollen wrists, ankles and digits. Therapeutic or control mAb (250 ug) was administered i.p. 4 h prior to injection of the anti-collagen mAbs on d 0, and again 4 h prior to LPS administration on d 3, and then continuing every $3^{rd}$ day for the length of the experiment. Beginning on d 3, mice were evaluated for the development of arthritis. Severity of arthritis in each limb was scored using a four point system. 0=normal; 1=mild redness, slight swelling of ankle or wrist; 2=moderate swelling of ankle or wrist; 3=severe swelling including some digits, ankle, and foot; 4=maximally inflamed.

Figure 6:
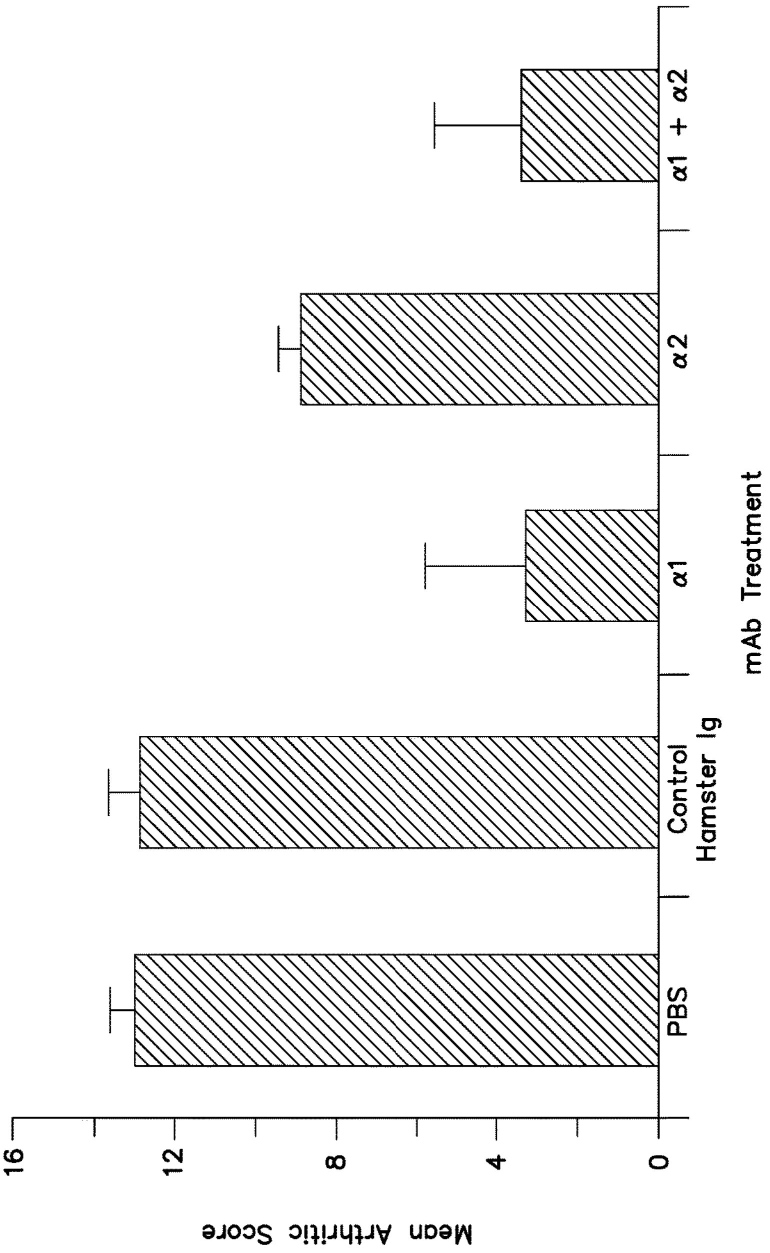
FIG. 6. Effect of anti-α1 and α2mAbs in collagen mAb-induced arthritis. Mice were injected i.p. with anti-collagen mAbs at d 0, followed by LPS on day 3. Mice were injected i.p. with indicated mAbs every $3^{rd}$ day starting on d 0. Clinical arthritis was apparent 2-3 d following LPS injection and continued for several weeks. Each limb was evaluated on a 0 to 4 scale every $3^{rd}$ day as illustrated in Example 6 and results are expressed as the mean arthritic score between d 9 and d 15 (±SEM) of all four limbs. These data represent a summary of four experiments with each experiment consisting of groups of three to four mice per condition.

Severe arthritis in Balb/c mice developed within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 6). In contrast, treatment with anti-α1 mAb alone resulted in a marked reduction (78%) in arthritis, lasting the duration of the experiment. Treatment with anti-α2 mAb alone also had a beneficial effect, resulting in a 32% decrease in the arthritic score as compared to control b-treated mice. The combination of anti-α1 and anti-α2 mAbs resulted in a similar degree of inhibition as seen with anti-α1 mAb alone.

Example 7

Histological analysis of effect of anti-α1 and anti-α2 mAb treatment on the inflammatory cellular infiltrate. Further histological analysis of the SRBC-induced DTH response confirmed the ability of anti-α1 and anti-α2 mAb treatment to modulate the elicited inflammatory response. An unchallenged footpad from an SRBC-sensitized mouse showed virtually no inflammatory cellular infiltrate when compared to an SRBC-challenged footpad from the same mouse. Treatment of SRBC-sensitized mice with anti-α1 and anti-α2 mAbs either alone or combined greatly reduced the number of these infiltrating cells found in SRBC-challenged footpads when compared to control mAb-treated mice. Closer examination of the infiltrating cells revealed most cells to be composed of neutrophils, with some monocytes and lymphocytes present, and confirmed that anti-α1 and anti-α2 mAb treatment greatly decreased the numbers of these cells.

Example 8

Immunohistochemical demonstration of α1-expressing cells in the inflammatory cellular infiltrate. Immunohistochemistry was performed to more precisely determine the nature of the infiltrating cells and whether they express collagen-binding integrins. Infiltrating cells from an inflamed footpad of an untreated mouse were examined for expression of α1β1 integrin and cell lineage markers. α1β1 integrin was found to be expressed on many infiltrating leukocytes. Dual immunohistochemistry was utilized to identify the nature of the infiltrating cells and the distribution of α1β1 expression. Using cell lineage markers, the infiltrate was found to be composed largely of granulocyte/monocytes (Mac-1+), with many of these cells being neutrophils (Gr1+), along with a smaller number of T lymphocytes (CD3+). Expression of α1β1 integrin was found among all three subsets of cells, with al expressed on a subset of Mac-1+ granulocyte/monocytes, a subset of Gr1+ neutrophils, and on the majority of infiltrating CD3+ T lymphocytes. Detailed immunohistochemical analysis revealed that although anti-α1 and anti-α2 mAb treatment reduced the numbers of infiltrating cells, no change in the cellular composition of the infiltrate was seen (data not shown). Immunohistochemistry staining with a FITC anti-hamster mAb confirmed the ability of the anti-α1 and antis α2 mAb to localize to the inflamed footpad (data not shown).

Example 9

Figure 7:
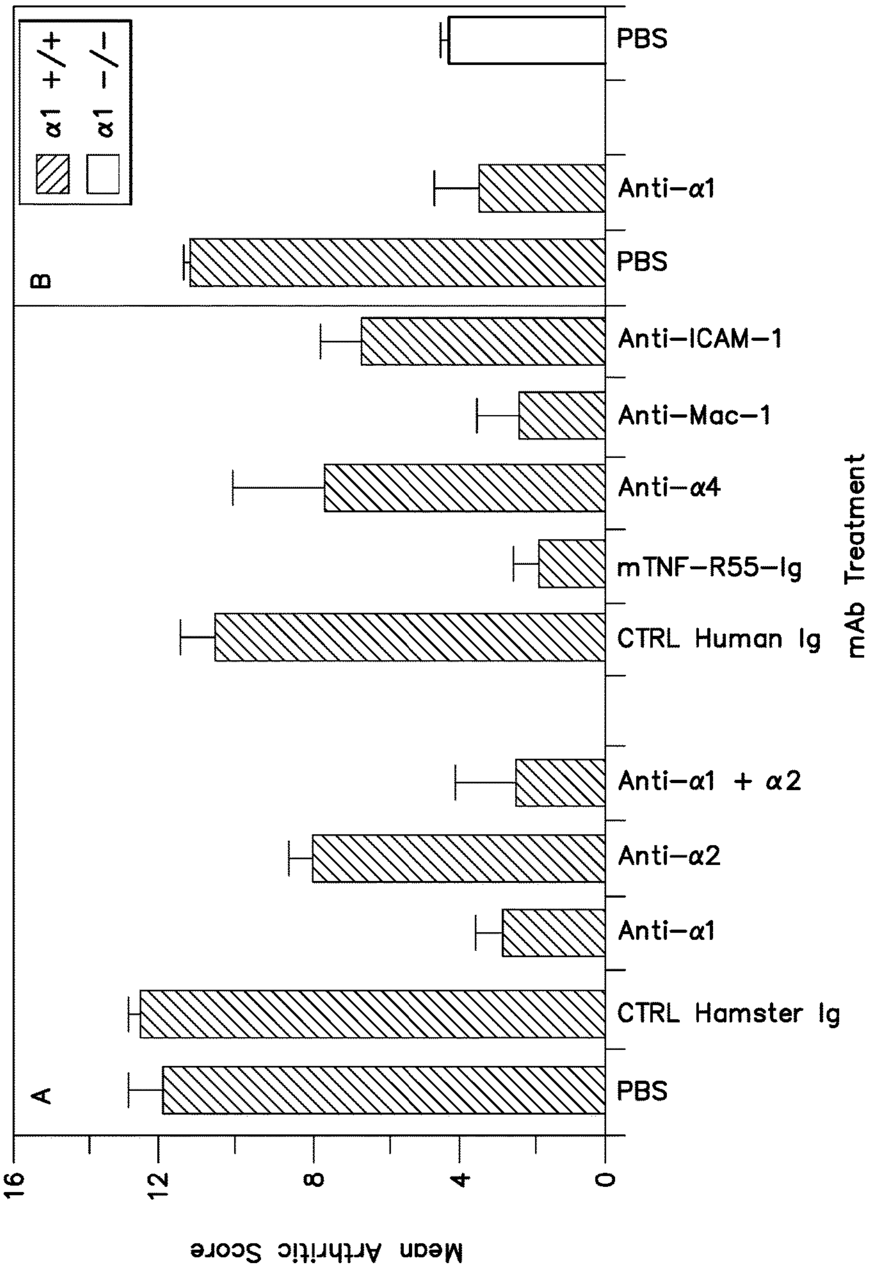
FIG. 7. Effect of anti-α1 and α2 mAbs in collagen mAb-induced arthritis. A. Preventative treatment of mice with either anti-α1 or anti-α2 mAb decreases arthritic score. Mice were treated with anti-collagen mAbs at d 0, followed by LPS on d 3. Arthritis was apparent by d 6 and continued for several weeks. Mice were treated with the indicated mAbs every $3^{rd}$ day starting on d 0. Each limb was evaluated and scored on a 0 to 4 scale every $3^{rd}$ day. Results are expressed as the mean arthritic score between d 9 and d 15 (±SEM) of all four limbs (maximum score of 16). Groups of 4 mice per condition were used; the average of 12 experiments is shown. B. α1-deficient mice have a reduced arthritic score comparable to anti-α1 mAb-treated wild-type mice. Experimental details and scoring are as outlined above. Groups of 4 mice per condition were used; the average of 2 experiments is shown.

Inhibition of arthritis by mAbs to α1β1 and α2β1 and in α1-deficient mice. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, J. Immunol 148:2103-2108; Terato et al., 1995, Autoimmunity 22:137-147). This model involves injection of a cocktail of anti-collagen type II mAbs into mice, followed later by LPS administration, resulting in the development of arthritis over the next 3-7 d. Mice were given mAb every $3^{rd}$ day starting at d 0, and scored for the development of arthritis every $3^{rd}$ day. Severe arthritis developed in all mice within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 7). In contrast, treatment with anti-α1 mAb alone resulted in a marked reduction (79% and higher) in arthritis, lasting the duration of the experiment. Treatment with anti-α2 mAb alone also had a beneficial effect, resulting in a 37% decrease in the arthritic score as compared to control mAb-treated mice. The combination of anti-α1 and anti-α2 mAbs resulted in a similar degree of inhibition as seen with anti-α1 mAb alone. Reduction of arthritic score with anti-α1 mAb treatment was seen in all mice and compares favorably with several other mAb-based treatments for arthritis such as soluble TNF receptor Ig fusion protein (Mori et al., 1996, J. Immunol. 157:3178-3182), anti-Mac-1 (Taylor et al., 1996, Immunology. 88:315-321), anti-α4 (Seiffge, 1996, J. Rheumatol. 23:2086-2091), and anti-ICAM-1 (Kakimoto et al., 1992, Cell Immunol. 142:326-337). In agreement with mAb-based data showing an important role for α1β1 in arthritis, untreated α1-deficient mice showed significant reduction in arthritic score when compared to wild-type mice.

Example 10

Effect of anti-α1 mAb treatment on the immunopathology of arthritic joints. Joints from wild-type arthritic mice (day 8) receiving either control mAb or anti-α1 mAb treatment were compared visually and histologically to joints from a normal untreated mouse. Visually, joints from control mAb-treated mice demonstrated redness and swelling of the entire foot including digits, while anti-α1 mAb-treated mice showed little if any signs of inflammation in either joints or digits. Histologic examination showed severe changes in control mAb-treated arthritic joints, with extensive infiltration of the subsynovial tissue with inflammatory cells, adherence of cells to the joint surface, and marked cartilage destruction as evidenced by proteoglycan loss. Consistent with previous reports (Terato et al., 1992, J. Immunol 148:2103-2108; Terato et al., 1995, Autoimmunity 22:137-147), the majority of the infiltrating cells in this model are neutrophils. Anti-α1 mAb treatment of mice dramatically reduced the amount of inflammatory infiltrate and the degree of cartilage destruction.

Example 11

Figure 8:
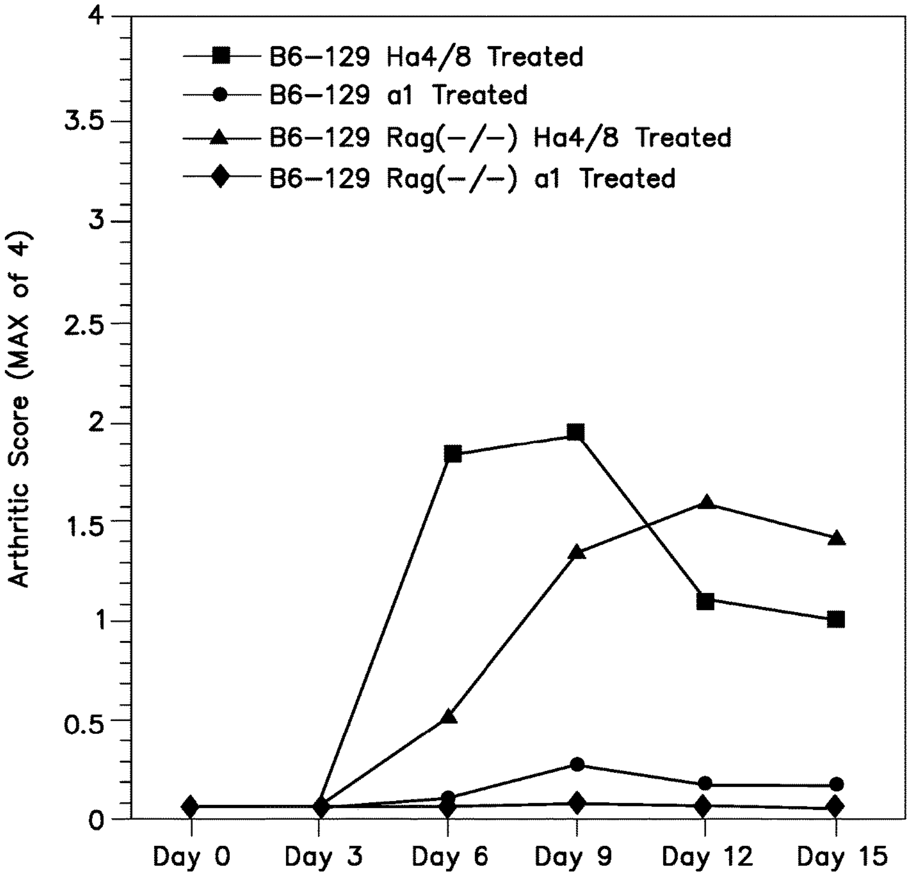
FIG. 8. Development of arthritis is delayed in the absence of lymphocytes and inhibition of arthritis by anti-α1 mAb occurs in the absence of lymphocytes. Wild-type B6,129 or RAG-1-deficient B6,129 mice were treated with anti-collagen mAbs at day 0, followed by LPS on day 3. Arthritis was apparent by day 6 and continued for several weeks. Mice were treated with the indicated mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Development of arthritis is delayed in the absence of lymphocytes and inhibition of arthritis by anti-α1 mAb occurs in the absence of lymphocytes. To determine what cell types might be important in the collagen mAb-induced arthritis model we compared the ability of wild-type B6-129 mice and RAG-1-deficient B6-129 mice to develop arthritis (FIG. 8). Genetic deletion of the RAG-1 (recombination activating gene-1) gene results in a complete loss of mature T and B lymphocytes (Mombaerts et al., 1992, Cell 68:869-877). Both the wild-type and RAG-1-deficient mice developed arthritis, though the kinetics of induction in the RAG-1-deficient mice is significantly slower (FIG. 8). These results suggest that while lymphocytes are involved in this model of arthritis, they are not required for the development and progression of the disease. Published reports examining the effect of the RAG-1-deficient mice in other models of arthritis also found that loss of T and B lymphocytes delayed the onset of arthritis (Plows et al., 1999, J. Immunol. 162:1018-1023). Treatment of either wild-type or RAG-1-deficient mice with anti-α1 mAb completely inhibited arthritis (FIG. 8). These results demonstrate that the effectiveness of anti-α1 mAb in this model is not dependent on the presence of lymphocytes, and that as suggested by previous experiments (FIG. 7), the efficacy of anti-α1 mAb in preventing disease may be through its action on other α1-expressing cells, such as macrophages and neutrophils.

Example 12

Figure 9:
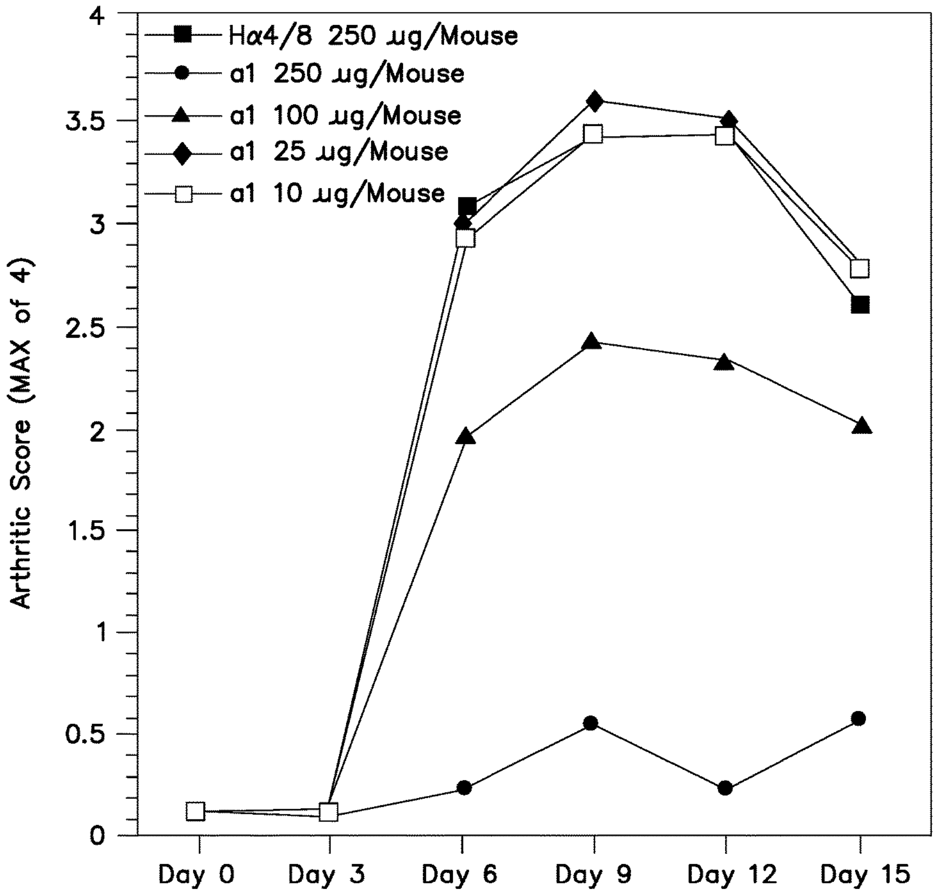
FIG. 9. Dose response of anti-α1 mAb inhibition of arthritis. Wild-type Balb/c mice were treated with anti-collagen mAbs at day 0, followed by LPS on day 3. Arthritis was apparent by day 6 and continued for several weeks. Mice were treated i.p. with the indicated dose of either Ha4/8 (isotype control) or Ha31/8 (anti-α1) mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Dose response of anti-α1 mAb inhibition of arthritis. Given the striking effects of anti-α1 mAb treatment on preventing arthritis, we extended these studies to include a dose response analysis (FIG. 9). Different doses of mAb were administered i.p. every 3$^{rd}$ day starting at day 0. In agreement with earlier data, a 250 ug dose of anti-α1 mAb resulted in near complete prevention of arthritis. A lower dose of 100 ug of anti-α1 mAb was partially effective at preventing arthritis in this model, while lower doses did not have any discernable effect on arthritic score (FIG. 9).

Example 13

Figure 10:
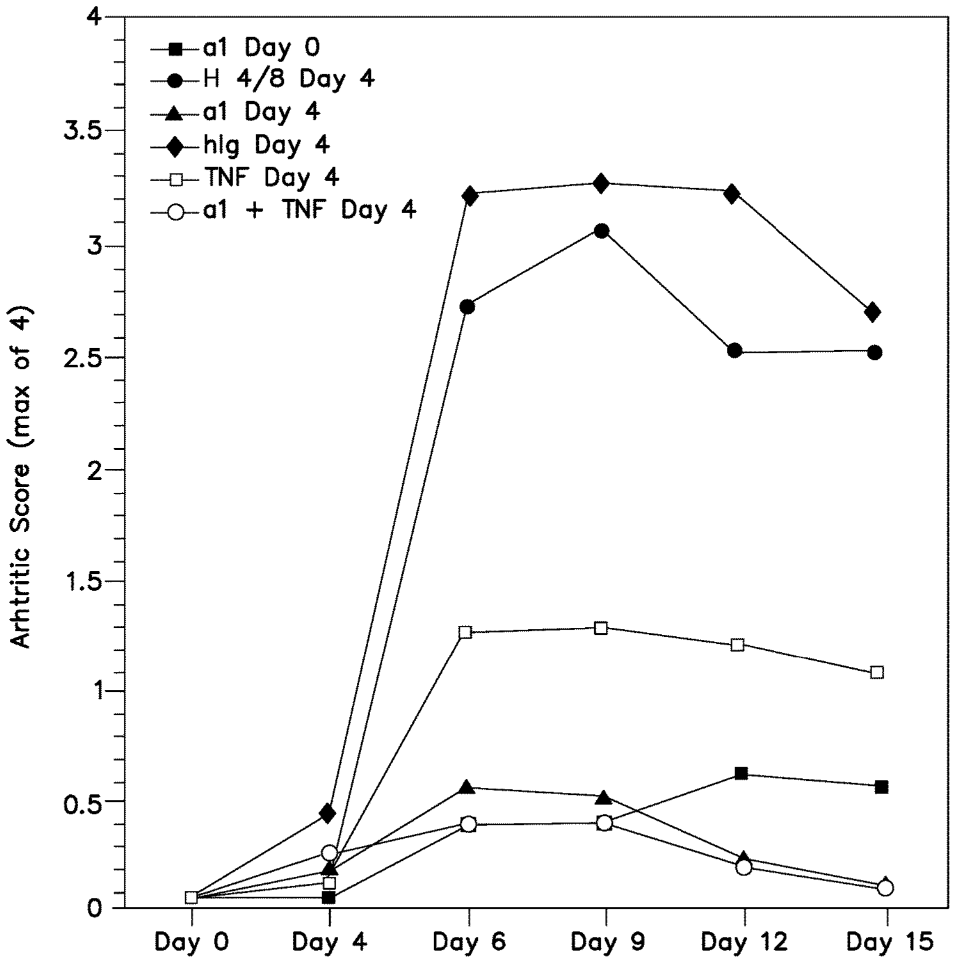
FIG. 10. Therapeutic treatment with anti-α1 mAb can decrease arthritic score. Wild-type Balb/c mice were treated with anti-collagen mAbs at day 0, followed by LPS on day 3. Arthritis was apparent by day 6 and continued for several weeks. Mice were treated i.p. with mAbs (250 μg) or Ig fusion protein (200 μg) every $3^{rd}$ day starting on day 4. Mice received either mAb (Ha4/8 isotype control or Ha31/8 anti-α1), Ig fusion protein (Isotype control Ig or TNF-R55-Ig) or a combination of both (250 ug Ha31/8 and 200 ug TNF-R55-Ig). Each limb was evaluated and scored on a 0 to 4 scale every $3^{rd}$ day. Results are expressed as the mean arthritic score per limb (maximum score of 4). Groups of 4 mice per condition were used.

Therapeutic treatment with anti-α1 mAb can decrease arthritic score. Given the effectiveness of anti-α1 mAb in preventing arthritis, we attempted to treat mice that are on their way to develop disease. Arthritis was induced in mice by injection of a cocktail of anti-collagen type II mAbs on day 0, followed by LPS administration on day 3. Mice were then treated with either anti-α1 mAb or a soluble TNF receptor Ig fusion protein starting on day 4. Progression of arthritis was completely blocked in mice receiving anti-α1 mAb starting at day 4, when compared to mice receiving control hamster mAb starting at day 4 (FIG. 10). The degree of inhibition seen with therapeutic administration of anti-α1 mAb was complete and was equal to that seen with preventative treatment of anti-α1 mAb (started at day 0) (FIG. 10). In comparison, treatment with TN receptor Ig fusion protein from day 4 onwards resulted in only a 60-70% inhibition in arthritic score when compared to control Ig fusion protein (FIG. 10). Combined treatment of anti-α1 mAb and TNF receptor Ig fusion together was effective at completely inhibiting arthritic score, which is not surprising given the complete effectiveness of anti-α1 mAb treatment alone in suppressing arthritis. In summary, these results indicate that therapeutic treatment with anti-α1 mAb is effective at inhibiting arthritic score, and compares favorably to therapeutic treatment with a TNF antagonist.

Example 14

Cloning and mutagenesis of the α1-I domain. Human and rat α1β1 integrin I domain sequences were amplified from full length cDNAs (Kem, et al., 1994, J. Biol. Chem. 269, 22811-22816; Ignatius et al., 1990, J. Cell Biol. 111, 709-720) by the polymerase chain reaction (PCR) (PCR CORE Kit; Boehringer Mannheim, GmbH Germany), using either human specific primers, 5'-CAGGATCCGTCAGCCCCA-CATTTCAA-3' [forward] (SEQ ED NO:7), and 5'-TCCTC-GAGGGCTTGCAGGGCAAATAT-3' [reverse] (SEQ ID NO:8), or rat specific primers, 5'-CAGGATCCGTCAGTC-CTACATTTCAA-3' [forward] (SEQ ID NO:9), and 5'-TC-CTCGAGCGCTTCCAAAGCGAATAT-3' [reverse] (SEQ ID NO:10).

The resulting PCR amplified products were purified, ligated into pGEX4t-i (Pharmacia), and transformed into competent DH5α cells (Life Technologies). Ampicillin resistant colonies were screened for the expression of the .about.45 kDa glutathione S-transferase-I domain fusion protein. The sequences from inserts of plasmid DNA of clones that were selected for further characterization were confirmed by DNA sequencing.

A rat/human chimeric α1-I domain (RΔH) was generated (MORPH Mutagenesis kit; 5 prime-3 prime), exchanging the rat residues G91, R92, Q93, and L96 (FIG. 11A) for the corresponding human residues, V, Q, R, and R, respectively. Clones harboring the RΔH I domain were identified by the loss of a diagnostic Stu 1 restriction enzyme site, and the inserts confirmed by DNA sequencing. The amino acid sequence of the human α1-I domain is shown in FIG. 12.

Example 15

Generation of mAbs specific to the α1-I domain. Monoclonal antibodies have proved to be very useful probes in studying the relationship between structure and function of integrin subunits. For example, mAbs were used extensively to study regions of the β1 subunit associated with an activated conformation (Qu, A., and Leahy, D. J. (1996) Structure 4, 931-942). Thus, to identify potential probes for conformational changes of the α1-I domain, we generated a panel of mAbs to the human α1-I domain.

Generation of anti-α1 I domain Monoclonal Antibodies. Female Robertsonian mice (Jackson Labs) were immunized intraperitoneally (i.p.) with 25 μg of purified human α1β1 (Edwards et al., 1995, J. Biol. Chem. 270, 12635-12640; Gotwals et al., 1999, Biochemistry 38:8280-8) emulsified with complete Freund's adjuvant (LifeTechnologies). They were boosted three times i.p. with 25 μg of α1β1 emulsified with incomplete Freund's adjuvant (LifeTechnologies). The mouse with the highest anti-α1-I domain titer was boosted i.p. with 100 μg of α1β1 three days prior to fusion, and intravenously with 50 μg of α1β1 one day prior to fusion. Spleen cells were fused with FL653 myeloma cells at a 1:6 ratio and were plated at 100,000 and 33,000 per well into 96 well tissue culture plates.

Supernatants were assessed for binding to the α1β1 integrin by single color FACS. Prior to FACS analysis, supernatants were incubated with untransfected K562 cells to eliminate IgG that bound solely to the D subunit. Subsequently, 3-5×10^4 K562 cells transfected with the α1 integrin subunit (K562-α1) suspended in FACS buffer (1% fetal calf serum (FCS) in PBS containing 0.5% $NaN_3$) were incubated with supernatant for 45 minutes at 4° C., washed and incubated with antis mouse IgG conjugated to phycoerythrin. After washing twice with FACS buffer, cells were analyzed in a Becton Dickinson Flow Cytometer.

Supernatants from the resulting hybridomas were screened for binding to the α1-I domain. Briefly, 50 μl of 30 μg/ml human α1-I-domain-(GST fusion in PBS was coated onto wells of a 96-well plate (Nunc) overnight at 4° C. The plates were washed with PBS, blocked with 1% BSA in PBS and the hybridoma supernatant was incubated with the I domain at room temperature for 1 hour. After extensive washing with PBS containing 0.03% Tween 20, alkaline phosphatase linked anti-mouse IgG (Jackson ImmunoResearch) was added for an additional hour. After a final wash, 1 mg/ml p-nitrophenylphosphate (pNPP) in 0.1 M glycine, 1 mM $ZnCl_2$, and 1 mM $MgCl_2$ was added for 30 minutes at room temperature, and the plates were read at O.D. 405.

Selected supernatants were tested for their ability to inhibit K562-α1 dependent adhesion to Collagen IV. K562-α1 cells were labeled with 2 mM 2',7' (bis-2-carboxyethyl-5 and 6) carboxyfluorescein penta acetoxymethylester (BCECF; Molecular Probes) in DMEM containing 0.25% BSA at 37° C. for 30 minutes. Labeled cells were washed with binding buffer (10 mM Hepes, pH 7.4; 0.9% NaCl; and 2% glucose) and resuspended in binding buffer plus 5 mM $MgCl_2$ at a final concentration of $1\times10^6$ cells/mL. 50 μl of supernatant was incubated with an equal volume of $2\times10^5$ K562-α1 cells in wells of a 96 well plate. The plate was then centrifuged and the supernatants removed. Cells were resuspended in binding buffer and transferred to wells of a collagen-coated plate and incubated for 1 hour at 37° C. Following incubation, the non-adherent cells were removed by washing three times with binding buffer. Attached cells were analyzed on a Cytofluor (Millipore).

Figure 13A:
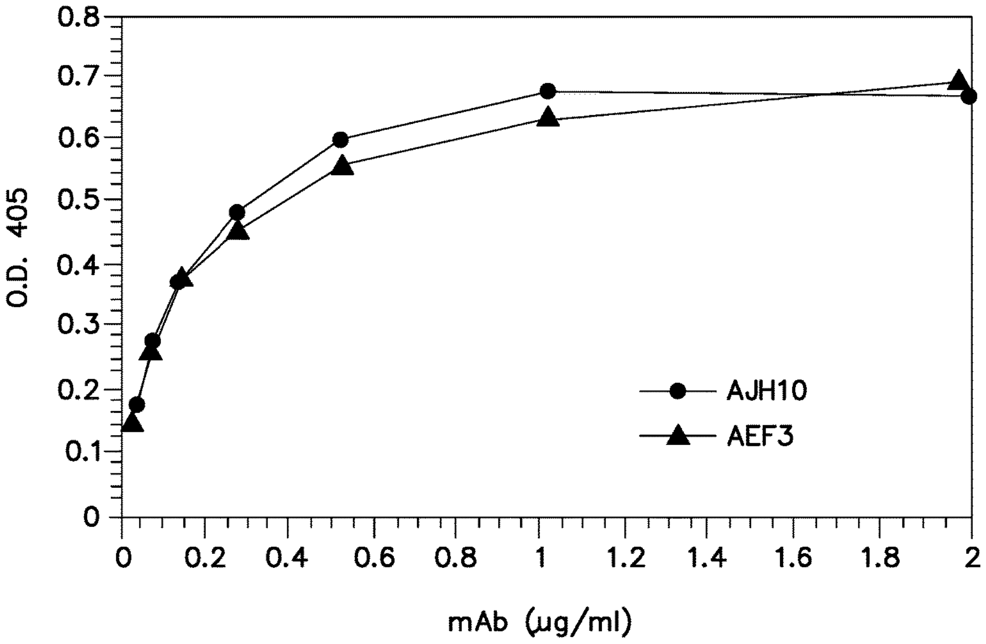
FIG. 13A-C. Identification of a blocking mAb to the α1-I domain.
Figure 13B:
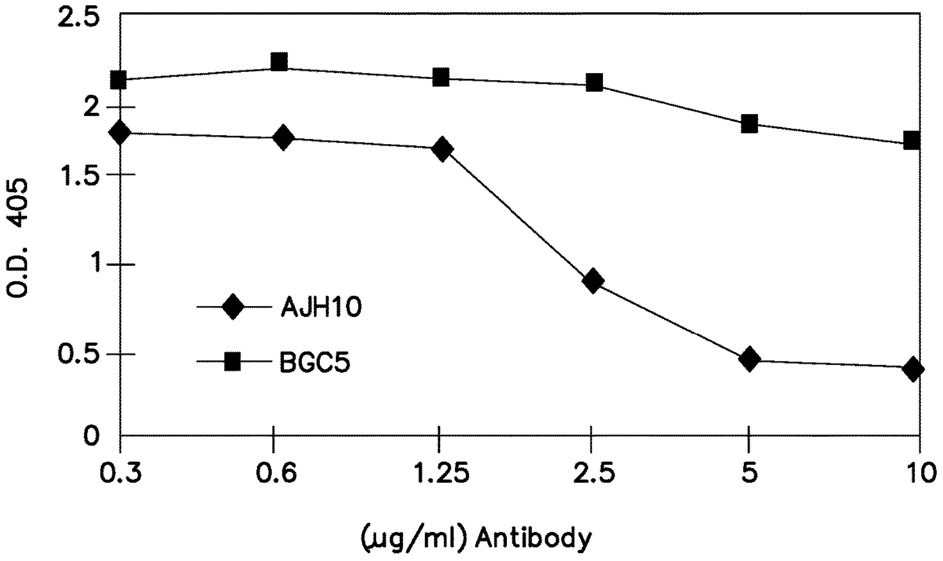
Figure 13C:
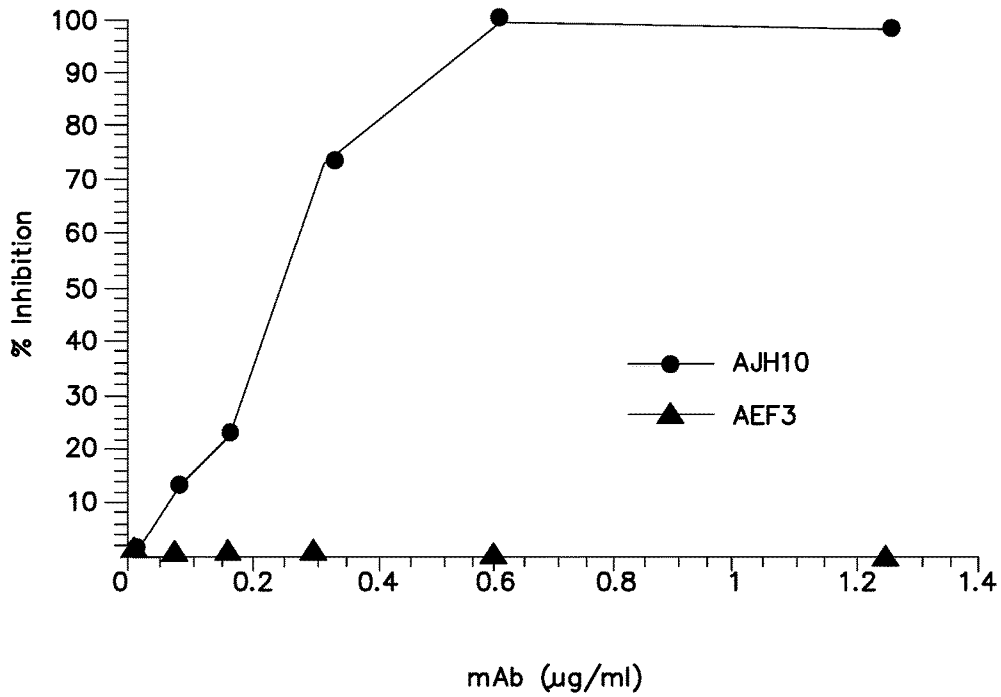
Figure 16A:
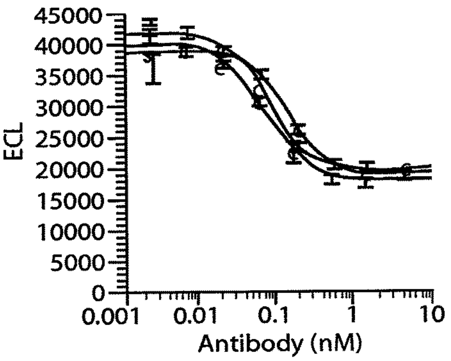
FIG. 16A-D. Characterization of Humanized AQC2 Forms. mAQC2 (triangles), chAQC2 (circles), hAQC2 (inverted triangles) and hAQC2' (squares) were evaluated.
Figure 16B:
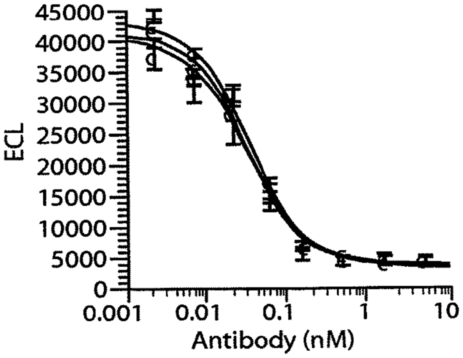
Figure 16C:
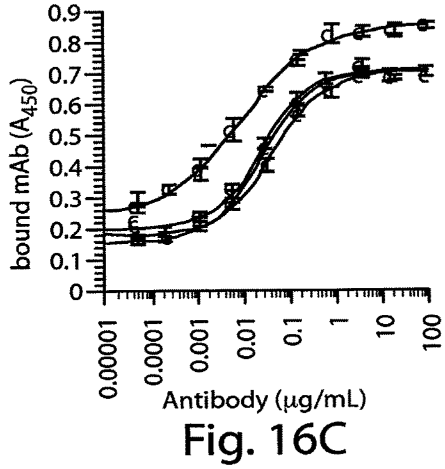
Figure 16D:
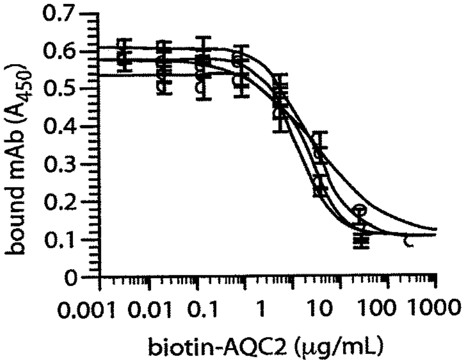

We initially identified 19 hybridomas, the supernatants of which bound to human leukemia K562 cells expressing the α1β1 integrin (K562-α1) and to the α1-I domain. The immunoglobulins were purified from each of these hybridomas and tested for the ability to block either K562-α1 or α1-I domain binding to collagen IV. The mAbs fall into two classes: those that block and those that do not block α1β1 function. For example, while the mAbs produced by clones AEF3, BGCS, AQC2 and AJH10 bind the α1-I domain (FIG. 13A, data not shown for BGCS), only mAbs AJH10 and AQC2 inhibit α1-I domain-dependent (FIG. 13B; FIG. 16B) or K562-α1 (FIG. 13C; FIG. 16C) adhesion to collagen IV.

Sequencing of the Complementarity Determining Regions. To establish the clonal origin of this panel of mAbs, we amplified by PCR and sequenced the CDRs from 12 of the 19 antibodies (data not shown).

2 μg of mRNA, isolated from $10^7$ hybridomas (FastTrack mRNA isolation kit, Invitrogen), was reverse transcribed (Ready-To-Go You Prime First Strand Kit, Pharmacia Biotech) using 25 pM each of the following primers: heavy chain VH1FOR-2 (Michishita et al., 1993, Cell 72:857-867); light chain, VK4FOR, which defines four separate oligos (Kern et al., 1994, J. Biol. Chem. 269:22811-22816). For each hybridoma, heavy and light chains were amplified in four separate PCR reactions using various combination of the following oligos: 1) Heavy chain: VH1FR1K (Kamata et al., 1995, J. of Biol. Chem. 270:12531-12535), VH1BACK, VH1BACK (Baldwin et al. (1998) Structure 6, 923-935), $V_H$fr1a, $V_H$fr1b, $V_H$fr1e, $V_H$fr1f, $V_H$fr1g (Ignatius et al. (1990) J. Cell Biol. 111, 709-720), or VH1FOR-2 (Michishita, M., Videm, V., and Arnaout, M. A. (1993) Cell 72, 857-867); 2) Light chain: VK1BACK (Baldwin et al. (1998) Structure 6, 923-935), VK4FOR, VK2BACK oligos (Kern et al. (1994) J. Biol. Chem. 269, 22811-22816), or $V_K$fr1a, $V_H$fr1c, $V_H$fr1e, $V_H$fr1f (Ignatius et al. (1990) J. Cell Biol. 111, 709-720). Products were amplified (5 min at 95° C., 50 cycles of 1 min at 94° C., 2 min at 55° C., 2 min at 72° C., and a final cycle of 10 min at 72° C.), gel purified (QIAquick, Qiagen), and sequenced directly using various of the listed oligos on an ABI 377 Sequencer.

Sequences from clones producing function-blocking mAbs were nearly identical across all the complementarity-determining regions (CDRs) and the intervening framework regions suggesting that these hybridomas are clonally related.

Example 16

Immunoblotting and FACS Analysis. Sequences of the variable regions of the non-blocking antibodies were markedly different from the clonally related family of sequences found for the blocking antibodies. As the blocking antibodies appear to originate from a single clone, we chose two (AJH10 and AQC2) to characterize further.

Immunoblotting. The smooth muscle cell layer dissected from sheep aorta, and K562-α1 cells were extracted with 1% Triton X-100 in 50 mM Hepes, pH 7.5, 150 mM NaCl, 10 mM phenylmethylsulfonyl flouride (PMSF), 20 μg/ml aprotinin, 10 μg/ml leupeptin, 10 mM ethylenediaminetetraacetic acid (EDTA). Samples were subjected to 4-20% gradient SDS-PAGE, and electroblotted onto nitrocellulose membranes. The blots were blocked with 5% dry milk in TBS; washed in TBS containing 0.03% Tween-20, and incubated with antibodies in blocking buffer containing 0.05% $NaN_3$ for 2 hours. Blots were then washed as before, incubated with horseradish peroxidase conjugated anti-mouse IgG for one hour, washed again and then treated with ECL reagent (Amersham). Blots were then exposed to film (Kodak) for 30 to 60 seconds, and developed.

Figure 14:
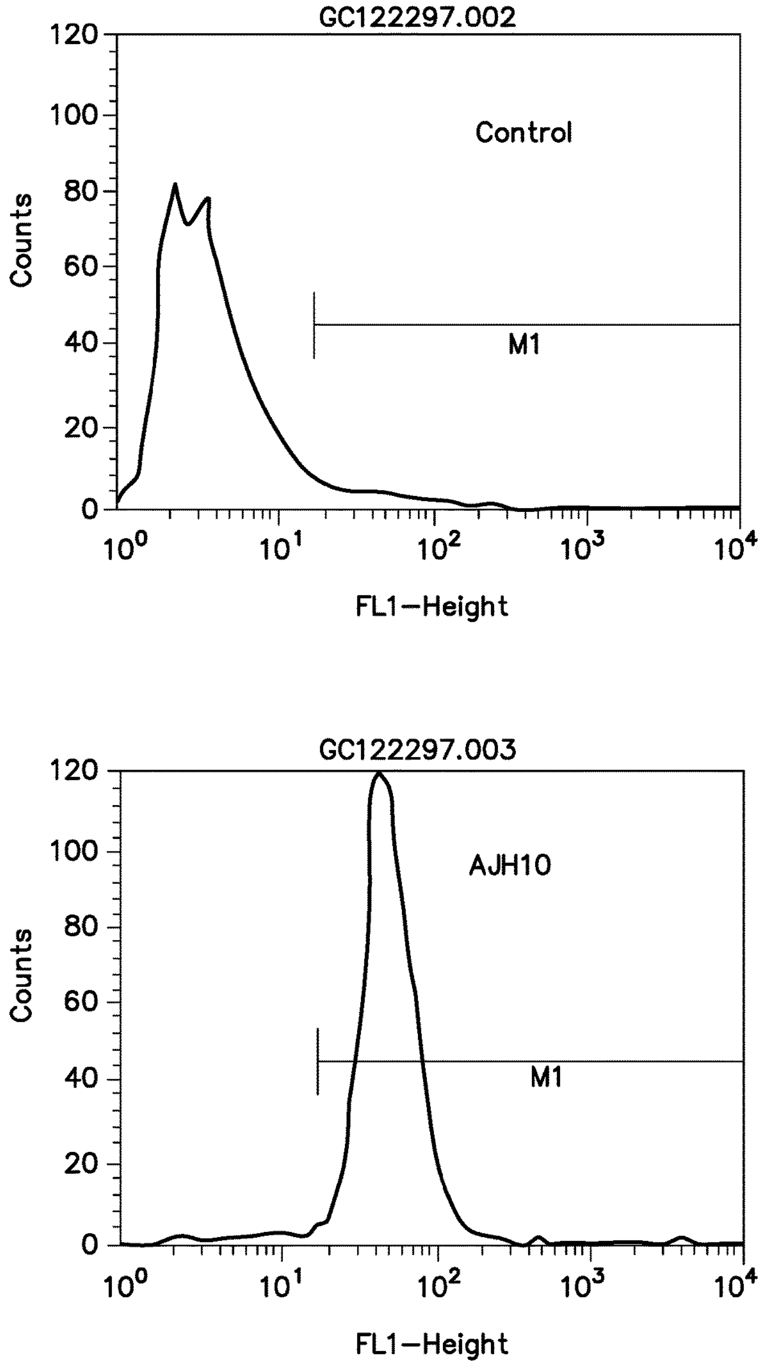
FIG. 14. Species Cross-reactivity of the blocking mAbs analyzed by fluorescence activated cell sorter (FACS). Rabbit vascular smooth muscle cells were incubated with either mAb AJH10 (bottom) or murine IgG control (top) and analyzed by fluorescence activated cell sorter (FACS).

Immunoblotting and FACS analysis (FIG. 14) demonstrate that AJH10 reacts with human, rabbit, and sheep, but not rat α1β1 integrin suggesting that the blocking mAbs bind to an evolutionarily conserved, linear epitope. The non-blocking mAbs were neither efficient at immunoblotting nor did they react with species other than human.

Example 17

Binding of the α1-I Domain to Collagen is Divalent Cation-Dependent

A. Purification of the α1-I Domains.

The α1-I domains were expressed in *E. coli* as GST (glutathione-S-transferase) fusion proteins containing a thrombin cleavage site at the junction of the sequences. The clarified supernatant from cells lysed in PBS was loaded onto a glutathione Sepharose 4B column (Pharmacia) which was washed extensively with PBS. The α1-I domain-GST fusion protein was eluted with 50 mM Tris-HCl, pH 8.0, 5 mM glutathione (reduced). For denaturation studies, the I domain was cleaved with thrombin in 50 mM Tris, pH 7.5, and purified from the GST fusion partner. DTT was added to 2 mM and the sample was loaded on a glutathione Sepharose 4B column. The flow-through and wash fractions were pooled and loaded onto a Q Sepharose FF column (Pharmacia). The α1-I domain was eluted with 50 mM Tris HCl, pH 7.5, 10 mM 2-mercaptoethanol, 75 mM NaCl. The purified I domain displayed its predicted mass (Lee et al. (1995) Structure 3, 1333-1340, 871 Da) by electrospray ionization-mass spectrometry (ESI-MS), migrated as a single band by SDS-PAGE, and the protein eluted as a single peak of appropriate size by size exclusion chromotography on a Superose 6 FPLC column (Pharmacia).

B. Functional Analysis 96 well plates were coated overnight at 4° C. with 1 μg/ml collagen IV (Sigma) or collagen Type I (Collaborative Biomedical), washed with Triton buffer (0.1% Triton X-100; 1 mM $MnCl_2$; 25 mM Tris-HCl; 150 mM NaCl), and blocked with 3% bovine serum albumin (BSA) in 25 mM Tris-HCl; 150 mM NaCl (TBS). Serial dilutions of the α1-I domain-GST fusion protein in TBS containing 1 mM MnCl-.sub.2 and 3% BSA were incubated on the coated plates at room temperature for 1 hour, and washed in Triton buffer. Bound α1-I domain was detected with serial additions of 10 μg/ml biotinylated anti-GST polyclonal antibody (Pharmacia); ExtrAvidin-horseradish peroxidase (Sigma) diluted 1:3000 in TBS containing 1 mM $MnCl_2$ and 3% BSA, and 1-Step ABTS (2,2'-Azine-di[3-ethylbenzthiazoline sulfonate]; Pierce). Plates were read at O.D. 405 on a microplate reader (Molecular Devices).

Results.

Figure 15A:
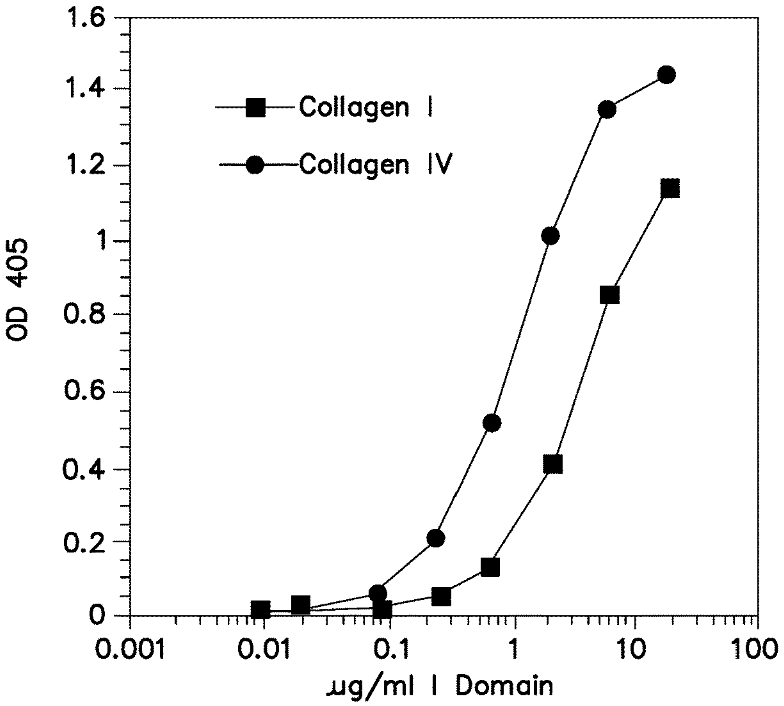
FIG. 15A-C. The α1-I domain binds collagen.
Figure 15B:
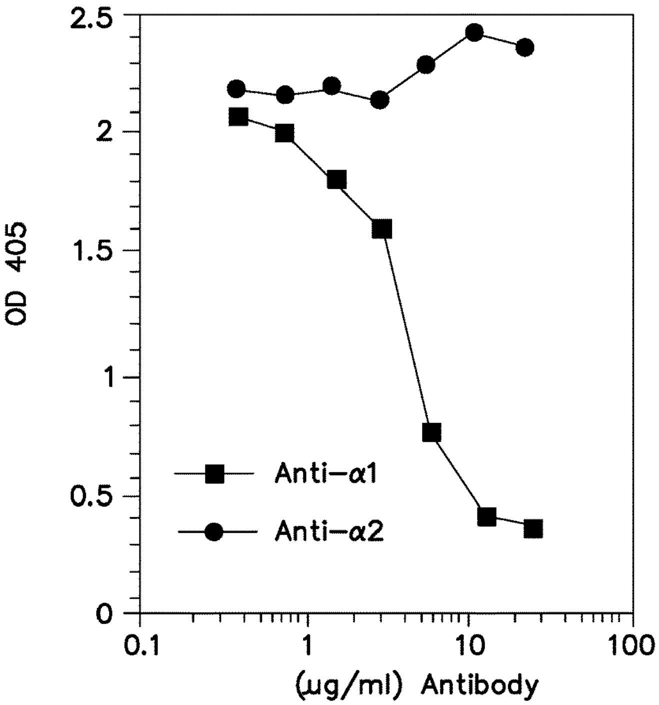
Figure 15C:
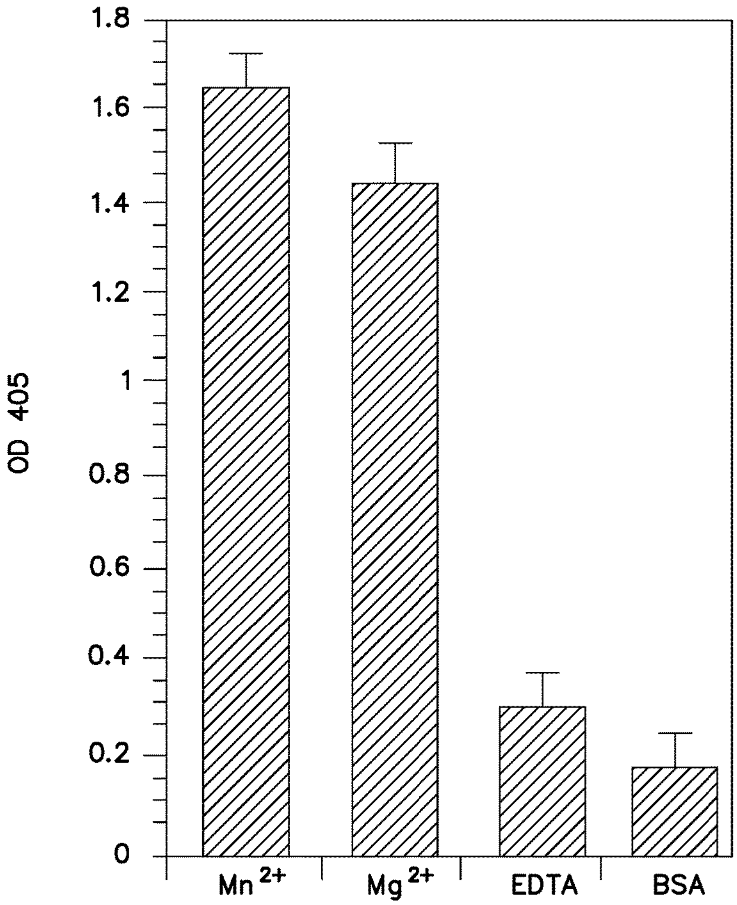

The human and rat (95% identity to human) α1-I domains were expressed in *E. coli* as GST-fusion proteins and purified over glutathione sepharose. Both proteins were examined for binding to collagen I and IV using a variation of an ELISA-based assay previously described (Qu, A., and Leahy, D. J. (1995) Proc. Natl. Acad. Sci. USA 92, 10277-10281). The human α1-I domain binds collagen IV with better efficiency than collagen I (FIG. 15A). An antibody specific to the α1-I domain, but not an antibody specific to the α2-I domain (FIG. 15B) abrogated binding to both ligands (data for collagen I is not shown). Both $Mn^{2+}$ and $Mg^{2+}$ stimulated binding, and EDTA reduced binding to background levels (FIG. 15C). No measurable differences in ligand binding were detected between the human and rat α1-I domains suggesting that the sequence differences between species are not functionally relevant (data not shown). Thus, the α1-I domain, specifically, require cation for efficient ligand binding.

Example 18

Figures 11A, 11B:
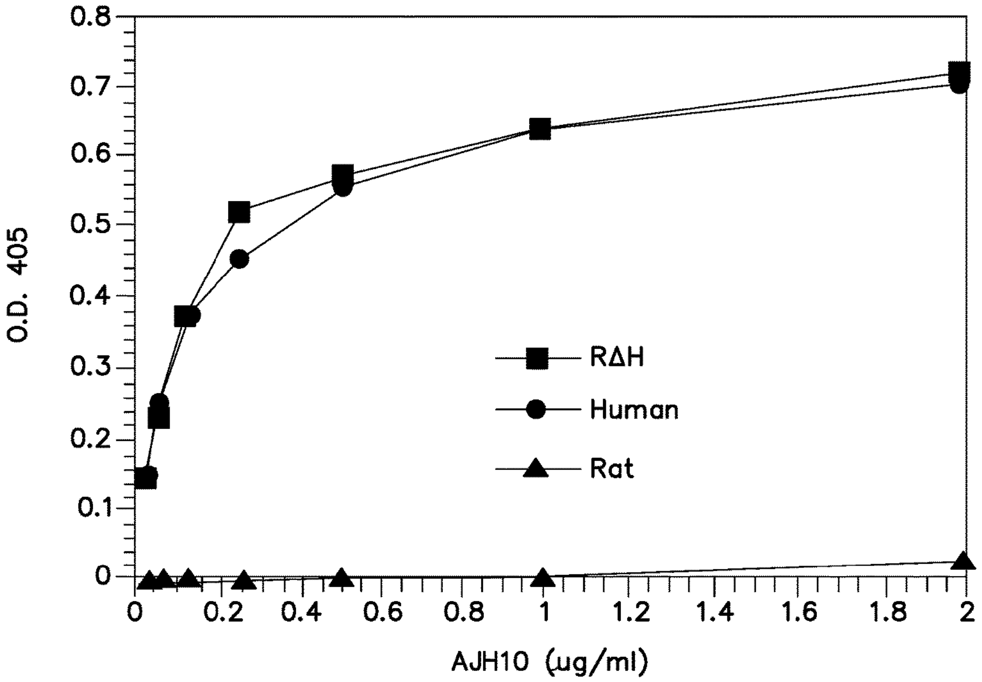
FIG. 11A-B. Location of the Epitope for the anti-α1 I domain Blocking mAbs.

A Cation-Dependent Epitope Resides near the MIDAS motif. We exploited the observation that AJH10 recognizes the human, but not the rat α1-I domain sequences to map the epitope for the α1β1 function-blocking mAbs. The human and rat sequences differ by only 12 amino acids, 4 of which lie in a stretch of 6 amino acids (aa 92-97, FIG. 11A) adjacent to the critical threonine (FIG. 11A, aa 98) within the MIDAS motif. To test the hypothesis that the 6 amino acid residues, Val-Gln-Arg-Gly-Gly-Arg (residues 91-96 of SEQ ID NO:64), comprise the epitope for the blocking mAbs, we constructed a chimeric I domain (RΔH), exchanging the rat residues G91, R92, Q93, and L96, for the corresponding human residues, V, Q, R, and R, respectively. AJH10, along with all the function-blocking mAbs, recognizes the chimeric I domain (RΔH; FIG. 11B).

To orient these residues with respect to the MIDAS domain in the tertiary structure of the α1-I domain, we modeled the α1-I domain using the coordinates of the crystal structure of the α2 I domain.

A homology model of the human α2 I-domain was built using the X ray crystal structure of the human α2 I-domain (Ward et al. (1989) Nature 341, 544-546). The model was built using the homology modeling module of Insight II (version 2.3.5; Biosym Technologies). The program CHARMM (Clackson et al. (1991) Nature 352, 624-628) was used with the all-hydrogen parameter set 22 with a distant dependent dielectric constant of two times the atom separation distance. We first did 1000 steps of steepest descent minimization with mass-weighted harmonic positional constraints of 1 kcal/(mol $Å^2$) on all atoms of the α1-I domain. This minimization was followed by another 1000 steps of steepest descent and 5000 steps of Adopted-Basis Newton Raphson with constraints of 0.1 kcal/(mol $Å^2$) on the C-α atoms of the α1-I domain to avoid significant deviations from the α2-I domain X-ray crystal structure.

The α1β1 and α2β1 integrin sequences exhibit 51% identity with no insertions or deletions, suggesting that the overall structure of the two I domains will be similar. The metal coordination site is predicted to be the same in the α1-I domain as in the α2-I domain, and the residues that comprise the epitope for the blocking mAbs lie on a loop between helix α3 and helix α4 which contains the threonine within the MIDAS motif critical for cation binding. The α1-I domain model predicts that the amide nitrogen of Q92 (FIG. 11A) hydrogen bonds with the carbonyl group of 133, the residue adjacent to S32. Thus, the loop that contains the epitope may play a functional role in stabilizing the MIDAS region.

Example 19

Monoclonal antibody AQC2 (i.e., mAQC2; "m" for murine) (Example 15, supra) is an $IgG_1$, kappa antibody. To identify the nucleotide sequences encoding the heavy and light chains of this antibody, total cellular RNA from AQC2 murine hybridoma cells was obtained by using a QIAGEN RNEASY midi kit in accordance with the manufacturer's instructions. Then cDNAs encoding the variable regions of the heavy and light chains were cloned by RT-PCR from total cellular RNA using a GIBCO BRL SUPERSCRIPT Preamplification System for First Strand cDNA Synthesis following the manufacturer's recommended protocol. Random hexamers were used for priming.

The heavy chain variable domain of mAQC2 was amplified by PCR from the first strand cDNA with the primers: 5' TGA GGA GAC GGT GAC CGT GGC CCT TGG CCC C 3' (SEQ ID NO:11) and 5' AGG TSM ARC TGC AGS AGT CWG G 3' (S=C/G, M=A/C, R=A/G, and W=A/T) (SEQ ID NO:12). The PCR was subjected to 30 cycles using Clontech's Advantage Taq polymerase: denature 30 sec at 94° C., anneal 1 min at 50° C., and elongate 1.5 min at 68° C. The mAQC2 light chain with its signal sequence was amplified by PCR using the primers: 5' ACT AGT CGA CAT GGA TTT WCA GGT GCA GAT TWT CAG CTT C 3' (W=A/T) (SEQ ID NO:13) and 5' ACT GGA TGG TGG GAA GAT GGA 3' (SEQ ID NO:14). The PCR was subjected to 30 cycles using Stratagene's cloned Pfu polymerase: denature 1 min at 94° C., anneal 1 min at 50° C., and elongate 2 min at 72° C. The PCR products for the heavy and light chains were gel-purified using a QIAGEN QIAQUICK gel extraction kit following the manufacturer's recommended protocol.

Purified heavy chain product was subcloned into Invitrogen's pCR2.1-TOPO TA vector using its TOPO TA cloning kit. Purified light chain was subcloned into Invitrogen's pCRbluntIITOPO vector using its Zero blunt TOPO cloning kit following the manufacturer's recommended protocol. Inserts from multiple independent subclones were sequenced. With the exception of degenerate positions within the PCR primers, the insert sequences of the independent subclones were identical.

The polypeptide sequences of mAQC2 were deduced from their coding sequences. The N-terminal amino acid sequence for the mature light chain predicted by the cDNA sequence from the PCR product amplified with a signal sequence exactly matched the N-terminal sequence of purified mAQC2 light chain derived from Edman degradation (DVKVVESGG; SEQ ID NO:15). BLAST analyses of the variable domain sequences confirmed their immunoglobulin identity.

The polypeptide sequence of the light chain variable domain of mAQC2 is shown below:

```
                                       (SEQ ID NO: 1)
 1 QIVLTQFPAL MSASPGEKVT MTCSASSSVN HMFWYQQKPK

41 SSPKPWIYLT SNLASGVPAR FSGSGSGTSY SLTISSMEAE

81 DAATYYCQQW SGNPWTFGGG TKLEIK             106
```

The CDRs are shown in boldface. The CDRs are defined according to Kabat et al., Sequences of Proteins of Immunological Interest, 5th Edition, The United States Department of Health and Human Services, The United States Government Printing Office, 1991. Using the Kabat numbering system, SEQ ID NO:1 is represented as follows, where a dash denotes the absence of an amino acid:

```
1    QIVLTQFPAL MSASPGEKVT MTCSASS-SV NHMFWYQQKP

41   KSSPKPWIYL TSNLASGVPA RFSGSGSGTS YSLTISSMEA

81   EDAATYYCQQ WSGNPWTFGG GTKLEIK            107
```

The polypeptide sequence of the heavy chain variable domain of mAQC2 is:

```
                                        (SEQ ID NO: 2)
 1   DVKVVESGGG LVKPGGSLKL ACAASGFSFS RYTMSWVRQI

41   PEKRLEWVAT ISGGGHTYYL DSVKGRFTIS RDNAKNTLYL

81   QMSSLRSEDT AMYYCTRGFG DGGYFDVWGQ GTTVTVSS
```

The CDRs are shown in boldface. Using the Kabat numbering system, SEQ ID NO:2 is represented as follows, where positions numbers are consecutive numerals unless otherwise indicated:

```
1       DVKVVESGGG LVKPGGSLKL ACAASGFSFS RYTMSWVRQI

41      PEKRLEWVAT ISGGGHTYYL DSVKGRFTIS RDNAKNTLYL

81      QM

82a-c   SSL

83      RSEDTAMY YCTRGFGDGG

100a-b  YF

101     DVWGQGTTVT VSS 113
```

As used herein, residue position numbers of variable domains are designated in accordance with the Kabat numbering system unless otherwise indicated.

Example 20

This example describes the generation of a murine-human chimeric antibody, chAQC2.

The cDNAs encoding the variable regions of the mAQC2 heavy and light chains were used to construct chAQC2 expression vectors, in which the mAQC2 variable regions were linked to human $IgG_1$ and kappa constant regions.

The heavy chain chimera was constructed as follows. A 0.33 kb PstI-BstEII fragment from the mAQC2 heavy chain plasmid pAND083 was subcloned into the phosphatased 2.82 kb PstI-BstEU vector fragment from the 5a8 heavy chain plasmid pLCB7, so as to add a murine heavy chain signal-encoding sequence and a murine splice donor site to the cDNA of the mAQC2 heavy chain variable region. 5a8 is a molecularly cloned CD4-specific mAb (see, e.g., Boon et al., 2002, Toxicology 172:191-203). In the mature heavy chain encoded by the resultant plasmid (pAND092), the N-terminus differed by five residues from the N-terminus (DVKVVE; SEQ ID NO:16) of the cognate mAQC2 heavy chain.

To correct the heavy chain N-terminus, pAND092 was subjected to unique site elimination (USE) mutagenesis using an USE mutagenesis kit (Amersham Pharmacia Biotech) following the manufacturer's recommended protocol. The Q1D, Q3K, L4V, Q5V, Q6E substitutions were encoded by the mutagenic primer 5' GCA CCA GGT GCC CAC TCC GAC GTC AAG GTG GTG GAG TCA GGG GGA GGC TTA GTG 3' (SEQ ID NO:17). Mutated plasmid clones were identified by their new AatII and HinfI sites and eliminated PstI site. The heavy chain coding sequence was then confirmed by DNA sequencing. The correctly mutated plasmid was called pAND094. The 0.43 kb NotI-HindIII fragment from pAND094 and the 1.21 kb HindIII-NotI fragment from the plasmid pEAG964 (containing a coding sequence for a human $IgG_1$ constant region) were subcloned into the NotI site of pCH269, a plasmid derived from the pCEP4 EBV expression vector (Invitrogen). The resultant plasmid was named pAND099.

The light chain chimera was generated as follows. A 0.46 kb EcoRI fragment from the mAQC2 light chain variable domain plasmid pAND081 was subcloned into the phosphatased 2.7 kb vector fragment of the pUC-derived pNN09 cloning vector, to add a 5' NotI site. The resulting plasmid, pAND091, was subjected to mutagenesis using the Amersham USE kit (supra) to introduce a BglII site at the 3' end of the coding sequence. The mutagenic primer had the sequence 5' GGA GGC ACC AAG CTG GAG ATC TAA CGG GCT GAT GCT GC 3' (SEQ TD NO: 18). The correctly mutated plasmid was identified by its BglII and BstYI site changes. The light chain coding sequence in the resultant plasmid pAND093 was confirmed by DNA sequencing. Then the 0.44 kb NotI-BglII light chain variable domain fragment from pAND093 and the 0.68 kb BclI-NotI fragment from the plasmid pEAG963 (containing a coding sequence for a human kappa light chain constant domain) were subcloned into the NotI site of pCH269 (supra), producing plasmid pAND102. To create an unblocked kappa light chain (Q1E), pAND093 was subjected to USE mutagenesis with the mutagenic primer 5' CAT MT GTC CAG GGG AGA AAT TGT TCT CAC CCA G 3' (SEQ ID NO:19), to introduce an XmnI site. The mutated plasmid was identified by screening for an XmnI site change. The light chain sequence in the resultant plasmid pAND097 was confirmed by DNA sequencing. The 0.44 kb NotI-BglII light chain variable domain fragment from pAND097 and the 0.68 kb BclI-NotI fragment from the plasmid pEAG963 (containing a human kappa light chain constant domain) were subcloned into the NotI site of pCH269, producing plasmid pAND098.

To generate chAQC2 antibodies, expression vectors (chAQC2 heavy chain vector pAND099-I chAQC2 light chain vector pAND102, and chAQC2 heavy chain vector pAND099+chAQC2 unblocked light chain vector pAND098) were co-transfected into 293-EBNA cells. The transfectants were tested for antibody secretion and specificity. The controls were cells transfected with the corresponding vectors without an insert or with DNA constructs encoding ch5c8 (a molecularly cloned CD154-specific mAb described in, e.g., Elster et al., 2001, Transplantation 72:1473-1478) or chCBE11 (a molecularly cloned LTβR-specific mAb described in, e.g., Browning et al., 1996, J. Biol. Chem. 271:24934-24938).

Then transfectants with the desired antibody secretion were lysed, and protein A immunoprecipitation was performed on the lysates and conditioned medium. Western blot analysis of the precipitates performed with anti-human heavy and light chain antibodies indicated that chAQC2-transfected cells synthesized and efficiently secreted heavy and light chains at levels similar to ch5c8-transfected and chCBE11-transfected cells. Further, huVLA-1-expressing K562α1 cells were stained with the conditioned medium from the transfected cells, and FACS analysis was performed on the stained cells. The results indicated that the chAQC2 antibody produced staining patterns similar to those of mAQC2, while conditioned media from mock-transfected and ch5c8-transfected cells failed to stain K562α1 cells. Chimeric AQC2 produced from scaled-up transient transfection was purified and shown to bind to VLA-1 by FACS titration. Chimeric AQC2 with either a wildtype or a genetically unblocked light chain bound to VLA-1. See also FIGS. 16A-D (discussed below).

Example 21

This example describes a method of humanizing the mAQC2 monoclonal antibody.

Analysis of the mAQC2 variable domains. The variable domains in the light and heavy chains of mAQC2 were compared with the consensus sequences for mouse and human subgroups (Kabat et al, supra) using the software program FASTA. The light chain variable domain was found to be a member of mouse subgroup VI with 89% identity in a 109 amino acid overlap. This domain also corresponded to human subgroup I with 72% identity in a 113 amino acid overlap. The heavy chain variable domain was found to be a member of mouse subgroup IIId with 86% identity in a 129 amino acid overlap. This heavy chain variable domain also corresponded to human subgroup III with 79% identity in a 130 amino acid overlap.

The CDRs were categorized into canonical classes according to Chothia et al., Nature 342, pp. 877-883 (1989). The key residues defining each canonical class determine to a large extent the structural conformation of the CDR loop, and thus should be retained in the reshaped antibody. The L1 loop of mAQC2 fell into canonical class 1 (10 residue loop), L2 into class 1 (7 residue loop) and L3 into class 1 (9 residue loop). The H1 loop fell into class 1 (5 residue loop) and the H2 loop into class 1 (16 residue loop) residues. The H3 loop did not seem to belong to any canonical class. The canonical residues important for these classes were all included in the humanized antibodies.

Unusual framework residues in mAQC2 were determined by analyzing all mouse and human variable chain sequences in the September 1999 version of the Kabat database. It was believed that mAQC2-specific differences might indicate somatic mutations that enhance binding affinity if these differences were close to the binding site. Unusual mAQC2 residues further away from the binding site and unusual human framework residues were removed in case they would create immunogenic epitopes in the humanized antibody. Unusual framework residues found in mAQC2 were 7(F), 10(L), and 41(K) in the light chain; and 4(V), 21(A), and 40(I) in the heavy chain. None of these unusual mouse framework residues were retained the humanized antibodies.

Modeling the structure of the variable regions. The light and heavy chains of mAQC2 were aligned against a nonredundant database to determine which structural frames to use to construct three-dimensional models of the mAQC2 light and heavy chains. Using FASTA, the light chain was found to have 82% sequence identity to monoclonal murine antibody ab57 (1CLOL), whereas the heavy chain was found to have 76% sequence identity to murine 6d9 Fab fragment (1HYY). Using the molecular modeling software package SYBYL (Tripos Inc.), the approximate three dimensional structures of the mAQC2 light and heavy chains were built using the light chain of ab57 and the heavy chain of 6d9, respectively. The structural integrity of the models was assessed at the console and was found to be reasonable.

Design of the reshaped variable regions. Two approaches were used to choose human acceptor frameworks to "accept" mAQC2's CDRs. The first approach was by homology matching and the other by using consensus human Ig sequences. Under the homology approach, the Kabat database, the nonredundant database from NCBI, ENTREZ (The National Institutes of Health), and the Incyte database were searched using the software programs FASTA and BLAST. The choice of human acceptor frameworks was made based on sequence identity between mAQC2 frameworks and human frameworks (excluding frameworks from previously humanized antibodies) and the source of the antibody.

The frameworks from an immunoglobulin variable region gene having a GENBANK accession number of gi:587330 (human kappa subgroup I Vκ-1c147) were eventually chosen for the light chain of the humanized antibody (Welschof et al., J. Immunol. Meth. 179:203-14 (1995)). The frameworks from Amulc11 (Kabat E D 044469; human subgroup III) were chosen for the heavy chain of the humanized antibody (Huang et al., J. Immunol. 151:5290-300 (1993)).

Back mutations of the human frameworks. Strategies for determining which back mutations to make are available on the Humanization by Design web sites under mirrored urls on the worldwide web at mathbio.nimr.mrc.ac.uk/jsaldan and cryst.bbk.ac.uk/~ubcg07s. Previous experiments have shown that it is important to retain canonical residues, interface packing residues and unusual murine residues that are close to the binding site. In addition, residues in the "Vernier Zone," which forms a platform on which the CDRs rest (Foote et al., J. Mol. Biol. 224, p. 487 (1992)) and those close to CDR H3 should be considered.

Four reshaped versions were designed for each of the variable light and heavy chains, as shown in Table 1. Two of the four versions for each chain were designed by homology matching (designated huAQC2-h1 and -h2) and the other two versions by consensus matching (huAQC2-c1 and c2). It should be noted that the sequences for huAQC-h1 heavy chain and huAQC-c1 heavy chain are identical.

TABLE 1

Sequences of mAQC2, huAQC2, and human frameworks

LIGHT CHAIN

|  | FR1 |  |
|---|---|---|
| Vκ-1c147 | D--M--S-SSL---V-DR--I--* |  |
| huAQC2-h2 | ------S-SSL---V-DR--I-- |  |
| huAQC2-h1 | ------S-SSL---V-DR--I-- |  |
| mAQC2 | QIVLTQFPALMSASPGEKVTMTC |  |
| huAQC2-c1 | --Q---S-SSL---V-DR--I-- |  |
| huAQC2-c2 | --Q---S-SSL---V-DR--I-- |  |

|  | CDR1 | FR2 |
|---|---|---|
| Vκ-1c147 | R---Q-ISYLN | ------GKA--LL-- |
| huAQC2-h2 | ----------- | ------GKA--LL-- |
| huAQC2-h1 | ----------- | ------GKA------ |
| mAQC2 | SASSSVNHMF | WYQQKPKSSPKPWIY |
| huAQC2-c1 | ----------- | ------GKA------ |
| huAQC2-c2 | ----------- | ------GKA--LL-- |

|  | CDR2 | FR3 |
|---|---|---|
| Vκ-1c147 | AA-S-Q- | -S---------DFT-----LQP-F----- |
| huAQC2-h2 | ------- | -S---------D-T-----LQP-F----- |
| huAQC2-h1 | ------- | -S---------D-T-----LQP-F----- |
| mAQC2 | LTSNLAS | GVPARFSGSGSGTSYSLTISSMEAEDAATYYC |
| huAQC2-c1 | ------- | -S---------D-T-----LQP-F----- |
| huAQC2-c2 | ------- | -S---------D-T-----LQP-F----- |

|  | CDR3 | FR4 | Framework Changes |
|---|---|---|---|
| Vκ-1c147 | --SYST-L- | ------V--- | 25 |
| huAQC2-h2 | ------- | ------V--- | 21 |
| huAQC2-h1 | ------- | ------V--- | 19 |
| mAQC2 | QQWSGNPWT | FGGGTKLEIK** | 0 |
| huAQC2-c1 | ------- | --Q---V--- | 21 |
| huAQC2-c2 | ------- | --Q---V--- | 23 |

SEQ ID NOs: 65, 51, 49, 1, 66, and 54, respectively, in order of appearance.

HEAVY CHAIN:

|  | FR1 | CDR1 |
|---|---|---|
| AMU1C11 | E-QL-------IQ-----R-S------TV- | SNY-- |
| huAQC2-h2 | E-QL-------IQ-----R-S------T-- | ----- |
| huAQC2-h1 | ---QL-------Q-----R-S--------- | ----- |
| mAQC2 | DVKVVESGGGLVKPGGSLKLACAASGFSFS | RYTMS |
| huAQC2-c1 | ---QL-------Q-----R-S--------- | ----- |
| huAQC2-c2 | E--QL-------Q-----R-S------T-- | ----- |

|  | FR2 | CDR2 |
|---|---|---|
| AMU1C11 | ----A-G-G----S | V-YS--S---A----- |
| huAQC2-h2 | ----A-G-G----- | ---------------- |

TABLE 1-continued

Sequences of mAQC2, huAQC2, and human frameworks

| | | |
|---|---|---|
| huAQC2-h1 | ----A-G-G----- | ---------------- |
| mAQC2 | WVRQIPEKRLEWVA | TISGGGHTYYLDSVKG |
| huAQC2-c1 | ----A-G-G----- | ---------------- |
| huAQC2-c2 | ----A-G-G----- | ---------------- |
| | FR3 | CDR3 |
| AMU1C11 | --------S--------N---A----V---AS | IRFLEWS--Y |
| huAQC2-h2 | --------S--------N---A----V----- | ---------- |
| huAQC2-h1 | --------S--------N---A----V----- | ---------- |
| mAQC2 | RFTISRDNAKNTLYLQMSSLRSEDTAMYYCTR | GFGDGGYFDV |
| huAQC2-c1 | --------S--------N---A----V----- | ---------- |
| huAQC2-c2 | --------S--------N---A----V----- | ---------- |
| | FR4 | Framework changes |
| AMU1C11 | -----L----- | 20 |
| huAQC2-h2 | -----L----- | 16 |
| huAQC2-h1 | -----L----- | 13 |
| mAQC2 | WGQGTTVTVSS*** | 0 |
| huAQC2-c1 | -----L----- | 13 |
| huAQC2-c2 | -----L----- | 15 |

*Dashes indicate identity with the mAQC2 amino acid sequence.
*Part of SEQ ID NO: 1.
***Part of SEQ ID NO: 2.
SEQ ID NOs: 67, 44, 42, 2, 42 and 68, respectively, in order of appearance.

Some of the back mutations are discussed below.

(1) Light Chain:

1 D→Q This mutation was made in all versions since previous reshaping experiments (e.g. Kolbinger et al, Protein Eng. 6, p. 971 (1993)) suggested its importance for antigen binding.

4 M→L This is a vernier residue and was retained in all versions,

46 L→P This residue is both an interfacial and vernier residue and was retained only in h1 and c1.

47 L→W This is a vernier residue and was retained only in h1 and c1.

71 F>Y This residue is in an important canonical position and was retained in all versions.

(2) Heavy Chain:

1 E→D This back mutation was made in h1 (i.e., c1) only.

12 I→V The residue I is unusual in human and was retained in the h2 only.

28 T→S This is a vernier residue and was retained in h1 only.

29 V→F This is a canonical residue and was retained in all versions.

49 S→A This is a vernier residue and was retained in all versions.

93 A→T This is a vernier residue and interfacial and was retained in all versions.

94 S→R This is a canonical residue and was retained in both versions.

The huAQC2 variable regions were made by USE mutagenesis as described above, using the chAQC2 variable domain plasmids as starting templates. The human acceptor framework ("FR") cDNA sequences were Kabat #Z37334 for the light chain and Kabat #U00490 for the heavy chain. To facilitate identification of mutated plasmids, silent mutations were introduced to change restriction sites. Mutated plasmids were identified by the restriction site changes. The variable region cDNA sequences in the resultant plasmids were confirmed by DNA sequencing.

The h1 and c1 versions of heavy chain (which were identical) were made by using plasmid pAND094 as template. The mutagenic primers were: FR1 primer 5'GGT GCC CAC TCC GAC GTC CAG CTG GTC GAG TCA GGG GGA GGC TTA GTC CAC CCT GGA GGG TCC CTG AGA CTC TCC TGT GCA GCC TCT GGA TTC 3' (SEQ ID NO:20), which introduced TaqI and PvuII sites, and eliminated a DdeI site; FR2 primer 5' ATG TCT TGG GTT CGC CAG GCT CCG GGG AAG GGG CTG GAG TGG GTC GCA ACC 3' (SEQ ID NO:21), which introduced a NciI site, and eliminated BspEI and EarI sites; FR3 primer 5' TTC ACC ATC TCC AGA GAC AAT TCC AAG AAC ACC CTG TAC CTG CAG ATG AAC AGT CTG AGG GCC GAG GAC ACA GCC GTG TAT TAC TGT ACA AGA 3' (SEQ ID NO:22), which introduced PstI and DdeI sites; and FR4 primer 5' TGG GGC CAA GGT ACC CTG GTC ACC GTC TCC TCA GGT GAG 3' (SEQ ID NO:23), which introduced KpnI and Eco0109I sites. The resultant h1 (i.e., c1) heavy chain plasmid was designated pAND104.

The c2 version of heavy chain were made by using pAND104 as template with the following mutagenic primers: FR1 primer 5' TCC TGT GCA GCC TCT GGA TTC ACC TTC AGT AGG TAT ACT ATG TCT TGG GTT 3' (SEQ ID NO:24), which introduced an AccI site; and FR1 primer 5' GCA CCA GGT GCG CAC TCC GAG GTC CAG CTG GTC GAG TCA 3' (SEQ ID NO:25), which introduced an FspI site and eliminated an AatII site. The resultant c2 heavy chain plasmid was designated pAND115.

The h2 version of heavy chain were made by using pAND115 as template with the following primer: FR1 primer 5' GAG TCA GGG GGA GGC TTA ATC CAG CCT GGA GGG TCC CTG 3' (SEQ ID NO:26), which eliminated a DdeI site. The resultant h2 heavy chain plasmid was designated pAND113.

To generate expression vectors for the huAQC2 heavy chains, the 0.43 kb NotI-HindIII heavy chain variable domain fragment from pAND104, pAND115, or pAND113, and the 1.21 kb HindIII-NotI fragment from pEAG964 (supra) were subcloned into the NotI site of pCH269 (supra). The resultant heavy chain expression plasmids were designated pAND114 (h1), pAND121 (c2), and pAND124 (h2), respectively.

The h1 version of light chain were made by using plasmid pAND093 as template. The mutagenic primers were: FR1 primer 5' CAA ATT GTT CTC ACC CAG TCT CCA TCC TCC CTG TCT GCG TCT GTA GGG GAC AGA GTC ACC ATC ACA TGC AGT GCC AGC TCA 3' (SEQ ID NO:27), which removed BstEII and PstI sites; FW primer 5' TTC TGG TAT CAG CAG AAG CCC GGG AAA GCC CCC AAA CCC TGG ATT 3' (SEQ ID NO:28), which introduced an NciI site; FR3 primer 5 GCT TCT GGA GTC CCT TCA CGC TTC AGT GGC AGT GGG TCT GGG ACA GAT TAC ACT CTC ACA ATC AGC AGC CTG CAA CCT GAA GAT TTT GCC ACT TAT TAC TGC CAG 3' (SEQ ID NO:29), which introduced a DdeI site and eliminated Eco0109I and AvaII sites; and FR4 primer 5S GGT GGA GGC ACT AAG GTG GAG ATC TAA CGG GCT 3' (SEQ ID NO:30), which introduced DdeI and StyI sites. The resultant h1 light chain plasmid was designated pAND103.

The h2 version of light chain were made by using pAND103 as template with the following primer: FR2 primer 5' CCC GGG AAA GCG CCC AAA CTC CTG ATT TAT CTC ACA TCC 3' (SEQ ID NO:31), which introduced HhaI and HaeII sites. The resultant h2 light chain plasmid was designated pAND116.

The c1 version of light chain used plasmid pAND103 template with the following primers: FR1 primer 5' GCC TCA GTC ATA ATG TCC CGG GGA CAA ATT CAG CTC ACC CAG TCT CCA TCC 3' (SEQ ID NO:32), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:33), which introduced a Bsp1286I site. The resultant c1 light chain plasmid was designated pAND118.

The c2 version of light chain were made by using plasmid pAND116 template with the following primers: FR1 primer 5' GCC TCA GTC ATA ATG TCC CGG GGA CAA ATT CAG CTC ACC CAG TCT CCA TCC 3' (SEQ ID NO:34), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:35), which introduced a Bsp1286I site. The resultant c2 light chain plasmid was designated pAND119.

To generate expression vectors for the huAQC2 light chains, the 0.44 kb NotI-BglII light chain variable domain fragment from pAND103, pAND116, pAND118, or pAND119, and the 0.68 kb BclI-NotI fragment from pEAG963 (supra) were subcloned into the NotI site of pCH269 (supra). The resultant light chain expression vectors were designated pAND117 (h1), pAND120 (h2), pAND122 (c1), and pAND123 (c2), respectively.

The expression vectors were co-transfected into 293-EBNA cells, and transfected cells were tested for antibody secretion and specificity. Cells transfected with an empty vector served as negative control. The whole cell lysates and the conditioned medium were immuno-precipitated with protein A. Western blot analysis of the precipitates (developed with anti-human heavy and light chain antibodies) indicated that huAQC2-transfected cells synthesized and efficiently secreted heavy and light chains at levels similar to chAQC2-transfected cells.

FACS analysis of VLA-1 expressing K 562α1 cells stained with conditioned medium from the transfected cells was then performed. To do so, the K562α1 cells were incubated with the conditioned medium on ice for 120 min. The cells were then washed three times with a FACS buffer (PBS with 5% FBS and 0.05% sodium azide). The washed cells were resuspended in the buffer and incubated with PE-conjugated anti-human IgG (H+L) (Jackson ImmunoResearch Laboratories, Inc.) on ice for 30 min on ice. After the incubation, the cells were washed three times with the FACS buffer, and resuspended in the FACS buffer for analysis. The data are shown in Table 2, in which HuAQC2-h1 refers to an mAb consisting of the h1 version of the huAQC2 heavy chain (HC) and the h1 version of the huAQC2 light chain (LC) (see Table 1). Likewise, huAQC-h2 is an mAb consisting of the h2 versions of the heavy and light chains, huAQC2-c1 the c1 versions, and huAQC2-c2 the c2 versions. In the table, relative MFI refers to mean MFI normalized to that observed for chAQC2 blocked. Data shown represents the average from two independent transfections. These data indicated that the huAQC2-h2 and -c2 mAbs bound less well than huAQC2-h1 and -c1 relative to chAQC2.

TABLE 2

FACS staining of K562α1 cells by chAQC2 and huAQC2

| | Light chain | Heavy chain | Relative MFI |
|---|---|---|---|
| chAQC2 | pAND102 | pAND099 | 1.00 |
| huAQC2-h1 | pAND117 | pAND114 | 1.50 |
| huAQC2-h2 | pAND120 | pAND124 | 0.64 |
| huAQC2-c1 | pAND122 | pAND114 | 1.50 |
| huAQC2-c2 | pAND123 | pAND121 | 0.68 |
| huAQC2 LC c1/HC c2 | pAND122 | pAND121 | 2.21 |
| huAQC2 LC c2/HC c1 | pAND123 | pAND114 | 0.76 |
| huAQC2 LC unblocked c1/HC c2 | pAND150* | pAND121 | 0.75 |
| huAQC2 LC L46P c2/HC c2 | pAND133** | pAND121 | 1.50 |
| huAQC2 LC L47W c2/HC c2 | pAND132*** | pAND121 | 1.00 |

*It encodes huAQC2 LC c1 with an unblocked N-terminus Q1D.
**It encodes huAQC2 LC c2 with L46P.
***It encodes huAQC2 LC c2 with L47W.

Co-transfections of 293-EBNA cells with chAQC2 and huAQC2h1, -h2, -c1 and -c2 were scaled up. Antibodies in the conditioned media were purified with Protein A-Sepharose. Purified mAbs were assayed by FACS for activity. The protocol as follows.

1. Count cells from flask that was split 1:4 on the day prior to the assay.
2. Pellet cells and resuspend at 2.5e5 cells/ml in FACS buffer (5% FBS in PBS with 0.02% NaAzide).
3. Pipette 100 μl of cells into the wells of a 96 well V bottom plate.
4. Prepare 1:3 serial dilutions of AQC2 starting at 3 μg/ml in FACS buffer.
5. Pellet the cells for 5 minutes at 800×g and flick plate to remove buffer.
6. Resuspend the cells in 100 μl of the diluted antibody series.
7. Incubate for 2 hours on ice.
8. Wash plate. Pellet the cells for 3 minutes at 800×g and flick plate to remove buffer.
9. Resuspend the cells in 100 μl of secondary antibody (diluted 1:100 in FACS buffer).
10. Incubate for 30 minutes on ice.
11. Wash plate (see above).
12. Resuspend cells in 25 μl of FACS buffer.
13. Centrifuge the FACS tubes briefly to ensure that the 50 μl is in the bottom of the tubes.
14. Vortex each tube vigorously and collect 5000 events.

Figure 17:
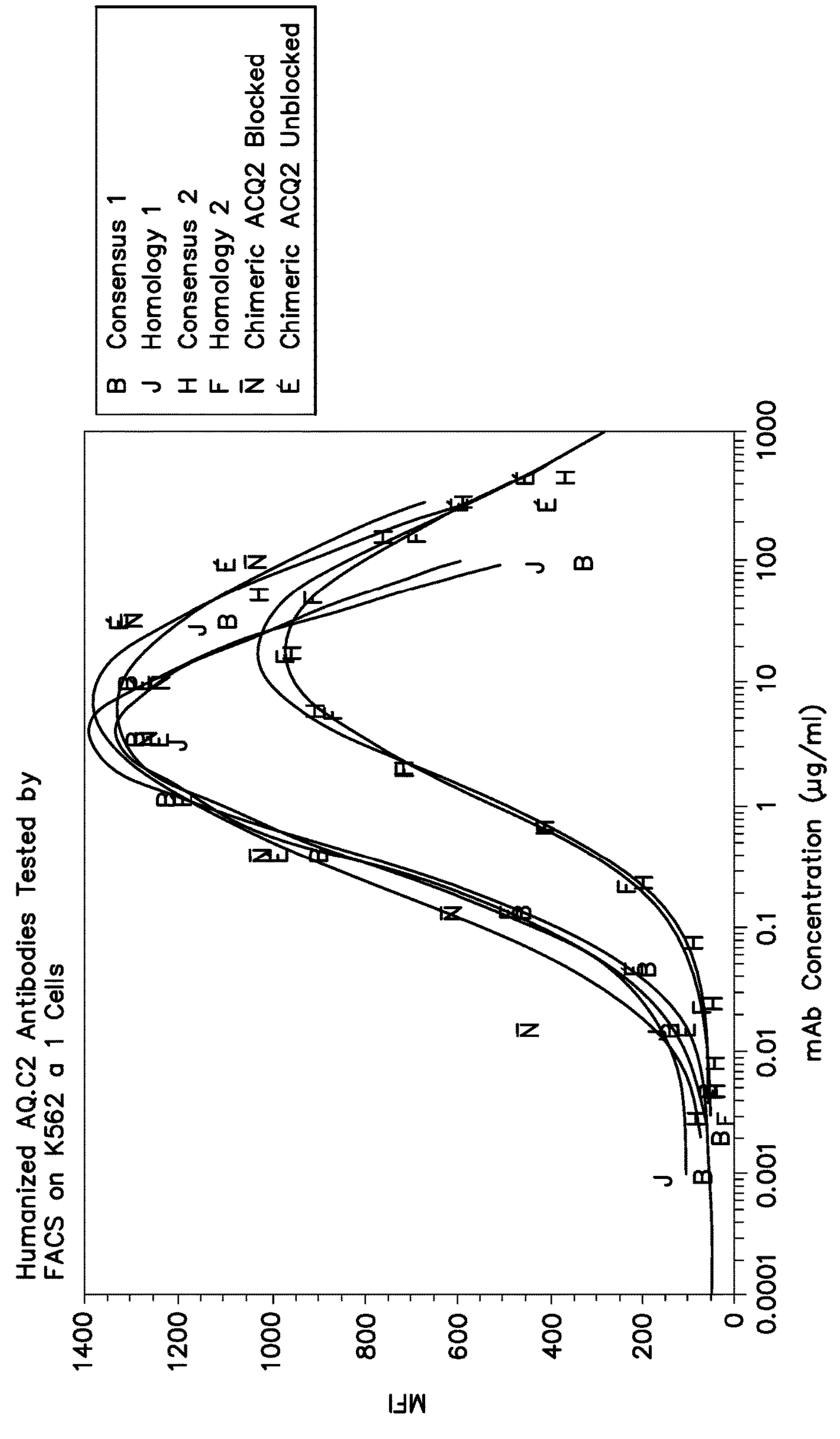
FIG. 17. Characterization of Humanized AQC2 Forms by FACS.

The data are shown in FIG. 17. These data confirmed that huAQC2-h2 and -c2 bound less well than huAQC2-h1 and c1 relative to chAQC2.

The consensus versions of huAQC2 were studied further because they would be less immunogenic when used to treat patients with chronic indications. Mix-and-match cotransfections were performed to identify whether a single chain was responsible for the apparent decrease in binding seen with huAQC2-c2. The co-transfections suggested that the reduction could be attributed to the c2 light chain (encoded by pAND123), which differed from the c1 light chain (encoded by pAND122) at only two residues in the FR region: P46L and W47L.

To examine the individual contributions of each of these two changes, new c2 light chain expression vectors were constructed. Plasmid pAND125, the LA7W variant of the c2 light chain was made using pAND119 as a template with the following mutagenic primer: FR2 primer 5' GGG AAA GCA CCC AAA CTC TGG ATC TAT CTC ACA TCC AAC 3' (SEQ ID NO:36), which introduced HhaI and HaeII sites. Plasmid pAND126, the L46P variant of the c2 light chain, was made by using pAND119 as a template with the following mutagenic primer: FR2 primer 5' AAG CCC GGG AAG GCG CCC AAA CCC CTG ATT TAT CTC ACA TCC AAC 3' (SEQ ID NO:37), which introduced BsaHI, BanI, and NarI sites. Expression vectors for these new huAQC2 light chains were made by subcloning the 0.44 kb NotI-BglII light chain variable domain fragment from pAND125 or pAND126, and the 0.68 kb BclI-NotI fragment from pEAG963 (supra) into the NotI site of pCH269 (supra). The resultant plasmids were designated pAND132 (c2 with L47W) (SEQ ID NO:47), and pAND133 (c2 with L46P) (SEQ ID NO:70), respectively.

Co-transfections of the new light chain plasmids with each of the huAQC2 heavy chain plasmids were performed. VLA-1 binding was examined by FACS. The data demonstrate that the L47W back mutation failed to improve binding. The LA6P mutation improved the peak of the binding curve, but the EC50 was still right-shifted relative to the behavior of huAQC2 version 1 (Table 2, supra). These results suggested that both back mutations were needed for full binding activity.

A genetically unblocked c1 light chain was also made, since the Q1D variant would be one residue more "humanized." The Q1D mutant, designated pAND148, was made with the template pAND118 with the following mutagenic primer: FR1 primer 5' GTC ATA ATG TCC CGG GGA GAT ATC CAG CTC ACC CAG TCT 3' (SEQ ID NO:38), which introduced a new EcoRI site and removed an ApoI site. An expression vector for this last variant of the huAQC2 light chain was made by subcloning the 0.44 kb NotI-BglII light chain variable domain fragment from pAND148 and the 0.68 kb BclI-NotI fragment from pEAG963 into the NotI site of pCH269, producing the light chain expression vector pAND150 (c1 with unblocked N-terminus Q1D). Co-expression of the genetically unblocked light chain with the c2 heavy chain (i.e., "huAQC2 LC c1 unblocked/HC c2"; designated huAQC2c4) was equivalent to that of "huAQC2 LC c1/HC c2" (designated as huAQC2-c3). VLA-1 binding was confirmed by FACS on VLA1-expressing K562α1 cells (Table 2).

Figure 18:
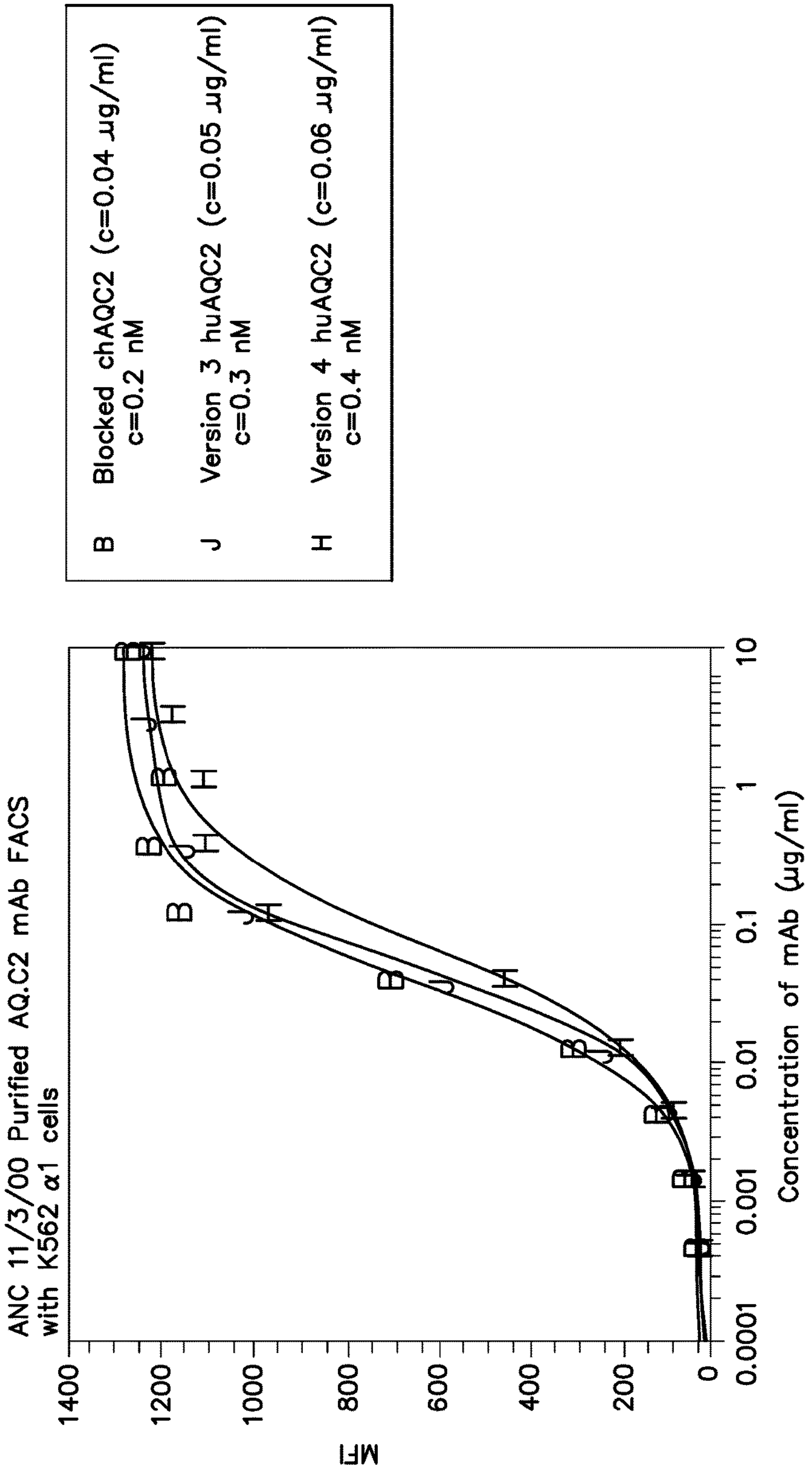
FIG. 18. Characterization of Humanized AQC2 Forms by FACS.

Co-transfections of 293EBNA cells with chAQC2 and huAQC2h1, -h2, -c1, -c2, -c3, and -c4 Antibodies in the conditioned media were purified on Protein A-Sepharose. The purified mAbs were assayed for activity (FIGS. 17 and 18). HuAQC2-c3 was chosen as the drug candidate, since its properties were more similar to chAQC2. Vectors were then designed for stable expression of huAQC2-c3 in CHO cells. The vectors contained a cDNA for the huAQC2 c1 LC or c2 HC, with the 5' and 3' UTRs eliminated and the heavy chain C-terminal lysine genetically deleted to ensure product homogeneity. The final vectors were pAND162 (light chain), pAND160 (heavy chain). As used herein, huAQC2-c3 is also called hAQC2.

The full polypeptide sequences of hAQC2 are as follows.

```
Light Chain (Plasmid: pAND162)
                                                      (SEQ ID NO: 3)
  1    QIQLTQSPSS LSASVGDRVT ITCSASSSVN HMFWYQQKPG KAPKPWIYLT

 51    SNLASGVPSR FSGSGSGTDY TLTISSLQPE DFATYYCQQW SGNPWTFGQG

101    TKVEIKRTVA APSVFIFPPS DEQLKSGTAS VVCLLNNFYP REAKVQWKVD

151    NALQSGNSQE SVTEQDSKDS TYSLSSTLTL SKADYEKHKV YACEVTHQGL

201    SSPVTKSNR GEC

Heavy Chain (Plasmid: pAND160) (SEQ ID NO: 4)
                                                      (SEQ ID NO: 4)
  1    EVQLVFSGGG LVQPGGSLRL SCAASGFTFS RYTMSWVRQA PGKGLEWVAT

 51    ISGGGHTYYL DSVKGRFTIS RDNSKNTLYL QMNSLRAEDT AVYYCTRGFG

101    DGGYFDVNGQ GTLVTVSSAS TKGPSVFPLA PSSKSTSGGT AALGCLVKDY

151    FPEPVTVSWN SGALTSGVHT PPAVLQSSGL YSLSSVVTVP SSSLGTQTYI

201    CNVNHKPSNT KVDKKVEPKS CDKTHTCPPC PAPELLGGPS VFLFPPKPKD

251    TLMISRTPEV TCVVVDVSHE DPEVKFNWYV DGVEVHNAKT KPREEQYNST

301    YRVVSVLTVL HQDWLNGKEY KCKVSNKALP APIEKTISKA KGQPREPQVY

351    TLPPSRDELT KHQVSLTCLV KGFYPSDTAV EWESNGQPEN NYKTTPPVLD

401    SDGSFFLYSK LTVDKSRWQQ GNVFSCSVMH EALHNHYTQK SLSLSPG
```

Other heavy and light chain polypeptide and nucleotide sequences are shown below.

A. chAQC2 heavy chain (Pand099) (SEQ ID NOs:39 and 40. The former No refers to the nucleotide sequence and the latter to the polypeptide sequence. The same order is used in the following numbering.)

```
  1     GACGTCAAGGTGGTGGAGTCAGGGGGAGGCTTAGTGAAGCCTGGAGGGTCC
        CTGAAACTCDVKVVESGGGLVKPGGSLKL

 61     GCCTGTGCAGCCTCTGGATTCAGTTTCAGTAGATATACTATGTCTTGGGTTCG
        CCAGATTACAASGFSFSRYTMSWVRQI

121     CCGGAGAAGAGGCTGGAGTGGGTCGCAACCATTAGTGGTGGTGGTCACACCT
        ACTATCTAPEKRLEWVATISGGGHTYYL

181     GACAGTGTGAAGGGCCGATTCACCATCTCCAGAGACAATGCCAAGAACACCC
        TGTACCTGDSVKGRFTISRDNAKNTLYL

241     CAAATGAGCAGTCTGAGGTCTGAGGACACAGCCATGTATTACTGTACAAGAG
        GTTTTGGAQMSSLRSEDTAMYYCTRGFG

301     GACGGGGGGTACTTCGATGTCTGGGGCCAAGGGACCACGGTCACCGTCTCCT
        CADGGYFDVWGQGTTVTVSS
```

B. hAQC2 HC h1 and c1 (pAND114)

(SEQ ID NOs: 41 and 42)

```
  1     GACGTCCAGCTGGTCGACTCAGGGGGAGGCTTAGTCCAGCCTGGAGGGTCCC
        TGAGACTCDVQLVESGGGLVQPGGSLRL

 61     TCCTGTGCACCCTCTGGATTCAGTTTCAGTAGATATACTATGTCTTGGGTTCG
        CCAGGCTSCAASGFSFSRYTMSWVRQA

121     CCGGGGAAGGGGCTGGAGTGGGTCGCAACCATTAGTGGTGGTGGTCACACCT
        ACTATCTAPGKGLEWVATISGGGHTYYL

181     GACAGTGTGAAGGGCCGATTCACCATCTCCAGAGACAATTCCAAGAACACCC
        TGTACCTGDSVKGRFTISRDNSKNTLYL

241     CAGATGAACAGTCTGAGGGCCGAGGACACAGCCGTGTATTACTGTACAAGAG
        GTTTTGGAQMNSLRAEDTAVYYCTRGFG

301     GACGGGGGGTACTTCGATGTCTGGGGCCAAGGTACCCTGGTCACCGTCTCCT
        CADGGYFDVWGQGTLVTVSS
```

C. hAQC2 h2 heavy chain (pAND124)

(SEQ ID NOs: 43 and 44)

```
  1     GAGGTCCAGCTGGTCGAGTCAGGGGGAGGCTTAATCCAGCCTGGAGGGTCCC
        TGAGACTCEVQLVESGGGLIQPGGSLRL

 61     TCCTGTGCAGCCTCTGGATTCACCTTCAGTAGGTATACTATGTCTTGGGTTCG
        CCAGGCTSCAASGFTFSRYTMSWVRQA

121     CCGGGGAAGGGGCTGGAGTGGGTCGCAACCATTAGTGGTGGTGGTCACACCT
        ACTATCTAPGKGLEWVATISGGGHTYYL

181     GACAGTGTGAAGGGCCGATTCACCATCTCCAGAGACAATTCCAAGAACACCC
        TGTACCTGDSVKGRFTISRDNSKNTLYL

241     CAGATGAACAGTCTGAGGGCCGAGGACACAGCCGTGTATTACTGTACAAGAG
        GTTTTGGAQMNSLRAEDTAVYYCTRGFG

301     GACGGGGGGTACTTCGATGTCTGGGGCCAAGGTACCCTGGTCACCGTCTCCT
        CAGGDGGYFDVWGQGTLVTVSS
```

D. hAQC2 c2 heavy chain (pAND121)

(SEQ ID NOs: 45 and 68)

```
  1     GAGGTCCAGCTGGTCGAGTCAGGGGGAGGCTTAGTCCAGCCTGGAGGGTCCC
        TGAGACTCEVQLVESGGGLVQPGGSLRL

 61     TCCTGTGCAGCCTCTGGATTCACCTTCAGTAGGTATACTATGTCTTGGGTTCG
        CCAGGCTSCAASGFTFSRYTMSWVRQA

121     CCGGGGAAGGGGCTGGAGTGGGTCGCAACCATTAGTGGTGGTGGTCACACCT
        ACTATCTAPGKGLEWVATISGGGHTYYL

181     GACAGTGTGAAGGGCCGATTCACCATCTCCAGAGACAATTCCAAGAACACCC
        TGTACCTGDSVKGRFTISRDNSKNTLYL

241     CAGATGAACAGTCTGAGGGCCGAGGACACAGCCGTGTATTACTGTACAAGAG
        GTTTTGGAQMNSLRAEDTAVYYCTRGFG

301     GACGGGGGGTACTTCGATGTCTGGGGCCAAGGTACCCTGGTCACCGTCTCCT
        CAGGDGGYFDVWGQGTLVTVSS
```

-continued

E. chAQC2 blocked light chain (Pand102)

(SEQ ID NOs: 46 and 1)

```
  1     CAAATTGTTCTCACCCAGTTTCCAGCACTCATGTCTGCGTCTCCAGGGGAGAA
        GCTCACCQIVLTQFPALMSASPGEKVT

 61     ATGACCTGCAGTGCCAGCTCAAGTGTAAATCACATGTTCTGGTATCAGCAGA
        AGCCAAAAMTCSASSSVNHMFWYQQKPK

121     TCCTCCCCCAAACCCTGGATTTATCTCACATCCAACCTGGCTTCTGGAGTCCC
        TGCTCGCSSPKPWIYLTSNLASGVPAR

181     TTCAGTGGCAGTGGGTCTGGGACCTCTTACTCTCTCACAATCAGCAGCATGGA
        GGCTGAAFSGSGSGTSYSLTISSMEAE

241     GATGCTGCCACTTATTACTGCCAGCAGTGGAGTGGTAACCCGTGGACGTTCG
        GTGGAGGCDAATYYCQQWSGNPWTFGGG

301     ACCAAGCTGGAGATCAAA TKLEIK
```

F. hAQC2 h1 light chain (pAND117)

(SEQ ID NOs: 48 and 49)

```
  1     CAAATTGTTCTCACCCAGTCTCCATCCTCCCTGTCTGCGTCTGTAGGgGACAG
        AGTCACCQIVLTQSPSSLSASVGDRVT

 61     ATCACATGCAGTGCCAGCTCAAGTGTAAATCACATGTTCTGGTATCAGCAGA
        AGCCCGGGITCSASSSVNHMFWYQQKPG

121     AAAGCCCCCAAACCCTGGATTTATCTCACATCCAACCTGGCTTCTGGAGTCCC
        TTCACGCKAPKPWIYLTSNLASGVPSR

181     TTCAGTGGCAGTGGGTCTGGGACAGATTACACTCTCACAATCAGCAGCCTGC
        AACCTGAAFSGSGSGTDYTLTISSLQPE

241     GATTTTGCCACTTATTACTGCCAGCAGTGGAGTGGTAACCCGTGGACGTTCGG
        TGGAGGCDFATYYCQQWSGNPWTFGGG

301     ACTAAGGTGGAGATCAAA TKVEIK
```

G. hAQC2 h2 light chain (pAND120)

(SEQ ID NOs: 50 and 51)

```
  1     CAAATTGTTCTCACCCAGTCTCCATCCTCCCTGTCTGCGTCTGTAGGGGACAG
        AGTCACCQIVLTQSPSSLSASVGDRVT

 61     ATCACATGCAGTGCCAGCTCAAGTGTAAATCACATGTTCTGGTATCAGCAGA
        AGCCCGGGITCSASSSVNHMFWYQQKPG

121     AAAGCGCCCAAACTCCTGATTTATCTCACATCCAACCTGGCTTCTGGAGTCCC
        TTCACGCKAPKLLIYLTSNLASGVPSR

181     TTCAGTGGCAGTGGGTCTGGGACAGATTACACTCTCACAATCAGCAGCCTGC
        AACCTGAAFSGSGSGTDYTLTISSLQPE

241     GATTTTGCCACTTATTACTGCCAGCAGTGGAGTGGTAACCCGTGGACGTTCGG
        TGGAGGCDFATYYCQQWSGNPWTFGGG

301     ACTAAGGTGGAGATCAAA TKVEIK
```

H. hAQC2 c1 light chain (pAND122)

(SEQ ID NOs: 52 and 66)

```
  1     CAAATTCAGCTCACCCAGTCTCCATCCTCCCTGTCTGCGTCTGTAGGGGACAG
        AGTCACCQIQLTQSPSSLSASVGDRVT

 61     ATCACATGCAGTGCCAGCTCAAGTGTAAATCACATGTTCTGGTATCAGCAGA
        AGCCCGGGITCSASSSVNHMFWYQQKPG

121     AAAGCCCCCAAACCCTGGATTTATCTCACATCCAACCTGGCTTCTGGAGTCCC
        TTCACGCKAPKPWIYLTSNLASGVPSR

181     TTCACTGGCAGTGGGTCTGGGACAGATTACACTCTCACAATCAGCAGCCTGC
        AACCTGAAFSGSGSGTDYTLTISSLQPE

241     GATTTTGCCACTTATTACTGCCAGCAGTGGAGTGGTAACCCGTGGACGTTCGG
        TCAGGGCDFATYYCQQWSGNPWTFGQG

301     ACTAAGGTGGAGATCAAA TKVEIK
```

I. hAQC2 c2 light chain (pAND123)

(SEQ ID NOs: 53 and 54)

```
  1     CAAATTCAGCTCACCCAGTCTCCATCCTCCCTGTCTGCGTCTGTAGGGGACAG
        AGTCACCQIQLTQSPSSLSASVGDRVT
```

-continued

```
 61     ATCACATGCAGTGCCAGCTCAAGTGTAAATCACATGTTCTGGTATCAGCAGA
        AGCCCGGGITCSASSSVNHMFWYQQKPG

121     AAAGCGCCCAAACTCCTGATTTATCTCACATCCAACCTGGCTTCTGGAGTCCC
        TTCACGCKAPKLLIYLTSNLASGVPSR

181     TTCAGTGGCAGTGGGTCTGGGACAGATTACACTCTCACAATCAGCAGCCTGC
        AACCTGAAFSGSGSGTDYTLTISSLQPE

241     GATTTTGCCACTTATTACTGCCAGCAGTGGAGTGGTAACCCGTGGACGTTCGG
        TCAGGGCDFATYYCQQWSGNPWTFGQG

301     ACTAAGGTGGAGATCAAA TKVEIK
```

J. chAQC2 unblocked light chain (pAND098)
(SEQ ID NOs: 55 and 56)

```
  1     GAAATTGTTCTCACCCAGTTTCCAGCACTCATGTCTGCGTCTCCAGGGGAGAA
        GGTCACCEIVLTQFPALMSASPGEKVT

 61     ATGACCTGCAGTGCCAGCTCAAGTGTAAATCACATGTTCTGGTATCAGCAGA
        AGCCAAAAMTCSASSSVNHMFWYQQKPK

121     TCCTCCCCCAAACCCTGGATTTATCTCACATCCAACCTGGCTTCTGGAGTCCC
        TGCTCGCSSPKPWIYLTSNLASGVPAR

181     TTCAGTGGCAGTGGGTCTGGGACCTCTTACTCTCTCACAATCAGCAGCATGGA
        GGCTGAAFSGSGSGTSYSLTISSMEAE

241     GATGCTGCCACTTATTACTGCCAGCAGTGGAGTGGTAACCCGTGGACGTTCG
        GTGGAGGCDAATYYCQQWSGNPWTFGGG

301     ACCAAGCTGGAGATCAAA TKLEIK
```

K. huAQC2 unblocked c1 light chain (pAND150)
(SEQ ID NOs: 57 and 58)

```
  1     GATATCCAGCTCACCCAGTCTCCATCCTCCCTGTCTGCGTCTGTAGGGGACAG
        AGTCACCDIQLTQSPSSLSASVGDRVT

 61     ATCACATGCAGTGCCAGCTCAAGTGTAAATCACATGTTCTGGTATCAGCAGA
        AGCCCGGGITCSASSSVNHMFWYQQKPG

121     AAAGCCCCCAAACCCTGGATTTATCTCACATCCAACCTGGCTTCTGGAGTCCC
        TTCACGCKAPKPWIYLTSNLASGVPSR

181     TTCAGTGGCAGTGGGTCTGGGACAGATTACACTCTCACAATCAGCAGCCTGC
        AACCTGAAFSGSGSGTDYTLTISSLQPE

241     GATTTTGCCACTTATTACTGCCAGCAGTGGAGTGGTAACCCGTGGACGTTCGG
        TCAGGGCDFATYYCQQWSGNPWTFGQG

301     ACTAAGGTGGAGATCAAATKVEIK
```

Example 22

This example describes the characterization of various AQC2 antibodies of the invention.

Solid-phase assay for α1 I domain binding. Fifty μl of 10 mg/ml α1 I domain-GST fusion protein was added to a CORNING COSTAR EASY WASH polystyrene 96-well plate (Gotwals et al., Biochemistry, 38, 8280-8 (1999)). Following incubation at 4° C. for 16 hrs, the plate was washed four times with 350 μl of 0.1% Tween-20 in PBS in a plate washer. The plate was blocked by addition of 180 μl of 3% BSA in TBS at 25° C. for 60 min, and then washed as above. Dilutions of antibodies (50 μl/well) in TBS containing 1 mg/ml BSA (assay buffer) were prepared in a 96-well roundbottom plate, transferred to the α1 I domain-coated plate, and incubated for 60 min at 25° C. Following a final wash, 100 μl/well of TMB reagent (Pierce) was added. After 10 min, 100 μl of 1 M sulfuric acid was added, and the absorbance at 450 nm was read on a UV-Vis 96-well spectrophotometer.

Electrochemiluminescence assays for binding of α1β1 integrin or α1 I domain to collagen. Tosyl-activated DYNABEADS M-280 (Dynal, Inc.) were coated with 100 μg/ml type IV collagen (Sigma) according to the manufacturer's instructions. Cell lysates from α1-transfected K562 cells were prepared as follows. Cells were collected by centrifugation, resuspended at $10^8$ cells/ml in a lysis buffer containing 25 mM Tris, pH 7.4, 1% NP-40, 1 mM CaCl.sub.2, 1 mM MnCl.sub.2, 1 mM MgCl.sub.2, 2% BSA, and 1 mM PMSF, and incubated at 4° C. for 60 ruin. Cell debris was removed by centrifugation at 12,000 rpm for 30 min and the resulting supernatant was used in subsequent experiments. Anti-β1 activating antibody TS2/16 and polyclonal anti-GST antibody (Pharmacia) were labeled with TAG-NHS ester (IGEN International, Inc., Gaithersburg, Md.) according to the manufacturer's instructions. Labeled antibodies were purified by gel filtration chromatography on SEPHADEX G25M (Pharmacia).

To carry out the binding assay, collagen-coated beads (1 mg/ml) were blocked for 5 min with 8% Lewis rat plasma in an assay buffer containing 50 mM HEPES, pH 7.5, 150 mM NaCl, and 0.1% Triton X-100. For the α1β1 binding assay, serial dilutions of antibodies were incubated with 10 μg of beads, cell lysate prepared from $10^5$ α1-transfected K562 cells (supra), and 0.1 μg/ml of TAG-TS2/16 in an assay buffer containing 1 mM $MnCl_2$. For the α1 I domain binding assay, the antibodies were incubated with 10 μg of beads, 0.1 μg/ml α1 I domain GST fusion protein, and 1 μg/ml of TAG-anti-GST in an assay buffer containing 1 mM $MnCl_2$. After one to two hours of agitation at room temperature, 200 μl of the assay buffer was added and the samples were read on an ORIGEN 1.5 electrochemiluminescence detector (IGEN). Plots are presented with arbitrary electrochemiluminescence units (ECL) on the ordinate axis.

Biotinylated mAQC2 competition assay. A 96-well plate was coated with 50 μl of 5 μg/ml α1 I domain GST fusion protein and blocked with 3% BSA in TBS as described above. Dilutions of antibodies (60 μl/well) in the assay buffer were prepared in a 96-well roundbottom plate, and 60 μl of 0.1 μg/ml biotinylated murine AQC2 in the assay buffer was added. Fifty microliters from each well was transferred to the coated plate and incubated for 3 hrs at 25° C. The plate was then washed as above, 50 μl of 1 μg/ml peroxidase-conjugated EXTRAVIDIN (Sigma) was added, and the plate was incubated another 2 hrs at 25° C. After a final wash, 100 μl/well of TMB reagent (Pierce) was added. After 10 min, 100 μl of 1 M sulfuric acid was added, and the absorbance at 450 nm was read on a UV-Vis 96-well spectrophotometer.

Experimental results. The experimental results are shown in FIGS. 16A-D and Table 3. The ability of mAQC2, chAQC2, hAQC2, and hAQC2' (i.e., huAQC2-c4; differing from hAQC2 only in that residue 1 of the hAQC2' light chain was D instead of Q) to (1) bind to human α1-transfected K562 cells (by FACS); (2) bind to immobilized α1-I domain (by ELISA); (3) compete with mAQC2 for binding to α1-I domain (ELISA); (4) block α1β1 domain binding to collagen (Electrochemiluminescence assay); or (5) block a α1β1 integrin binding to collagen (Electrochemiluminescence assay) was determined. The results are shown in FIGS. 16A-D, and calculated IC50 (for inhibition) or EC50 (for binding) values are given in Table 3. In each assay, each of the humanized AQC2 forms showed a similar ability to either bind VLA1 (or the α1 domain) or block binding to collagen (Note that in panel C, the observed difference in intensity between mAQC2 and the humanized forms derives from the use of an anti-murine-IgG secondary antibody, instead of an anti-human-IgG).

TABLE 3

Summary of assay results (all values in nM)

| Antibody | FACS (EC50) | VLA1 Inhibition (IC50) | α1I Inhibition (IC50) | ELISA (EC50) | Competition with biotin-AQC2 (IC50) |
|---|---|---|---|---|---|
| mAQC2 | n.d. | 0.0726 (±0.014) | 0.029 (±0.011) | 0.061 (±0.015) | 38 (±8.7) |

TABLE 3-continued

Summary of assay results (all values in nM)

| Antibody | FACS (EC50) | VLA1 Inhibition (IC50) | α1I Inhibition (IC50) | ELISA (EC50) | Competition with biotin-AQC2 (IC50) |
|---|---|---|---|---|---|
| Chimera | 0.25 | 0.071 (±0.002) | 0.027 (±0.007) | 0.176 (±0.058) | 30 (±6.9) |
| hAQC2 | 0.29 | 0.129 (±0.005) | 0.035 (±0.005) | 0.190 (±0.010) | 65 (±2.2) |
| hAQC2' | 0.43 | 0.125 (±0.018) | 0.037 (±0.001) | 0.313 (±0.072) | 69 (±25.7) |

We next tested whether changes at certain conservative residues in the CDRs could preserve the VLA-1 binding activity of hAQC2, DNA constructs encoding variants of hAQC2 with the following mutations were made by site-directed mutagenesis: (1) G55S in the heavy chain CDR2; (2) S24N in the light chain CDR1 (introducing an occupied N-linked glycosylation site); (3) G92S in the light chain CDR3; (4) a combination of (1) and (2); and (5) a combination of (1) and (3). The DNA constructs encoding both the heavy and light chains were then co-transfected into 293-EBNA cells, and the conditioned medium of the transfectants was assayed for antibody expression by Western blot and ELISA. The results indicated that the hAQC2 variants were expressed as efficiently as cognate h-AQC2. FACS analysis using VLA-1-expressing K562 cells further showed that the VLA-1 binding activities of these variants were similar to hAQC2 itself. In sum, the amino acid substitutions did not alter the VLA-1 binding activity of hAQC2. Indeed, X-ray crystal structure of the RΔH/hAQC2 Fab complex (infra) shows that S24 and G92 of the light chain and G55 of the heavy chain are not in the binding pocket that is in contact with the α1-I domain.

Example 23

The effector functions of an immunoglobulin couple the immunoglobulin's antigen-binding activity to the inflammatory, cytotoxic and stimulatory arms of the immune system. Effector functions may impair the safety and efficacy of an immunoglobulin therapeutic product. To reduce the potential effector functions of h-AQC2, mutations of L234A and L235A were made to its heavy chain to generate hsAQC2. For the same reason, a single mutation of N298Q (numbering according to SEQ ID NO:5) was made in the heavy chain of hAQC2 to generate an aglycosylated form of hAQC2, named haAQC2. Studies can be done to compare their efficacy, residual effector function, stability and immunogenicity to cognate hAQC2. Unless otherwise indicated, residue position numbers in constant regions as used herein are designated in accordance with the EU numbering convention.

The heavy chain polypeptide sequence of haAQC2 is as follows (Plasmid: pAND161):

```
                                                              (SEQ ID NO: 5)
  1    EVQLVESGGG LVQPGGSLRL SCAASGFTFS RYTMSWVRQA PGKGLEWVAT

 51    ISGGGHTYYL DSVKGRFTIS RDNSKNTLYL QMNSLRAEDT AVYYCTRGFG

101    DGGYFDVWGQ GTLVTVSSAS TKGPSVFPLA PSSKSTSGGT AALGCLVKDY

151    FPEPVTVSWN SGALTSGVHT FPAVLQSSGL YSLSSVVTVP SSSLGTQTYI

201    CNVNHKPSNT KVDKKVEPKS CDKTHTCPPC PAPELLGGPS VFLFPPKPKD

251    TLMISRTPEV TCVVVDVSHE DPEVKFNWYV DGVEVHNAKT KPREEQYQST
```

-continued

```
301     YRVVSVLTVL HQDWLNGKEY KCKVSNKALP APIEKTISKA KGQPREPQVY

351     TLPPSRDELT KNQVSLTCLV KGFYPSDIAV EWESNGQPEN NYKTTPPVLD

401     SDGSFFLYSK LTVDKSRWQQ GNVFSCSVMH EALHNHYTQK SLSLSPG
```

The heavy chain polypeptide sequence of hsAQC2 is as follows (Plasmid: pAND171):

```
                                                   (SEQ ID NO: 6)
  1     EVQLVESGGG LVQPGGSLRL SCAASGFTFS RYTMSWVRQA PGKGLEWVAT

 51     ISGGGHTYYL DSVKGRFTIS RDNSKNTLYL QMNSLRAEDT AVYYCTRGFG

101     DGGYPDVWCQ GTLVTVSSAS TKGPSVFPLA PSSKSTSGGT AALGCLVKDY

151     FPEPVTVSWN SGALTSGVHT FPAVLQSSGL YSLSSVVTVP SSSLGTQTYI

201     CNVNHKPSNT KVDKKVEPKS CDKTHTCPPC PAPEAAGGPS VFLFPPKPKD

251     TLMISRTPEV TCVVVDVSHE DPEVKFNWYV DGVEVHNAKT KPREEQYNST

301     YRVVSVLTVL HQDWLNGKEY KCKVSNKALP APIEKTISKA KGQPREPQVY

351     TLPPSRDELT KNQVSLTCLV KGFYPLDIAV EWESNGQPEN NYKTTPPVLD

401     SDGSFFLYSK LTVDKSRWQQ GNVFSCSVMH EALHNHYTQK SLSLSPG
```

Example 24

This example describes a method for determining the crystal structure of the complex of a rat/human chimeric α1-I domain of the α1β1 integrin and the hAQC2 Fab fragment.

Preparation of the Protein Complex

The hAQC2 Fab fragment was prepared from hAQC2 antibody using a variation of the procedure of the IMMUNOPURE.®. Fab preparation kit (Cat#44885, Pierce, Rockford, Ill.). The intact hAQC2 antibody was concentrated to 12 mg/ml in a buffer containing 20 mM phosphate, 10 mM EDTA and 25 mM cysteine (pH 7.0). Immobilized papain was added at an enzyme to substrate ratio of 1:50, and digestion was allowed to occur overnight at 37° C. The immobilized papain was removed and the crude digest was dialyzed against 20 mM sodium acetate buffer (pH 4.5). The Fab fragment was separated from residual intact antibody, dimeric Fab fragment, and Fc fragment by cation exchange chromatography using a S-column (Poros HS/M, PERSEPTIVE Biosystems #PO42M26) with a shallow salt gradient. The Fab fragment was then exchanged into 0.1 M Hepes buffer (pH 8.0).

The chimeric α1-I domain used in the present invention is a rat/human chimeric I domain construct (mutant RΔH) containing residues Thr145-Phe336 of the rat α1 integrin chain, where residues Gly217, Arg218, Gln219 and Leu222 (crystal numbering) have been substituted with equivalent human residues Val, Gln, Arg and Arg, respectively, in order to restore antibody binding. The amino acid sequences of chimeric RΔH, rat, and human α1-I domains are given below in SEQ ID NOs:59, 60 and 61, respectively. Recombinant α1-I domain was expressed in *E. coli* as a GST-fusion protein. The RΔH α1-I domain was cleaved with thrombin and purified from a *Pichia pastoris* clone as described previously (Gotwals et al., 1999, Biochemistry 38:8280-8288).

```
                                             (SEQ ID NO: 59)
145     TQLDIV

151     IVLDGSNSIY PWESVIAFLN DLLKRMDIGP KQTQVGIVQY
```

-continued

```
191     GENVTHEFNL NKYSSTEEVL VAANKIVQRG GRQTMTALGI

231     DTARKEAFTE ARGARRGVKK VMVIVTDGES HDNYRLKQVI

271     QDCEDENIQR FSIAILGHYN RGNLSTEKFV EEIKSIASEP

311     TEKHFFNVSD ELALVTIVKA LGERIF

                                             (SEQ ID NO: 60)
145     TQLDIV

151     IVLDGSNSIY PWESVIAFLN DLLKRMDIGP KQTQVGIVQY

191     GENVTHEFNL NKYSSTEEVL VAANKIGRQG GLQTMTALGI

231     DTARKEAFTE ARGARRGVKK VMVIVTDGES HDNYRLKQVI

271     QDCEDENIQR FSIAILGHYN RGNLSTEKFV EEIKSIASEP

311     TEKHFFNVSD ELALVTIVKA LGERIF

                                             (SEQ ID NO: 61)
145     TQLDIV

151     IVLDGSNSIY PWDSVTAFLN DLLKRMDIGP KQTQVGIVQY

191     GENVTHEFNL NKYSSTEEVL VAAKKIVQRG GRQTMTALGI

231     DTARKEAFTE ARGARRGVKK VMVIVTDGES HDNHRLKKVI

271     QDCEDENIQR FSIAILGSYN RGNLSTEKFV EEIKSIASEP

311     TEKHFFNVSD EIALVTIVKT LGERIF
```

The hAQC2 Fab fragment was mixed with excess chimeric α1-I domain and incubated at 37° C. for 15 minutes. The saturated α1/Fab complexes were separated from uncomplexed α1-I domain by size exclusion chromatography using a S200 Sephacryl column (Pharmacia, Gibco). The complex was further concentrated to 11 mg/ml in a 20 mM Tris (pH 7.4) 150 mM NaCl 1 mM $MnCl_2$, 5 mM β-mercaptoethanol.

Preparation of Crystals

Crystallization conditions were found using the CRYSTAL SCREEN™ KITs from Hampton Research (Laguna Niguel, Calif.). Crystals of the complex described above were grown at 20° C. by vapor diffusion using an equal amount of protein complex solution and a 20-30% PEG 1500 reservoir solution. Typically, 2 μL of protein complex was added to 2 μL of well solution to yield drops of 4 μL. Crystals grew in two to seven days as hexagonal rods with dimensions 0.8×0.05×0.05 $mm^3$. The presence of the α1-I domain and hAQC2 Fab fragment was confirmed by SDS-PAGE analysis of dissolved crystals. In order to reduce the inherent radiation damage during data collection, X-ray diffraction data was collected at approximately 100 K. To prepare the crystals for data collection at this low temperature, crystals were gradually equilibrated into a cryoprotectant solution containing 25% PEG 400 and 30% PEG 1500, and flash cooled in liquid nitrogen.

Structure Determination

Native X-ray diffraction data to 2.8 Å resolution were collected from a single crystal at about 100 K using an ADSC Quantum 4 charged-coupled device detector at beamline X4A of the Brookhaven National Laboratory (BNL) National Synchrotron Light Source (NSLS). Data was processed using the software programs DENZO and SCALEPACK (Otwinowski & Minor, 1997, Methods in Enzymol. 276:307-326). Crystals belonged to the space group P6.sub.1 or its enantiomorph P6.sub.5, with unit cell dimensions a=b=255.09 Å, c=38.64 Å. The data set was 96.6% complete and had an R-merge of 8.3%. The Matthews coefficient (Matthews, 1968, J. Mol. Biol. 33:491-497) was 2.59 $Å^3$ $Da^{-1}$ with a solvent content of 52.1%, which indicated that there were two complexes in the asymmetric unit. The two complexes in the asymmetric unit were related by non-crystallographic 2-fold symmetry. Data statistics are shown in Table 4.

Molecular replacement searches were done with the program AMoRe (Navaza, 1994, Acta Cryst. A50:157-163) from the CCP4 program package (Collaborative Computational Project No. 4. The CCP4 Suite: programs for protein crystallography. 1994, Acta Cryst. D50:760-763), and molecular graphics manipulations were done with the program QUANTA. A single α1-I domain from the structure of the rat α1-I domain of α1β1 integrin (Protein Data Bank (PDB) accession number 1ck4; Nolte et al., 1999, FEBS Lett. 452:379-385) was used as a model or probe for rotation and translation searches. The translation function search indicated that the $1^{st}$ and $9^{th}$ highest peaks of the rotation function corresponded to the correct solutions for the two α1-I domains in the asymmetric unit (correlation coefficient (cc)=21.1%, R=53.1%) and that the space group was $P6_5$. Subsequently, searches for the hAQC2 Fab fragments were done, keeping the I domain solutions fixed and using a model of the Fv domain of the hAQC2 Fab as a search probe. A clear solution was found for one of the two Fv domains (cc=22.1%, R=52.6%), but the second Fv could not be located. The position of the second Fv was derived using the non-crystallographic 2-fold symmetry. Rigid body refinement of the two I domains and two Fv domains reduced the R-factor to 43.6% (R-free=42.7%). An 2Fo-Fc electron density map showed clear electron density for the constant domain (Fconst) of the first Fab fragment, but no density for the Fconst domain of the second Fab fragment. A model of the Fconst domain of the first Fab was manually fit in the observed electron density. Subsequent rigid body refinement with the software program CNX (Accelrys Inc., San Diego, Calif. ©2000; Brunger, 1998, Acta Cryst. D54: 905-921), using data in the 500-2.8 Å resolution range, optimized the position of all domains, reducing the R-factor to 39.7% (R-free=38.9%).

All subsequent refinement steps were carried out with the CNX program. To reduce model bias, partial models were used for 2Fo-Fc map calculation and model refinement. The initial partial model, was subjected to simulated annealing and grouped B-factor refinement with non-crystallographic symmetry restraints. The R-working and R-free factors dropped to 28.3% and 32.9%, respectively. Several cycles consisting of iterative model building, maximum likelihood positional refinement and B-factor refinement followed. Only model adjustments that resulted in a drop in the K-free factor were accepted. A bulk-solvent correction was employed after the complete model was built. The R-working and K-free factors of the final model are 21.3% and 27.2%, respectively for the data (F>2σ) in the 500-2.8 Å resolution range.

The final 2Fo-Fc electron density map is of good quality for most of the complex with the exception of amino acid residues 288-295 of one I domain fragment (molecule A in FIG. 19A-1 to A-109) that are associated with weak electron density and have not been included in the model. In addition, the entire constant domain of one Fab fragment has no visible electron density, which indicates that it is disordered. This appears to be consequence of the absence of crystal contacts for the constant domain of the Fab fragment due to its position within a large solvent channel. This domain was also not included in the final model that consists of 1030 amino acid residues, constituting 6 polypeptide chains, and 2 manganese ions. The r.m.s. positional deviation between equivalent residues from the two complexes in the asymmetric unit is small (0.37 Å for 1660 equivalent main chain atoms). Stereochemistry statistics were calculated with the software programs PROCHECK (Laskowski et al., 1993, J. Appl. Cryst. 26:283-291; Morris et al., 1992, Proteins 12:345-364) and CNX. Hydrogen bonds (<3.6 Å) were found with the program CONTACT (Tadeusz Skarzvnski, Imperial College, London, Jan. 12, 1988; Collaborative Computational Project No. 4. The CCP4 Suite: programs for protein crystallography. 1994, Acta Cryst. D50, 760-763). All non-glycine residues (except residue Thr50 of the L chain that will be discussed below) are in the allowed regions of the Ramachandran diagram and 86% of the residues are in the most favored regions. The average B-factor of the main chain atoms is 38.5 $A^2$. Crystallographic analysis data are in Table 4.

TABLE 4

Summary of Data Statistics and Crystallographic Analysis

| | |
|---|---|
| **Data collection** | |
| Cell dimensions a, b, c (Å) | 255.09, 255.09, 38.64 |
| Space group | $P6_5$ |
| Resolution (Å) | 500-2.8 (2.9-2.8)$^\dagger$ |
| Unique reflections | 35275 |
| Completeness (%) | 96.6 (87.7)$^\dagger$ |
| Average I/s | 11.92 (2.29)$^\dagger$ |
| Rmerge* (%) | 8.3 (30.9)$^\dagger$ |
| **Model** | |
| Number of non-H atoms | 7950 |
| Number of protein residues | 1030 |
| Contents of asymmetric unit | 2 I domains, 1 Fab fragment, 1 Fv domain |
| Average B-factor ($Å^2$) | 38.5 |
| **Refinement** | |
| Resolution range used (F > 2σ[[δ]]) | 500-2.8 |
| R-factor (R-working) (%) | 21.3 |
| R-free$^{\dagger\dagger}$ (%) | 27.2 |

TABLE 4-continued

| Summary of Data Statistics and Crystallographic Analysis | |
|---|---|
| Stereochemistry | |
| RMS deviations | |
| Bond lengths (Å) | 0.007 |
| Angles (°) | 1.43 |

*Rmerge = $\Sigma_h\Sigma_i|I_{hi} - I_h|/\Sigma_{hi}I_{hi}$

†Values for the highest resolution shell given in parenthesis.

††8% of the data were allocated for the calculation of R-free factor.

Example 25

This example describes the crystal structure of the complex of a rat/human chimeric α1-I domain of the α1β1 integrin and the hAQC2 Fab fragment.

Architecture of Crystal Structure

The crystal structure of the complex of the rat/human chimeric α1-I domain of the α1β1 integrin and the hAQC2 Fab fragment has an elongated shape (FIG. 20). The dimensions of the complex are 100 Å×50 Å×35 Å.

The Fab fragment exhibits the typical immunoglobulin fold. The light chain and heavy chains of the Fab fragment each form two broad sheets of anti-parallel β-strands which pack tightly together to form a scaffold for the complementarity determining region (CDR) loops which extend from the packed sheets. Both the light chain and the heavy chain contain three CDR loops. The light chain loops are called L1, L2 and L3, while the heavy chain loops are referred to as H1, H2 and H3. The complementarity determining region (CDR) loops correspond to canonical structure 1 for light chain L1, L2 and L3 loops and for heavy chain H1 and H2 loops (Chothia et al., 1989, Nature 342:877-883). The heavy chain H3 loop has a tight β-hairpin-like conformation that is stabilized by internal hydrogen bonds as well as two aromatic residues (Tyr104 and Phe105) that are packed against the light chain. Residue Thr50 of L2 adopts mainchain dihedral angles that fall in the disallowed regions of the Ramachandran diagram. The same observation for the corresponding residue has been made for other antibodies (Muller et al., 1998, Structure 6, pp. 1153-11567) which indicates that this is a natural characteristic of L2 loops.

The α1-I domain in the present invention has a structure very similar to the uncomplexed α1-I domain (PDB accession number 1ck4; Nolte et al., 1999, FEBS Lett. 452:379-385; PDB accession code 1qc5; Rich et al., 1999, J. Biol. Chem. 274:24906-24913). The I domain structure exhibits a "dinucleotide-binding" or "Rossman" fold (Rao & Rossman, 1973, J. Mol. Biol. 76:241-256) in which a central sheet of five parallel β-strands and one small antiparallel-strand is surrounded on both sides by a total of seven α-helices. The six β-strands of the structure in this invention will be referred to as βA, βB, βC, βD, βE, and βF and the seven α-helices are called α1, α2, α3, α4, α5, α6 and α7.

Three characteristic structural features exist for 1 domains. The first characteristic feature is the presence of an inserted small helix in the βE-α6 loop, termed as the C helix. Most of the C helix loop of molecule A (FIG. 19A-1 to A-109) in the present invention is associated with weak electron density, which suggests disorder. This appears to be a consequence of absence of crystal contacts or contacts with the Fab that would have stabilized the loop. However, the same loop in molecule B (FIG. 19A-1 to A-109) in the present invention has well-defined electron density and has been included in the model. The second characteristic feature of α1-I domains is the MIDAS or Metal-Ion-Dependent-Adhesion-Site where metal ions and ligands are implicated to bind to the I domain. Five key residues which form part of the MIDAS are referred to as the "DxSxS-T-D" motif. These residues, which are completely conserved among I domains, coordinate the metal ion (Gotwals et al., 1999, Biochemistry 38:8280-8288). The crystals in the present invention were grown in the presence of manganese and the MIDAS site of the I domain in this structure is observed to contain a $Mn^{+2}$ metal ion. The ion is directly coordinated by the side chains of residues Ser156, Ser158 and Thr224. The 2Fo-Fc electron density map shows no evidence that MIDAS residues Asp 154 and Asp257 make water-mediated indirect coordination of the metal ion (FIG. 20). However, the apparent absence of water molecules could be a consequence of the limited resolution (2.8 Å) of the electron density map. The third feature of X domains is that all determined structures of I domains belong to one of two conformations called "open" and "closed". The differences between the open and closed conformation include a different mode of metal ion coordination and a significant (about 10 Å) positional shift of the C-terminal helix of the I domain. The I domain in the complex in the present invention is in the closed conformation.

In the structure of the complex in the present invention, the Fab fragment binds to its epitope on the front upper surface of the I domain with a footprint 35 Å by 30 Å. The total buried surface area in the antibody-antigen interface is 1534 .$Å^2$ which is typical of other antibody-antigen complexes (Davies et al., 1996, Proc. Natl. Acad. Sci. USA 93:7-12; Jones & Thornton, 1996, Proc. Natl. Acad. Sci. USA 93:13-20). The surface is 25% hydrophobic and 75% hydrophilic in character. The heavy chain contributes 65% of the buried surface area for the complex, while the remaining 35% is contributed by the light chain. The antibody epitope consists of residues located in four loops of the I domain (Emsley et al., 2000, Cell 101:47-56). Three of the loops form the MIDAS site: loop 1 (βA-α1) which contains the conserved DXSXS sequence, loop 2 (α3-α4) which contains the MIDAS Thr224 and loop 3 (βD-α5) that contains MIDAS residue Asp257. The fourth loop is the C-helix loop and is involved in only in minor contacts.

The central feature of the antigen-antibody interaction is the coordination of the MIDAS site metal ion by Asp101 from the CDR H3 of the antibody (FIG. 20). The distance between the ion and O61 of Asp101 is 2.4 Å. In addition, the Oβ2 atom of Asp101 is interacting with His261 of the I domain. Interestingly, the CDR H3 contains several glycine residues adjacent to Asp101 (sequence GFGDGGY) (SEQ ID NO:62), presumably to allow enough flexibility to the CDR loop to permit proper coordination of the metal ion. The CDR H3 sequence is essentially invariant in monoclonal antibodies that were raised against the same antigen and found to belong in the same class. Most of the antibody residues that are involved in antibody-antigen contacts are located in L3, H1, H2 and H3CDR loops. A few residues from the L1 (Asn30) and L2 (Tyr48) loops appear to form minor Van Der Waals contacts. L3 primarily contributes to contacts through two large hydrophobic residues, Trp90 and Trp95. In addition, Asn93 from L3 forms hydrogen bonds with Gln223 of the I domain. The side chains of His56 and Tyr58 from the H2 loop form hydrogen bonds with main chain atoms of loop 2 of the I domain. Arg31 of H1 is in contact with Arg291 of loop 4 of the I domain. Arg222 from loop 2 of the I domain is sandwiched between several antibody residues including Tyr58, Trp95 and Asn93. This is the only residue out of the four mutated in the RΔH I domain, that is involved in contacts with the Fab. It is therefore likely to be the only residue responsible for restoring the binding of the antibody after the mutagenesis.

Comparison of the Crystal Structure of the Complex of a Rat/Human Chimeric α1-I Domain and the hAQC2 Fab Fragment with Other I Domain Structures The chimeric RΔH α1-I domain has four sequence differences with the rat α1-I domain (rat residues: 217G, 218R, 219Q and 222L), eight sequence differences with the human α1-I domain (human residues: 163D, 166T, 214K, 264H, 268K, 288S, 322I and 380T), and ten sequence differences with the clone used in the crystal structure studies of human α1-I domain (clone residues: 163D, 166T, 174E, 214K, 230I, 264H, 268K, 288S, 322I and 380T). In the unliganded rat α1β1 α1-I domain crystal structure (PDB accession code 1ck4; Nolte et al., 1999, FEBS Lett. 452:379-385), the α1-I domain contains no bound metal ions and adopts the "closed" conformation. In the unliganded human α1-I domain crystal structure (accession code 1qc5; Rich et al., 1999, J. Biol. Chem. 274:24906-24913), the α1-I domain contains bound $Mg^{+2}$ and similarly adopts the closed conformation. Superimposition of these two structures with the complexed chimeric α1-I domain indicates that there are only minor conformational changes upon hAQC2 antibody binding. The r.m.s. positional deviation between the rat and chimeric α1-I domain is 1.04 Å for all 768 main chain atoms. The r.m.s. positional deviation between the human and chimeric α1-I domain is 0.69 Å for all 764 main chain atoms. The biggest differences (human and chimeric α1-I domain pair) are observed in loop 1 (r.m.s. deviations 1.24 Å for main chain atoms of residues 154-161) and the loop 4 (C helix loop) of the α1-I domain (r.m.s. deviations 1.55 Å for main chain atoms of residues 288-296). However, these differences can be more accurately described as shifts of the whole secondary structure elements rather than complex conformational changes. These are likely to be within the normal range of conformational flexibility of proteins. The r.m.s. positional deviation between the human and chimeric α1-I domain for backbone atoms of amino acid residues Glu192, Gln218, Arg219, Gly220, and Gly221 (crystal numbering) is 0.33 Å. The r.m.s. positional deviation between the rat and chimeric α1-I domain for backbone atoms of amino acid residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering) is 0.97 Å.

The I domain maintains the "closed" I domain conformation that has been observed only for unliganded I domains crystallized in the absence of ligands or pseudo-ligands bound to the MIDAS site. The r.m.s. positional deviation of the C-terminal helices of the human and chimeric I domains (calculated for the main chain atoms of residues 321-335) is 0.64 Å. A simulated annealing omit map calculated for the final refined model unambiguously confirms that the position of the C-terminal helix and adjacent structural elements are consistent with the closed conformation.

In order to investigate the effects of ligand binding to the modes of metal ion coordination, the structure of the present invention was superimposed with the structures of the unliganded α2-I domain (PDB accession code 1aox; Emsley et al., 1997, J. Biol. Chem. 272:28512-28517) and the α2-I domain complexed with a collagen peptide (PDB accession code 1dzi; Emsley et al., 2000, Cell 101:47-56). The coordination of the metal ion by Asp101 from the antibody is remarkably similar to the coordination of the metal ion of the α2-I domain by a glutamic acid from the collagen peptide. Another feature that is conserved is the simultaneous interaction of the acidic group with His261 (His258 in the α2-I domain). All MIDAS residues of the I domain-Fab complex except Ser156 and Ser158 adopt conformations very similar to those observed in the unliganded I domain. In contrast, the side chains of Ser156 and Ser158, as well as the metal, adopt conformations similar with those of the liganded I domain. It is clear that the coordination of the metal ion by Asp101 does not allow the ion to maintain the position and coordination distances that are observed in the unliganded state. Thus, the metal ion is not directly coordinated by Asp257, a fact that permits the ion to maintain high electrophilicity.

Biological Implications

In the present invention, there is no direct coordination of the metal by Asp257, which may permit high affinity binding by lowering the energy barrier between a closed (no ligand bound) and open (ligand bound) conformation. However, the coordination of the metal by an aspartic acid from the antibody is not sufficient to induce the open conformation to the I domain in the present invention. The I domain-Fab complex structure indicates that it is possible to have strong binding to the I domain that adopts the closed conformation and that coordination of the metal ion by an acidic residue from the ligand may be necessary but not sufficient to induce a conformational change to the open state. Binding of the antibody is expected to stabilize the low affinity state of the integrin and prevent the outside-in signaling that would have accompanied integrin binding to collagen.

Although the foregoing invention has been described in some detail by way of illustration and example for purposes of clarity of understanding, it will be apparent to those skilled in the art that certain changes and modifications will be practiced.

Therefore, the description and examples should not be construed as limiting the scope of the invention.

What is claimed is:

1. A method of treating a subject having psoriasis, comprising administering to the subject a composition comprising an anti-VLA-1 antibody or antigen binding fragment thereof, and a pharmaceutically acceptable carrier, wherein the antibody or antigen binding fragment thereof comprises light chain complementarity determining regions defined by amino acid residues 24 to 33, 49 to 55 and 88 to 96 of SEQ ID NO:1, and heavy chain complementarity determining regions defined by amino acid residues 31 to 35, 50 to 65 and 98 to 107 of SEQ ID NO:2.

2. The method of claim 1, wherein the anti-VLA-1 antibody or antigen binding fragment thereof comprises a light chain variable domain sequence of SEQ ID NO:1 and a heavy chain variable domain sequence of SEQ ID NO:2.

3. The method of claim 1, wherein the anti-VLA-1 antibody or antigen binding fragment thereof comprises the same heavy and light chain polypeptide sequences as an antibody produced by hybridoma mAQC2 which is deposited under ATCC accession number PTA3273.

4. The method of claim 1, wherein the anti-VLA-1 antibody or antigen binding fragment thereof is humanized.

5. The method of claim 4, wherein the anti-VLA-1 antibody or antigen binding fragment thereof comprises at least one of the following residues in its light chain: Q1, L4, P45, W46 and Y70 according to SEQ ID NO:1; or at least one of the following residues in its heavy chain: D1, V12, S28, F29, A49, T96, and R97 according to SEQ ID NO:2.

6. The method of claim 4, wherein the anti-VLA-1 antibody or antigen binding fragment thereof comprises a light chain variable domain sequence defined by amino acid residues 1 to 106 of SEQ ID NO:3, and a heavy chain variable domain sequence defined by amino acid residues 1 to 118 of SEQ ID NO:4.

7. The method of claim 4, wherein the anti-VLA-1 antibody or antigen binding fragment thereof comprises the same heavy and light chain polypeptide sequences as an antibody produced by cell line hAQC2 which is deposited under ATCC accession number PTA3275.

8. The method of claim 4, wherein the anti-VLA-1 antibody or antigen binding fragment thereof comprises the same heavy and light chain polypeptide sequences as an antibody produced by cell line hsAQC2 which is deposited under ATCC accession number PTA3356.

9. The method of claim 4, wherein the anti-VLA-1 antibody or antigen binding fragment thereof comprises the same heavy and light chain polypeptide sequences as an antibody produced by cell line haAQC2 which is deposited under ATCC accession number PTA3274.

10. The method of claim 4, wherein the anti-VLA-1 antibody or antigen binding fragment thereof comprises a antibody or antigen-binding fragment thereof that has an alanine at amino acid position 235 and an alanine at amino acid position 236 as set forth in SEQ ID NO:6.

11. The method of claim 4, wherein the anti-VLA-1 antibody or antigen binding fragment thereof comprises an antibody or antigen-binding fragment thereof that has a glutamine at amino acid position 298 as set forth in SEQ ID NO:5.

12. The method of claim 1, wherein the subject is a human.

13. A method of treating a subject having psoriasis, the method comprising administering to the subject a composition comprising an anti-VLA-1 antibody or antigen binding fragment thereof, and a pharmaceutically acceptable carrier, wherein the antibody or antigen-binding fragment thereof comprises a light chain and a heavy chain selected from one of the following light chain and heavy chain pairs:

(i) a light chain of an anti-VLA-1 antibody, or antigen-binding fragment thereof, which has the sequence of SEQ ID NO:3, and a heavy chain of an anti-VLA-1 antibody, or antigen-binding fragment thereof, which has the sequence of SEQ ID NO:4;

(ii) a light chain of an anti-VLA-1 antibody, or antigen-binding fragment thereof, whose light chain variable domain has the sequence of SEQ ID NO:49, and a heavy chain of an anti-VLA-1 antibody, or antigen-binding fragment thereof, whose heavy chain variable domain has the sequence of SEQ ID NO:42;

(iii) a light chain of an anti-VLA-1 antibody, or antigen-binding fragment thereof, whose light chain variable domain has the sequence of SEQ ID NO:51, and a heavy chain of an anti-VLA-1 antibody, or antigen-binding fragment thereof, whose heavy chain variable domain has the sequence of SEQ ID NO:44;

(iv) a light chain of an anti-VLA-1 antibody, or antigen-binding fragment thereof, whose light chain variable domain has the sequence of SEQ ID NO:54, and a heavy chain of an anti-VLA-1 antibody, or antigen-binding fragment thereof, whose heavy chain variable domain has the sequence of SEQ ID NO:42;

(v) a light chain of an anti-VLA-1 antibody, or antigen-binding fragment thereof, whose light chain variable domain has the sequence of SEQ ID NO:58, and a heavy chain of an anti-VLA-1 antibody, or antigen-binding fragment thereof, whose heavy chain variable domain has the sequence of SEQ ID NO:68;

(vi) a light chain of an anti-VLA-1 antibody, or antigen-binding fragment thereof, whose light chain variable domain has the sequence of SEQ ID NO:70, and a heavy chain of an anti-VLA-1 antibody, or antigen-binding fragment thereof, whose heavy chain variable domain has the sequence of SEQ ID NO:68;

(vii) a light chain of an anti-VLA-1 antibody, or antigen-binding fragment thereof, whose light chain variable domain has the sequence of SEQ ID NO:66, and a heavy chain of an anti-VLA-1 antibody, or antigen-binding fragment thereof, whose heavy chain variable domain has the sequence of SEQ ID NO:42;

(viii) a light chain of an anti-VLA-1 antibody, or antigen-binding fragment thereof, whose light chain variable domain has the sequence of SEQ ID NO:54, and a heavy chain of an anti-VLA-1 antibody, or antigen-binding fragment thereof, whose heavy chain variable domain has the sequence of SEQ ID NO:68;

(ix) a light chain of an anti-VLA-1 antibody, or antigen-binding fragment thereof, whose light chain variable domain has the sequence of SEQ ID NO:47, and a heavy chain of an anti-VLA-1 antibody, or antigen-binding fragment thereof, whose heavy chain variable domain has the sequence of SEQ ID NO:68;

(x) a light chain of an antibody produced by hybridoma mAQC2 (ATCC accession number PTA3273), and a heavy chain of an antibody produced by hybridoma mAQC2 (ATCC accession number PTA3273);

(xi) a light chain of an antibody produced by cell line hAQC2 (ATCC accession number PTA3275), and a heavy chain of an antibody produced by cell line hAQC2 (ATCC accession number PTA3275);

(xii) a light chain of an antibody produced by cell line haAQC2 (ATCC accession number PTA3274), and a heavy chain of an antibody produced by cell line haAQC2 (ATCC accession number PTA3274);

(xiii) a light chain of an antibody produced by cell line hsAQC2 (ATCC accession number PTA3356), and a heavy chain of an antibody produced by cell line hsAQC2 (ATCC accession number PTA3356); or (xiv) a light chain of an anti-VLA-1 antibody, or antigen-binding fragment thereof, whose light chain variable domain has the sequence of SEQ ID NO:66, and a heavy chain of an anti-VLA-1 antibody, or antigen-binding fragment thereof, whose heavy chain variable domain has the sequence of SEQ ID NO:68.

14. The method of claim 13, wherein the anti-VLA-1 antibody or antigen binding fragment thereof comprises a light chain having the sequence of SEQ ID NO:3 and a heavy chain having the sequence of SEQ ID NO:4.

15. The method of claim 13, wherein the subject is human.

* * * * *

SEQUENCE LISTING

```
<160> NUMBER OF SEQ ID NOS: 70

<210> SEQ ID NO 1
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 1

Gln Ile Val Leu Thr Gln Phe Pro Ala Leu Met Ser Ala Ser Pro Gly
1               5                   10                  15
```

-continued

```
Glu Lys Val Thr Met Thr Cys Ser Ala Ser Ser Ser Val Asn His Met
            20                  25                  30

Phe Trp Tyr Gln Gln Lys Pro Lys Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105


<210> SEQ ID NO 2
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 2

Asp Val Lys Val Val Glu Ser Gly Gly Gly Leu Val Lys Pro Gly Gly
1               5                   10                  15

Ser Leu Lys Leu Ala Cys Ala Ala Ser Gly Phe Ser Phe Ser Arg Tyr
            20                  25                  30

Thr Met Ser Trp Val Arg Gln Ile Pro Glu Lys Arg Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
            100                 105                 110

Thr Val Thr Val Ser Ser
        115


<210> SEQ ID NO 3
<211> LENGTH: 213
<212> TYPE: PRT
<213> ORGANISM: Artificial Sequence
<220> FEATURE:
<223> OTHER INFORMATION: Synthetically generated peptide

<400> SEQUENCE: 3

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95
```

```
Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 4
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 5
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 5

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Thr Met Ser Trp Val Arg Gln Ala Pro Gly Lys Gly Leu Glu Trp Val
35 40 45

Ala Thr Ile Ser Gly Gly Gly His Thr Tyr Tyr Leu Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Thr
85 90 95

Arg Gly Phe Gly Asp Gly Gly Tyr Phe Asp Val Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

-continued

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 6
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80
```

```
Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 7
<211> LENGTH: 26
<212> TYPE: DNA
<213> ORGANISM: Homo sapiens

<400> SEQUENCE: 7
caggatccgt cagccccaca tttcaa 26

-continued

<210> SEQ ID NO 8
<211> LENGTH: 26
<212> TYPE: DNA
<213> ORGANISM: Homo sapiens

<400> SEQUENCE: 8
tcctcgaggg cttgcagggc aaatat 26

<210> SEQ ID NO 9
<211> LENGTH: 26
<212> TYPE: DNA
<213> ORGANISM: Rattus sp.

<400> SEQUENCE: 9
caggatccgt cagtcctaca tttcaa 26

<210> SEQ ID NO 10
<211> LENGTH: 26
<212> TYPE: DNA
<213> ORGANISM: Rattus sp.

<400> SEQUENCE: 10
tcctcgagcg cttccaaagc gaatat 26

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
tgaggagacg gtgaccgtgg cccttggccc c 31

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aggtsmarct gcagsagtcw gg 22

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
actagtcgac atggatttwc aggtgcagat twtcagcttc 40

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
actggatggt gggaagatgg a 21

<210> SEQ ID NO 15
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 15

Asp Val Lys Val Val Glu Ser Gly Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 16

Asp Val Lys Val Val Glu
1               5

<210> SEQ ID NO 17
<211> LENGTH: 54
<212> TYPE: DNA
<213> ORGANISM: Artificial Sequence
<220> FEATURE:
<223> OTHER INFORMATION: Primer

<400> SEQUENCE: 17
gcaccaggtg cccactccga cgtcaaggtg gtggagtcag ggggaggctt agtg 54

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
ggaggcacca agctggagat ctaacgggct gatgctgc 38

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
cataatgtcc aggggagaaa ttgttctcac ccag 34

<210> SEQ ID NO 20
<211> LENGTH: 93
<212> TYPE: DNA
<213> ORGANISM: Artificial Sequence
<220> FEATURE:
<223> OTHER INFORMATION: Primer

<400> SEQUENCE: 20
ggtgcccact ccgacgtcca gctggtcgag tcagggggag gcttagtcca gcctggaggg 60
tccctgagac tctcctgtgc agcctctgga ttc 93

<210> SEQ ID NO 21
<211> LENGTH: 51

<212> TYPE: DNA
<213> ORGANISM: Artificial Sequence
<220> FEATURE:
<223> OTHER INFORMATION: Primer

<400> SEQUENCE: 21
atgtcttggg ttcgccaggc tccggggaag gggctggagt gggtcgcaac c 51

<210> SEQ ID NO 22
<211> LENGTH: 93
<212> TYPE: DNA
<213> ORGANISM: Artificial Sequence
<220> FEATURE:
<223> OTHER INFORMATION: Primer

<400> SEQUENCE: 22
ttcaccatct ccagagacaa ttccaagaac accctgtacc tgcagatgaa cagtctgagg 60
gccgaggaca cagccgtgta ttactgtaca aga 93

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
tggggccaag gtaccctggt caccgtctcc tcaggtgag 39

<210> SEQ ID NO 24
<211> LENGTH: 51
<212> TYPE: DNA
<213> ORGANISM: Artificial Sequence
<220> FEATURE:
<223> OTHER INFORMATION: Primer

<400> SEQUENCE: 24
tcctgtgcag cctctggatt caccttcagt aggtatacta tgtcttgggt t 51

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
gcaccaggtg cgcactccga ggtccagctg gtcgagtca 39

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
gagtcagggg gaggcttaat ccagcctgga gggtccctg 39

<210> SEQ ID NO 27
<211> LENGTH: 81
<212> TYPE: DNA
<213> ORGANISM: Artificial Sequence
<220> FEATURE:
<223> OTHER INFORMATION: Primer

<400> SEQUENCE: 27
caaattgttc tcacccagtc tccatcctcc ctgtctgcgt ctgtagggga cagagtcacc 60
atcacatgca gtgccagctc a 81

<210> SEQ ID NO 28
<211> LENGTH: 45
<212> TYPE: DNA
<213> ORGANISM: Artificial Sequence
<220> FEATURE:
<223> OTHER INFORMATION: Primer

<400> SEQUENCE: 28
ttctggtatc agcagaagcc cgggaaagcc cccaaaccct ggatt 45

<210> SEQ ID NO 29
<211> LENGTH: 105
<212> TYPE: DNA
<213> ORGANISM: Artificial Sequence
<220> FEATURE:
<223> OTHER INFORMATION: Primer

<400> SEQUENCE: 29
gcttctggag tcccttcacg cttcagtggc agtgggtctg ggacagatta cactctcaca 60
atcagcagcc tgcaacctga agattttgcc acttattact gccag 105

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
ggtggaggca ctaaggtgga gatctaacgg gct 33

<210> SEQ ID NO 31
<211> LENGTH: 39
<212> TYPE: DNA
<213> ORGANISM: Artificial Sequence
<220> FEATURE:
<223> OTHER INFORMATION: Primer

<400> SEQUENCE: 31
cccgggaaag cgcccaaact cctgatttat ctcacatcc 39

<210> SEQ ID NO 32
<211> LENGTH: 51
<212> TYPE: DNA
<213> ORGANISM: Artificial Sequence
<220> FEATURE:
<223> OTHER INFORMATION: Primer

<400> SEQUENCE: 32
gcctcagtca taatgtcccg gggacaaatt cagctcaccc agtctccatc c 51

<210> SEQ ID NO 33
<211> LENGTH: 51
<212> TYPE: DNA
<213> ORGANISM: Artificial Sequence
<220> FEATURE:
<223> OTHER INFORMATION: Primer

<400> SEQUENCE: 33
ggtaacccgt ggacgttcgg tcagggcact aaggtggaga tctaacgggc t 51

<210> SEQ ID NO 34
<211> LENGTH: 51
<212> TYPE: DNA
<213> ORGANISM: Artificial Sequence
<220> FEATURE:
<223> OTHER INFORMATION: Primer

<400> SEQUENCE: 34
gcctcagtca taatgtcccg gggacaaatt cagctcaccc agtctccatc c 51

<210> SEQ ID NO 35
<211> LENGTH: 51
<212> TYPE: DNA
<213> ORGANISM: Artificial Sequence
<220> FEATURE:
<223> OTHER INFORMATION: Primer

<400> SEQUENCE: 35
ggtaacccgt ggacgttcgg tcagggcact aaggtggaga tctaacgggc t 51

<210> SEQ ID NO 36
<211> LENGTH: 39
<212> TYPE: DNA
<213> ORGANISM: Artificial Sequence
<220> FEATURE:
<223> OTHER INFORMATION: Primer

<400> SEQUENCE: 36
gggaaagcac ccaaactctg gatctatctc acatccaac 39

<210> SEQ ID NO 37
<211> LENGTH: 45
<212> TYPE: DNA
<213> ORGANISM: Artificial Sequence
<220> FEATURE:
<223> OTHER INFORMATION: Primer

<400> SEQUENCE: 37
aagcccggga aggcgcccaa acccctgatt tatctcacat ccaac 45

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
gtcataatgt cccggggaga tatccagctc acccagtct 39

<210> SEQ ID NO 39
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 39

```
gac gtc aag gtg gtg gag tca ggg gga ggc tta gtg aag cct gga ggg       48
Asp Val Lys Val Val Glu Ser Gly Gly Gly Leu Val Lys Pro Gly Gly
1               5                   10                  15

tcc ctg aaa ctc gcc tgt gca gcc tct gga ttc agt ttc agt aga tat       96
```

-continued

```
Ser Leu Lys Leu Ala Cys Ala Ala Ser Gly Phe Ser Phe Ser Arg Tyr
            20                  25                  30

act atg tct tgg gtt cgc cag att ccg gag aag agg ctg gag tgg gtc      144
Thr Met Ser Trp Val Arg Gln Ile Pro Glu Lys Arg Leu Glu Trp Val
        35                  40                  45

gca acc att agt ggt ggt ggt cac acc tac tat cta gac agt gtg aag      192
Ala Thr Ile Ser Gly Gly Gly His Thr Tyr Tyr Leu Asp Ser Val Lys
    50                  55                  60

ggc cga ttc acc atc tcc aga gac aat gcc aag aac acc ctg tac ctg      240
Gly Arg Phe Thr Ile Ser Arg Asp Asn Ala Lys Asn Thr Leu Tyr Leu
65                  70                  75                  80

caa atg agc agt ctg agg tct gag gac aca gcc atg tat tac tgt aca      288
Gln Met Ser Ser Leu Arg Ser Glu Asp Thr Ala Met Tyr Tyr Cys Thr
                85                  90                  95

aga ggt ttt gga gac ggg ggg tac ttc gat gtc tgg ggc caa ggg acc      336
Arg Gly Phe Gly Asp Gly Gly Tyr Phe Asp Val Trp Gly Gln Gly Thr
            100                 105                 110

acg gtc acc gtc tcc tca                                              354
Thr Val Thr Val Ser Ser
        115


<210> SEQ ID NO 40
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 40

Asp Val Lys Val Val Glu Ser Gly Gly Gly Leu Val Lys Pro Gly Gly
1               5                   10                  15

Ser Leu Lys Leu Ala Cys Ala Ala Ser Gly Phe Ser Phe Ser Arg Tyr
            20                  25                  30

Thr Met Ser Trp Val Arg Gln Ile Pro Glu Lys Arg Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
            100                 105                 110

Thr Val Thr Val Ser Ser
        115


<210> SEQ ID NO 41
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 41

gac gtc cag ctg gtc gag tca ggg gga ggc tta gtc cag cct gga ggg       48
Asp Val Gln Leu Val Glu Ser Gly Gly Gly Leu Val Gln Pro Gly Gly
1               5                   10                  15

tcc ctg aga ctc tcc tgt gca gcc tct gga ttc agt ttc agt aga tat       96
```

```
Ser Leu Arg Leu Ser Cys Ala Ala Ser Gly Phe Ser Phe Ser Arg Tyr
            20                  25                  30

act atg tct tgg gtt cgc cag gct ccg ggg aag ggg ctg gag tgg gtc      144
Thr Met Ser Trp Val Arg Gln Ala Pro Gly Lys Gly Leu Glu Trp Val
        35                  40                  45

gca acc att agt ggt ggt ggt cac acc tac tat cta gac agt gtg aag      192
Ala Thr Ile Ser Gly Gly Gly His Thr Tyr Tyr Leu Asp Ser Val Lys
    50                  55                  60

ggc cga ttc acc atc tcc aga gac aat tcc aag aac acc ctg tac ctg      240
Gly Arg Phe Thr Ile Ser Arg Asp Asn Ser Lys Asn Thr Leu Tyr Leu
65                  70                  75                  80

cag atg aac agt ctg agg gcc gag gac aca gcc gtg tat tac tgt aca      288
Gln Met Asn Ser Leu Arg Ala Glu Asp Thr Ala Val Tyr Tyr Cys Thr
                85                  90                  95

aga ggt ttt gga gac ggg ggg tac ttc gat gtc tgg ggc caa ggt acc      336
Arg Gly Phe Gly Asp Gly Gly Tyr Phe Asp Val Trp Gly Gln Gly Thr
            100                 105                 110

ctg gtc acc gtc tcc tca                                              354
Leu Val Thr Val Ser Ser
        115


<210> SEQ ID NO 42
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 42

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115


<210> SEQ ID NO 43
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 43

gag gtc cag ctg gtc gag tca ggg gga ggc tta atc cag cct gga ggg       48
Glu Val Gln Leu Val Glu Ser Gly Gly Gly Leu Ile Gln Pro Gly Gly
1               5                   10                  15

tcc ctg aga ctc tcc tgt gca gcc tct gga ttc acc ttc agt agg tat       96
```

-continued

```
Ser Leu Arg Leu Ser Cys Ala Ala Ser Gly Phe Thr Phe Ser Arg Tyr
            20                  25                  30

act atg tct tgg gtt cgc cag gct ccg ggg aag ggg ctg gag tgg gtc      144
Thr Met Ser Trp Val Arg Gln Ala Pro Gly Lys Gly Leu Glu Trp Val
        35                  40                  45

gca acc att agt ggt ggt ggt cac acc tac tat cta gac agt gtg aag      192
Ala Thr Ile Ser Gly Gly Gly His Thr Tyr Tyr Leu Asp Ser Val Lys
    50                  55                  60

ggc cga ttc acc atc tcc aga gac aat tcc aag aac acc ctg tac ctg      240
Gly Arg Phe Thr Ile Ser Arg Asp Asn Ser Lys Asn Thr Leu Tyr Leu
65                  70                  75                  80

cag atg aac agt ctg agg gcc gag gac aca gcc gtg tat tac tgt aca      288
Gln Met Asn Ser Leu Arg Ala Glu Asp Thr Ala Val Tyr Tyr Cys Thr
                85                  90                  95

aga ggt ttt gga gac ggg ggg tac ttc gat gtc tgg ggc caa ggt acc      336
Arg Gly Phe Gly Asp Gly Gly Tyr Phe Asp Val Trp Gly Gln Gly Thr
            100                 105                 110

ctg gtc acc gtc tcc tca gg                                           356
Leu Val Thr Val Ser Ser
        115


<210> SEQ ID NO 44
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 44

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115


<210> SEQ ID NO 45
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 45

gag gtc cag ctg gtc gag tca ggg gga ggc tta gtc cag cct gga ggg       48
Glu Val Gln Leu Val Glu Ser Gly Gly Gly Leu Val Gln Pro Gly Gly
1               5                   10                  15

tcc ctg aga ctc tcc tgt gca gcc tct gga ttc acc ttc agt agg tat       96
```

```
Ser Leu Arg Leu Ser Cys Ala Ala Ser Gly Phe Thr Phe Ser Arg Tyr
            20                  25                  30

act atg tct tgg gtt cgc cag gct ccg ggg aag ggg ctg gag tgg gtc      144
Thr Met Ser Trp Val Arg Gln Ala Pro Gly Lys Gly Leu Glu Trp Val
        35                  40                  45

gca acc att agt ggt ggt ggt cac acc tac tat cta gac agt gtg aag      192
Ala Thr Ile Ser Gly Gly Gly His Thr Tyr Tyr Leu Asp Ser Val Lys
    50                  55                  60

ggc cga ttc acc atc tcc aga gac aat tcc aag aac acc ctg tac ctg      240
Gly Arg Phe Thr Ile Ser Arg Asp Asn Ser Lys Asn Thr Leu Tyr Leu
65                  70                  75                  80

cag atg aac agt ctg agg gcc gag gac aca gcc gtg tat tac tgt aca      288
Gln Met Asn Ser Leu Arg Ala Glu Asp Thr Ala Val Tyr Tyr Cys Thr
                85                  90                  95

aga ggt ttt gga gac ggg ggg tac ttc gat gtc tgg ggc caa ggt acc      336
Arg Gly Phe Gly Asp Gly Gly Tyr Phe Asp Val Trp Gly Gln Gly Thr
            100                 105                 110

ctg gtc acc gtc tcc tca gg                                           356
Leu Val Thr Val Ser Ser
        115


<210> SEQ ID NO 46
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 46

caa att gtt ctc acc cag ttt cca gca ctc atg tct gcg tct cca ggg       48
Gln Ile Val Leu Thr Gln Phe Pro Ala Leu Met Ser Ala Ser Pro Gly
1               5                   10                  15

gag aag gtc acc atg acc tgc agt gcc agc tca agt gta aat cac atg       96
Glu Lys Val Thr Met Thr Cys Ser Ala Ser Ser Ser Val Asn His Met
            20                  25                  30

ttc tgg tat cag cag aag cca aaa tcc tcc ccc aaa ccc tgg att tat      144
Phe Trp Tyr Gln Gln Lys Pro Lys Ser Ser Pro Lys Pro Trp Ile Tyr
        35                  40                  45

ctc aca tcc aac ctg gct tct gga gtc cct gct cgc ttc agt ggc agt      192
Leu Thr Ser Asn Leu Ala Ser Gly Val Pro Ala Arg Phe Ser Gly Ser
    50                  55                  60

ggg tct ggg acc tct tac tct ctc aca atc agc agc atg gag gct gaa      240
Gly Ser Gly Thr Ser Tyr Ser Leu Thr Ile Ser Ser Met Glu Ala Glu
65                  70                  75                  80

gat gct gcc act tat tac tgc cag cag tgg agt ggt aac ccg tgg acg      288
Asp Ala Ala Thr Tyr Tyr Cys Gln Gln Trp Ser Gly Asn Pro Trp Thr
                85                  90                  95

ttc ggt gga ggc acc aag ctg gag atc aaa                              318
Phe Gly Gly Gly Thr Lys Leu Glu Ile Lys
            100                 105


<210> SEQ ID NO 47
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 47

Gln Ile Gln Leu Thr Gln Ser Pro Ser Ser Leu Ser Ala Ser Val Gly
```

-continued

```
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Leu Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105
```

<210> SEQ ID NO 48
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 48

```
caa att gtt ctc acc cag tct cca tcc tcc ctg tct gcg tct gta ggg       48
Gln Ile Val Leu Thr Gln Ser Pro Ser Ser Leu Ser Ala Ser Val Gly
1               5                   10                  15

gac aga gtc acc atc aca tgc agt gcc agc tca agt gta aat cac atg       96
Asp Arg Val Thr Ile Thr Cys Ser Ala Ser Ser Ser Val Asn His Met
            20                  25                  30

ttc tgg tat cag cag aag ccc ggg aaa gcc ccc aaa ccc tgg att tat      144
Phe Trp Tyr Gln Gln Lys Pro Gly Lys Ala Pro Lys Pro Trp Ile Tyr
        35                  40                  45

ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
    50                  55                  60

ggg tct ggg aca gat tac act ctc aca atc agc agc ctg caa cct gaa      240
Gly Ser Gly Thr Asp Tyr Thr Leu Thr Ile Ser Ser Leu Gln Pro Glu
65                  70                  75                  80

gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                85                  90                  95

ttc ggt gga ggc act aag gtg gag atc aaa                              318
Phe Gly Gly Gly Thr Lys Val Glu Ile Lys
            100                 105
```

<210> SEQ ID NO 49
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 49

```
Gln Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45
```

```
Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gly Gly Thr Lys Val Glu Ile Lys
            100                 105


<210> SEQ ID NO 50
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 50

caa att gtt ctc acc cag tct cca tcc tcc ctg tct gcg tct gta ggg       48
Gln Ile Val Leu Thr Gln Ser Pro Ser Ser Leu Ser Ala Ser Val Gly
1               5                   10                  15

gac aga gtc acc atc aca tgc agt gcc agc tca agt gta aat cac atg       96
Asp Arg Val Thr Ile Thr Cys Ser Ala Ser Ser Ser Val Asn His Met
            20                  25                  30

ttc tgg tat cag cag aag ccc ggg aaa gcg ccc aaa ctc ctg att tat      144
Phe Trp Tyr Gln Gln Lys Pro Gly Lys Ala Pro Lys Leu Leu Ile Tyr
        35                  40                  45

ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
    50                  55                  60

ggg tct ggg aca gat tac act ctc aca atc agc agc ctg caa cct gaa      240
Gly Ser Gly Thr Asp Tyr Thr Leu Thr Ile Ser Ser Leu Gln Pro Glu
65                  70                  75                  80

gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                85                  90                  95

ttc ggt gga ggc act aag gtg gag atc aaa                              318
Phe Gly Gly Gly Thr Lys Val Glu Ile Lys
            100                 105


<210> SEQ ID NO 51
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 51

Gln Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Leu Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80
```

```
Asp Phe Ala Thr Tyr Tyr Cys Gln Gln Trp Ser Gly Asn Pro Trp Thr
                85                  90                  95

Phe Gly Gly Gly Thr Lys Val Glu Ile Lys
            100                 105


<210> SEQ ID NO 52
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 52

caa att cag ctc acc cag tct cca tcc tcc ctg tct gcg tct gta ggg       48
Gln Ile Gln Leu Thr Gln Ser Pro Ser Ser Leu Ser Ala Ser Val Gly
1               5                   10                  15

gac aga gtc acc atc aca tgc agt gcc agc tca agt gta aat cac atg       96
Asp Arg Val Thr Ile Thr Cys Ser Ala Ser Ser Ser Val Asn His Met
            20                  25                  30

ttc tgg tat cag cag aag ccc ggg aaa gcc ccc aaa ccc tgg att tat      144
Phe Trp Tyr Gln Gln Lys Pro Gly Lys Ala Pro Lys Pro Trp Ile Tyr
        35                  40                  45

ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
    50                  55                  60

ggg tct ggg aca gat tac act ctc aca atc agc agc ctg caa cct gaa      240
Gly Ser Gly Thr Asp Tyr Thr Leu Thr Ile Ser Ser Leu Gln Pro Glu
65                  70                  75                  80

gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                85                  90                  95

ttc ggt cag ggc act aag gtg gag atc aaa                              318
Phe Gly Gln Gly Thr Lys Val Glu Ile Lys
            100                 105


<210> SEQ ID NO 53
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 53

caa att cag ctc acc cag tct cca tcc tcc ctg tct gcg tct gta ggg       48
Gln Ile Gln Leu Thr Gln Ser Pro Ser Ser Leu Ser Ala Ser Val Gly
1               5                   10                  15

gac aga gtc acc atc aca tgc agt gcc agc tca agt gta aat cac atg       96
Asp Arg Val Thr Ile Thr Cys Ser Ala Ser Ser Ser Val Asn His Met
            20                  25                  30

ttc tgg tat cag cag aag ccc ggg aaa gcc ccc aaa ctc ctg att tat      144
Phe Trp Tyr Gln Gln Lys Pro Gly Lys Ala Pro Lys Leu Leu Ile Tyr
        35                  40                  45

ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
    50                  55                  60

ggg tct ggg aca gat tac act ctc aca atc agc agc ctg caa cct gaa      240
Gly Ser Gly Thr Asp Tyr Thr Leu Thr Ile Ser Ser Leu Gln Pro Glu
65                  70                  75                  80
```

```
gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                85                  90                  95

ttc ggt cag ggc act aag gtg gag atc aaa                              318
Phe Gly Gln Gly Thr Lys Val Glu Ile Lys
            100                 105


<210> SEQ ID NO 54
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 54

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Leu Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105


<210> SEQ ID NO 55
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 55

gaa att gtt ctc acc cag ttt cca gca ctc atg tct gcg tct cca ggg       48
Glu Ile Val Leu Thr Gln Phe Pro Ala Leu Met Ser Ala Ser Pro Gly
1               5                   10                  15

gag aag gtc acc atg acc tgc agt gcc agc tca agt gta aat cac atg       96
Glu Lys Val Thr Met Thr Cys Ser Ala Ser Ser Ser Val Asn His Met
            20                  25                  30

ttc tgg tat cag cag aag cca aaa tcc tcc ccc aaa ccc tgg att tat      144
Phe Trp Tyr Gln Gln Lys Pro Lys Ser Ser Pro Lys Pro Trp Ile Tyr
        35                  40                  45

ctc aca tcc aac ctg gct tct gga gtc cct gct cgc ttc agt ggc agt      192
Leu Thr Ser Asn Leu Ala Ser Gly Val Pro Ala Arg Phe Ser Gly Ser
    50                  55                  60

ggg tct ggg acc tct tac tct ctc aca atc agc agc atg gag gct gaa      240
Gly Ser Gly Thr Ser Tyr Ser Leu Thr Ile Ser Ser Met Glu Ala Glu
65                  70                  75                  80

gat gct gcc act tat tac tgc cag cag tgg agt ggt aac ccg tgg acg      288
Asp Ala Ala Thr Tyr Tyr Cys Gln Gln Trp Ser Gly Asn Pro Trp Thr
                85                  90                  95

ttc ggt gga ggc acc aag ctg gag atc aaa                              318
Phe Gly Gly Gly Thr Lys Leu Glu Ile Lys
```

```
        100                 105


<210> SEQ ID NO 56
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 56

Glu Ile Val Leu Thr Gln Phe Pro Ala Leu Met Ser Ala Ser Pro Gly
1               5                   10                  15

Glu Lys Val Thr Met Thr Cys Ser Ala Ser Ser Ser Val Asn His Met
            20                  25                  30

Phe Trp Tyr Gln Gln Lys Pro Lys Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105


<210> SEQ ID NO 57
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 57

gat atc cag ctc acc cag tct cca tcc tcc ctg tct gcg tct gta ggg       48
Asp Ile Gln Leu Thr Gln Ser Pro Ser Ser Leu Ser Ala Ser Val Gly
1               5                   10                  15

gac aga gtc acc atc aca tgc agt gcc agc tca agt gta aat cac atg       96
Asp Arg Val Thr Ile Thr Cys Ser Ala Ser Ser Ser Val Asn His Met
            20                  25                  30

ttc tgg tat cag cag aag ccc ggg aaa gcc ccc aaa ccc tgg att tat      144
Phe Trp Tyr Gln Gln Lys Pro Gly Lys Ala Pro Lys Pro Trp Ile Tyr
        35                  40                  45

ctc aca tcc aac ctg gct tct gga gtc cct tca cgc ttc agt ggc agt      192
Leu Thr Ser Asn Leu Ala Ser Gly Val Pro Ser Arg Phe Ser Gly Ser
    50                  55                  60

ggg tct ggg aca gat tac act ctc aca atc agc agc ctg caa cct gaa      240
Gly Ser Gly Thr Asp Tyr Thr Leu Thr Ile Ser Ser Leu Gln Pro Glu
65                  70                  75                  80

gat ttt gcc act tat tac tgc cag cag tgg agt ggt aac ccg tgg acg      288
Asp Phe Ala Thr Tyr Tyr Cys Gln Gln Trp Ser Gly Asn Pro Trp Thr
                85                  90                  95

ttc ggt cag ggc act aag gtg gag atc aaa                              318
Phe Gly Gln Gly Thr Lys Val Glu Ile Lys
            100                 105


<210> SEQ ID NO 58
<211> LENGTH: 106
<212> TYPE: PRT
<213> ORGANISM: Artificial Sequence
```

<220> FEATURE:
<223> OTHER INFORMATION: Synthetically generated peptide

<400> SEQUENCE: 58

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 59
<211> LENGTH: 192
<212> TYPE: PRT
<213> ORGANISM: Artificial Sequence
<220> FEATURE:
<223> OTHER INFORMATION: Rat and human chimeric I domain construct

<400> SEQUENCE: 59

Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Asn
            20                  25                  30

Asp Ile Gly Pro Lys Gln Thr Gln Val Gly Ile Val Gln Tyr Gly Glu
        35                  40                  45

Asn Val Thr His Glu Phe Asn Leu Asn Lys Tyr Ser Ser Thr Glu Glu
    50                  55                  60

Val Leu Val Ala Ala Asn Lys Ile Val Gln Arg Gly Gly Arg Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
        115                 120                 125

Cys Glu Asp Glu Asn Ile Gln Arg Phe Ser Ile Ala Ile Leu Gly His
    130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Thr Val Lys Ala Leu Gly Glu Arg Ile Phe
            180                 185                 190

<210> SEQ ID NO 60
<211> LENGTH: 192
<212> TYPE: PRT
<213> ORGANISM: Rattus sp.

<400> SEQUENCE: 60

```
Thr Gln Leu Asp Ile Val Ile Val Leu Asp Gly Ser Asn Ser Ile Tyr
1               5                   10                  15

Pro Trp Glu Ser Val Ile Ala Phe Leu Asn Asp Leu Leu Lys Arg Met
            20                  25                  30

Asp Ile Gly Pro Lys Gln Thr Gln Val Gly Ile Val Gln Tyr Gly Glu
        35                  40                  45

Asn Val Thr His Glu Phe Asn Leu Asn Lys Tyr Ser Ser Thr Glu Glu
    50                  55                  60

Val Leu Val Ala Ala Asn Lys Ile Gly Arg Gln Gly Gly Leu Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
        115                 120                 125

Cys Glu Asp Glu Asn Ile Gln Arg Phe Ser Ile Ala Ile Leu Gly His
    130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Ile Val Lys Ala Leu Gly Glu Arg Ile Phe
            180                 185                 190
```

<210> SEQ ID NO 61
<211> LENGTH: 192
<212> TYPE: PRT
<213> ORGANISM: Homo sapiens

<400> SEQUENCE: 61

```
Thr Gln Leu Asp Ile Val Ile Val Leu Asp Gly Ser Asn Ser Ile Tyr
1               5                   10                  15

Pro Trp Asp Ser Val Thr Ala Phe Leu Asn Asp Leu Leu Lys Arg Met
            20                  25                  30

Asp Ile Gly Pro Lys Gln Thr Gln Val Gly Ile Val Gln Tyr Gly Glu
        35                  40                  45

Asn Val Thr His Glu Phe Asn Leu Asn Lys Tyr Ser Ser Thr Glu Glu
    50                  55                  60

Val Leu Val Ala Ala Lys Lys Ile Val Gln Arg Gly Gly Arg Gln Thr
65                  70                  75                  80

Met Thr Ala Leu Gly Ile Asp Thr Ala Arg Lys Glu Ala Phe Thr Glu
                85                  90                  95

Ala Arg Gly Ala Arg Arg Gly Val Lys Lys Val Met Val Ile Val Thr
            100                 105                 110

Asp Gly Glu Ser His Asp Asn His Arg Leu Lys Lys Val Ile Gln Asp
        115                 120                 125

Cys Glu Asp Glu Asn Ile Gln Arg Phe Ser Ile Ala Ile Leu Gly Ser
    130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Ile Ala Leu Val Thr Ile Val Lys Thr Leu Gly Glu Arg Ile Phe
```

180 185 190

<210> SEQ ID NO 62
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 62

Gly Phe Gly Asp Gly Gly Tyr
1 5

<210> SEQ ID NO 63
<211> LENGTH: 214
<212> TYPE: PRT
<213> ORGANISM: Rattus sp.

<400> SEQUENCE: 63

Val Ser Pro Thr Phe Gln Val Val Asn Ser Phe Ala Pro Val Gln Glu
1 5 10 15

Cys Ser Thr Gln Leu Asp Ile Val Ile Val Leu Asp Gly Ser Asn Ser
20 25 30

Ile Tyr Pro Trp Glu Ser Val Ile Ala Phe Leu Asn Asp Leu Leu Lys
35 40 45

Arg Met Asp Ile Gly Pro Lys Gln Thr Gln Val Gly Ile Val Gln Tyr
50 55 60

Gly Glu Asn Val Thr His Glu Phe Asn Leu Asn Lys Tyr Ser Ser Thr
65 70 75 80

Glu Glu Val Leu Val Ala Ala Lys Lys Ile Gly Arg Gln Gly Gly Leu
85 90 95

Gln Thr Met Thr Ala Leu Gly Ile Asp Thr Ala Arg Lys Glu Ala Phe
100 105 110

Thr Glu Ala Arg Gly Ala Arg Arg Gly Val Lys Lys Val Met Val Ile
115 120 125

Val Thr Asp Gly Glu Ser His Asp Asn Tyr Arg Leu Lys Gln Val Ile
130 135 140

Gln Asp Cys Glu Asp Glu Asn Ile Gln Arg Phe Ser Ile Ala Ile Leu
145 150 155 160

Gly His Tyr Asn Arg Gly Asn Leu Ser Thr Glu Lys Phe Val Glu Glu
165 170 175

Ile Lys Ser Ile Ala Ser Glu Pro Thr Glu Lys His Phe Phe Asn Val
180 185 190

Ser Asp Glu Leu Ala Leu Val Thr Ile Val Lys Ala Leu Gly Glu Arg
195 200 205

Ile Phe Ala Leu Glu Ala
210

<210> SEQ ID NO 64
<211> LENGTH: 214
<212> TYPE: PRT
<213> ORGANISM: Homo sapiens

<400> SEQUENCE: 64

Val Ser Pro Thr Phe Gln Val Val Asn Ser Ile Ala Pro Val Gln Glu
1 5 10 15

Cys Ser Thr Gln Leu Asp Ile Val Ile Val Leu Asp Gly Ser Asn Ser
20 25 30

Ile Tyr Pro Trp Asp Ser Val Thr Ala Phe Leu Asn Asp Leu Leu Lys
35 40 45

Arg Met Asp Ile Gly Pro Lys Gln Thr Gln Val Gly Ile Val Gln Tyr
50 55 60

Gly Glu Asn Val Thr His Glu Phe Asn Leu Asn Lys Tyr Ser Ser Thr
65 70 75 80

Glu Glu Val Leu Val Ala Ala Lys Lys Ile Val Gln Arg Gly Gly Arg
85 90 95

Gln Thr Met Thr Ala Leu Gly Thr Asp Thr Ala Arg Lys Glu Ala Phe
100 105 110

Thr Glu Ala Arg Gly Ala Arg Arg Gly Val Lys Lys Val Met Val Ile
115 120 125

Val Thr Asp Gly Glu Ser His Asp Asn His Arg Leu Lys Lys Val Ile
130 135 140

Gln Asp Cys Glu Asp Glu Asn Ile Gln Arg Phe Ser Ile Ala Ile Leu
145 150 155 160

Gly Ser Tyr Asn Arg Gly Asn Leu Ser Thr Glu Lys Phe Val Glu Glu
165 170 175

Ile Lys Ser Ile Ala Ser Glu Pro Thr Glu Lys His Phe Phe Asn Val
180 185 190

Ser Asp Glu Leu Ala Leu Val Thr Ile Val Lys Thr Leu Gly Glu Arg
195 200 205

Ile Phe Ala Leu Glu Ala
210

<210> SEQ ID NO 65
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 65

Asp Ile Val Met Thr Gln Ser Pro Ser Ser Leu Ser Ala Ser Val Gly
1 5 10 15

Asp Arg Val Thr Ile Thr Cys Arg Ala Ser Gln Ser Ile Ser Tyr Leu
20 25 30

Asn Trp Tyr Gln Gln Lys Pro Gly Lys Ala Pro Lys Leu Leu Ile Tyr
35 40 45

Ala Ala Ser Ser Leu Gln Ser Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys Gln Gln Ser Tyr Ser Thr Pro Leu Thr
85 90 95

Phe Gly Gly Gly Thr Lys Val Glu Ile Lys
100 105

<210> SEQ ID NO 66
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 66

Gln Ile Gln Leu Thr Gln Ser Pro Ser Ser Leu Ser Ala Ser Val Gly
1 5 10 15

```
Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105


<210> SEQ ID NO 67
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 67

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Ile Arg Phe Leu Glu Trp Ser Phe Asp Tyr Trp Gly Gln Gly Thr
            100                 105                 110

Leu Val Thr Val Ser Ser
        115


<210> SEQ ID NO 68
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
```

-continued

```
                85                  90                  95

Arg Gly Phe Gly Asp Gly Gly Tyr Phe Asp Val Trp Gly Gln Gly Thr
            100                 105                 110

Leu Val Thr Val Ser Ser
        115


<210> SEQ ID NO 69
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115


<210> SEQ ID NO 70
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 70

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105
```